(12) United States Patent
Guo et al.

(10) Patent No.: US 10,654,909 B2
(45) Date of Patent: May 19, 2020

(54) SOLUBLE ALPHA KLOTHO AND SERUM ALBUMIN FUSION PROTEIN

(71) Applicant: Novartis AG, Basel (CH)

(72) Inventors: Donglin Guo, Wellesley, MA (US); Chikwendu Ibebunjo, Newton, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/532,634

(22) PCT Filed: Dec. 2, 2015

(86) PCT No.: PCT/IB2015/059294
§ 371 (c)(1),
(2) Date: Jun. 2, 2017

(87) PCT Pub. No.: WO2016/088059
PCT Pub. Date: Jun. 9, 2016

(65) Prior Publication Data
US 2018/0037623 A1 Feb. 8, 2018

Related U.S. Application Data

(60) Provisional application No. 62/087,516, filed on Dec. 4, 2014.

(51) Int. Cl.
*C07K 14/71* (2006.01)
*C12N 15/62* (2006.01)

(52) U.S. Cl.
CPC .............. *C07K 14/71* (2013.01); *C12N 15/62* (2013.01); *C07K 2319/00* (2013.01); *C07K 2319/30* (2013.01)

(58) Field of Classification Search
None
See application file for complete search history.

(56) References Cited

U.S. PATENT DOCUMENTS

| | | |
|---|---|---|
| 5,408,038 A | 4/1995 | Smith et al. |
| 5,541,094 A | 7/1996 | Anton et al. |
| 6,579,850 B1 | 6/2003 | Nabeshima et al. |
| 7,060,479 B2 | 6/2006 | Dumas Milne Edwards et al. |
| 7,217,798 B2 | 5/2007 | Hinton et al. |
| 7,223,563 B2 | 5/2007 | Econs et al. |
| 7,259,248 B2 | 8/2007 | Itoh et al. |
| 7,745,406 B2 | 6/2010 | Econs et al. |
| 8,420,088 B2 | 4/2013 | Glass et al. |
| 8,461,111 B2 | 6/2013 | Blaber et al. |
| 8,481,031 B2 | 7/2013 | Glass et al. |
| 8,932,589 B2 | 1/2015 | Glass et al. |
| 9,458,209 B2 | 10/2016 | Glass et al. |
| 9,475,857 B2 | 10/2016 | Glass et al. |
| 2005/0004348 A1 | 1/2005 | Miyamoto et al. |
| 2006/0160181 A1 | 7/2006 | Luethy et al. |
| 2006/0281679 A1 | 12/2006 | Itoh et al. |
| 2009/0192087 A1 | 7/2009 | Glass et al. |
| 2010/0215657 A1 | 8/2010 | Glass et al. |
| 2010/0298220 A1 | 11/2010 | Blaber et al. |
| 2011/0195077 A1 | 8/2011 | Glass et al. |
| 2011/0195895 A1 | 8/2011 | Walker et al. |
| 2012/0064544 A1 | 3/2012 | Econs et al. |
| 2013/0122004 A1 | 5/2013 | Glass et al. |
| 2013/0224196 A1 | 8/2013 | Glass et al. |
| 2013/0324458 A1 | 12/2013 | Glass et al. |
| 2014/0323395 A1 | 10/2014 | Belouski et al. |
| 2016/0030585 A1 | 2/2016 | Barnes et al. |
| 2016/0031961 A1 | 2/2016 | Glass et al. |
| 2017/0166618 A1 | 6/2017 | Glass et al. |
| 2017/0233446 A1 | 8/2017 | Glass et al. |

FOREIGN PATENT DOCUMENTS

| | | |
|---|---|---|
| AU | 2011209380 B2 | 9/2013 |
| JP | 2004201691 A | 7/2004 |
| JP | 2004527253 A | 9/2004 |
| JP | 2006238894 A | 9/2006 |
| JP | 2008194039 A | 8/2008 |
| WO | 01/61007 A2 | 8/2001 |

(Continued)

OTHER PUBLICATIONS

Muller et al. J. Biol. Chem. 282(17): 12650-12660, 2007.*
Goetz et al.; "Molecular Insights into the Klotho-Dependent, Endocrine Mode of Action of Fibroblast Growth Factor 19 Subfamily Members"; Molecular and Cellular Biology; 27(9):3417-3428 (2007).
Hessell et al.; "Fc receptor but not complement binding is important in antibody protection against HIV"; Nature—Letters; 449:101-105 (2007).
Kurosu et al.; "Regulation of Fibroblast Growth Factor-23 Signaling by Klotho"; The Journal of Biological Chemistry; 281(10):6120-6123 (2006).
Lode et al.; "Gene therapy with a single chain interleukin 12 fusion protein induces T cell-dependent protective immunity in a syngeneic model of murine neuroblastoma"; Proc. Natl. Acad. Sci. USA; 95:2475-2480 (1998).

(Continued)

*Primary Examiner* — Christine J Saoud
(74) *Attorney, Agent, or Firm* — Kun Wang; Genomics Institute of the Novartis Research Foundation

(57) ABSTRACT

The present disclosure is directed to compositions and methods related to an alpha sKlotho variant or fragment, in which 1 to up to about 20 amino acids have been deleted from the C-terminus, optionally also having mutations at V563 and/or K795. The present disclosure also pertains to an alpha sKlotho polypeptide variant or fragment, having mutations at V563 and/or K795, wherein the polypeptide variant or fragment is full-length, or optionally 1 to up to about 20 amino acids have been deleted from the C-terminus. The present disclosure also pertains to fusion polypeptides comprising: (a) an alpha sKlotho, in which 1 to up to about 20 amino acids have been deleted from the C-terminus, optionally also having mutations at V563 and/or K795; (b) a linker; and (c) FGF23, optionally having a mutation at R179, C206 and/or C244, or (c) serum albumin.

6 Claims, 21 Drawing Sheets
Specification includes a Sequence Listing.

(56) References Cited

FOREIGN PATENT DOCUMENTS

| WO | 02/08271 A1 | 1/2002 |
|---|---|---|
| WO | 02/088358 A2 | 11/2002 |
| WO | 2009/095372 | 8/2009 |
| WO | 2009/117622 | 9/2009 |
| WO | 2011/092234 A1 | 8/2011 |
| WO | 2013/027191 A1 | 2/2013 |
| WO | 2015/200078 A1 | 12/2015 |

OTHER PUBLICATIONS

Ray; "Klotho Gets Around"; Science STKE; 2006(365):tw416 (2006)[Abstract].

Razzaque, M.S. "Therapeutic potential of klothoFGF23 fusion polypeptides: WO2009095372", Expert Opinion on Therapeutic Patents, in Forma Healthcare, GB, vol . 20, No. 7, pp. 981-985, (2010).

Tohyama et al.; "Klotho Is a Novel Beta-Glucuronidase Capable of Hydrolyzing Steroid Beta-Glucuronides"; The Journal of Biological Chemistry; 279(11):9777-9784 (2004).

Torres et al.; "Klotho: An antiaging protein involved in mineral and vitamin D metabolism"; Kidney International; 71:730-737 (2007).

Urakawa et al.; "Klotho converts canonical FGF receptor into a specific receptor for FGF23"; Nature—Letters; 444:770-774 (2006).

Wu et al.; "Co-receptor Requirements for Fibroblast Growth Factor-19 Signaling"; The Journal of Biological Chemistry; 282(40):29069-29072 (2007).

The ADHR Consortium; "Autosomal dominant hypophosphataemic rickets is associated with mutations in FGF23"; Nature Genetics; 26:345-348 (2000).

Bai et al.; "The Autosomal Dominant Hypophosphatemic Rickets R176Q Mutation in Fibroblast Growth Factor 23 Resists Proteolytic Cleavage and Enhances in Vivo Biological Potency"; The Journal of Biological Chemistry; 278(11):9843-9849 (2003).

Bai et al.; "Transgenic Mice Overexpressing Human Fibroblast Growth Factor 23 (R176Q) Delineate a Putative Role for Parathyroid Hormone in Renal Phosphate Wasting Disorders"; Endocrinology; 145(11):5269-5279 (2004).

Bai et al.; "Klotho ablation converts the biochemical and skeletal alterations in FGF23 (R176Q) transgenic mice to a Klotho-deficient phenotype"; Am. J. Physiol. Endocrinol. Metab.; 296:E79-E88 (2009).

Ben-Dov et al.; "The parathyroid is a target organ for FGF23 in rats"; The Journal of Clinical Investigation—Research Article; 117(12):4003-4008 (2007).

Berndt et al.; "Biological activity of FGF-23 fragments"; Pflugers Arch—Eur. J. Physiol.; 454:615-623 (2007).

Carpenter et al.; "Circulating Levels of Soluble Klotho and FGF23 in X-Linked Hypophosphatemia: Circadian Variance, Effects of Treatment, and Relationship to Parathyroid Status"; J. Clin. Endocrinol. Metab.; 95:E352-E357 (2010).

Drueke et al.; "Klotho spins the thread of life-what does Klotho do to the receptors of fibroblast growth factor-23 (FGF23)?"; Nephrol Dial. Transplant; 22:1524-1526 (2007).

KURO-O; "Overview of the FGF23-Klotho axis"; Pediatr. Nephrol.; 25:583-590 (2010).

Shimada et al.; "Mutant FGF-23 responsible for autosomal dominant hypophosphatemic rickets is resistant to proteolytic cleavage and causes hypophosphatemia in vivo"; Endocrinology; 143(8):3179-3182 (2002).

Strewler; "FGF23, hypophosphatemia, and rickets: Has phosphatonin been found?"; PNAS—Commentary; 98(11):5945-5946 (2001).

Urakawa et al; "Klotho converts canonical FGF receptor into a specific receptor for FGF23"; Nature; 444:770-774 (2006)[Supplemental Data List; Supplemental Figures 1-6; Supplemental Discussion; Supplemental Methods and Supplemental Table].

White et al.; "Autosomal-dominant hypophosphatemic rickets (ADHR) mutations stabilize FGF-23"; Kidney International; 60:2079-2086 (2001).

Yu et al.; "FGF23 and disorders of phosphate homeostasis"; Cytokine & Growth Factor Reviews; 16:221-232 (2005).

Gasparian et al., Biochemistry, 74(2):221-225 (2009).

Beenken et al., (Adv. Exp. Med. Biol. 728: 1-24, 2012).

Wu, X. et al., "C-terminal Tail of FGF-19 Determines Its Specificity toward Klotho Co-receptors", The Journal of Biological Chemistry, 283(48):33304-33309, (2008).

Garringer, H.J. et al., "Molecular genetic and biochemical analyses of FGF23 mutations in familial tumoral calcinosis", Am. J. Physiol. Endocrinol. Metab., 295(4):E929-E937 (2008).

R. Goetz, et al. "Isolated C-terminal tail of FGF23 alleviates hypophosphatemia inhibiting FGF23-FGFR-Klotho complex formation", Proceedings of the National Academy of Sciences, vol. 107, No. 1, pp. 407-412, (E-published: Dec. 2009 [Pending Verification]) Print Publication Date: Jan. 2010.

Ito, et al. "Molecular cloning and expression analyses of mouse bklotho, which encodes a novel Klotho family protein" Mech. Dev., 98:115-119 (2000).

\* cited by examiner

▨ : Klotho (extracellular domain) or active fragment of Klotho;

▨ : FGF23 (R179Q), FGF23, FGF 19, FGF21; ▨ : linker; ▨ : IgG signal peptide.

lane 1, Ctrl; lane 2, FGF23; lane 3, sKlotho; lanes 4-6, sKlotho-FGF23 lane 1, Ctrl; lane 2, FGF23; lane 3, sKlotho; lanes 4-6, sKlotho-FGF23 lane 1, purified sKlotho-FGF23-6xHis; lane 2, molecular weight marker

A

B 1. pcDNA3.1-sKlotho-FGF23
2. pcDNA3.1-FGF23-sKlotho(del c-20)
3. pcDNA3.1-sKlotho(del c-20)-FGF23

A

B

SOLUBLE ALPHA KLOTHO AND SERUM ALBUMIN FUSION PROTEIN

CROSS REFERENCE TO RELATED APPLICATIONS

This application is a U.S. National Phase Application under 35 U.S.C. § 371 of International Application PCT/IB2015/059294, filed on Dec. 2, 2015, which claims priority to U.S. Application No. 62/087,516, filed on Dec. 4, 2014, the contents of which are hereby incorporated by reference in their entireties.

SEQUENCE LISTING

The instant application contains a Sequence Listing, which has been submitted electronically in ASCII format and is hereby incorporated by reference in its entirety. Said ASCII copy, created on Aug. 18, 2017, is named PAT056577-US-PCT_SEQ_LSTG and is 477,508 bytes in size.

1. BACKGROUND

Fibroblast growth factors (FGFs) constitute a family of homologous polypeptide growth factors expressed in many organisms (Ornitz and Itoh, Genome Biol. 2: reviews, 3005.1-3005.12 (2001)). Among vertebrate species, FGFs are highly conserved in both gene structure and amino-acid sequence, having between 13-71% amino acid identity with one another. In humans, there are 22 known members of the FGF family (FGF15 is the mouse ortholog of human FGF19, hence there is no human FGF15). During early development, FGFs regulate cell proliferation, migration, and differentiation, but in the adult organism, FGFs maintain homeostasis, function in tissue repair, and respond to injury.

FGFs function as growth factors by binding and thereby activating cell-surface FGF receptors. FGF receptors (FGFRs) are tyrosine kinase receptors that activate signal transduction through autophosphorylation of FGFR, phosphorylation of FRS2 (FGF receptor substrate 2) and ERK1/2 (extracellular signal-regulated protein kinase 1/2), and activating Egr-1 (early growth response-1). FGFs also have a high affinity for heparin sulfate proteoglycans. When bound to FGFs, heparin sulfate enhances the activation of FGFRs.

The alpha-Klotho gene encodes a 130 kDa single pass type I transmembrane protein with an extracellular domain and a short cytoplasmic domain. The extracellular domain of alpha-Klotho protein comprises two subdomains termed, KL-D1 and KL-D2. These two subdomains share sequence homology to β-glucosidase of bacteria and plants. The extracellular domain of the alpha-Klotho protein may be bound to the cell surface by the transmembrane domain or may be cleaved and released into the extracellular milieu. Cleavage of the extracellular domain appears to be facilitated by local low extracellular $Ca^{2+}$ concentrations.

In addition to alpha-Klotho, a homolog of alpha-Klotho, beta-Klotho, has been identified (Ito et al., Mech. Dev. 98:115-9 (2000)). Beta-Klotho is also a single pass type I transmembrane protein with extracellular KL-D1 and KL-D2 subdomains.

Modulation of alpha-Klotho expression has been demonstrated to produce aging related characteristics in mammals. Mice homozygous for a loss of function mutation in the alpha-Klotho gene develop characteristics resembling human aging, including shortened lifespan, skin atrophy, muscle wasting, arteriosclerosis, pulmonary emphysema and osteoporosis (Kuro-o et al., Nature, 390:45-51 (1997)). In contrast, overexpression of the alpha-Klotho gene in mice extends lifespan and increases resistance to oxidative stress relative to wild-type mice (Kurosu et al., Science 309:1829-1833 (2005); Yamamoto et al., J. Biol. Chem. 280:38029-38034 (2005)).

Recent studies have demonstrated strikingly similar biological characteristics between FGF23-deficient mice and alpha-Klotho-deficient mice (Shimada et al., J. Clin. Invest. 113:561-568 (2004); Yoshida et al. Endocrinology 143:683-689 (2002)), indicating functional crosstalk between FGF23 and alpha-Klotho. These studies led to the identification of alpha-Klotho as an obligatory partner of FGF23, in terms of both binding and signaling through its cognate FGF receptors (Urakawa et al., Nature 22:1524-6 (2007)). The alpha-Klotho gene is mainly expressed in kidney, parathyroid gland and choroid plexus. It is hypothesized that the tissue-specific expression of alpha-Klotho restricts activation of FGF23 signaling to those tissues.

Similar to FGF23/alpha-Klotho, beta-Klotho is an obligatory partner of FGF19 and FGF21, both in binding and in signaling through their respective cognate FGF receptors (Ogawa et al., Proc. Natl. Acad. Sci. USA 104:7432-7 (2007); Lin et al., J Biol Chem. 282:27227-84 (2007); and Wu et al., J. Biol. Chem. 282:29069-72 (2007)). Such studies have also demonstrated the involvement of beta-Klotho in regulating tissue-specific metabolic activity. Beta-Klotho was initially shown to act with FGF21 as a cofactor for regulating carbohydrate and lipid metabolism in adipose tissue. Beta-Klotho in conjunction with FGF19 regulates bile acid metabolism in liver, thus explaining elevated bile synthesis in beta-Klotho deficient mice (Ito et al., J Clin Invest. 2005 August; 115(8):2202-8).

U.S. Pat. No. 6,579,850 describes polypeptides and compositions comprising an alpha-Klotho polypeptide. Human and mouse alpha-Klotho polypeptides are disclosed. The patent also disclosed that compositions comprising the polypeptides are useful in treating a syndrome resembling premature aging, treating adult diseases, and suppressing aging.

U.S. Pat. No. 7,223,563 describes isolated nucleic acids encoding the FGF23 polypeptide sequence or recombinant cells comprising such an isolated nucleic acid. The patent further relates to methods of diagnosing and treating hypophosphatemic and hyperphosphatemic disorders, osteoporosis, dermatomyositis, and coronary artery disease.

U.S. Pat. No. 7,259,248 describes isolated nucleic acids encoding the FGF21 polypeptide sequence. The patent further relates to methods of diagnosing and treating liver disease, conditions related to thymic function, and methods of treating conditions of the testis.

There yet exists the need for novel artificial variants of alpha-Klotho, FGF23 and fusion polypeptides comprising these components.

2. SUMMARY OF THE DISCLOSURE

The present disclosure is directed to methods, uses, kits and compositions for preventing or treating age-related conditions or metabolic disorders with polypeptides, fusion polypeptides or soluble polypeptides.

A polypeptide of the disclosure comprises, for example, a Klotho variant, such as an alpha sKlotho delta C-20 (in which 1 to about 20 amino acids, about 20 amino acids, or 20 amino acids, have been deleted from the C-terminus), optionally also having mutations at V563 and/or K795. As another example, the polypeptide is an alpha sKlotho variant having a mutation at V563 and/or K795, which is full-length, or wherein optionally 1 to about 20 amino acids, about 20 amino acids or 20 amino acids have been deleted from the C-terminus. Any such polypeptide is a Klotho C-terminal deletion variant. Such a Klotho C-terminal deletion variant can be further modified, e.g., by the addition of PEG, and/or fused to other polypeptides. Suitable fusion polypeptides include, inter alia, FGF23 or a variant thereof, or serum albumin or a variant thereof. Thus: The fusion polypeptide of the present disclosure comprises, as a non-limiting example, in N-terminal to C-terminal order: (a) an alpha sKlotho delta C-20 (in which 1 to about 20 amino acids, about 20 amino acids, or 20 amino acids, have been deleted from the C-terminus), optionally also having mutations at V563 and/or K795; and (b) another polypeptide, e.g., FGF23 (without the FGF23 signal peptide), optionally having a mutation at R179, C206 and/or C244, or (b) serum albumin; and optionally, (c) a linker interposed between (a) and (b). Thus: The fusion polypeptide of the present disclosure comprises, as a non-limiting example, in N-terminal to C-terminal order: (a) an alpha sKlotho variant having mutations at V563 and/or K795 and optionally being full-length or being delta C-20 (in which 1 to about 20 amino acids, about 20 amino acids, or 20 amino acids, have been deleted from the C-terminus); and (b) another polypeptide, e.g., FGF23 (without the FGF23 signal peptide), optionally having a mutation at R179, C206 and/or C244, or (b) serum albumin; and optionally, (c) a linker interposed between (a) and (b). In some embodiments, the fusion polypeptide comprises, in N-terminal to C-terminal order: (a) an alpha sKlotho (e.g., alpha Klotho lacking the transmembrane domain and optionally lacking the signal peptide), in which 1 to about 20 amino acids, about 20 amino acids, or 20 amino acids have been deleted from the C-terminus, optionally also having mutations at V563 and/or K795; (b) a linker (e.g., about 10, about 20, about 30, or about 40 amino acids in length); and (c) FGF23, optionally having a mutation at R179, C206 and/or C244. In some embodiments, the FGF23 component has a mutation at C206 and/or C244. In some embodiments of these fusions, the alpha sKlotho has the mutations at V563 and/or K795. In some embodiments, the sKlotho delta C-20 is represented by SEQ ID NO: 77 or 78 (the latter having the mutations V563A and K795E). In some embodiments, the fusion polypeptide comprises a signal peptide N-terminal to the alpha sKlotho. In various embodiments, the signal peptide is a Klotho signal peptide. In some embodiments, the signal peptide is represented by the bold, underlined portion of SEQ ID NO: 81. In various embodiment, the linker is any type of linker known in the art capable of connecting two peptides. In various embodiments, the linker comprises one or more amino acids. In various embodiments, the linker comprises any sequence of SEQ ID NOs: 11 to 18, or any number or combination thereof. In various embodiments, the linker comprises 1, 2, 3 or more copies of SEQ ID NO: 12. In various embodiments, the linker comprises 3 copies of SEQ ID NO: 12. In some embodiments, the fusion polypeptide is represented by SEQ ID NOs: 79, 80, 81 or 82.

The polypeptides and fusion polypeptides of the present disclosure can be used for treating or preventing FGF23-related or Klotho-related diseases such as age-related condition (selected from the group consisting of sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss), a metabolic disorder (selected from the group consisting of Type II Diabetes, Metabolic Syndrome, hyperglycemia, and obesity), hyperphosphatemia, calcinosis, chronic renal disease, chronic renal failure, cancer, breast cancer, and/or muscle atrophy. In various embodiments, the Klotho variant polypeptides and fusion polypeptides of the disclosure can be used in various methods of treating kidney diseases.

In some embodiments of the fusion polypeptide, the FGF23 is mutated. In some embodiments, the fusion polypeptide comprises a wild-type FGF23. In some embodiments, the FGF23 component of the fusion polypeptide is represented by SEQ ID NO: 42 or 43 or the bold portion of any of SEQ ID NOs: 79 to 82, or a functionally active variant, fragment or derivative of any of these. In one embodiment of the present disclosure, the fusion polypeptide comprises: a polypeptide comprising a functionally active variant of FGF23 having mutations at any of R179, Y154, C206, and C244. The data shown in Examples 7 and 8 and FIGS. 12 and 13 showed that these mutations reduce aggregation, reduce undesired protease-induced cleavage, and increase production. The FGF23 R179/Y154/C206/C244 mutant produced more protein but much less degradation product and retained FGF23 activity.

In various embodiments, the fusion polypeptide further comprises a modified Fc fragment having decreased affinity for Fc-gamma-receptor and/or increased serum half-life. For example, the fusion polypeptide can comprise a Klotho variant [e.g., a Klotho or alpha sKlotho delta C-20 (in which 1 to about 20 amino acids, about 20 amino acids, or 20 amino acids, have been deleted from the C-terminus), optionally also having mutations at V563 and/or K795; or Klotho or an alpha sKlotho variant having a mutation at V563 and/or K795, which is full-length, or wherein optionally 1 to about 20 amino acids, about 20 amino acids or 20 amino acids have been deleted from the C-terminus] and a modified Fc fragment having decreased affinity for Fc-gamma-receptor and/or increased serum half-life.

In some embodiments, the present disclosure provides a Klotho fusion polypeptide comprising a Klotho protein or an active fragment or variant thereof and a fibroblast growth factor or an active fragment or variant thereof. In some embodiments, the fusion polypeptide comprises a Klotho polypeptide, a FGF (such as FGF23) and a modified Fc fragment. The Fc fragment can, for example, have decreased binding to Fc-gamma-receptor and increased serum half-life. Fusion proteins comprising sKlotho, FGF23 and FcLALA (a modified Fc fragment having decreased affinity for Fc-gamma-receptor and/or increased serum half-life) are described in SEQ ID NOs. 46, 47, 48, and 49.

In some embodiments, the fusion polypeptide or protein comprises a FGF (e.g., FGF23), or a functionally active variant or derivative (e.g., a variant comprising at least one conservative amino acid substitution and/or one amino acid deletion) thereof and a modified Fc fragment, or a functionally active variant or derivative (e.g., a variant comprising at least one conservative amino acid substitution and/or one amino acid deletion) thereof. Fusion proteins comprising FGF23 and FcLALA are described in SEQ ID NOs. 50, 51, 52 and 53. In some embodiments, the fusion polypeptide has one or more mutations in FGF23 which decrease aggregation and/or protease-mediated cleavage.

In a first aspect, the disclosure provides a fusion polypeptide having at least one extracellular subdomain of a Klotho protein or active fragment or variant thereof and a fibroblast growth factor or an active fragment or variant thereof. In some embodiments, the fusion further comprises a modified Fc fragment having decreased affinity (e.g., decreased Ka or increased Kd) for Fc-gamma-receptor and/or increased serum half-life. The Klotho extracellular domain may be derived from either the alpha or beta Klotho isoforms. Further, although the FGF component of the Klotho fusion polypeptide is described primarily with reference to fibroblast growth factor-19, fibroblast growth factor-21 and fibroblast growth factor-23, it is contemplated that any of the twenty-three known FGFs can be used in practicing the disclosure. The reader of the instant application may assume that each of every combination of alpha or beta extracellular domain with each human FGF protein or an active fragment or variant thereof are individually and specifically contemplated.

According to the present disclosure, the extracellular domain of the Klotho protein can include one or both of the KL-D1 and KL-D2 domains of a Klotho protein, or a functionally active variant or derivative (e.g., a variant comprising at least one conservative amino acid substitution and/or one amino acid deletion) thereof. In some embodiments, the Klotho fusion polypeptide of the disclosure has at least two extracellular subdomains of a Klotho protein, or a functionally active variant or derivative (e.g., a variant comprising at least one conservative amino acid substitution and/or one amino acid deletion) thereof. For example, the at least two extracellular subdomains can be at least two KL-D1 domains in tandem repeats, at least two KL-D2 domains in tandem repeats, or at least one KL-D1 domain and at least one KL-D2 domain. In various embodiments, the fusion polypeptide of the disclosure comprises amino acids 28-292 of the full length alpha Klotho protein, or amino acids 28-982 (SEQ ID NO: 7). In another embodiment, the fusion polypeptide of the disclosure comprises amino acids 52-997 of the full length beta Klotho protein.

In one embodiment of the present disclosure, the components of a fusion polypeptide comprise: (a) a polypeptide comprising fibroblast growth factor 23 (FGF23), or a functionally active variant or derivative (e.g., a variant comprising at least one conservative amino acid substitution and/or one amino acid deletion) thereof, wherein FGF23 has a mutation at one or more of the positions R179, Y154, Q156, C206 and C244; and (b) either a modified Fc fragment having decreased affinity for Fc-gamma-receptor and/or increased serum half-life, or a polypeptide comprising at least one extracellular subdomain of a Klotho protein, or a functionally active variant or derivative (e.g., a variant comprising at least one conservative amino acid substitution and/or one amino acid deletion) thereof; and, optionally (c) a linker. The results, shown in Example 8 and FIGS. 12 and 13, showed that the FGF23 R179/Y154/C206/C244 mutant produced more protein but much less degradation product but retained significant FGF23 activity.

Not all combinations of mutations of FGF23 were equally effective. In addition, not all mutations at a particular site are equally effective. The mutations at S155 produced much more degradation product than the mutations at Y154. In addition, the mutation of Y154D produced less degradation product than the mutation of Y154H or Y154N. Therefore:

In one embodiment of the present disclosure, the the disclosure provides a composition comprising a fusion polypeptide comprising: (a) a polypeptide comprising a functionally active variant of FGF23 having mutations at R179, Y154, C206, and C244, and (b) a modified Fc fragment having decreased affinity for Fc-gamma-receptor and/or increased serum half-life, and, optionally, (c) a linker, wherein the FGF23 does not have a mutation at S155.

In one embodiment of the present disclosure, the the disclosure provides a composition comprising a fusion polypeptide comprising: (a) a polypeptide comprising a functionally active variant of FGF23 having mutations at R179, Y154, C206, and C244, and (b) a modified Fc fragment having decreased affinity for Fc-gamma-receptor and/or increased serum half-life, and, optionally, (c) a linker, wherein the mutation at Y154 is Y154D.

In one embodiment of the present disclosure, the the disclosure provides a composition comprising a fusion polypeptide comprising: (a) a polypeptide comprising a functionally active variant of FGF23 having mutations at R179, Y154, C206, and C244, and (b) a modified Fc fragment having decreased affinity for Fc-gamma-receptor and/or increased serum half-life, and, optionally, (c) a linker, wherein the mutation at Y154 is Y154D and wherein the FGF23 does not have a mutation at S155.

Further additional embodiments are disclosed below.

In one embodiment of the present disclosure, the components of a fusion polypeptide comprise: (a) a polypeptide comprising a functionally active variant of FGF23 having mutations at R179, Y154, C206, and C244; and (b) either a modified Fc fragment having decreased affinity for Fc-gamma-receptor and/or increased serum half-life, or a polypeptide comprising at least one extracellular subdomain of a Klotho protein, or a functionally active variant or derivative (e.g., a variant comprising at least one conservative amino acid substitution and/or one amino acid deletion) thereof; and, optionally, (c) a linker.

In one embodiment of the present disclosure, the components of a fusion polypeptide comprise: (a) a polypeptide comprising a functionally active variant of FGF23 having mutations at R179, Y154, C206, and C244; and (b) a modified Fc fragment having decreased affinity for Fc-gamma-receptor and/or increased serum half-life; and, optionally, (c) a linker.

In one embodiment of the present disclosure, the components of a fusion polypeptide comprise: (a) a polypeptide comprising a functionally active variant of FGF23 having mutations R179Q, Y154D, C206S, and C244S; and (b) a modified Fc fragment having decreased affinity for Fc-gamma-receptor and/or increased serum half-life; and, optionally, (c) a linker. An example of this embodiment is provided in SEQ ID NOs: 70 and 74.

In one embodiment of the present disclosure, the components of a fusion polypeptide comprise: (a) a polypeptide comprising a functionally active variant of FGF23 having mutations R179Q, Y154C, C206S, and C244S; and (b) a modified Fc fragment having decreased affinity for Fc-gamma-receptor and/or increased serum half-life; and, optionally, (c) a linker. An example of this embodiment is provided in SEQ ID NOs: 72 and 76.

The components can be, for example, chemically linked or fused in frame by a peptide bond. They may also linked via a linker. Non-limiting examples of polypeptide linker are SEQ ID NOs: 11, 12, 13, 14, 15, 16, 17, and 18. Such linkers may comprise at least one and up to about 30 repeats of SEQ ID NOs:11, 12, 13, 14, 15, 16, 17 and 18. In another non-limiting embodiment, the fusion comprises (2) a FGF or an active fragment or variant thereof and (3) a modified Fc fragment. The various components of the fusion can be operatively linked in any order; the polypeptide (1) can be operatively linked to the N-terminus of the polypeptide for (2) or (3); the polypeptide for (2) can be operatively linked to the N-terminus of the polypeptide for (1) or (3); the polypeptide for (3) can be operatively linked to the N-terminus of the polypeptide for (1) or (2).

According to the present disclosure, the extracellular subdomain of a Klotho protein, the fibroblast growth factor and the (optional) modified Fc fragment having decreased affinity for Fc-gamma-receptor and/or increased serum half-life can be operatively linked to one another in a variety of orientations and manners. For example, the extracellular subdomain of the Klotho protein can be operatively linked to the N-terminus of the fibroblast growth factor or alternatively the fibroblast growth factor can be operatively linked to the N-terminus of an extracellular subdomain of the Klotho protein.

In one embodiment, the present disclosure provides a fusion polypeptide comprising a sKlotho of a Klotho protein and a linker. In another embodiment, the present disclosure provides a fusion polypeptide comprising a sKlotho of the alpha Klotho protein and a linker. In another embodiment, the present disclosure provides a fusion polypeptide comprising a sKlotho of the beta Klotho protein and a linker. In yet another embodiment, the present disclosure provides a human FGF protein or an active fragment or variant thereof (e.g., without signal peptide) and a linker. In one embodiment the disclosure provides fusion proteins, nucleic acid molecules or pharmaceutical composition for use in therapy or as medicament for use in the treatment of a pathological disorder. Pharmaceutical compositions comprising the fusion proteins of the disclosure and their uses for treating or preventing age-related conditions or metabolic disorders are also encompassed by the present disclosure. In some embodiments, the fusion protein further comprises a modified Fc fragment having decreased affinity for Fc-gamma-receptor and/or increased serum half-life.

In one embodiment, the present disclosure provides a fusion polypeptide comprising a sKlotho of alpha Klotho protein with signal peptide fused (directly or indirectly via a linker) to FGF-23. In another embodiment, the present disclosure provides a fusion polypeptide comprising a sKlotho of alpha Klotho protein without signal peptide fused (directly or indirectly via a linker) to FGF-23. In another embodiment, the present disclosure provides sKlotho of alpha Klotho protein with signal peptide fused (directly or indirectly via a linker) to FGF-23 without signal peptide. In another embodiment, the present disclosure provides a fusion polypeptide comprising sKlotho of alpha Klotho protein without signal peptide fused (directly or indirectly via a linker) to FGF-23 without signal peptide. In some embodiments, the fusion protein further comprises a modified Fc fragment having decreased affinity for Fc-gamma-receptor and/or increased serum half-life.

In one embodiment, the present disclosure provides a fusion polypeptide comprising a sKlotho of alpha Klotho protein with signal peptide fused (directly or indirectly via a linker) to FGF-23 (R179Q) variant. In another embodiment, the present disclosure provides a fusion polypeptide comprising a sKlotho of alpha Klotho protein without signal peptide fused (directly or indirectly via a linker) to FGF-23 (R179Q) variant. In another embodiment, the present disclosure provides sKlotho of alpha Klotho protein with signal peptide fused (directly or indirectly via a linker) to FGF-23 (R179Q) variant without signal peptide. In another embodiment, the present disclosure provides a fusion polypeptide comprising sKlotho of alpha Klotho protein without signal peptide fused (directly or indirectly via a linker) to FGF-23 (R179Q) variant without signal peptide. In some embodiments, the fusion protein further comprises a modified Fc fragment having decreased affinity for Fc-gamma-receptor and/or increased serum half-life.

In one embodiment, the present disclosure provides a fusion polypeptide comprising: (a) a polypeptide comprising fibroblast growth factor 23 (FGF23), or a functionally active variant or derivative (e.g., a variant comprising at least one conservative amino acid substitution and/or one amino acid deletion) thereof, wherein FGF23 has a mutation at one or more of the positions Y154, Q156, C206 and C244; and (b) either a modified Fc fragment having decreased affinity for Fc-gamma-receptor and/or increased serum half-life, or a polypeptide comprising at least one extracellular subdomain of a Klotho protein, or a functionally active variant or derivative (e.g., a variant comprising at least one conservative amino acid substitution and/or one amino acid deletion) thereof; and, optionally (c) a linker. Such fusion polypeptides are disclosed in SEQ ID NOs: 54, 55, 56, 57, 58, 59, 60, 61, 62, 63, 64, 65, 66, 67, and 68.

In one embodiment, the present disclosure provides a fusion polypeptide comprising (1) sKlotho of alpha Klotho protein with signal peptide, or a functionally active variant or derivative (e.g., a variant comprising at least one conservative amino acid substitution and/or one amino acid deletion) thereof, (2) a linker; and (3) FGF-23 (R179Q) variant without signal peptide, or a functionally active variant or derivative (e.g., a variant comprising at least one conservative amino acid substitution and/or one amino acid deletion) thereof. In another embodiment, the present disclosure provides a fusion polypeptide comprising (1) sKlotho of alpha Klotho protein without signal peptide, or a functionally active variant or derivative (e.g., a variant comprising at least one conservative amino acid substitution and/or one amino acid deletion) thereof (2) a linker; and (3) FGF-23 (R179Q) variant without signal peptide, or a functionally active variant or derivative (e.g., a variant comprising at least one conservative amino acid substitution and/or one amino acid deletion) thereof. In some embodiments, the fusion polypeptides of the disclosure are glycosylated. In some embodiments, the fusion protein further comprises a modified Fc fragment having decreased affinity for Fc-gamma-receptor and/or increased serum half-life.

In one embodiment, the present disclosure provides a fusion polypeptide comprising (1) sKlotho of alpha Klotho protein with signal peptide (SEQ ID NO: 44 or SEQ ID NO: 45), or a functionally active variant or derivative (e.g., a variant comprising at least one conservative amino acid substitution and/or one amino acid deletion) thereof (2) a linker comprising SEQ ID NO: 11; and (3) FGF-23 (R179Q) variant without signal peptide (SEQ ID NO: 43), or a functionally active variant or derivative (e.g., a variant comprising at least one conservative amino acid substitution and/or one amino acid deletion) thereof. In another embodiment, the present disclosure provides a fusion polypeptide comprising (1) sKlotho of alpha Klotho protein without signal peptide (SEQ ID NO: 7), or a functionally active variant or derivative (e.g., a variant comprising at least one conservative amino acid substitution and/or one amino acid deletion) thereof (2) a linker comprising SEQ ID NO: 11; and (3) FGF-23 (R179Q) variant without signal peptide (SEQ ID NO: 43), or a functionally active variant or derivative (e.g., a variant comprising at least one conservative amino acid substitution and/or one amino acid deletion) thereof. In one embodiment, the present disclosure provides a fusion polypeptide comprising the amino acid sequence of SEQ ID NO: 19, 20, 40, or 41. In some embodiments, the fusion polypeptides of the disclosure are glycosylated.

In one embodiment, the present disclosure provides a fusion polypeptide comprising sKlotho of alpha Klotho protein with signal peptide (SEQ ID NO: 44 or SEQ ID NO:

45), or a functionally active variant or derivative (e.g., a variant comprising at least one conservative amino acid substitution and/or one amino acid deletion) thereof and a linker comprising SEQ ID NO: 11. In another embodiment, the present disclosure provides a fusion polypeptide comprising sKlotho of alpha Klotho protein without signal peptide (SEQ ID NO: 7); and a linker comprising SEQ ID NO: 11. In some embodiments, the fusion polypeptides of the disclosure are glycosylated. In some embodiments, the fusion protein further comprises a modified Fc fragment having decreased affinity for Fc-gamma-receptor and/or increased serum half-life.

In one embodiment, the present disclosure provides a fusion polypeptide comprising a human FGF protein or an active fragment or variant thereof (e.g., without the signal peptide); and a linker comprising SEQ ID NO: 11. In some embodiments, the fusion polypeptides of the disclosure are glycosylated. In some embodiments, the fusion protein further comprises a modified Fc fragment having decreased affinity for Fc-gamma-receptor and/or increased serum half-life.

In one embodiment, the present disclosure provides a fusion polypeptide comprising a human FGF protein (e.g., FGF23) or an active fragment or variant thereof (e.g., without the signal peptide); a linker (e.g., a linker comprising SEQ ID NO: 11); and sKlotho (with or without a signal peptide), or a functionally active variant or derivative (e.g., a variant comprising at least one conservative amino acid substitution and/or one amino acid deletion) thereof) or a Fc-gramma-receptor (e.g., FcLALA); wherein the FGF (e.g., FGF23) has one or more mutations at these residues: R179, Y154, Q156, C206, and/or C244. In various embodiments, the mutations are R179Q, Y154D, Q156A, C206S, and/or C244S. Even though these mutations are conserved in the human, rhesus, bovine, mouse and rat FGF23, mutating them does not prevent FGF23 activity. Rather, mutating these amino acids unexpectedly enhances the qualities of the proteins, by reducing aggregation, reducing undesired protease-induced cleavage, and increasing protein production from cells. In various embodiments, the fusion protein comprising one or more FGF23 mutation is glycosylated.

In one embodiment, the present disclosure provides a pharmaceutical composition (e.g., in an intra-muscular administering form) comprising (e.g., as a sole pharmaceutically active ingredient) a fusion polypeptide (e.g., glycosylated or non-glycosylated) that comprises (1) FGF-23 (R179Q) variant without signal peptide (SEQ ID NO: 43), or a variant comprising additional mutations which reduce aggregation and/or protease-mediated cleavage, or a functionally active variant or derivative (e.g., a variant comprising at least one conservative amino acid substitution and/or one amino acid deletion) thereof (2) optionally, a linker comprising SEQ ID NO: 11; and (3) sKlotho of alpha Klotho protein with signal peptide (SEQ ID NO: 44 or SEQ ID NO: 45), or a functionally active variant or derivative (e.g., a variant comprising at least one conservative amino acid substitution and/or one amino acid deletion) thereof or a modified Fc fragment having decreased affinity for Fc-gamma-receptor and/or increased serum half-life; and uses of the pharmaceutical composition in therapy or as medicament for the treatment of a pathological disorder, for example treating and/or preventing age-related conditions, such as muscular atrophy. In another embodiment, the present disclosure provides a pharmaceutical composition (e.g., in an intra-muscular administering form) comprising (e.g., as a sole pharmaceutically active ingredient) a fusion polypeptide (e.g., glycosylated or non-glycosylated) that comprises (1) FGF-23 (R179Q) variant without signal peptide (SEQ ID NO: 43), or a variant comprising additional mutations which reduce aggregation and/or protease-mediated cleavage, or a functionally active variant or derivative (e.g., a variant comprising at least one conservative amino acid substitution and/or one amino acid deletion) thereof (2) a linker comprising SEQ ID NO: 11; and (3) sKlotho of alpha Klotho protein without signal peptide (SEQ ID NO: 7), or a functionally active variant or derivative (e.g., a variant comprising at least one conservative amino acid substitution and/or one amino acid deletion) thereof, or a modified Fc fragment having decreased affinity for Fc-gamma-receptor and/or increased serum half-life, or a functionally active variant or derivative (e.g., a variant comprising at least one conservative amino acid substitution and/or one amino acid deletion) thereof; and uses of the pharmaceutical composition in therapy or as medicament for the treatment of a pathological disorder, for example treating and/or preventing age-related conditions, such as muscular atrophy. In one embodiment, the present disclosure provides a pharmaceutical composition (e.g., in an intra-muscular administering form) comprising (e.g., as a sole pharmaceutically active ingredient) a fusion polypeptide (e.g., glycosylated or non-glycosylated) comprising the amino acid sequence of SEQ ID NO: 19, 20, 40, or 41; and uses of the pharmaceutical composition in therapy or as medicament for the treatment of a pathological disorder, for example treating and/or preventing age-related conditions, such as muscular atrophy.

In one embodiment, the present disclosure provides a pharmaceutical composition (e.g., in an intra-muscular administering form) comprising (e.g., as a sole pharmaceutically active ingredient) a fusion polypeptide (e.g., glycosylated or non-glycosylated) that comprises sKlotho of alpha Klotho protein with signal peptide (SEQ ID NO: 44 or SEQ ID NO: 45); and a linker comprising SEQ ID NO: 11; and uses of the pharmaceutical composition for treating and/or preventing age-related conditions, such as muscular atrophy. In another embodiment, the present disclosure provides a pharmaceutical composition (e.g., in an intra-muscular administering form) comprising (e.g., as a sole pharmaceutically active ingredient) a fusion polypeptide (e.g., glycosylated or non-glycosylated) comprising sKlotho of alpha Klotho protein without signal peptide (SEQ ID NO: 7); and a linker comprising SEQ ID NO: 11; and uses of the pharmaceutical composition in therapy or as medicament for the treatment of a pathological disorder, for example treating and/or preventing age-related conditions, such as muscular atrophy. In some embodiments, the fusion protein further comprises a modified Fc fragment.

In one embodiment, the present disclosure provides a pharmaceutical composition comprising (e.g., as a sole pharmaceutically active ingredient) a fusion polypeptide (e.g., glycosylated or non-glycosylated) that comprises a human FGF protein or an active fragment or variant thereof (e.g., without the signal peptide); and a linker comprising SEQ ID NO: 11.

Pharmaceutical compositions comprising the fusion proteins of the disclosure and their uses in therapy or as medicament for the treatment of a pathological disorder therapy, for example treating or preventing age-related conditions (e.g., muscle atrophy) or metabolic disorders (e.g., diabete) are also encompassed by the present disclosure.

In one embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% identical to SEQ ID NO: 19. In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% identical to SEQ ID NO: 20.

In one embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% identical to SEQ ID NO: 40. In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% identical to SEQ ID NO: 41.

In one embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 46. In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 47.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 48. In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 49.

In one embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 50. In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 51.

In one embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 52. In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 53.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 54.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 55.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 56.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 57.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 58.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 59.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 60.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 61.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 62.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 63.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 64.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 65.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 66.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 67.

In another embodiment, the present disclosure provides a fusion polypeptide that is at least 85%, at least 90%, at least 91%, at least 92%, at least 93%, at least 94%, at least 95%, at least 96%, at least 96%, at least 97%, at least 98%, at least 99% or 100% identical to SEQ ID NO: 68.

In one embodiment, the present disclosure provides a fusion polypeptide comprising a sKlotho of beta Klotho protein with signal peptide fused (directly or indirectly via a linker) to FGF-19 or an active fragment or variant thereof. In some embodiments, the fusion further comprises a modified Fc fragment having decreased affinity for Fc-gamma-receptor and/or increased serum half-life. In another embodiment, the present disclosure provides a fusion polypeptide comprising a sKlotho of beta Klotho protein without signal peptide fused (directly or indirectly via a linker) to FGF-19 or an active fragment or variant thereof. In another embodiment, the present disclosure provides a fusion polypeptide comprising a sKlotho of beta Klotho protein with signal peptide fused (directly or indirectly via a linker) to FGF-21 or an active fragment or variant thereof. In another embodiment, the present disclosure provides a fusion polypeptide comprising a sKlotho of beta Klotho protein without signal peptide fused (directly or indirectly via a linker) to FGF-21 or an active fragment or variant thereof.

The disclosure provides nucleic acid sequences encoding any of the Klotho fusion polypeptides described herein and host cells containing the nucleic acids. In some embodiments, the fusion further comprises a modified Fc fragment having decreased affinity for Fc-gamma-receptor and/or increased serum half-life.

In some embodiments, the disclosure encompasses a nucleic acid encoding any polypeptide described herein. In some embodiments, the disclosure encompasses a nucleic acid encoding any fusion polypeptide described herein. In some embodiments, the disclosure encompasses any Klotho or Klotho variant described herein. In some embodiments, the disclosure encompasses any FGF or FGF23 or FGF or FGF23 variant described herein.

The disclosure also provides composition having any of the Klotho fusion polypeptides contemplated herein. The compositions of the disclosure can further include heparin. In some embodiments, the fusion further comprises a modified Fc fragment having decreased affinity for Fc-gamma-receptor and/or increased serum half-life.

The disclosure also provides variants of Klotho. These include variants of alpha sKlotho (soluble Klotho, which lacks transmembrane domain and lacks the signal peptide, but retains Klotho domains 1 and 2 (KL-D1 and KL-D2), wherein up to about 20 amino acids have been deleted from the C-terminus (delta C-20 or ΔC20). A non-limiting example of Klotho delta C-20 (alpha sKlotho ΔC20) is provided in SEQ ID NO: 77. In various embodiments, the Klotho delta C-20 can optionally have mutations at V563 and/or K795. A non-limiting example of Klotho delta C-20 (alpha sKlotho ΔC20) with mutations at V563 and K795 is provided in SEQ ID NO: 78. The disclosure also contemplates fusion polypeptides comprising a Klotho delta C-20.

Thus: A polypeptide of the disclosure is, for example, an alpha sKlotho delta C-20 (in which 1 to about 20 amino acids, about 20 amino acids, or 20 amino acids, have been deleted from the C-terminus), optionally also having mutations at V563 and/or K795. As another example, the polypeptide is an alpha sKlotho variant having a mutation at V563 and/or K795, which is full-length, or wherein optionally 1 to about 20 amino acids, about 20 amino acids or 20 amino acids have been deleted from the C-terminus. Any such polypeptide is a Klotho C-terminal deletion variant. Such a Klotho C-terminal deletion variant can be fused to other polypeptides, such as FGF23 or a variant thereof, or serum albumin or a variant thereof.

The disclosure also provides a method for treating or preventing an age-related condition in an individual. An individual (e.g., human) is administered a therapeutically effective dose of a pharmaceutical composition containing a Klotho variant or a fusion polypeptide comprising a Klotho variant, e.g., having at least one extracellular subdomain of a Klotho protein (e.g., alpha Klotho protein) or an active fragment or variant thereof and a fibroblast growth factor or an active fragment or variant thereof so as to treat or prevent the age-related condition. In some embodiments, the fusion further comprises a modified Fc fragment having decreased affinity for Fc-gamma-receptor and/or increased serum half-life. In particular, the disclosure provides a method of treating or preventing muscle wasting comprising administering to an individual (e.g., human) an therapeutically effective amount of a polypeptide or fusion polypeptide having at least one extracellular subdomain of an alpha Klotho protein or an active fragment or variant thereof and a fibroblast growth factor (or an active fragment or variant thereof).

Additionally, the disclosure provides a method for treating or preventing a metabolic disorder in an individual. An individual is administered a therapeutically effective dose of a pharmaceutical composition containing a polypeptide or fusion polypeptide of the disclosure, e.g., having at least one extracellular subdomain of a Klotho protein and a fibroblast growth factor (or an active fragment or variant thereof) so as to treat the metabolic disorder. In some embodiments, the fusion further comprises a modified Fc fragment having decreased affinity for Fc-gamma-receptor and/or increased serum half-life. In particular, a fusion polypeptide of the disclosure having at least one extracellular subdomain of a beta-Klotho protein and a fibroblast growth factor 21 is useful for treating a metabolic disorder.

Klotho-FGF23 fusion polypeptides of the disclosure can be used for treating or preventing hyperphosphatemia or calcinosis in an individual. In some embodiments, the fusion further comprises a modified Fc fragment having decreased affinity for Fc-gamma-receptor and/or increased serum half-life. A pharmacologically effective dose of a pharmaceutical composition containing the Klotho fusion polypeptide of the disclosure, having at least one extracellular subdomain of a Klotho protein and a fibroblast growth factor, is administered to treat or prevent hyperphosphatemia or calcinosis. In particular, a Klotho fusion polypeptide of the disclosure having at least one extracellular subdomain of an alpha Klotho protein and a fibroblast growth factor 23 is useful for treating hyperphosphatemia or calcinosis.

Klotho-FGF23 fusion polypeptides of the disclosure can be used for treating or preventing chronic renal disease or chronic renal failure in an individual. In some embodiments, the fusion further comprises a modified Fc fragment having decreased affinity for Fc-gamma-receptor and/or increased serum half-life. A therapeutically effective dose of a pharmaceutical composition containing the Klotho fusion polypeptide of the disclosure, having at least one extracellular subdomain of a Klotho protein (e.g., alpha Klotho protein) and a fibroblast growth factor, is administered to treat or prevent chronic renal disease or chronic renal failure.

Klotho-FGF23 fusion polypeptides of the disclosure can be used for treating or preventing cancer (e.g., breast cancer) in an individual. In some embodiments, the fusion further comprises a modified Fc fragment having decreased affinity for Fc-gamma-receptor and/or increased serum half-life. A therapeutically effective dose of a pharmaceutical composition containing the Klotho fusion polypeptide of the disclosure, having at least one extracellular subdomain of a Klotho protein (e.g., alpha Klotho protein) and a fibroblast growth factor, is administered to treat or prevent cancer or breast cancer.

The present disclosure provides fusion polypeptides comprising at least one extracellular subdomain of Klotho protein or an active fragment or variant thereof and a FGF or an active fragment or variant thereof for use in medicine. In some embodiments, the fusion further comprises a modified Fc fragment having decreased affinity for Fc-gamma-receptor and/or increased serum half-life. In one embodiment, the present disclosure provides fusion polypeptides comprising at least one extracellular subdomain of Klotho protein or an active fragment or variant thereof and a FGF or an active fragment or variant thereof for use in treating or preventing muscle atrophy. The present disclosure also provides a method of treating or preventing an age related condition (e.g., muscle atrophy) comprising administering to an individual in need thereof a therapeutically effective dose of a pharmaceutical composition comprising a polypeptide or fusion polypeptide of the disclosure, e.g., one comprising a soluble Klotho protein or active fragment or variant thereof.

The disclosure furthermore provides the above described peptides and fusion polypeptides or pharmaceutical compositions comprising said peptides for use in therapy, as a medicament or for use in the treatment of a pathological disorder, for example age-related condition, metabolic disorder, hyperphosphatemia or calcinosis, chronic renal disease or chronic renal failure or to prevent cancer or breast cancer, in an individual. Additionally, the disclosure further provides use of a polypeptide, nucleic acid or pharmaceutical composition of the invention in the manufacture of a medicament for the treatment of a pathological disorder, particularly for the treatment of the above mentioned disorders, preferably age related conditions like muscle atrophy.

The disclosure also includes kits for treating or preventing an age-related disorder or metabolic disorder in an individual. The kit includes instructions for use and a purified Klotho fusion polypeptide having at least one extracellular subdomain of a Klotho protein and a fibroblast growth factor. In some embodiments, the fusion further comprises a modified Fc fragment having decreased affinity for Fc-gamma-receptor and/or increased serum half-life.

The disclosure also provides a kit for producing a Klotho fusion polypeptide of the disclosure. The kit of the disclosure includes instructions for use and a nucleic acid encoding a Klotho fusion polypeptide, having at least one extracellular subdomain of Klotho protein and a fibroblast growth factor. In some embodiments, the fusion further comprises a modified Fc fragment having decreased affinity for Fc-gamma-receptor and/or increased serum half-life.

In one embodiment of the disclosure, the fusion polypeptide comprises: (a) a polypeptide comprising a fibroblast growth factor, or a functionally active variant or derivative (e.g., a variant comprising at least one conservative amino acid substitution and/or one amino acid deletion) thereof; and (b) a modified Fc fragment, or a functionally active variant or derivative (e.g., a variant comprising at least one conservative amino acid substitution and/or one amino acid deletion) thereof, having decreased affinity for Fc-gamma-receptor and/or increased serum half-life.

In one embodiment of the disclosure, the polypeptide of (a) and the polypeptide of (b) are connected by a polypeptide linker. The linker can be repeated 1 to 30 times, or more.

In one embodiment of the disclosure, the polypeptide linker comprises an amino acid sequence selected from the group consisting of: SEQ ID NO: 11, SEQ ID NO: 12, SEQ ID NO: 13, SEQ ID NO: 14, SEQ ID NO: 15, SEQ ID NO: 16, SEQ ID NO: 17, and SEQ ID NO: 18.

In one embodiment of the disclosure, the polypeptide of (a) is connected by a peptide bond to the N-terminus of said polypeptide linker, and the polypeptide of (b) is connected by a peptide bond to the C-terminus of said polypeptide linker.

In one embodiment of the disclosure, the fusion polypeptide further comprises a signal peptide.

In one embodiment of the disclosure, the signal peptide is the IgG signal peptide.

In one embodiment of the disclosure, the fibroblast growth factor is fibroblast growth factor-23 or a fibroblast growth factor-23 variant (R179Q).

In one embodiment of the disclosure, the fibroblast growth factor is fibroblast growth factor-19 or fibroblast growth factor-21.

In one embodiment of the disclosure, fusion polypeptide comprises an amino acid sequence which is 95% or more identical to the amino acid sequence of SEQ ID NO: 51, or SEQ ID NO: 53.

In one embodiment of the disclosure, fusion polypeptide comprises the amino acid sequence of SEQ ID NO: 51, or SEQ ID NO: 53.

In one embodiment of the disclosure, fusion polypeptide comprises FcLALA.

3. BRIEF DESCRIPTION OF THE DRAWINGS

FIG. 1 illustrates several different embodiments of the Klotho fusion polypeptides of the disclosure. The represented fusion polypeptides include one or more Klotho extracellular subdomains operatively linked to a fibroblast growth factor. Polypeptides containing one or more Klotho extracellular subdomains include, for example, an extracellular domain of Klotho (e.g., aa 1 to 982 of human Klotho), or an active fragment of Klotho.

FIGS. 2A-2C depict protein expression of an sKlotho-FGF23 fusion protein. FIG. 2A shows that sKlotho-FGF23 fusion protein was detected in conditioned media by Western blotting with anti-FGF23 antibodies. FIG. 2B shows that sKlotho-FGF23 fusion protein was detected in conditioned media by SDS-PAGE and Coomassie blue staining FIG. 2C shows a highly purified sKlotho-FGF23-6×His fusion protein, analyzed by SDS-PAGE and Coomassie blue staining.

FIG. 3 illustrates the results of an Egr-1 luciferase assay comparing the activation level of Egr-1 in cells treated with conditioned media containing either a Klotho fusion polypeptide, a FGF 23 polypeptide only, a soluble Klotho (sKlotho) polypeptide only, and a soluble Klotho polypeptide in combination with a FGF 23 polypeptide in the absence or presence of heparin (20 μg/ml).

FIGS. 4A-4B depict the results of an Egr-1 luciferase assay comparing the activation level of Egr-1 in cells treated with purified Klotho fusion polypeptide, FGF 23 polypeptide, or soluble Klotho polypeptide in the absence or presence of heparin. FIG. 4A shows an the results of an experiment comparing the activation level of Egr-1 in cells treated with FGF 23 alone, sKlotho-His (10 nM or 20 nM) and a combination of FGF 23 and sKlotho-His (10 nM or 20 nM) in the absence or presence of heparin (20 μg/ml). FIG. 4B shows Egr-1 luciferase reporter activity in cells treated with sKlotho-FGF23-His fusion (0 nM, 0.6 nM, 1.21 nM, 2.41 nM, 4.83 nM, 9.65 nM, and 19.3 nM).

FIGS. 5A-5B illustrate the effect of treatment with a purified sKlotho fusion polypeptide on C2C12 muscle cells. FIG. 5A shows measurements of myotube diameter in C2C12 muscle cells treated with either IGF-1 (10 nM), FGF2 (20 ng/ml), or a purified Klotho fusion polypeptide (20 nM), in the absence or presence of dexamethasone (100 µM). FIG. 5B shows the phosphorylation of signaling pathway proteins in C2C12 muscle cells by IGF-1 (10 nM), FGF2 (20 ng/ml), or a purified Klotho fusion polypeptide (20 nM), in the absence or presence of rapamycin (40 nM).

Figure 10:
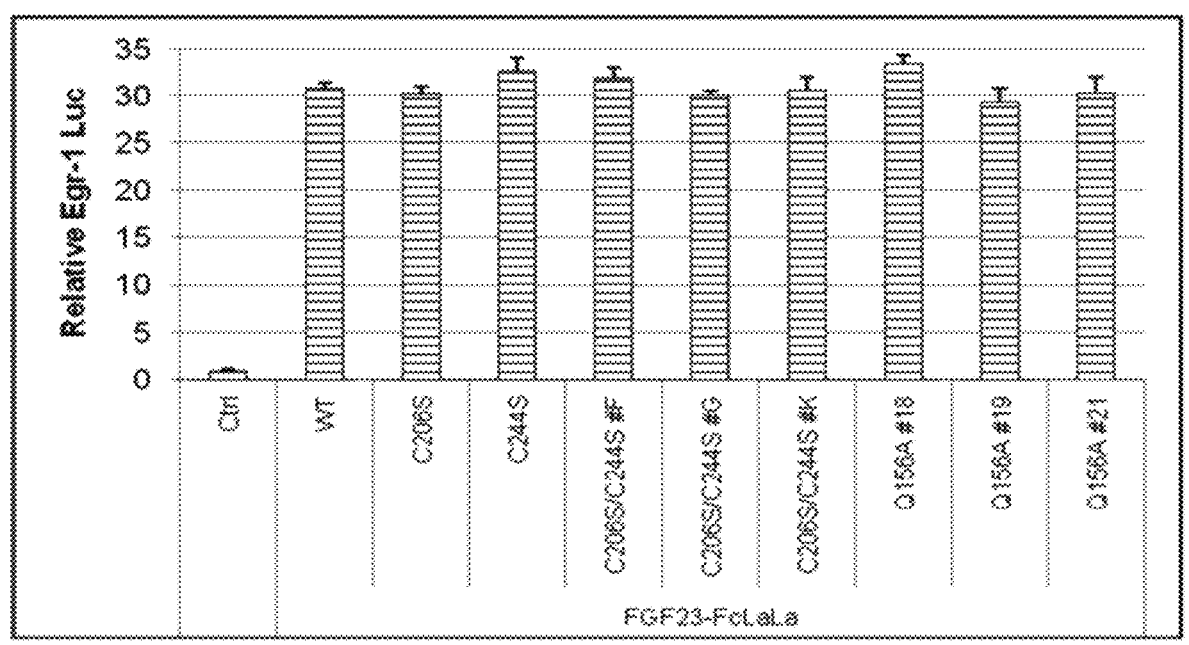

FIG. 10. This figure shows activation of EGR-1-luc reporter gene by FGF23(R179Q)-FcLALA and Q156A, C206S, C244S and C206S/C244S mutants.

Figure 11:
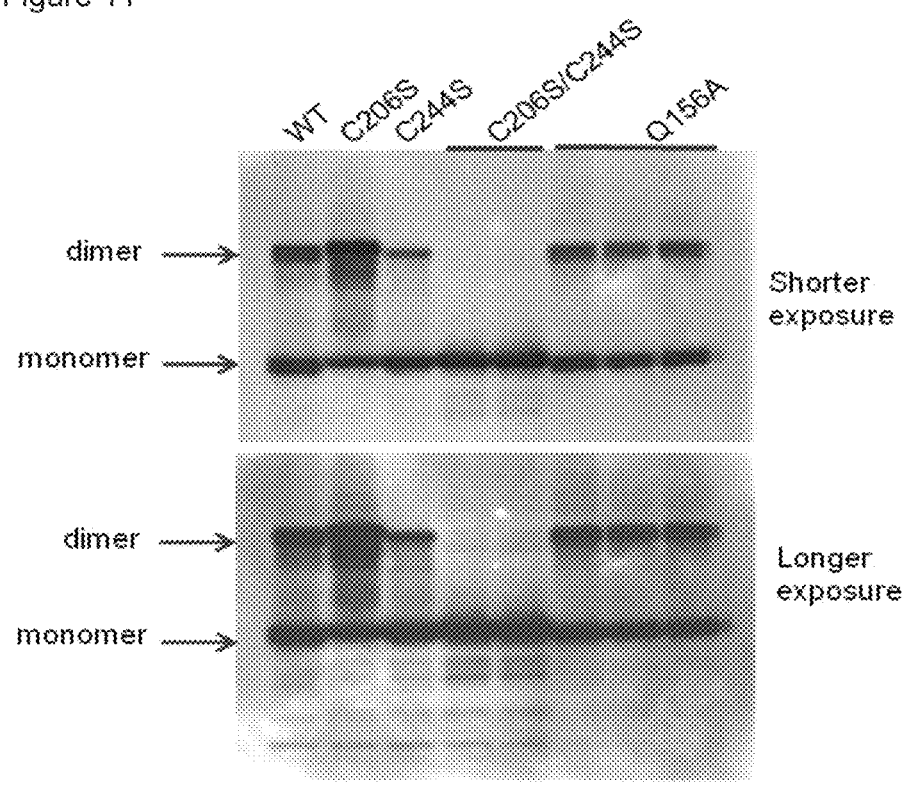

FIG. 11 shows protein qualities and dimerization of WT (wild-type), Q156A, C206S, C244S and C206S/C244S mutants of FGF23(R179Q)-FcLaLa.

Figure 12:
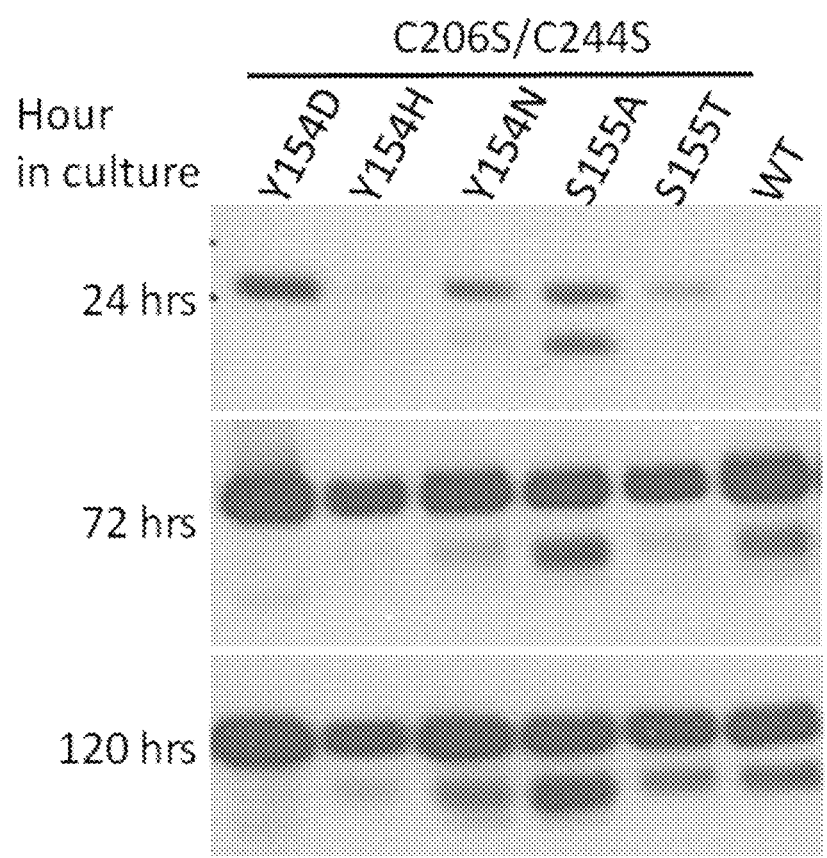

FIG. 12 shows the protein qualities of WT, Y154D/C206S/C244S, Y154H/C206S/C244S, Y154N/C206S/C244S, S155A/C206S/C244S, S155T/C206S/C244S, of FGF23(R179Q)-FcLaLa. All FGF23 variants in this figure (including "WT") have the R179Q mutation.

Figure 13:
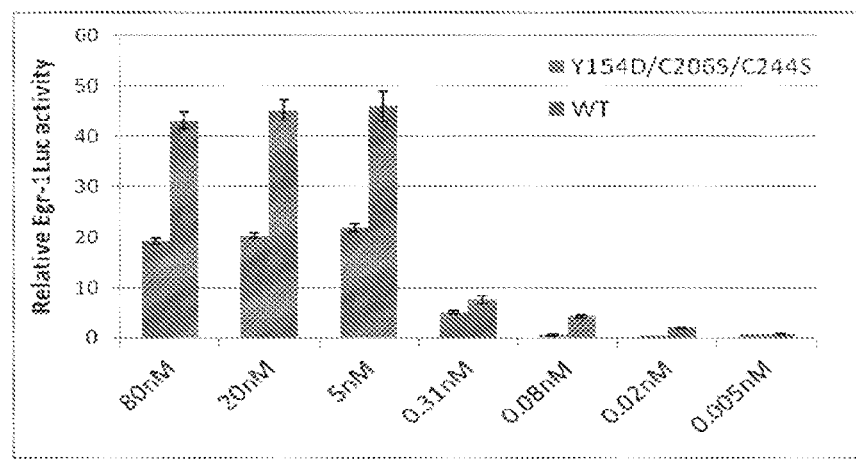

FIG. 13 shows the activation of Egr-1-luc reporter gene by FGF23(R179Q)-FcLALA and FGF23(R179Q)-Y154D/C206S/C244S mutant.

Figure 14:
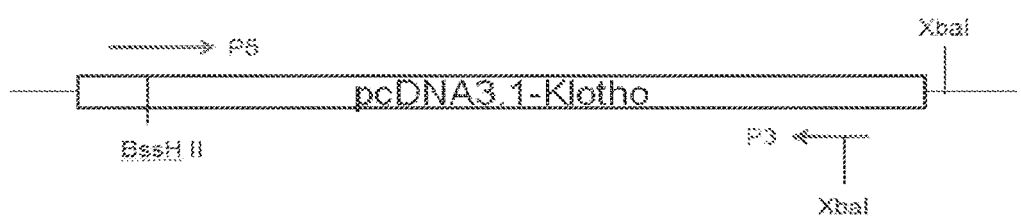
Figure 14:
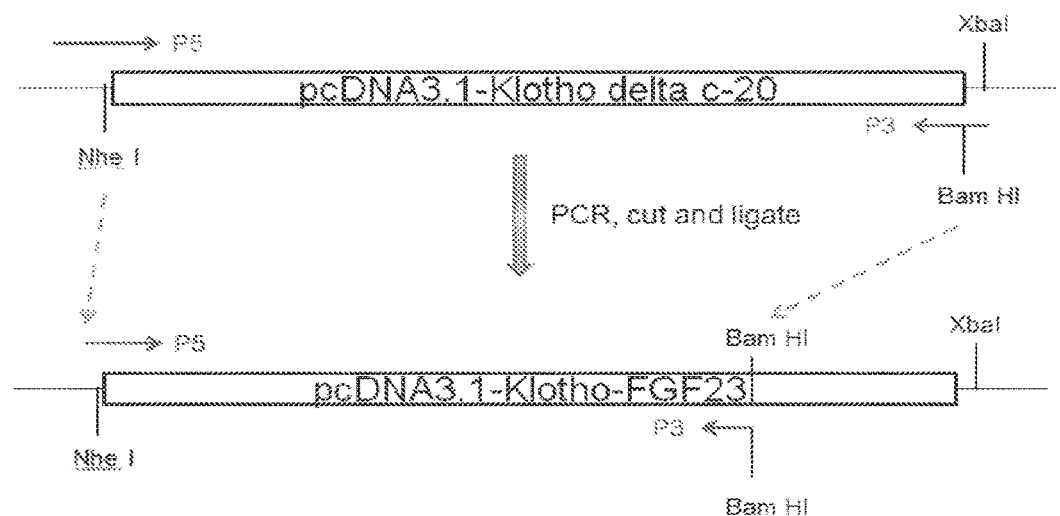

FIGS. 14A-14B show the construction of various constructs. FIG. 14A shows the strategy for constructing sKlotho variants having C-terminal deletions of about 20, about 40, about 60, about 80, about 100, about 120, about 140, about 160, about 180, about 200, about 220, about 240, about 260, about 280, about 300, about 320, about 340, about 360, about 380, about 400, about 420, about 440, about 460, about 480 amino acids. Primer P5 (SEQ ID NO: 83) was used as the 5' primer. Any of a series of 24 primers designated C-20, C-40, C-60 . . . C-480 (SEQ ID NOs: 84 to 107) were used to truncate about 20, about 40, about 60 . . . about 480 amino acids from the C-terminus. Of all the sKlotho truncations, only the one with a deletion of about 20 aa (sKlotho del c-20) was efficacious; a fusion of this sKlotho truncation and FGF23 was created, as shown in FIG. 14B. FIG. 14B shows the strategy for constructing the sKlotho (del c-20)-FGF23 fusion polypeptide. The P5 primer was used in combination with the C-20 primer in PCR (polymerase chain reaction) to prepare the fragment having the sKlotho truncation. This fragment was cleaved with restriction endonucleases and ligated into a vector encoding the FGF23 to construct sKlotho (del c-20)-FGF23 fusion polypeptide.

Figure 15:
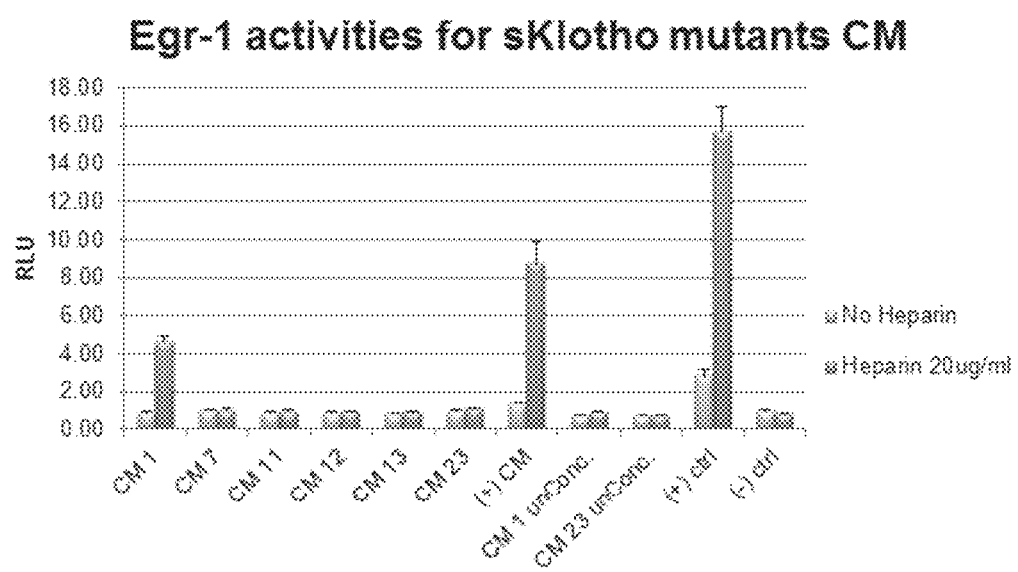

FIG. 15 shows the Egr-1 activities of sKlotho mutants. Conditioned medium (CM) was collected from various Hek293 cells, each having a vector encoding a fusion of a sKlotho truncation and FGF23. Only CM from cells producing useful amounts of fusion were used. Fusions used: CM1: sKlotho truncation of about 20 amino acids (aa); CM7: sKlotho truncation of about 140 amino acids (aa); CM11: sKlotho truncation of about 220 amino acids (aa); CM12: sKlotho truncation of about 240 amino acids (aa); CM13: sKlotho truncation of about 260 amino acids (aa); CM23: sKlotho truncation of about 460 amino acids (aa). Positive controls: conditioned medium from cells producing a fusion of sKlotho and FGF23 [(+) CM]; purified fusion of sKlotho and FGF23 [(+) ctrl]. "unConc." indicates experiments wherein less protein was used. Negative control: (−) ctrl. RLU, relative luciferase units. This experiment showed that the deletion of about 20 amino acids from the C-terminus decreased activity of sKlotho.

Figure 16A:
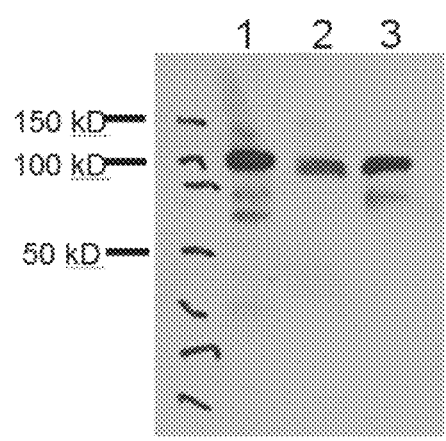
Figure 16B:
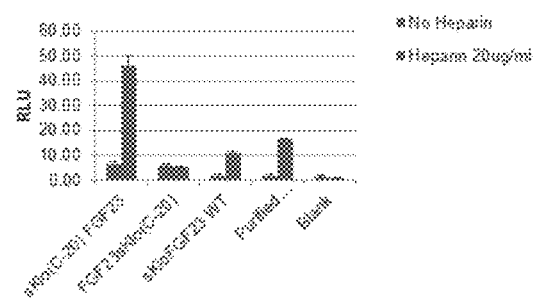

FIG. 16 shows that deleting about 20 amino acids from the C-terminus of sKlotho increased activity of a sKlotho-FGF23 fusion polypeptide. FIG. 16A shows a Western blot of relative amounts of various fusions comprising a sKlotho or sKlotho delta C-20 and FGF23. Lane 1, sKlotho-FGF23 fusion. Lane 2, FGF23-sKlotho delta C-20 (del c-20) fusion. Lane 3, sKlotho delta C-20 (del c-20)-FGF23 fusion. Size markers are also indicated. A polyclonal antibody against Klotho was used. FIG. 16B shows the activity of these fusion polypeptides in the Egr-1-Luc assay.

Figure 17:
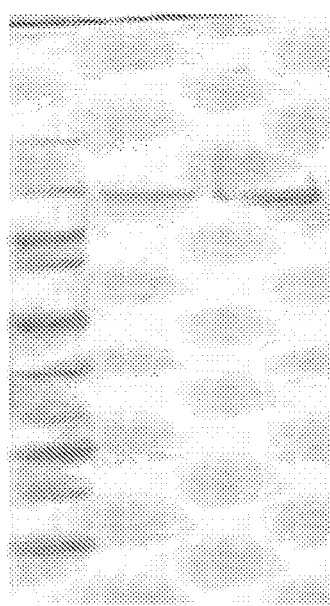
Figure 17:
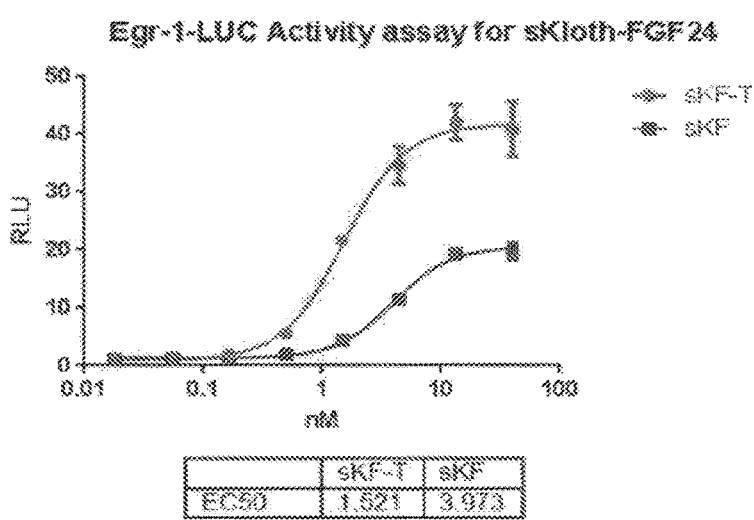

FIG. 17 shows an experiment with purified protein, reiterating the finding that deleting about 20 amino acids from the C-terminus of sKlotho increased activity of a sKlotho-FGF23 fusion polypeptide. FIG. 17A shows a protein gel showing the purity of the sKlotho del c-20-FGF23 fusion (lanes 2 and 3). Lane 1, size markers. FIG. 17B shows a Egr-1 assay using purified sKlotho del c-20-FGF23 fusion (sKF-T) and sKlotho-FGF23 fusion (sKF). The EC50 of the proteins is also shown. In these figures and in the specification, the terms sKF-T, Klotho del c-20-FGF23, sKlotho del c-20-FGF23, klotho (delta C-20)-FGF23, Alpha sKlotho ΔC20-FGF23 and the like all indicate a fusion polypeptide comprising, in N-terminus to C-terminus order: alpha sKlotho with a truncation of about 20 amino acids from the C-terminus, an optional linker, and a FGF23.

Figure 18:
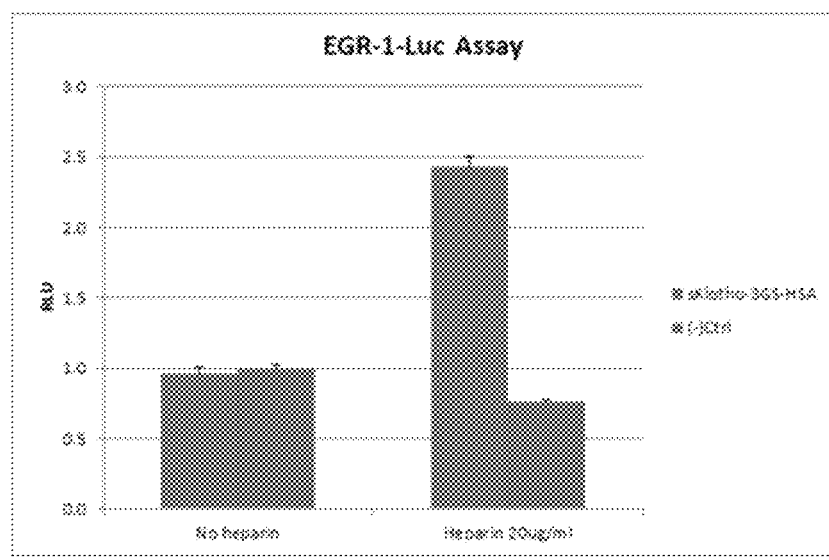

FIG. 18 shows shows that a fusion polypeptide comprising a sKlotho del (deletion) C-20 and mouse serum albumin has efficacy in an Egr-1 assay.

4. DETAILED DESCRIPTION

The present disclosure is directed to methods, kits and compositions for preventing or treating age-related conditions and metabolic disorders; and to the use of said compostions in therapy, as a medicament or for use in the treatment of a pathological disorder. The polypeptides and fusion polypeptides of the disclosure include a Klotho protein or active fragment or variant thereof. In some embodiments, the polypeptides and fusion polypeptides of the disclosure include a Klotho protein or an active fragment or variant thereof operatively linked to a fibroblast growth factor polypeptide or active fragment or variant thereof.

The fusion polypeptide of the present disclosure comprises, as a non-limiting example, in N-terminal to C-terminal order: (a) an alpha sKlotho delta C-20 (in which about 20 amino acids, 20 amino acids, or from 1 up to about 20 amino acids have been deleted from the C-terminus); and (b) FGF23, optionally having a mutation at R179; and optionally, (c) a linker interposed between (a) and (b). In some embodiments, the fusion polypeptide comprises, in N-terminal to C-terminal order: (a) an alpha sKlotho (e.g., alpha Klotho lacking the transmembrane domain and the signal peptide), in which about 20 amino acids have been deleted from the C-terminus; (b) a linker; and (c) FGF23, optionally having a mutation at R179, C206 and/or C244. In some embodiments, the FGF23 component has a mutation at C206 and/or C244. In some embodiments of these fusions, the alpha sKlotho has the mutations at V563 and/or K795. In some embodiments, the sKlotho delta C-20 is represented by SEQ ID NO: 77 or 78 (the latter having the mutations V563A and K795E). In some embodiments, the fusion polypeptide further comprises a signal peptide N-terminal to the alpha sKlotho. In various embodiments, the signal peptide is a Klotho signal peptide. In some embodiments, the signal peptide is represented by the bold, underlined portion of SEQ ID NO: 81. In various embodiment, the linker is any type of linker known in the art capable of connecting two peptides. In various embodiments, the linker comprises one or more amino acids. In various embodiments, the linker comprises any sequence of SEQ ID NOs: 11 to 18, or any number or combination thereof. In various embodiments, the linker comprises 1, 2, 3 or more copies of SEQ ID NO: 12. In various embodiments, the linker comprises 3 copies of SEQ ID NO: 12. In some embodiments, the fusion polypeptide is represented by SEQ ID NOs: 79, 80, 81 or 82.

In some embodiments, the fusion further comprises a modified Fc fragment with decreased ability to bind FcRn and/or increased stability in serum. In another embodiment, the fusion polypeptide comprises a FGF (e.g., FGF23) and a modified Fc fragment with decreased ability to bind FcRn and/or increased stability in serum.

The fusion proteins or sKlotho of the present disclosure are useful in the treatment and prevention of a variety of age-related conditions including sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss; and metabolic disorders including Type II Diabetes, Metabolic Syndrome, hyperglycemia, and obesity.

The present disclosure is based at least in part on the finding that despite the physical constraints (e.g., large size of both the Klotho and FGF polypeptides) the Klotho-FGF fusion polypeptides are highly effective in activating an FGF receptor. This finding is unexpected given that fusion of these two proteins would likely interfere with the heterodimerization and thus the activities of the proteins; e.g., the binding domains of the proteins may be perturbed by the fusion or the proteins may be mis-oriented spatially if put together in a "cis" formation.

The fusion polypeptides described herein are advantageous because they allow the administration of a single therapeutic protein that has enhanced activity compared to Klotho or FGF administered alone or together as separate polypeptides. The use of Klotho and FGF as a single fusion polypeptide rather than as two separate polypeptides (i.e., a Klotho polypeptide and a separate FGF polypeptide) is more effective at activating the FGF receptor.

The fusion polypeptide of the present disclosure comprises, as a non-limiting example, in N-terminal to C-terminal order: (a) an alpha sKlotho delta C-20 (in which about 20 amino acids, 20 amino acids, or from 1 up to about 20 amino acids have been deleted from the C-terminus); and (b) FGF23, optionally having a mutation(s) at R179, C206 and/or C244; and optionally, (c) a linker interposed between (a) and (b). In some embodiments, the fusion polypeptide comprises, in N-terminal to C-terminal order: (a) an alpha sKlotho (e.g., alpha Klotho lacking the transmembrane domain and the signal peptide), in which about 20 amino acids have been deleted from the C-terminus; (b) a linker; and (c) FGF23, optionally having a mutation(s) at R179, C206 and/or C244.

The fusion polypeptide of the present disclosure comprises, as a non-limiting example, in N-terminal to C-terminal order: (a) an alpha sKlotho delta C-20 (in which about 20 amino acids, 20 amino acids, or from 1 up to about 20 amino acids have been deleted from the C-terminus); and (b) serum albumin; and optionally, (c) a linker interposed between (a) and (b). In some embodiments, the fusion polypeptide comprises, in N-terminal to C-terminal order: (a) an alpha sKlotho (e.g., alpha Klotho lacking the transmembrane domain and the signal peptide), in which about 20 amino acids, 20 amino acids, or from 1 up to about 20 amino acids have been deleted from the C-terminus; (b) a linker; and (c) serum albumin. In various embodiments, the serum albumin can be human, mouse, or of any animal origin. A non-limiting example of a fusion comprising human Klotho and mouse serum albumin is provided in SEQ ID NO: 108. The activity of a fusion polypeptide comprising Klotho and serum albumin is shown in FIG. 18. One reason the mouse serum albumin may be used experimentally is that the human serum albumin is not recycled in the mouse system, so it is may have decreased efficacy as a half life extension moiety. For a therapeutic polypeptide, it would be desirable to use a fusion polypeptide comprising human serum albumin (or a variant thereof), and a human Klotho variant (e.g., a human Klotho C-terminal deletion variant; or a human Klotho having a mutation at V563 and/or K795; or a human Klotho variant having a C-terminal deletion and a mutation at V563 and/or K795).

As shown in Example 9, various deletions were made in the C-terminus of alpha sKlotho. These sKlotho mutants deleted about 20, about 40, about 60, about 80, about 100, about 120, about 140, about 160, about 180, about 200, about 220, about 240, about 260, about 280, about 300, about 320, about 340, about 360, about 380, about 400, about 420, about 440, about 460, about 480 from the C-terminus. These are designated, respectively, delta C-20, delta C-40, delta C-60, etc., and produced using primers C-20, C-40, C-60, etc., listed in SEQ ID NOs: 84-107. As noted in Example 9, many of these constructs did not express useful quantities of sKlotho mutant. Of those that did, C-20 (also known as 1), C-140 (7), C-220 (11), C-240 (12), C260 (13) and C-460 (23) were tested for Klotho activity. Conditioned medium from cells producing the proteins were used, in a Egr-1 assay, with relative luciferase activity (RLA) measured. C-20 showed some Klotho activity, though less than wild-type Klotho from conditioned medium or purified wild-type Klotho. The other C-terminal sKlotho deletions (C-140, C-220, C-240, C260 and C-460) did not shown significant Klotho activity.

Even though the alpha sKlotho delta C-20 showed less activity than wild-type sKlotho, the former was more active than the later in the context of a fusion with FGF23.

In other words, deleting about 20 amino acids from sKlotho decreased activity of sKlotho, but surprisingly increased activity of the sKlotho-FGF23 fusion. These unexpected results are shown in Example 9. As noted above, alpha sKlotho delta C-20 was less active than wild-type alpha sKlotho. However, the alpha sKlotho delta C-20-FGF23 fusion is more active than the alpha sKlotho (wild-type)-FGF23 fusion. The data shown in this Figure used polypeptides from conditioned medium. The alpha sKlotho delta C-20-FGF23 fusion polypeptide was then purified and the experiment was repeated, and the phenomenon was reproduced. FIG. 17, using purified polypeptides, again showed that alpha sKlotho delta C-20-FGF23 fusion is more active than the alpha sKlotho (wild-type)-FGF23 fusion.

Thus, the deletion of about 20 amino acids surprisingly decreased activity of the isolated sKlotho, but increased activity of the sKlotho-FGF23 fusion polypeptide.

Definitions

"Klotho polypeptide", "Klotho protein", or "Klotho" as used herein, includes active fragments, derivatives, mimetics, variants and chemically modified compounds or hybrids thereof of wild-type "Klotho". A Klotho active fragment has the ability to bind to an FGF polypeptide. Generally, a Klotho active polypeptide contains at least a Klotho subdomain (e.g., KL-D1 and KL-D2). Wild-type Klotho has the amino acid sequence as is found in nature. Example Klotho polypeptides suitable for use with the present disclosure include alpha-Klotho (SEQ ID NO: 2) and beta-Klotho (SEQ ID NO: 4). Nucleotide and amino acid sequences of the alpha-Klotho and beta-Klotho are found in the GenBank database at Accession No. NM_004795; NP_004786 and NM_175737; NP_783864, respectively. Klotho polypeptides include those described in U.S. Pat. No. 6,579,850, the content of which is herein incorporated by reference in its entirety. The Klotho polypeptides include those from other species besides humans, including alpha-Klotho from mouse (NP_038851), rat (NP_112626), rabbit (NP_001075692) and beta-Klotho from mouse (NP_112457). Species predicted to have alpha-Klotho include chimpanzee (XP_522655), macaque (XP_001101127), horse (XP_001495662), cow (XP_001252500), platypus (XP_001510981), and chicken (XP_417105). Species predicted to have beta-Klotho include chimpanzee (XP_526550), macaque (XP_001091413), horse (XP_001495248), dog (XP_536257), rat (XP_001078178), platypus (XP_001512722), and chicken (XP_423224). The Klotho polypeptides have an amino acid sequence that is substantially identical to the amino acid sequence of SEQ ID NO: 2 or SEQ ID NO: 4; i.e., at least 70%, 75%, 80%, 85%, 90%, 95%, 96%, 97%, 98%, 99% or more identical at the amino acid sequences of SEQ ID NO: 2 or SEQ ID NO: 4, or active fragment or variant thereof.

"Fusion polypeptide" or "fusion protein", as used herein, shall mean a polypeptide comprising two or more different polypeptides or active fragments thereof that are not naturally present in the same polypeptide. In some embodiments, the two or more different polypeptides are operatively linked together covalently, e.g., chemically linked or fused in frame by a peptide bond. As used herein a "Klotho fusion polypeptide" is a fusion polypeptide which includes an amino acid sequence from a Klotho polypeptide or active fragment or variant thereof. A fusion polypeptide can comprise, as non-limiting examples, Klotho (e.g., sKlotho), FGF (e.g., FG23), and (optionally) a modified Fc fragment (e.g., a modified Fc fragment with decreased binding affinity to FC-gamma-receptor and/or increased serum half-life). Examples of this type of fusion polypeptide are presented in SEQ ID NOs. 46 to 49. In another embodiment, the fusion proteins comprise FGF (e.g., FGF23) and a modified Fc (e.g., FcLALA). Fusion proteins comprising FGF23 and FcLALA are described in SEQ ID NOs. 50, 51, 52 and 53. FcLALA is a Fc fragment with a LALA mutation (L234A, L235A), which triggers ADCC with lowered efficiency, and binds and activates human complement weakly. Hessell et al. 2007 Nature 449:101-104.

"Fibroblast growth factor" and "FGF" are used interchangeably herein and shall refer to polypeptides that regulate cell proliferation, migration, differentiation, homeostasis, tissue repair and response to injury in an animal, including a human subject. FGFs have the ability to bind to a fibroblast growth factor receptor and regulate its activity, including autophosphorylation of FGFR, phosphorylation of FRS2 (FGF receptor substrate 2) and ERK1/2 (extracellular signal-regulated protein kinase 1/2), and activating Egr-1 (early growth response-1). The term "FGF" includes active fragments, derivatives, mimetics, variants and chemically modified compounds or hybrids thereof of wild-type "FGF", e.g., as known in the art and as described in U.S. Pat. Nos. 7,223,563 and 7,259,248, the contents of which are incorporated by reference in their entirety. Wild-type FGF has an amino acid sequence as is found in nature. Example fibroblast growth factors suitable for use with the present disclosure include fibroblast growth factor-19 (FGF19; SEQ ID NO: 31), fibroblast growth factor-21 (FGF21; SEQ ID NO: 33), and fibroblast growth factor-23 (FGF23; SEQ ID NO: 35). The FGF polypeptides include those from other species besides humans, including murine FGFs. Generally, FGF polypeptides have an amino acid sequence that is substantially identical to the amino acid sequence of SEQ ID NO: 31, SEQ ID NO: 33 or SEQ ID NO: 35; i.e., having an amino acid sequence is which is at least 70%, 75%, 80%, 85%, 90%, 95%, 96%, 97%, 98%, 99% or more or 100% identical to the amino acid sequences of SEQ ID NO: 31 SEQ ID NO: 33 or SEQ ID NO: 35, or active fragments thereof. Additional non-limiting examples of FGF, particularly FGF23, are provided at aa 1002-1228 of SEQ ID NO: 47; aa 1002-1228 of SEQ ID NO: 49; aa 1-251 of SEQ ID NO: 51, and aa 1-251 of SEQ ID NO: 53; and sequences which are at least 70%, 75%, 80%, 85%, 90%, 95%, 96%, 97%, 98%, 99% or more or 100% identical to these sequences. Nucleotides encoding these sequences are provided in SEQ ID NOs: 46, 48, 50 and 52.

The term "FGF", includes active fragments of the full-length polypeptide. Active FGF fragments that are able to bind to their corresponding FGF receptors are known in the art and also contemplated for use in the present disclosure. One skilled in the art would appreciate, based on the sequences disclosed herein, that overlapping fragments of the FGFs can be generated using standard recombinant technology, for example, that described in Sambrook et al. (1989, Molecular Cloning: A Laboratory Manual, Cold Spring Harbor Laboratory Press, New York) and Ausubel et al. (1997, Current Protocols in Molecular Biology, Green & Wiley, New York). One skilled in the art would appreciate, based on the disclosure presented herein, that the biological activity of FGF fragments could be tested by methods well known in the art and described herein, including binding to the FGF receptor. Similarly, cell culture models which possess the necessary FGF signal transduction machinery (i.e. FGF receptor) may be transfected with FGF fragments and subsequently tested for alterations in FGF signaling, relative to wild type FGF.

FGFs are grouped into seven subfamilies based on the homology of the FGF core homology domain (approximately 120 amino acids long), which is flanked by N- and C-terminal sequences that are highly variable in both length and primary sequence, particularly among different FGF subfamilies (Goetz et al., Molecular and Cellular Biology, 2007, Vol. 27, 3417-3428). An FGF active polypeptide generally contains at least an FGF core homology domain. In some embodiments, an FGF active polypeptide may contain, in addition to an FGF core homology domain, flanking sequences which may confer additional specificity in binding FGF receptors. FGF19, FGF21, and FGF23 are grouped in the FGF19 subfamily because the core region of these ligands share high sequence identity relative to other FGFs (FGF19 v. FGF21: 38% identity; FGF19 v. FGF23: 36% identity). FGF19 subfamily members act analogously to signaling molecules of the endocrine system and regulate diverse physiological processes uncommon to classical FGFs (e.g., FGF19: energy and bile acid homeostasis; FGF21: glucose and lipid metabolism; and FGF 23: phosphate and vitamin D homeostasis).

"Fibroblast growth factor receptor" and "FGFR" as used herein refer to any one of FGFRs 1-4 known in the art, or splice variants thereof (e.g., FGFR1c). Example fibroblast growth factor receptors suitable for use with the present disclosure include fibroblast growth factor receptor-19 (e.g., FGFR4-beta Klotho), fibroblast growth factor receptor-21 (e.g., FGFR1c-alpha Klotho), and fibroblast growth factor receptor-23 (e.g., FGFR1c-alpha Klotho, FGFR3-alpha Klotho, FGFR4-alpha Klotho).

"Extracellular domain", as used herein, refers to the fragment of a transmembrane protein existing outside of a cell (e.g., not including the intracellular or transmembrane region). The "extracellular domain of the Klotho protein", "soluble Klotho", or "sKlotho" (e.g., SEQ ID NO: 7; SEQ ID NO: 39), refers to an extracellular domain of the Klotho polypeptide that is capable of binding a fibroblast growth factor, and/or capable of enabling the binding of a fibroblast growth factor to a fibroblast growth factor receptor by binding to the fibroblast growth factor. The Klotho extracellular domain corresponds to amino acid residues 28-982 of the full length alpha Klotho sequence (SEQ ID NO: 2) and to amino acid residues 52-997 of the full length beta Klotho sequence (SEQ ID NO: 4).

"Extracellular subdomain of Klotho protein" and "extracellular subdomain of Klotho protein" are used interchangeably herein and shall refer to a region in the extracellular domain of the Klotho polypeptide that is capable of binding a fibroblast growth factor, and/or is capable of enabling the binding of a fibroblast growth factor to a fibroblast growth factor receptor by binding to the fibroblast growth factor. In various embodiments, the fusion comprises a polypeptide comprising at least one extracellular subdomain of a Klotho protein; a polypeptide comprising a fibroblast growth factor; and, optionally, a modified Fc fragment having decreased affinity for Fc-gamma-receptor and/or increased serum half-life. The Klotho extracellular domain has two homologous subdomains that are repeated, i.e., KL-D1 (SEQ ID NO: 5) and KL-D2 (SEQ ID NO: 6). KL-D1 and KL-D2 correspond respectively to amino acid residues 58-506 and 517-953 of the full length alpha Klotho polypeptide (SEQ ID NO: 2) and respectively to amino acid residues 77-508 and 571-967 of the full length beta Klotho polypeptide (SEQ ID NO: 4) and are suitable for use with the present disclosure. Generally, a polypeptide that contains at least one Klotho subdomain is a Klotho active polypeptide. The Klotho extracellular subdomain for use with the polypeptide of the disclosure may be an alpha Klotho or beta Klotho KL-D1 domain with an amino acid sequence that is substantially identical to the amino acid sequence of SEQ ID NO: 5 or SEQ ID NO: 37, respectively. Further, the Klotho KL-D1 domain may have an amino acid sequence that is at least 70%, 75%, 80%, 85%, 90%, 95%, 96%, 97%, 98%, 99% or more identical to the amino acid sequence of SEQ ID NO: 5 or SEQ ID NO: 37. The Klotho extracellular subdomain may also be an alpha or beta Klotho polypeptide KL-D2 domain that is substantially identical to the amino acid sequence of SEQ ID NO: 6 or SEQ ID NO: 38, respectively. In a further embodiment, the KL-D2 domain has an amino acid sequence that is at least at least 70%, 75%, 80%, 85%, 90%, 95%, 96%, 97%, 98%, 99% or more identical to the amino acid sequence of SEQ ID NO: 6 or SEQ ID NO: 38. In some embodiments, the fusion comprises at least two extracellular subdomains of the Klotho protein (e.g., KL-D1 and KL-D2; KL-D1 and KL-D1 in tandem repeats; KL-D2 and KL-D2 in tandem repeats, etc.).

"Modified Fc fragment", as used herein, shall mean an Fc fragment of an antibody comprising a modified sequence. The Fc fragment is a portion of an antibody comprising the CH2, CH3 and part of the hinge region. The modified Fc fragment can be derived from, for example, IgG1, IgG2, IgG3, or IgG4. FcLALA is a modified Fc fragment with a LALA mutation (L234A, L235A), which triggers ADCC with lowered efficiency, and binds and activates human complement weakly. Hessell et al. 2007 Nature 449:101-104. Additional modifications to the Fc fragment are described in, for example, U.S. Pat. No. 7,217,798. For example, in various modified Fc fragments: (a) amino acid residue 250 is glutamic acid and amino acid residue 428 is phenylalanine; or (b) amino acid residue 250 is glutamine and amino acid residue 428 is phenylalanine; or (c) amino acid residue 250 is glutamine and amino acid residue 428 is leucine. In some embodiments, amino acid residues 250 and 428 differ from the residues present in an unmodified Fc-fusion protein by amino acid residue 250 being glutamic acid or glutamine and amino acid residue 428 being leucine or phenylalanine, and wherein amino acid residues are numbered by the EU numbering system, as described in U.S. Pat. No. 7,217,798. In some embodiments, the modified Fc-fusion protein has a higher affinity for FcRn at pH 6.0 than at pH 8.0. Preferably, the modified Fc fragment has decreased affinity to FcRn and/or increased serum half-life. Non-limiting examples of modified Fc fragments include that at aa (amino acids) 1234-1459 of SEQ ID NO: 47; aa 1234 to 1450 of SEQ ID NO: 49; aa 257 to 482 of SEQ ID NO: 51; and aa 257 to 473 of SEQ ID NO: 53; and sequences which are at least 70%, 75%, 80%, 85%, 90%, 95%, 96%, 97%, 98%, 99% or more or 100% identical to these sequences. Nucleotides encoding these sequences are provided in SEQ ID NOs: 46, 48, 50 and 52.

"Signal peptide", as used herein, shall mean a peptide chain (3-60 amino acids long) that directs the post-translational transport of a protein to the endoplasmic reticulum and may be cleaved off. Example signal peptides suitable for use with the present disclosure include the Klotho signal peptide (SEQ ID NO: 19) and the IgG signal peptide (SEQ ID NO: 20). Note that upon secretion and cleavage by the producer cell line, the signal peptide (e.g., of the peptides corresponding to SEQ ID NO: 19 and SEQ ID NO: 20) is cleaved off. Thus, after secretion and cleavage of the signal peptide by the producer cell lines, the peptide of SEQ ID NO: 19 would generate the peptide of SEQ ID NO: 41.

"Linker", as used herein, shall mean a functional group (e.g., chemical or polypeptide) that covalently attaches two or more polypeptides or nucleic acids so that they are connected with one another.

As used herein, a "peptide linker" refers to one or more amino acids used to couple two proteins together (e.g., to couple the extracellular domain of Klotho and fibroblast growth factor-23). Peptide linkers suitable for use with the present disclosure include, but are not limited to, polypeptides with amino acid sequences represented by SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18.

A polypeptide linker can comprise at least 1 and up to about 30 repeats of any of these amino acid sequences.

"Operatively linked", as used herein, shall mean the linking of two or more biomolecules so that the biological functions, activities, and/or structure associated with the biomolecules are at least retained. In reference to polypeptides, the term means that the linking of two or more polypeptides results in a fusion polypeptide that retains at least some of the respective individual activities of each polypeptide component. The two or more polypeptides may be linked directly or via a linker. In reference to nucleic acids, the term means that a first polynucleotide is positioned adjacent to a second polynucleotide that directs transcription of the first polynucleotide when appropriate molecules (e.g., transcriptional activator proteins) are bound to the second polynucleotide.

"Specifically binds", as used herein, shall refer to the ability of a first molecule to bind to a target molecule out of many, different types of molecules to which it may be exposed because of the ability of the first molecule to adopt a particular structure conducive to forming non-covalent interactions between itself and the other target molecule. The first molecule binds to the target forming a stable complex while there is substantially less recognition, contact, or complex formation of the first molecule with any other non-specific molecules.

"Polypeptide variant" or "protein variant", as used herein, refers to polypeptides in which one or more amino acids have been substituted by different amino acids from a reference sequence. It is well understood in the art that some amino acids may be substituted by others with broadly similar properties without changing the nature of the activity of the polypeptide (conservative substitutions) as described hereinafter. These terms also encompass polypeptides in which one or more amino acids have been added or deleted, or replaced with different amino acids, e.g., protein isoforms. An example variant of fibroblast growth factor-23 suitable for use with the present disclosure is the fibroblast growth factor-23 variant (R179Q).

"Pharmaceutical composition", as used herein, shall mean a composition containing a compound (e.g., a fusion polypeptide of the disclosure) that may be administered to treat or prevent a disease or disorder in an individual.

"Individual" or "subject", as used herein, shall refer to a mammal, including, but not limited to, a human or non-human mammal, such as a bovine, equine, canine, ovine, or feline.

"Treat", as used herein, shall mean decrease, suppress, attenuate, diminish, arrest, or stabilize the development or progression of a disease. In the context of the disclosure, the administration of the polypeptides of the disclosure may be used to treat age-related conditions, including sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss; and metabolic disorders, including Type II Diabetes, Metabolic Syndrome, hyperglycemia, and obesity.

"Prevent", as used herein, shall refer to a decrease in the occurrence of a disorder or decrease in the risk of acquiring a disorder or its associated symptoms in a subject. In the context of the disclosure, the administration of the polypeptides of the disclosure may be used to prevent age-related conditions, including sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss; and metabolic disorders, including Type II Diabetes, Metabolic Syndrome, hyperglycemia, and obesity. The prevention may be complete, e.g., the total absence of an age-related condition or metabolic disorder. The prevention may also be partial, such that the likelihood of the occurrence of the age-related condition or metabolic disorder in a subject is less likely to occur than had the subject not received the present disclosure.

"Disease", as used herein, shall mean any condition or disorder that damages or interferes with the normal function of a cell, tissue, or organ.

"Age-related condition", as used herein, shall mean any disease or disorder whose incidence in a population or severity in an individual correlates with the progression of age. In one embodiment, the age-related condition is a disease or disorder whose incidence is at least 1.5 fold higher among human individuals greater than 60 years of age relative to human individuals between the ages of 30-40 and in a selected population of greater than 100,000 individuals. Age-related conditions relevant to the present disclosure include, but are not limited to, sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss.

"Metabolic disorder", as used herein, shall mean any disease or disorder that damages or interferes with normal function in a cell, tissue, or organ by affecting the production of energy in cells or the accumulation of toxins in a cell, tissue, organ, or individual. Metabolic disorders relevant to the present disclosure include, but are not limited to, Type II Diabetes, Metabolic Syndrome, hyperglycemia, and obesity.

An "effective dose" or "effective amount" is an amount sufficient to effect a beneficial or desired clinical result. In the context of the disclosure, it is an amount of a Klotho fusion polypeptide or sKlotho effective to produce the intended pharmacological, therapeutic or preventive result. A therapeutically effective dose results in the prevention or amelioration of the disorder or one or more symptoms of the disorder, (e.g., an age-related condition or metabolic disorder). Therapeutically effective doses will vary depending upon the subject and disease condition being treated, the weight and age of the subject, the severity of the disease condition, the manner of administration and the like which can be readily be determined by one of ordinary skill in the art.

"Klotho nucleic acid molecule", as used herein is a gene encoding a Klotho protein. An example human Klotho gene is provided at GenBank Accession No. NM_004795 (SEQ ID NO: 1). Additional non-limiting examples of Klotho are provided at aa 1-982 of SEQ ID NO: 47 and aa 1-982 of SEQ ID NO: 49; and sequences which are at least 70%, 75%, 80%, 85%, 90%, 95%, 96%, 97%, 98%, 99% or more or 100% identical to these sequences.

"Fragment", as used herein, refers to a portion of a polypeptide or nucleic acid molecule. This portion contains, preferably, at least 10%, 20%, 30%, 40%, 50%, 60%, 70%, 80%, 90% or more of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000 or up to 3000 nucleotides or amino acids.

The term "substantially identical" refers to a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, 70%, 75%, 80% or 85%, 90%, 91%, 92%, 93%, 94%, 95%, 96%, 97%, 98%, 99% or more identical at the amino acid level or nucleic acid to the sequence used for comparison.

The present disclosure is directed to methods, kits and compositions for preventing or treating age-related conditions and metabolic disorders; and to the use of said compostions in therapy, as a medicament or for use in the treatment of a pathological disorder. In some embodiments, the disclosure provides a polypeptide and a fusion polypeptide having at least one extracellular subdomain of a Klotho protein. In some embodiments, the fusion polypeptides further comprise a fibroblast growth factor, serum album, Fc, or other polypeptide, or an active fragment or variant thereof. In some embodiments, the fusion further comprises a modified Fc fragment having decreased affinity for Fc-gamma-receptor and/or increased serum half-life. In other embodiments, the fusion comprises an FGF (e.g., FGF19, FGF21, FGF23 or FGF23 variant R179Q) fused to a modified Fc (e.g., FcLALA). FcLALA is a Fc fragment with a LALA mutation (L234A, L235A), which triggers ADCC with lowered efficiency, and binds and activates human complement weakly. The Klotho extracellular domain may be derived from either the alpha or beta Klotho isoforms. Further, although the FGF component of the Klotho fusion polypeptide is described primarily with reference to fibroblast growth factor-19, fibroblast growth factor-21 and fibroblast growth factor-23, it is contemplated that any of the twenty-three known FGFs or an active fragment or variant thereof can be used in practicing the disclosure.

The extracellular domain of the Klotho protein can include one or both of the KL-D1 and KL-D2 domains of a Klotho protein. In some embodiments, the Klotho fusion polypeptide has at least two extracellular subdomains of a Klotho protein. For example, the at least two extracellular subdomains can be at least two KL-D1 domains in tandem repeats, at least two KL-D2 domains in tandem repeats, or at least one KL-D1 domain and at least one KL-D2 domain.

The extracellular subdomain of a Klotho protein or an active fragment or variant thereof and the fibroblast growth factor (or an active fragment or variant thereof) can be operatively linked to one another in a variety of orientations and manners. For example, the extracellular subdomain of the Klotho protein can be operatively linked to the N-terminus of the fibroblast growth factor or alternatively the fibroblast growth factor can be operatively linked to the N-terminus of the at least one extracellular subdomain of the Klotho protein.

The fusion polypeptide of the disclosure may include one or both of the Klotho extracellular domains, i.e., KL-D1 (SEQ ID NO: 5) and KL-D2 (SEQ ID NO: 6). KL-D1 and KL-D2 correspond respectively to amino acid residues 58-506 and 517-953 of the full length alpha Klotho polypeptide (SEQ ID NO: 2) and to amino acid residues 77-508 and 571-967 of the full length beta Klotho polypeptide (SEQ ID NO: 4) and are suitable for use with the present disclosure. The Klotho fusion polypeptide may have a KL-D1 domain of an alpha Klotho polypeptide having an amino acid sequence that is substantially identical to the amino acid sequence of SEQ ID NO: 5 or of a beta Klotho polypeptide having an amino acid sequence that is substantially identical to the amino acid sequence of SEQ ID NO: 37. Specifically, the Klotho fusion polypeptide may have an amino acid sequence that is at least 70%, 75%, 80%, 85%, 90%, 95%, 96%, 97%, 98%, 99% or more identical to SEQ ID NO: 5 or SEQ ID NO: 37. The Klotho fusion polypeptide may have a KL-D2 domain of an alpha Klotho polypeptide with an amino acid sequence that is substantially identical to the amino acid sequence of SEQ ID NO: 6 or of a beta Klotho polypeptide having an amino acid sequence that is substantially identical to the amino acid sequence of SEQ ID NO: 38. Specifically, the Klotho fusion polypeptide may have an amino acid sequence that is at least at least 70%, 75%, 80%, 85%, 90%, 95%, 96%, 97%, 98%, 99% or more identical to SEQ ID NO: 6 or SEQ ID NO: 38, respectively.

In some embodiments, the Klotho fusion polypeptide of the disclosure is soluble and is capable of binding to an FGF receptor.

The Klotho fusion polypeptides of the disclosure can contain a polypeptide linker which connects the polypeptide having at least one extracellular subdomain of a Klotho protein and the fibroblast growth factor and the (optional) modified Fc fragment. Suitable linkers are well known in the art and generally contain several Gly and several Ser residues, e.g., $(Gly_4 Ser)_3$ (SEQ ID NO: 11), $Gly_4$ Ser polypeptide (SEQ ID NO: 12), Gly (SEQ ID NO: 13), Gly Gly (SEQ ID NO: 14), Gly Ser (SEQ ID NO: 15), $Gly_2$ Ser (SEQ ID NO: 16), Ala (SEQ ID NO: 17), and Ala Ala (SEQ ID NO: 18). In some embodiments, the linker will have at least 2 and up to about 30 repeats of an amino acid sequence represented by any one of SEQ ID NO: 12, SEQ ID NO: 13, SEQ ID NO: 14, SEQ ID NO: 15, SEQ ID NO: 16, SEQ ID NO: 17, or SEQ ID NO: 18.

When a polypeptide linker is present in the Klotho fusion polypeptide of the disclosure, the polypeptide having at least one extracellular subdomain of a Klotho protein may be connected by a peptide bond to the N-terminus of the linker polypeptide with the FGF connected by a peptide bond to the C-terminus of the polypeptide linker. Alternatively, the FGF may be connected by a peptide bond to the N-terminus of the linker polypeptide with the polypeptide having at least one extracellular subdomain of Klotho connected by a peptide bond to the C-terminus of the polypeptide linker. A chemical linker can also be used to link the two polypeptides.

The Klotho fusion polypeptide of the disclosure may include a signal peptide. Example signal peptides for use with the Klotho fusion polypeptide include, but are not limited to the Klotho signal peptide (SEQ ID NO: 8) and the IgG signal peptide (SEQ ID NO: 9).

In some embodiments, the disclosure provides a fusion between a FGF (e.g., FGF19, FGF21, FGF23, or FGF23 variant R179Q) and a modified Fc (e.g., FcLALA). The fusion can also optionally comprise linkers between the FGF and Fc portions. The fusion can also optionally comprise a signal peptide. In various embodiments, the disclosure encompasses nucleic acids encoding these fusion polypeptides, vectors comprising these nucleic acids, and host cells containing these nucleic acids.

4.1. Klotho and Fibroblast Growth Factor Polypeptides

The Klotho fusion polypeptides of the disclosure are expected to exhibit biological activities comparable to FGF in nature, such as binding to an FGF receptor and inducing the phosphorylation of an FGF receptor, FRS2 (FGF receptor substrate 2) and ERK1/2 (extracellular signal-regulated protein kinase 1/2) and activating Egr-1 (early growth response-1) gene. FGF is a secreted peptide growth factor that binds the FGF receptor. The amino acid and nucleic acid sequences of FGF are readily available to those of skill in the art. For example, example nucleotide sequences for FGF19, FGF21, and FGF23 can be found in the GenBank database at Accession numbers: NM_005117, NM_019113, and NM_020638, respectively, and herein as SEQ ID NOs: 30, 32, and 34, respectively. Example amino sequences for FGF19, FGF21, and FGF23 can be found in the GenBank database at Accession numbers: NP_005108, NP_061986, and NP_065689, respectively, and herein as SEQ ID NOs: 31, 35, and 35, respectively. Additionally, FGF may include one or more alterations which aid in the expression of the protein, e.g., the FGF23 (R179Q) variant (SEQ ID NO: 36).

The Klotho protein is a 130 kDa single pass type I transmembrane protein with an extracellular domain and a short cytoplasmic domain. The amino acid and nucleic acid sequences of Klotho are readily available to those of skill in the art. For example, example nucleotide sequences for alpha-Klotho and beta-Klotho can be found in the GenBank database at Accession numbers: NM_004795 and NM_175737, respectively, and herein as SEQ ID NOs: 7 and 8, respectively. Example amino acid sequences for alpha-Klotho and beta-Klotho can be found in the GenBank database at Accession numbers: NP_004786 and NP_783864, respectively, and herein as SEQ ID NOs: 2 and 4, respectively.

The Klotho fusion polypeptide of the disclosure can bind to a fibroblast growth factor receptor and has an alpha-Klotho or beta-Klotho extracellular domain operatively linked to either fibroblast growth factor-19 (SEQ ID NO: 31), fibroblast growth factor-21 (SEQ ID NO: 33), fibroblast growth factor-23 (SEQ ID NO: 35), or variants thereof (which include fibroblast growth factor-23 variant (R179Q) (SEQ ID NO: 36)).

Specifically, the Klotho fusion polypeptide of the disclosure may include an alpha-Klotho (SEQ ID NO: 2) which is operatively coupled to fibroblast growth factor-23 (SEQ ID NO: 35) or fibroblast growth factor-23 variant (R179Q) (SEQ ID NO: 36). Additionally, the Klotho fusion polypeptide of the disclosure may have beta-Klotho (SEQ ID NO: 4), which is operatively coupled to fibroblast growth factor-19 (SEQ ID NO: 31). The Klotho fusion polypeptide of the disclosure may include a beta-Klotho (SEQ ID NO: 4), which is operatively coupled to fibroblast growth factor-21 (SEQ ID NO: 33).

The disclosure includes homologs of the various Klotho and FGF genes and proteins encoded by those genes. A "homolog," in reference to a gene refers to a nucleotide sequence that is substantially identical over at least part of the gene or to its complementary strand or a part thereof, provided that the nucleotide sequence encodes a protein that has substantially the same activity/function as the protein encoded by the gene which it is a homolog of Homologs of the genes described herein can be identified by percent identity between amino acid or nucleotide sequences for putative homologs and the sequences for the genes or proteins encoded by them (e.g., nucleotide sequences for genes encoding Klotho and FGF or their complementary strands). Percent identity may be determined, for example, by visual inspection or by using various computer programs known in the art or as described herein. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative amino acid substitutions typically include substitutions within the following groups:
glycine and alanine;
valine, isoleucine and leucine;
aspartic acid, glutamic acid, asparagine and glutamine;
serine and threonine;
lysine and arginine; and
phenylalanine and tyrosine.

Thus, mutating a glycine to alanine would be a conservative amino acid substitution, as would mutating an alanine to a glycine; mutating a valine to an isoleucine or leucine would be a conservative amino acid substation, as would replacing an isoleucine with valine or leucine, as would replacing leucine with valine or isoleucine, etc. The disclosure provides variants of all the amino acid sequences disclosed herein with at least one conservative amino acid substitution.

In an example approach to determining the degree of identity, a BLAST program may be used, with a probability score between $e^{-3}$ and $e^{-100}$ indicating a closely related sequence.

In one embodiment, the present disclosure provides a fusion polypeptide of SEQ ID NO: 19.

In another embodiment, the present disclosure provides a fusion polypeptide of SEQ ID NO: 20.

In one embodiment, the present disclosure provides a fusion polypeptide of SEQ ID NO: 40.

In another embodiment, the present disclosure provides a fusion polypeptide of SEQ ID NO: 41, or a variant thereof comprising at least one conservative amino acid substitution.

In one embodiment, the present disclosure provides a fusion polypeptide of SEQ ID NO: 46.

In another embodiment, the present disclosure provides a fusion polypeptide of SEQ ID NO: 47, or a variant thereof comprising at least one conservative amino acid substitution.

In another embodiment, the present disclosure provides a fusion polypeptide of SEQ ID NO: 48.

In another embodiment, the present disclosure provides a fusion polypeptide of SEQ ID NO: 49, or a variant thereof comprising at least one conservative amino acid substitution.

In one embodiment, the present disclosure provides a fusion polypeptide of SEQ ID NO: 50.

In another embodiment, the present disclosure provides a fusion polypeptide of SEQ ID NO: 51, or a variant thereof comprising at least one conservative amino acid substitution.

In one embodiment, the present disclosure provides a fusion polypeptide of SEQ ID NO: 52.

In another embodiment, the present disclosure provides a fusion polypeptide of SEQ ID NO: 53, or a variant thereof comprising at least one conservative amino acid substitution.

In another embodiment, the present disclosure provides a fusion polypeptide of SEQ ID NO: 54, or a variant thereof comprising at least one conservative amino acid substitution.

In another embodiment, the present disclosure provides a fusion polypeptide of SEQ ID NO: 55, or a variant thereof comprising at least one conservative amino acid substitution.

In another embodiment, the present disclosure provides a fusion polypeptide of SEQ ID NO: 56, or a variant thereof comprising at least one conservative amino acid substitution.

In another embodiment, the present disclosure provides a fusion polypeptide of SEQ ID NO: 57, or a variant thereof comprising at least one conservative amino acid substitution.

In another embodiment, the present disclosure provides a fusion polypeptide of SEQ ID NO: 58, or a variant thereof comprising at least one conservative amino acid substitution.

In another embodiment, the present disclosure provides a fusion polypeptide of SEQ ID NO: 59, or a variant thereof comprising at least one conservative amino acid substitution.

In another embodiment, the present disclosure provides a fusion polypeptide of SEQ ID NO: 60, or a variant thereof comprising at least one conservative amino acid substitution.

In another embodiment, the present disclosure provides a fusion polypeptide of SEQ ID NO: 61, or a variant thereof comprising at least one conservative amino acid substitution.

In another embodiment, the present disclosure provides a fusion polypeptide of SEQ ID NO: 62, or a variant thereof comprising at least one conservative amino acid substitution.

In another embodiment, the present disclosure provides a fusion polypeptide of SEQ ID NO: 63, or a variant thereof comprising at least one conservative amino acid substitution.

In another embodiment, the present disclosure provides a fusion polypeptide of SEQ ID NO: 64, or a variant thereof comprising at least one conservative amino acid substitution.

In another embodiment, the present disclosure provides a fusion polypeptide of SEQ ID NO: 65, or a variant thereof comprising at least one conservative amino acid substitution.

In another embodiment, the present disclosure provides a fusion polypeptide of SEQ ID NO: 66, or a variant thereof comprising at least one conservative amino acid substitution.

In another embodiment, the present disclosure provides a fusion polypeptide of SEQ ID NO: 67, or a variant thereof comprising at least one conservative amino acid substitution.

In another embodiment, the present disclosure provides a fusion polypeptide of SEQ ID NO: 68, or a variant thereof comprising at least one conservative amino acid substitution.

As used herein, the terms "homology" and "homologous" are not limited to designate proteins having a theoretical common genetic ancestor, but includes proteins which may be genetically unrelated that have, nonetheless, evolved to perform similar functions and/or have similar structures. Functional homology to the various proteins described herein also encompasses proteins that have an activity of the corresponding protein of which it is a homolog. For proteins to have functional homology, it is not required that they have significant identity in their amino acid sequences, but, rather, proteins having functional homology are so defined by having similar or identical activities. For example, with respect to a Klotho molecule, the polypeptide should have the functional characteristics of binding to an FGF polypeptide and enable the binding of the FGF to an FGFR. With respect to an FGF molecule, the polypeptide should have the functional characteristics of binding to an FGFR and causing the activation of FGFR (e.g., phosphorylation). Assays for assessing FGF binding to the FGF receptor and/or activation of the FGF signaling pathway are known in the art and described herein (See Example 2). Assays for assessing Klotho activity are also known in the art and described herein (e.g., binding to a FGF polypeptide). Proteins with structural homology are defined as having analogous tertiary (or quaternary) structure and do not necessarily require amino acid identity or nucleic acid identity for the genes encoding them. In certain circumstances, structural homologs may include proteins which maintain structural homology only at the active site or binding site of the protein.

In addition to structural and functional homology, the present disclosure further encompasses proteins having amino acid identity to the various Klotho and FGF amino acid sequences described herein. To determine the percent identity/homology of two amino acid sequences, the sequences are aligned for optimal comparison purposes (e.g., gaps can be introduced in the amino acid sequence of one protein for optimal alignment with the amino acid sequence of another protein). The amino acid residues at corresponding amino acid positions are then compared. When a position in one sequence is occupied by the same amino acid residue as the corresponding position in the other, then the molecules are identical at that position. The percent identity between the two sequences is a function of the number of identical positions shared by the sequences (i.e., % identity=# of identical positions/total # of positions multiplied by 100).

The amino acid sequences of molecules of the disclosure described herein have an amino acid sequence which is at least about 60%, 70%, 80%, 90%, 95%, 96%, 97%, 98%, 99% or more identical or homologous to an amino acid sequence described herein.

The nucleic acid sequences of molecules of the disclosure described herein have a nucleotide sequence which hybridizes to or is at least about 60%, 70%, 80%, 90%, 95%, 96%, 97%, 98%, 99% or more identical or homologous to a nucleotide sequence described herein.

Nucleic acid molecules appropriate for use in the fusion polypeptides of the disclosure may have a Klotho or FGF nucleotide sequence which hybridizes under stringent conditions to the complement of a nucleic acid molecule encoding Klotho or FGF, respectively. As used herein, the term "hybridizes under stringent conditions" is intended to describe conditions for hybridization and washing under which nucleotide sequences at least about 70%, 80%, 85%, 90% or more homologous to each other typically remain hybridized to each other. Such stringent conditions are known to those skilled in the art and can be found in Ausubel et al. *Current Protocols in Molecular Biology*, Wiley Interscience, New York (2001), 6.3.1-6.3.6. A specific, non-limiting example of stringent hybridization conditions are hybridization in 6× sodium chloride/sodium citrate (SSC) at about 45° C., followed by one or more washes in 0.2×SSC, 0.1% SDS at 50-65° C.

4.2. Klotho-FGF Fusion Polypeptides of the Disclosure

In some embodiments of the disclosure, a Klotho fusion polypeptide has a polypeptide chain having a first polypeptide sequence of a Klotho polypeptide or an active fragment or variant thereof and a second polypeptide sequence encoding FGF or an active fragment or variant thereof. In some embodiments, the fusion further comprises a modified Fc fragment having decreased affinity for Fc-gamma-receptor and/or increased serum half-life.

The disclosure includes fusion polypeptides which are at least about 95% or more homologous to an amino acid sequence presented in SEQ ID NO: 19-28. The amino acid sequence of SEQ ID NO: 19 encodes a Klotho fusion polypeptide having a Klotho extracellular domain N-terminally linked to the FGF23 (R179Q) variant (SEQ ID NO: 36). The amino acid sequence of SEQ ID NO: 20 encodes a Klotho fusion polypeptide having an IgG signal peptide N-terminally linked to a Klotho extracellular domain lacking a signal peptide N-terminally linked to the FGF23 (R179Q) variant. The amino acid sequence of SEQ ID NO: 21 encodes a Klotho fusion polypeptide having a KL-D1 extracellular subdomain N-terminally linked to the FGF23 (R179Q) variant. The amino acid sequence of SEQ ID NO: 22 encodes a Klotho fusion polypeptide having a KL-D2 extracellular subdomain N-terminally linked to the FGF23 (R179Q) variant. The amino acid sequence of SEQ ID NO: 23 encodes a Klotho fusion polypeptide having two KL-D1 extracellular subdomains N-terminally linked to the FGF23 (R179Q) variant. The amino acid sequence of SEQ ID NO: 24 encodes a Klotho fusion polypeptide having two KL-D2 extracellular subdomains N-terminally linked to the FGF23 (R179Q) variant. The amino acid sequence of SEQ ID NO: 25 encodes a Klotho fusion polypeptide having the FGF23 (R179Q) variant N-terminally linked to a Klotho extracellular domain. The amino acid sequence of SEQ ID NO: 26 encodes a Klotho fusion polypeptide having the FGF23 (R179Q) variant N-terminally linked to a KL-D1 extracellular subdomain. The amino acid sequence of SEQ ID NO: 27 encodes a Klotho fusion polypeptide having the FGF23 (R179Q) variant N-terminally linked to a KL-D2 extracellular subdomain. The amino acid sequence of SEQ ID NO: 28 encodes a Klotho fusion polypeptide having the FGF23 (R179Q) variant N-terminally linked to two KL-D1 extracellular subdomains. The amino acid sequence of SEQ ID NO: 29 encodes a Klotho fusion polypeptide having the FGF23 (R179Q) variant N-terminally linked to two KL-D2 extracellular subdomains. In some embodiments, the fusion further comprises a modified Fc fragment having decreased affinity for Fc-gamma-receptor and/or increased serum half-life.

The Klotho fusion polypeptide of the disclosure may include an amino acid sequence which is at least about 95% identical to the amino acid sequence set forth in SEQ ID NO: 7. The amino acid sequence of SEQ ID NO: 7 encodes a Klotho extracellular domain lacking a signal peptide. In some embodiments, the fusion further comprises a modified Fc fragment having decreased affinity for Fc-gamma-receptor and/or increased serum half-life.

The subject fusion proteins are described herein and can be made using methods known in the art. For example, the fusion polypeptides of the disclosure may be constructed as described in U.S. Pat. No. 6,194,177. The use of Klotho polypeptides is described in U.S. Pat. No. 6,579,850. The use of FGF nucleic acid molecules is described in U.S. Pat. No. 7,223,563.

In some embodiments, a nucleic acid molecule encoding the Klotho is cloned by PCR and ligated, in frame, with a nucleic acid molecule encoding FGF. In some embodiments, the fusion further comprises a modified Fc fragment having decreased affinity for Fc-gamma-receptor and/or increased serum half-life. The nucleic acid encoding the fusion polypeptide is operatively linked to a promoter to allow for expression. The nucleic acid molecule encoding the fusion polypeptide is subsequently transfected into a host cell for expression. The sequence of the final construct can be confirmed by sequencing.

When preparing the fusion proteins of the present disclosure, a nucleic acid molecule encoding an extracellular subdomain of Klotho will be fused in frame to the nucleic acid molecule encoding FGF and the (optional) nucleic acid encoding the modified Fc fragment. Expression of the resulting nucleic acid molecule results in the extracellular subdomain of Klotho being fused N-terminal in relation to the FGF polypeptide. Fusions are also possible in which the extracellular subdomain of Klotho is fused C-terminal in relation to the FGF polypeptide. Methods for making fusion proteins are well known in the art.

The fusion polypeptides of the disclosure have at least two polypeptides that are covalently linked, in which one polypeptide comes from one protein sequence or domain, e.g., Klotho, and the other polypeptide comes from another protein sequence or domain, e.g., FGF. In some embodiments, the fusion further comprises a modified Fc fragment having decreased affinity for Fc-gamma-receptor and/or increased serum half-life. In another embodiment, the disclosure comprises a FGF fused to a modified Fc fragment. Klotho and/or FGF and/or the (optional) modified Fc fragment, of the fusion polypeptides of the disclosure, can be joined by methods well known to those of skill in the art. These methods include both chemical and recombinant means.

Nucleic acids encoding the domains to be incorporated into the fusion polypeptides of the disclosure can be obtained using routine techniques in the field of recombinant genetics. Basic texts disclosing the general methods of use in this disclosure include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994-1999). In nucleic acids encoding a Klotho fusion polypeptide of the disclosure, the nucleic acid sequence encoding alpha-Klotho or beta-Klotho, represented by SEQ ID NO: 1 and SEQ ID NO: 3, respectively, may be used. In nucleic acids encoding a Klotho fusion polypeptide, the nucleic acid sequence encoding FGF19, FGF21, or FGF23, represented by SEQ ID NO: 30, SEQ ID NO: 32 and SEQ ID NO: 34, respectively, may be used. Nucleic acid sequences of molecules of the disclosure described herein comprise a nucleotide sequence which hybridizes to or is at least about 60%, 70%, 80%, 90%, 95%, 96%, 97%, 98%, 99% or more identical or homologous to SEQ ID NO: 1, SEQ ID NO: 3, SEQ ID NO: 30, SEQ ID NO: 32, or SEQ ID NO: 34.

Nucleic acid sequences that encode the various components of the fusion [Klotho, and/or FGF peptide and/or the (optional) modified Fc fragment] can be obtained using any of a variety of methods. For example, the nucleic acid sequences encoding the polypeptides may be cloned from cDNA and genomic DNA libraries by hybridization with probes, or isolated using amplification techniques with oligonucleotide primers. More commonly, amplification techniques are used to amplify and isolate the Klotho and FGF sequences using a DNA or RNA template (see, e.g., Dieffenfach & Dveksler, PCR Primers: A Laboratory Manual (1995)). Alternatively, overlapping oligonucleotides can be produced synthetically and joined to produce one or more of the domains. Nucleic acids encoding Klotho or FGF can also be isolated from expression libraries using antibodies as probes.

According to the present disclosure, the various components of the fusion [Klotho, and/or, FGF and/or the (optional) modified Fc fragment] can be linked either directly or via a covalent linker, including amino acid linkers, such as a polyglycine linker, or another type of chemical linker, including, carbohydrate linkers, lipid linkers, fatty acid linkers, polyether linkers, such as PEG, etc. (See for example, Hermanson, Bioconjugate techniques (1996)). The polypeptides forming the fusion/fusion polypeptide are typically linked C-terminus to N-terminus, although they can also be linked C-terminus to C-terminus, N-terminus to N-terminus, or N-terminus to C-terminus. One or more polypeptide domains may be inserted at an internal location within a fusion polypeptide of the disclosure. The polypeptides of the fusion protein can be in any order. The fusion polypeptides may be produced by covalently linking a chain of amino acids from one protein sequence, e.g., an extracellular subdomain of Klotho, to a chain of amino acids from another protein sequence, e.g., FGF, by preparing a recombinant polynucleotide contiguously encoding the fusion protein. The different chains of amino acids in a fusion protein may be directly spliced together or may be indirectly spliced together via a chemical linking group or an amino acid linking group. The amino acid linking group can be about 200 amino acids or more in length, or generally 1 to 100 amino acids. In some embodiments, proline residues are incorporated into the linker to prevent the formation of significant secondary structural elements by the linker. Linkers can often be flexible amino acid subsequences that are synthesized as part of a recombinant fusion protein. Such flexible linkers are known to persons of skill in the art.

According to the present disclosure, the amino acid sequences of the fusion [an extracellular subdomain of Klotho and/or the FGF and/or the (optional) modified Fc fragment] may be linked via a peptide linker. Example peptide linkers are well known in the art and described herein. For example, peptide linkers generally include several Gly and several Ser residues, such as: $(Gly_4 Ser)_3$ (SEQ ID NO: 11), $Gly_4$ Ser polypeptide (SEQ ID NO: 12), Gly (SEQ ID NO: 13), Gly Gly (SEQ ID NO: 14), Gly Ser (SEQ ID NO: 15), $Gly_2$ Ser (SEQ ID NO: 16), Ala (SEQ ID NO: 17), and Ala Ala (SEQ ID NO: 18). Specifically, a peptide linker for use in a fusion protein of the disclosure may act as a flexible hinge.

The signal sequence of Klotho or FGF may be excluded prior to incorporation of Klotho into a fusion protein of the disclosure. The signal sequence for Klotho or FGF of the fusion protein may be included, e.g., the polypeptide represented by SEQ ID NO: 19. However, such sequences may also be omitted and replaced with the signal sequence of a different protein, e.g., the IgG signal sequence (SEQ ID NO: 9). Generally, the pharmaceutical compositions of the disclosure will contain the mature form of Klotho and FGF.

Generally, introns are excluded from either one or both the Klotho or the FGF moieties prior to incorporation into a fusion polypeptide.

The fusion polypeptides of the disclosure may include one or more polymers covalently attached to one or more reactive amino acid side chains. By way of example, not limitation, such polymers include polyethylene glycol (PEG), which can be attached to one or more free cysteine sulfhydryl residues, thereby blocking the formation of disulfide bonds and aggregation when the protein is exposed to oxidizing conditions. In addition, PEGylation of the fusion polypeptides of the disclosure is expected to provide such improved properties as increased half-life, solubility, and protease resistance. The fusion polypeptides of the disclosure may alternatively be modified by the covalent addition of polymers to free amino groups such as the lysine epsilon or the N-terminal amino group. Particular specific cysteines and lysines for covalent modification will be those not involved in receptor binding, heparin binding, or in proper protein folding. It will be apparent to one skilled in the art that the methods for assaying the biochemical and/or biological activity of the fusion polypeptides may be employed in order to determine if modification of a particular amino acid residue affects the activity of the protein as desired. Other similar suitable modifications are contemplated and known in the art.

The disclosure is also directed to the expression of a fusion polypeptide that is at least about 95% or more homologous to an amino acid sequence presented in SEQ ID NO: 19-28.

The present disclosure encompasses a fusion polypeptide comprising: (a) a polypeptide comprising at least one extracellular subdomain of a Klotho protein, or a functionally active variant or derivative thereof; (b) a polypeptide comprising a fibroblast growth factor, or a functionally active variant or derivative thereof; and (c) a modified Fc fragment having decreased affinity for Fc-gamma-receptor and/or increased serum half-life. By "a functionally active variant or derivative thereof" is meant a variant or derivative comprising a longer, shorter or altered amino acid sequence than the corresponding wild-type polypeptide, while retaining the biological activity. Thus "a functionally active variant or derivative" of an extracellular subdomain of a Klotho protein or a fibroblast growth factor comprises fewer, more, or an altered amino acid sequence than a wild-type extracellular subdomain of a Klotho protein or a fibroblast growth factor, but still retains at least one biological activity of the wild-type polypeptide sequence. A functionally active variant or derivative of a polypeptide disclosed herein can also comprise the same amino acid sequence of a polypeptide disclosed herein, but vary in post-translational modification (e.g., pegylation, methylation and/or glycosylation), or have additional moieties or elements added to it. In various embodiments, the variant or derivative of FGF23 comprises R179Q or does not.

In one embodiment, a functionally active variant or derivative polypeptide includes an amino acid sequence at least about 60% identical to a sequence disclosed herein (e.g., at least one extracellular domain of a Klotho protein or a fibroblast growth factor). Preferably, the polypeptide is at least 55%, 60%, 65%, 70%, 75%, 80%, 85%, 90%, 95%, 98%, 99% or more identical to a sequence disclosed herein.

As used herein, percent identity of two amino acid sequences (or of two nucleic acid sequences) is determined using the algorithm of Karlin and Altschul (PNAS USA 87:2264-2268, 1990), modified as in Karlin and Altschul, PNAS USA 90:5873-5877, 1993). Such an algorithm is incorporated into the NBLAST and XBLAST programs of Altschul et al. (J. Mol. Biol. 215:403-410, 1990). BLAST nucleotide searches are performed with the NBLAST program, score=100, wordlength=12. BLAST protein searches are performed with the XBLAST program, score=50, wordlength=3. To obtain gapped alignment for comparison purposes GappedBLAST is utilized as described in Altschul et al. (Nucleic Acids Res. 25:3389-3402, 1997). When utilizing BLAST and GappedBLAST programs the default parameters of the respective programs (e.g., XBLAST and NBLAST) are used to obtain nucleotide sequences homologous to a nucleic acid molecule of the invention.

Identity or identical means amino acid sequence (or nucleic acid sequence) similarity and has an art recognized meaning. Sequences with identity share identical or similar amino acids (or nucleic acids). Thus, a candidate sequence sharing 85% amino acid sequence identity with a reference sequence requires that, following alignment of the candidate sequence with the reference sequence, 85% of the amino acids in the candidate sequence are identical to the corresponding amino acids in the reference sequence, and/or constitute conservative amino acid changes.

Functionally active variants of a polypeptide disclosed herein retain substantially the same functional activity of the original polypeptide or fragment. Naturally occurring functionally active variants such as allelic variants and species variants and non-naturally occurring functionally active variants are included in the invention and can be produced by, for example, mutagenesis techniques or by direct synthesis.

A functionally active variant or derivative differs by about or at least, for example, 1, 2, 3, 4, 5, 6, 7, 8, 9, 10, 11, 12, 13, 14, 15, 16, 17, 18, 19, 20, 25, 30, 35, 40, 45, 50, 55, 60 or more amino acid residues from a polypeptide disclosed herein. Where this comparison requires alignment the sequences are aligned for maximum homology. The site of variation can occur anywhere in the polypeptide, as long as activity substantially similar to a polypeptide disclosed herein.

Guidance concerning how to make variants and derivatives with phenotypically silent amino acid substitutions is provided in Bowie et al., Science, 247:1306-1310 (1990), which teaches that there are two main strategies for studying the tolerance of an amino acid sequence to change.

The first strategy exploits the tolerance of amino acid substitutions by natural selection during the process of evolution. By comparing amino acid sequences in different species, the amino acid positions which have been conserved between species can be identified. See e.g., FIG. 4. These conserved amino acids are likely important for protein function. In contrast, the amino acid positions in which substitutions have been tolerated by natural selection indicate positions which are not critical for protein function. Thus, positions tolerating amino acid substitution can be modified while still maintaining specific binding activity of the polypeptide.

The second strategy uses genetic engineering to introduce amino acid changes at specific positions of a cloned gene to identify regions critical for protein function. For example, site-directed mutagenesis or alanine-scanning mutagenesis (the introduction of single alanine mutations at every residue in the molecule) can be used (Cunningham et al., Science, 244:1081-1085 (1989)).

Methods of introducing a mutation into amino acids of a protein is well known to those skilled in the art. See, e.g., Ausubel (ed.), Current Protocols in Molecular Biology, John Wiley and Sons, Inc. (1994); T. Maniatis, E. F. Fritsch and J. Sambrook, Molecular Cloning: A Laboratory Manual, Cold Spring Harbor laboratory, Cold Spring Harbor, N.Y. (1989)). Mutations can also be introduced using commercially available kits such as "QuikChange™ Site-Directed Mutagenesis Kit" (Stratagene). The generation of a polypeptide functionally active variant or derivative to a polypeptide by replacing an amino acid that does not influence the function of a polypeptide can be accomplished by one skilled in the art.

A variant or derivative can have, for example, one or more conservative substitutions while still retaining at least one biological activity. A conservative substitution is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Particular example variants and derivatives include, without limitation, functionally active variants and derivatives of a polypeptide comprising at least one extracellular subdomain of a Klotho protein, e.g., a polypeptide comprising at least about 100, 150, 200, 250, 300, 350, 375, 400, or 425 contiguous amino acids of an extracellular domain of Klotho (e.g., SEQ ID NO: 5 or 6), with no more than about 1, 2, 3, 4, 5, 6, 7, 8, 9, 10, 11, 12, 13, 14, 15, 16, 17, 18, 19, 20, 25, 30, 35, 40, 45, 50, 55, 60 or more amino acid residue differences from the wild-type sequence (as disclosed in SEQ ID NO: 5 or 6), while retaining at least one biological activity of the wild-type polypeptide. For example, a functionally active variant or derivative of a polypeptide comprising at least one extracellular subdomain of a Klotho protein comprises a polypeptide comprising at least about 400 contiguous amino acids of SEQ ID NO: 5 or 6, with no more than about 100 amino acid residue differences. For example, a functionally active variant or derivative of a polypeptide comprising at least one extracellular subdomain of a Klotho protein comprises a polypeptide comprising at least about 400 contiguous amino acids of SEQ ID NO: 5 or 6, with no more than about 50 amino acid residue differences. For example, a functionally active variant or derivative of a polypeptide comprising at least one extracellular subdomain of a Klotho protein comprises a polypeptide comprising at least about 425 contiguous amino acids of SEQ ID NO: 5 or 6, with no more than about 25 amino acid residue differences. For example, a functionally active variant or derivative of a polypeptide comprising at least one extracellular subdomain of a Klotho protein comprises a polypeptide comprising at least about 425 contiguous amino acids of SEQ ID NO: 5 or 6, with no more than about 10 amino acid residue differences. In another example, a functionally active variant or derivative of a polypeptide comprising at least one extracellular subdomain of a Klotho protein comprises a polypeptide comprising at least about 100, 150, 200, 250, 300, 350, 400, 450, 500, 550, 600, 650, 700, 750, 800, 850, 900, 925, 950 or 982 contiguous amino acids of SEQ ID NO: 7, with no more than about 1, 2, 3, 4, 5, 6, 7, 8, 9, 10, 11, 12, 13, 14, 15, 16, 17, 18, 19, 20, 25, 30, 35, 40, 45, 50, 55, 60, 70, 75, 80, 85, 90, 95, 100, 110, 120, 140, 150, 160, 170, 180, 190, or 200 amino acid residue differences from the wild-type sequence. For example, a functionally active variant or derivative of a polypeptide comprising at least one extracellular subdomain of a Klotho protein comprises a polypeptide comprising at least about 500 contiguous amino acids of SEQ ID NO: 7, with no more than about 100 amino acid residue differences. For example, a functionally active variant or derivative of a polypeptide comprising at least one extracellular subdomain of a Klotho protein comprises a polypeptide comprising at least about 600 contiguous amino acids of SEQ ID NO: 7, with no more than about 100 amino acid residue differences. For example, a functionally active variant or derivative of a polypeptide comprising at least one extracellular subdomain of a Klotho protein comprises a polypeptide comprising at least about 700 contiguous amino acids of SEQ ID NO: 7, with no more than about 100 amino acid residue differences. For example, a functionally active variant or derivative of a polypeptide comprising at least one extracellular subdomain of a Klotho protein comprises a polypeptide comprising at least about 800 contiguous amino acids of SEQ ID NO: 7, with no more than about 100 amino acid residue differences. For example, a functionally active variant or derivative of a polypeptide comprising at least one extracellular subdomain of a Klotho protein comprises a polypeptide comprising at least about 900 contiguous amino acids of SEQ ID NO: 7, with no more than about 100 amino acid residue differences. For example, a functionally active variant or derivative of a polypeptide comprising at least one extracellular subdomain of a Klotho protein comprises a polypeptide comprising at least about 900 contiguous amino acids of SEQ ID NO: 7, with no more than about 50 amino acid residue differences.

Particular example variants and derivatives include, without limitation, functionally active variants and derivatives of a polypeptide comprising a fibroblast growth factor, e.g., a polypeptide comprising at least about 100, 125, 150, 150, 175, 200, 225, or 250 contiguous amino acids of a fibroblast growth factor, e.g., FGF19 (SEQ ID NO: 31), FGF21 (SEQ ID NO: 33), or FGF23 (SEQ ID NO: 35), with no more than about 1, 2, 3, 4, 5, 6, 7, 8, 9, 10, 11, 12, 13, 14, 15, 16, 17, 18, 19, 20, 25, 30, 35, 40, 45, 50, 55, 60 or more amino acid residue differences from the wild-type sequence (as disclosed in SEQ ID NOs: 31, 33 or 35), while retaining at least one biological activity of the wild-type polypeptide. In various embodiments, the variant or derivative can comprise the R179Q variation or not. For example, a functionally active variant or derivative of a polypeptide comprising a fibroblast growth factor comprises a polypeptide comprising at least about 150 contiguous amino acids of SEQ ID NOs: 31, 33 or 35, with no more than about 25 amino acid residue differences. For example, a functionally active variant or derivative of a polypeptide comprising a fibroblast growth factor comprises a polypeptide comprising at least about 175 contiguous amino acids of SEQ ID NOs: 31, 33 or 35, with no more than about 25 amino acid residue differences. For example, a functionally active variant or derivative of a polypeptide comprising a fibroblast growth factor comprises a polypeptide comprising at least about 200 contiguous amino acids of SEQ ID NOs: 31, 33 or 35, with no more than about 25 amino acid residue differences. For example, a functionally active variant or derivative of a polypeptide comprising a fibroblast growth factor comprises a polypeptide comprising at least about 225 contiguous amino acids of SEQ ID NO: 35, with no more than about 50 amino acid residue differences. For example, a functionally active variant or derivative of a polypeptide comprising a fibroblast growth factor comprises a polypeptide comprising at least about 225 contiguous amino acids of SEQ ID NO: 35, with no more than about 25 amino acid residue differences.

4.3. Expression of Fusion Polypeptides of the Disclosure

In order to express the fusion protein of the disclosure, DNA molecules obtained by any of the methods described herein or those that are known in the art, can be inserted into appropriate expression vectors by techniques well known in the art. For example, a double stranded cDNA can be cloned into a suitable vector by homopolymeric tailing or by restriction enzyme linking involving the use of synthetic DNA linkers or by blunt-ended ligation. DNA ligases are usually used to ligate the DNA molecules and undesirable joining can be avoided by treatment with alkaline phosphatase.

Therefore, the disclosure includes vectors (e.g., recombinant plasmids and bacteriophages) that include nucleic acid molecules (e.g., genes or recombinant nucleic acid molecules encoding genes) as described herein. The term "recombinant vector" includes a vector (e.g., plasmid, phage, phasmid, virus, cosmid, fosmid, or other purified nucleic acid vector) that has been altered, modified or engineered such that it contains greater, fewer or different nucleic acid sequences than those included in the native or natural nucleic acid molecule from which the recombinant vector was derived. For example, a recombinant vector may include a nucleotide sequence encoding a Klotho-FGF23 fusion operatively linked to regulatory sequences, e.g., promoter sequences, terminator sequences and/or artificial ribosome binding sites (RBSs), as defined herein. Recombinant vectors which allow for expression of the genes or nucleic acids included in them are referred to as "expression vectors."

For eukaryotic hosts, different transcriptional and translational regulatory sequences may be employed, depending on the nature of the host. They may be derived from viral sources, such as adenovirus, bovine papilloma virus, Simian virus or the like, where the regulatory signals are associated with a particular gene which has a high level of expression. Examples include, but are not limited to, the TK promoter of the Herpes virus, the SV40 early promoter, the yeast gal4 gene promoter, etc. Transcriptional initiation regulatory signals may be selected which allow for repression or activation, so that expression of the genes can be modulated.

In some of the molecules of the disclosure described herein, one or more DNA molecules having a nucleotide sequence encoding one or more polypeptide chains of a fusion polypeptide are operatively linked to one or more regulatory sequences, which are capable of integrating the desired DNA molecule into a host cell. Cells which have been stably transformed by the introduced DNA can be selected, for example, by introducing one or more markers which allow for selection of host cells which contain the expression vector. A selectable marker gene can either be linked directly to a nucleic acid sequence to be expressed, or be introduced into the same cell by co-transfection. Additional elements may also be needed for optimal synthesis of proteins described herein. It would be apparent to one of ordinary skill in the art which additional elements to use.

Factors of importance in selecting a particular plasmid or viral vector include, but are not limited to, the ease with which recipient cells that contain the vector are recognized and selected from those recipient cells which do not contain the vector; the number of copies of the vector which are desired in a particular host; and whether it is desirable to be able to "shuttle" the vector between host cells of different species.

Once the vector(s) is constructed to include a DNA sequence for expression, it may be introduced into an appropriate host cell by one or more of a variety of suitable methods that are known in the art, including but not limited to, for example, transformation, transfection, conjugation, protoplast fusion, electroporation, calcium phosphate-precipitation, direct microinjection, etc.

Host cells may either be prokaryotic or eukaryotic. Examples of eukaryotic host cells include, for example, mammalian cells, such as human, monkey, mouse, and Chinese hamster ovary (CHO) cells. Such cells facilitate post-translational modifications of proteins, including, for example, correct folding or glycosylation. Additionally, yeast cells can also be used to express fusion polypeptides of the disclosure. Like most mammalian cells, yeast cells also enable post-translational modifications of proteins, including, for example, glycosylation. A number of recombinant DNA strategies exist which utilize strong promoter sequences and high copy number plasmids that can be utilized for production of proteins in yeast. Yeast transcription and translation machinery can recognize leader sequences on cloned mammalian gene products, thereby enabling the secretion of peptides bearing leader sequences (i.e., pre-peptides). A particular method of high-yield production of the fusion polypeptides of the disclosure is through the use of dihydrofolate reductase (DHFR) amplification in DHFR-deficient CHO cells, by the use of successively increasing levels of methotrexate as described in U.S. Pat. No. 4,889,803. The polypeptide obtained may be in a glycosylated form.

After the introduction of one or more vector(s), host cells are usually grown in a selective medium, which selects for the growth of vector-containing cells. Purification of the recombinant proteins can be carried out by any of the methods known in the art or described herein, for example, any conventional procedures involving extraction, precipitation, chromatography and electrophoresis. A further purification procedure that may be used for purifying proteins is affinity chromatography using monoclonal antibodies which bind a target protein. Generally, crude preparations containing a recombinant protein are passed through a column on which a suitable monoclonal antibody is immobilized. The protein usually binds to the column via the specific antibody while the impurities pass through. After washing the column, the protein is eluted from the gel by changing pH or ionic strength, for example.

4.4. Assays for Assessing Fusion Polypeptide Activity

Assays described herein (See Example 2) and those known in the art can be used for detecting Klotho or FGF activity of the fusion polypeptides of the disclosure. Suitable activity assays include receptor binding assays, cellular proliferation assays and cell signaling assays. For example, a binding assay which may be used for determining whether a fusion polypeptide has Klotho or FGF activity includes, assaying the binding of a fusion polypeptide to an FGF receptor. FGF receptor binding assays include, but are not limited to, both competitive and non-competitive assay. For example, FGF receptor binding can be detected by contacting cells expressing an FGF receptor with a labeled FGF (for example, radio-active label) and increasing concentrations of an unlabeled Klotho-FGF fusion polypeptide. The two ligands that compete for binding to the same receptor are added to a reaction mixture containing the cell. The cells are subsequently washed and labeled FGF is measured. A decrease in the amount of the labeled FGF to its receptor in the presence of the unlabeled fusion polypeptide is indicative of binding of the Klotho-FGF fusion polypeptide to the receptor. Alternatively, the Klotho-FGF fusion polypeptide may be labeled and direct binding of the fusion polypeptide to the cell is detected.

Klotho or FGF activity can also be measured by determining whether the fusion polypeptide induces a cellular response. For example, in some embodiments, an assay for detecting the biological activity of a Klotho-FGF fusion polypeptide involves contacting cells which express an FGF receptor with a fusion polypeptide, assaying a cellular response such as, for example, cell proliferation or Egr-1 activation, myotube diameter in C2C12 cells, and comparing the cellular response in the presence and absence of the fusion polypeptide. An increase in the cellular response in the presence of the fusion polypeptide complex relative to the absence indicates that the fusion polypeptide has biological activity. Also, an increase in a downstream signaling event from the receptor can also be measured as indicia of biological activity (e.g., phosphorylation of FGFR, FRS2, ERK1/2, p70S6K etc.).

4.5 Pharmaceutical Compositions and Methods of Treatment

The disclosure also pertains to pharmaceutical compositions containing one or more fusion polypeptides of the disclosure and a pharmaceutically acceptable diluent or carrier. The pharmaceutical compositions can further include a pharmaceutically effective dose of heparin. Such pharmaceutical compositions may be included in a kit or container. Such kit or container may be packaged with instructions pertaining to the extended in vivo half-life or the in vitro shelf life of the fusion polypeptides. Optionally associated with such kit or container(s) can be a notice in the form prescribed by a governmental agency regulating the manufacture, use or sale of pharmaceuticals or biological products, which notice reflects approval by the agency of manufacture, use or sale for human administration. Such compositions may be used in methods of treating, preventing, or ameliorating a disease or a disease symptom (e.g., age-related condition or metabolic disorder) in a patient, preferably a mammal and most preferably a human, by administering the pharmaceutical composition comprising a polypeptide or fusion polypeptide of the disclosure to the patient.

In general, a therapeutically effective amount of a pharmaceutical composition of the disclosure is from about 0.0001 mg/kg to 0.001 mg/kg; 0.001 mg/kg to about 10 mg/kg body weight or from about 0.02 mg/kg to about 5 mg/kg body weight. Commonly, a therapeutically effective amount of a fusion polypeptide is from about 0.001 mg to about 0.01 mg, about 0.01 mg to about 100 mg, or from about 100 mg to about 1000 mg, for example. Preferably, a therapeutically effective amount of a fusion polypeptide is from about 0.001 mg/kg to 2 mg/kg.

The optimal pharmaceutical formulations for a fusion polypeptide can be determined by one or ordinary skilled in the art depending upon the route of administration and desired dosage. (See, for example, Remington's Pharmaceutical Sciences, 18th Ed. (1990), Mack Publishing Co., Easton, Pa., the entire disclosure of which is hereby incorporated by reference).

The fusion polypeptides of the disclosure may be administered as a pharmaceutical composition that may be in the form of a solid, liquid or gas (aerosol). Typical routes of administration may include, without limitation, oral, topical, parenteral, sublingual, rectal, vaginal, intradermal and intranasal. Parenteral administration includes subcutaneous injections, intravenous, intramuscular, intraperitoneal, intrapleural, intrasternal injection or infusion techniques. Preferably, the compositions are administered parenterally. More preferably, the compositions are administered intravenously. Pharmaceutical compositions of the disclosure can be formulated so as to allow a polypeptide of the disclosure to be bioavailable upon administration of the composition to a subject. Compositions can take the form of one or more dosage units, where, for example, a tablet can be a single dosage unit, and a container of a polypeptide of the disclosure in aerosol form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the overall health of the subject, the type of age-related condition or metabolic disorder the subject in need of treatment of, the use of the composition as part of a multi-drug regimen, the particular form of the polypeptide of the disclosure, the manner of administration, and the composition employed.

The pharmaceutically acceptable carrier or vehicle may be particulate, so that the compositions are, for example, in tablet or powder form. The carrier(s) can be liquid, with the compositions being, for example, an oral syrup or injectable liquid. In addition, the carrier(s) can be gaseous, so as to provide an aerosol composition useful in, e.g., inhalatory administration.

The term "carrier" refers to a diluent, adjuvant or excipient, with which a polypeptide of the disclosure is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to a subject, the polypeptides of the disclosure and pharmaceutically acceptable carriers are sterile. Water is a particular carrier when the polypeptide of the disclosure is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The composition may be intended for oral administration, and if so, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as ethyl cellulose, carboxymethylcellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the pharmaceutical composition is in the form of a capsule, e.g., a gelatin capsule, it can contain, in addition to materials of the above type, a liquid carrier such as polyethylene glycol, cyclodextrin or a fatty oil.

The pharmaceutical composition can be in the form of a liquid, e.g., an elixir, syrup, solution, emulsion or suspension. The liquid can be useful for oral administration or for delivery by injection. When intended for oral administration, a composition can contain one or more of a sweetening agent, preservatives, dye/colorant and flavour enhancer. In a composition for administration by injection, one or more of a surfactant, preservative, wetting agent, dispersing agent, suspending agent, buffer, stabilizer and isotonic agent can also be included.

The liquid compositions of the disclosure, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. A parenteral composition can be enclosed in an ampoule, a disposable syringe or a multiple-dose vial made of glass, plastic or other material. Physiological saline is a particular specific adjuvant. An injectable composition is preferably sterile.

The pharmaceutical compositions contain an effective amount of a compound of the disclosure (e.g., fusion polypeptide) such that a suitable dosage will be obtained. The pharmaceutical compositions may contain the known effective amount of the compounds as currently prescribed for their respective disorders.

The route of administration of the polypeptide of the disclosure used in the prophylactic and/or therapeutic regimens which will be effective in the prevention, treatment, and/or management of a age-related condition or metabolic disorder can be based on the currently prescribed routes of administration for other therapeutics known in the art. The polypeptides of the disclosure can be administered by any convenient route, for example, by infusion or bolus injection, by absorption through epithelial or mucocutaneous linings (e.g., oral mucosa, rectal and intestinal mucosa, etc.). Administration can be systemic or local. Various delivery systems are known, e.g., microparticles, microcapsules, capsules, etc., and may be useful for administering a polypeptide of the disclosure. More than one polypeptides of the disclosure may be administered to a subject. Methods of administration may include, but are not limited to, oral administration and parenteral administration; parenteral administration including, but not limited to, intradermal, intramuscular, intraperitoneal, intravenous, subcutaneous, intranasal, epidural, sublingual, intranasal, intracerebral, intraventricular, intrathecal, intravaginal, transdermal, rectally, by inhalation, or topically to the ears, nose, eyes, or skin.

The polypeptides of the disclosure may be administered parenterally. Specifically, the polypeptides of the disclosure may be administered intravenously.

Pulmonary administration can also be employed, e.g., by use of an inhaler or nebulizer, and formulation with an aerosolizing agent, or via perfusion in a fluorocarbon or synthetic pulmonary surfactant. The polypeptides of the disclosure can also be formulated as a suppository, with traditional binders and carriers such as triglycerides. The polypeptides of the disclosure can be delivered in a controlled release system.

For example, a pump can be used (see Sefton, *CRC Crit. Ref. Biomed. Eng.* 1987, 14, 201; Buchwald et al., Surgery 1980, 88: 507; Saudek et al., *N Engl. J. Med.* 1989, 321: 574). Polymeric materials can also be used for controlled release of the polypeptides of the disclosure (see *Medical Applications of Controlled Release*, Langer and Wise (eds.), CRC Pres., Boca Raton, Fla., 1974; *Controlled Drug Bioavailability, Drug Product Design and Performance*, Smolen and Ball (eds.), Wiley, New York, 1984; Ranger and Peppas, *J. Macromol. Sci. Rev. Macromol. Chem.* 1983, 23, 61; see also Levy et al., *Science* 1985, 228, 190; During et al., *Ann. Neurol.*, 1989, 25, 351; Howard et al., *J. Neurosurg.*, 1989, 71, 105). Specifically, a controlled-release system can be placed in proximity of the target of the polypeptides of the disclosure, e.g., the brain, thus requiring only a fraction of the systemic dose (see, e.g., Goodson, in *Medical Applications of Controlled Release*, supra, vol. 2, 1984, pp. 115-138). Other controlled-release systems discussed in the review by Langer (*Science* 1990, 249, 1527-1533) can be used.

Polymeric materials used to achieve controlled or sustained release of the polypeptides of the disclosure are disclosed, e.g., in U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. Preferably, the polymer used in a sustained release formulation is inert, free of leachable impurities, stable on storage, sterile, and biodegradable.

In general, a therapeutically effective amount of a pharmaceutical composition of the disclosure is from about 0.0001 mg/kg to 0.001 mg/kg; 0.001 mg/kg to about 10 mg/kg body weight or from about 0.02 mg/kg to about 5 mg/kg body weight.

In other embodiments, the prophylactic and/or therapeutic regimen involves administering to a patient one or more doses of an effective amount of a polypeptide of the disclosure, wherein the dose of an effective amount achieves a plasma level of at least 0.01 µg/mL to at least 400 µg/mL of the polypeptide of the disclosure.

A prophylactic and/or therapeutic regimen may involve administering to a patient a plurality of doses of an effective amount of a polypeptide of the disclosure, wherein the plurality of doses maintains a plasma level of at least 0.01 µg/mL, to 400 µg/mL of the polypeptide of the disclosure. The prophylactic and/or therapeutic regimen may be administered for at least 1 day, 1 month, 2 months, 3 months, 4 months, 5 months, 6 months, 7 months, 8 months or 9 months.

The prophylactic and/or therapeutic regimen may involve administration of a polypeptide of the disclosure in combination with one or more additional therapeutics. The recommended dosages of the one or more therapeutics currently used for the prevention, treatment, and/or management of an age-related condition or metabolic disorder can be obtained from any reference in the art including, but not limited to, Hardman et al., eds., *Goodman & Gilman's The Pharmacological Basis Of Basis Of Therapeutics,* 10th ed., McGraw-Hill, New York, 2001; *Physician's Desk Reference* (60th ed., 2006), which is incorporated herein by reference in its entirety.

The disclosure includes methods of treating disorders wherein agonistic activity of Klotho protein and FGF are desirable. The disclosure furthermore includes the use of the disclosed proteins, fusion proteins, nucleic acid molecules or pharmaceutical composition in therapy or as medicament for the treatment of a pathological disorder wherein agonistic activity of Klotho protein and FGF are desirable. Examples of such methods or uses of the disclosure include, but are not limited to age-related condition or metabolic disorders.

The disclosure includes methods for treating or preventing an age-related condition in an individual; and the use of the disclosed proteins (polypeptides), fusion proteins, nucleic acid molecules or pharmaceutical composition in therapy or as medicament for treating or preventing an age-related condition in an individual. An individual in need of treatment is administered a pharmacologically effective dose of a pharmaceutical composition containing a Klotho fusion polypeptide, having at least one extracellular subdomain of a Klotho protein and a fibroblast growth factor and an (optional) modified Fc fragment, so as to treat or prevent the age-related condition. In some embodiments, the Klotho fusion polypeptide is co-administered with a pharmacologically effective dose of heparin. Age-related conditions include sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss. In some embodiments, the Klotho fusion polypeptide contains at least one extracellular domain of an alpha Klotho protein. In a particular embodiment, a Klotho fusion protein containing at least one extracellular domain of alpha Klotho protein and fibroblast growth factor 23 is administered to an individual in need of treatment for muscle wasting.

The disclosure is also directed to a method for treating or preventing a metabolic disorder in an individual; and to the use of the disclosed proteins (polypeptides), fusion proteins (polypeptides), nucleic acid molecules or pharmaceutical composition in therapy or as medicament for treating or preventing metabolic disorder in an individual. An individual in need of treatment is administered a pharmacologically effective dose of a pharmaceutical composition containing a Klotho fusion polypeptide, having at least one extracellular subdomain of a Klotho protein and a fibroblast growth factor so as to treat the metabolic disorder, and an (optional) modified Fc fragment having decreased binding to FcRn and/or increased serum half-life and/or stability. In some embodiments, the Klotho fusion polypeptide is co-administered with a pharmacologically effective dose of heparin. The method may be used in the treatment or prevention of Type II Diabetes, Metabolic Syndrome, hyperglycemia, and obesity. In a particular embodiment, a Klotho fusion protein containing at least one extracellular domain of a beta-Klotho protein and fibroblast growth factor 21 is administered to an individual in need of treatment for a metabolic disorder.

The disclosure also provides methods for treating or preventing hyperphosphatemia or calcinosis in an individual; and the use of the disclosed proteins, fusion proteins, nucleic acid molecules or pharmaceutical composition in therapy or as medicament for treating or preventing hyperphosphatemia or calcinosis in an individual. An individual in need of treatment is administered a pharmacologically effective dose of a pharmaceutical composition containing a Klotho fusion polypeptide, having at least one extracellular subdomain of a Klotho protein, a fibroblast growth factor and an (optional) modified Fc fragment so as to treat hyperphosphatemia or calcinosis. In some embodiments, the Klotho fusion polypeptide is co-administered with a pharmacologically effective dose of heparin. In a particular embodiment, a Klotho fusion protein containing at least one extracellular domain of an alpha Klotho protein and fibroblast growth factor 23 and an (optional) modified Fc fragment is administered to an individual in need of treatment for a hyperphosphatemia or calcinosis.

The disclosure is also directed to a method for treating or preventing chronic renal disease or chronic renal failure in an individual; and to the use of the disclosed proteins, fusion proteins, nucleic acid molecules or pharmaceutical composition in therapy or as medicament for treating or preventing chronic renal disease or chronic renal failure in an individual. An individual in need of treatment is administered a pharmacologically effective dose of a pharmaceutical composition containing a Klotho fusion polypeptide, having at least one extracellular subdomain of a Klotho protein, a fibroblast growth factor and an (optional) modified Fc fragment so as to treat chronic renal disease or chronic renal failure. In some embodiments, the Klotho fusion polypeptide is co-administered with a pharmacologically effective dose of heparin. In some embodiments, a Klotho fusion protein containing at least one extracellular domain of an alpha Klotho protein is administered to an individual in need of treatment for chronic renal disease or chronic renal failure.

The disclosure also includes methods for treating or preventing cancer in an individual; and the use of the disclosed proteins, fusion proteins, nucleic acid molecules or pharmaceutical composition in therapy or as medicament for treating or preventing cancer in an individual. An individual in need of treatment is administered a pharmacologically effective dose of a pharmaceutical composition containing a Klotho fusion polypeptide, having at least one extracellular subdomain of a Klotho protein, a fibroblast growth factor and an (optional) modified Fc fragment so as to treat cancer. The method may be used in the treatment or prevention of breast cancer. In some embodiments, the Klotho fusion polypeptide is co-administered with a pharmacologically effective dose of heparin. In some embodiments, a Klotho fusion protein containing at least one extracellular domain of an alpha Klotho protein is administered to an individual in need of treatment for cancer.

In methods of treating disorders by administering a pharmaceutical composition containing a Klotho variant or Klotho fusion polypeptide; or when using pharmaceutical composition containing a Klotho variant or Klotho fusion polypeptide in therapy, the Klotho fusion polypeptide and an (optional) modified Fc fragment has at least one extracellular subdomain of a Klotho protein and a fibroblast growth factor. In a particular embodiment, the Klotho fusion protein contains at least one extracellular domain of a beta Klotho protein and fibroblast growth factor 21.

In another embodiment, the fusion comprises a FGF (e.g., FGF19, FGF21, FGF23 or FGF23 variant) and a modified Fc fragment with decreased binding to FcRn and/or increased serum stability. This type of fusion can be used in various diseases, as described above, or used to treat or prevent any FGF-related disease known in the art.

The fusion can be administered to an individual in need thereof. The fusion polypeptide compositions can be administered according to any method of administration known to those of skill in the art and described herein. Particular specific methods of administration include subcutaneous or intravenous. Other effective modes of administration are described herein.

4.6. Methods of Treatment and Assays for Assessing Efficacy

Methods or uses of the disclosure which provide administering the fusion polypeptides described herein to an individual can be used to treat a variety of disorders including an age-related disorder or a metabolic disorder. Without being limited by any particular theory, fusion polypeptides may be used to treat disorders in which there is dysregulation of Klotho or FGF. Example disorders include metabolic disorders and age-related disorders. For example, both FGF23 or Klotho knock-out mice display a variety of similar phenotypes including, low physical activity, growth retardation, muscle wasting, skin atrophy, atherosclerosis, short life spans, etc. (See Razzaque and Lanske, *J. of Endrocrinology*, 194:1-10 (2007), which is herein incorporated by reference).

In particular, fusion polypeptides of the disclosure are particularly useful in the treatment of aging-related disorders, including muscle wasting. Without being bound to theory, the ability of Klotho and FGF23 to control mineral (e.g., phosphate and calcium) and vitamin D homeostasis may be the means by which these proteins modulate aging and muscle atrophy.

On the other hand, fusion polypeptides of the disclosure may be used for treating a metabolic disorder. For example, beta-Klotho and FGF19 have been shown to control bile acid homeostasis by regulating cholesterol 7-α-hydroxylase (CYP7A1). A non-limiting example of bile homeostasis disorder is cholestasis. The beta-Klotho and FGF21 have been shown to induce lipolysis in adipocytes and, therefore, reduced fat storage and increased glucose uptake. Non-limiting examples of lipolysis/fat storage disorders are obesity and associated metabolic and cardiovascular diseases.

Based at least in part on the finding that FGF23 is able to stimulate excretion of phosphate in the urine and thereby reduce phosphate levels in the serum, Klotho-FGF23 fusion polypeptides of the disclosure can be used for treating or preventing hyperphosphatemia or calcinosis in an individual. For example, it has been shown that a homozygous missense mutation in Klotho resulting in a deficiency in Klotho in a patient can cause severe tumoral calcinosis and artery calcification (Ichikawa et al., *J. Clin. Invest.* 117: 2684-2691 (2007), which is herein incorporated by reference). An individual is administered a pharmacologically effective dose of a pharmaceutical composition containing the Klotho fusion polypeptide, having at least one extracellular subdomain of a Klotho protein, a fibroblast growth factor and an (optional) modified Fc fragment so as to treat or prevent hyperphosphatemia or calcinosis. In particular, a Klotho fusion polypeptide containing at least one extracellular domain of an alpha Klotho protein, a fibroblast growth factor and an (optional) modified Fc fragment is useful for treating hyperphosphatemia or calcinosis.

Klotho fusion polypeptides of the disclosure can also be used for treating or preventing chronic renal disease or chronic renal failure in an individual. For example, it has been shown that Klotho expression is reduced in kidney of patients with chronic renal failure, compared to that in unaffected kidneys (Koh et al., *Biochem. Biophys. Res. Comm.* 280:1015-1020 (2001), which is herein incorporated by reference). An individual is administered a pharmacologically effective dose of a pharmaceutical composition containing the Klotho fusion polypeptide, having at least one extracellular subdomain of a Klotho protein, a fibroblast growth factor and an (optional) modified Fc fragment so as to treat or prevent chronic renal disease or chronic renal failure. In particular, a Klotho polypeptide or fusion polypeptide containing at least one extracellular domain of an alpha Klotho protein or variant thereof is useful for treating chronic renal disease or chronic renal failure.

Klotho fusion polypeptides of the disclosure can also be used for treating or preventing cancer in an individual. For example, it has been shown that Klotho expression is reduced in breast cancer tissue, compared to normal breast cancer tissue (Wolf et al., *Oncogene* (2008) advance online publication, which is herein incorporated by reference). An individual is administered a pharmacologically effective dose of a pharmaceutical composition containing the Klotho fusion polypeptide, having at least one extracellular subdomain of a Klotho protein, a fibroblast growth factor and an (optional) modified Fc fragment so as to treat or prevent cancer or breast cancer. In particular, a Klotho fusion protein containing at least one extracellular domain of an alpha Klotho protein is useful for treating cancer or breast cancer.

Methods for evaluating the efficacy and/or determining the effective dose of a Klotho fusion polypeptide of the disclosure on an age-related disorder or metabolic disorder include organismal based assays, e.g., using a mammal (e.g., a mouse, rat, primate, or some other non-human), or other animal (e.g., Xenopus, zebrafish, or an invertebrate such as a fly or nematode). The Klotho fusion polypeptide can be administered to the organism once or as a regimen (regular or irregular). A parameter of the organism is then evaluated, e.g., an age-associated parameter. Klotho fusion polypeptides that are of interest result in a change in the parameter relative to a reference, e.g., a parameter of a control organism. Other parameters (e.g., related to toxicity, clearance, and pharmacokinetics) can also be evaluated.

The Klotho fusion polypeptide of the disclosure may be evaluated using an animal that has a particular disorder, e.g., a disorder described herein, e.g., an age-related disorder, a metabolic disorder. These disorders can also provide a sensitized system in which the test polypeptide's effects on physiology can be observed. Example disorders include: denervation, disuse atrophy; metabolic disorders (e.g., disorder of obese and/or diabetic animals such as db/db mouse and ob/ob mouse); cerebral, liver ischemia; cisplatin/taxol/ vincristine models; various tissue (xenograph) transplants; transgenic bone models; pain syndromes (include inflammatory and neuropathic disorders); Paraquat, genotoxic, and oxidative stress models; and tumor I models.

For measuring an age-related disorder, the animal model can be an animal that has an altered phenotype when calorically restricted. For example, F344 rats provide a useful assay system for evaluating a Klotho fusion polypeptide. When calorically restricted, F344 rats have a 0 to 10% incidence of nephropathy. However, when fed ad libitum, they have a 60 to 100% incidence of nephropathy.

To evaluate a Klotho fusion polypeptide of the disclosure, it is administered to the animal (e.g., an F344 rat or other suitable animal) and a parameter of the animal is evaluated, e.g., after a period of time. The animal can be fed ad libitum or normally (e.g., not under caloric restriction, although some parameters can be evaluated under such conditions). Typically, a cohort of such animals is used for the assay. Generally, a test polypeptide can be indicated as favorably altering lifespan regulation in the animal if the test polypeptide affects the parameter in the direction of the phenotype of a similar animal subject to caloric restriction. Such test polypeptides may cause at least some of the lifespan regulatory effects of caloric restriction, e.g., a subset of such effects, without having to deprive the organism of caloric intake.

The parameter to be tested may be an age-associated or disease associated parameter, e.g., a symptom of the disorder associated with the animal model. For example, the test polypeptide can be administered to a SH Rat, and blood pressure is monitored. A test polypeptide that is favorably indicated can cause an amelioration of the symptom relative to a similar reference animal not treated with the polypeptide. Other parameters relevant to a disorder or to aging can include: antioxidant levels (e.g.. antioxidant enzyme levels or activity), stress resistance (e.g., paraquat resistance), core body temperature, glucose levels, insulin levels, thyroid-stimulating hormone levels, prolactin levels, and leutinizing hormone levels.

To measure the effectiveness of the polypeptides of the disclosure for treating an age-related disorder, an animal having decreased Klotho expression may be used, e.g., a mouse with a mutant Klotho; See Kuroo, et al. Nature, 390; 45 (1997) and U.S. Pub. No. 2003/0119910, both of which are herein incorporated by reference in their entirety. For example, the test polypeptide is administered to the mutant mouse and age-related parameters are monitored. A test polypeptide that is favorably indicated can cause an amelioration of the symptom relative to a similar reference animal not treated with the polypeptide. A parameter relevant to a metabolic disorder or to aging can be assessed by measurement of body weight, examination on the acquisition of reproductive ability, measurement of blood sugar level, observation of life span, observation of skin, observation of motor functions such as walking, and the like. The assessment can also be made by measurement of thymus weight, observation of the size of calcified nodules formed on the inner surface of thoracic cavity, and the like. Further, quantitative determination of mRNA for the Klotho gene or Klotho protein is also useful for the assessment.

Still other in vivo models and organismal assays include evaluating an animal for a metabolic parameter, e.g., a parameter relevant to an insulin disorder, type II diabetes. Example metabolic parameters include: glucose concentration, insulin concentration, and insulin sensitivity.

Another example system features tumors, e.g., in an animal model. The tumors can be spontaneous or induced. For example, the tumors can be developed from cells that have a variety of genetic constitutions, e.g., they can be p53+ or p53−. It is also possible to use organisms that an autoimmune disorder, e.g., an NZB mouse, which is predisposed to SLE. To evaluate features of bone disease, it is possible, for example, to use an animal that has an ovariectomy as a model, e.g., for osteoporosis. Similarly, for joint disease, the model can be based on adjuvant arthritis (e.g., mice can be immunized with cartilage proteoglycans, high mobility group proteins, streptococcal cell wall material, or collagens); for kidney disease, kd/kd mice can be used. Animal models of cognition, particularly learning and memory are also available. Animal models of diabetes and its complications are also available, e.g., the streptozotocin model. Canine models can be used, for example, for evaluating stroke and ischemia.

In assessing whether a test polypeptide is capable of altering life span regulation, a number of age-associated parameters or biomarkers can be monitored or evaluated. Example age associated parameters include: (i) lifespan of the cell or the organism; (ii) presence or abundance of a gene transcript or gene product in the cell or organism that has a biological age dependent expression pattern; (iii) resistance of the cell or organism to stress; (iv) one so or more metabolic parameters of the cell or organism (example parameters include circulating insulin levels, blood glucose levels; fat content; core body temperature and so forth); (v) proliferative capacity of the cell or a set of cells present in the organism; and (vi) physical appearance or behavior of the cell or organism.

The term "average lifespan" refers to the average of the age of death of a cohort of organisms. In some cases, the "average lifespan" is assessed using a cohort of genetically identical organisms under controlled environmental conditions. Deaths due to mishap are discarded. Where average lifespan cannot be determined (e.g., for humans) under controlled environmental conditions, reliable statistical information (e.g., from actuarial tables) for a sufficiently large population can be used as the average lifespan.

Characterization of molecular differences between two such organisms, e.g., one reference organism and one organism treated with a Klotho fusion polypeptide can reveal a difference in the physiological state of the organisms. The reference organism and the treated organism are typically the same chronological age. The term "chronological age" as used herein refers to time elapsed since a preselected event, such as conception, a defined embryological or fetal stage, or, more preferably, birth. A variety of criteria can be used to determine whether organisms are of the "same" chronological age for the comparative analysis. Typically, the degree of accuracy required is a function of the average lifespan of a wildtype organism. For example, for the nematode C. elegans, for which the laboratory wildtype strain N2 lives an to average of about 16 days under some controlled conditions, organisms of the same age may have lived for the same number of days. For mice, organism of the same age may have lived for the same number of weeks or months; for primates or humans, the same number of years (or within 2, 3, or 5 years); and so forth. Generally, organisms of the same chronological age may have lived for an amount of time within 15, 10, 5, 3, 2 or 1% of the average lifespan of a wildtype organism of that species. Preferably, the organisms are adult organisms, e.g., the organisms have lived for at least an amount of time in which the average wildtype organism has matured to an age at which it is competent to reproduce.

The organismal screening assay can be performed before the organisms exhibit overt physical features of aging. For example, the organisms may be adults that have lived only 10, 30, 40, 50, 60, or 70% of the average lifespan of a wildtype organism of the same species. Age-associated changes in metabolism, immune competence, and chromosomal structure have been reported. Any of these changes can be evaluated, either in a test subject (e.g., for an organism based assay), or for a patient (e.g., prior, during or after treatment with a therapeutic described herein.

A marker associated with caloric restriction can also be evaluated in a subject organism of a screening assay (or a treated subject). Although these markers may not be age-associated, they may be indicative of a physiological state that is altered when the Klotho pathway is modulated. The marker can be an mRNA or protein whose abundance changes in calorically restricted animals. WO01/12851 and U.S. Pat. No. 6,406,853 describe example markers. Cellular models derived from cells of an animal described herein or analogous to an animal model described herein can be used for a cell-based assay.

Models for evaluating the effect of a test polypeptide on muscle atrophy include: 1) rat medial gastrocnemius muscle mass loss resulting from denervation, e.g., by severing the right sciatic nerve at mid-thigh; 2) rat medial gastrocnemius muscle mass loss resulting from immobilization, e.g., by fixed the right ankle joint at 90 degrees of flexion; 3) rat medial gastrocnemius muscle mass loss resulting from hind limb suspension; (see, e.g., U.S. 2003-0129686); 4) skeletal muscle atrophy resulting from treatment with the cachectic cytokine, interleukin-1 (IL-1) (R. N. Cooney, S. R. Kimball, T. C. Vary, Shock 7, 1-16 (1997)); and 5) skeletal muscle atrophy resulting from treatment with the glucocorticoid, dexamethasone (A. L. Goldberg, J. Biol. Chem. 244, 3223-9 (1969).)

Example animal models for AMD include: laser-induced mouse model simulating exudative (wet) macular degeneration Bora et al., Proc. Natl. Acad. Sci. USA., 100:2679-84 (2003); a transgenic mouse expressing a mutated form of cathepsin D resulting in features associated with the "geographic atrophy" form of AMD (Rakoczy et al., Am. J. Pathol., 161:1515-24 (2002)); and a transgenic mouse over expressing VEGF in the retinal pigment epithelium resulting in CNV. Schwesinger et al., Am. J. Pathol. 158:1161-72 (2001).

Example animal models of Parkinson's disease include primates rendered Parkinsonian by treatment with the dopaminergic neurotoxin 1-methyl-4 phenyl 1,2,3,6-tetrahydropyridine (MPTP) (see, e.g., U.S. Patent Publication No. 20030055231 and Wichmann et al., Ann. N.Y. Acad. Sci., 991:199-213 (2003); 6-hydroxydopamine-lesioned rats (e.g., Lab. Anim. Sci., 49:363-71 (1999)); and transgenic invertebrate models (e.g., Lakso et al., J. Neurochem. 86:165-72 (2003) and Link, Mech. Ageing Dev., 122:1639-49 (2001)).

Example molecular models of Type II diabetes include: a transgenic mouse having defective Nkx-2.2 or Nkx-6.1; (U.S. Pat. No. 6,127,598); Zucker Diabetic Fatty fa/fa (ZDF) rat. (U.S. Pat. No. 6,569,832); and Rhesus monkeys, which spontaneously develop obesity and subsequently frequently progress to overt type 2 diabetes (Hotta et al., Diabetes, 50:1126-33 (2001); and a transgenic mouse with a dominant-negative IGF-I receptor (KR-IGF-IR) having Type 2 diabetes-like insulin resistance.

Example animal and cellular models for neuropathy include: vincristine induced sensory-motor neuropathy in mice (U.S. Pat. No. 5,420,112) or rabbits (Ogawa et al., Neurotoxicology, 21:501-11 (2000)); a streptozotocin (STZ)-diabetic rat for study of autonomic neuropathy (Schmidt et al., Am. J. Pathol., 163:21-8 (2003)); and a progressive motor neuropathy (pmn) mouse (Martin et al., Genomics, 75:9-16 (2001)).

Example animal models of hyperphosphatemia or tumoral calcinosis include Klotho knockout mice and FGF23 knockout mice (Yoshida et al., Endocrinology 143:683-689 (2002)).

Example animal models of chronic renal disease or chronic renal failure include COL4A3+/− mice (Beirowski et al., J. Am. Soc. Nephrol. 17:1986-1994 (2006)).

Example animal models of cancer include the transplantation or implantation of cancer cells or tissue into nude mice, as is known in the art (Giovanella et al., Adv. Cancer Res. 44:69-120 (1985)). For example, animal models of breast cancer include nude mice transplanted or implanted with breast cancer cells or tissue (e.g., Yue et al., Cancer Res. 54:5092-5095 (1994); Glinsky et al., Cancer Res. 56:5319-5324 (1996); Visonneau Am. J. Path. 152:1299-1311 (1998)).

The compositions can be administered to a subject, e.g., an adult subject, particularly a healthy adult subject or a subject having an age-related disease. In the latter case, the method can include evaluating a subject, e.g., to characterize a symptom of an age-related disease or other disease marker, and thereby identifying a subject as having a neurodegenerative disease, e.g., Alzheimer's or an age-related disease or being pre-disposed to such a disease.

Skeletal Muscle Atrophy

Methods or uses of the disclosure which provide administering the Klotho polypeptide or fusion polypeptide to an individual can be used to treat skeletal muscle atrophy. Muscle atrophy includes numerous neuromuscular, metabolic, immunological and neurological disorders and diseases as well as starvation, nutritional deficiency, metabolic stress, diabetes, aging, muscular dystrophy, or myopathy. Muscle atrophy occurs during the aging process. Muscle atrophy also results from reduced use or disuse of the muscle. Symptoms include a decline in skeletal muscle tissue mass. In human males, muscle mass declines by one-third between the ages of 50 and 80. Some molecular features of muscle atrophy include the upregulation of ubiquitin ligases, and the loss of myofibrillar proteins (Furuno et al., *J. Biol. Chem.*, 265:8550-8557, 1990). The breakdown of these proteins can be followed, e.g., by measuring 3-methyl-histidine production, which is a specific constituent of actin, and in certain muscles of myosin (Goodman, Biochem. J. 241:121-12, 1987 and Lowell, et al., Metabolism, 35:1121-112, 1986; Stein and Schluter, *Am. J. Physiol. Endocrinol. Metab.* 272: E688-E696, 1997). Release of creatine kinase (a cell damage marker) (Jackson, et al., Neurology, 41: 101 104, 1991) can also be indicative.

Non-Insulin-Dependent Diabetes

Methods or uses of the disclosure which provide administering the Klotho polypeptide or fusion polypeptide to an individual can be used to treat Non-insulin-dependent Diabetes. Non-insulin-dependent Diabetes is also called "adult onset" diabetes and Type 2 diabetes. Type 2 diabetes also includes "non-obese type 2" and "obese type 2." Type II diabetes can be characterized by (1) reduced pancreatic-beta-islet-cell secretion of insulin such that less than necessary amounts of insulin are produced to keep blood glucose levels in balance and/or (2) "insulin resistance," wherein the body fails to respond normally to insulin. (U.S. Pat. Nos. 5,266,561 and 6,518,069). For example, glucose-stimulated insulin levels typically fail to rise above 4.0 nmol/L. (U.S. Pat. No. 5,266,561). Example symptoms of Type II diabetes include: hyperglycemia while fasting (U.S. Pat. No. 5,266, 561); fatigue; excessive thirst; frequent urination; blurred vision; and an increased rate of infections. Molecular indications of Type II diabetes include islet amyloid deposition in the pancreases.

Neuropathy

Neuropathy can include a central and/or peripheral nerve dysfunction caused by systemic disease, hereditary condition or toxic agent affecting motor, sensory, sensorimotor or autonomic nerves. (see, e.g., US Patent Application No. 20030013771). Symptoms can vary depending upon the cause of the nerve damage and the particular types of nerves affected. For example, symptoms of motor neuropathy include clumsiness in performing physical tasks or as muscular weakness, exhaustion after minor exertion, difficulty in standing or walking and attenuation or absence of a neuromuscular reflex. (U.S. Patent Application No. 20030013771) symptoms of autonomic neuropathy include constipation, cardiac irregularities and attenuation of the postural hypotensive reflex. (U.S. Patent Application No. 20030013771), symptoms of sensory neuropathy include pain and numbness; tingling in the hands, legs or feet; and extreme sensitivity to touch, and symptoms of retinopathy include blurred vision, sudden loss of vision, black spots, and flashing lights.

Alzheimer's Disease

Methods or uses of the disclosure which provide administering the Klotho polypeptide or fusion polypeptide to an individual can be used to treat Alzheimer's Disease (AD). Alzheimer's Disease is a complex neurodegenerative disease that results in the irreversible loss of neurons. It provides merely one example of a neurodegenerative disease that is also an age-related condition. Clinical hallmarks of Alzheimer's Disease include progressive impairment in memory, judgment, orientation to physical surroundings, and language. Neuropathological hallmarks of AD include region-specific neuronal loss, amyloid plaques, and neurofibrillary tangles. Amyloid plaques are extracellular plaques containing the amyloid peptide (also known as Ap, or Ap42) which is a cleavage product of the, 8-amyloid precursor protein (also known as APP). Neurofibrillary tangles are insoluble intracellular aggregates composed of filaments of the abnormally hyperphosphorylated microtubule-associated protein, taut Amyloid plaques and neurofibrillary tangles may contribute to secondary events that lead to neuronal loss by apoptosis (Clark and Karlawish, *Ann. Intern. Med.* 138(5):400-410 (2003). For example, p-amyloid induces caspase-2-dependent apoptosis in cultured neurons (Troy et al. *J Neurosci.* 20(4):1386-1392). The deposition of plaques in viva may trigger apoptosis of proximal neurons in a similar manner.

A variety of criteria, including genetic, biochemical, physiological, and cognitive criteria, can be used to evaluate AD in a subject. Symptoms and diagnosis of AD are known to medical practitioners. Some example symptoms and markers of AD are presented below. Information about these indications and other indications known to be associated with AD can be used as an "AD-related parameter." An AD related parameter can include qualitative or quantitative information. An example of quantitative information is a numerical value of one or more dimensions, e.g., a concentration of a protein or a tomographic map. Qualitative information can include an assessment, e.g., a physician's comments or a binary ("yes"/"no") and so forth. An AD-related parameter includes information that indicates that the subject is not diagnosed with AD or does not have a particular indication of AD, e.g., a cognitive test result that is not typical of AD or a genetic APOE polymorphism not associated with AD.

Progressive cognitive impairment is a hallmark of AD. This impairment can present as decline in memory, judgment, decision making, orientation to physical surroundings, and language (Nussbaum and Ellis, *New Eng J. Med.* 348(14):1356 35 1364 (2003)). Exclusion of other forms of dementia can assist in making a diagnosis of AD. Neuronal death leads to progressive cerebral atrophy in AD patients. Imaging techniques (e.g., magnetic resonance imaging, or computer assisted tomography) can be used to detect AD-associated lesions in the brain and/or brain atrophy.

AD patients may exhibit biochemical abnormalities that result from the pathology of the disease. For example, levels of tan protein in the cerebrospinal fluid is elevated in AD patients (Andreasen, N. et al. *Arch Neurol.* 58:349-350 (2001)).

Levels of amyloid beta 42 (A,B42) peptide can be reduced in CSF of AD patients. Levels of Ap42 can be increased in the plasma of AD patients (Ertekein-Taner, N., et al. *Science* 290:2303 2304 (2000)). Techniques to detect biochemical abnormalities in a sample from a subject include cellular, immunological, and other biological methods known in the art. For general guidance, see, e.g., techniques described in Sambrook & Russell, Molecular Cloning: A Laboratory Manual, 3rd Edition, Cold Spring Harbor Laboratory, N.Y. (2001), Ausubel et al., Current Protocols in Molecular Biology (Greene Publishing Associates and Wiley Interscience, N.Y. (1989), (Harrow, E. and Lane, D. (1988) Antibodies: A Laboratory Manual, Cold Spring Harbor Laboratory Press, Cold Spring Harbor, N.Y.), and updated editions thereof.

For example, antibodies, other immunoglobulins, and other specific binding ligands can be used to detect a biomolecule, e.g., a protein or other antigen associated with AD. For example, one or more specific antibodies can be used to probe a sample. Various formats are possible, e.g., ELISAs, fluorescence-based assays, Western blots, and protein arrays. Methods of producing polypeptide arrays are described in the art, e.g., in De Wildt et al. (2000). *Nature Biotech.* 18, 989-994; Lucking et al. (1999). *Anal. Biochem.*

270, 103-111; Ge, H. (2000). *Nucleic Acids Res.* 28, e3, I-VII; MacBeath, G., and Schreiber, S. L. (2000). *Science* 289, 1760 to 1 763; and WO 99/5 1 773A1.

In one assay, a non-human animal model of AD (e.g., a mouse model) is used, e.g., to evaluate a polypeptide or a therapeutic regimen. For example, U.S. Pat. No. 6,509,515 describes one such model animal which is naturally able to be used with learning and memory tests. The animal expresses an amyloid precursor protein (APP) sequence at a level in brain tissues such that the animal develops a progressive necrologic disorder within a short period of time from birth, generally within a year from birth, preferably within 2 to 6 months, from birth. The APP protein sequence is introduced into the animal, or an ancestor of the animal, at an embryonic stage, preferably the one cell, or fertilized oocyte, stage, and generally not later than about the 8-cell stage. The zygote or embryo is then developed to term in a pseudo-pregnant as foster female. The amyloid precursor protein genes are introduced into an animal embryo so as to be chromosomally incorporated in a state which results in super endogenous expression of the amyloid precursor protein and the development of a progressive necrologic disease in the cortico-limbic areas of the brain, areas of the brain which are prominently affected in progressive necrologic disease states such as AD. The gliosis and clinical manifestations in affected transgenic animals model necrologic disease. The progressive aspects of the neurologic disease are characterized by diminished exploratory and/or locomotor behavior and diminished deoxyglucose uptake/utilization and hypertrophic gliosis in the cortico-limbic regions of the brain. Further, the changes that are seen are similar to those that are seen in some aging animals. Other animal models are also described in U.S. Pat. Nos. 5,387,742; 5,877,399; 6,358,752; and 6, 187,992.

Parkinson's Disease

Methods or uses of the disclosure which provide administering the Klotho polypeptide or fusion polypeptide to an individual can be used to treat Parkinson's Disease. Parkinson's disease includes neurodegeneration of dopaminergic neurons in the substantia nigra resulting in the degeneration of the nigrostriatal dopamine system that regulates motor function. This pathology, in turn, leads to motor dysfunctions. (see, e.g., and Lotharius et al., *Nat. Rev. Neurosci.*, 3:932-42 (2002)). Example motor symptoms include: akinesia, stooped posture, gait difficulty, postural instability, catalepsy, muscle rigidity, and tremor. Example non-motor symptoms include: depression, lack of motivation, passivity, dementia and gastrointestinal dysfunction (see, e. g., Fahn, *Ann. N.Y. Acad. Sci.*, 991:1-14 (2003) and Pfeiffer, *Lancet Neurol.*, 2:107-16 (2003)) Parkinson's has been observed in 0.5 to 1 percent of persons 65 to 69 years of age and 1 to 3 percent among persons 80 years of age and older. (see, e.g., Nussbaum et al., *N. Engl. J. Med.*, 348:1356-64 (2003)). Molecular markers of Parkinson's disease include reduction in aromatic L amino acid decarboxylase (AADC) (see, e.g., US App. No. 20020172664); and loss of dopamine content in the nigrostriatal neurons (see, e.g., Fahn, Ann. *N.Y. Acad. Sci.*, 991:1-14 (2003) and Lotharius et al., Nat. Rev. Neurosci., 3:932-42 (2002)). In some familial cases, PD is linked to mutations in single genes encoding alpha-synuclein and parkin (an E3 ubiquitin ligase) proteins. (e.g., Riess et al., J. Neurol. 250 Suppl 1:13 10 (2003) and Nussbaum et al., N. Engl. J. Med., 348:1356-64 (2003)). A missense mutation in a neuron-specific C-terminal ubiquitin hydrolase gene is also associated with Parkinson's. (e.g., Nussbaum et al., N. Engl. J. Med., 348:1356-64 (2003))

Huntington's Disease

Methods or uses of the disclosure which provide administering the Klotho polypeptide or fusion polypeptide to an individual can be used to treat Huntington's Disease. Methods for evaluating the efficacy and/or determining the effective dose of a Klotho fusion polypeptide on Huntington's Disease include organismal based assays, e.g., using a mammal (e.g., a mouse, rat, primate, or some other non-human), or other animal (e.g., *Xenopus*, zebrafish, or an invertebrate such as a fly or nematode). A number of animal model system for Huntington's disease are available. See, e.g., Brouillet, Functional *Neurology* 15(4): 239-251 (2000); Ona et al. *Nature* 399: 263-267 (1999), Bates et al. *Hum Mol Genet.* 6(10):1633-7 (1997); Hansson et al. *J. of Neurochemistry* 78: 694-703; and Rubinsztein, D. C., *Trends in Genetics*, Vol. 1S, No. 4, pp. 202-209 (a review on various animal and non-human models of HD).

An example of such an animal model is the transgenic mouse strain is the R6/2 line (Mangiarini et al. Cell 87: 493-506 (1996)). The R6/2 mice are transgenic Huntington's disease mice, which over-express exon 1 of the human HD gene (under the control of the endogenous promoter). The exon 1 of the R6/2 human HD gene has an expanded CAG/polyglutamine repeat lengths (150 CAG repeats on average). These mice develop a progressive, ultimately fatal neurological disease with many features of human Huntington's disease. Abnormal aggregates, constituted in part by the N terminal part of Huntingtin (encoded by HD exon 1), are observed in R6/2 mice, both 45 in the cytoplasm and nuclei of cells (Davies et al. *Cell* 90: 537-548 (1997)). For example, the human Huntingtin protein in the transgenic animal is encoded by a gene that includes at least 55 CAG repeats and more preferably about 150 CAG repeats. These transgenic animals can develop a Huntington's disease-like phenotype.

These transgenic mice are characterized by reduced weight gain, reduced lifespan and motor impairment characterized by abnormal gait, resting tremor, hindlimb clasping and hyperactivity from 8 to 10 weeks after birth (for example the R6/2 strain; see Mangiarini et al. *Cell* 87: 493-506 (1996)). The phenotype worsens progressively toward hypokinesia. The brains of these transgenic mice also demonstrate neurochemical and histological abnormalities, such as changes in neurotransmitter receptors (glutamate, dopaminergic), decreased concentration of N-acetylaspartate (a marker of neuronal integrity) and reduced striatum and brain size. Accordingly, evaluating can include assessing parameters related to neurotransmitter levels, neurotransmitter receptor levels, brain size and striatum size. In addition, abnormal aggregates containing the transgenic part of or full-length human Huntingtin protein are present in the brain tissue of these animals (e.g., the R6/2 transgenic mouse strain). See, e.g., Mangiarini et al. *Cell* 87: 493-506 (1996), Davies et al. *Cell* 90: 537-548 (1997), Brouillet, Functional Neurology 15(4): 239-251 (2000) and Cha et al. *Proc. Natl. Acad. Sci. USA* 95: 6480-6485 (1998).

To test the effect of the test polypeptide or known polypeptide described in the application in an animal model, different concentrations of test polypeptide are administered to the transgenic animal, for example by injecting the test polypeptide into circulation of the animal. A Huntington's disease-like symptom may be evaluated in the animal. The progression of the Huntington's disease-like symptoms, e.g., as described above for the mouse model, is then monitored to determine whether treatment with the test polypeptide results in reduction or delay of symptoms. In another assay, disaggregation of the Huntingtin protein aggregates in these animals is monitored. The animal can then be sacrificed and brain slices are obtained. The brain slices are then analyzed for the presence of aggregates containing the transgenic human Huntingtin protein, a portion thereof, or a fusion protein comprising human Huntingtin protein, or a portion thereof. This analysis can includes, for example, staining the slices of brain tissue with anti-Huntingtin antibody and adding a secondary antibody conjugated with FITC which recognizes the anti-Huntington's antibody (e.g., the anti-Huntingtin antibody is mouse anti-human antibody and the secondary antibody is specific for human antibody) and visualizing the protein aggregates by fluorescent microscopy.

A variety of methods are available to evaluate and/or monitor Huntington's disease. A variety of clinical symptoms and indicia for the disease are known. Huntington's disease causes a movement disorder, psychiatric difficulties and cognitive changes. The degree, age of onset, and manifestation of these symptoms can vary. The movement disorder can include quick, random, dance-like movements called chorea.

Example motor evaluations include: ocular pursuit, saccade initiation, saccade velocity, dysarthria, tongue protrusion, finger tap ability, pronate/supinate, a lo fist-hand-palm sequence, rigidity of arms, bradykinesia, maximal dystonia (trunk, upper and lower extremities), maximal chorea (e.g., trunk, face, upper and lower extremities), gait, tandem walking, and retropulsion. An example treatment can cause a change in the Total Motor Score 4 (TMS-4), a subscale of the UHDRS, e.g., over a one-year period.

Cancer

Methods or uses of the disclosure which provide administering the Klotho polypeptide or fusion polypeptide to an individual can be used to treat cancer. Cancer includes any disease that is caused by or results in inappropriately high levels of cell division, inappropriately low levels of apoptosis, or both. Examples of cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). Lymphoproliferative disorders are also considered to be proliferative diseases.

Embodiments

In one embodiment, the disclosure pertains to: a composition comprising a fusion polypeptide comprising, in N-terminal to C-terminal order: (a) an alpha sKlotho, in which about 20 amino acids have been deleted from the C-terminus, optionally also having mutations at V563 and/or K795; (b) a linker; and (c) FGF23, optionally having a mutation at R179, C206 and/or C244.

In one embodiment, (a) the alpha sKlotho, in which about 20 amino acids have been deleted from the C-terminus, has a mutation at V563.

In one embodiment, (a) the alpha sKlotho, in which about 20 amino acids have been deleted from the C-terminus, has a mutation at K795.

In one embodiment, (a) the alpha sKlotho, in which about 20 amino acids have been deleted from the C-terminus, has mutations at V563 and K795.

In one embodiment, (a) the alpha sKlotho, in which about 20 amino acids have been deleted from the C-terminus, has the sequence of SEQ ID NO: 77.

In one embodiment, (a) the alpha sKlotho, in which about 20 amino acids have been deleted from the C-terminus, has the sequence of SEQ ID NO: 78.

In one embodiment, (c) the FGF23 has a mutation at R179.

In one embodiment, (c) the FGF23 has a mutation at C206.

In one embodiment, (c) the FGF23 has a mutation at C244.

In one embodiment, (c) the FGF23 has a mutation at R179 and a mutation at C206 or C244.

In one embodiment, (c) the FGF23 has mutations at R179, C206 and C244.

In one embodiment, (c) the FGF23 has the sequence of YPNASPLLGSSWGGLIHLYTATARNSYHLQIH-KNGHVDGAPHQTIYSALMIRSEDAGFVV ITGVMSR-RYLCMDFRGNIFGSHYFDPENCRFQHQTLENGYD-VYHSPQYHFLVSLGRAKR AFLPGMNPPPYSQFLSRRNEIPLIHFNTPIPRRHTQ-SAEDDSERDPLNVLKPRARMTPAPAS CSQELPSAE-DNSPMASDPLGVVRGGRVNTHAGGTGPEGCRP-FAKFI (a portion of SEQ ID NO: 80).

In one embodiment, (a) the alpha sKlotho, in which about 20 amino acids have been deleted from the C-terminus, has the sequence of SEQ ID NO: 77 or 78.

In one embodiment, (a) the alpha sKlotho, in which about 20 amino acids have been deleted from the C-terminus, has the sequence of SEQ ID NO: 77.

In one embodiment, (a) the alpha sKlotho, in which about 20 amino acids have been deleted from the C-terminus, has the sequence of SEQ ID NO: 78.

In one embodiment, the linker is a polypeptide linker.

In one embodiment, the polypeptide linker comprises an amino acid sequence comprising one or more copies of a linker selected from the group consisting of: SEQ ID NO: 11, SEQ ID NO: 12, SEQ ID NO: 13, SEQ ID NO: 14, SEQ ID NO: 15, SEQ ID NO: 16, SEQ ID NO: 17, and SEQ ID NO: 18.

In one embodiment, the fusion polypeptide further comprises a signal peptide.

In one embodiment, the fusion polypeptide comprises the amino acid sequence of SEQ ID NO: 80 or SEQ ID NO: 82.

In one embodiment, the composition further comprises a pharmaceutically acceptable carrier.

In one embodiment, the disclosure pertains to: a nucleic acid comprising a sequence that encodes fusion polypeptide of any embodiment described herein.

In one embodiment, the host cell comprises the nucleic acid of any embodiment described herein.

In one embodiment, the vector comprises the nucleic acid of any embodiment described herein.

In one embodiment, the disclosure pertains to: a method of treating or preventing a FGF23-related disease, comprising the step of administering to an individual in need thereof a therapeutically effective dose of a composition comprising a fusion polypeptide comprising, in N-terminal to C-terminal order: (a) an alpha sKlotho, in which about 20 amino acids have been deleted from the C-terminus, optionally also having mutations at V563 and/or K795; (b) a linker; and (c) FGF23, optionally having a mutation at R179, C206 and/or C244.

In one embodiment, the disclosure pertains to: a method of treating or preventing a FGF23-related disease, comprising the step of administering to an individual in need thereof a therapeutically effective dose of a composition of any embodiment described herein.

In one embodiment, the FGF23-related disease is selected from the group consisting of: an age-related condition, a metabolic disorder, hyperphosphatemia, calcinosis, chronic renal disease, chronic renal failure, cancer, breast cancer, and muscle atrophy.

In one embodiment, the age-related condition is selected from the group consisting of sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss.

In one embodiment, the metabolic disorder is selected from the group consisting of Type II Diabetes, Metabolic Syndrome, hyperglycemia, and obesity.

All patents, patent applications, and published references cited herein are hereby incorporated by reference in their entirety. While this disclosure has been particularly shown and described with references to embodiments thereof, it will be understood by those skilled in the art that various changes in form and details may be made therein without departing from the scope of the disclosure encompassed by the appended claims.

5. Examples

Example 1. Expression and Purification of Klotho Fusion Polypeptides

Expression of the Klotho Fusion Polypeptide

Figure 1:
Figure 1:
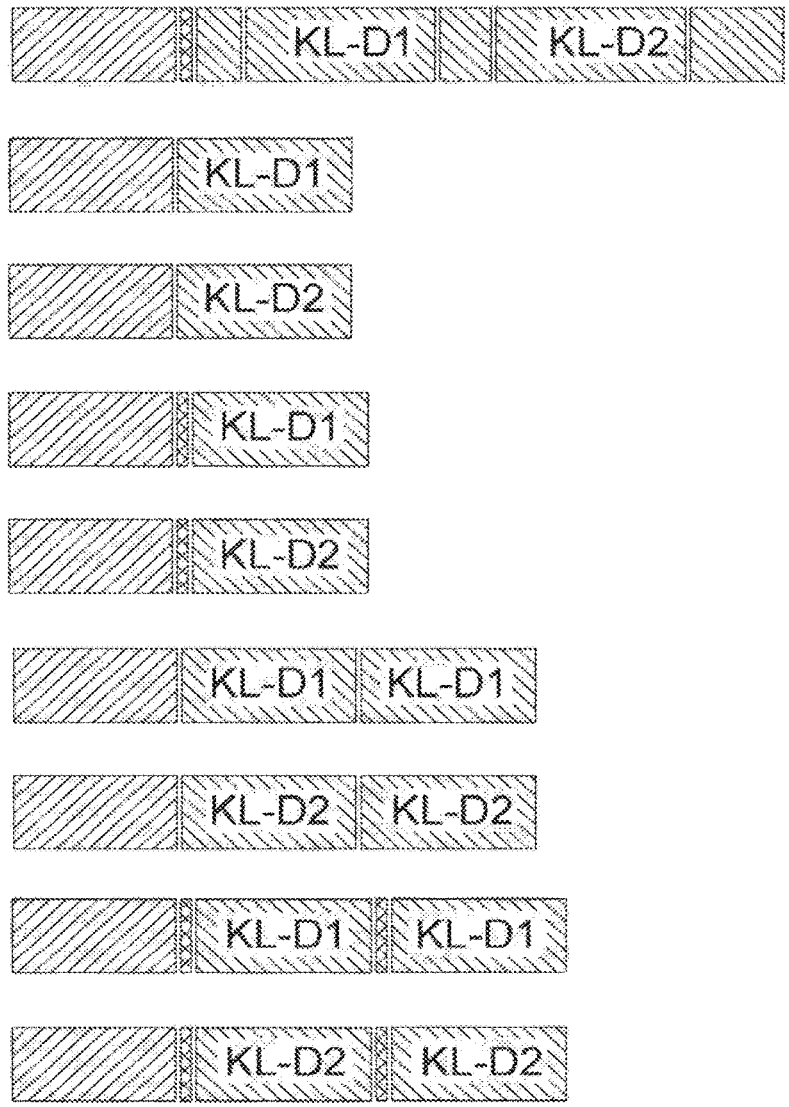
Figure 2A:
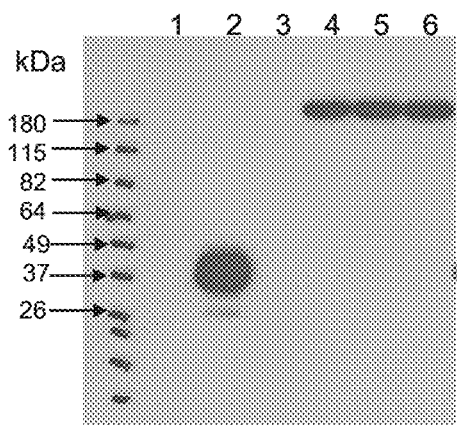
Figure 2B:
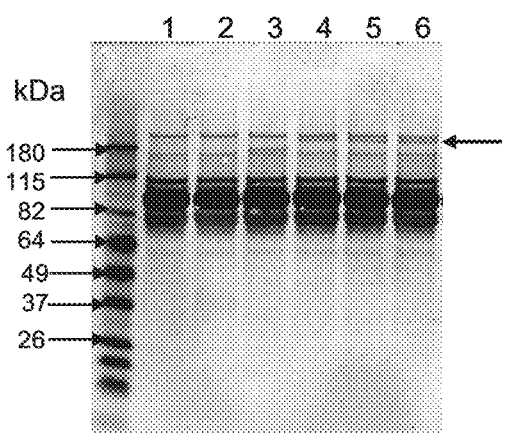

The polypeptides of the disclosure were made by transiently transfecting HEK293T cells with an expression vector encoding a Klotho fusion polypeptide having the extracellular domain of alpha Klotho and the FGF23 (R179Q) variant. Conditioned media containing expressed polypeptides were generated by transient transfection of the respective expression plasmids for Klotho, FGF23, and the Klotho-FGF23(R179Q) fusion protein. The transfections were performed in 6-well plates using Lipofectamine 2000 (Invitrogen, Cat #11668-019). Five hours after transfection, the transfection mix was replaced with 3 ml DMEM plus 1% FBS. Conditioned media were collected 72 hours after the addition of 3 ml DMEM plus 1% FBS. Samples of conditioned medium from various transiently transfected HEK293T cells were separated by SDS-polyacrylamide gel electrophoresis (SDS-PAGE) and analyzed by Western blot (FIG. 2A) or stained with Coomassie blue (FIG. 2B).

SDS-polyacrylamide gel electrophoresis was performed on various samples (lane 1, Control; lane 2, FGF23; lane 3, sKlotho; lanes 4-6, sKlotho-FGF23). Coomassie blue staining revealed the expression of a high, >180 kDa band (FIG. 2B, indicated by arrow on the right) that was not present in lanes 1-3, which contained samples that had not been transfected with the vector encoding the Klotho fusion polypeptide. The quality of the Klotho fusion polypeptide secreted into the media was evaluated by Western blot (FIG. 2A). An anti-FGF23 rat monoclonal IgG2A (R&D Systems, Cat # MAB26291) was used as the primary antibody to detect the Klotho fusion polypeptides by Western blot. The Western blot confirmed that the additional bands observed in the Coomassie stained gels were Klotho fusion polypeptides. The Western blot confirmed that the Klotho fusion polypeptides had the expected molecular weight for the Klotho fusion polypeptide. This analysis shows the expression of the Klotho-FGF23(R179Q) fusion protein.

Purification of the Klotho Fusion Polypeptide

Figure 2C:
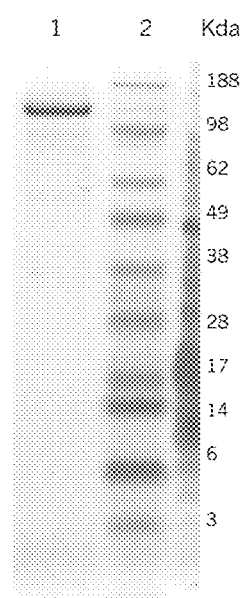

The polypeptides of the disclosure were purified from conditioned media from a culture of HEK293T cells transiently transfected with an expression vector encoding a Klotho fusion polypeptide having the extracellular domain of alpha Klotho and the FGF23 R179Q variant. To generate conditioned medium, an expression vector encoding sKlotho-FGF23-6×His was transfected (500 µg DNA in 18 ml of OptiMEM 1 (GIBCO, Cat #11058) mixed with 18 ml of 2 µg/ml polyethlinimine (PEI) into HEK293 cells grown in suspension in expression medium (464 ml of HEK293T cells at $10^6$ cells/ml in Freestype 293 expression medium (GIBCO, Cat #12338)). After transfection, the culture was allowed to grow (120 hours; 37° C. in a 5% $CO_2$ incubator; shaking at 125 rpm). At the end of incubation, conditioned medium was harvested by centrifugation (1000 rpm for five minutes). The conditioned medium was then applied to a nickel-agarose column. The sKlotho-FGF23-6×His bound tightly to the column and was eluted with 50 mM imidazole. The resulting purified material was then dialyzed in PBS to remove imidazole. A sample of the purified sKlotho-FGF23-6×His was separated by SDS-PAGE (lane 1, purified sKlotho-FGF23-6×His; lane 2, molecular weight marker) and analyzed by staining with Coomassie blue (FIG. 2C). The stained SDS-PAGE gel confirmed that the purified sKlotho-FGF23-6×His had the expected molecular weight. The inability to detect bands corresponding to proteins other than full-length sKlotho-FGF23-6×His in the lane loaded with the purified material also showed that the sKlotho-FGF23-6×His was purified.

Figure 3:
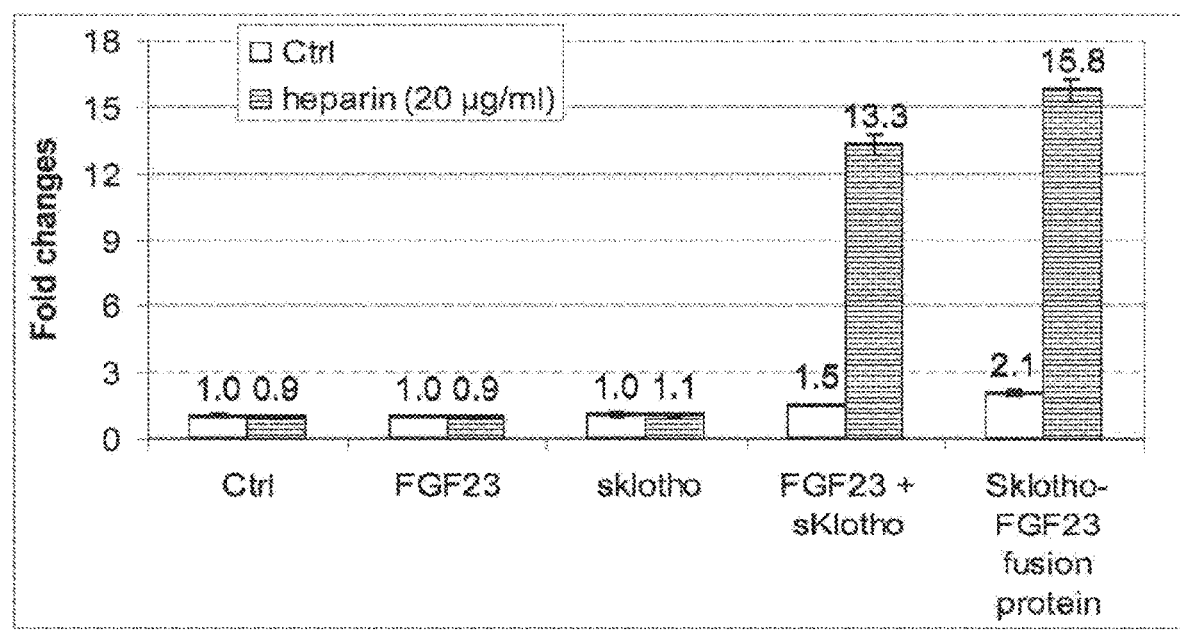
Figure 4A:
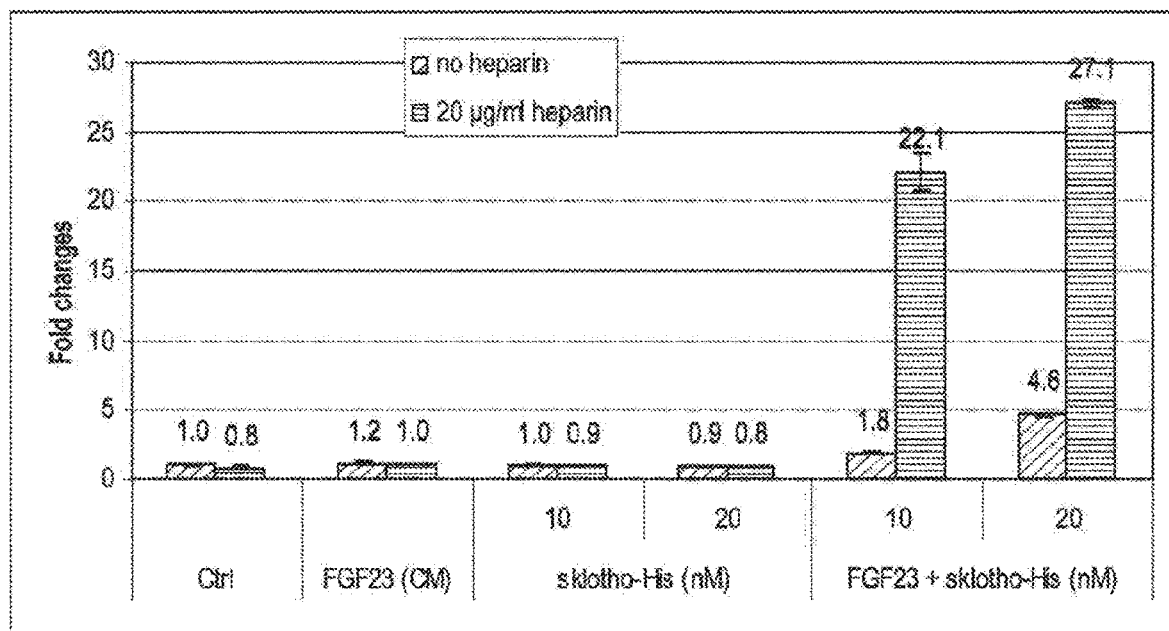
Figure 4B:
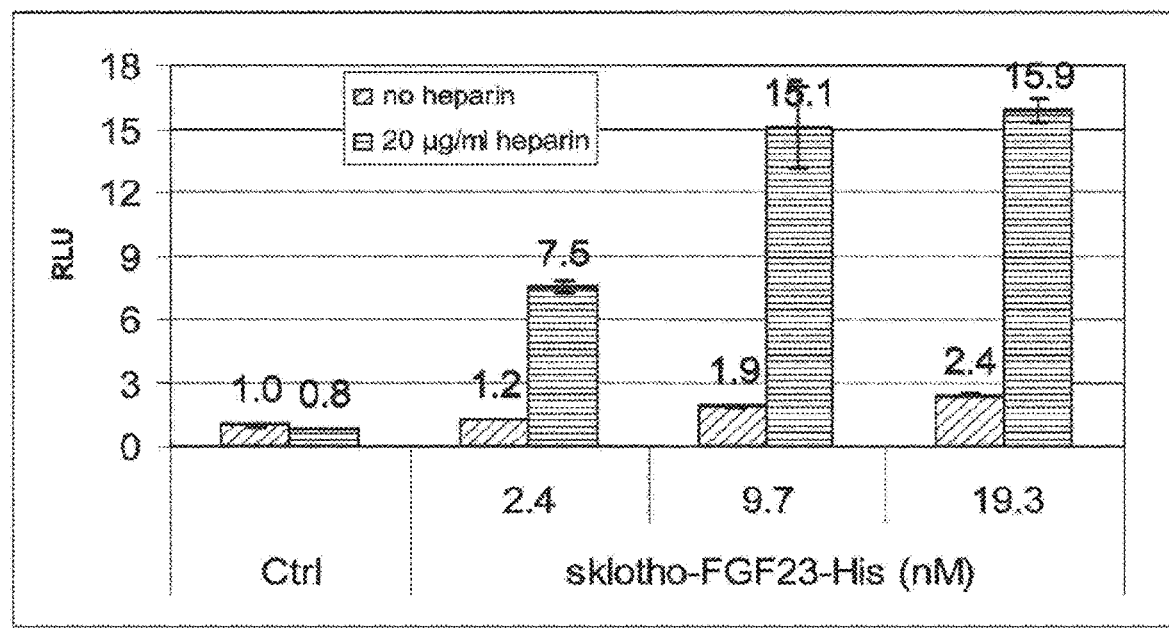
Figure 5A:
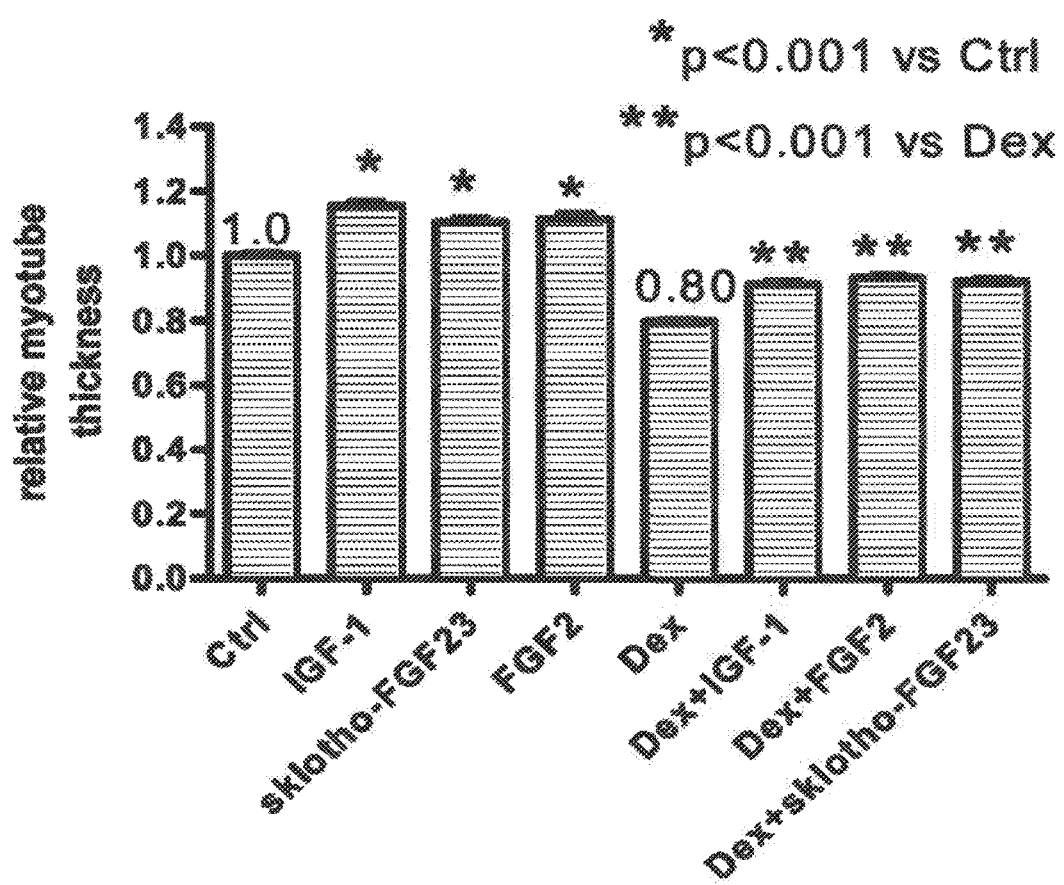
Figure 5B:
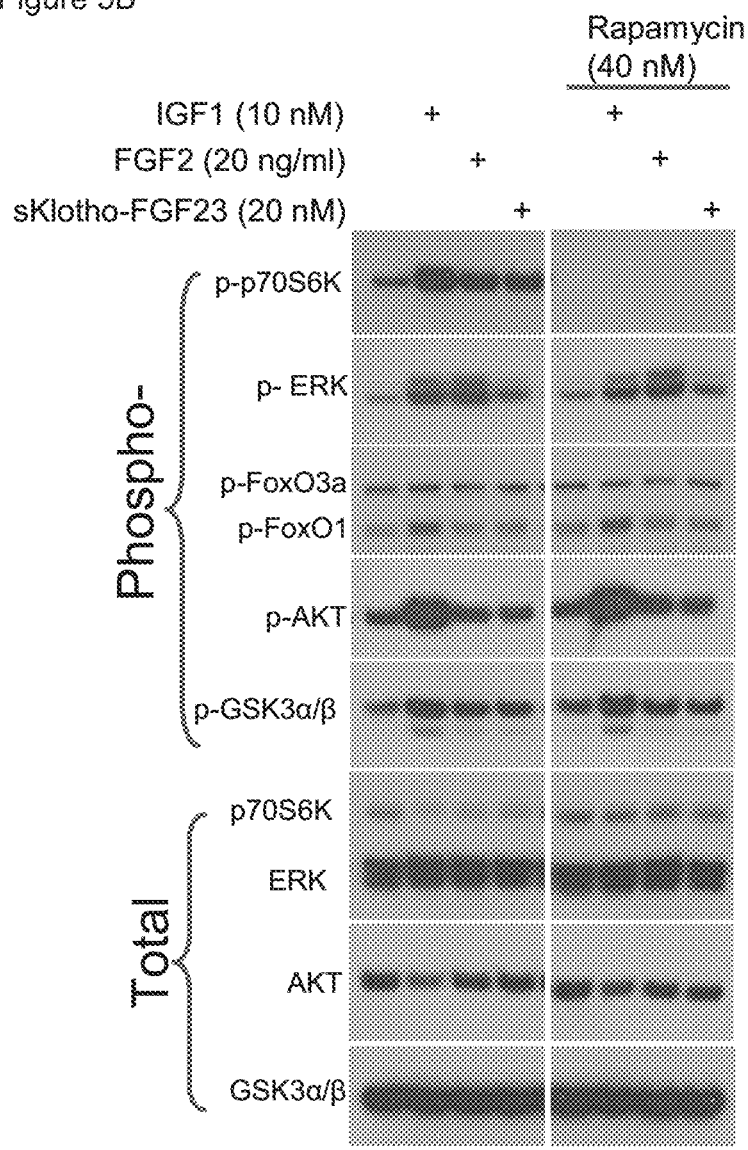

Example 2. In Vitro Assay Assessing the Activity of the Klotho Fusion Polypeptide Egr-1-Luciferase The biological activity of the expressed alpha Klotho fusion polypeptide was tested in Egr-1-luciferase reporter assays. Binding of the Klotho fusion polypeptide to the FGF23 receptor resulted in the downstream activation of Egr-1 and the expression of a luciferase reporter regulated by the Egr-1 promoter. The Egr-1-luciferase reporter gene was constructed based on that reported by Urakawa et al. (Nature, 2006, Vol 444, 770-774). HEK293T cells seeded in 48-well poly-D-lysine plate were transfected with the Egr-1-luciferase reporter gene together with a transfection normalization reporter gene (Renilla luciferase). Five hours after transfection of the Egr-1 luciferase reporter gene, the transfection mix was replaced with 3 ml DMEM plus 1% FBS. Conditioned media were collected 72 hours after the addition of 3 ml DMEM plus 1% FBS. Five hours later, the transfection mix was replaced with a sample to be tested for activity. In initial experiments, 50% conditioned medium (alone or containing Klotho, FGF23, Klotho and FGF23, and the Klotho-FGF23(R179Q) fusion protein) and 50% DMEM with 1% FBS in the presence or absence of 20 µg/ml heparin (Sigma, Cat #H8537; dissolved in DMEM as 2 mg/ml stock) were tested in the Egr-1-luciferase reporter assays (FIG. 3). Further experiments used defined quantities of the purified polypeptides (FIGS. 4A and 4B). Cells were lysed 20 hours later in passive lysis buffer (Promega, Cat #E194A) and luciferase activities were determined using Dual-Glo Luciferase Assay System (Promega, Cat #E2940).

In initial experiments, Klotho fusion polypeptide activity was demonstrated in unfractionated conditioned medium. Using the Egr-1-luciferase reporter gene (FIG. 3) these experiments quantified the fold changes in the expression of the luciferase reporter. Conditioned medium containing a combination of FGF23 and the extracellular domain of Klotho protein activated Egr-1-luciferase, but conditioned medium containing only FGF23 or conditioned medium containing only the extracellular domain of Klotho, did not activate Egr-1-luciferase. Conditioned medium containing the fusion protein sKlotho-FGF23(R179Q) activated the Egr-1-luciferase reporter gene in contrast to conditioned media containing either FGF23 or Klotho alone. In these experiments, conditioned medium containing the fusion protein sKlotho-FGF23(R179Q) activated the Egr-1-luciferase reporter gene significantly better than conditioned medium containing a combination of FGF23 and Klotho. In the presence of heparin, the inductions by conditioned medium containing the fusion protein sKlotho-FGF23 (R179Q) and the conditioned medium containing a combination of FGF23 and Klotho were significantly enhanced. Table 1 lists the relative expression of various FGF-Klotho fusion polypeptides in conditioned medium and the relative activity of the unfractionated conditioned medium corresponding to the various FGF-Klotho fusion polypeptides in Egr-1-luciferase reporter assays.

TABLE 1

Expression and Activities of sKlotho-FGF23 fusion variants

| | sKlotho-FGF23 fusion constructs | Expression | Activity in Egr-1-luc reporter gene |
|---|---|---|---|
| 1 | sKlotho-FGF23 | good | yes |
| 2 | IgG sp-sKlotho-FGF23 | good | yes |
| 3 | sKL-D1-FGF23 | good | no |
| 4 | sKL-D2-FGF23 | no | n.a. |
| 5 | s(KL-D1)2-FGF23 | good | no |
| 6 | sKL-D1/D2-FGF23 | no | n.a. |
| 7 | ssKlotho(ΔN-26)-FGF23 | poor | no* |
| 8 | sKLD1-D2(Δ692-965)-FGF23 | poor | no* |
| 9 | sKL-D1-D2(Δ507-798)-FGF23 | poor | no* |
| 10 | FGF23-sKlotho | poor | no* |

*lack of activity may be the result of low expression

Egr-1-luciferase reporter assays were also performed using defined quantities of proteins purified from the conditioned medium, using the purification procedure as described in Example 1. Consistent with previous results using unfractionated conditioned medium containing the expressed polypeptides, treatment with a combination of purified FGF23 and sKlotho resulted in luciferase reporter activity, but treatment with purified FGF23 alone did not (FIG. 4A). The luciferase reporter activity from the combination of purified FGF23 and sKlotho was further dependent on the dose of purified sKlotho, and the effect could be enhanced by the presence of heparin (20 µg/ml). An effect of the sKlotho-FGF23-6×His fusion polypeptide on luciferase activity could be detected at concentrations as low as about 1.21 nM (1.2 fold change) and at least up to about 19.3 nM (2.4 fold change) in Egr-1-luciferase reporter assays (FIG. 4B). The activity of the sKlotho-FGF23-6×His fusion polypeptide on luciferase activity was significantly enhanced in the presence of heparin (20 µg/ml). In the presence of heparin, the effect of the sKlotho-FGF23-6×His fusion polypeptide on luciferase activity could be detected at a concentration as low as about 0.6 nM (2.0 fold change). The result showed that purified sKlotho-FGF23-6×His dose-dependently induced the EGR-1-luc reporter gene, and that treatment with sKlotho-FGF23-6×His.

Example 3. In Vitro Assay Assessing the Effect of the Klotho Fusion Polypeptide on Muscle Cells The biological effect of the expressed Klotho fusion polypeptide was tested on C2C12 myoblasts. Treatment of C2C12 myoblasts with IGF-1, FGF2, or sKlotho-FGF23 resulted in myotube growth and phosphorylation of signaling proteins. C2C12 myoblasts were seeded at a density of 40,000 cells/well in 6-well poly-D-lysine and fibronectin coated plates in growth medium (3 parts DMEM and 1 part F12), 10% FBS, 1% Glut; 1% P/S; 1% Linolic acid; 0.1% ITS: [insulin (10 mg/ml), transferrin (5.5 mg/ml), and selenium (5 ng/ml)]. After myoblasts reached confluence (3 days), medium was changed into differentiation medium (DMED with 2% horse serum; 1% Glut; 1% P/S).

For the myotube diameter experiments, three days after confluent media was changed into differentiation medium, cells were treated with IGF-1 (10 nM), FGF2 (20 ng/ml) or sKlotho-FGF23 (20 nM) in the absence or presence of dexamethasone (100 µM) for 24 hours in differentiation medium. At the end of treatment, cells were fixed with glutaraldehyde (5% in PBS) and multiple fluorescent images were collected. Myotube diameter was measured using the Pipeline Pilot program to determine hypertrophy or atrophy.

For the signaling protein phosphorylation, experiments, three days after confluent media was changed into differentiation medium, cells were starved for four hours with DMEM without FBS and then treated with IGF-1 (10 nM), FGF2 (20 ng/ml) or sKlotho-FGF23 (20 nM) in the absence or presence of Rapamycin (40 nM) for 30 min. Cells were lysed in RIPA buffer in the presence of protease and phosphatase inhibitors. Western blot analysis was carried out and membranes were probed with different antibodies as indicated in the figure and developed on X-ray films, which were scanned.

The results of this study showed that sKlotho-FGF23 resulted in an increase in myotube diameter compared to the control and induced C2C12 myotube hypertrophy similar to results for IGF-1 and FGF2 (FIG. 4A). In addition, treatment with sKlotho-FGF23, IGF-1, and FGF2 could partially reverse myotube atrophy induced by dexamethasone, based on measurements of myotube diameter. No difference was observed between sKlotho-FGF23 and FGF2 on myotube morphology (measured by thickness of the myotubes) in the absence or presence of dexamethasone. The trophic effects of sKlotho-FGF23, IGF-1, and FGF2 were statistically significant.

Consistent with the effects on C2C12 myotubes, sKlotho-FGF23 fusion protein signaling led to the phosphorylation of p70S6K and ERK, but not AKT or FoxO, in C2C12 myotubes (FIG. 4B). The effect of sKlotho-FGF23 on signaling was similar to that of FGF2, but was distinct from that of IGF-1. The extent of ERK phosphorylation by sKlotho-FGF23 was observed to be less than that of IGF-1 or FGF2. The phosphorylation of p70S6K by sKlotho-FGF23 was rapamycin sensitive. In the experiments involving C2C12 cells, heparin was not required to activate signaling. These results show that a sKlotho-FGF23 fusion polypeptide activated signaling in C2C12 myotubes.

Example 4. Fusion Polypeptides Comprising sKlotho, FGF23 and FcLALA

Various fusion polypeptides are constructed using sKlotho, FGF23, and a modified Fc fragment of an antibody. These modified Fc molecules have altered (decreased) binding to FcRn and thus increased serum half-life. They also have modified bioavailability and altered transport to mucosal surfaces and other targets in the body. In this example, the FGF23 and sKlotho are fused to FcLALA, which is described in U.S. Pat. No. 7,217,798 and Hessell et al. 2007 Nature 449:101-104, Intervening between the various components of these fusion polypeptides are linkers, as described in Lode et al. 1998 Proc. Natl. Acad. Sci. USA 95: 2475-2480. These fusions are inserted into constructs, e.g., pcDNA3.1 (Invitrogen, Carlsbad, Calif.), and expressed in HEK293 cells.

A. sKlotho-FGF23-FcLALA v1

A fusion is constructed which comprises: sKlotho, a linker, FGF23, another linker, and FcLALA. This embodiment, designated sKlotho-FGF23-FcLALA v1, is presented in SEQ ID NOs: 46 and 47, below.

The nucleotide sequence of sKlotho-FGF23-FcLALA v1 (wherein initiation ATG as 1) is presented as SEQ ID NO: 46.

The amino acid sequence of sKlotho-FGF23-FcLALA v1 is presented below as SEQ ID NO: 47.

In this sequence, the various components of the fusion are as follows:

sKlotho: 1-982; Linker1: 983-1001; FGF23: 1002-1228; Linker 2; 1229-1233; FcLALA: 1234-1459.

B. sKlotho-FGF23-FcLALA v2

A fusion is constructed which comprises: sKlotho, a linker, FGF23, another linker, and FcLALA. This embodiment is designated sKlotho-FGF23-FcLALA v2 and presented as SEQ ID NOs: 48 and 49, below.

The nucleotide sequence of sKlotho-FGF23-FcLALA v2 (wherein initiation ATG as 1) is presented as SEQ ID NO: 48.

The amino acid sequence of sKlotho-FGF23-FcLALA v2 is presented below as SEQ ID NO: 49.

In this sequence, the various components of the fusion are as follows:

sKlotho: (aa or amino acids) 1-982; Linker 1: 983-1001; FGF23: 1002-1228; Linker 2; 1229-1233; FcLALA: 1234-1450.

Other fusion polypeptides can be constructed by combining in various combinations the FGF, Klotho, modified Fc fragments, and (optionally) linker sequences, and variants and derivatives thereof, as described herein or known in the art.

Example 5. Fusion Polypeptides Comprising FGF23 and FcLALA

Various fusion polypeptides are constructed using FGF23, and a modified Fc fragment of an antibody, as described in U.S. Pat. No. 7,217,798. These modified Fc molecules have altered (decreased) binding to FcRn and thus increased serum half-life. They also have modified bioavailability and altered transport to mucosal surfaces and other targets in the body. In this example, FGF23 is fused to FcLALA, Intervening between the various components of these fusion polypeptides are linkers, as described in Lode et al. 1998 Proc. Natl. Acad. Sci. USA 95: 2475-2480. These fusions are inserted constructs, e.g., pcDNA3.1 (Invitrogen, Carlsbad, Calif.), and expressed in HEK293 cells.

C. FGF23-FcLALA v1

A fusion is constructed which comprises: FGF23, a linker, and FcLALA. This construct is designated FGF23-FcLALA v1 and presented below as SEQ ID NOs: 50 and 51.

The nucleotide sequence of FGF23-FcLALA v1 (wherein initiation ATG as 1) is presented below as SEQ ID NO: 50.

The amino acid sequence of FGF23(R179Q)-FcLALAv1 is presented below as SEQ ID NO: 51.

In this sequence, the various components of the fusion are as follows:

FGF23: (aa) 1-251; Linker: 252-256; FcLALA: 257-482.

D. FGF23-FcLALA v2

A fusion is constructed which comprises: FGF23-FcLALA v2, which comprises FGF23 and FcLALA.

The nucleotide sequence of FGF23-FcLALA v2 (wherein initiation ATG as 1) is presented below as SEQ ID NO: 52.

The amino acid sequence of FGF23(R179Q)-FcLALAv2 is presented below as SEQ ID NO: 53.

In this sequence, the various components of the fusion are as follows:

FGF23: 1-251; Linker: 252-256; FcLALA: 257-473.

Other fusion polypeptides can be constructed by combining in various combinations the FGF sequences, modified Fc fragments, and (optionally) linkers, and variants and derivatives thereof, as described herein or known in the art.

E. Activation of Egr-1-luc reporter gene by sKlotho-FGF23(R179Q)-FcLALA fusion proteins; activation of Egr-1-luc reporter gene by FGF23(R179Q)-FcLALA proteins; and pharmacokinetic profile of FGF23(R179Q) vs FGF23 (R179Q)-FcLaLav2 are determined.

Figure 6:
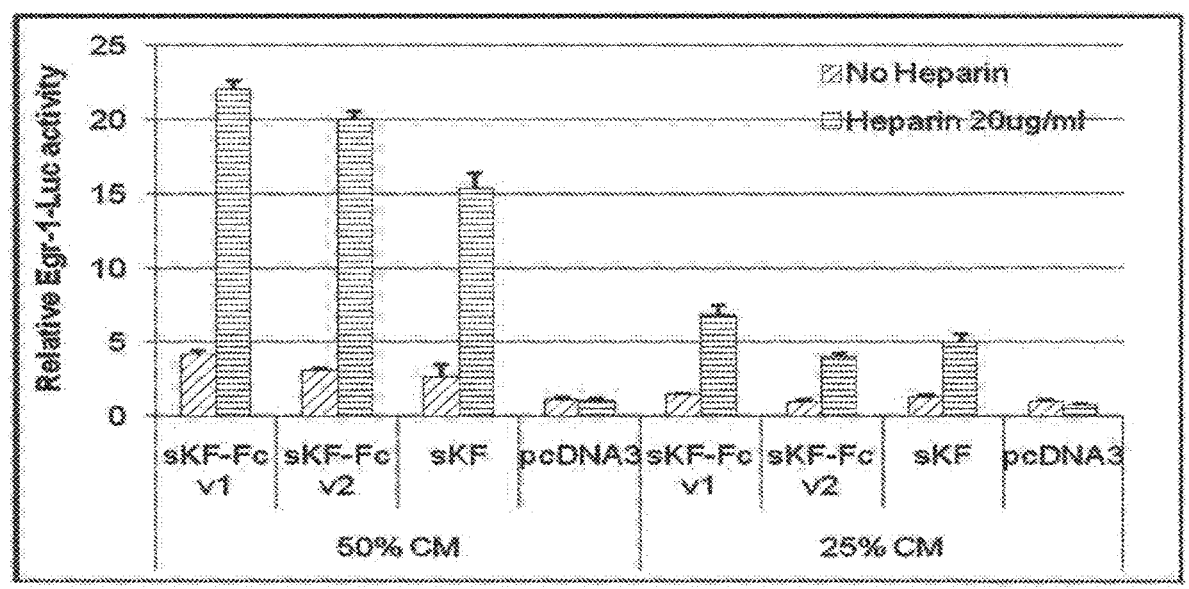
FIG. 6 shows activation of EGR-1-luc reporter gene by sKlotho-FGF23(R179Q)-FcLALA fusion proteins.

FIG. 6 shows the activation of Egr-1-luc reporter gene by sKlotho-FGF23(R179Q)-FcLALA fusion proteins. HEK293T cells are transiently transfected with the Egr-1-luc reporter gene and incubated with the indicated conditioned media in the absence or presence of 20 µg/ml heparin. Luciferase activities are then determined 18 hours later. The result shows that sklotho-FGF23-FcLALA fusion proteins induces the reporter gene activity. These inductions are significantly enhanced in the presence of heparin. sKF-Fcv1: sKlotho-FGF23-FcLALAv1; sKF-Fcv2: sKlotho-FGF23-FcLALAv2

Figure 7:
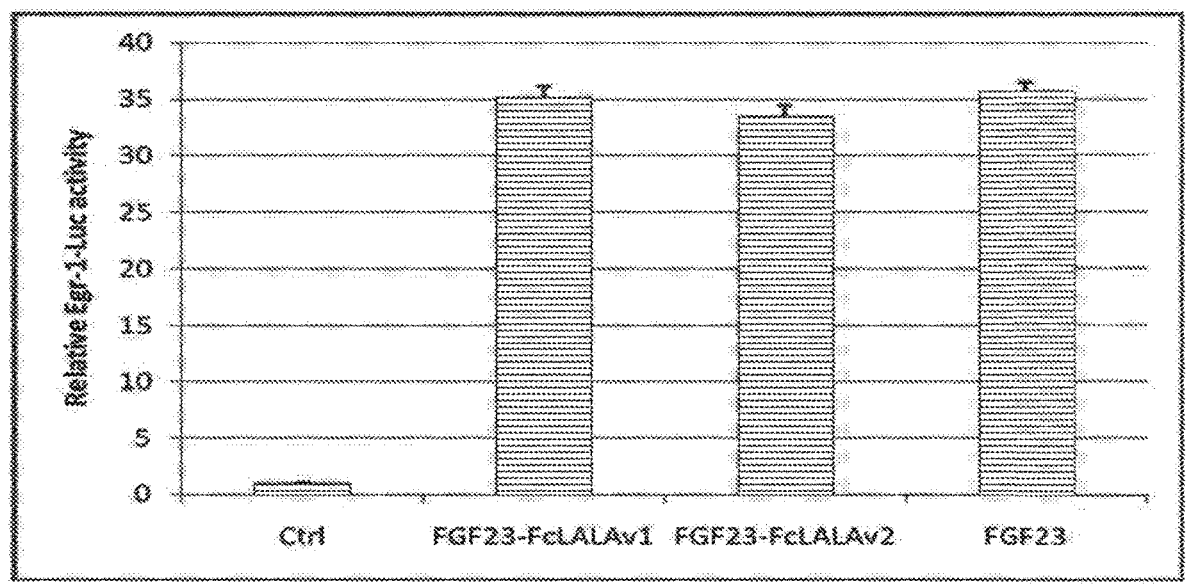
FIG. 7 shows the activation of EGR-1-luc reporter gene by FGF23(R179Q)-FcLALA proteins.

FIG. 7 shows the activation of Egr-1-luc reporter gene by FGF23(R179Q)-FcLALA proteins. HEK293T cells are transiently transfected with the Egr-1-luc reporter gene together with the full-length transmembrane form of Klotho and incubated with the indicated 30% conditioned media. Luciferase activities are then determined 18 hours later. The results show that FGF23-FcLALA fusion proteins induce the reporter gene activity in a similar manner as the FGF23.

Figure 8:
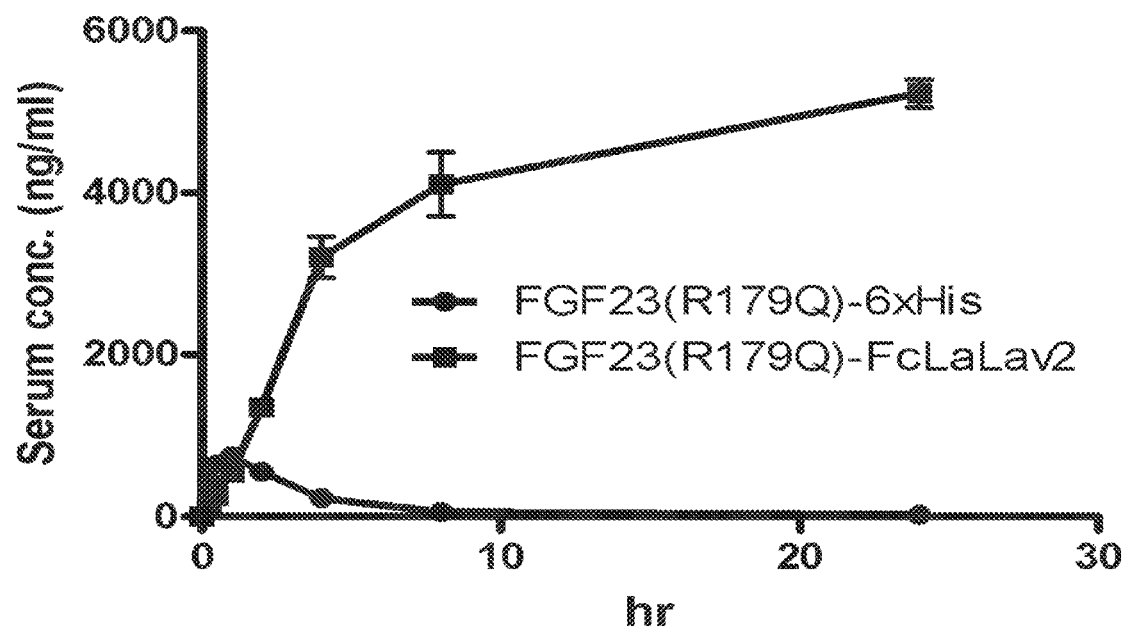
FIG. 8 shows the pharmacokinetic profile of FGF23 (R179Q) vs FGF23(R179Q)-FcLALAv2.

FIG. 8 shows the pharmacokinetic profile of FGF23 (R179Q) vs FGF23(R179Q)-FcLALAv2. Four mice per group are injected subcutaneously with FGF23(R179Q)-6× His or FGF23(R179Q)-FcLALAv2 at 2 mg/kg. At the indicated times, serum samples are collected and analyzed for FGF23 by ELISA. FGF23(R179Q)-FcLALA concentration in serum remains elevated at the 24 hr time point, while FGF23(R179Q)-6×His is back to basal level. This results indicate that with the addition of FcLALA, the in vivo half-life of FGF23(R179Q) is significantly improved.

Example 6. In Vivo Efficacy of sKlotho-FGF23 Fusion in Enhancing Muscle Growth after Dexamethasone-Induced Muscle Atrophy Experimental data shows that intramuscular injection of sKlotho-FGF23 significantly enhanced growth of muscle mass after dexamethasone-induced muscle atrophy. In this experiment, the peptide corresponding to that of SEQ ID NO: 41 is used.

Figure 9:
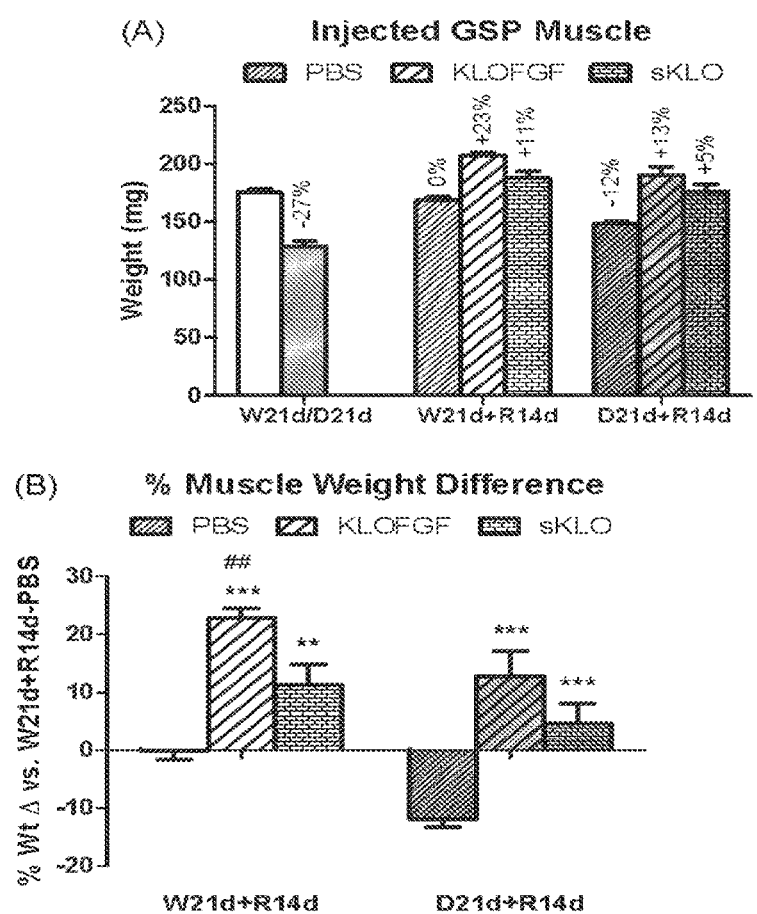
FIGS. 9A and 9B show the in vivo efficacy of sKlotho-FGF23 fusion in enhancing muscle growth after dexamethasone-induced muscle atrophy.

FIG. 9 shows absolute weights (A) and percent weight change (B) of the gastrocnemius-soleus-plantaris (GSP) muscles showing that intramuscular injection of sKlotho-FGF23 (KLOFGF) significantly enhanced regrowth of muscle mass after dexamethasone (DEX)-induced muscle atrophy compared with intramuscular injection of sKlotho (sKLO) or phosphate buffered saline (PBS).

Eighty male C57BL/6 mice, aged 15 weeks, are randomized by body weight into 8 groups each of 10 mice. Four groups receive water without DEX (W21d) while the other four receive DEX in drinking water at 2.4 mg/kg/day for three weeks (D21d). After the three weeks, DEX treatment is stopped and one W21d and one D21d group is immediately sacrificed to establish the degree of muscle atrophy induced by the DEX treatment. The remaining three groups of W21d or D21d mice are allowed to recover for another 14 days (R14d) during which period they receive an intramuscular injection of 2×50 µl of PBS, sKlotho-FGF23 (KLOFGF; 1.6 mg/ml), or sKlotho (sKLO; 1.6 mg/ml), respectively, every other day into the right gastrocnemius-soleus-plantaris muscle complex. The mice are sacrificed 24 h after the last intramuscular injection and the muscle weights determined and expressed as absolute weight (A) or percent change compared to the W21d+PBS group.

These data show the in vivo efficacy of sKlotho-FGF23 fusion in enhancing muscle growth after dexamethasone-induced muscle atrophy.

Example 7. Additional Mutations in the FGF23 Portion of Fusion Proteins which Reduce Aggregation, Reduce Undesired Protease-Induced Cleavage, and Increase Production Several mutations are investigated within the FGF23 portion of sKlotho-FGF23 and FGF23-FcLaLa fusion polypeptides. These include Q156, C206 and C244 (wherein the number is based on the FGF23 amino acid sequence). Example individual mutations include Q156A, C206S and C244S, and mutations at any of these sites can be combined with a mutation at R179 (e.g., R179Q). Example sequences are provided in SEQ ID NO: 54 to 68.

C206 and C244 are suspected to be involved in dimerization; and Q156 is a site identified by the inventors as a protease sensitive site. Mutating these amino acids to any other amino acid enhances the qualities of the proteins, by reducing aggregation, reducing undesired protease-induced cleavage, and increasing protein production from cells, without interfering with FGF23 activity. This is an unexpected result, as these three positions are conserved in the FGF23 proteins found in human, rhesus, bovine, mouse and rat. This conservation is shown below in the comparison between SEQ ID NOs: 69, 70, 71, 72 and 73, with the Q156, C206 and C244 in bold, underlined font.

```
hFGF23  MLGARLRLWVCALCSVCSMSVLRAYPNASPLLGSSWGGLIHLYTATARNSYHLQIHKNGH rhesus  MLGARLRLWVCALCSVCSMSVIRAYPNASPLLGSSWGGLIHLYTATARNSYHLQIHKNGH bovine  MLGARLGLWVCTLSCV-----VQAYPNSSPLLGSSWGGLTHLYTATARNSYHLQIHGDGH mouse   MLGTCLRLLVGVLCTVCSLGTARAYPDTSPLLGSNWGSLTHLYTATARTSYHLQIHRDGH rat     MLGACLRLLVGALCTVCSLGTARAYSDTSPLLGSNWGSLTHLYTATARNSYHLQIHRDGH hFGF23  VDGAPHQTIYSALMIRSEDAGFVVITGVMSRRYLCMDFRGNIFGSHYFDPENCRFQHQTL rhesus  VDGAPHQTIYSALMIRSEDAGFVVITGVMSRRYLCMDFRGNIFGSHYFNPENCRFRHWTL bovine  VDGSPQQTVYSALMIRSEDAGFVVITGVMSRRYLCMDFTGNIFGSHHFSPESCRFRQRTL mouse   VDGTPHQTIYSALMITSEDAGSVVITGAMTRRFLCMDLHGNIFGSLHFSPENCKFRQWTL rat     VDGTPHQTIYSALMITSEDAGSVVIIGAMTRRFLCMDLRGNIFGSYHFSPENCRFRQWTL hFGF23  ENGYDVYHSPQYHFLVSLGRAKRAFLPGMNPPPYSQFLSRRNEIPLIHFNTPI-PRRHTR rhesus  ENGYDVYHSPQHHFLVSLGRAKRAFLPGMNPPPYSQFLSRRNEIPLIHFNTPR-PRRHTR bovine  ENGYDVYHSPQHRFLVSLGRAKRAFLPGTNPPPYAQFLSRRNEIPLPHFAATARPRRHTR mouse   ENGYDVYLSQKHRYLVSLGRAKRIFQPGTNPPPFSQFLARRNEVPLLHFYTVR-PRRHTR rat     ENGYDVYLSPKHHYLVSLGRSKRIFQPGTNPPPFSQFLARENEVPLLHFYTAR-PRRHTR hFGF23  SAEDDSERDPLNVLKPRARMIPAPASCSQELPSAEDNSPMASDPLGVVRGGRVNTHAGGT rhesus  SAEDDSERDPLNVLKPRARMTPAPASCSQELPSAEDNSPVASDPLGVVRGGRVNTHAGGT bovine  SAHDSG--DPLSVLKPRARATPVPAACSQELPSAEDSGPAASDPLGVLRGHRLDVRAGSA mouse   SAEDPPERDPLNVLKPRPRATPVPVSCSRELPSAEEGGPAASDPLGVLRRGRGDARGGAG rat     SAEDPPERDPLNVLKPRPRATPIPVSCSRELPSAEEGGPAASDPLGVLRRGRGDARRGAG hFGF23  GPEGCRPFAKFI (SEQ ID NO: 69)
```

```
rhesus  GPEACRPFPKFI   (SEQ ID NO: 70)

bovine  GAERCRPFPGFA   (SEQ ID NO: 71)

mouse   GADRCRPFPRFV   (SEQ ID NO: 72)

rat     GTDRCRPFPRFV   (SEQ ID NO: 73)
```

The fact that these three mutations do not prevent FGF23 activity is shown in FIG. 10. This figure shows activation of Egr-1-luc reporter gene by FGF23(R179Q)-FcLALA and Q156A, C206S, C244S and C206S/C244S mutants.

HEK293T cells are transiently transfected with the EGR-1-luc reporter gene together with the full-length transmembrane form of Klotho and indicated FGF23-FcLaLa mutants. Luciferase activities are then determined 18 hours later. The results show that C206S, C244S, C206S/C244S (three independent clones) and Q156A (three independent clones) mutants are equally effective as FGF23-FcLALA fusion proteins in activating EGR-1-Luc reporter gene activity.

Data showing that mutating C244 and C206 alter dimerization and aggregation of FGF23 is shown in FIG. 11. This figure shows protein qualities of WT, Q156A, C206S, C244S and C206S/C244S mutants of FGF23(R179Q)-FcLaLa. Conditioned medium from HEK293T cells transient transfected with the indicated FGF23-FcLaLa expression vectors are analyzed by Western blot using an FGF23 antibody. The result shows that C206S/C244S mutation prevents protein dimerization and Q156A mutation has reduced proteolytic fragments.

Thus, surprisingly, even though these Q156, C206 and C244 residues are conserved across species, they can mutated without reducing FGF23 activity and can enhance the qualities of the protein by reducing aggregation and cleavage and by improving production.

Example 8. Additional Mutations in the FGF23 Portion of Fusion Proteins which Produce More Protein but Less Degradation Product, and Allow FGF23 Activity Several additional mutations are investigated within the FGF23 portion of FGF23-FcLaLa fusion polypeptides. These include Y154 and S155 (wherein the number is based on the FGF23 amino acid sequence). Example individual mutations include Y154D, Y154H, S155A, S155T, C206S, and C244S, and mutations at any of these sites can be combined with a mutation at R179 (e.g., R179Q). Example sequences are provided in SEQ ID NO: 69 to 76.

FIG. 12 shows the protein qualities of WT (R179Q), Y154D/C206S/C244S, Y154H/C206S/C244S, Y154N/C206S/C244S, S155A/C206S/C244S, S155T/C206S/C244S, of FGF23(R179Q)-FcLaLa. Conditioned medium from HEK293 cells transient transfected with the indicated FGF23-FcLaLa expression vectors and for the indicated times were analyzed by Western blot using an FGF23 antibody. The result showed that the FGF23 R179Q/Y154D/C206S/C244S mutant produced more protein but much less degradation product. All the FGF23 variants used in this experiment (including "WT") have the R179Q mutation.

Thus, the mutation at Y154 produced much less degradation product than the mutation at S155, when FGF23 with mutations at R179/Y154/C206/C244 was compared with FGF23 with mutations at R179/S155/C206/C244. Also, in this context, the mutation of Y154D produced much less degradation product than the mutation of Y154H or Y154N.

FIG. 13 shows the activation of Egr-1-luc reporter gene by FGF23(R179Q)-FcLALA and FGF23(R179Q)-Y154D/C206S/C244S mutant. HEK293T cells were transiently transfected with the Egr-1-luc reporter gene together with the full-length transmembrane form of Klotho. Five hours after transfection, the respective purified proteins were added. Luciferase activities were then determined 18 hours later. The result showed that FGF23(R179Q)-Y154D/C206S/C244S mutant retains partial (~50%) activity. "WT" indicates FGF23 with R179Q mutation.

Example 9. Deletion of about 20 Amino Acids from the C-Terminus of sKlotho Decreases the Activity of sKlotho, but Increases the Activity of a sKlotho-FGF23 Fusion Polypeptide Various truncations from the C-terminal end of sKlotho were created. FIGS. 14A-14B show the construction of various constructs. FIG. 14A shows the strategy for constructing sKlotho variants having C-terminal deletions of about 20, about 40, about 60, about 80, about 100, about 120, about 140, about 160, about 180, about 200, about 220, about 240, about 260, about 280, about 300, about 320, about 340, about 360, about 380, about 400, about 420, about 440, about 460, about 480 amino acids. Primer P5 (SEQ ID NO: 83) was used as the 5' primer. Any of a series of 24 primers designated C-20, C-40, C-60 . . . C-480 (SEQ ID NOs: 84 to 107) were used to truncate about 20, about 40, about 60 . . . about 480 amino acids from the C-terminus. Of all the sKlotho truncations, only the one with a deletion of about 20 aa (sKlotho del c-20) was efficacious; a fusion of this sKlotho truncation and FGF23 was created, as shown in FIG. 14B. FIG. 14B shows the strategy for constructing the sKlotho (del c-20)-FGF23 fusion polypeptide. The P5 primer was used in combination with the C-20 primer in PCR (polymerase chain reaction) to prepare the fragment having the sKlotho truncation. This fragment was cleaved with restriction endonucleases and ligated into a vector encoding the FGF23 to construct sKlotho (del c-20)-FGF23 fusion polypeptide.

The activity of various truncations from the C-terminus of sKlotho were tested. The deletion of about 20 amino acids from the C-terminus decreased activity of sKlotho, but this construct retained some activity. FIG. 15 shows the Egr-1 activities of sKlotho mutants. Conditioned medium (CM) was collected from various Hek293 cells, each having a vector encoding a fusion of a sKlotho truncation and FGF23. Only CM from cells producing useful amounts of fusion were used. Fusions used: CM1: sKlotho truncation of about 20 amino acids (aa); CM7: sKlotho truncation of about 140 amino acids (aa); CM11: sKlotho truncation of about 220 amino acids (aa); CM12: sKlotho truncation of about 240 amino acids (aa); CM13: sKlotho truncation of about 260 amino acids (aa); CM23: sKlotho truncation of about 460 amino acids (aa). Positive controls: conditioned medium from cells producing a fusion of sKlotho and FGF23 [(+) CM]; purified fusion of sKlotho and FGF23 [(+) ctrl]. "unConc." indicates experiments wherein less protein was used. Negative control: (−) ctrl. RLU, relative luciferase units. This experiment showed that the deletion of about 20 amino acids from the C-terminus decreased activity of sKlotho.

Even though the deletion of about 20 amino acids from the C-terminus of sKlotho decreased sKlotho activity, this deletion increased activity of a sKlotho-FGF23 fusion polypeptide. FIG. 16 shows that deleting about 20 amino acids from the C-terminus of sKlotho increased activity of a sKlotho-FGF23 fusion polypeptide. FIG. 16A shows a Western blot of relative amounts of various fusions comprising a sKlotho or sKlotho delta C-20 and FGF23. Lane 1, sKlotho-FGF23 fusion. Lane 2, FGF23-sKlotho delta C-20 (del c-20) fusion. Lane 3, sKlotho delta C-20 (del c-20)-FGF23 fusion. Size markers are also indicated. A polyclonal antibody against Klotho was used. FIG. 16B shows the activity of these fusion polypeptides in the Egr-1-Luc assay.

FIG. 17 shows an experiment with purified protein, reiterating the finding that deleting about 20 amino acids from the C-terminus of sKlotho increased activity of a sKlotho-FGF23 fusion polypeptide. FIG. 17A shows a protein gel showing the purity of the sKlotho del c-20-FGF23 fusion (lanes 2 and 3). Lane 1, size markers. FIG. 17B shows a Egr-1 assay using purified sKlotho del c-20-FGF23 fusion (sKF-T) and sKlotho-FGF23 fusion (sKF). The EC50 of the proteins is also shown. In these figures and in the specification, the terms sKF-T, Klotho del c-20-FGF23, sKlotho del c-20-FGF23, klotho (delta C-20)-FGF23, Alpha sKlotho ΔC20-FGF23 and the like all indicate a fusion polypeptide comprising, in N-terminus to C-terminus order: alpha sKlotho with a truncation of about 20 amino acids from the C-terminus, a linker, and FGF23.

FIG. 18 shows that a fusion polypeptide comprising a sKlotho del (deletion) C-20 and mouse serum albumin has efficacy in an Egr-1 assay. The fusion polypeptide was expressed in HEK293 cells transfected with an expression plasmid encoding the fusion polypeptide.

It is noted that, while the sKlotho delta C-20 (del c-20)-FGF23 fusion used in the experiments illustrated in FIGS. 16 and 17 was predicted to have the amino acid sequence of SEQ ID NO: 80, amino acid sequencing of the fusion showed that it had the amino acid sequence of SEQ ID NO: 82, which has two mutations unintentionally introduced by the PCR step, namely, V563A and K795E. These two mutations are not present in the sKlotho delta C-20 (del c-20), which, other than the deletion, has the wild-type sKlotho sequence.

Unless defined otherwise, the technical and scientific terms used herein have the same meaning as that usually understood by a specialist familiar with the field to which the disclosure belongs.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein.

Claims to the invention are non-limiting and are provided below.

Although particular embodiments and claims have been disclosed herein in detail, this has been done by way of example for purposes of illustration only, and is not intended to be limiting with respect to the scope of the appended claims, or the scope of subject matter of claims of any corresponding future application. In particular, it is contemplated by the inventors that various substitutions, alterations, and modifications may be made to the disclosure without departing from the spirit and scope of the disclosure as defined by the claims. The choice of nucleic acid starting material or clone of interest is believed to be a matter of routine for a person of ordinary skill in the art with knowledge of the embodiments described herein. Other aspects, advantages, and modifications considered to be within the scope of the following claims. Redrafting of claim scope in later filed corresponding applications may be due to limitations by the patent laws of various countries and should not be interpreted as giving up subject matter of the claims.

```
SEQUENCE LISTING
Human Klotho nucleic acid sequence (NM_004795)
(SEQ ID NO: 1)
Protein coding region: 9-3047
    1 cgcgcagcat gcccgccagc gccccgccgc gccgccgcg gccgccgccg ccgtcgctgt 61 cgctgctgct ggtgctgctg ggcctgggcg gccgccgcct ggtgcggag ccgggcgacg 121 gcgcgcagac ctgggcccgt ttctcgcggc ctcctgcccc cgaggccgcg ggcctcttcc 181 agggcacctt ccccgacggc ttcctctggg ccgtgggcag cgccgcctac cagaccgagg 241 gcggctggca gcagcacggc aagggtgcgt ccatctggga tacgttcacc caccaccccc 301 tggcaccccc gggagactcc cggaacgcca gtctgccgtt gggcgccccg tcgccgctgc 361 agcccgccac cggggacgta gccagcgaca gctacaacaa cgtcttccgc gacacggagg 421 cgctgcgcga gctcggggtc actcactacc gcttctccat ctcgtgggcg cgagtgctcc 481 ccaatggcag cgcgggcgtc cccaaccgcg aggggctgcg ctactaccgg cgcctgctgg 541 agcggctgcg ggagctgggc gtgcagcccg tggtcacccct gtaccactgg gacctgcccc 601 agcgcctgca ggacgcctac ggcggctggg ccaaccgcgc cctggccgac cacttcaggg 661 attacgcgga gctctgcttc cgccacttcg gcggtcaggt caagtactgg atcaccatcg 721 acaaccccta cgtggtggcc tggcacggct acgccaccgg cgcctggcc ccggcatcc 781 ggggcagccc gcggctcggg tacctggtgg cgcacaacct cctcctggct catgccaaag
```

-continued

```
 841 tctggcatct ctacaatact tctttccgtc ccactcaggg aggtcaggtg tccattgccc
 901 taagctctca ctggatcaat cctcgaagaa tgaccgacca cagcatcaaa gaatgtcaaa
 961 aatctctgga ctttgtacta ggttggtttg ccaaacccgt atttattgat ggtgactatc
1021 ccgagagcat gaagaataac ctttcatcta ttctgcctga ttttactgaa tctgagaaaa
1081 agttcatcaa aggaactgct gactttttg ctctttgctt tggacccacc ttgagttttc
1141 aacttttgga ccctcacatg aagttccgcc aattggaatc tcccaacctg aggcaactgc
1201 tttcctggat tgaccttgaa tttaaccatc ctcaaatatt tattgtggaa atggctggt
1261 ttgtctcagg gaccaccaag agagatgatg ccaaatatat gtattacctc aaaaagttca
1321 tcatggaaac cttaaaagcc atcaagctgg atggggtgga tgtcatcggg tataccgcat
1381 ggtccctcat ggatggtttc gagtggcaca gaggttacag catcaggcgt ggactcttct
1441 atgttgactt tctaagccag gacaagatgt tgttgccaaa gtcttcagcc ttgttctacc
1501 aaaagctgat agagaaaaat ggcttccctc ctttacctga aaatcagccc ctagaaggga
1561 catttccctg tgactttgct tggggagttg ttgacaacta cattcaagta gataccactc
1621 tgtctcagtt taccgacctg aatgtttacc tgtgggatgt ccaccacagt aaaaggctta
1681 ttaaagtgga tggggttgtg accaagaaga ggaaatccta ctgtgttgac tttgctgcca
1741 tccagcccca gatcgcttta ctccaggaaa tgcacgttac acatttttcgc ttctccctgg
1801 actgggccct gattctccct ctgggtaacc agtcccaggt gaaccacacc atcctgcagt
1861 actatcgctg catggccagc gagcttgtcc gtgtcaacat cacccagtg gtggccctgt
1921 ggcagcctat ggccccgaac caaggactgc cgcgcctcct ggccaggcag ggcgcctggg
1981 agaacccta cactgccctg gcctttgcag agtatgcccg actgtgcttt caagagctcg
2041 gccatcacgt caagctttgg ataacgatga atgagccgta tacaaggaat atgacataca
2101 gtgctggcca caaccttctg aaggcccatg ccctggcttg gcatgtgtac aatgaaaagt
2161 ttaggcatgc tcagaatggg aaaatatcca tagccttgca ggctgattgg atagaacctg
2221 cctgcccttt ctcccaaaag acaaagagg tggccgagag agttttggaa tttgacattg
2281 gctggctggc tgagcccatt ttcggctctg gagattatcc atgggtgatg agggactggc
2341 tgaaccaaag aaacaatttt cttcttcctt atttcactga agatgaaaaa aagctaatcc
2401 agggtacctt tgacttttg gctttaagcc attataccac catccttgta gactcagaaa
2461 aagaagatcc aataaaatac aatgattacc tagaagtgca agaaatgacc gacatcacgt
2521 ggctcaactc ccccagtcag gtggcggtag tgccctgggg gttgcgcaaa gtgctgaact
2581 ggctgaagtt caagtacgga gacctcccca tgtacataat atccaacgga atcgatgacg
2641 ggctgcatgc tgaggacgac cagctgaggg tgtattatat gcagaattac ataaacgaag
2701 ctctcaaagc ccacatactg gatggtatca atctttgcgg atactttgct tattcgttta
2761 acgaccgcac agctccgagg tttggcctct atcgttatgc tgcagatcag tttgagccca
2821 aggcatccat gaaacattac aggaaaatta ttgacagcaa tggtttcccg ggcccagaaa
2881 ctctggaaag attttgtcca gaagaattca ccgtgtgtac tgagtgcagt ttttttcaca
2941 cccgaaagtc tttactggct ttcatagctt ttctattttt tgcttctatt atttctctct
3001 cccttatatt ttactactcg aagaaaggca gaagaagtta caaatagttc tgaacatttt
3061 tctattcatt cattttgaaa taattatgca gacacatcag ctgttaacca tttgcacctc
3121 taagtgttgt gaaactgtaa atttcataca tttgacttct agaaaacatt tttgtggctt
3181 atgacagagg ttttgaaatg ggcataggtg atcgtaaaat attgaataat gcgaatagtg
```

-continued

```
3241 cctgaatttg ttctcttttt gggtgattaa aaaactgaca ggcactataa tttctgtaac
3301 acactaacaa agcatgaaa ataggaacc acaccaatgc aacatttgtg cagaaatttg
3361 aatgacaaga ttaggaatat tttcttctgc acccacttct aaatttaatg ttttttctgga
3421 agtagtaatt gcaagagttc gaatagaaag ttatgtacca agtaaccatt tctcagctgc
3481 cataataatg cctagtggct tcccctctgt caaatctagt ttcctatgga aagaagatg
3541 gcagatacag gagagacgac agagggtcct aggctggaat gttcctttcg aaagcaatgc
3601 ttctatcaaa tactagtatt aatttatgta tctggttaat gacatacttg gagagcaaat
3661 tatggaaatg tgtatttat atgatttttg aggtcctgtc taaaccctgt gtccctgagg
3721 gatctgtctc actggcatct tgttgaggc cttgcacata ggaaacttt gataagtatc
3781 tgcggaaaaa caaacatgaa tcctgtgata ttgggctctt caggaagcat aaagcaattg
3841 tgaaatacag tataccgcag tggctctagg tggaggaaag gaggaaaaag tgcttattat
3901 gtgcaacatt atgattaatc tgattataca ccattttga gcagatcttg aatgaatga
3961 catgaccttt ccctagagaa taaggatgaa ataatcactc attctatgaa cagtgacact
4021 actttctatt ctttagctgt actgtaattt ctttgagttg atagttttac aaaattcttaa
4081 taggttcaaa agcaatctgg tctgaataac actggatttg tttctgtgat ctctgaggtc
4141 tattttatgt ttttgctgct acttctgtgg aagtagcttt gaactagttt tactttgaac
4201 tttcacgctg aaacatgcta gtgatatcta gaaagggcta attaggtctc atcctttaat
4261 gccccttaaa taagtcttgc tgattttcag acagggaagt ctctctatta cactggagct
4321 gttttataga taagtcaata ttgtatcagg caagataaac caatgtcata acaggcattg
4381 ccaacctcac tgacacaggg tcatagtgta ataataata ctgtactata taatatatca
4441 tctttagagg tatgattttt tcatgaaaga taagcttttg gtaatattca ttttaaagtg
4501 gacttattaa aattggatgc tagagaatca gtttattt atgtatatat ttttctgatt
4561 ataagagtaa tatatgttca ttgtaaaaat ttttaaaaca cagaaactat atgcaaagaa
4621 aaaataaaaa ttatctataa tctcagaacc cagaaatagc cactattaac atttcctacg
4681 tattttattt tacatagatc atattgtata tagttagtat ctttattaat ttttattatg
4741 aaactttcct ttgtcattat tagtcttcaa aagcatgatt tttaatagtt gttgagtatt
4801 ccaccacagg aatgtatcac aacttaaccg ttcccgtttg ttagactagt ttcttattaa
4861 tgttgatgaa tgttgtttaa aaataatttt gttgctacat ttactttaat ttccttgact
4921 gtaaagagaa gtaattttgc tccttgataa agtattatat taataataaa tctgcctgca
4981 acttttgcc ttctttcata atc
```

Klotho amino acid sequence (NP_004786)
(SEQ ID NO: 2)

```
  1 MPASAPPRRP RPPPPSLSLL LVLLGLGGRR LRAEPGDGAQ TWARFSRPPA PEAAGLFQGT
 61 FPDGFLWAVG SAAYQTEGGW QQHGKGASIW DTFTHHPLAP PGDSRNASLP LGAPSPLQPA
121 TGDVASDSYN NVFRDTEALR ELGVTHYRFS ISWARVLPNG SAGVPNREGL RYYRRLLERL
181 RELGVQPVVT LYHWDLPQRL QDAYGGWANR ALADHFRDYA ELCFRHFGGQ VKYWITIDNP
241 YVVAWHGYAT GRLAPGIRGS PRLGYLVAHN LLLAHAKVWH LYNTSFRPTQ GGQVSIALSS
301 HWINPRRMTD HSIKECQKSL DFVLGWFAKP VFIDGDYPES MKNNLSSILP DFTESEKKFI
361 KGTADFFALC FGPTLSFQLL DPHMKFRQLE SPNLRQLLSW IDLEFNHPQI FIVENGWFVS
421 GTTKRDDAKY MYYLKKFIME TLKAIKLDGV DVIGYTAWSL MDGFEWHRGY SIRRGLFYVD
481 FLSQDKMLLP KSSALFYQKL IEKNGFPPLP ENQPLEGTFP CDFAWGVVDN YIQVDTTLSQ
541 FTDLNVYLWD VHHSKRLIKV DGVVTKKRKS YCVDFAAIQP QIALLQEMHV THFRFSLDWA
```

```
601 LILPLGNQSQ VNHTILQYYR CMASELVRVN ITPVVALWQP MAPNQGLPRL LARQGAWENP

661 YTALAFAEYA RLCFQELGHH VKLWITMNEP YTRNMTYSAG HNLLKAHALA WHVYNEKFRH

721 AQNGKISIAL QADWIEPACP FSQKDKEVAE RVLEFDIGWL AEPIFGSGDY PWVMRDWLNQ

781 RNNFLLPYFT EDEKKLIQGT FDFLALSHYT TILVDSEKED PIKYNDYLEV QEMTDITWLN

841 SPSQVAVVPW GLRKVLNWLK FKYGDLPMYI ISNGIDDGLH AEDDQLRVYY MQNYINEALK

901 AHILDGINLC GYFAYSFNDR TAPRFGLYRY AADQFEPKAS MKHYRKIIDS NGFPGPETLE

961 RFCPEEFTVC TECSFFHTRK SLLAFIAFLF FASIISLSLI FYYSKKGRRS YK
``` beta-Klotho nucleic acid sequence (NM_175737)
(SEQ ID NO: 3)
Protein coding region: 98-3232

```
   1 atcctcagtc tcccagttca agctaatcat tgacagagct ttacaatcac aagcttttac 61 tgaagctttg ataagacagt ccagcagttg gtggcaaatg aagccaggct gtgcggcagg 121 atctccaggg aatgaatgga ttttcttcag cactgatgaa ataaccacac gctataggaa 181 tacaatgtcc aacgggggat tgcaaagatc tgtcatcctg tcagcactta ttctgctacg 241 agctgttact ggattctctg gagatggaag agctatatgg tctaaaaatc ctaattttac 301 tccggtaaat gaaagtcagc tgtttctcta tgacactttc cctaaaaact ttttctgggg 361 tattgggact ggagcattgc aagtggaagg gagttggaag aaggatggaa aaggaccttc 421 tatatgggat catttcatcc acacacacct taaaaatgtc agcagcacga atggttccag 481 tgacagttat attttctgg aaaaagactt atcagccctg gattttatag gagtttcttt 541 ttatcaattt tcaatttcct ggccaaggct ttccccgat ggaatagtaa cagttgccaa 601 cgcaaaaggt ctgcagtact acagtactct tctggacgct ctagtgctta gaaacattga 661 acctatagtc actttatacc actgggattt gcctttggca ctacaagaaa atatgggggg 721 gtggaaaaat gataccataa tagatatctt caatgactat gccacatact gtttccagat 781 gtttgggac cgtgtcaaat attggattac aattcacaac ccatatctag tggcttggca 841 tgggtatggg acaggtatgc atgcccctgg agagaaggga aatttagcag ctgtctacac 901 tgtgggacac aacttgatca aggctcactc gaaagtttgg cataactaca acacacattt 961 ccgcccacat cagaagggtt ggttatcgat cacgttggga tctcattgga tcgagccaaa 1021 ccggtcggaa aacacgatgg atatattcaa atgtcaacaa tccatggttt ctgtgcttgg 1081 atggtttgcc aaccctatcc atggggatgg cgactatcca gagggatga gaaagaagtt 1141 gttctccgtt ctacccattt tctctgaagc agagaagcat gagatgagag cacagctga 1201 tttctttgcc ttttctttg gacccaacaa cttcaagccc ctaaacacca tggctaaaat 1261 gggacaaaat gtttcactta atttaagaga gcgctgaac tggattaaac tggaatacaa 1321 caaccctcga atcttgattg ctgagaatgg ctggttcaca gacagtcgtg tgaaaacaga 1381 agacaccacg gccatctaca tgatgaagaa tttcctcagc caggtgcttc aagcaataag 1441 gttagatgaa atacgagtgt ttggttatac tgcctggtct ctcctggatg gctttgaatg 1501 gcaggatgct tacaccatcc gccgaggatt attttatgtg gattttaaca gtaaacagaa 1561 agagcggaaa cctaagtctt cagcacacta ctacaaacag atcatacgag aaaatggttt 1621 ttctttaaaa gagtccacgc cagatgtgca gggccagttt ccctgtgact tctcctgggg 1681 tgtcactgaa tctgttctta agcccgagtc tgtggcttcg tccccacagt tcagcgatcc 1741 tcatctgtac gtgtggaacg ccactggcaa cagactgttg caccgagtgg aagggggtgag 1801 gctgaaaaca cgacccgctc aatgcacaga ttttgtaaac atcaaaaac aacttgagat 1861 gttggcaaga atgaaagtca cccactaccg gtttgctctg gattgggcct cggtccttcc
```

-continued

```
1921 cactggcaac ctgtccgcgg tgaaccgaca ggccctgagg tactacaggt gcgtggtcag 1981 tgaggggctg aagcttggca tctccgcgat ggtcaccctg tattatccga cccacgccca 2041 cctaggcctc cccgagcctc tgttgcatgc cgacgggtgg ctgaacccat cgacggccga 2101 ggccttccag gcctacgctg gctgtgctt ccaggagctg ggggacctgg tgaagctctg 2161 gatcaccatc aacgagccta accggctaag tgacatctac aaccgctctg caacgacac 2221 ctacggggcg gcgcacaacc tgctggtggc ccacgccctg gctggcgcc tctacgaccg 2281 gcagttcagg ccctcacagc gcggggccgt gtcgctgtcg ctgcacgcgg actgggcgga 2341 acccgccaac ccctatgctg actcgcactg gagggcggcc gagcgcttcc tgcagttcga 2401 gatcgcctgg ttcgccgagc cgctcttcaa gaccggggac taccccgcgg ccatgaggga 2461 atacattgcc tccaagcacc gacggggct tccagctcg ccctgccgc gcctcaccga 2521 ggccgaaagg aggctgctca agggcacggt cgacttctgc gcgctcaacc acttcaccac 2581 taggttcgtg atgcacgagc agctggccgg cagccgctac gactcggaca gggacatcca 2641 gtttctgcag gacatcaccc gcctgagctc ccccacgcgc ctggctgtga ttccctgggg 2701 ggtgcgcaag ctgctgcggt gggtccggag gaactacggc gacatggaca tttacatcac 2761 cgccagtggc atcgacgacc aggctctgga ggatgaccgg ctccggaagt actacctagg 2821 gaagtacctt caggaggtgc tgaaagcata cctgattgat aaagtcagaa tcaaaggcta 2881 ttatgcattc aaactggctg aagagaaatc taaacccaga tttggattct tcacatctga 2941 ttttaaagct aaatcctcaa tacaatttta caacaaagtg atcagcagca ggggcttccc 3001 ttttgagaac agtagttcta gatgcagtca gacccaagaa aatacagagt gcactgtctg 3061 cttattcctt gtgcagaaga accactgat attcctgggt tgttgcttct tctccaccct 3121 ggttctactc ttatcaattg ccattttttca aaggcagaag agaagaaagt tttggaaagc 3181 aaaaaactta caacacatac cattaaagaa aggcaagaga gttgttagct aaactgatct 3241 gtctgcatga tagacagttt aaaaattcat cccagttcc
``` beta-Klotho amino acid sequence (NP_783864)
(SEQ ID NO: 4)

```
  1 mkpgcaagsp gnewiffstd eittryrntm snqqlqrsvi lsalillrav tgfsqdgrai 61 wsknpnftpv nesqlflydt fpknffwgig tgalqvegsw kkdgkgpsiw dhfihthlkn 121 vsstngssds yiflekdlsa ldfigvsfyq fsiswprlfp dgivtvanak glqyystlld 181 alvlrniepi vtlyhwdlpl alqekyggwk ndtiidifnd yatycfqmfg drvkywitih 241 npylvawhgy gtgmhapgek gnlaavytvg hnlikahskv whnynthfrp hqkgwlsitl 301 gshwiepnrs entmdifkcq qsmvsvlgwf anpihgdgdy pegmrkklfs vlpifseaek 361 hemrgtadff afsfgpnnfk plntmakmgq nvslnlreal nwikleynnp riliaengwf 421 tdsrvktedt taiymmknfl sqvlqairld eirvfgytaw slldgfewqd aytirrglfy 481 vdfnskqker kpkssahyyk qiirengfsl kestpdvqgq fpcdfswgvt esvlkpesva 541 sspqfsdphl yvwnatgnrl lhrvegvrlk trpaqctdfv nikkqlemla rmkvthyrfa 601 ldwasvlptg nlsavnrqal ryyrcvvseg lklgisamvt lyypthahlg lpepllhadg 661 wlnpstaeaf qayaglcfqe lgdlvklwit inepnrlsdi ynrsgndtyg aahnllvaha 721 lawrlydrqf rpsqrgaysl slhadwaepa npyadshwra aerflqfeia wfaeplfktg 781 dypaamreyi askhrrglss salprlteae rrllkgtvdf calnhfttrf vmheqlagsr 841 ydsdrdiqfl qditrlsspt rlavipwgvr kllrwvrrny gdmdlyitas giddqaledd 901 rlrkyylgky lqevlkayli dkvrikgyya fklaeekskp rfgfftsdfk akssiqfynk
```

```
 961 vissrgfpfe nsssrcsqtq entectvclf lvqkkplifl gccffstlvl llsialfqrq 1021 krrkfwkakn lqhiplkkgk rvvs
```

Human Klotho domain 1 (KL-D1) amino acid sequence
(SEQ ID NO: 5)
```
  58                                                           qgt 61 fpdgflwavg saayqteggw qqhgkgasiw dtfthhplap pgdsrnaslp lgapsplqpa 121 tgdvasdsyn nvfrdtealr elgvthyrfs iswarvlpng sagvpnregl ryyrrllerl 181 relgvqpvvt lyhwdlpqrl qdayggwanr aladhfrdya elcfrhfggq vkywitidnp 241 yvvawhgyat grlapgirgs prlgylvahn lllahakvwh lyntsfrptq ggqvsialss 301 hwinprrmtd hsikecqksl dfvlgwfakp vfidgdypes mknnlssilp dftesekkfi 361 kgtadffalc fgptlsfqll dphmkfrqle spnlrqllsw idlefnhpqi fivengwfvs 421 gttkrddaky myylkkfime tlkaikldgv dvigytawsl mdgfewhrgy sirrglfyvd 481 flsqdkmllp kssalfyqkl lekngf
```

Human Klotho domain 2 (KL-D2) amino acid sequence
(SEQ ID NO: 6)
```
 517                                      gtfp cdfawgvvdn yiqvdttlsq 541 ftdlnvylwd vhhskrlikv dgvvtkkrks ycvdfaalqp qiallqemhv thfrfsldwa 601 lilplgnqsq vnhtilqyyr cmaselvrvn itpvvalwqp mapnqglprl larqgawenp 661 ytalafaeya rlcfqelghh vklwitmnep ytrnmtysag hnllkahala whvynekfrh 721 aqngkisial qadwiepacp fsqkdkevae rvlefdigwl aeplfgsgdy pwvmrdwlnq 781 rnnfllpyft edekkliqgt fdflalshyt tilvdseked pikyndylev qemtditwln 841 spsqvavvpw glrkvinwlk fkygdlpmyi isngiddglh aeddqlrvyy mqnyinealk 901 ahildginlc gyfaysfndr taprfglyry aadqfepkas mkhyrkilds ngf
```

Klotho extracellular domain (without signal peptide) amino acid sequence
(SEQ ID NO: 7)
```
  28                                      epgdgaq twarfsrppa peaaglfqgt 61 fpdgflwavg saayqteggw qqhgkgasiw dtfthhplap pgdsrnaslp lgapsplqpa 121 tgdvasdsyn nvfrdtealr elgvthyrfs iswarvlpng sagvpnregl ryyrrllerl 181 relgvqpvvt lyhwdlpqrl qdayggwanr aladhfrdya elcfrhfggq vkywitidnp 241 yvvawhgyat grlapgirgs prlgylvahn lllahakvwh lyntsfrptq ggqvsialss 301 hwinprrmtd hsikecqksl dfvlgwfakp vfidgdypes mknnlssilp dftesekkfi 361 kgtadffalc fgptlsfqll dphmkfrqle spnlrqllsw idlefnhpqi fivengwfvs 421 gttkrddaky myylkkfime tlkalkldgv dvigytawsl mdgfewhrgy sirrglfyvd 481 flsqdkmllp kssalfyqkl iekngfpplp enqplegtfp cdfawgvvdn yiqvdttlsq 541 ftdlnvylwd vhhskrlikv dgvvtkkrks ycvdfaaiqp qiallqemhv thfrfsldwa 601 lilplgnqsq vnhtilqyyr cmaselvrvn itpvvalwqp mapnqglprl larqgawenp 661 ytalafaeya rlcfqelghh vklwitmnep ytrnmtysag hnllkahala whvynekfrh 721 aqngkisial qadwiepacp fsqkdkevae rvlefdigwl aepifgsgdy pwvmrdwlnq 781 rnnfllpyft edekkliqgt fdflalshyt tilvdseked pikyndylev qemtditwln 841 spsqvavvpw glrkvlnwlk fkygdlpmyi isngiddglh aeddqlrvyy mqnyinealk 901 ahildginlc gyfaysfndr taprfglyry aadqfepkas mkhyrkiids ngfpgpetle 961 rfcpeeftvc tecsffhtrk sl
```

```
Klotho signal peptide amino acid sequence
(SEQ ID NO: 8)
   1 mpasapprrp rppppslsll lvllglggrr lra IgG signal peptide amino acid sequence
(SEQ ID NO: 9)
   1 msvltqvlal lllwltgtrc rrlra (Gly4 Ser)3 polypeptide linker nucleic acid sequence
(SEQ ID NO: 10)
   1 ggaggtggag gttcaggagg tggaggttca ggaggtggag gttca (Gly4 Ser)3 polypeptide linker amino acid sequence
(SEQ ID NO: 11)
   1 GGGGSGGGGS GGGGS (Gly4 Ser) polypeptide linker amino acid sequence
(SEQ ID NO: 12)
   1 GGGGS (Gly) polypeptide linker amino acid sequence
(SEQ ID NO: 13)
   1 G (Gly Gly) polypeptide linker amino acid sequence
(SEQ ID NO: 14)
   1 GG (Gly Ser) polypeptide linker amino acid sequence
(SEQ ID NO: 15)
   1 GS (Gly2 Ser) polypeptide linker amino acid sequence
(SEQ ID NO: 16)
   1 GGS (Ala) polypeptide linker amino acid sequence
(SEQ ID NO: 17)
   1 A (Ala Ala) polypeptide linker amino acid sequence
(SEQ ID NO: 18)
   1 AA Klotho signal peptide-Klotho extracellular domain-FGF23
(R179Q) amino acid sequence
(SEQ ID NO: 19)
     1 MPASAPPRRP RPPPPSLSLL LVLLGLGGRR LRAEPGDGAQ TWARFSRPPA

51 PEAAGLFQGT FPDGFLWAVG SAAYQTEGGW QQHGKGASIW DTFTHHPLAP

101 PGDSRNASLP LGAPSPLQPA TGDVASDSYN NVFRDTEALR ELGVTHYRFS

151 ISWARVLPNG SAGVPNREGL RYYRRLLERL RELGVQPVVT LYHWDLPQRL

201 QDAYGGWANR ALADHFRDYA ELCFRHFGGQ VKYWITIDNP YVVAWHGYAT

251 GRLAPGIRGS PRLGYLVAHN LLLAHAKVWH LYNTSFRPTQ GGQVSIALSS

301 HWINPRRMTD HSIKECQKSL DFVLGWFAKP VFIDGDYPES MKNNLSSILP

351 DFTESEKKFI KGTADFFALC FGPTLSFQLL DPHMKFRQLE SPNLRQLLSW

401 IDLEFNHPQI FIVENGWFVS GTTKRDDAKY MYYLKKFIME TLKAIKLDGV

451 DVIGYTAWSL MDGFEWHRGY SIRRGLFYVD FLSQDKMLLP KSSALFYQKL

501 IEKNGFPPLP ENQPLEGTFP CDFAWGVVDN YIQVDTTLSQ FTDLNVYLWD

551 VHHSKRLIKV DGVVTKKRKS YCVDFAAIQP QIALLQEMHV THFRFSLDWA

601 LILPLGNQSQ VNHTILQYYR CMASELVRVN ITPVVALWQP MAPNQGLPRL

651 LARQGAWENP YTALAFAEYA RLCFQELGHH VKLWITMNEP YTRNMTYSAG

701 HNLLKAHALA WHVYNEKFRH AQNGKISIAL QADWIEPACP FSQKDKEVAE

751 RVLEFDIGWL AEPIFGSGDY PWVMRDWLNQ RNNFLLPYFT EDEKKLIQGT

801 FDFLALSHYT TILVDSEKED PIKYNDYLEV QEMTDITWLN SPSQVAVVPW
```

-continued

```
 851 GLRKVLNWLK FKYGDLPMYI ISNGIDDGLH AEDDQLRVYY MQNYINEALK

901 AHILDGINLC GYFAYSFNDR TAPRFGLYRY AADQFEPKAS MKHYRKIIDS

951 NGFPGPETLE RFCPEEFTVC TECSFFHTRK SLGSGGGGSG GGGSGGGGSL

1001 KYPNASPLLG SSWGGLIHLY TATARNSYHL QIHKNGHVDG APHQTIYSAL

1051 MIRSEDAGFV VITGVMSRRY LCMDFRGNIF GSHYFDPENC RFQHQTLENG

1101 YDVYHSPQYH FLVSLGRAKR AFLPGMNPPP YSQFLSRRNE IPLIHFNTPI

1151 PRRHTQSAED DSERDPLNVL KPRARMTPAP ASCSQELPSA EDNSPMASDP

1201 LGVVRGGRVN THAGGTGPEG CRPFAKFI*
```

IgG signal peptide-Klotho extracellular domain-FGF23
(R179Q) amino acid sequence
(SEQ ID NO: 20)

```
   1 MSVLTQVLAL LLLWLTGLGG RRLRAEPGDG AQTWARFSRP PAPEAAGLFQ

51 GTFPDGFLWA VGSAAYQTEG GWQQHGKGAS IWDTFTHHPL APPGDSRNAS

101 LPLGAPSPLQ PATGDVASDS YNNVFRDTEA LRELGVTHYR FSISWARVLP

151 NGSAGVPNRE GLRYYRRLLE RLRELGVQPV VTLYHWDLPQ RLQDAYGGWA

201 NRALADHFRD YAELCFRHFG GQVKYWITID NPYVVAWHGY ATGRLAPGIR

251 GSPRLGYLVA HNLLLAHAKV WHLYNTSFRP TQGGQVSIAL SSHWINPRRM

301 TDHSIKECQK SLDFVLGWFA KPVFIDGDYP ESMKNNLSSI LPDFTESEKK

351 FIKGTADFFA LCFGPTLSFQ LLDPHMKFRQ LESPNLRQLL SWIDLEFNHP

401 QIFIVENGWF VSGTTKRDDA KYMYYLKKFI METLKAIKLD GVDVIGYTAW

451 SLMDGFEWHR GYSIRRGLFY VDFLSQDKML LPKSSALFYQ KLIEKNGFPP

501 LPENQPLEGT FPCDFAWGVV DNYIQVDTTL SQFTDLNVYL WDVHHSKRLI

551 KVDGVVTKKR KSYCVDFAAI QPQIALLQEM HVTHFRFSLD WALILPLGNQ

601 SQVNHTILQY YRCMASELVR VNITPVVALW QPMAPNQGLP RLLARQGAWE

651 NPYTALAFAE YARLCFQELG HHVKLWITMN EPYTRNMTYS AGHNLLKAHA

701 LAWHVYNEKF RHAQNGKISI ALQADWIEPA CPFSQKDKEV AERVLEFDIG

751 WLAEPIFGSG DYPWVMRDWL NQRNNFLLPY FTEDEKKLIQ GTFDFLALSH

801 YTTILVDSEK EDPIKYNDYL EVQEMTDITW LNSPSQVAVV PWGLRKVLNW

851 LKFKYGDLPM YIISNGIDDG LHAEDDQLRV YYMQNYINEA LKAHILDGIN

901 LCGYFAYSFN DRTAPRFGLY RYAADQFEPK ASMKHYRKII DSNGFPGPET

951 LERFCPEEFT VCTECSFFHT RKSLGSGGGG SGGGGSGGGG SLKYPNASPL

1001 LGSSWGGLIH LYTATARNSY HLQIHKNGHV DGAPHQTIYS ALMIRSEDAG

1051 FVVITGVMSR RYLCMDFRGN IFGSHYFDPE NCRFQHQTLE NGYDVYHSPQ

1101 YHFLVSLGRA KRAFLPGMNP PPYSQFLSRR NEIPLIHFNT PIPRRHTQSA

1151 EDDSERDPLN VLKPRARMTP APASCSQELP SAEDNSPMAS DPLGVVRGGR

1201 VNTHAGGTGP EGCRPFAKFI *
```

KL-D1-FGF23 (R179Q) amino acid sequence
(SEQ ID NO: 21)

```
   1 MPASAPPRRP RPPPPSLSLL LVLLGLGGRR LRAEPGDGAQ TWARFSRPPA

51 PEAAGLFQGT FPDGFLWAVG SAAYQTEGGW QQHGKGASIW DTFTHHPLAP

101 PGDSRNASLP LGAPSPLQPA TGDVASDSYN NVFRDTEALR ELGVTHYRFS

151 ISWARVLPNG SAGVPNREGL RYYRRLLERL RELGVQPVVT LYHWDLPQRL

201 QDAYGGWANR ALADHFRDYA ELCFRHFGGQ VKYWITIDNP YVVAWHGYAT
```

```
251 GRLAPGIRGS PRLGYLVAHN LLLAHAKVWH LYNTSFRPTQ GGQVSIALSS

301 HWINPRRMTD HSIKECQKSL DFVLGWFAKP VFIDGDYPES MKNNLSSILP

351 DFTESEKKFI KGTADFFALC FGPTLSFQLL DPHMKFRQLE SPNLRQLLSW

401 IDLEFNHPQI FIVENGWFVS GTTKRDDAKY MYYLKKFIME TLKAIKLDGV

451 DVIGYTAWSL MDGFEWHRGY SIRRGLFYVD FLSQDKMLLP KSSALFYQKL

501 IEKNGFPPLP ENQPLEGSGG GGSGGGGSGG GGSLKYPNAS PLLGSSWGGL

551 IHLYTATARN SYHLQIHKNG HVDGAPHQTI YSALMIRSED AGFVVITGVM

601 SRRYLCMDFR GNIFGSHYFD PENCRFQHQT LENGYDVYHS PQYHFLVSLG

651 RAKRAFLPGM NPPPYSQFLS RRNEIPLIHF NTPIPRRHTQ SAEDDSERDP

701 LNVLKPRARM TPAPASCSQE LPSAEDNSPM ASDPLGVVRG GRVNTHAGGT

751 GPEGCRPFAK FI*
```

KL-D2-FGF23 (R179Q) amino acid sequence
(SEQ ID NO: 22)
```
  1 MPASAPPRRP RPPPPSLSLL LVLLGLGGRR LPLPENQPLE GTFPCDFAWG

51 VVDNYIQVDT TLSQFTDLNV YLWDVHHSKR LIKVDGVVTK KRKSYCVDFA

101 AIQPQIALLQ EMHVTHFRFS LDWALILPLG NQSQVNHTIL QYYRCMASEL

151 VRVNITPVVA LWQPMAPNQG LPRLLARQGA WENPYTALAF AEYARLCFQE

201 LGHHVKLWIT MNEPYTRNMT YSAGHNLLKA HALAWHVYNE KFRHAQNGKI

251 SIALQADWIE PACPFSQKDK EVAERVLEFD IGWLAEPIFG SGDYPWVMRD

301 WLNQRNNFLL PYFTEDEKKL IQGTFDFLAL SHYTTILVDS EKEDPIKYND

351 YLEVQEMTDI TWLNSPSQVA VVPWGLRKVL NWLKFKYGDL PMYIISNGID

401 DGLHAEDDQL RVYYMQNYIN EALKAHILDG INLCGYFAYS FNDRTAPRFG

451 LYRYAADQFE PKASMKHYRK IIDSNGFPGP ETLERFCPEE FTVCTECSFF

501 HTRKSLGSGG GGSGGGGSGG GGSLKYPNAS PLLGSSWGGL IHLYTATARN

551 SYHLQIHKNG HVDGAPHQTI YSALMIRSED AGFVVITGVM SRRYLCMDFR

601 GNIFGSHYFD PENCRFQHQT LENGYDVYHS PQYHFLVSLG RAKRAFLPGM

651 NPPPYSQFLS RRNEIPLIHF NTPIPRRHTQ SAEDDSERDP LNVLKPRARM

701 TPAPASCSQE LPSAEDNSPM ASDPLGVVRG GRVNTHAGGT GPEGCRPFAK

751 FI*
```

(KL-D1)$_2$-FGF23 (R179Q) amino acid sequence
(SEQ ID NO: 23)
```
  1 MPASAPPRRP RPPPPSLSLL LVLLGLGGRR LRAEPGDGAQ TWARFSRPPA

51 PEAAGLFQGT FPDGFLWAVG SAAYQTEGGW QQHGKGASIW DTFTHHPLAP

101 PGDSRNASLP LGAPSPLQPA TGDVASDSYN NVFRDTEALR ELGVTHYRFS

151 ISWARVLPNG SAGVPNREGL RYYRRLLERL RELGVQPVVT LYHWDLPQRL

201 QDAYGGWANR ALADHFRDYA ELCFRHFGGQ VKYWITIDNP YVVAWHGYAT

251 GRLAPGIRGS PRLGYLVAHN LLLAHAKVWH LYNTSFRPTQ GGQVSIALSS

301 HWINPRRMTD HSIKECQKSL DFVLGWFAKP VFIDGDYPES MKNNLSSILP

351 DFTESEKKFI KGTADFFALC FGPTLSFQLL DPHMKFRQLE SPNLRQLLSW

401 IDLEFNHPQI FIVENGWFVS GTTKRDDAKY MYYLKKFIME TLKAIKLDGV

451 DVIGYTAWSL MDGFEWHRGY SIRRGLFYVD FLSQDKMLLP KSSALFYQKL

501 IEKNGFPPLP ENQPLEGSGT FPDGFLWAVG SAAYQTEGGW QQHGKGASIW
```

```
 551 DTFTHHPLAP PGDSRNASLP LGAPSPLQPA TGDVASDSYN NVFRDTEALR

601 ELGVTHYRFS ISWARVLPNG SAGVPNREGL RYYRRLLERL RELGVQPVVT

651 LYHWDLPQRL QDAYGGWANR ALADHFRDYA ELCFRHFGGQ VKYWITIDNP

701 YVVAWHGYAT GRLAPGIRGS PRLGYLVAHN LLLAHAKVWH LYNTSFRPTQ

751 GGQVSIALSS HWINPRRMTD HSIKECQKSL DFVLGWFAKP VFIDGDYPES

801 MKNNLSSILP DFTESEKKFI KGTADFFALC FGPTLSFQLL DPHMKFRQLE

851 SPNLRQLLSW IDLEFNHPQI FIVENGWFVS GTTKRDDAKY MYYLKKFIME

901 TLKAIKLDGV DVIGYTAWSL MDGFEWHRGY SIRRGLFYVD FLSQDKMLLP

951 KSSALFYQKL IEKNGFPEFG SGGGGSGGGG SGGGGSLKYP NASPLLGSSW

1001 GGLIHLYTAT ARNSYHLQIH KNGHVDGAPH QTIYSALMIR SEDAGFVVIT

1051 GVMSRRYLCM DFRGNIFGSH YFDPENCRFQ HQTLENGYDV YHSPQYHFLV

1101 SLGRAKRAFL PGMNPPPYSQ FLSRRNEIPL IHFNTPIPRR HTQSAEDDSE

1151 RDPLNVLKPR ARMTPAPASC SQELPSAEDN SPMASDPLGV VRGGRVNTHA

1201 GGTGPEGCRP FAKFI*
```

(KL-D2)$_2$-FGF23 (R179Q) amino acid sequence
(SEQ ID NO: 24)

```
   1 MPASAPPRRP RPPPPSLSLL LVLLGLGGRR LPLPENQPLE GTFPCDFAWG

51 VVDNYIQVDT TLSQFTDLNV YLWDVHHSKR LIKVDGVVTK KRKSYCVDFA

101 AIQPQIALLQ EMHVTHFRFS LDWALILPLG NQSQVNHTIL QYYRCMASEL

151 VRVNITPVVA LWQPMAPNQG LPRLLARQGA WENPYTALAF AEYARLCFQE

201 LGHHVKLWIT MNEPYTRNMT YSAGHNLLKA HALAWHVYNE KFRHAQNGKI

251 SIALQADWIE PACPFSQKDK EVAERVLEFD IGWLAEPIFG SGDYPWVMRD

301 WLNQRNNFLL PYFTEDEKKL IQGTFDFLAL SHYTTILVDS EKEDPIKYND

351 YLEVQEMTDI TWLNSPSQVA VVPWGLRKVL NWLKFKYGDL PMYIISNGID

401 DGLHAEDDQL RVYYMQNYIN EALKAHILDG INLCGYFAYS FNDRTAPRFG

451 LYRYAADQFE PKASMKHYRK IIDSNGFPGP ETLERFCPEE FTVCTECSFF

501 HTRKSLGTFP CDFAWGVVDN YIQVDTTLSQ FTDLNVYLWD VHHSKRLIKV

551 DGVVTKKRKS YCVDFAAIQP QIALLQEMHV THFRFSLDWA LILPLGNQSQ

601 VNHTILQYYR CMASELVRVN ITPVVALWQP MAPNQGLPRL LARQGAWENP

651 YTALAFAEYA RLCFQELGHH VKLWITMNEP YTRNMTYSAG HNLLKAHALA

701 WHVYNEKFRH AQNGKISIAL QADWIEPACP FSQKDKEVAE RVLEFDIGWL

751 AEPIFGSGDY PWVMRDWLNQ RNNFLLPYFT EDEKKLIQGT FDFLALSHYT

801 TILVDSEKED PIKYNDYLEV QEMTDITWLN SPSQVAVVPW GLRKVLNWLK

851 FKYGDLPMYI ISNGIDDGLH AEDDQLRVYY MQNYINEALK AHILDGINLC

901 GYFAYSFNDR TAPRFGLYRY AADQFEPKAS MKHYRKIIDS NGFGSGGGGS

951 GGGGSGGGGS LKYPNASPLL GSSWGGLIHL YTATARNSYH LQIHKNGHVD

1001 GAPHQTIYSA LMIRSEDAGF VVITGVMSRR YLCMDFRGNI FGSHYFDPEN

1051 CRFQHQTLEN GYDVYHSPQY HFLVSLGRAK RAFLPGMNPP PYSQFLSRRN

1101 EIPLIHFNTP IPRRHTQSAE DDSERDPLNV LKPRARMTPA PASCSQELPS

1151 AEDNSPMASD PLGVVRGGRV NTHAGGTGPE GCRPFAKFI*
```

FGF23 (R179Q)-Klotho extracellular domain amino acid
sequence
(SEQ ID NO: 25)
```
   1 MLGARLRLWV CALCSVCSMS VLRAYPNASP LLGSSWGGLI HLYTATARNS
  51 YHLQIHKNGH VDGAPHQTIY SALMIRSEDA GFVVITGVMS RRYLCMDFRG
 101 NIFGSHYFDP ENCRFQHQTL ENGYDVYHSP QYHFLVSLGR AKRAFLPGMN
 151 PPPYSQFLSR RNEIPLIHFN TPIPRRHTQS AEDDSERDPL NVLKPRARMT
 201 PAPASCSQEL PSAEDNSPMA SDPLGVVRGG RVNTHAGGTG PEGCRPFAKF
 251 IGSGGGGSGG GGSGGGGSLK EPGDGAQTWA RFSRPPAPEA AGLFQGTFPD
 301 GFLWAVGSAA YQTEGGWQQH GKGASIWDTF THHPLAPPGD SRNASLPLGA
 351 PSPLQPATGD VASDSYNNVF RDTEALRELG VTHYRFSISW ARVLPNGSAG
 401 VPNREGLRYY RRLLERLREL GVQPVVTLYH WDLPQRLQDA YGGWANRALA
 451 DHFRDYAELC FRHFGGQVKY WITIDNPYVV AWHGYATGRL APGIRGSPRL
 501 GYLVAHNLLL AHAKVWHLYN TSFRPTQGGQ VSIALSSHWI NPRRMTDHSI
 551 KECQKSLDFV LGWFAKPVFI DGDYPESMKN NLSSILPDFT ESEKKFIKGT
 601 ADFFALCFGP TLSFQLLDPH MKFRQLESPN LRQLLSWIDL EFNHPQIFIV
 651 ENGWFVSGTT KRDDAKYMYY LKKFIMETLK AIKLDGVDVI GYTAWSLMDG
 701 FEWHRGYSIR RGLFYVDFLS QDKMLLPKSS ALFYQKLIEK NGFPPLPENQ
 751 PLEGTFPCDF AWGVVDNYIQ VDTTLSQFTD LNVYLWDVHH SKRLIKVDGV
 801 VTKKRKSYCV DFAAIQPQIA LLQEMHVTHF RFSLDWALIL PLGNQSQVNH
 851 TILQYYRCMA SELVRVNITP VVALWQPMAP NQGLPRLLAR QGAWENPYTA
 901 LAFAEYARLC FQELGHHVKL WITMNEPYTR NMTYSAGHNL LKAHALAWHV
 951 YNEKFRHAQN GKISIALQAD WIEPACPFSQ KDKEVAERVL EFDIGWLAEP
1001 IFGSGDYPWV MRDWLNQRNN FLLPYFTEDE KKLIQGTFDF LALSHYTTIL
1051 VDSEKEDPIK YNDYLEVQEM TDITWLNSPS QVAVVPWGLR KVLNWLKFKY
1101 GDLPMYIISN GIDDGLHAED DQLRVYYMQN YINEALKAHI LDGINLCGYF
1151 AYSFNDRTAP RFGLYRYAAD QFEPKASMKH YRKIIDSNGF PGPETLERFC
1201 PEEFTVCTEC SFFHTRKSL*
```
FGF23 (R179Q)-KL-D1 amino acid sequence
(SEQ ID NO: 26)
```
   1 MLGARLRLWV CALCSVCSMS VLRAYPNASP LLGSSWGGLI HLYTATARNS
  51 YHLQIHKNGH VDGAPHQTIY SALMIRSEDA GFVVITGVMS RRYLCMDFRG
 101 NIFGSHYFDP ENCRFQHQTL ENGYDVYHSP QYHFLVSLGR AKRAFLPGMN
 151 PPPYSQFLSR RNEIPLIHFN TPIPRRHTQS AEDDSERDPL NVLKPRARMT
 201 PAPASCSQEL PSAEDNSPMA SDPLGVVRGG RVNTHAGGTG PEGCRPFAKF
 251 IQGTFPDGFL WAVGSAAYQT EGGWQQHGKG ASIWDTFTHH PLAPPGDSRN
 301 ASLPLGAPSP LQPATGDVAS DSYNNVFRDT EALRELGVTH YRFSISWARV
 351 LPNGSAGVPN REGLRYYRRL LERLRELGVQ PVVTLYHWDL PQRLQDAYGG
 401 WANRALADHF RDYAELCFRH FGGQVKYWIT IDNPYVVAWH GYATGRLAPG
 451 IRGSPRLGYL VAHNLLLAHA KVWHLYNTSF RPTQGGQVSI ALSSHWINPR
 501 RMTDHSIKEC QKSLDFVLGW FAKPVFIDGD YPESMKNNLS SILPDFTESE
 551 KKFIKGTADF FALCFGPTLS FQLLDPHMKF RQLESPNLRQ LLSWIDLEFN
 601 HPQIFIVENG WFVSGTTKRD DAKYMYYLKK FIMETLKAIK LDGVDVIGYT
```

```
651 AWSLMDGFEW HRGYSIRRGL FYVDFLSQDK MLLPKSSALF YQKLIEKNGF

652 *

FGF23 (R179Q)-KL-D2 amino acid sequence
(SEQ ID NO: 27)
   1 MLGARLRLWV CALCSVCSMS VLRAYPNASP LLGSSWGGLI HLYTATARNS

51 YHLQIHKNGH VDGAPHQTIY SALMIRSEDA GFVVITGVMS RRYLCMDFRG

101 NIFGSHYFDP ENCRFQHQTL ENGYDVYHSP QYHFLVSLGR AKRAFLPGMN

151 PPPYSQFLSR RNEIPLIHFN TPIPRRHTQS AEDDSERDPL NVLKPRARMT

201 PAPASCSQEL PSAEDNSPMA SDPLGVVRGG RVNTHAGGTG PEGCRPFAKF

251 IGTFPCDFAW GVVDNYIQVD TTLSQFTDLN VYLWDVHHSK RLIKVDGVVT

301 KKRKSYCVDF AAIQPQIALL QEMHVTHFRF SLDWALILPL GNQSQVNHTI

351 LQYYRCMASE LVRVNITPVV ALWQPMAPNQ GLPRLLARQG AWENPYTALA

401 FAEYARLCFQ ELGHHVKLWI TMNEPYTRNM TYSAGHNLLK AHALAWHVYN

451 EKFRHAQNGK ISIALQADWI EPACPFSQKD KEVAERVLEF DIGWLAEPIF

501 GSGDYPWVMR DWLNQRNNFL LPYFTEDEKK LIQGTFDFLA LSHYTTILVD

551 SEKEDPIKYN DYLEVQEMTD ITWLNSPSQV AVVPWGLRKV LNWLKFKYGD

601 LPMYIISNGI DDGLHAEDDQ LRVYYMQNYI NEALKAHILD GINLCGYFAY

651 SFNDRTAPRF GLYRYAADQF EPKASMKHYR KIIDSNGF*

FGF23 (R179Q)-(KL-D1)₂ amino acid sequence
(SEQ ID NO: 28)
   1 MLGARLRLWV CALCSVCSMS VLRAYPNASP LLGSSWGGLI HLYTATARNS

51 YHLQIHKNGH VDGAPHQTIY SALMIRSEDA GFVVITGVMS RRYLCMDFRG

101 NIFGSHYFDP ENCRFQHQTL ENGYDVYHSP QYHFLVSLGR AKRAFLPGMN

151 PPPYSQFLSR RNEIPLIHFN TPIPRRHTQS AEDDSERDPL NVLKPRARMT

201 PAPASCSQEL PSAEDNSPMA SDPLGVVRGG RVNTHAGGTG PEGCRPFAKF

251 IQGTFPDGFL WAVGSAAYQT EGGWQQHGKG ASIWDTFTHH PLAPPGDSRN

301 ASLPLGAPSP LQPATGDVAS DSYNNVFRDT EALRELGVTH YRFSISWARV

351 LPNGSAGVPN REGLRYYRRL LERLRELGVQ PVVTLYHWDL PQRLQDAYGG

401 WANRALADHF RDYAELCFRH FGGQVKYWIT IDNPYVVAWH GYATGRLAPG

451 IRGSPRLGYL VAHNLLLAHA KVWHLYNTSF RPTQGGQVSI ALSSHWINPR

501 RMTDHSIKEC QKSLDFVLGW FAKPVFIDGD YPESMKNNLS SILPDFTESE

551 KKFIKGTADF FALCFGPTLS FQLLDPHMKF RQLESPNLRQ LLSWIDLEFN

601 HPQIFIVENG WFVSGTTKRD DAKYMYYLKK FIMETLKAIK LDGVDVIGYT

651 AWSLMDGFEW HRGYSIRRGL FYVDFLSQDK MLLPKSSALF YQKLIEKNGF

701 QGTFPDGFLW AVGSAAYQTE GGWQQHGKGA SIWDTFTHHP LAPPGDSRNA

751 SLPLGAPSPL QPATGDVASD SYNNVFRDTE ALRELGVTHY RFSISWARVL

801 PNGSAGVPNR EGLRYYRRLL ERLRELGVQP VVTLYHWDLP QRLQDAYGGW

851 ANRALADHFR DYAELCFRHF GGQVKYWITI DNPYVVAWHG YATGRLAPGI

901 RGSPRLGYLV AHNLLLAHAK VWHLYNTSFR PTQGGQVSIA LSSHWINPRR

951 MTDHSIKECQ KSLDFVLGWF AKPVFIDGDY PESMKNNLSS ILPDFTESEK

1001 KFIKGTADFF ALCFGPTLSF QLLDPHMKFR QLESPNLRQL LSWIDLEFNH
```

```
1051  PQIFIVENGW  FVSGTTKRDD  AKYMYYLKKF  IMETLKAIKL  DGVDVIGYTA

1101  WSLMDGFEWH  RGYSIRRGLF  YVDFLSQDKM  LLPKSSALFY  QKLIEKNGF*
```

FGF23 (R179Q)-(KL-D2)$_2$ amino acid sequence
(SEQ ID NO: 29)
```
   1  MLGARLRLWV  CALCSVCSMS  VLRAYPNASP  LLGSSWGGLI  HLYTATARNS

51  YHLQIHKNGH  VDGAPHQTIY  SALMIRSEDA  GFVVITGVMS  RRYLCMDFRG

101  NIFGSHYFDP  ENCRFQHQTL  ENGYDVYHSP  QYHFLVSLGR  AKRAFLPGMN

151  PPPYSQFLSR  RNEIPLIHFN  TPIPRRHTQS  AEDDSERDPL  NVLKPRARMT

201  PAPASCSQEL  PSAEDNSPMA  SDPLGVVRGG  RVNTHAGGTG  PEGCRPFAKF

251  IGTFPCDFAW  GVVDNYIQVD  TTLSQFTDLN  VYLWDVHHSK  RLIKVDGVVT

301  KKRKSYCVDF  AAIQPQIALL  QEMHVTHFRF  SLDWALILPL  GNQSQVNHTI

351  LQYYRCMASE  LVRVNITPVV  ALWQPMAPNQ  GLPRLLARQG  AWENPYTALA

401  FAEYARLCFQ  ELGHHVKLWI  TMNEPYTRNM  TYSAGHNLLK  AHALAWHVYN

451  EKFRHAQNGK  ISIALQADWI  EPACPFSQKD  KEVAERVLEF  DIGWLAEPIF

501  GSGDYPWVMR  DWLNQRNNFL  LPYFTEDEKK  LIQGTFDFLA  LSHYTTILVD

551  SEKEDPIKYN  DYLEVQEMTD  ITWLNSPSQV  AVVPWGLRKV  LNWLKFKYGD

601  LPMYIISNGI  DDGLHAEDDQ  LRVYYMQNYI  NEALKAHILD  GINLCGYFAY

651  SFNDRTAPRF  GLYRYAADQF  EPKASMKHYR  KIIDSNGFGT  FPCDFAWGVV

701  DNYIQVDTTL  SQFTDLNVYL  WDVHHSKRLI  KVDGVVTKKR  KSYCVDFAAI

751  QPQIALLQEM  HVTHFRFSLD  WALILPLGNQ  SQVNHTILQY  YRCMASELVR

801  VNITPVVALW  QPMAPNQGLP  RLLARQGAWE  NPYTALAFAE  YARLCFQELG

851  HHVKLWITMN  EPYTRNMTYS  AGHNLLKAHA  LAWHVYNEKF  RHAQNGKISI

901  ALQADWIEPA  CPFSQKDKEV  AERVLEFDIG  WLAEPIFGSG  DYPWVMRDWL

951  NQRNNFLLPY  FTEDEKKLIQ  GTFDFLALSH  YTTILVDSEK  EDPIKYNDYL

1001  EVQEMTDITW  LNSPSQVAVV  PWGLRKVLNW  LKFKYGDLPM  YIISNGIDDG

1051  LHAEDDQLRV  YYMQNYINEA  LKAHILDGIN  LCGYFAYSFN  DRTAPRFGLY

1101  RYAADQFEPK  ASMKHYRKII  DSNGF*
```

FGF19 nucleic acid sequence (NM_005117)
(SEQ ID NO: 30)
Protein coding region (464-1114)
```
   1  gctcccagcc  aagaacctcg  gggccgctgc  gcggtgggga  ggagttcccc  gaaaccggc 61  cgctaagcga  ggcctcctcc  tcccgcagat  ccgaacggcc  tgggcggggt  caccccggct 121  gggacaagaa  gccgccgcct  gcctgcccgg  gccggggag  ggggctgggg  ctggggccgg 181  aggcggggtg  tgagtgggtg  tgtgcggggg  gcggaggctt  gatgcaatcc  cgataagaaa 241  tgctcgggtg  tcttgggcac  ctacccgtgg  ggcccgtaag  cgctactat  ataaggctgc 301  cggcccggag  ccgccgcgcc  gtcagagcag  gagcgctgcg  tccaggatct  agggccacga 361  ccatcccaac  ccggcactca  cagccccgca  gcgcatcccg  gtcgccgccc  agcctcccgc 421  accccatcg  ccggagctgc  gccgagagcc  cagggaggt  gccatgcgga  gcgggtgtgt 481  ggtggtccac  gtatggatcc  tggccggcct  ctggctggcc  gtggccgggc  gccccctcgc 541  cttctcggac  gcggggcccc  acgtgcacta  cggctgggc  gacccccatcc  gcctgcggca 601  cctgtacacc  tccggccccc  acgggctctc  cagctgcttc  ctgcgcatcc  gtgccgacgg 661  cgtcgtggac  tgcgcgcggg  gccagagcgc  gcacagtttg  ctgagaatca  aggcagtcgc 721  tctgcggacc  gtggccatca  agggcgtgca  cagcgtgcgg  tacctctgca  tgggcgccga
```

```
 781 cggcaagatg caggggctgc ttcagtactc ggaggaagac tgtgctttcg aggaggagat 841 ccgcccagat ggctacaatg tgtaccgatc cgagaagcac cgcctcccgg tctccctgag 901 cagtgccaaa cagcggcagc tgtacaagaa cagaggcttt cttccactct ctcatttcct 961 gcccatgctg cccatggtcc cagaggagcc tgaggacctc aggggccact tggaatctga 1021 catgttctct tcgcccctgg agaccgacag catggaccca tttgggcttg tcaccggact 1081 ggaggccgtg aggagtccca gctttgagaa gtaactgaga ccatgcccgg gcctcttcac 1141 tgctgccagg ggctgtggta cctgcagcgt gggggacgtg cttctacaag aacagtcctg 1201 agtccacgtt ctgtttagct ttaggaagaa acatctagaa gttgtacata ttcagagttt 1261 tccattggca gtgccagttt ctagccaata gacttgtctg atcataacat tgtaagcctg 1321 tagcttgccc agctgctgcc tgggccccca ttctgctccc tcgaggttgc tggacaagct 1381 gctgcactgt ctcagttctg cttgaatacc tccatcgatg gggaactcac ttcctttgga 1441 aaaattctta tgtcaagctg aaattctcta atttttctc atcacttccc caggagcagc 1501 cagaagacag gcagtagttt taatttcagg aacaggtgat ccactctgta aaacagcagg 1561 taaatttcac tcaaccccat gtgggaattg atctatatct ctacttccag ggaccatttg 1621 cccttcccaa atccctccag gccagaactg actggagcag gcatggccca ccaggcttca 1681 ggagtagggg aagcctggag ccccactcca gccctgggac aacttgagaa ttccccctga 1741 ggccagttct gtcatggatg ctgtcctgag ataacttgc tgtcccggtg tcacctgctt 1801 ccatctccca gcccaccagc cctctgccca cctcacatgc ctccccatgg attggggcct 1861 cccaggcccc ccaccttatg tcaacctgca cttcttgttc aaaaatcagg aaaagaaaag 1921 atttgaagac cccaagtctt gtcaataact tgctgtgtgg aagcagcggg ggaagaccta 1981 gaaccctttc cccagcactt ggttttccaa catgatattt atgagtaatt tattttgata 2041 tgtacatctc ttattttctt acattattta tgcccccaaa ttatatttat gtatgtaagt 2101 gaggtttgtt ttgtatatta aaatggagtt tgtttgtaaa aaaaaaaaaa aaaaaaa
```
FGF19 amino acid sequence (NP_005108)
(SEQ ID NO: 31)
```
  1 MRSGCVVVHV WILAGLWLAV AGRPLAFSDA GPHVHYGWGD PIRLRHLYTS GPHGLSSCFL

61 RIRADGVVDC ARGQSAHSLL EIKAVALRTV AIKGVHSVRY LCMGADGKMQ GLLQYSEEDC

121 AFEEEIRPDG YNVYRSEKHR LPVSLSSAKQ RQLYKNRGFL PLSHFLPMLP MVPEEPEDLR

181 GHLESDMFSS PLETDSMDPF GLVTGLEAVR SPSFEK
```
FGF21 nucleic acid sequence (NM_019113)
(SEQ ID NO: 32)
Protein coding region 151-780
```
  1 CTGTCAGCTG AGGATCCAGC CGAAAGAGGA GCCAGGCACT CAGGCCACCT GAGTCTACTC

61 ACCTGGACAA CTGGAATCTG GCACCAATTC TAAACCACTC AGCTTCTCCG AGCTCACACC

121 CCGGAGATCA CCTGAGGACC CGAGCCATTG ATGGACTCGG ACGAGACCGG GTTCGAGCAC

181 TCAGGACTGT GGGTTTCTGT GCTGGCTGGT CTTCTGCTGG GAGCCTGCCA GGCACACCCC

241 ATCCCTGACT CCAGTCCTCT CCTGCAATTC GGGGGCCAAG TCCGGCAGCG GTACCTCTAC

301 ACAGATGATG CCCAGCAGAC AGAAGCCCAC CTGGAGATCA GGGAGGATGG GACGGTGGGG

361 GGCGCTGCTG ACCAGAGCCC CGAAAGTCTC CTGCAGCTGA AAGCCTTGAA GCCGGGAGTT

421 ATTCAAATCT GGGAGTCAAG ACATCCAGG TTCCTGTGCC AGCGGCCAGA TGGGGCCCTG

481 TATGGATCGC TCCACTTTGA CCCTGAGGCC TGCAGCTTCC GGGAGCTGCT TCTTGAGGAC

541 GGATACAATG TTTACCAGTC CGAAGCCCAC GGCCTCCCGC TGCACCTGCC AGGGAACAAG

601 TCCCCACACC GGGACCCTGC ACCCCGAGGA CCAGCTCGCT TCCTGCCACT ACCAGGCCTG
```

```
661 CCCCCCGCAC TCCCGGAGCC ACCCGGAATC CTGGCCCCCC AGCCCCCCGA TGTGGGCTCC

721 TCGGACCCTC TGAGCATGGT GGGACCTTCC CAGGGCCGAA GCCCCAGCTA CGCTTCCTGA

781 AGCCAGAGGC TGTTTACTAT GACATCTCCT CTTTATTTAT TAGGTTATTT ATCTTATTTA

841 TTTTTTTATT TTTCTTACTT GAGATAATAA AGAGTTCCAG AGGAGAAAAA AAAAAAAAA

901 AAAAAAAAAA AAAAAAAAA AAAAAAAAA AAAAAAAAA
```

FGF21 amino acid sequence (NP_061986)
(SEQ ID NO: 33)
```
  1 MDSDETGFEH SGLWVSVLAG LLLGACQAHP IPDSSPLLQF GGQVRQRYLY TDDAQQTEAH

61 LEIREDGTVG GAADQSPESL LQLKALKPGV IQILGVKTSR FLCQRPDGAL YGSLHFDPEA

121 CSFRELLLED GYNVYQSEAH GLPLHLPGNK SPHRDPAPRG PARFLPLPGL PPALPEPPGI

181 LAPQPPDVGS SDPLSMVGPS QGRSPSYAS
```

FGF23 nucleic acid sequence (NM_020638)
(SEQ ID NO: 34)
Protein coding region 147-902
```
   1 cggcaaaaag gagggaatcc agtctaggat cctcacacca gctacttgca agggagaagg 61 aaaaggccag taaggcctgg gccaggagag tcccgacagg agtgtcaggt ttcaatctca 121 gcaccagcca ctcagagcag gcacgatgt tgggggcccg cctcaggctc tgggtctgtg 181 ccttgtgcag cgtctgcagc atgagcgtcc tcagagccta tcccaatgcc tccccactgc 241 tcggctccag ctggggtggc ctgatccacc tgtacacagc cacagccagg aacagctacc 301 acctgcagat ccacaagaat ggccatgtgg atggcgcacc ccatcagacc atctacagtg 361 ccctgatgat cagatcagag gatgctggct tgtggtgat acaggtgtg atgagcagaa 421 gatacctctg catggatttc agaggcaaca ttttggatc acactatttc gacccggaga 481 actgcaggtt ccaacaccag acgctggaaa acgggtacga cgtctaccac tctcctcagt 541 atcacttcct ggtcagtctg ggccgggcga agagagcctt cctgccaggc atgaacccac 601 ccccgtactc ccagttcctg tcccggagga acgagatccc cctaattcac ttcaacaccc 661 ccataccacg gcggcacacc cggagcgccg aggacgactc ggagcgggac cccctgaacg 721 tgctgaagcc ccgggcccgg atgacccggg ccccggcctc ctgttcacag gagctcccga 781 gcgccgagga caacagcccg atggccagtg acccattagg ggtggtcagg ggcggtcgag 841 tgaacacgca cgctggggga acgggccggg aaggctgccg ccccttcgcc aagttcatct 901 agggtcgctg gaagggcacc ctctttaacc catccctcag caaacgcagc tcttcccaag 961 gaccaggtcc cttgacgttc cgaggatggg aaaggtgaca ggggcatgta tggaatttgc 1021 tgcttctctg gggtccttc cacaggaggt cctgtgagaa ccaacctttg aggcccaagt 1081 catgggtttt caccgccttc ctcactccat atagaacacc tttcccaata ggaaacccca 1141 acaggtaaac tagaaatttc cccttcatga aggtagagag aagggtctc tcccaacata 1201 tttctcttcc ttgtgcctct cctctttatc acttttaagc ataaaaaaaa aaaaaaaaaa 1261 aaaaaaaaaa aaaagcagtg ggttcctgag ctcaagactt tgaaggtgta gggaagagga 1321 aatcggagat cccagaagct tctccactgc cctatgcatt tatgttagat gccccgatcc 1381 cactggcatt tgagtgtgca aaccttgaca ttaacagctg aatggggcaa gttgatgaaa 1441 acactacttt caagccttcg ttcttccttg agcatctctg gggaagagct gtcaaaagac 1501 tggtggtagg ctggtgaaaa cttgacagct agacttgatg cttgctgaaa tgaggcagga 1561 atcataatag aaaactcagc ctccctacag ggtgagcacc ttctgtctcg ctgtctccct 1621 ctgtgcagcc acagccagag ggcccagaat ggcccactc tgttcccaag cagttcatga 1681 tacagcctca ccttttggcc ccatctctgg ttttgaaaa tttggtctaa ggaataaata
```

-continued

```
1741 gcttttacac tggctcacga aaatctgccc tgctagaatt tgcttttcaa aatggaaata 1801 aattccaact ctcctaagag gcatttaatt aaggctctac ttccaggttg agtaggaatc 1861 cattctgaac aaactacaaa aatgtgactg ggaaggggc tttgagagac tgggactgct 1921 ctgggttagg ttttctgtgg actgaaaaat cgtgtccttt tctctaaatg aagtggcatc 1981 aaggactcag ggggaaagaa atcaggggac atgttataga agttatgaaa agacaaccac 2041 atggtcaggc tcttgtctgt ggtctctagg gctctgcagc agcagtggct cttcgattag 2101 ttaaaactct cctaggctga cacatctggg tctcaatccc cttggaaatt cttggtgcat 2161 taaatgaagc cttaccccat tactgcggtt cttcctgtaa gggggctcca ttttcctccc 2221 tctcttttaaa tgaccaccta aaggacagta tattaacaag caaagtcgat tcaacaacag 2281 cttcttccca gtcacttttt tttttctcac tgccatcaca tactaacctt atactttgat 2341 ctattctttt tggttatgag agaaatgttg gcaactgtt tttacctgat ggttttaagc 2401 tgaacttgaa ggactggttc ctattctgaa acagtaaaac tatgtataat agtatatagc 2461 catgcatggc aaatatttta atatttctgt tttcatttcc tgttggaaat attatcctgc 2521 ataatagcta ttggaggctc ctcagtgaaa gatcccaaaa ggattttggt ggaaaactag 2581 ttgtaatctc acaaactcaa cactaccatc aggggttttc tttatggcaa agccaaaata 2641 gctcctacaa tttcttatat ccctcgtcat gtggcagtat ttatttattt atttggaagt 2701 ttgcctatcc ttctatattt atagatattt ataaaaatgt aacccctttt tcctttcttc 2761 tgtttaaaat aaaaataaaa tttatctcag cttctgttag cttatcctct ttgtagtact 2821 acttaaaagc atgtcggaat ataagaataa aaaggattat gggaggggaa cattagggaa 2881 atccagagaa ggcaaaattg aaaaaaagat tttagaattt taaaatttc aaagatttct 2941 tccattcata aggagactca atgattttaa ttgatctaga cagaattatt taagttttat 3001 caatattgga tttctggt
```

FGF23 amino acid sequence (NP_065689)
(SEQ ID NO: 35)

```
  1 MLGARLRLWV CALCSVCSMS VLRAYPNASP LLGSSWGGLI HLYTATARNS YHLQIHKNGH

61 VDGAPHQTIY SALMIRSEDA GFVVITGVMS RRYLCMDFRG NIFGSHYFDP ENCRFQHQTL

121 ENGYDVYHSP QYHFLVSLGR AKRAFLPGMN PPPYSQFLSR RNEIPLIHFN TPIPRRHIRS

181 AEDDSERDPL NVLKPRARMT PAPASCSQEL PSAEDNSPMA SDPLGVVRGG RVNTHAGGTG

241 PEGCRPFAKF I
```

FGF23 (R179Q) amino acid sequence
(SEQ ID NO: 36)

```
  1 MLGARLRLWV CALCSVCSMS VLRAYPNASP LLGSSWGGLI HLYTATARNS YHLQIHKNGH

61 VDGAPHQTIY SALMIRSEDA GFVVITGVMS RRYLCMDFRG NIFGSHYFDP ENCRFQHQTL

121 ENGYDVYHSP QYHFLVSLGR AKRAFLPGMN PPPYSQFLSR RNEIPLIHFN TPIPRRHTQS

181 AEDDSERDPL NVLKPRARMT PAPASCSQEL PSAEDNSPMA SDPLGVVRGG RVNTHAGGTG

241 PEGCRPFAKF I
```

Human beta-Klotho domain 1 (b-KL-D1) amino acid sequence
(SEQ ID NO: 37)

```
 77                         ydt fpknffwgig tgalqvegsw kkdgkgpsiw dhfihthlkn 121 vsstngssds yiflekdlsa ldfigvsfyq fsiswprlfp dgivtvanak glqyystlld 181 alvlrniepi vtlyhwdlpl alqekyggwk ndtildifnd yatycfqmfg drvkywitih 241 npylvawhgy gtgmhapgek gnlaavytvg hnlikahskv whnynthfrp hqkgwlsitl 301 gshwiepnrs entmdifkcq qsmvsvlgwf anpihgdgdy pegmrkklfs vlpifseaek
```

-continued

```
361 hemrgtadff afsfgpnnfk pintmakmgq nvslnlreal nwikleynnp riliaengwf 421 tdsrvktedt taiymmknfl sqvlqairld eirvfgytaw slldgfewqd aytirrglfy 481 vdfnskqker kpkssahyyk qiirengf
```

Human beta-Klotho domain 2 (b-KL-D2) amino acid sequence
(SEQ ID NO: 38)
```
571                                trpaqctdfv nikkqlemla rmkvthyrfa 601 ldwasvlptg nlsavnrqal ryyrcvvseg lklgisamvt lyypthahlg lpepllhadg 661 wlnpstaeaf qayaglcfqe lgdlvklwit inepnrlsdi ynrsgndtyg aahnllvaha 721 lawrlydrqf rpsqrgavsl slhadwaepa npyadshwra aerflqfeia wfaeplfktg 781 dypaamreyi askhrrglss salprlteae rrllkgtvdf calnhfttrf vmheqlagsr 841 ydsdrdiqfl qditrlsspt rlavipwgvr kllrwvrrny gdmdiyitas giddqaledd 901 rlrkyylgky lqevlkayli dkvrikgyya fklaeekskp rfgfftsdfk akssiqfynk 961 vissrgf
```

Beta-Klotho extracellular domain (without signal peptide) amino acid sequence
(SEQ ID NO: 39)
```
 52                                                     gfsgdgrai 61 wsknpnftpv nesqlflydt fpknffwgig tgalqvegsw kkdgkgpsiw dhfihthlkn 121 vsstngssds yiflekdlsa ldfigvsfyq fsiswprlfp dgivtvanak glqyystlld 181 alvlrniepi vtlyhwdlpl alqekyggwk ndtiidifnd yatycfqmfg drvkywitih 241 npylvawhgy gtgmhapgek gnlaavytvg hnlikahskv whnynthfrp hqkgwlsitl 301 gshwiepnrs entmdifkcq qsmvsvlgwf anpihgdgdy pegmrkklfs vlpifseaek 361 hemrgtadff afsfgpnnfk plntmakmgq nvslnlreal nwikleynnp riliaengwf 421 tdsrvktedt talymmknfl sqvlqairld eirvfgytaw slldgfewqd aytirrglfy 481 vdfnskqker kpkssahyyk qiirengfsl kestpdvqgq fpcdfswgvt esvlkpesva 541 sspqfsdphl yvwnatgnrl lhrvegvrlk trpaqctdfv nikkqlemla rmkvthyrfa 601 ldwasvlptg nlsavnrqal ryyrcvvseg lklgisamvt lyypthahlg lpepllhadg 661 wlnpstaeaf qayaglcfqe lgdlvklwit inepnrlsdi ynrsgndtyg aahnllvaha 721 lawrlydrqf rpsqrgavsl slhadwaepa npyadshwra aerflqfeia wfaeplfktg 781 dypaamreyi askhrrglss salprlteae rrllkgtvdf calnhfttrf vmheqlagsr 841 ydsdrdiqfl qditrlsspt rlavipwgvr kllrwvrrny gdmdlyitas giddqaledd 901 rlrkyylgky lqevlkayli dkvrikgyya fklaeekskp rfgfftsdfk akssiqfynk 961 vissrgfpfe nsssrcsqtq entectvclf lvqkkpl
``` sKlotho without signal peptide - FGF23 amino acid sequence (without signal peptide)
(SEQ ID NO: 40)
```
                                 EPGDGAQ TWARFSRPPA

51 PEAAGLFQGT FPDGFLWAVG SAAYQTEGGW QQHGKGASIW DTFTHHPLAP

101 PGDSRNASLP LGAPSPLQPA TGDVASDSYN NVFRDTEALR ELGVTHYRFS

151 ISWARVLPNG SAGVPNREGL RYYRRLLERL RELGVQPVVT LYHWDLPQRL

201 QDAYGGWANR ALADHFRDYA ELCFRHFGGQ VKYWITIDNP YVVAWHGYAT

251 GRLAPGIRGS PRLGYLVAHN LLLAHAKVWH LYNTSFRPTQ GGQVSIALSS

301 HWINPRRMTD HSIKECQKSL DFVLGWFAKP VFIDGDYPES MKNNLSSILP

351 DFTESEKKFI KGTADFFALC FGPTLSFQLL DPHMKFRQLE SPNLRQLLSW

401 IDLEFNHPQI FIVENGWFVS GTTKRDDAKY MYYLKKFIME TLKAIKLDGV
```

```
 451 DVIGYTAWSL MDGFEWHRGY SIRRGLFYVD FLSQDKMLLP KSSALFYQKL

501 IEKNGFPPLP ENQPLEGTFP CDFAWGVVDN YIQVDTTLSQ FTDLNVYLWD

551 VHHSKRLIKV DGVVTKKRKS YCVDFAAIQP QIALLQEMHV THFRFSLDWA

601 LILPLGNQSQ VNHTILQYYR CMASELVRVN ITPVVALWQP MAPNQGLPRL

651 LARQGAWENP YTALAFAEYA RLCFQELGHH VKLWITMNEP YTRNMTYSAG

701 HNLLKAHALA WHVYNEKFRH AQNGKISIAL QADWIEPACP FSQKDKEVAE

751 RVLEFDIGWL AEPIFGSGDY PWVMRDWLNQ RNNFLLPYFT EDEKKLIQGT

801 FDFLALSHYT TILVDSEKED PIKYNDYLEV QEMTDITWLN SPSQVAVVPW

851 GLRKVLNWLK FKYGDLPMYI ISNGIDDGLH AEDDQLRVYY MQNYINEALK

901 AHILDGINLC GYFAYSFNDR TAPRFGLYRY AADQFEPKAS MKHYRKIIDS

951 NGFPGPETLE RFCPEEFTVC TECSFFHTRK SLGSGGGGSG GGGSGGGGSL

1001 KYPNASPLLG SSWGGLIHLY TATARNSYHL QIHKNGHVDG APHQTIYSAL

1051 MIRSEDAGFV VITGVMSRRY LCMDFRGNIF GSHYFDPENC RFQHQTLENG

1101 YDVYHSPQYH FLVSLGRAKR AFLPGMNPPP YSQFLSRRNE IPLIHFNTPI

1151 PRRHTRSAED DSERDPLNVL KPRARMTPAP ASCSQELPSA EDNSPMASDP

1201 LGVVRGGRVN THAGGTGPEG CRPFAKFI* sKlotho without signal peptide -FGF23 (R179Q)
(without signal peptide) amino acid sequence
(SEQ ID NO: 41)
                                       EPGDGAQ TWARFSRPPA

51 PEAAGLFQGT FPDGFLWAVG SAAYQTEGGW QQHGKGASIW DTFTHHPLAP

101 PGDSRNASLP LGAPSPLQPA TGDVASDSYN NVFRDTEALR ELGVTHYRFS

151 ISWARVLPNG SAGVPNREGL RYYRRLLERL RELGVQPVVT LYHWDLPQRL

201 QDAYGGWANR ALADHFRDYA ELCFRHFGGQ VKYWITIDNP YVVAWHGYAT

251 GRLAPGIRGS PRLGYLVAHN LLLAHAKVWH LYNTSFRPTQ GGQVSIALSS

301 HWINPRRMTD HSIKECQKSL DFVLGWFAKP VFIDGDYPES MKNNLSSILP

351 DFTESEKKFI KGTADFFALC FGPTLSFQLL DPHMKFRQLE SPNLRQLLSW

401 IDLEFNHPQI FIVENGWFVS GTTKRDDAKY MYYLKKFIME TLKAIKLDGV

451 DVIGYTAWSL MDGFEWHRGY SIRRGLFYVD FLSQDKMLLP KSSALFYQKL

501 IEKNGFPPLP ENQPLEGTFP CDFAWGVVDN YIQVDTTLSQ FTDLNVYLWD

551 VHHSKRLIKV DGVVTKKRKS YCVDFAAIQP QIALLQEMHV THFRFSLDWA

601 LILPLGNQSQ VNHTILQYYR CMASELVRVN ITPVVALWQP MAPNQGLPRL

651 LARQGAWENP YTALAFAEYA RLCFQELGHH VKLWITMNEP YTRNMTYSAG

701 HNLLKAHALA WHVYNEKFRH AQNGKISIAL QADWIEPACP FSQKDKEVAE

751 RVLEFDIGWL AEPIFGSGDY PWVMRDWLNQ RNNFLLPYFT EDEKKLIQGT

801 FDFLALSHYT TILVDSEKED PIKYNDYLEV QEMTDITWLN SPSQVAVVPW

851 GLRKVLNWLK FKYGDLPMYI ISNGIDDGLH AEDDQLRVYY MQNYINEALK

901 AHILDGINLC GYFAYSFNDR TAPRFGLYRY AADQFEPKAS MKHYRKIIDS

951 NGFPGPETLE RFCPEEFTVC TECSFFHTRK SLGSGGGGSG GGGSGGGGSL

1001 KYPNASPLLG SSWGGLIHLY TATARNSYHL QIHKNGHVDG APHQTIYSAL

1051 MIRSEDAGFV VITGVMSRRY LCMDFRGNIF GSHYFDPENC RFQHQTLENG

1101 YDVYHSPQYH FLVSLGRAKR AFLPGMNPPP YSQFLSRRNE IPLIHFNTPI
```

```
1151  PRRHTQSAED DSERDPLNVL KPRARMTPAP ASCSQELPSA EDNSPMASDP

1201  LGVVRGGRVN THAGGTGPEG CRPFAKFI*

FGF23 without signal peptide
(SEQ ID NO: 42)
                       YPNASP LLGSSWGGLI HLYTATARNS YHLQIHKNGH

61  VDGAPHQTIY SALMIRSEDA GFVVITGVMS RRYLCMDFRG NIFGSHYFDP ENCRFQHQTL

121  ENGYDVYHSP QYHFLVSLGR AKRAFLPGMN PPPYSQFLSR RNEIPLIHFN TPIPRRHTRS

181  AEDDSERDPL NVLKPRARMT PAPASCSQEL PSAEDNSPMA SDPLGVVRGG RVNTHAGGTG

241  PEGCRPFAKF I

FGF23(R179Q) without signal peptide
(SEQ ID NO: 43)
                       YPNASP LLGSSWGGLI HLYTATARNS YHLQIHKNGH

61  VDGAPHQTIY SALMIRSEDA GFVVITGVMS RRYLCMDFRG NIFGSHYFDP ENCRFQHQTL

121  ENGYDVYHSP QYHFLVSLGR AKRAFLPGMN PPPYSQFLSR RNEIPLIHFN TPIPRRHTQS

181  AEDDSERDPL NVLKPRARMT PAPASCSQEL PSAEDNSPMA SDPLGVVRGG RVNTHAGGTG

241  PEGCRPFAKF I sKlotho with Klotho signal peptide
(SEQ ID NO: 44)
   1  MPASAPPRRP RPPPPSLSLL LVLLGLGGRR LRAEPGDGAQ TWARFSRPPA

51  PEAAGLFQGT FPDGFLWAVG SAAYQTEGGW QQHGKGASIW DTFTHHPLAP

101  PGDSRNASLP LGAPSPLQPA TGDVASDSYN NVFRDTEALR ELGVTHYRFS

151  ISWARVLPNG SAGVPNREGL RYYRRLLERL RELGVQPVVT LYHWDLPQRL

201  QDAYGGWANR ALADHFRDYA ELCFRHFGGQ VKYWITIDNP YVVAWHGYAT

251  GRLAPGIRGS PRLGYLVAHN LLLAHAKVWH LYNTSFRPTQ GGQVSIALSS

301  HWINPRRMTD HSIKECQKSL DFVLGWFAKP VFIDGDYPES MKNNLSSILP

351  DFTESEKKFI KGTADFFALC FGPTLSFQLL DPHMKFRQLE SPNLRQLLSW

401  IDLEFNHPQI FIVENGWFVS GTTKRDDAKY MYYLKKFIME TLKAIKLDGV

451  DVIGYTAWSL MDGFEWHRGY SIRRGLFYVD FLSQDKMLLP KSSALFYQKL

501  IEKNGFPPLP ENQPLEGTFP CDFAWGVVDN YIQVDTTLSQ FTDLNVYLWD

551  VHHSKRLIKV DGVVTKKRKS YCVDFAAIQP QIALLQEMHV THFRFSLDWA

601  LILPLGNQSQ VNHTILQYYR CMASELVRVN ITPVVALWQP MAPNQGLPRL

651  LARQGAWENP YTALAFAEYA RLCFQELGHH VKLWITMNEP YTRNMTYSAG

701  HNLLKAHALA WHVYNEKFRH AQNGKISIAL QADWIEPACP FSQKDKEVAE

751  RVLEFDIGWL AEPIFGSGDY PWVMRDWLNQ RNNFLLPYFT EDEKKLIQGT

801  FDFLALSHYT TILVDSEKED PIKYNDYLEV QEMTDITWLN SPSQVAVVPW

851  GLRKVLNWLK FKYGDLPMYI ISNGIDDGLH AEDDQLRVYY MQNYINEALK

901  AHILDGINLC GYFAYSFNDR TAPRFGLYRY AADQFEPKAS MKHYRKIIDS

951  NGFPGPETLE RFCPEEFTVC TECSFFHTRK SL sKlotho with IgG Signal peptide
(SEQ ID NO: 45)
   1  MSVLTQVLAL LLLWLTGLGG RRLRAEPGDG AQTWARFSRP PAPEAAGLFQ

51  GTFPDGFLWA VGSAAYQTEG GWQQHGKGAS IWDTFTHHPL APPGDSRNAS

101  LPLGAPSPLQ PATGDVASDS YNNVFRDTEA LRELGVTHYR FSISWARVLP

151  NGSAGVPNRE GLRYYRRLLE RLRELGVQPV VTLYHWDLPQ RLQDAYGGWA
```

-continued

```
201 NRALADHFRD YAELCFRHFG GQVKYWITID NPYVVAWHGY ATGRLAPGIR

251 GSPRLGYLVA HNLLLAHAKV WHLYNTSFRP TQGGQVSIAL SSHWINPRRM

301 TDHSIKECQK SLDFVLGWFA KPVFIDGDYP ESMKNNLSSI LPDFTESEKK

351 FIKGTADFFA LCFGPTLSFQ LLDPHMKFRQ LESPNLRQLL SWIDLEFNHP

401 QIFIVENGWF VSGTTKRDDA KYMYYLKKFI METLKAIKLD GVDVIGYTAW

451 SLMDGFEWHR GYSIRRGLFY VDFLSQDKML LPKSSALFYQ KLIEKNGFPP

501 LPENQPLEGT FPCDFAWGVV DNYIQVDTTL SQFTDLNVYL WDVHHSKRLI

551 KVDGVVTKKR KSYCVDFAAI QPQIALLQEM HVTHFRFSLD WALILPLGNQ

601 SQVNHTILQY YRCMASELVR VNITPVVALW QPMAPNQGLP RLLARQGAWE

651 NPYTALAFAE YARLCFQELG HHVKLWITMN EPYTRNMTYS AGHNLLKAHA

701 LAWHVYNEKF RHAQNGKISI ALQADWIEPA CPFSQKDKEV AERVLEFDIG

751 WLAEPIFGSG DYPWVMRDWL NQRNNFLLPY FTEDEKKLIQ GTFDFLALSH

801 YTTILVDSEK EDPIKYNDYL EVQEMTDITW LNSPSQVAVV PWGLRKVLNW

851 LKFKYGDLPM YIISNGIDDG LHAEDDQLRV YYMQNYINEA LKAHILDGIN

901 LCGYFAYSFN DRTAPRFGLY RYAADQFEPK ASMKHYRKII DSNGFPGPET

951 LERFCPEEFT VCTECSFFHT RKSL* sKlotho-FGF23-FcLALA v1
(SEQ ID NO: 46)
    1 ATGCCCGCCA GCGCCCCGCC GCGCCGCCCG CGGCCGCCGC CGCCGTCGCT GTCGCTGCTG

61 CTGGTGCTGC TGGGCCTGGG CGGCCGCCGC CTGCGTGCGG AGCCGGGCGA CGGCGCGCAG

121 ACCTGGGCCC GTTTCTCGCG GCCTCCTGCC CCCGAGGCCG CGGGCCTCTT CCAGGGCACC

181 TTCCCCGACG GCTTCCTCTG GGCCGTGGGC AGCGCCGCCT ACCAGACCGA GGGCGGCTGG

241 CAGCAGCACG GCAAGGGTGC GTCCATCTGG GATACGTTCA CCCACCACCC CCTGGCACCC

301 CCGGGAGACT CCCGGAACGC CAGTCTGCCG TTGGGCGCCC CGTCGCCGCT GCAGCCCGCC

361 ACCGGGGACG TAGCCAGCGA CAGCTACAAC AACGTCTTCC GCGACACGGA GGCGCTGCGC

421 GAGCTCGGGG TCACTCACTA CCGCTTCTCC ATCTCGTGGG CGCGAGTGCT CCCCAATGGC

481 AGCGCGGGCG TCCCCAACCG CGAGGGGCTG CGCTACTACC GGCGCCTGCT GGAGCGGCTG

541 CGGGAGCTGG GCGTGCAGCC CGTGGTCACC CTGTACCACT GGGACCTGCC CCAGCGCCTG

601 CAGGACGCCT ACGGCGGCTG GGCCAACCGC GCCCTGGCCG ACCACTTCAG GGATTACGCG

661 GAGCTCTGCT TCCGCCACTT CGGCGGTCAG GTCAAGTACT GGATCACCAT CGACAACCCC

721 TACGTGGTGG CCTGGCACGG CTACGCCACC GGGCGCCTGG CCCCCGGCAT CCGGGGCAGC

781 CCGCGGCTCG GGTACCTGGT GGCGCACAAC CTCCTCCTGG CTCATGCCAA AGTCTGGCAT

841 CTCTACAATA CTTCTTTCCG TCCCACTCAG GGAGGTCAGG TGTCCATTGC CTAAGCTCT

901 CACTGGATCA ATCCTCGAAG AATGACCGAC CACAGCATCA AGAATGTCA AAAATCTCTG

961 GACTTTGTAC TAGGTTGGTT TGCCAAACCC GTATTTATTG ATGGTGACTA TCCCGAGAGC

1021 ATGAAGAATA ACCTTTCATC TATTCTGCCT GATTTTACTG AATCTGAGAA AAAGTTCATC

1081 AAAGGAACTG CTGACTTTTT TGCTCTTTGC TTTGGACCCA CCTTGAGTTT TCAACTTTTG

1141 GACCCTCACA TGAAGTTCCG CCAATTGGAA TCTCCCAACC TGAGGCAACT GCTTCCTGG

1201 ATTGACCTTG AATTTAACCA TCCTCAAATA TTTATTGTGG AAAATGGCTG GTTTGTCTCA

1261 GGGACCACCA AGAGAGATGA TGCCAAATAT ATGTATTACC TCAAAAAGTT CATCATGGAA

1321 ACCTTAAAAG CCATCAAGCT GGATGGGGTG GATGTCATCG GTATACCGC ATGGTCCCTC

1381 ATGGATGGTT TCGAGTGGCA CAGAGGTTAC AGCATCAGGC GTGGACTCTT CTATGTTGAC
```

```
1441 TTTCTAAGCC AGGACAAGAT GTTGTTGCCA AAGTCTTCAG CCTTGTTCTA CCAAAAGCTG

1501 ATAGAGAAAA ATGGCTTCCC TCCTTTACCT GAAAATCAGC CCCTAGAAGG GACATTTCCC

1561 TGTGACTTTG CTTGGGGAGT TGTTGACAAC TACATTCAAG TAGATACCAC TCTGTCTCAG

1621 TTTACCGACC TGAATGTTTA CCTGTGGGAT GTCCACCACA GTAAAAGGCT TATTAAAGTG

1681 GATGGGGTTG TGACCAAGAA GAGGAAATCC TACTGTGTTG ACTTTGCTGC CATCCAGCCC

1741 CAGATCGCTT TACTCCAGGA AATGCACGTT ACACATTTTC GCTTCTCCCT GGACTGGGCC

1801 CTGATTCTCC CTCTGGGTAA CCAGTCCCAG GTGAACCACA CCATCCTGCA GTACTATCGC

1861 TGCATGGCCA GCGAGCTTGT CCGTGTCAAC ATCACCCCAG TGGTGGCCCT GTGGCAGCCT

1921 ATGGCCCCGA ACCAAGGACT GCCGCGCCTC CTGGCCAGGC AGGGCGCCTG GGAGAACCCC

1981 TACACTGCCC TGGCCTTTGC AGAGTATGCC CGACTGTGCT TTCAAGAGCT CGGCCATCAC

2041 GTCAAGCTTT GGATAACGAT GAATGAGCCG TATACAAGGA ATATGACATA CAGTGCTGGC

2101 CACAACCTTC TGAAGGCCCA TGCCCTGGCT TGGCATGTGT ACAATGAAAA GTTTAGGCAT

2161 GCTCAGAATG GAAAATATC CATAGCCTTG CAGGCTGATT GGATAGAACC TGCCTGCCCT

2221 TTCTCCCAAA AGGACAAAGA GGTGGCCGAG AGAGTTTTGG AATTTGACAT TGGCTGGCTG

2281 GCTGAGCCCA TTTTCGGCTC TGGAGATTAT CCATGGGTGA TGAGGGACTG GCTGAACCAA

2341 AGAAACAATT TTCTTCTTCC TTATTTCACT GAAGATGAAA AAAAGCTAAT CCAGGGTACC

2401 TTTGACTTTT TGGCTTTAAG CCATTATACC ACCATCCTTG TAGACTCAGA AAAAGAAGAT

2461 CCAATAAAAT ACAATGATTA CCTAGAAGTG CAAGAAATGA CCGACATCAC GTGGCTCAAC

2521 TCCCCCAGTC AGGTGGCGGT AGTGCCCTGG GGGTTGCGCA AAGTGCTGAA CTGGCTGAAG

2581 TTCAAGTACG GAGACCTCCC CATGTACATA ATATCCAACG GAATCGATGA CGGGCTGCAT

2641 GCTGAGGACG ACCAGCTGAG GGTGTATTAT ATGCAGAATT ACATAAACGA AGCTCTCAAA

2701 GCCCACATAC TGGATGGTAT CAATCTTTGC GGATACTTTG CTTATTCGTT TAACGACCGC

2761 ACAGCTCCGA GGTTTGGCCT CTATCGTTAT GCTGCAGATC AGTTTGAGCC CAAGGCATCC

2821 ATGAAACATT ACAGGAAAAT TATTGACAGC AATGGTTTCC CGGGCCCAGA AACTCTGGAA

2881 AGATTTTGTC CAGAAGAATT CACCGTGTGT ACTGAGTGCA GTTTTTTTCA CACCCGAAAG

2941 TCTTTAGGAT CCGGAGGTGG AGGTTCAGGA GGTGGAGGTT CAGGAGGTGG AGGTTCACTT

3001 AAGTATCCCA ATGCCTCCCC ACTGCTCGGC TCCAGCTGGG GTGGCCTGAT CCACCTGTAC

3061 ACAGCCACAG CCAGGAACAG CTACCACCTG CAGATCCACA AGAATGGCCA TGTGGATGGC

3121 GCACCCCATC AGACCATCTA CAGTGCCCTG ATGATCAGAT CAGAGGATGC TGGCTTTGTG

3181 GTGATTACAG GTGTGATGAG CAGAAGATAC CTCTGCATGG ATTTCAGAGG CAACATTTTT

3241 GGATCACACT ATTTCGACCC GGAGAACTGC AGGTTCCAAC ACCAGACGCT GGAAAACGGG

3301 TACGACGTCT ACCACTCTCC TCAGTATCAC TTCCTGGTCA GTCTGGGCCG GGCGAAGAGA

3361 GCCTTCCTGC AGGCATGAA CCCACCCCCG TACTCCCAGT TCCTGTCCCG GAGGAACGAG

3421 ATCCCCCTAA TTCACTTCAA CACCCCCATA CCACGGCGGC ACACCCAGAG CGCCGAGGAC

3481 GACTCGGAGC GGGACCCCCT GAACGTGCTG AAGCCCCGGG CCCGGATGAC CCCGGCCCCG

3541 GCCTCCTGTT CACAGGAGCT CCCGAGCGCC GAGGACAACA GCCCGATGGC CAGTGACCCA

3601 TTAGGGGTGG TCAGGGGCGG TCGAGTGAAC ACGCACGCTG GGGAACGGGC CCGGAAGGC

3661 TGCCGCCCCT TCGCCAAGTT CATCGGAGGT GGAGGTTCAA AAACCCACAC GTGTCCTCCT

3721 TGTCCTGCCC CAGAAGCAGC AGGTGGTCCA TCAGTTTTTC TTTTCCCTCC CAAACCCAAG

3781 GATACGCTGA TGATCTCTCG CACGCCTGAG GTGACATGCG TCGTAGTAGA CGTGAGCCAC
```

```
3841 GAAGATCCCG AGGTGAAGTT CAATTGGTAT GTGGACGGAG TAGAAGTGCA TAACGCGAAA

3901 ACTAAGCCGC GCGAGGAACA ATATAACAGT ACTTACAGGG TGGTATCCGT GCTCACAGTC

3961 CTGCACCAGG ACTGGCTGAA CGGTAAGGAA TACAAGTGCA AGTAAGCAA CAAGGCACTT

4021 CCCGCGCCTA TTGAGAAAAC AATCTCCAAG GCGAAGGGAC AACCAAGAGA ACCTCAGGTT

4081 TACACTCTCC CGCCTTCCAG GGAAGAGATG ACCAAAAATC AAGTTTCCCT GACTTGCCTC

4141 GTCAAAGGAT TCTACCCTTC CGACATTGCT GTTGAATGGG AAAGCAATGG ACAACCAGAG

4201 AACAACTACA AGACAACACC CCCGGTGCTG GATAGTGACG GATCTTTCTT TCTCTACTCA

4261 AAGCTGACCG TGGATAAGTC CAGGTGGCAG CAGGGAAACG TGTTTTCCTG CTCTGTCATG

4321 CATGAAGCGC TGCATAATCA CTATACCCAG AAGTCTCTGA GCTTGAGCCC AGGCAAGTAA
``` sKlotho-FGF23-FcLALA v1
(SEQ ID NO: 47)
```
   1 MPASAPPRRP RPPPPSLSLL LVLLGLGGRR LRAEPGDGAQ TWARFSRPPA

51 PEAAGLFQGT FPDGFLWAVG SAAYQTEGGW QQHGKGASIW DTFTHHPLAP

101 PGDSRNASLP LGAPSPLQPA TGDVASDSYN NVFRDTEALR ELGVTHYRFS

151 ISWARVLPNG SAGVPNREGL RYYRRLLERL RELGVQPVVT LYHWDLPQRL

201 QDAYGGWANR ALADHFRDYA ELCFRHFGGQ VKYWITIDNP YVVAWHGYAT

251 GRLAPGIRGS PRLGYLVAHN LLLAHAKVWH LYNTSFRPTQ GGQVSIALSS

301 HWINPRRMTD HSIKECQKSL DFVLGWFAKP VFIDGDYPES MKNNLSSILP

351 DFTESEKKFI KGTADFFALC FGPTLSFQLL DPHMKFRQLE SPNLRQLLSW

401 IDLEFNHPQI FIVENGWFVS GTTKRDDAKY MYYLKKFIME TLKAIKLDGV

451 DVIGYTAWSL MDGFEWHRGY SIRRGLFYVD FLSQDKMLLP KSSALFYQKL

501 IEKNGFPPLP ENQPLEGTFP CDFAWGVVDN YIQVDTTLSQ FTDLNVYLWD

551 VHHSKRLIKV DGVVTKKRKS YCVDFAAIQP QIALLQEMHV THFRFSLDWA

601 LILPLGNQSQ VNHTILQYYR CMASELVRVN ITPVVALWQP MAPNQGLPRL

651 LARQGAWENP YTALAFAEYA RLCFQELGHH VKLWITMNEP YTRNMTYSAG

701 HNLLKAHALA WHVYNEKFRH AQNGKISIAL QADWIEPACP FSQKDKEVAE

751 RVLEFDIGWL AEPIFGSGDY PWVMRDWLNQ RNNFLLPYFT EDEKKLIQGT

801 FDFLALSHYT TILVDSEKED PIKYNDYLEV QEMTDITWLN SPSQVAVVPW

851 GLRKVLNWLK FKYGDLPMYI ISNGIDDGLH AEDDQLRVYY MQNYINEALK

901 AHILDGINLC GYFAYSFNDR TAPRFGLYRY AADQFEPKAS MKHYRKIIDS

951 NGFPGPETLE RFCPEEFTVC TECSFFHTRK SLGSGGGGSG GGGSGGGGSL

1001 KYPNASPLLG SSWGGLIHLY TATARNSYHL QIHKNGHVDG APHQTIYSAL

1051 MIRSEDAGFV VITGVMSRRY LCMDFRGNIF GSHYFDPENC RFQHQTLENG

1101 YDVYHSPQYH FLVSLGRAKR AFLPGMNPPP YSQFLSRRNE IPLIHFNTPI

1151 PRRHTQSAED DSERDPLNVL KPRARMTPAP ASCSQELPSA EDNSPMASDP

1201 LGVVRGGRVN THAGGTGPEG CRPFAKFIGG GGSKTHTCPP CPAPEAAGGP

1251 SVFLFPPKPK DTLMISRTPE VTCVVVDVSH EDPEVKFNWY VDGVEVHNAK

1301 TKPREEQYNS TYRVVSVLTV LHQDWLNGKE YKCKVSNKAL RAPIEKTISK

1351 AKGQPREPQV YTLPPSREEM TKNQVSLTCL VKGFYPSDIA VEWESNGQPE

1401 NNYKTTPPVL DSDGSFFLYS KLTVDKSRWQ QGNVFSCSVM HEALHNHYTQ

1451 KSLSLSPGK*
``` sKlotho-FGF23-FcLALA v2
(SEQ ID NO: 48)

```
   1 ATGCCCGCCA GCGCCCCGCC GCGCCGCCCG CGGCCGCCGC CGCCGTCGCT GTCGCTGCTG
  61 CTGGTGCTGC TGGGCCTGGG CGGCCGCCGC CTGCGTGCGG AGCCGGGCGA CGGCGCGCAG
 121 ACCTGGGCCC GTTTCTCGCG GCCTCCTGCC CCCGAGGCCG CGGGCCTCTT CCAGGGCACC
 181 TTCCCCGACG GCTTCCTCTG GGCCGTGGGC AGCGCCGCCT ACCAGACCGA GGGCGGCTGG
 241 CAGCAGCACG GCAAGGGTGC GTCCATCTGG GATACGTTCA CCCACCACCC CCTGGCACCC
 301 CCGGGAGACT CCCGGAACGC CAGTCTGCCG TTGGGCGCCC CGTCGCCGCT GCAGCCCGCC
 361 ACCGGGGACG TAGCCAGCGA CAGCTACAAC AACGTCTTCC GCGACACGGA GGCGCTGCGC
 421 GAGCTCGGGG TCACTCACTA CCGCTTCTCC ATCTCGTGGG CGCGAGTGCT CCCCAATGGC
 481 AGCGCGGGCG TCCCCAACCG CGAGGGGCTG CGCTACTACC GGCGCCTGCT GGAGCGGCTG
 541 CGGGAGCTGG GCGTGCAGCC CGTGGTCACC CTGTACCACT GGGACCTGCC CCAGCGCCTG
 601 CAGGACGCCT ACGGCGGCTG GGCCAACCGC GCCCTGGCCG ACCACTTCAG GGATTACGCG
 661 GAGCTCTGCT TCCGCCACTT CGGCGGTCAG GTCAAGTACT GGATCACCAT CGACAACCCC
 721 TACGTGGTGG CCTGGCACGG CTACGCCACC GGGCGCCTGG CCCCCGGCAT CCGGGGCAGC
 781 CCGCGGCTCG GGTACCTGGT GGCGCACAAC CTCCTCCTGG CTCATGCCAA AGTCTGGCAT
 841 CTCTACAATA CTTCTTTCCG TCCCACTCAG GGAGGTCAGG TGTCCATTGC CCTAAGCTCT
 901 CACTGGATCA ATCCTCGAAG AATGACCGAC CACAGCATCA AGAATGTCA AAAATCTCTG
 961 GACTTTGTAC TAGGTTGGTT TGCCAAACCC GTATTTATTG ATGGTGACTA TCCCGAGAGC
1021 ATGAAGAATA ACCTTTCATC TATTCTGCCT GATTTTACTG AATCTGAGAA AAAGTTCATC
1081 AAAGGAACTG CTGACTTTTT TGCTCTTTGC TTTGGACCCA CCTTGAGTTT CAACTTTTG
1141 GACCCTCACA TGAAGTTCCG CCAATTGGAA TCTCCCAACC TGAGGCAACT GCTTTCCTGG
1201 ATTGACCTTG AATTTAACCA TCCTCAAATA TTTATTGTGG AAAATGGCTG GTTTGTCTCA
1261 GGGACCACCA AGAGAGATGA TGCCAAATAT ATGTATTACC TCAAAAAGTT CATCATGGAA
1321 ACCTTAAAAG CCATCAAGCT GGATGGGGTG GATGTCATCG GTATACCGCA TGGTCCCTC
1381 ATGGATGGTT TCGAGTGGCA CAGAGGTTAC AGCATCAGGC GTGGACTCTT CTATGTTGAC
1441 TTTCTAAGCC AGGACAAGAT GTTGTTGCCA AAGTCTTCAG CCTTGTTCTA CCAAAAGCTG
1501 ATAGAGAAAA ATGGCTTCCC TCCTTTACCT GAAAATCAGC CCCTAGAAGG ACATTTCCC
1561 TGTGACTTTG CTTGGGGAGT TGTTGACAAC TACATTCAAG TAGATACCAC TCTGTCTCAG
1621 TTTACCGACC TGAATGTTTA CCTGTGGGAT GTCCACCACA GTAAAAGGCT TATTAAAGTG
1681 GATGGGGTTG TGACCAAGAA GAGGAAATCC TACTGTGTTG ACTTTGCTGC CATCCAGCCC
1741 CAGATCGCTT TACTCCAGGA AATGCACGTT ACACATTTTC GCTTCTCCCT GGACTGGGCC
1801 CTGATTCTCC CTCTGGGTAA CCAGTCCCAG GTGAACCACA CCATCCTGCA GTACTATCGC
1861 TGCATGGCCA GCGAGCTTGT CCGTGTCAAC ATCACCCCAG TGGTGGCCCT GTGGCAGCCT
1921 ATGGCCCCGA ACCAAGGACT GCCGCGCCTC CTGGCCAGGC AGGGCGCCTG GGAGAACCCC
1981 TACACTGCCC TGGCCTTTGC AGAGTATGCC CGACTGTGCT TTCAAGAGCT CGGCCATCAC
2041 GTCAAGCTTT GGATAACGAT GAATGAGCCG TATACAAGGA ATATGACATA CAGTGCTGGC
2101 CACAACCTTC TGAAGGCCCA TGCCCTGGCT TGGCATGTGT ACAATGAAAA GTTTAGGCAT
2161 GCTCAGAATG GGAAAATATC CATAGCCTTG CAGGCTGATT GGATAGAACC TGCCTGCCCT
2221 TTCTCCCAAA AGGACAAAGA GGTGGCCGAG AGAGTTTTGG AATTTGACAT TGGCTGGCTG
2281 GCTGAGCCCA TTTTCGGCTC TGGAGATTAT CCATGGGTGA TGAGGGACTG GCTGAACCAA
```

-continued

```
2341 AGAAACAATT TCTTCTTCC TTATTTCACT GAAGATGAAA AAAAGCTAAT CCAGGGTACC

2401 TTTGACTTTT TGGCTTTAAG CCATTATACC ACCATCCTTG TAGACTCAGA AAAAGAAGAT

2461 CCAATAAAAT ACAATGATTA CCTAGAAGTG CAAGAAATGA CCGACATCAC GTGGCTCAAC

2521 TCCCCCAGTC AGGTGGCGGT AGTGCCCTGG GGGTTGCGCA AAGTGCTGAA CTGGCTGAAG

2581 TTCAAGTACG GAGACCTCCC CATGTACATA ATATCCAACG GAATCGATGA CGGGCTGCAT

2641 GCTGAGGACG ACCAGCTGAG GGTGTATTAT ATGCAGAATT ACATAAACGA AGCTCTCAAA

2701 GCCCACATAC TGGATGGTAT CAATCTTTGC GGATACTTTG CTTATTCGTT TAACGACCGC

2761 ACAGCTCCGA GGTTTGGCCT CTATCGTTAT GCTGCAGATC AGTTTGAGCC CAAGGCATCC

2821 ATGAAACATT ACAGGAAAAT TATTGACAGC AATGGTTTCC CGGGCCCAGA AACTCTGGAA

2881 AGATTTTGTC CAGAAGAATT CACCGTGTGT ACTGAGTGCA GTTTTTTTCA CCCCGAAAG

2941 TCTTTAGGAT CCGGAGGTGG AGGTTCAGGA GGTGGAGGTT CAGGAGGTGG AGGTTCACTT

3001 AAGTATCCCA ATGCCTCCCC ACTGCTCGGC TCCAGCTGGG GTGGCCTGAT CCACCTGTAC

3061 ACAGCCACAG CCAGGAACAG CTACCACCTG CAGATCCACA GAATGGCCA TGTGGATGGC

3121 GCACCCCATC AGACCATCTA CAGTGCCCTG ATGATCAGAT CAGAGGATGC TGGCTTTGTG

3181 GTGATTACAG GTGTGATGAG CAGAAGATAC CTCTGCATGG ATTTCAGAGG CAACATTTTT

3241 GGATCACACT ATTTCGACCC GGAGAACTGC AGGTTCCAAC ACCAGACGCT GGAAAACGGG

3301 TACGACGTCT ACCACTCTCC TCAGTATCAC TTCCTGGTCA GTCTGGGCCG GGCGAAGAGA

3361 GCCTTCCTGC CAGGCATGAA CCCACCCCCG TACTCCCAGT TCCTGTCCCG GAGGAACGAG

3421 ATCCCCCTAA TTCACTTCAA CACCCCCATA CCACGGCGGC ACACCCAGAG CGCCGAGGAC

3481 GACTCGGAGC GGGACCCCCT GAACGTGCTG AAGCCCCGGG CCCGGATGAC CCCGGCCCCG

3541 GCCTCCTGTT CACAGGAGCT CCCGAGCGCC GAGGACAACA GCCCGATGGC CAGTGACCCA

3601 TTAGGGGTGG TCAGGGGCGG TCGAGTGAAC ACGCACGCTG GGGAACGGG CCCGGAAGGC

3661 TGCCGCCCCT TCGCCAAGTT CATCGGAGGT GGAGGTTCAG CCCCAGAAGC AGCAGGTGGT

3721 CCATCAGTTT TTCTTTTCCC TCCCAAACCC AAGGATACGC TGATGATCTC TCGCACGCCT

3781 GAGGTGACAT GCGTCGTAGT AGACGTGAGC CACGAAGATC CCGAGGTGAA GTTCAATTGG

3841 TATGTGGACG GAGTAGAAGT GCATAACGCG AAAACTAAGC CGCGCGAGGA ACAATATAAC

3901 AGTACTTACA GGGTGGTATC CGTGCTCACA GTCCTGCACC AGGACTGGCT GAACGGTAAG

3961 GAATACAAGT GCAAAGTAAG CAACAAGGCA CTTCCCGCGC CTATTGAGAA AACAATCTCC

4021 AAGGCGAAGG GACAACCAAG AGAACCTCAG GTTTACACTC TCCCGCCTTC CAGGGAAGAG

4081 ATGACCAAAA ATCAAGTTTC CCTGACTTGC CTCGTCAAAG GATTCTACCC TTCCGACATT

4141 GCTGTTGAAT GGGAAAGCAA TGGACAACCA GAGAACAACT ACAAGACAAC ACCCCCGGTG

4201 CTGGATAGTG ACGGATCTTT CTTTCTCTAC TCAAAGCTGA CCGTGGATAA GTCCAGGTGG

4261 CAGCAGGGAA ACGTGTTTTC CTGCTCTGTC ATGCATGAAG CGCTGCATAA TCACTATACC

4321 CAGAAGTCTC TGAGCTTGAG CCCAGGCAAG TAA
``` sKlotho-FGF23-FcLALA v2
(SEQ ID NO: 49)

```
  1 MPASAPPRRP RPPPPSLSLL LVLLGLGGRR LRAEPGDGAQ TWARFSRPPA

51 PEAAGLFQGT FPDGFLWAVG SAAYQTEGGW QQHGKGASIW DTFTHHPLAP

101 PGDSRNASLP LGAPSPLQPA TGDVASDSYN NVFRDTEALR ELGVTHYRFS

151 ISWARVLPNG SAGVPNREGL RYYRRLLERL RELGVQPVVT LYHWDLPQRL

201 QDAYGGWANR ALADHFRDYA ELCFRHFGGQ VKYWITIDNP YVVAWHGYAT

251 GRLAPGIRGS PRLGYLVAHN LLLAHAKVWH LYNTSFRPTQ GGQVSIALSS
```

```
301  HWINPRRMTD HSIKECQKSL DFVLGWFAKP VFIDGDYPES MKNNLSSILP
351  DFTESEKKFI KGTADFFALC FGPTLSFQLL DPHMKFRQLE SPNLRQLLSW
401  IDLEFNHPQI FIVENGWFVS GTTKRDDAKY MYYLKKFIME TLKAIKLDGV
451  DVIGYTAWSL MDGFEWHRGY SIRRGLFYVD FLSQDKMLLP KSSALFYQKL
501  IEKNGFPPLP ENQPLEGTFP CDFAWGVVDN YIQVDTTLSQ FTDLNVYLWD
551  VHHSKRLIKV DGVVTKKRKS YCVDFAAIQP QIALLQEMHV THFRFSLDWA
601  LILPLGNQSQ VNHTILQYYR CMASELVRVN ITPVVALWQP MAPNQGLPRL
651  LARQGAWENP YTALAFAEYA RLCFQELGHH VKLWITMNEP YTRNMTYSAG
701  HNLLKAHALA WHVYNEKFRH AQNGKISIAL QADWIEPACP FSQKDKEVAE
751  RVLEFDIGWL AEPIFGSGDY PWVMRDWLNQ RNNFLLPYFT EDEKKLIQGT
801  FDFLALSHYT TILVDSEKED PIKYNDYLEV QEMTDITWLN SPSQVAVVPW
851  GLRKVLNWLK FKYGDLPMYI ISNGIDDGLH AEDDQLRVYY MQNYINEALK
901  AHILDGINLC GYFAYSFNDR TAPRFGLYRY AADQFEPKAS MKHYRKIIDS
951  NGFPGPETLE RFCPEEFTVC TECSFFHTRK SLGSGGGGSG GGGSGGGGSL
1001 KYPNASPLLG SSWGGLIHLY TATARNSYHL QIHKNGHVDG APHQTIYSAL
1051 MIRSEDAGFV VITGVMSRRY LCMDFRGNIF GSHYFDPENC RFQHQTLENG
1101 YDVYHSPQYH FLVSLGRAKR AFLPGMNPPP YSQFLSRRNE IPLIHFNTPI
1151 PRRHTQSAED DSERDPLNVL KPRARMTPAP ASCSQELPSA EDNSPMASDP
1201 LGVVRGGRVN THAGGTGPEG CRPFAKFIGG GGSAPEAAGG PSVFLFPPKP
1251 KDTLMISRTP EVTCVVVDVS HEDPEVKFNW YVDGVEVHNA KTKPREEQYN
1301 STYRVVSVLT VLHQDWLNGK EYKCKVSNKA LPAPIEKTIS KAKGQPREPQ
1351 VYTLPPSREE MTKNQVSLTC LVKGFYPSDI AVEWESNGQP ENNYKTTPPV
1401 LDSDGSFFLY SKLTVDKSRW QQGNVFSCSV MHEALHNHYT QKSLSLSPGK
1451 *

FGF23-FcLALA v1
(SEQ ID NO: 50)
   1 ATGTTGGGGG CCCGCCTCAG GCTCTGGGTC TGTGCCTTGT GCAGCGTCTG CAGCATGAGC
  61 GTCCTCAGAG CCTATCCCAA TGCCTCCCCA CTGCTCGGCT CCAGCTGGGG TGGCCTGATC
 121 CACCTGTACA CAGCCACAGC CAGGAACAGC TACCACCTGC AGATCCACAA GAATGGCCAT
 181 GTGGATGGCG CACCCCATCA GACCATCTAC AGTGCCCTGA TGATCAGATC AGAGGATGCT
 241 GGCTTTGTGG TGATTACAGG TGTGATGAGC AGAAGATACC TCTGCATGGA TTTCAGAGGC
 301 AACATTTTTG GATCACACTA TTTCGACCCG GAGAACTGCA GGTTCCAACA CCAGACGCTG
 361 GAAAACGGGT ACGACGTCTA CCACTCTCCT CAGTATCACT TCCTGGTCAG TCTGGGCCGG
 421 GCGAAGAGAG CCTTCCTGCC AGGCATGAAC CCACCCCCGT ACTCCCAGTT CCTGTCCCGG
 481 AGGAACGAGA TCCCCCTAAT TCACTTCAAC ACCCCCATAC CACGGCGGCA CACCCAGAGC
 541 GCCGAGGACG ACTCGGAGCG GGACCCCCTG AACGTGCTGA AGCCCCGGGC CCGGATGACC
 601 CCGGCCCCGG CCTCCTGTTC ACAGGAGCTC CCGAGCGCCG AGGACAACAG CCCGATGGCC
 661 AGTGACCCAT TAGGGGTGGT CAGGGGCGGT CGAGTGAACA CGCACGCTGG GGGAACGGGC
 721 CCGGAAGGCT GCCGCCCCTT CGCCAAGTTC ATCGGAGGTG GAGGTTCAAA ACCCACACG
 781 TGTCCTCCTT GTCCTGCCCC AGAAGCAGCA GGTGGTCCAT CAGTTTTTCT TTTCCCTCCC
 841 AAACCCAAGG ATACGCTGAT GATCTCTCGC ACGCCTGAGG TGACATGCGT CGTAGTAGAC
```

-continued

```
 901 GTGAGCCACG AAGATCCCGA GGTGAAGTTC AATTGGTATG TGGACGGAGT AGAAGTGCAT

961 AACGCGAAAA CTAAGCCGCG CGAGGAACAA TATAACAGTA CTTACAGGGT GGTATCCGTG

1021 CTCACAGTCC TGCACCAGGA CTGGCTGAAC GGTAAGGAAT ACAAGTGCAA AGTAAGCAAC

1081 AAGGCACTTC CCGCGCCTAT TGAGAAAACA ATCTCCAAGG CGAAGGGACA ACCAAGAGAA

1141 CCTCAGGTTT ACACTCTCCC GCCTTCCAGG GAAGAGATGA CCAAAAATCA GTTTCCCTG

1201 ACTTGCCTCG TCAAAGGATT CTACCCTTCC GACATTGCTG TTGAATGGGA AAGCAATGGA

1261 CAACCAGAGA ACAACTACAA GACAACACCC CCGGTGCTGG ATAGTGACGG ATCTTTCTTT

1321 CTCTACTCAA AGCTGACCGT GGATAAGTCC AGGTGGCAGC AGGGAAACGT GTTTTCCTGC

1381 TCTGTCATGC ATGAAGCGCT GCATAATCAC TATACCCAGA AGTCTCTGAG CTTGAGCCCA

1441 GGCAAGTAA
```

FGF23(R179Q)-FcLALAv1
(SEQ ID NO: 51)

```
   1 MLGARLRLWV CALCSVCSMS VLRAYPNASP LLGSSWGGLI HLYTATARNS

51 YHLQIHKNGH VDGAPHQTIY SALMIRSEDA GFVVITGVMS RRYLCMDFRG

101 NIFGSHYFDP ENCRFQHQTL ENGYDVYHSP QYHFLVSLGR AKRAFLPGMN

151 PPPYSQFLSR RNEIPLIHFN TPIPRRHTQS AEDDSERDPL NVLKPRARMT

201 PAPASCSQEL PSAEDNSPMA SDPLGVVRGG RVNTHAGGTG PEGCRPFAKF

251 IGGGGSKTHT CPPCPAPEAA GGPSVFLFPP KPKDTLMISR TPEVTCVVVD

301 VSHEDPEVKF NWYVDGVEVH NAKTKPREEQ YNSTYRVVSV LTVLHQDWLN

351 GKEYKCKVSN KALPAPIEKT ISKAKGQPRE PQVYTLPPSR EEMTKNQVSL

401 TCLVKGFYPS DIAVEWESNG QPENNYKTTP PVLDSDGSFF LYSKLTVDKS

451 RWQQGNVFSC SVMHEALHNH YTQKSLSLSP GK*
```

FGF23-FcLALA v2
(SEQ ID NO: 52)

```
   1 ATGTTGGGGG CCCGCCTCAG GCTCTGGGTC TGTGCCTTGT GCAGCGTCTG CAGCATGAGC

61 GTCCTCAGAG CCTATCCCAA TGCCTCCCCA CTGCTCGGCT CCAGCTGGGG TGGCCTGATC

121 CACCTGTACA CAGCCACAGC CAGGAACAGC TACCACCTGC AGATCCACAA GAATGGCCAT

181 GTGGATGGCG CACCCCATCA GACCATCTAC AGTGCCCTGA TGATCAGATC AGAGGATGCT

241 GGCTTTGTGG TGATTACAGG TGTGATGAGC AGAAGATACC TCTGCATGGA TTTCAGAGGC

301 AACATTTTTG GATCACACTA TTTCGACCCG GAGAACTGCA GGTTCCAACA CCAGACGCTG

361 GAAAACGGGT ACGACGTCTA CCACTCTCCT CAGTATCACT TCCTGGTCAG TCTGGGCCGG

421 GCGAAGAGAG CCTTCCTGCC AGGCATGAAC CCACCCCCGT ACTCCCAGTT CCTGTCCCGG

481 AGGAACGAGA TCCCCCTAAT TCACTTCAAC ACCCCCATAC CACGGCGGCA CACCCAGAGC

541 GCCGAGGACG ACTCGGAGCG GGACCCCCTG AACGTGCTGA AGCCCCGGGC CCGGATGACC

601 CCGGCCCCGG CCTCCTGTTC ACAGGAGCTC CCGAGCGCCG AGGACAACAG CCCGATGGCC

661 AGTGACCCAT TAGGGGTGGT CAGGGGCGGT CGAGTGAACA CGCACGCTGG GGGAACGGGC

721 CCGGAAGGCT GCCGCCCCTT CGCCAAGTTC ATCGGAGGTG GAGGTTCAGC CCCAGAAGCA

781 GCAGGTGGTC CATCAGTTTT TCTTTTTCCCT CCCAAACCCA AGGATACGCT GATGATCTCT

841 CGCACGCCTG AGGTGACATG CGTCGTAGTA GACGTGAGCC ACGAAGATCC CGAGGTGAAG

901 TTCAATTGGT ATGTGGACGG AGTAGAAGTG CATAACGCGA AAACTAAGCC GCGCGAGGAA

961 CAATATAACA GTACTTACAG GGTGGTATCC GTGCTCACAG TCCTGCACCA GGACTGGCTG

1021 AACGGTAAGG AATACAAGTG CAAAGTAAGC AACAAGGCAC TTCCCGCGCC TATTGAGAAA

1081 ACAATCTCCA AGGCGAAGGG ACAACCAAGA GAACCTCAGG TTTACACTCT CCCGCCTTCC
```

-continued

```
1141 AGGGAAGAGA TGACCAAAAA TCAAGTTTCC CTGACTTGCC TCGTCAAAGG ATTCTACCCT

1201 TCCGACATTG CTGTTAATG GGAAAGCAAT GGACAACCAG AGAACAACTA CAAGACAACA

1261 CCCCCGGTGC TGGATAGTGA CGGATCTTTC TTTCTCTACT CAAAGCTGAC CGTGGATAAG

1321 TCCAGGTGGC AGCAGGGAAA CGTGTTTTCC TGCTCTGTCA TGCATGAAGC GCTGCATAAT

1381 CACTATACCC AGAAGTCTCT GAGCTTGAGC CCAGGCAAGT AA
```

FGF23(R179Q)-FcLALAv2
(SEQ ID NO: 53)

```
  1 MLGARLRLWV CALCSVCSMS VLRAYPNASP LLGSSWGGLI HLYTATARNS

51 YHLQIHKNGH VDGAPHQTIY SALMIRSEDA GFVVITGVMS RRYLCMDFRG

101 NIFGSHYFDP ENCRFQHQTL ENGYDVYHSP QYHFLVSLGR AKRAFLPGMN

151 PPPYSQFLSR RNEIPLIHFN TPIPRRHTQS AEDDSERDPL NVLKPRARMT

201 PAPASCSQEL PSAEDNSPMA SDPLGVVRGG RVNTHAGGTG PEGCRPFAKF

251 IGGGGSAPEA AGGPSVFLFP PKPKDTLMIS RTPEVTCVVV DVSHEDPEVK

301 FNWYVDGVEV HNAKTKPREE QYNSTYRVVS VLTVLHQDWL NGKEYKCKVS

351 NKALPAPIEK TISKAKGQPR EPQVYTLPPS REEMTKNQVS LTCLVKGFYP

401 SDIAVEWESN GQPENNYKTT PPVLDSDGSF FLYSKLTVDK SRWQQGNVFS

451 CSVMHEALHN HYTQKSLSLS PGK*
```

Amino acid sequence of sKlotho-FGF23 (R1156Q, C1183S)
(SEQ ID NO: 54)
sKlotho: aa [amino acid] 1-982; Linker1: aa 983-1001;
FGF23: aa 1002-1228

```
   1 MPASAPPRRP RPPPPSLSLL LVLLGLGGRR LRAEPGDGAQ TWARFSRPPA

51 PEAAGLFQGT FPDGFLWAVG SAAYQTEGGW QQHGKGASIW DTFTHHPLAP

101 PGDSRNASLP LGAPSPLQPA TGDVASDSYN NVFRDTEALR ELGVTHYRFS

151 ISWARVLPNG SAGVPNREGL RYYRRLLERL RELGVQPVVT LYHWDLPQRL

201 QDAYGGWANR ALADHFRDYA ELCFRHFGGQ VKYWITIDNP YVVAWHGYAT

251 GRLAPGIRGS PRLGYLVAHN LLLAHAKVWH LYNTSFRPTQ GGQVSIALSS

301 HWINPRRMTD HSIKECQKSL DFVLGWFAKP VFIDGDYPES MKNNLSSILP

351 DFTESEKKFI KGTADFFALC FGPTLSFQLL DPHMKFRQLE SPNLRQLLSW

401 IDLEFNHPQI FIVENGWFVS GTTKRDDAKY MYYLKKFIME TLKAIKLDGV

451 DVIGYTAWSL MDGFEWHRGY SIRRGLFYVD FLSQDKMLLP KSSALFYQKL

501 IEKNGFPPLP ENQPLEGTFP CDFAWGVVDN YIQVDTTLSQ FTDLNVYLWD

551 VHHSKRLIKV DGVVTKKRKS YCVDFAAIQP QIALLQEMHV THFRFSLDWA

601 LILPLGNQSQ VNHTILQYYR CMASELVRVN ITPVVALWQP MAPNQGLPRL

651 LARQGAWENP YTALAFAEYA RLCFQELGHH VKLWITMNEP YTRNMTYSAG

701 HNLLKAHALA WHVYNEKFRH AQNGKISIAL QADWIEPACP FSQKDKEVAE

751 RVLEFDIGWL AEPIFGSGDY PWVMRDWLNQ RNNFLLPYFT EDEKKLIQGT

801 FDFLALSHYT TILVDSEKED PIKYNDYLEV QEMTDITWLN SPSQVAVVPW

851 GLRKVLNWLK FKYGDLPMYI ISNGIDDGLH AEDDQLRVYY MQNYINEALK

901 AHILDGINLC GYFAYSFNDR TAPRFGLYRY AADQFEPKAS MKHYRKIIDS

951 NGFPGPETLE RFCPEEFTVC TECSFFHTRK SLGSGGGGSG GGGSGGGGSL

1001 KYPNASPLLG SSWGGLIHLY TATARNSYHL QIHKNGHVDG APHQTIYSAL

1051 MIRSEDAGFV VITGVMSRRY LCMDFRGNIF GSHYFDPENC RFQHQTLENG
```

```
1101 YDVYHSPQYH FLVSLGRAKR AFLPGMNPPP YSQFLSRRNE IPLIHFNTPI

1151 PRRHTQSAED DSERDPLNVL KPRARMTPAP ASSSQELPSA EDNSPMASDP

1201 LGVVRGGRVN THAGGTGPEG CRPFAKFI*
```

Amino acid sequence of sKlotho-FGF23 (R1156Q, C1221S)
(SEQ ID NO: 55)
sKlotho: 1-982; Linker1: 983-1001; FGF23: 1002-1228;

```
   1 MPASAPPRRP RPPPPSLSLL LVLLGLGGRR LRAEPGDGAQ TWARFSRPPA

51 PEAAGLFQGT FPDGFLWAVG SAAYQTEGGW QQHGKGASIW DTFTHHPLAP

101 PGDSRNASLP LGAPSPLQPA TGDVASDSYN NVFRDTEALR ELGVTHYRFS

151 ISWARVLPNG SAGVPNREGL RYYRRLLERL RELGVQPVVT LYHWDLPQRL

201 QDAYGGWANR ALADHFRDYA ELCFREFGGQ VKYWITIDNP YVVAWHGYAT

251 GRLAPGIRGS PRLGYLVAHN LLLAHAKVWH LYNTSFRPTQ GGQVSIALSS

301 HWINPRRMTD HSIKECQKSL DFVLGWFAKP VFIDGDYPES MKNNLSSILP

351 DFTESEKKFI KGTADFFALC FGPTLSFQLL DPHMKFRQLE SPNLRQLLSW

401 IDLEFNHPQI FIVENGWFVS GTTKRDDAKY MYYLKKFIME TLKAIKLDGV

451 DVIGYTAWSL MDGFEWHRGY SIRRGLFYVD FLSQDKMLLP KSSALFYQKL

501 IEKNGFPPLP ENQPLEGTFP CDFAWGVVDN YIQVDTTLSQ FTDLNVYLWD

551 VHHSKRLIKV DGVVTKKRKS YCVDFAAIQP QIALLQEMHV THFRFSLDWA

601 LILPLGNQSQ VNHTILQYYR CMASELVRVN ITPVVALWQP MAPNQGLPRL

651 LARQGAWENP YTALAFAEYA RLCFQELGHH VKLWITMNEP YTRNMTYSAG

701 HNLLKAHALA WHVYNEKFRH AQNGKISIAL QADWIEPACP FSQKDKEVAE

751 RVLEFDIGWL AEPIFGSGDY PWVMRDWLNQ RNNFLLPYFT EDEKKLIQGT

801 FDFLALSHYT TILVDSEKED PIKYNDYLEV QEMTDITWLN SPSQVAVVPW

851 GLRKVLNWLK FKYGDLPMYI ISNGIDDGLH AEDDQLRVYY MQNYINEALK

901 AHILDGINLC GYFAYSFNDR TAPRFGLYRY AADQFEPKAS MKHYRKIIDS

951 NGFPGPETLE RFCPEEFTVC TECSFFHTRK SLGSGGGGSG GGGSGGGGSL

1001 KYPNASPLLG SSWGGLIHLY TATARNSYHL QIHKNGHVDG APHQTIYSAL

1051 MIRSEDAGFV VITGVMSRRY LCMDFRGNIF GSHYFDPENC RFQHQTLENG

1101 YDVYHSPQYH FLVSLGRAKR AFLPGMNPPP YSQFLSRRNE IPLIHFNTPI

1151 PRRHTQSAED DSERDPLNVL KPRARMTPAP ASCSQELPSA EDNSPMASDP

1201 LGVVRGGRVN THAGGTGPEG SRPFAKFI*
```

Amino acid sequence of sKlotho-FGF23 (R1156Q, Q1133A)
(SEQ ID NO: 56)
sKlotho: 1-982; Linker1: 983-1001; FGF23: 1002-1228

```
   1 MPASAPPRRP RPPPPSLSLL LVLLGLGGRR LRAEPGDGAQ TWARFSRPPA

51 PEAAGLFQGT FPDGFLWAVG SAAYQTEGGW QQHGKGASIW DTFTHHPLAP

101 PGDSRNASLP LGAPSPLQPA TGDVASDSYN NVFRDTEALR ELGVTHYRFS

151 ISWARVLPNG SAGVPNREGL RYYRRLLERL RELGVQPVVT LYHWDLPQRL

201 QDAYGGWANR ALADHFRDYA ELCFRHFGGQ VKYWITIDNP YVVAWHGYAT

251 GRLAPGIRGS PRLGYLVAHN LLLAHAKVWH LYNTSFRPTQ GGQVSIALSS

301 HWINPRRMTD HSIKECQKSL DFVLGWFAKP VFIDGDYPES MKNNLSSILP

351 DFTESEKKFI KGTADFFALC FGPTLSFQLL DPHMKFRQLE SPNLRQLLSW

401 IDLEFNHPQI FIVENGWFVS GTTKRDDAKY MYYLKKFIME TLKAIKLDGV

451 DVIGYTAWSL MDGFEWHRGY SIRRGLFYVD FLSQDKMLLP KSSALFYQKL
```

```
501 IEKNGFPPLP ENQPLEGTFP CDFAWGVVDN YIQVDTTLSQ FTDLNVYLWD

551 VHHSKRLIKV DGVVTKKRKS YCVDFAAIQP QIALLQEMHV THFRFSLDWA

601 LILPLGNQSQ VNHTILQYYR CMASELVRVN ITPVVALWQP MAPNQGLPRL

651 LARQGAWENP YTALAFAEYA RLCFQELGHH VKLWITMNEP YTRNMTYSAG

701 HNLLKAHALA WHVYNEKFRH AQNGKISIAL QADWIEPACP FSQKDKEVAE

751 RVLEFDIGWL AEPIFGSGDY PWVMRDWLNQ RNNFLLPYFT EDEKKLIQGT

801 FDFLALSHYT TILVDSEKED PIKYNDYLEV QEMTDITWLN SPSQVAVVPW

851 GLRKVLNWLK FKYGDLPMYI ISNGIDDGLH AEDDQLRVYY MQNYINEALK

901 AHILDGINLC GYFAYSFNDR TAPRFGLYRY AADQFEPKAS MKHYRKIIDS

951 NGFPGPETLE RFCPEEFTVC TECSFFHTRK SLGSGGGGSG GGGSGGGGSL

1001 KYPNASPLLG SSWGGLIHLY TATARNSYHL QIHKNGHVDG APHQTIYSAL

1051 MIRSEDAGFV VITGVMSRRY LCMDFRGNIF GSHYFDPENC RFQHQTLENG

1101 YDVYHSPQYH FLVSLGRAKR AFLPGMNPPP YSAFLSRRNE IPLIHFNTPI

1151 PRRHTQSAED DSERDPLNVL KPRARMTPAP ASCSQELPSA EDNSPMASDP

1201 LGVVRGGRVN THAGGTGPEG CRPFAKFI*
```

Amino acid sequence of sKlotho-FGF23 (R1156Q, C1183S, C1221S)
(SEQ ID NO: 57)
sKlotho: 1-982; Linker1: 983-1001; FGF23: 1002-1228

```
  1 MPASAPPRRP RPPPPSLSLL LVLLGLGGRR LRAEPGDGAQ TWARFSRPPA

51 PEAAGLFQGT FPDGFLWAVG SAAYQTEGGW QQHGKGASIW DTFTHHPLAP

101 PGDSRNASLP LGAPSPLQPA TGDVASDSYN NVFRDTEALR ELGVTHYRFS

151 ISWARVLPNG SAGVPNREGL RYYRRLLERL RELGVQPVVT LYHWDLPQRL

201 QDAYGGWANR ALADHFRDYA ELCFRHFGGQ VKYWITIDNP YVVAWHGYAT

251 GRLAPGIRGS PRLGYLVAHN LLLAHAKVWH LYNTSFRPTQ GGQVSIALSS

301 HWINPRRMTD HSIKECQKSL DFVLGWFAKP VFIDGDYPES MKNNLSSILP

351 DFTESEKKFI KGTADFFALC FGPTLSFQLL DPHMKFRQLE SPNLRQLLSW

401 IDLEFNHPQI FIVENGWFVS GTTKRDDAKY MYYLKKFIME TLKAIKLDGV

451 DVIGYTAWSL MDGFEWHRGY SIRRGLFYVD FLSQDKMLLP KSSALFYQKL

501 IEKNGFPPLP ENQPLEGTFP CDFAWGVVDN YIQVDTTLSQ FTDLNVYLWD

551 VHHSKRLIKV DGVVTKKRKS YCVDFAAIQP QIALLQEMHV THFRFSLDWA

601 LILPLGNQSQ VNHTILQYYR CMASELVRVN ITPVVALWQP MAPNQGLPRL

651 LARQGAWENP YTALAFAEYA RLCFQELGHH VKLWITMNEP YTRNMTYSAG

701 HNLLKAHALA WHVYNEKFRH AQNGKISIAL QADWIEPACP FSQKDKEVAE

751 RVLEFDIGWL AEPIFGSGDY PWVMRDWLNQ RNNFLLPYFT EDEKKLIQGT

801 FDFLALSHYT TILVDSEKED PIKYNDYLEV QEMTDITWLN SPSQVAVVPW

851 GLRKVLNWLK FKYGDLPMYI ISNGIDDGLH AEDDQLRVYY MQNYINEALK

901 AHILDGINLC GYFAYSFNDR TAPRFGLYRY AADQFEPKAS MKHYRKIIDS

951 NGFPGPETLE RFCPEEFTVC TECSFFHTRK SLGSGGGGSG GGGSGGGGSL

1001 KYPNASPLLG SSWGGLIHLY TATARNSYHL QIHKNGEVDG APHQTIYSAL

1051 MIRSEDAGFV VITGVMSRRY LCMDFRGNIF GSHYFDPENC RFQHQTLENG

1101 YDVYHSPQYH FLVSLGRAKR AFLPGMNPPP YSQFLSRRNE IPLIHFNTPI
```

```
1151 PRRHTQSAED DSERDPLNVL KPRARMTPAP ASSSQELPSA EDNSPMASDP

1201 LGVVRGGRVN THAGGTGPEG SRPFAKFI*
```

Amino acid sequence of sKlotho-FGF23 (R1156Q, C1183S,
C1221S, Q1133A)
(SEQ ID NO: 58)
sKlotho: 1-982; Linker1: 983-1001; FGF23: 1002-1228

```
   1 MPASAPPRRP RPPPPSLSLL LVLLGLGGRR LRAEPGDGAQ TWARFSRPPA

51 PEAAGLFQGT FPDGFLWAVG SAAYQTEGGW QQHGKGASIW DTFTHHPLAP

101 PGDSRNASLP LGAPSPLQPA TGDVASDSYN NVFRDTEALR ELGVTHYRFS

151 ISWARVLPNG SAGVPNREGL RYYRRLLERL RELGVQPVVT LYHWDLPQRL

201 QDAYGGWANR ALADHFRDYA ELCFRHFGGQ VKYWITIDNP YVVAWHGYAT

251 GRLAPGIRGS PRLGYLVAHN LLLAHAKVWH LYNTSFRPTQ GGQVSIALSS

301 HWINPRRMTD HSIKECQKSL DFVLGWFAKP VFIDGDYPES MKNNLSSILP

351 DFTESEKKFI KGTADFFALC FGPTLSFQLL DPHMKFRQLE SPNLRQLLSW

401 IDLEFNHPQI FIVENGWFVS GTTKRDDAKY MYYLKKFIME TLKAIKLDGV

451 DVIGYTAWSL MDGFEWHRGY SIRRGLFYVD FLSQDKMLLP KSSALFYQKL

501 IEKNGFPPLP ENQPLEGTFP CDFAWGVVDN YIQVDTTLSQ FTDLNVYLWD

551 VHHSKRLIKV DGVVTKKRKS YCVDFAAIQP QIALLQEMHV THFRFSLDWA

601 LILPLGNQSQ VNHTILQYYR CMASELVRVN ITPVVALWQP MAPNQGLPRL

651 LARQGAWENP YTALAFAEYA RLCFQELGHH VKLWITMNEP YTRNMTYSAG

701 HNLLKAHALA WHVYNEKFRH AQNGKISIAL QADWIEPACP FSQKDKEVAE

751 RVLEFDIGWL AEPIFGSGDY PWVMRDWLNQ RNNFLLPYFT EDEKKLIQGT

801 FDFLALSHYT TILVDSEKED PIKYNDYLEV QEMTDITWLN SPSQVAVVPW

851 GLRKVLNWLK FKYGDLPMYI ISNGIDDGLH AEDDQLRVYY MQNYINEALK

901 AHILDGINLC GYFAYSFNDR TAPRFGLYRY AADQFEPKAS MKHYRKIIDS

951 NGFPGPETLE RFCPEEFTVC TECSFFHTRK SLGSGGGGSG GGGSGGGGSL

1001 KYPNASPLLG SSWGGLIHLY TATARNSYHL QIHKNGHVDG APHQTIYSAL

1051 MIRSEDAGFV VITGVMSRRY LCMDFRGNIF GSHYFDPENC RFQHQTLENG

1101 YDVYHSPQYH FLVSLGRAKR AFLPGMNPPP YSAFLSRRNE IPLIHFNTPI

1151 PRRHTQSAED DSERDPLNVL KPRARMTPAP ASSSQELPSA EDNSPMASDP

1201 LGVVRGGRVN THAGGTGPEG SRPFAKFI*
```

Amino acid sequence of FGF23(R179Q; C206S)-FcLALAv1
(SEQ ID NO: 59)
FGF23: 1-251; Linker: 252-256; FcLALA: 257-482

```
   1 MLGARLRLWV CALCSVCSMS VLRAYPNASP LLGSSWGGLI HLYTATARNS

51 YHLQIHKNGH VDGAPHQTIY SALMIRSEDA GFVVITGVMS RRYLCMDFRG

101 NIFGSHYFDP ENCRFQHQTL ENGYDVYHSP QYHFLVSLGR AKRAFLPGMN

151 PPPYSQFLSR RNEIPLIHFN TPIPRRHTQS AEDDSERDPL NVLKPRARMT

201 PAPASSSQEL PSAEDNSPMA SDPLGVVRGG RVNTHAGGTG PEGCRPFAKF

251 IGGGGSKTHT CPPCPAPEAA GGPSVFLFPP KPKDTLMISR TPEVTCVVVD

301 VSHEDPEVKF NWYVDGVEVH NAKTKPREEQ YNSTYRVVSV LTVLHQDWLN

351 GKEYKCKVSN KALPAPIEKT ISKAKGQPRE PQVYTLPPSR EEMTKNQVSL

401 TCLVKGFYPS DIAVEWESNG QPENNYKTTP PVLDSDGSFF LYSKLTVDKS

451 RWQQGNVFSC SVMHEALHNH YTQKSLSLSP GK*
```

```
Amino acid sequence of FGF23(R179Q, C244S)-FcLALAv1
(SEQ ID NO: 60)
FGF23: 1-251; Linker: 252-256; FcLALA: 257-482
  1 MLGARLRLWV CALCSVCSMS VLRAYPNASP LLGSSWGGLI HLYTATARNS

51 YHLQIHKNGH VDGAPHQTIY SALMIRSEDA GFVVITGVMS RRYLCMDFRG

101 NIFGSHYFDP ENCRFQHQTL ENGYDVYHSP QYHFLVSLGR AKRAFLPGMN

151 PPPYSQFLSR RNEIPLIHFN TPIPRRHTQS AEDDSERDPL NVLKPRARMT

201 PAPASCSQEL PSAEDNSPMA SDPLGVVRGG RVNTHAGGTG PEGSRPFAKF

251 IGGGGSKTHT CPPCPAPEAA GGPSVFLFPP KPKDTLMISR TPEVTCVVVD

301 VSHEDPEVKF NWYVDGVEVH NAKTKPREEQ YNSTYRVVSV LTVLHQDWLN

351 GKEYKCKVSN KALPAPIEKT ISKAKGQPRE PQVYTLPPSR EEMTKNQVSL

401 TCLVKGFYPS DIAVEWESNG QPENNYKTTP PVLDSDGSFF LYSKLTVDKS

451 RWQQGNVFSC SVMHEALHNH YTQKSLSLSP GK*

Amino acid sequence of FGF23(R179Q, Q156A)-FcLALAv1
(SEQ ID NO: 61)
FGF23: 1-251; Linker: 252-256; FcLALA: 257-482
  1 MLGARLRLWV CALCSVCSMS VLRAYPNASP LLGSSWGGLI HLYTATARNS

51 YHLQIHKNGH VDGAPHQTIY SALMIRSEDA GFVVITGVMS RRYLCMDFRG

101 NIFGSHYFDP ENCRFQHQTL ENGYDVYHSP QYHFLVSLGR AKRAFLPGMN

151 PPPYSAFLSR RNEIPLIHFN TPIPRRHTQS AEDDSERDPL NVLKPRARMT

201 PAPASCSQEL PSAEDNSPMA SDPLGVVRGG RVNTHAGGTG PEGCRPFAKF

251 IGGGGSKTHT CPPCPAPEAA GGPSVFLFPP KPKDTLMISR TPEVTCVVVD

301 VSHEDPEVKF NWYVDGVEVH NAKTKPREEQ YNSTYRVVSV LTVLHQDWLN

351 GKEYKCKVSN KALPAPIEKT ISKAKGQPRE PQVYTLPPSR EEMTKNQVSL

401 TCLVKGFYPS DIAVEWESNG QPENNYKTTP PVLDSDGSFF LYSKLTVDKS

451 RWQQGNVFSC SVMHEALHNH YTQKSLSLSP GK*

Amino acid sequence of FGF23(R179Q, C206S, C244S)-FcLALAv1
(SEQ ID NO: 62)
FGF23: 1-251; Linker: 252-256; FcLALA: 257-482
  1 MLGARLRLWV CALCSVCSMS VLRAYPNASP LLGSSWGGLI HLYTATARNS

51 YHLQIHKNGH VDGAPHQTIY SALMIRSEDA GFVVITGVMS RRYLCMDFRG

101 NIFGSHYFDP ENCRFQHQTL ENGYDVYHSP QYHFLVSLGR AKRAFLPGMN

151 PPPYSQFLSR RNEIPLIHFN TPIPRRHTQS AEDDSERDPL NVLKPRARMT

201 PAPASSSQEL PSAEDNSPMA SDPLGVVRGG RVNTHAGGTG PEGSRPFAKF

251 IGGGGSKTHT CPPCPAPEAA GGPSVFLFPP KPKDTLMISR TPEVTCVVVD

301 VSHEDPEVKF NWYVDGVEVH NAKTKPREEQ YNSTYRVVSV LTVLHQDWLN

351 GKEYKCKVSN KALPAPIEKT ISKAKGQPRE PQVYTLPPSR EEMTKNQVSL

401 TCLVKGFYPS DIAVEWESNG QPENNYKTTP PVLDSDGSFF LYSKLTVDKS

451 RWQQGNVFSC SVMHEALHNH YTQKSLSLSP GK*

Amino acid sequence of FGF23(R179Q, C206S, C244S,
Q156A)-FcLALAv1
(SEQ ID NO: 63)
FGF23: 1-251; Linker: 252-256; FcLALA: 257-482
  1 MLGARLRLWV CALCSVCSMS VLRAYPNASP LLGSSWGGLI HLYTATARNS

51 YHLQIHKNGH VDGAPHQTIY SALMIRSEDA GFVVITGVMS RRYLCMDFRG

101 NIFGSHYFDP ENCRFQHQTL ENGYDVYHSP QYHFLVSLGR AKRAFLPGMN

151 PPPYSAFLSR RNEIPLIHFN TPIPRRHTQS AEDDSERDPL NVLKPRARMT
```

```
201 PAPASSSQEL PSAEDNSPMA SDPLGVVRGG RVNTHAGGTG PEGSRPFAKF

251 IGGGGSKTHT CPPCPAPEAA GGPSVFLFPP KPKDTLMISR TPEVTCVVVD

301 VSHEDPEVKF NWYVDGVEVH NAKTKPREEQ YNSTYRVVSV LTVLHQDWLN

351 GKEYKCKVSN KALPAPIEKT ISKAKGQPRE PQVYTLPPSR EEMTKNQVSL

401 TCLVKGFYPS DIAVEWESNG QPENNYKTTP PVLDSDGSFF LYSKLTVDKS

451 RWQQGNVFSC SVMHEALHNH YTQKSLSLSP GK*

Amino acid sequence of FGF23(R179Q, C206S)-FcLALAv2
(SEQ ID NO: 64)
FGF23: 1-251; Linker: 252-256; FcLALA: 257-473
  1 MLGARLRLWV CALCSVCSMS VLRAYPNASP LLGSSWGGLI HLYTATARNS

51 YHLQIHKNGH VDGAPHQTIY SALMIRSEDA GFVVITGVMS RRYLCMDFRG

101 NIFGSHYFDP ENCRFQHQTL ENGYDVYHSP QYHFLVSLGR AKRAFLPGMN

151 PPPYSQFLSR RNEIPLIHFN TPIPRRHTQS AEDDSERDPL NVLKPRARMT

201 PAPASSSQEL PSAEDNSPMA SDPLGVVRGG RVNTHAGGTG PEGCRPFAKF

251 IGGGGSAPEA AGGPSVFLFP PKPKDTLMIS RTPEVTCVVV DVSHEDPEVK

301 FNWYVDGVEV HNAKTKPREE QYNSTYRVVS VLTVLHQDWL NGKEYKCKVS

351 NKALPAPIEK TISKAKGQPR EPQVYTLPPS REEMTKNQVS LTCLVKGFYP

401 SDIAVEWESN GQPENNYKTT PPVLDSDGSF FLYSKLTVDK SRWQQGNVFS

451 CSVMHEALHN HYTQKSLSLS PGK*

Amino acid sequence of FGF23(R179Q, C244S)-FcLALAv2
(SEQ ID NO: 65)
FGF23: 1-251; Linker: 252-256; FcLALA: 257-473
  1 MLGARLRLWV CALCSVCSMS VLRAYPNASP LLGSSWGGLI HLYTATARNS

51 YHLQIHKNGH VDGAPHQTIY SALMIRSEDA GFVVITGVMS RRYLCMDFRG

101 NIFGSHYFDP ENCRFQHQTL ENGYDVYHSP QYHFLVSLGR AKRAFLPGMN

151 PPPYSQFLSR RNEIPLIHFN TPIPRRHTQS AEDDSERDPL NVLKPRARMT

201 PAPASCSQEL PSAEDNSPMA SDPLGVVRGG RVNTHAGGTG PEGSRPFAKF

251 IGGGGSAPEA AGGPSVFLFP PKPKDTLMIS RTPEVTCVVV DVSHEDPEVK

301 FNWYVDGVEV HNAKTKPREE QYNSTYRVVS VLTVLHQDWL NGKEYKCKVS

351 NKALPAPIEK TISKAKGQPR EPQVYTLPPS REEMTKNQVS LTCLVKGFYP

401 SDIAVEWESN GQPENNYKTT PPVLDSDGSF FLYSKLTVDK SRWQQGNVFS

451 CSVMHEALHN HYTQKSLSLS PGK*

Amino acid sequence of FGF23(R179Q, Q156A)-FcLALAv2
(SEQ ID NO: 66)
FGF23: 1-251; Linker: 252-256; FcLALA: 257-473
  1 MLGARLRLWV CALCSVCSMS VLRAYPNASP LLGSSWGGLI HLYTATARNS

51 YHLQIHKNGH VDGAPHQTIY SALMIRSEDA GFVVITGVMS RRYLCMDFRG

101 NIFGSHYFDP ENCRFQHQTL ENGYDVYHSP QYHFLVSLGR AKRAFLPGMN

151 PPPYSAFLSR RNEIPLIHFN TPIPRRHTQS AEDDSERDPL NVLKPRARMT

201 PAPASCSQEL PSAEDNSPMA SDPLGVVRGG RVNTHAGGTG PEGCRPFAKF

251 IGGGGSAPEA AGGPSVFLFP PKPKDTLMIS RTPEVTCVVV DVSHEDPEVK

301 FNWYVDGVEV HNAKTKPREE QYNSTYRVVS VLTVLHQDWL NGKEYKCKVS

351 NKALPAPIEK TISKAKGQPR EPQVYTLPPS REEMTKNQVS LTCLVKGFYP

401 SDIAVEWESN GQPENNYKTT PPVLDSDGSF FLYSKLTVDK SRWQQGNVFS

451 CSVMHEALHN HYTQKSLSLS PGK*
```

-continued

Amino acid sequence of FGF23(R179Q, C206S, C244S)-FcLALAv2
(SEQ ID NO: 67)
FGF23: 1-251; Linker: 252-256; FcLALA: 257-473

```
  1 MLGARLRLWV CALCSVCSMS VLRAYPNASP LLGSSWGGLI HLYTATARNS

51 YHLQIHKNGH VDGAPHQTIY SALMIRSEDA GFVVITGVMS RRYLCMDFRG

101 NIFGSHYFDP ENCRFQHQTL ENGYDVYHSP QYHFLVSLGR AKRAFLPGMN

151 PPPYSQFLSR RNEIPLIHFN TPIPRRHTQS AEDDSERDPL NVLKPRARMT

201 PAPASSSQEL PSAEDNSPMA SDPLGVVRGG RVNTHAGGTG PEGSRPFAKF

251 IGGGGSAPEA AGGPSVFLFP PKPKDTLMIS RTPEVTCVVV DVSHEDPEVK

301 FNWYVDGVEV HNAKTKPREE QYNSTYRVVS VLTVLHQDWL NGKEYKCKVS

351 NKALPAPIEK TISKAKGQPR EPQVYTLPPS REEMTKNQVS LTCLVKGFYP

401 SDIAVEWESN GQPENNYKTT PPVLDSDGSF FLYSKLTVDK SRWQQGNVFS

451 CSVMHEALHN HYTQKSLSLS PGK*
```

Amino acid sequence of FGF23(R179Q, C206S, C244S, Q156A)-FcLALAv2
(SEQ ID NO: 68)
FGF23: 1-251; Linker: 252-256; FcLALA: 257-473

```
  1 MLGARLRLWV CALCSVCSMS VLRAYPNASP LLGSSWGGLI HLYTATARNS

51 YHLQIHKNGH VDGAPHQTIY SALMIRSEDA GFVVITGVMS RRYLCMDFRG

101 NIFGSHYFDP ENCRFQHQTL ENGYDVYHSP QYHFLVSLGR AKRAFLPGMN

151 PPPYSAFLSR RNEIPLIHFN TPIPRRHTQS AEDDSERDPL NVLKPRARMT

201 PAPASSSQEL PSAEDNSPMA SDPLGVVRGG RVNTHAGGTG PEGSRPFAKF

251 IGGGGSAPEA AGGPSVFLFP PKPKDTLMIS RTPEVTCVVV DVSHEDPEVK

301 FNWYVDGVEV HNAKTKPREE QYNSTYRVVS VLTVLHQDWL NGKEYKCKVS

351 NKALPAPIEK TISKAKGQPR EPQVYTLPPS REEMTKNQVS LTCLVKGFYP

401 SDIAVEWESN GQPENNYKTT PPVLDSDGSF FLYSKLTVDK SRWQQGNVFS

451 CSVMHEALHN HYTQKSLSLS PGK*
```

In the following sequences, certain mutations in FGF23
(e.g., Y154D, Y154C, C206S, C244S) are underlined.
Amino acid sequence of FGF23(R179Q, Y154D)-FcLALAv2
(SEQ ID NO: 69):
FGF23: 1-251; Linker: 252-256; FcLALA: 257-473

```
  1 MLGARLRLWV CALCSVCSMS VLRAYPNASP LLGSSWGGLI HLYTATARNS

51 YHLQIHKNGH VDGAPHQTIY SALMIRSEDA GFVVITGVMS RRYLCMDFRG

101 NIFGSHYFDP ENCRFQHQTL ENGYDVYHSP QYHFLVSLGR AKRAFLPGMN

151 PPPDSQFLSR RNEIPLIHFN TPIPRRHTQS AEDDSERDPL NVLKPRARMT

201 PAPTSCSQEL PSAEDNSPMA SDPLGVVRGG RVNTHAGGTG PEGCRPFAKF

251 IGGGGSAPEA AGGPSVFLFP PKPKDTLMIS RTPEVTCVVV DVSHEDPEVK

301 FNWYVDGVEV HNAKTKPREE QYNSTYRVVS VLTVLHQDWL NGKEYKCKVS

351 NKALPAPIEK TISKAKGQPR EPQVYTLPPS REEMTKNQVS LTCLVKGFYP

401 SDIAVEWESN GQPENNYKTT PPVLDSDGSF FLYSKLTVDK SRWQQGNVFS

451 CSVMHEALHN HYTQKSLSLS PGK*
```

Amino acid sequence of FGF23(R179Q, Y154D, C206S, C244S)-FcLALAv2
(SEQ ID NO: 70)
FGF23: 1-251; Linker: 252-256; FcLALA: 257-473

```
  1 MLGARLRLWV CALCSVCSMS VLRAYPNASP LLGSSWGGLI HLYTATARNS

51 YHLQIHKNGH VDGAPHQTIY SALMIRSEDA GFVVITGVMS RRYLCMDFRG

101 NIFGSHYFDP ENCRFQHQTL ENGYDVYHSP QYHFLVSLGR AKRAFLPGMN
```

-continued

```
151 PPPDSQFLSR RNEIPLIHFN TPIPRRHTQS AEDDSERDPL NVLKPRARMT

201 PAPASSSQEL PSAEDNSPMA SDPLGVVRGG RVNTHAGGTG PEGSRPFAKF

251 IGGGGSAPEA AGGPSVFLFP PKPKDTLMIS RTPEVTCVVV DVSHEDPEVK

301 FNWYVDGVEV HNAKTKPREE QYNSTYRVVS VLTVLHQDWL NGKEYKCKVS

351 NKALPAPIEK TISKAKGQPR EPQVYTLPPS REEMTKNQVS LTCLVKGFYP

401 SDIAVEWESN GQPENNYKTT PPVLDSDGSF FLYSKLTVDK SRWQQGNVFS

451 CSVMHEALHN HYTQKSLSLS PGK*
```

Amino acid sequence of FGF23(R179Q, Y154C)-FcLALAv2
(SEQ ID NO: 71)
FGF23: 1-251; Linker: 252-256; FcLALA: 257-473

```
  1 MLGARLRLWV CALCSVCSMS VLRAYPNASP LLGSSWGGLI HLYTATARNS

51 YHLQIHKNGH VDGAPHQTIY SALMIRSEDA GFVVITGVMS RRYLCMDFRG

101 NIFGSHYFDP ENCRFQHQTL ENGYDVYHSP QYHFLVSLGR AKRAFLPGMN

151 PPPCSQFLSR RNEIPLIHFN TPIPRRHTQS AEDDSERDPL NVLKPRARMT

201 PAPASCSQEL PSAEDNSPMA SDPLGVVRGG RVNTHAGGTG PEGCRPFAKF

251 IGGGGSAPEA AGGPSVFLFP PKPKDTLMIS RTPEVTCVVV DVSHEDPEVK

301 FNWYVDGVEV HNAKTKPREE QYNSTYRVVS VLTVLHQDWL NGKEYKCKVS

351 NKALPAPIEK TISKAKGQPR EPQVYTLPPS REEMTKNQVS LTCLVKGFYP

401 SDIAVEWESN GQPENNYKTT PPVLDSDGSF FLYSKLTVDK SRWQQGNVFS

451 CSVMHEALHN HYTQKSLSLS PGK*
```

Amino acid sequence of FGF23(R179Q, Y154C, C206S, C244S)-FcLALAv2
(SEQ ID NO: 72):
FGF23: 1-251; Linker: 252-256; FcLALA: 257-473

```
  1 MLGARLRLWV CALCSVCSMS VLRAYPNASP LLGSSWGGLI HLYTATARNS

51 YHLQIHKNGH VDGAPHQTIY SALMIRSEDA GFVVITGVMS RRYLCMDFRG

101 NIFGSHYFDP ENCRFQHQTL ENGYDVYHSP QYHFLVSLGR AKRAFLPGMN

151 PPPCSQFLSR RNEIPLIHFN TPIPRRHTQS AEDDSERDPL NVLKPRARMT

201 PAPASSSQEL PSAEDNSPMA SDPLGVVRGG RVNTHAGGTG PEGSRPFAKF

251 IGGGGSAPEA AGGPSVFLFP PKPKDTLMIS RTPEVTCVVV DVSHEDPEVK

301 FNWYVDGVEV HNAKTKPREE QYNSTYRVVS VLTVLHQDWL NGKEYKCKVS

351 NKALPAPIEK TISKAKGQPR EPQVYTLPPS REEMTKNQVS LTCLVKGFYP

401 SDIAVEWESN GQPENNYKTT PPVLDSDGSF FLYSKLTVDK SRWQQGNVFS

451 CSVMHEALHN HYTQKSLSLS PGK*
```

Nucleotide sequence of FGF23(R179Q, Y154D)-FcLALAv2
(SEQ ID NO: 73)

```
  1 ATGTTGGGGG CCCGCCTCAG GCTCTGGGTC TGTGCCTTGT GCAGCGTCTG CAGCATGAGC

61 GTCCTCAGAG CCTATCCCAA TGCCTCCCCA CTGCTCGGCT CCAGCTGGGG TGGCCTGATC

121 CACCTGTACA CAGCCACAGC CAGGAACAGC TACCACCTGC AGATCCACAA GAATGGCCAT

181 GTGGATGGCG CACCCCATCA GACCATCTAC AGTGCCCTGA TGATCAGATC AGAGGATGCT

241 GGCTTTGTGG TGATTACAGG TGTGATGAGC AGAAGATACC TCTGCATGGA TTTCAGAGGC

301 AACATTTTTG GATCACACTA TTTCGACCCG GAGAACTGCA GGTTCCAACA CCAGACGCTG

361 GAAAACGGGT ACGACGTCTA CCACTCTCCT CAGTATCACT TCCTGGTCAG TCTGGGCCGG

421 GCGAAGAGAG CCTTCCTGCC AGGCATGAAC CCACCCCCGG ACTCCCAGTT CCTGTCCCGG

481 AGGAACGAGA TCCCCCTAAT TCACTTCAAC ACCCCCATAC CACGGCGGCA CACCCAGAGC
```

```
541 GCCGAGGACG ACTCGGAGCG GGACCCCCTG AACGTGCTGA AGCCCCGGGC CCGGATGACC

601 CCGGCCCCGG CCTCCTGTTC ACAGGAGCTC CCGAGCGCCG AGGACAACAG CCCGATGGCC

661 AGTGACCCAT TAGGGGTGGT CAGGGGCGGT CGAGTGAACA CGCACGCTGG GGGAACGGGC

721 CCGGAAGGCT GCCGCCCCTT CGCCAAGTTC ATCGGAGGTG GAGGTCAGC CCCAGAAGCA

781 GCAGGTGGTC CATCAGTTTT TCTTTTCCCT CCCAAACCCA AGGATACGCT GATGATCTCT

841 CGCACGCCTG AGGTGACATG CGTCGTAGTA GACGTGAGCC ACGAAGATCC CGAGGTGAAG

901 TTCAATTGGT ATGTGGACGG AGTAGAAGTG CATAACGCGA AAACTAAGCC GCGCGAGGAA

961 CAATATAACA GTACTTACAG GGTGGTATCC GTGCTCACAG TCCTGCACCA GGACTGGCTG

1021 AACGGTAAGG AATACAAGTG CAAAGTAAGC AACAAGGCAC TTCCCGCGCC TATTGAGAAA

1081 ACAATCTCCA AGGCGAAGGG ACAACCAAGA GAACCTCAGG TTTACACTCT CCCGCCTTCC

1141 AGGGAAGAGA TGACCAAAAA TCAAGTTTCC CTGACTTGCC TCGTCAAAGG ATTCTACCCT

1201 TCCGACATTG CTGTTGAATG GGAAAGCAAT GGACAACCAG AGAACAACTA CAAGACAACA

1261 CCCCCGGTGC TGGATAGTGA CGGATCTTTC TTTCTCTACT CAAAGCTGAC CGTGGATAAG

1321 TCCAGGTGGC AGCAGGGAAA CGTGTTTTCC TGCTCTGTCA TGCATGAAGC GCTGCATAAT

1381 CACTATACCC AGAAGTCTCT GAGCTTGAGC CCAGGCAAGT AA

Nucleotide sequence of FGF23(R179Q, Y154D, C206S, C244S)-FcLALAv2
(SEQ ID NO: 74)
   1 ATGTTGGGGG CCCGCCTCAG GCTCTGGGTC TGTGCCTTGT GCAGCGTCTG CAGCATGAGC

61 GTCCTCAGAG CCTATCCCAA TGCCTCCCCA CTGCTCGGCT CCAGCTGGGG TGGCCTGATC

121 CACCTGTACA CAGCCACAGC CAGGAACAGC TACCACCTGC AGATCCACAA GAATGGCCAT

181 GTGGATGGCG CACCCCATCA GACCATCTAC AGTGCCCTGA TGATCAGATC AGAGGATGCT

241 GGCTTTGTGG TGATTACAGG TGTGATGAGC AGAAGATACC TCTGCATGGA TTTCAGAGGC

301 AACATTTTTG GATCACACTA TTTCGACCCG GAGAACTGCA GGTTCCAACA CCAGACGCTG

361 GAAAACGGGT ACGACGTCTA CCACTCTCCT CAGTATCACT TCCTGGTCAG TCTGGGCCGG

421 GCGAAGAGAG CCTTCCTGCC AGGCATGAAC CCACCCCCGG AC**TCCCAGTT CCTGTCCCGG

481 AGGAACGAGA TCCCCCTAAT TCACTTCAAC ACCCCCATAC CACGGCGGCA CACCCAGAGC

541 GCCGAGGACG ACTCGGAGCG GGACCCCCTG AACGTGCTGA AGCCCCGGGC CCGGATGACC

601 CCGGCCCCGG CCTCCTCTTC ACAGGAGCTC CCGAGCGCCG AGGACAACAG CCCGATGGCC

661 AGTGACCCAT TAGGGGTGGT CAGGGGCGGT CGAGTGAACA CGCACGCTGG GGGAACGGGC

721 CCGGAAGGCT CCCGCCCCTT CGCCAAGTTC ATCGGAGGTG GAGGTCAGC CCCAGAAGCA

781 GCAGGTGGTC CATCAGTTTT TCTTTTCCCT CCCAAACCCA AGGATACGCT GATGATCTCT

841 CGCACGCCTG AGGTGACATG CGTCGTAGTA GACGTGAGCC ACGAAGATCC CGAGGTGAAG

901 TTCAATTGGT ATGTGGACGG AGTAGAAGTG CATAACGCGA AAACTAAGCC GCGCGAGGAA

961 CAATATAACA GTACTTACAG GGTGGTATCC GTGCTCACAG TCCTGCACCA GGACTGGCTG

1021 AACGGTAAGG AATACAAGTG CAAAGTAAGC AACAAGGCAC TTCCCGCGCC TATTGAGAAA

1081 ACAATCTCCA AGGCGAAGGG ACAACCAAGA GAACCTCAGG TTTACACTCT CCCGCCTTCC

1141 AGGGAAGAGA TGACCAAAAA TCAAGTTTCC CTGACTTGCC TCGTCAAAGG ATTCTACCCT

1201 TCCGACATTG CTGTTGAATG GGAAAGCAAT GGACAACCAG AGAACAACTA CAAGACAACA

1261 CCCCCGGTGC TGGATAGTGA CGGATCTTTC TTTCTCTACT CAAAGCTGAC CGTGGATAAG

1321 TCCAGGTGGC AGCAGGGAAA CGTGTTTTCC TGCTCTGTCA TGCATGAAGC GCTGCATAAT

1381 CACTATACCC AGAAGTCTCT GAGCTTGAGC CCAGGCAAGT AA
```

-continued

Nucleotide sequence of FGF23(R179Q, Y154C)-FcLALAv2
(SEQ ID NO: 75)

```
   1 ATGTTGGGGG CCCGCCTCAG GCTCTGGGTC TGTGCCTTGT GCAGCGTCTG CAGCATGAGC
  61 GTCCTCAGAG CCTATCCCAA TGCCTCCCCA CTGCTCGGCT CCAGCTGGGG TGGCCTGATC
 121 CACCTGTACA CAGCCACAGC CAGGAACAGC TACCACCTGC AGATCCACAA GAATGGCCAT
 181 GTGGATGGCG CACCCCATCA GACCATCTAC AGTGCCCTGA TGATCAGATC AGAGGATGCT
 241 GGCTTTGTGG TGATTACAGG TGTGATGAGC AGAAGATACC TCTGCATGGA TTTCAGAGGC
 301 AACATTTTTG GATCACACTA TTTCGACCCG GAGAACTGCA GGTTCCAACA CCAGACGCTG
 361 GAAAACGGGT ACGACGTCTA CCACTCTCCT CAGTATCACT TCCTGGTCAG TCTGGGCCGG
 421 GCGAAGAGAG CCTTCCTGCC AGGCATGAAC CCACCCCCGT GCTCCCAGTT CCTGTCCCGG
 481 AGGAACGAGA TCCCCCTAAT TCACTTCAAC ACCCCCATAC CACGGCGGCA CACCCAGAGC
 541 GCCGAGGACG ACTCGGAGCG GGACCCCCTG AACGTGCTGA AGCCCCGGGC CCGGATGACC
 601 CCGGCCCCGG CCTCCTGTTC ACAGGAGCTC CCGAGCGCCG AGGACAACAG CCCGATGGCC
 661 AGTGACCCAT TAGGGGTGGT CAGGGGCGGT CGAGTGAACA CGCACGCTGG GGGAACGGGC
 721 CCGGAAGGCT GCCGCCCCTT CGCCAAGTTC ATCGGAGGTG GAGGTTCAGC CCCAGAAGCA
 781 GCAGGTGGTC CATCAGTTTT TCTTTTCCCT CCCAAACCCA AGGATACGCT GATGATCTCT
 841 CGCACGCCTG AGGTGACATG CGTCGTAGTA GACGTGAGCC ACGAAGATCC CGAGGTGAAG
 901 TTCAATTGGT ATGTGGACGG AGTAGAAGTG CATAACGCGA AAACTAAGCC GCGCGAGGAA
 961 CAATATAACA GTACTTACAG GGTGGTATCC GTGCTCACAG TCCTGCACCA GGACTGGCTG
1021 AACGGTAAGG AATACAAGTG CAAAGTAAGC AACAAGGCAC TTCCCGCGCC TATTGAGAAA
1081 ACAATCTCCA AGGCGAAGGG ACAACCAAGA GAACCTCAGG TTTACACTCT CCCGCCTTCC
1141 AGGGAAGAGA TGACCAAAAA TCAAGTTTCC CTGACTTGCC TCGTCAAAGG ATTCTACCCT
1201 TCCGACATTG CTGTTGAATG GGAAAGCAAT GGACAACCAG AGAACAACTA CAAGACAACA
1261 CCCCCGGTGC TGGATAGTGA CGGATCTTTC TTTCTCTACT CAAAGCTGAC CGTGGATAAG
1321 TCCAGGTGGC AGCAGGGAAA CGTGTTTTCC TGCTCTGTCA TGCATGAAGC GCTGCATAAT
1381 CACTATACCC AGAAGTCTCT GAGCTTGAGC CCAGGCAAGT AA
```

Nucleotide sequence of FGF23(R179Q, Y154C, C206S, C244S)-FcLALAv2
(SEQ ID NO: 76):

```
   1 ATGTTGGGGG CCCGCCTCAG GCTCTGGGTC TGTGCCTTGT GCAGCGTCTG CAGCATGAGC
  61 GTCCTCAGAG CCTATCCCAA TGCCTCCCCA CTGCTCGGCT CCAGCTGGGG TGGCCTGATC
 121 CACCTGTACA CAGCCACAGC CAGGAACAGC TACCACCTGC AGATCCACAA GAATGGCCAT
 181 GTGGATGGCG CACCCCATCA GACCATCTAC AGTGCCCTGA TGATCAGATC AGAGGATGCT
 241 GGCTTTGTGG TGATTACAGG TGTGATGAGC AGAAGATACC TCTGCATGGA TTTCAGAGGC
 301 AACATTTTTG GATCACACTA TTTCGACCCG GAGAACTGCA GGTTCCAACA CCAGACGCTG
 361 GAAAACGGGT ACGACGTCTA CCACTCTCCT CAGTATCACT TCCTGGTCAG TCTGGGCCGG
 421 GCGAAGAGAG CCTTCCTGCC AGGCATGAAC CCACCCCCGT GCTCCCAGTT CCTGTCCCGG
 481 AGGAACGAGA TCCCCCTAAT TCACTTCAAC ACCCCCATAC CACGGCGGCA CACCCAGAGC
 541 GCCGAGGACG ACTCGGAGCG GGACCCCCTG AACGTGCTGA AGCCCCGGGC CCGGATGACC
 601 CCGGCCCCGG CCTCCTCTTC ACAGGAGCTC CCGAGCGCCG AGGACAACAG CCCGATGGCC
 661 AGTGACCCAT TAGGGGTGGT CAGGGGCGGT CGAGTGAACA CGCACGCTGG GGGAACGGGC
 721 CCGGAAGGCT CCCGCCCCTT CGCCAAGTTC ATCGGAGGTG GAGGTTCAGC CCCAGAAGCA
 781 GCAGGTGGTC CATCAGTTTT TCTTTTCCCT CCCAAACCCA AGGATACGCT GATGATCTCT
 841 CGCACGCCTG AGGTGACATG CGTCGTAGTA GACGTGAGCC ACGAAGATCC CGAGGTGAAG
```

```
 901 TTCAATTGGT ATGTGGACGG AGTAGAAGTG CATAACGCGA AAACTAAGCC GCGCGAGGAA
 961 CAATATAACA GTACTTACAG GGTGGTATCC GTGCTCACAG TCCTGCACCA GGACTGGCTG
1021 AACGGTAAGG AATACAAGTG CAAAGTAAGC AACAAGGCAC TTCCCGCGCC TATTGAGAAA
1081 ACAATCTCCA AGGCGAAGGG ACAACCAAGA GAACCTCAGG TTTACACTCT CCCGCCTTCC
1141 AGGGAAGAGA TGACCAAAAA TCAAGTTTCC CTGACTTGCC TCGTCAAAGG ATTCTACCCT
1201 TCCGACATTG CTGTTGAATG GGAAAGCAAT GGACAACCAG AGAACAACTA CAAGACAACA
1261 CCCCCGGTGC TGGATAGTGA CGGATCTTTC TTTCTCTACT CAAAGCTGAC CGTGGATAAG
1321 TCCAGGTGGC AGCAGGGAAA CGTGTTTTCC TGCTCTGTCA TGCATGAAGC GCTGCATAAT
1381 CACTATACCC AGAAGTCTCT GAGCTTGAGC CCAGGCAAGT AA
```

Klotho delta C-20: Alpha sKlotho ΔC20
(SEQ ID NO: 77)
EPGDGAQTWARFSRPPAPEAAGLFQGTFPDGFLWAVGSAAYQTEGGWQQHGKGASIWDTFTHHPLAPP

GDSRNASLPLGAPSPLQPATGDVASDSYNNVFRDTEALRELGVTHYRFSISWARVLPNGSAGVPNREG

LRYYRRLLERLRELGVQPVVTLYHWDLPQRLQDAYGGWANRALADHFRDYAELCFRHFGGQVKYWITI

DNPYVVAWHGYATGRLAPGIRGSPRLGYLVAHNLLLAHAKVWHLYNTSFRPTQGGQVSIALSSHWINP

RRMTDHSIKECQKSLDFVLGWFAKPVFIDGDYPESMKNNLSSILPDFTESEKKFIKGTADFFALCFGP

TLSFQLLDPHMKFRQLESPNLRQLLSWIDLEFNHPQIFIVENGWFVSGTTKRDDAKYMYYLKKFIMET

LKAIKLDGVDVIGYTAWSLMDGFEWHRGYSIRRGLFYVDFLSQDKMLLPKSSALFYQKLIEKNGFPPL

PENQPLEGTFPCDFAWGVVDNYIQVDTTLSQFTDLNVYLWDVHHSKRLIKVDGVVTKKRKSYCVDFAA

IQPQIALLQEMHVTHFRFSLDWALILPLGNQSQVNHTILQYYRCMASELVRVNITPVVALWQPMAPNQ

GLPRLLARQGAWENPYTALAFAEYARLCFQELGHHVKLWITMNEPYTRNMTYSAGHNLLKAHALAWHV

YNEKFRHAQNGKISIALQADWIEPACPFSQKDKEVAERVLEFDIGWLAEPIFGSGDYPWVMRDWLNQR

NNFLLPYFTEDEKKLIQGTFDFLALSHYTTILVDSEKEDPIKYNDYLEVQEMTDITWLNSPSQVAVVP

WGLRKVLNWLKFKYGDLPMYIISNGIDDGLHAEDDQLRVYYMQNYINEALKAHILDGINLCGYFAYSF

NDRTAPRFGLYRYAADQFEPKASMKHYRKIIDSNGFPGPETLERF

Klotho delta C-20 with two mutations: Alpha sKlotho ΔC20 with V563A
and K795E (underlined)
(SEQ ID NO: 78)
EPGDGAQTWARFSRPPAPEAAGLFQGTFPDGFLWAVGSAAYQTEGGWQQHGKGASIWDTFTHHPLAPP

GDSRNASLPLGAPSPLQPATGDVASDSYNNVFRDTEALRELGVTHYRFSISWARVLPNGSAGVPNREG

LRYYRRLLERLRELGVQPVVTLYHWDLPQRLQDAYGGWANRALADHFRDYAELCFRHFGGQVKYWITI

DNPYVVAWHGYATGRLAPGIRGSPRLGYLVAHNLLLAHAKVWHLYNTSFRPTQGGQVSIALSSHWINP

RRMTDHSIKECQKSLDFVLGWFAKPVFIDGDYPESMKNNLSSILPDFTESEKKFIKGTADFFALCFGP

TLSFQLLDPHMKFRQLESPNLRQLLSWIDLEFNHPQIFIVENGWFVSGTTKRDDAKYMYYLKKFIMET

LKAIKLDGVDVIGYTAWSLMDGFEWHRGYSIRRGLFYVDFLSQDKMLLPKSSALFYQKLIEKNGFPPL

PENQPLEGTFPCDFAWGVVDNYIQVDTTLSQFTDLNVYLWDVHHSKRLIKVDG_A_VTKKRKSYCVDFAA

IQPQIALLQEMHVTHFRFSLDWALILPLGNQSQVNHTILQYYRCMASELVRVNITPVVALWQPMAPNQ

GLPRLLARQGAWENPYTALAFAEYARLCFQELGHHVKLWITMNEPYTRNMTYSAGHNLLKAHALAWHV

YNEKFRHAQNGKISIALQADWIEPACPFSQKDKEVAERVLEFDIGWLAEPIFGSGDYPWVMRDWLNQR

NNFLLPYFTEDE_KE_LIQGTFDFLALSHYTTILVDSEKEDPIKYNDYLEVQEMTDITWLNSPSQVAVVP

WGLRKVLNWLKFKYGDLPMYIISNGIDDGLHAEDDQLRVYYMQNYINEALKAHILDGINLCGYFAYSF

NDRTAPRFGLYRYAADQFEPKASMKHYRKIIDSNGFPGPETLERF

-continued

Klotho delta C-20-FGF23: Alpha sKlotho ΔC20 (not Bold or Italics);
linker (italics); FGF23 R179Q (bold, not italics)
(SEQ ID NO: 79)
EPGDGAQTWARFSRPPAPEAAGLFQGTFPDGFLWAVGSAAYQTEGGWQQHGKGASIWDTFTHHPLAPP

GDSRNASLPLGAPSPLQPATGDVASDSYNNVFRDTEALRELGVTHYRFSISWARVLPNGSAGVPNREG

LRYYRRLLERLRELGVQPVVTLYHWDLPQRLQDAYGGWANRALADHFRDYAELCFRHFGGQVKYWITI

DNPYVVAWHGYATGRLAPGIRGSPRLGYLVAHNLLLAHAKVWHLYNTSFRPTQGGQVSIALSSHWINP

RRMTDHSIKECQKSLDFVLGWFAKPVFIDGDYPESMKNNLSSILPDFTESEKKFIKGTADFFALCFGP

TLSFQLLDPHMKFRQLESPNLRQLLSWIDLEFNHPQIFIVENGWFVSGTTKRDDAKYMYYLKKFIMET

LKAIKLDGVDVIGYTAWSLMDGFEWHRGYSIRRGLFYVDFLSQDKMLLPKSSALFYQKLIEKNGFPPL

PENQPLEGTFPCDFAWGVVDNYIQVDTTLSQFTDLNVYLWDVHHSKRLIKVDGVVTKKRKSYCVDFAA

IQPQIALLQEMHVTHFRFSLDWALILPLGNQSQVNHTILQYYRCMASELVRVNITPVVALWQPMAPNQ

GLPRLLARQGAWENPYTALAFAEYARLCFQELGHHVKLWITMNEPYTRNMTYSAGHNLLKAHALAWHV

YNEKFRHAQNGKISIALQADWIEPACPFSQKDKEVAERVLEFDIGWLAEPIFGSGDYPWVMRDWLNQR

NNFLLPYFTEDEKKLIQGTFDFLALSHYTTILVDSEKEDPIKYNDYLEVQEMTDITWLNSPSQVAVVP

WGLRKVLNWLKFKYGDLPMYIISNGIDDGLHAEDDQLRVYYMQNYINEALKAHILDGINLCGYFAYSF

NDRTAPRFGLYRYAADQFEPKASMKHYRKIIDSNGFPGPETLERF*GSGGGGSGGGGSGGGGSLK*YPNA

SPLLGSSWGGLIHLYTATARNSYHLQIHKNGHVDGAPHQTIYSALMIRSEDAGFVVITGVMSRRYLCM

DFRGNIFGSHYFDPENCRFQHQTLENGYDVYHSPQYHFLVSLGRAKRAFLPGMNPPPYSQFLSRRNEI

PLIHFNTPIPRRHTQSAEDDSERDPLNVLKPRARMTPAPASCSQELPSAEDNSPMASDPLGVVRGGRV

NTHAGGTGPEGCRPFAKFI

Klotho-FGF23: Alpha sKlotho (not Bold or Italics); linker (italics);
FGF23 R179Q (bold, not italics)
(SEQ ID NO: 80)
EPGDGAQTWARFSRPPAPEAAGLFQGTFPDGFLWAVGSAAYQTEGGWQQHGKGASIWDTFTHHPLAPP

GDSRNASLPLGAPSPLQPATGDVASDSYNNVFRDTEALRELGVTHYRFSISWARVLPNGSAGVPNREG

LRYYRRLLERLRELGVQPVVTLYHWDLPQRLQDAYGGWANRALADHFRDYAELCFRHFGGQVKYWITI

DNPYVVAWHGYATGRLAPGIRGSPRLGYLVAHNLLLAHAKVWHLYNTSFRPTQGGQVSIALSSHWINP

RRMTDHSIKECQKSLDFVLGWFAKPVFIDGDYPESMKNNLSSILPDFTESEKKFIKGTADFFALCFGP

TLSFQLLDPHMKFRQLESPNLRQLLSWIDLEFNHPQIFIVENGWFVSGTTKRDDAKYMYYLKKFIMET

LKAIKLDGVDVIGYTAWSLMDGFEWHRGYSIRRGLFYVDFLSQDKMLLPKSSALFYQKLIEKNGFPPL

PENQPLEGTFPCDFAWGVVDNYIQVDTTLSQFTDLNVYLWDVHHSKRLIKVDGVVTKKRKSYCVDFAA

IQPQIALLQEMHVTHFRFSLDWALILPLGNQSQVNHTILQYYRCMASELVRVNITPVVALWQPMAPNQ

GLPRLLARQGAWENPYTALAFAEYARLCFQELGHHVKLWITMNEPYTRNMTYSAGHNLLKAHALAWHV

YNEKFRHAQNGKISIALQADWIEPACPFSQKDKEVAERVLEFDIGWLAEPIFGSGDYPWVMRDWLNQR

NNFLLPYFTEDEKKLIQGTFDFLALSHYTTILVDSEKEDPIKYNDYLEVQEMTDITWLNSPSQVAVVP

WGLRKVLNWLKFKYGDLPMYIISNGIDDGLHAEDDQLRVYYMQNYINEALKAHILDGINLCGYFAYSF

NDRTAPRFGLYRYAADQFEPKASMKHYRKIIDSNGFPGPETLERFCPEEFTVCTECSFFHTRKSL*GSG*

*GGGSGGGGSGGGGSLK*YPNASPLLGSSWGGLIHLYTATARNSYHLQIHKNGHVDGAPHQTIYSALMIR

SEDAGFVVITGVMSRRYLCMDFRGNIFGSHYFDPENCRFQHQTLENGYDVYHSPQYHFLVSLGRAKRA

FLPGMNPPPYSQFLSRRNEIPLIHFNTPIPRRHTQSAEDDSERDPLNVLKPRARMTPAPASCSQELPS

AEDNSPMASDPLGVVRGGRVNTHAGGTGPEGCRPFAKFI

-continued

Klotho (with two mutations)-FGF23: Klotho signal peptide (bold, italics); Alpha sKlotho (not Bold or Italics) with V563A and K795E (underlined); linker (italics); FGF23 R179Q (bold, not italics)
(SEQ ID NO: 81)

MPASAPPRRPRPPPPSLSLLLVLLGLGGRRLRAEPGDGAQTWARFSRPPAPEAAGLFQGTFPDGFLWA

VGSAAYQTEGGWQQHGKGASIWDTFTHHPLAPPGDSRNASLPLGAPSPLQPATGDVASDSYNNVFRDT

EALRELGVTHYRFSISWARVLPNGSAGVPNREGLRYYRRLLERLRELGVQPVVTLYHWDLPQRLQDAY

GGWANRALADHFRDYAELCFRHFGGQVKYWITIDNPYVVAWHGYATGRLAPGIRGSPRLGYLVAHNLL

LAHAKVWHLYNTSFRPTQGGQVSIALSSHWINPRRMTDHSIKECQKSLDFVLGWFAKPVFIDGDYPES

MKNNLSSILPDFTESEKKFIKGTADFFALCFGPTLSFQLLDPHMKFRQLESPNLRQLLSWIDLEFNHP

QIFIVENGWFVSGTTKRDDAKYMYYLKKFIMETLKAIKLDGVDVIGYTAWSLMDGFEWHRGYSIRRGL

FYVDFLSQDKMLLPKSSALFYQKLIEKNGFPPLPENQPLEGTFPCDFAWGVVDNYIQVDTTLSQFTDL

NVYLWDVHHSKRLIKVDG<u>A</u>VTKKRKSYCVDFAAIQPQIALLQEMHVTHFRFSLDWALILPLGNQSQVN

HTILQYYRCMASELVRVNITPVVALWQPMAPNQGLPRLLARQGAWENPYTALAFAEYARLCFQELGHH

VKLWITMNEPYTRNMTYSAGHNLLKAHALAWHVYNEKFRHAQNGKISIALQADWIEPACPFSQKDKEV

AERVLEFDIGWLAEPIFGSGDYPWVMRDWLNQRNNFLLPYFTEDE<u>K</u>ELIQGTFDFLALSHYTTILVDS

EKEDPIKYNDYLEVQEMTDITWLNSPSQVAVVPWGLRKVLNWLKFKYGDLPMYIISNGIDDGLHAEDD

QLRVYYMQNYINEALKAHILDGINLCGYFAYSFNDRTAPRFGLYRYAADQFEPKASMKHYRKIIDSNG

FPGPETLERF*GSGGGGSGGGGSGGGGSLK*YPNASPLLGSSWGGLIHLYTATARNSYHLQIHKNGHVDG

APHQTIYSALMIRSEDAGFVVITGVMSRRYLCMDFRGNIFGSHYFDPENCRFQHQTLENGYDVYHSPQ

YHFLVSLGRAKRAFLPGMNPPPYSQFLSRRNEIPLIHFNTPIPRRHTQSAEDDSERDPLNVLKPRARM

TPAPASCSQELPSAEDNSPMASDPLGVVRGGRVNTHAGGTGPEGCRPFAKFI

Klotho-FGF23: Klotho signal peptide (bold, italics); Alpha sKlotho (not Bold or Italics) with V563A and K795E (underlined); linker (italics); FGF23 R179Q (bold, not italics)
(SEQ ID NO: 82)

EPGDGAQTWARFSRPPAPEAAGLFQGTFPDGFLWAVGSAAYQTEGGWQQHGKGASIWDTFTHHPLAPP

GDSRNASLPLGAPSPLQPATGDVASDSYNNVFRDTEALRELGVTHYRFSISWARVLPNGSAGVPNREG

LRYYRRLLERLRELGVQPVVTLYHWDLPQRLQDAYGGWANRALADHFRDYAELCFRHFGGQVKYWITI

DNPYVVAWHGYATGRLAPGIRGSPRLGYLVAHNLLLAHAKVWHLYNTSFRPTQGGQVSIALSSHWINP

RRMTDHSIKECQKSLDFVLGWFAKPVFIDGDYPESMKNNLSSILPDFTESEKKFIKGTADFFALCFGP

TLSFQLLDPHMKFRQLESPNLRQLLSWIDLEFNHPQIFIVENGWFVSGTTKRDDAKYMYYLKKFIMET

LKAIKLDGVDVIGYTAWSLMDGFEWHRGYSIRRGLFYVDFLSQDKMLLPKSSALFYQKLIEKNGFPPL

PENQPLEGTFPCDFAWGVVDNYIQVDTTLSQFTDLNVYLWDVHHSKRLIKVDG<u>A</u>VTKKRKSYCVDFAA

IQPQIALLQEMHVTHFRFSLDWALILPLGNQSQVNHTILQYYRCMASELVRVNITPVVALWQPMAPNQ

GLPRLLARQGAWENPYTALAFAEYARLCFQELGHHVKLWITMNEPYTRNMTYSAGHNLLKAHALAWHV

YNEKFRHAQNGKISIALQADWIEPACPFSQKDKEVAERVLEFDIGWLAEPIFGSGDYPWVMRDWLNQR

NNFLLPYFTEDE<u>K</u>ELIQGTFDFLALSHYTTILVDSEKEDPIKYNDYLEVQEMTDITWLNSPSQVAVVP

WGLRKVLNWLKFKYGDLPMYIISNGIDDGLHAEDDQLRVYYMQNYINEALKAHILDGINLCGYFAYSF

NDRTAPRFGLYRYAADQFEPKASMKHYRKIIDSNGFPGPETLERF*GSGGGGSGGGGSGGGGSLK*YPNA

SPLLGSSWGGLIHLYTATARNSYHLQIHKNGHVDGAPHQTIYSALMIRSEDAGFVVITGVMSRRYLCM

DFRGNIFGSHYFDPENCRFQHQTLENGYDVYHSPQYHFLVSLGRAKRAFLPGMNPPPYSQFLSRRNEI

PLIHFNTPIPRRHTQSAEDDSERDPLNVLKPRARMTPAPASCSQELPSAEDNSPMASDPLGVVRGGRV

NTHAGGTGPEGCRPFAKFI

-continued

```
PRIMERS
5' primer:
(SEQ ID NO: 83)
P5; gacggcgcgcagacctgggc

3' primers:
(SEQ ID NO: 84)
C-20; TAGCTCTAGACTAAAATCTTTCCAGAGTTTCTG (SEQ ID NO: 85)
C-40; TAGCTCTAGACTATTTCATGGATGCCTTGGGCT (SEQ ID NO: 86)
C-60; TAGCTCTAGACTAAGCTGTGCGGTCGTTAAACG (SEQ ID NO: 87)
C-80; TAGCTCTAGACTAGTGGGCTTTGAGAGCTTCGT (SEQ ID NO: 88)
C-100; TAGCTCTAGACTACTCAGCATGCAGCCCGTCAT (SEQ ID NO: 89)
C-120; TAGCTCTAGACTACTTGAACTTCAGCCAGTTCA (SEQ ID NO: 90)
C-140; TAGCTCTAGACTAGGGGGAGTTGAGCCACGTGA (SEQ ID NO: 91)
C-160; TAGCTCTAGACTATATTGGATCTTCTTTTTCTG (SEQ ID NO: 92)
C-180; TAGCTCTAGACTAGTCAAAGGTACCCTGGATTA (SEQ ID NO: 93)
C-200; TAGCTCTAGACTAGTTTCTTTGGTTCAGCCAGT (SEQ ID NO: 94)
C-220; TAGCTCTAGACTACTCAGCCAGCCAGCCAATGT (SEQ ID NO: 95)
C-240; TAGCTCTAGACTAGGAGAAAGGGCAGGCAGGTT (SEQ ID NO: 96)
C-260; TAGCTCTAGACTACTGAGCATGCCTAAACTTTT (SEQ ID NO: 97)
C-280; TAGCTCTAGACTAGTTGTGGCCAGCACTGTATG (SEQ ID NO: 98)
C-300; TAGCTCTAGACTACTTGACGTGATGGCCGAGCT (SEQ ID NO: 99)
C-320; TAGCTCTAGACTAAGTGTAGGGGTTCTCCCAGG (SEQ ID NO: 100)
C-340; TAGCTCTAGACTAGGCCATAGGCTGCCACAGGG (SEQ ID NO: 101)
C-360; TAGCTCTAGACTACATGCAGCGATAGTACTGCA (SEQ ID NO: 102)
C-380; TAGCTCTAGACTAAATCAGGGCCCAGTCCAGGG (SEQ ID NO: 103)
C-400; TAGCTCTAGACTAGATCTGGGGCTGGATGGCAG (SEQ ID NO: 104)
C-420; TAGCTCTAGACTACCCATCCACTTTAATAAGCC (SEQ ID NO: 105)
C-440; TAGCTCTAGACTAGGTAAACTGAGACAGAGTGG (SEQ ID NO: 106)
C-460; TAGCTCTAGACTAGTCACAGGGAAATGTCCCTT
```

(SEQ ID NO: 107)
C-480; TAGCTCTAGACTACTCTATCAGCTTTTGGTAGA
Klotho-serum albumin fusion: Human soluble Klotho and mouse
serum Albumin fusion protein: Human Klotho Signal Peptide
(Bold, Italics, starting at MPAS (SEQ ID NO: 116)); Human
Klotho (not Bold or Italics, starting at EPGD(SEQ ID NO:
117)); linker (italics, starting at GSGG (SEQ ID NO: 113));
mouse Albumin (bold, underlined, starting at LKEA (SEQ ID NO:
114)):
(SEQ ID NO: 108)
*MPASAPPRRPRPPPPSLSLLLVLLGLGGRRLRA*EPGDGAQTWARFSRPPAPEAAGLFQGTFP

DGFLWAVGSAAYQTEGGWQQHGKGASIWDTFTHHPLAPPGDSRNASLPLGAPSPLQPATSDV

ASDSYNNVFRDTEALRELGVTHYRFSISWARVLPNGSAGVPNREGLRYYRLLERLRELGVQ

HSIKECQKSLDFVLGWFAKPVFIDGDYPESMKNNLSSILPDFTESEKKFIKGTADFFALCFG

PTLSFQLLDPHMKFRQLESPNLRQLLSWIDLEFNHPQIFIVENGWFVSGTTKRDDAKYMYYL

KKFIMETLKAIKLDGVDVIGYTAWSLMDGFEWHRGYSIRRGLFYVDFLSQDKMLLPKSSALF

YQKLIEKNGFPPLPENQPLEGTFPCDFAWGVVDNYIQVDTTLSQFTDLNVYLWDVHHSKRLI

KVDGVVTKKRKSYCVDFAAIQPQIALLQEMHVTHFRFSLDWALILPLGNQSQVNHTILQYYR

CMASELVRVNITPVVALWQPMAPNQGLPRLLARQGAWENPYTALAFAEYARLCFQELGHHVK

LWITMNEPYTRNMTYSAGHNLLKAHALAWHVYNEKFRHAQNGKISIALQADWIEPACPFSQK

DKEVAERVLEFDIGWLAEPIFGSGDYPWVMRDWLNQRNNFLLPYFTEDEKKLIQGTFDFLAL

SHYTTILVDSEKEDPIKYNDYLEVQEMTDITWLNSPSQVAVVPWGLRKVLNWLKFKYGDLPM

YIISNGIDDGLHAEDDQLRVYYMQNYINEALKAHILDGINLCGYFAYSFNDRTAPRFGLYRY

AADQFEPKASMKHYRKIIDSNGFPGPETLERFCPEEFTVCTECSFFHTRKS*LGSGGGGSGGG*

*GSGGGGS*<u>LKEAHKSEIAHRYNALGEQHFKGLVLTAFSQYLQKASYDEHAKLVQEVTDFAKTC</u>

<u>VADESAANCDKSLHTLFGDKLCAIPNLRENYGELADCCTKQEPERNECFLQHKDDNPSLPPF</u>

<u>ERPEAEAMCTSFKENPTTFMGHYLHEVARRHPYFYAPELLYYAEQYNEILTQCCAEADKESC</u>

<u>LTPKLDGVKEKALVSSVRQRMKCSSMQKFGERAFKAWAVARLSQTFPNADFAEITKLATDLT</u>

<u>KVNKECCHGDLLECADDRAELAKYMCENQATISSKLQTCCDKPLLKKAHCLSEVEHDTMPAD</u>

<u>LPAIAADFVEDQEVCKNYAEAKDVFLGTFLYEYSRRHPDYSVSLLLRLAKKYEATLEKCCAE</u>

<u>ANPPACYGTVLAEFQPLVEEPKNLVKTNCDLYEKLGEYGFQNAILVRYTQKAPQVSTPTLVE</u>

<u>AARNLGRVGTKCCTLPEDQRLPCVEDYLSAILNRVCLLHEKTPVSEHVTKCCSGSLVERRPC</u>

<u>FSALTVDETYVPKEFKAETFTFHSDICTLPEKEKQIKKQTALAELVKHKPKATAEQLKTVMD</u>

DFAQFLDTCCKAADKDTCFSTEGPNLVTRAKDALA

---

What is claimed is:

1. A composition comprising a fusion polypeptide comprising, in N-terminal to C-terminal order: (a) an alpha sKlotho, in which 20 amino acids have been deleted from the C-terminus, having the sequence of SEQ ID NO: 77, and having mutations at V563A and K795E; (b) a linker; and (c) serum albumin.

2. The composition of claim 1, wherein the alpha sKlotho has the sequence of SEQ ID NO: 78.

3. The composition of claim 1, wherein the linker is a polypeptide linker.

4. The composition of claim 3, wherein the polypeptide linker comprises an amino acid sequence comprising one or more copies of a linker selected from the group consisting of: SEQ ID NO: 11, SEQ ID NO: 12, SEQ ID NO: 13, SEQ ID NO: 14, SEQ ID NO: 15, SEQ ID NO: 16, SEQ ID NO: 17, and SEQ ID NO: 18.

5. The composition of claim 1, wherein the fusion polypeptide further comprises a signal peptide.

6. The composition of claim 1, further comprising a pharmaceutically acceptable carrier.

* * * * *

SEQUENCE LISTING

<160> NUMBER OF SEQ ID NOS: 117

<210> SEQ ID NO 1
<211> LENGTH: 5003
<212> TYPE: DNA
<213> ORGANISM: Homo sapiens

<400> SEQUENCE: 1
cgcgcagcat gcccgccagc gccccgccgc cgccccgcg gccgccgccg ccgtcgctgt    60
cgctgctgct ggtgctgctg ggcctgggcg gccgccgcct gcgtgcggag ccgggcgacg   120
gcgcgcagac ctgggcccgt ttctcgcggc ctcctgcccc cgaggccgcg ggcctcttcc   180
agggcacctt ccccgacggc ttcctctggg ccgtgggcag cgccgcctac cagaccgagg   240

```
gcggctggca gcagcacggc aagggtgcgt ccatctggga tacgttcacc caccacccccc    300 tggcaccccc gggagactcc cggaacgcca gtctgccgtt gggcgccccg tcgccgctgc    360
agcccgccac cggggacgta gccagcgaca gctacaacaa cgtcttccgc gacacggagg    420
cgctgcgcga gctcggggtc actcactacc gcttctccat ctcgtgggcg cgagtgctcc    480
ccaatggcag cgcgggcgtc cccaaccgcg aggggctgcg ctactaccgg cgcctgctgg    540
agcggctgcg ggagctgggc gtgcagcccg tggtcaccct gtaccactgg gacctgcccc    600
agcgcctgca ggacgcctac ggcggctggg ccaaccgcgc cctggccgac cacttcaggg    660
attacgcgga gctctgcttc cgccacttcg gcggtcaggt caagtactgg atcaccatcg    720 acaacccccta cgtggtggcc tggcacggct acgccaccgg gcgcctggcc cccggcatcc    780
ggggcagccc gcggctcggg tacctggtgg cgcacaacct cctcctggct catgccaaag    840
tctggcatct ctacaatact tctttccgtc ccactcaggg aggtcaggtg tccattgccc    900
taagctctca ctggatcaat cctcgaagaa tgaccgacca cagcatcaaa gaatgtcaaa    960
aatctctgga ctttgtacta ggttggtttg ccaaacccgt atttattgat ggtgactatc   1020
ccgagagcat gaagaataac cttccatcta ttctgcctga ttttactgaa tctgagaaaa   1080
agttcatcaa aggaactgct gacttttttg ctctttgctt tggacccacc ttgagttttc   1140
aacttttgga ccctcacatg aagttccgcc aattggaatc tcccaacctg aggcaactgc   1200
tttcctggat tgaccttgaa tttaaccatc tcaaatatt tattgtggaa atggctggt   1260 ttgtctcagg gaccaccaag agagatgatg ccaaatatat gtattacctc aaaaagttca   1320
tcatggaaac cttaaaagcc atcaagctgg atggggtgga tgtcatcggg tataccgcat   1380
ggtccctcat ggatggtttc gagtggcaca gaggttacag catcaggcgt ggactcttct   1440
atgttgactt tctaagccag gacaagatgt tgttgccaaa gtcttcagcc ttgttctacc   1500
aaaagctgat agagaaaaat ggcttccctc ctttacctga aaatcagccc ctagaaggga   1560
catttccctg tgactttgct tggggagttg ttgacaacta cattcaagta gataccactc   1620
tgtctcagtt taccgacctg aatgtttacc tgtgggatgt ccaccacagt aaaaggctta   1680
ttaaagtgga tggggttgtg accaagaaga ggaaatccta ctgtgttgac tttgctgcca   1740
tccagcccca gatcgcttta ctccaggaaa tgcacgttac acattttcgc ttctccctgg   1800
actgggccct gattctccct ctgggtaacc agtcccaggt gaaccacacc atcctgcagt   1860
actatcgctg catggccagc gagcttgtcc gtgtcaacat caccccagtg gtggccctgt   1920
ggcagcctat ggccccgaac caaggactgc cgcgcctcct ggccaggcag ggcgcctggg   1980
agaaccccta cactgccctg cctttgcag agtatgcccg actgtgcttt caagagctcg   2040
gccatcacgt caagctttgg ataacgatga atgagccgta caaggaat atgacataca   2100 gtgctggcca caaccttctg aaggcccatg ccctggcttg gcatgtgtac aatgaaaagt   2160
ttaggcatgc tcagaatggg aaaatatcca tagccttgca ggctgattgg atagaacctg   2220
cctgcccttt ctcccaaaag gacaaagagg tggccgagag agttttggaa tttgacattg   2280
gctggctggc tgagcccatt ttcggctctg gagattatcc atgggtgatg agggactggc   2340
tgaaccaaag aaacaatttt cttcttcctt atttcactga agatgaaaaa aagctaatcc   2400 agggtaccctt tgactttttg gctttaagcc attataccac catccttgta gactcagaaa   2460
aagaagatcc aataaaatac aatgattacc tagaagtgca agaaatgacc gacatcacgt   2520
ggctcaactc ccccagtcag gtggcggtag tgccctgggg gttgcgcaaa gtgctgaact   2580
```

```
ggctgaagtt caagtacgga gacctcccca tgtacataat atccaacgga atcgatgacg    2640
ggctgcatgc tgaggacgac cagctgaggg tgtattatat gcagaattac ataaacgaag    2700
ctctcaaagc ccacatactg gatggtatca atctttgcgg atactttgct tattcgttta    2760
acgaccgcac agctccgagg tttggcctct atcgttatgc tgcagatcag tttgagccca    2820
aggcatccat gaaacattac aggaaaatta ttgacagcaa tggtttcccg ggcccagaaa    2880
ctctggaaag attttgtcca gaagaattca ccgtgtgtac tgagtgcagt ttttttcaca    2940
cccgaaagtc tttactggct ttcatagctt ttctattttt tgcttctatt atttctctct    3000
cccttatatt ttactactcg aagaaaggca gaagaagtta caaatagttc tgaacatttt    3060
tctattcatt cattttgaaa taattatgca gacacatcag ctgttaacca tttgcacctc    3120
taagtgttgt gaaactgtaa atttcataca tttgacttct agaaaacatt tttgtggctt    3180
atgacagagg ttttgaaatg ggcataggtg atcgtaaaat attgaataat gcgaatagtg    3240
cctgaatttg ttctcttttt gggtgattaa aaaactgaca ggcactataa tttctgtaac    3300
acactaacaa aagcatgaaa aataggaacc acaccaatgc aacatttgtg cagaaatttg    3360
aatgacaaga ttaggaatat tttcttctgc acccacttct aaatttaatg ttttttctgga   3420 agtagtaatt gcaagagttc gaatagaaag ttatgtacca agtaaccatt tctcagctgc    3480
cataataatg cctagtggct tcccctctgt caaatctagt ttcctatgga aaagaagatg    3540
gcagatacag gagagacgac agagggtcct aggctggaat gttcctttcg aaagcaatgc    3600
ttctatcaaa tactagtatt aatttatgta tctggttaat gacatacttg gagagcaaat    3660
tatgaaaatg tgtatttat atgattttg aggtcctgtc taaaccctgt gtccctgagg      3720
gatctgtctc actggcatct tgttgagggc cttgcacata ggaaacttttt gataagtatc   3780 tgcgaaaaaa caaacatgaa tcctgtgata ttgggctctt caggaagcat aaagcaattg    3840
tgaaatacag tataccgcag tggctctagg tggaggaaag gaggaaaaag tgcttattat    3900
gtgcaacatt atgattaatc tgattataca ccatttttga gcagatcttg gaatgaatga    3960
catgaccttt ccctagagaa taaggatgaa ataatcactc attctatgaa cagtgacact    4020
actttctatt ctttagctgt actgtaattt ctttgagttg atagttttac aaattcttaa    4080
taggttcaaa agcaatctgg tctgaataac actggatttg tttctgtgat ctctgaggtc    4140
tattttatgt ttttgctgct acttctgtgg aagtagcttt gaactagttt tactttgaac    4200
tttcacgctg aaacatgcta gtgatatcta gaaagggcta attaggtctc atcctttaat    4260
gccccttaaa taagtcttgc tgattttcag acagggaagt ctctctatta cactggagct    4320
gttttataga taagtcaata ttgtatcagg caagataaac caatgtcata acaggcattg    4380
ccaacctcac tgcacagggg tcatagtgta ataatatata ctgtactata taatatatca    4440
tctttagagg tatgattttt tcatgaaaga taagcttttg gtaatattca ttttaaagtg    4500
gacttattaa aattggatgc tagagaatca agtttatttt atgtatatat ttttctgatt    4560
ataagagtaa tatatgttca ttgtaaaaat ttttaaaaca cagaaactat atgcaaagaa    4620
aaaataaaaa ttatctataa tctcagaacc cagaaatagc cactattaac atttcctacg    4680
tatttatttt tacatagatc atattgtata tagttagtat ctttattaat ttttattatg    4740
aaactttcct ttgtcattat tagtcttcaa aagcatgatt tttaatagtt gttgagtatt    4800
ccaccacagg aatgtatcac aacttaaccg ttcccgtttg ttagactagt ttcttattaa    4860
tgttgatgaa tgttgtttaa aaataatttt gttgctacat ttactttaat ttccttgact    4920
gtaaagagaa gtaattttgc tccttgataa agtattatat taataataaa tctgcctgca    4980
```

```
acttttttgcc ttctttcata atc                                              5003
```

<210> SEQ ID NO 2
<211> LENGTH: 1012
<212> TYPE: PRT
<213> ORGANISM: Homo sapiens

<400> SEQUENCE: 2

| Met | Pro | Ala | Ser | Ala | Pro | Pro | Arg | Arg | Pro | Pro | Pro | Pro | Pro | Pro | Ser |
|---|---|---|---|---|---|---|---|---|---|---|---|---|---|---|---|
| 1 | | | | 5 | | | | | 10 | | | | | 15 | |

| Leu | Ser | Leu | Leu | Leu | Val | Leu | Leu | Gly | Leu | Gly | Gly | Arg | Arg | Leu | Arg |
| | | | 20 | | | | | 25 | | | | | 30 | | |

| Ala | Glu | Pro | Gly | Asp | Gly | Ala | Gln | Thr | Trp | Ala | Arg | Phe | Ser | Arg | Pro |
| | | 35 | | | | | 40 | | | | | 45 | | | |

| Pro | Ala | Pro | Glu | Ala | Ala | Gly | Leu | Phe | Gln | Gly | Thr | Phe | Pro | Asp | Gly |
| | 50 | | | | | 55 | | | | | 60 | | | | |

| Phe | Leu | Trp | Ala | Val | Gly | Ser | Ala | Ala | Tyr | Gln | Thr | Glu | Gly | Gly | Trp |
| 65 | | | | 70 | | | | | 75 | | | | | 80 | |

| Gln | Gln | His | Gly | Lys | Gly | Ala | Ser | Ile | Trp | Asp | Thr | Phe | Thr | His | His |
| | | | | 85 | | | | | 90 | | | | | 95 | |

| Pro | Leu | Ala | Pro | Pro | Gly | Asp | Ser | Arg | Asn | Ala | Ser | Leu | Pro | Leu | Gly |
| | | | 100 | | | | | 105 | | | | | 110 | | |

| Ala | Pro | Ser | Pro | Leu | Gln | Pro | Ala | Thr | Gly | Asp | Val | Ala | Ser | Asp | Ser |
| | | 115 | | | | | 120 | | | | | 125 | | | |

| Tyr | Asn | Asn | Val | Phe | Arg | Asp | Thr | Glu | Ala | Leu | Arg | Glu | Leu | Gly | Val |
| | 130 | | | | | 135 | | | | | 140 | | | | |

| Thr | His | Tyr | Arg | Phe | Ser | Ile | Ser | Trp | Ala | Arg | Val | Leu | Pro | Asn | Gly |
| 145 | | | | 150 | | | | | 155 | | | | | 160 | |

| Ser | Ala | Gly | Val | Pro | Asn | Arg | Glu | Gly | Leu | Arg | Tyr | Tyr | Arg | Arg | Leu |
| | | | | 165 | | | | | 170 | | | | | 175 | |

| Leu | Glu | Arg | Leu | Arg | Glu | Leu | Gly | Val | Gln | Pro | Val | Val | Thr | Leu | Tyr |
| | | | 180 | | | | | 185 | | | | | 190 | | |

| His | Trp | Asp | Leu | Pro | Gln | Arg | Leu | Gln | Asp | Ala | Tyr | Gly | Gly | Trp | Ala |
| | | 195 | | | | | 200 | | | | | 205 | | | |

| Asn | Arg | Ala | Leu | Ala | Asp | His | Phe | Arg | Asp | Tyr | Ala | Glu | Leu | Cys | Phe |
| | 210 | | | | | 215 | | | | | 220 | | | | |

| Arg | His | Phe | Gly | Gly | Gln | Val | Lys | Tyr | Trp | Ile | Thr | Ile | Asp | Asn | Pro |
| 225 | | | | 230 | | | | | 235 | | | | | 240 | |

| Tyr | Val | Val | Ala | Trp | His | Gly | Tyr | Ala | Thr | Gly | Arg | Leu | Ala | Pro | Gly |
| | | | | 245 | | | | | 250 | | | | | 255 | |

| Ile | Arg | Gly | Ser | Pro | Arg | Leu | Gly | Tyr | Leu | Val | Ala | His | Asn | Leu | Leu |
| | | | 260 | | | | | 265 | | | | | 270 | | |

| Leu | Ala | His | Ala | Lys | Val | Trp | His | Leu | Tyr | Asn | Thr | Ser | Phe | Arg | Pro |
| | | 275 | | | | | 280 | | | | | 285 | | | |

| Thr | Gln | Gly | Gly | Gln | Val | Ser | Ile | Ala | Leu | Ser | Ser | His | Trp | Ile | Asn |
| | 290 | | | | | 295 | | | | | 300 | | | | |

| Pro | Arg | Arg | Met | Thr | Asp | His | Ser | Ile | Lys | Glu | Cys | Gln | Lys | Ser | Leu |
| 305 | | | | 310 | | | | | 315 | | | | | 320 | |

| Asp | Phe | Val | Leu | Gly | Trp | Phe | Ala | Lys | Pro | Val | Phe | Ile | Asp | Gly | Asp |
| | | | | 325 | | | | | 330 | | | | | 335 | |

| Tyr | Pro | Glu | Ser | Met | Lys | Asn | Asn | Leu | Ser | Ser | Ile | Leu | Pro | Asp | Phe |
| | | | 340 | | | | | 345 | | | | | 350 | | |

| Thr | Glu | Ser | Glu | Lys | Lys | Phe | Ile | Lys | Gly | Thr | Ala | Asp | Phe | Phe | Ala |
| | | 355 | | | | | 360 | | | | | 365 | | | |

```
Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
                420                 425                 430

Tyr Leu Lys Lys Phe Ile Met Glu Thr Leu Lys Ala Ile Lys Leu Asp
            435                 440                 445

Gly Val Asp Val Ile Gly Tyr Thr Ala Trp Ser Leu Met Asp Gly Phe
    450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
    515                 520                 525

Asp Asn Tyr Ile Gln Val Asp Thr Thr Leu Ser Gln Phe Thr Asp Leu
530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
            580                 585                 590

Phe Arg Phe Ser Leu Asp Trp Ala Leu Ile Leu Pro Leu Gly Asn Gln
    595                 600                 605

Ser Gln Val Asn His Thr Ile Leu Gln Tyr Tyr Arg Cys Met Ala Ser
610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
            660                 665                 670

Cys Phe Gln Glu Leu Gly His His Val Lys Leu Trp Ile Thr Met Asn
    675                 680                 685

Glu Pro Tyr Thr Arg Asn Met Thr Tyr Ser Ala Gly His Asn Leu Leu
690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
    755                 760                 765

Asp Tyr Pro Trp Val Met Arg Asp Trp Leu Asn Gln Arg Asn Asn Phe
770                 775                 780
```

| | | | | | | | | | | | | | | |
|---|---|---|---|---|---|---|---|---|---|---|---|---|---|---|
|Leu|Leu|Pro|Tyr|Phe|Thr|Glu|Asp|Glu|Lys|Lys|Leu|Ile|Gln|Gly|Thr|
|785| | | |790| | | |795| | | | |800| |

| | | | | | | | | | | | | |
|---|---|---|---|---|---|---|---|---|---|---|---|---|
|Phe|Asp|Phe|Leu|Ala|Leu|Ser|His|Tyr|Thr|Thr|Ile|Leu|Val|Asp|Ser|
| | | | |805| | | |810| | | |815| |

Glu Lys Glu Asp Pro Ile Lys Tyr Asn Asp Tyr Leu Glu Val Gln Glu
           820                825                830

Met Thr Asp Ile Thr Trp Leu Asn Ser Pro Ser Gln Val Ala Val Val
           835                840                845

Pro Trp Gly Leu Arg Lys Val Leu Asn Trp Leu Lys Phe Lys Tyr Gly
    850                855                860

Asp Leu Pro Met Tyr Ile Ile Ser Asn Gly Ile Asp Asp Gly Leu His
865                870                875                880

Ala Glu Asp Asp Gln Leu Arg Val Tyr Tyr Met Gln Asn Tyr Ile Asn
                885                890                895

Glu Ala Leu Lys Ala His Ile Leu Asp Gly Ile Asn Leu Cys Gly Tyr
                900                905                910

Phe Ala Tyr Ser Phe Asn Asp Arg Thr Ala Pro Arg Phe Gly Leu Tyr
                915                920                925

Arg Tyr Ala Ala Asp Gln Phe Glu Pro Lys Ala Ser Met Lys His Tyr
    930                935                940

Arg Lys Ile Ile Asp Ser Asn Gly Phe Pro Gly Pro Glu Thr Leu Glu
945                950                955                960

Arg Phe Cys Pro Glu Glu Phe Thr Val Cys Thr Glu Cys Ser Phe Phe
                965                970                975

His Thr Arg Lys Ser Leu Leu Ala Phe Ile Ala Phe Leu Phe Phe Ala
                980                985                990

Ser Ile Ile Ser Leu Ser Leu Ile  Phe Tyr Tyr Ser Lys  Lys Gly Arg
                995                1000                1005

Arg Ser  Tyr Lys
    1010

<210> SEQ ID NO 3
<211> LENGTH: 3279
<212> TYPE: DNA
<213> ORGANISM: Homo sapiens

<400> SEQUENCE: 3

| | | |
|---|---|---|
|atcctcagtc tcccagttca agctaatcat tgacagagct ttacaatcac aagcttttac|60|
|tgaagctttg ataagacagt ccagcagttg gtggcaaatg aagccaggct gtgcggcagg|120|
|atctccaggg aatgaatgga tttcttcag cactgatgaa ataaccacac gctataggaa|180|
|tacaatgtcc aacgggggat tgcaaagatc tgtcatcctg tcagcactta ttctgctacg|240|
|agctgttact ggattctctg gagatggaag agctatatgg tctaaaaatc ctaattttac|300|
|tccggtaaat gaaagtcagc tgtttctcta tgacactttc cctaaaaact ttttctgggg|360|
|tattgggact ggagcattgc aagtggaagg gagttggaag aaggatggaa aaggaccttc|420|
|tatatgggat catttcatcc acacacacct taaaaatgtc agcagcacga atggttccag|480|
|tgacagttat attttctgg aaaaagactt atcagccctg gatttatag gagtttcttt|540|
|ttatcaattt tcaatttcct ggccaaggct ttccccgat ggaatagtaa cagttgccaa|600|
|cgcaaaaggt ctgcagtact acagtactct tctggacgct ctagtgctta gaaacattga|660|
|acctatagtt actttatacc actgggatt gcctttggca ctacaagaaa aatatggggg|720|
|gtggaaaaat gataccataa tagatatctt caatgactat gccacatact gtttccagat|780|

```
gtttggggac cgtgtcaaat attggattac aattcacaac ccatatctag tggcttggca    840
tgggtatggg acaggtatgc atgcccctgg agagaaggga aatttagcag ctgtctacac    900
tgtgggacac aacttgatca aggctcactc gaaagtttgg cataactaca acacacattt    960
ccgcccacat cagaagggtt ggttatcgat cacgttggga tctcattgga tcgagccaaa   1020
ccggtcggaa aacacgatgg atatattcaa atgtcaacaa tccatggttt ctgtgcttgg   1080
atggtttgcc aaccctatcc atggggatgg cgactatcca gagggatga gaaagaagtt   1140 gttctccgtt ctacccattt tctctgaagc agagaagcat gagatgagag gcacagctga   1200 tttcttttgcc ttttcttttg gacccaacaa cttcaagccc ctaaacacca tggctaaaat   1260
gggacaaaat gtttcactta atttaagaga agcgctgaac tggattaaac tggaatacaa   1320
caaccctcga atcttgattg ctgagaatgg ctggttcaca gacagtcgtg tgaaaacaga   1380
agacaccacg gccatctaca tgatgaagaa tttcctcagc caggtgcttc aagcaataag   1440
gttagatgaa atacgagtgt ttggttatac tgcctggtct ctcctggatg gctttgaatg   1500
gcaggatgct tacaccatcc gccgaggatt atttatgtg gatttaaca gtaaacagaa   1560 agagcggaaa cctaagtctt cagcacacta ctacaaacag atcatacgag aaaatggttt   1620
ttctttaaaa gagtccacgc cagatgtgca gggccagttt ccctgtgact ctcctgggg   1680 tgtcactgaa tctgttctta agcccgagtc tgtggcttcg tccccacagt tcagcgatcc   1740
tcatctgtac gtgtggaacg ccactggcaa cagactgttg caccgagtgg aaggggtgag   1800
gctgaaaaca cgacccgctc aatgcacaga ttttgtaaac atcaaaaaac aacttgagat   1860
gttggcaaga atgaaagtca cccactaccg gtttgctctg gattgggcct cggtccttcc   1920
cactggcaac ctgtccgcgg tgaaccgaca ggccctgagg tactacaggt gcgtggtcag   1980
tgaggggctg aagcttggca tctccgcgat ggtcaccctg tattatccga cccacgccca   2040
cctaggcctc cccgagcctc tgttgcatgc cgacgggtgg ctgaacccat cgacggccga   2100
ggccttccag gcctacgctg ggctgtgctt ccaggagctg ggggacctgg tgaagctctg   2160
gatcaccatc aacgagccta accggctaag tgacatctac aaccgctctg caacgacac   2220 ctacggggcg cgcacaacc tgctggtggc ccacgccctg gcctggcgcc tctacgaccg   2280
gcagttcagg ccctcacagc gcggggccgt gtcgctgtcg ctgcacgcgg actgggcgga   2340
acccgccaac ccctatgctg actcgcactg gagggcggcc gagcgcttcc tgcagttcga   2400
gatcgcctgg ttcgccgagc cgctcttcaa gaccggggac taccccgcgg ccatgaggga   2460
atacattgcc tccaagcacc gacggggct ttccagctcg ccctgccgc gcctcaccga   2520 ggccgaaagg aggctgctca agggcacggt cgacttctgc gcgctcaacc acttcaccac   2580
taggttcgtg atgcacgagc agctggccgg cagccgctac gactcggaca gggacatcca   2640
gtttctgcag gacatcaccc gcctgagctc ccccacgcgc ctggctgtga ttccctgggg   2700
ggtgcgcaag ctgctgcggt gggtccggag gaactacggc gacatggaca tttacatcac   2760
cgccagtggc atcgacgacc aggctctgga ggatgaccgg ctccggaagt actacctagg   2820
gaagtacctt caggaggtgc tgaaagcata cctgattgat aaagtcagaa tcaaaggcta   2880
ttatgcattc aaactggctg aagagaaatc taaacccaga tttggattct tcacatctga   2940
ttttaaagct aaatcctcaa tacaatttta caacaaagtg atcagcagca ggggcttccc   3000
ttttgagaac agtagttcta gatgcagtca gacccaagaa aatacagagt gcactgtctg   3060
cttattcctt gtgcagaaga aaccactgat attcctgggt tgttgcttct tctccaccct   3120
ggttctactc ttatcaattg ccatttttca aaggcagaag agaagaaagt tttggaaagc   3180
```

```
aaaaaactta caacacatac cattaaagaa aggcaagaga gttgttagct aaactgatct    3240
gtctgcatga tagacagttt aaaaattcat cccagttcc                           3279
```

<210> SEQ ID NO 4
<211> LENGTH: 1044
<212> TYPE: PRT
<213> ORGANISM: Homo sapiens

<400> SEQUENCE: 4

```
Met Lys Pro Gly Cys Ala Ala Gly Ser Pro Gly Asn Glu Trp Ile Phe
 1               5                  10                  15

Phe Ser Thr Asp Glu Ile Thr Thr Arg Tyr Arg Asn Thr Met Ser Asn
            20                  25                  30

Gly Gly Leu Gln Arg Ser Val Ile Leu Ser Ala Leu Ile Leu Leu Arg
        35                  40                  45

Ala Val Thr Gly Phe Ser Gly Asp Gly Arg Ala Ile Trp Ser Lys Asn
    50                  55                  60

Pro Asn Phe Thr Pro Val Asn Glu Ser Gln Leu Phe Leu Tyr Asp Thr
65                  70                  75                  80

Phe Pro Lys Asn Phe Phe Trp Gly Ile Gly Thr Gly Ala Leu Gln Val
                85                  90                  95

Glu Gly Ser Trp Lys Lys Asp Gly Lys Gly Pro Ser Ile Trp Asp His
            100                 105                 110

Phe Ile His Thr His Leu Lys Asn Val Ser Ser Thr Asn Gly Ser Ser
        115                 120                 125

Asp Ser Tyr Ile Phe Leu Glu Lys Asp Leu Ser Ala Leu Asp Phe Ile
    130                 135                 140

Gly Val Ser Phe Tyr Gln Phe Ser Ile Ser Trp Pro Arg Leu Phe Pro
145                 150                 155                 160

Asp Gly Ile Val Thr Val Ala Asn Ala Lys Gly Leu Gln Tyr Tyr Ser
                165                 170                 175

Thr Leu Leu Asp Ala Leu Val Leu Arg Asn Ile Glu Pro Ile Val Thr
            180                 185                 190

Leu Tyr His Trp Asp Leu Pro Leu Ala Leu Gln Glu Lys Tyr Gly Gly
        195                 200                 205

Trp Lys Asn Asp Thr Ile Ile Asp Ile Phe Asn Asp Tyr Ala Thr Tyr
    210                 215                 220

Cys Phe Gln Met Phe Gly Asp Arg Val Lys Tyr Trp Ile Thr Ile His
225                 230                 235                 240

Asn Pro Tyr Leu Val Ala Trp His Gly Tyr Gly Thr Gly Met His Ala
                245                 250                 255

Pro Gly Glu Lys Gly Asn Leu Ala Ala Val Tyr Thr Val Gly His Asn
            260                 265                 270

Leu Ile Lys Ala His Ser Lys Val Trp His Asn Tyr Asn Thr His Phe
        275                 280                 285

Arg Pro His Gln Lys Gly Trp Leu Ser Ile Thr Leu Gly Ser His Trp
    290                 295                 300

Ile Glu Pro Asn Arg Ser Glu Asn Thr Met Asp Ile Phe Lys Cys Gln
305                 310                 315                 320

Gln Ser Met Val Ser Val Leu Gly Trp Phe Ala Asn Pro Ile His Gly
                325                 330                 335

Asp Gly Asp Tyr Pro Glu Gly Met Arg Lys Lys Leu Phe Ser Val Leu
            340                 345                 350
```

```
Pro Ile Phe Ser Glu Ala Glu Lys His Glu Met Arg Gly Thr Ala Asp
            355                 360                 365

Phe Phe Ala Phe Ser Phe Gly Pro Asn Asn Phe Lys Pro Leu Asn Thr
370                 375                 380

Met Ala Lys Met Gly Gln Asn Val Ser Leu Asn Leu Arg Glu Ala Leu
385                 390                 395                 400

Asn Trp Ile Lys Leu Glu Tyr Asn Asn Pro Arg Ile Leu Ile Ala Glu
                405                 410                 415

Asn Gly Trp Phe Thr Asp Ser Arg Val Lys Thr Glu Asp Thr Thr Ala
            420                 425                 430

Ile Tyr Met Met Lys Asn Phe Leu Ser Gln Val Leu Gln Ala Ile Arg
        435                 440                 445

Leu Asp Glu Ile Arg Val Phe Gly Tyr Thr Ala Trp Ser Leu Leu Asp
    450                 455                 460

Gly Phe Glu Trp Gln Asp Ala Tyr Thr Ile Arg Arg Gly Leu Phe Tyr
465                 470                 475                 480

Val Asp Phe Asn Ser Lys Gln Lys Glu Arg Lys Pro Lys Ser Ser Ala
                485                 490                 495

His Tyr Tyr Lys Gln Ile Ile Arg Glu Asn Gly Phe Ser Leu Lys Glu
            500                 505                 510

Ser Thr Pro Asp Val Gln Gly Gln Phe Pro Cys Asp Phe Ser Trp Gly
        515                 520                 525

Val Thr Glu Ser Val Leu Lys Pro Glu Ser Val Ala Ser Ser Pro Gln
    530                 535                 540

Phe Ser Asp Pro His Leu Tyr Val Trp Asn Ala Thr Gly Asn Arg Leu
545                 550                 555                 560

Leu His Arg Val Glu Gly Val Arg Leu Lys Thr Arg Pro Ala Gln Cys
                565                 570                 575

Thr Asp Phe Val Asn Ile Lys Lys Gln Leu Glu Met Leu Ala Arg Met
            580                 585                 590

Lys Val Thr His Tyr Arg Phe Ala Leu Asp Trp Ala Ser Val Leu Pro
        595                 600                 605

Thr Gly Asn Leu Ser Ala Val Asn Arg Gln Ala Leu Arg Tyr Tyr Arg
    610                 615                 620

Cys Val Val Ser Glu Gly Leu Lys Leu Gly Ile Ser Ala Met Val Thr
625                 630                 635                 640

Leu Tyr Tyr Pro Thr His Ala His Leu Gly Leu Pro Glu Pro Leu Leu
                645                 650                 655

His Ala Asp Gly Trp Leu Asn Pro Ser Thr Ala Glu Ala Phe Gln Ala
            660                 665                 670

Tyr Ala Gly Leu Cys Phe Gln Glu Leu Gly Asp Leu Val Lys Leu Trp
        675                 680                 685

Ile Thr Ile Asn Glu Pro Asn Arg Leu Ser Asp Ile Tyr Asn Arg Ser
    690                 695                 700

Gly Asn Asp Thr Tyr Gly Ala Ala His Asn Leu Leu Val Ala His Ala
705                 710                 715                 720

Leu Ala Trp Arg Leu Tyr Asp Arg Gln Phe Arg Pro Ser Gln Arg Gly
                725                 730                 735

Ala Val Ser Leu Ser Leu His Ala Asp Trp Ala Glu Pro Ala Asn Pro
            740                 745                 750

Tyr Ala Asp Ser His Trp Arg Ala Ala Glu Arg Phe Leu Gln Phe Glu
        755                 760                 765

Ile Ala Trp Phe Ala Glu Pro Leu Phe Lys Thr Gly Asp Tyr Pro Ala
```

```
                    770                 775                 780
Ala Met Arg Glu Tyr Ile Ala Ser Lys His Arg Arg Gly Leu Ser Ser
785                 790                 795                 800

Ser Ala Leu Pro Arg Leu Thr Glu Ala Glu Arg Arg Leu Leu Lys Gly
                805                 810                 815

Thr Val Asp Phe Cys Ala Leu Asn His Phe Thr Thr Arg Phe Val Met
            820                 825                 830

His Glu Gln Leu Ala Gly Ser Arg Tyr Asp Ser Asp Arg Asp Ile Gln
        835                 840                 845

Phe Leu Gln Asp Ile Thr Arg Leu Ser Ser Pro Thr Arg Leu Ala Val
    850                 855                 860

Ile Pro Trp Gly Val Arg Lys Leu Leu Arg Trp Val Arg Arg Asn Tyr
865                 870                 875                 880

Gly Asp Met Asp Ile Tyr Ile Thr Ala Ser Gly Ile Asp Asp Gln Ala
                885                 890                 895

Leu Glu Asp Asp Arg Leu Arg Lys Tyr Tyr Leu Gly Lys Tyr Leu Gln
            900                 905                 910

Glu Val Leu Lys Ala Tyr Leu Ile Asp Lys Val Arg Ile Lys Gly Tyr
        915                 920                 925

Tyr Ala Phe Lys Leu Ala Glu Glu Lys Ser Lys Pro Arg Phe Gly Phe
    930                 935                 940

Phe Thr Ser Asp Phe Lys Ala Lys Ser Ser Ile Gln Phe Tyr Asn Lys
945                 950                 955                 960

Val Ile Ser Ser Arg Gly Phe Pro Phe Glu Asn Ser Ser Arg Cys
                965                 970                 975

Ser Gln Thr Gln Glu Asn Thr Glu Cys Thr Val Cys Leu Phe Leu Val
            980                 985                 990

Gln Lys Lys Pro Leu Ile Phe Leu Gly Cys Cys Phe Phe Ser Thr Leu
        995                 1000                1005

Val Leu Leu Leu Ser Ile Ala Ile Phe Gln Arg Gln Lys Arg Arg
    1010                1015                1020

Lys Phe Trp Lys Ala Lys Asn Leu Gln His Ile Pro Leu Lys Lys
    1025                1030                1035

Gly Lys Arg Val Val Ser
    1040

<210> SEQ ID NO 5
<211> LENGTH: 449
<212> TYPE: PRT
<213> ORGANISM: Homo sapiens

<400> SEQUENCE: 5

Gln Gly Thr Phe Pro Asp Gly Phe Leu Trp Ala Val Gly Ser Ala Ala
1               5                   10                  15

Tyr Gln Thr Glu Gly Gly Trp Gln Gln His Gly Lys Gly Ala Ser Ile
                20                  25                  30

Trp Asp Thr Phe Thr His His Pro Leu Ala Pro Pro Gly Asp Ser Arg
            35                  40                  45

Asn Ala Ser Leu Pro Leu Gly Ala Pro Ser Pro Leu Gln Pro Ala Thr
        50                  55                  60

Gly Asp Val Ala Ser Asp Ser Tyr Asn Asn Val Phe Arg Asp Thr Glu
65                  70                  75                  80

Ala Leu Arg Glu Leu Gly Val Thr His Tyr Arg Phe Ser Ile Ser Trp
                85                  90                  95
```

```
Ala Arg Val Leu Pro Asn Gly Ser Ala Gly Val Pro Asn Arg Glu Gly
            100                 105                 110

Leu Arg Tyr Tyr Arg Arg Leu Leu Glu Arg Leu Arg Glu Leu Gly Val
        115                 120                 125

Gln Pro Val Val Thr Leu Tyr His Trp Asp Leu Pro Gln Arg Leu Gln
    130                 135                 140

Asp Ala Tyr Gly Gly Trp Ala Asn Arg Ala Leu Ala Asp His Phe Arg
145                 150                 155                 160

Asp Tyr Ala Glu Leu Cys Phe Arg His Phe Gly Gly Gln Val Lys Tyr
                165                 170                 175

Trp Ile Thr Ile Asp Asn Pro Tyr Val Val Ala Trp His Gly Tyr Ala
            180                 185                 190

Thr Gly Arg Leu Ala Pro Gly Ile Arg Gly Ser Pro Arg Leu Gly Tyr
        195                 200                 205

Leu Val Ala His Asn Leu Leu Leu Ala His Ala Lys Val Trp His Leu
    210                 215                 220

Tyr Asn Thr Ser Phe Arg Pro Thr Gln Gly Gly Gln Val Ser Ile Ala
225                 230                 235                 240

Leu Ser Ser His Trp Ile Asn Pro Arg Arg Met Thr Asp His Ser Ile
                245                 250                 255

Lys Glu Cys Gln Lys Ser Leu Asp Phe Val Leu Gly Trp Phe Ala Lys
            260                 265                 270

Pro Val Phe Ile Asp Gly Asp Tyr Pro Glu Ser Met Lys Asn Asn Leu
        275                 280                 285

Ser Ser Ile Leu Pro Asp Phe Thr Glu Ser Lys Lys Phe Ile Lys
    290                 295                 300

Gly Thr Ala Asp Phe Phe Ala Leu Cys Phe Gly Pro Thr Leu Ser Phe
305                 310                 315                 320

Gln Leu Leu Asp Pro His Met Lys Phe Arg Gln Leu Glu Ser Pro Asn
                325                 330                 335

Leu Arg Gln Leu Leu Ser Trp Ile Asp Leu Glu Phe Asn His Pro Gln
            340                 345                 350

Ile Phe Ile Val Glu Asn Gly Trp Phe Val Ser Gly Thr Thr Lys Arg
        355                 360                 365

Asp Asp Ala Lys Tyr Met Tyr Tyr Leu Lys Lys Phe Ile Met Glu Thr
370                 375                 380

Leu Lys Ala Ile Lys Leu Asp Gly Val Asp Val Ile Gly Tyr Thr Ala
385                 390                 395                 400

Trp Ser Leu Met Asp Gly Phe Glu Trp His Arg Gly Tyr Ser Ile Arg
                405                 410                 415

Arg Gly Leu Phe Tyr Val Asp Phe Leu Ser Gln Asp Lys Met Leu Leu
            420                 425                 430

Pro Lys Ser Ser Ala Leu Phe Tyr Gln Lys Leu Ile Glu Lys Asn Gly
        435                 440                 445

Phe

<210> SEQ ID NO 6
<211> LENGTH: 437
<212> TYPE: PRT
<213> ORGANISM: Homo sapiens

<400> SEQUENCE: 6

Gly Thr Phe Pro Cys Asp Phe Ala Trp Gly Val Val Asp Asn Tyr Ile
1               5                   10                  15
```

```
Gln Val Asp Thr Thr Leu Ser Gln Phe Thr Asp Leu Asn Val Tyr Leu
            20                  25                  30

Trp Asp Val His His Ser Lys Arg Leu Ile Lys Val Asp Gly Val Val
        35                  40                  45

Thr Lys Lys Arg Lys Ser Tyr Cys Val Asp Phe Ala Ala Ile Gln Pro
    50                  55                  60

Gln Ile Ala Leu Leu Gln Glu Met His Val Thr His Phe Arg Phe Ser
65                  70                  75                  80

Leu Asp Trp Ala Leu Ile Leu Pro Leu Gly Asn Gln Ser Gln Val Asn
                85                  90                  95

His Thr Ile Leu Gln Tyr Tyr Arg Cys Met Ala Ser Glu Leu Val Arg
                100                 105                 110

Val Asn Ile Thr Pro Val Val Ala Leu Trp Gln Pro Met Ala Pro Asn
            115                 120                 125

Gln Gly Leu Pro Arg Leu Leu Ala Arg Gln Gly Ala Trp Glu Asn Pro
        130                 135                 140

Tyr Thr Ala Leu Ala Phe Ala Glu Tyr Ala Arg Leu Cys Phe Gln Glu
145                 150                 155                 160

Leu Gly His His Val Lys Leu Trp Ile Thr Met Asn Glu Pro Tyr Thr
                165                 170                 175

Arg Asn Met Thr Tyr Ser Ala Gly His Asn Leu Leu Lys Ala His Ala
                180                 185                 190

Leu Ala Trp His Val Tyr Asn Glu Lys Phe Arg His Ala Gln Asn Gly
                195                 200                 205

Lys Ile Ser Ile Ala Leu Gln Ala Asp Trp Ile Glu Pro Ala Cys Pro
210                 215                 220

Phe Ser Gln Lys Asp Lys Glu Val Ala Glu Arg Val Leu Glu Phe Asp
225                 230                 235                 240

Ile Gly Trp Leu Ala Glu Pro Ile Phe Gly Ser Gly Asp Tyr Pro Trp
            245                 250                 255

Val Met Arg Asp Trp Leu Asn Gln Arg Asn Asn Phe Leu Leu Pro Tyr
                260                 265                 270

Phe Thr Glu Asp Glu Lys Lys Leu Ile Gln Gly Thr Phe Asp Phe Leu
            275                 280                 285

Ala Leu Ser His Tyr Thr Thr Ile Leu Val Asp Ser Glu Lys Glu Asp
        290                 295                 300

Pro Ile Lys Tyr Asn Asp Tyr Leu Glu Val Gln Glu Met Thr Asp Ile
305                 310                 315                 320

Thr Trp Leu Asn Ser Pro Ser Gln Val Ala Val Val Pro Trp Gly Leu
                325                 330                 335

Arg Lys Val Leu Asn Trp Leu Lys Phe Lys Tyr Gly Asp Leu Pro Met
                340                 345                 350

Tyr Ile Ile Ser Asn Gly Ile Asp Asp Gly Leu His Ala Glu Asp Asp
            355                 360                 365

Gln Leu Arg Val Tyr Tyr Met Gln Asn Tyr Ile Asn Glu Ala Leu Lys
        370                 375                 380

Ala His Ile Leu Asp Gly Ile Asn Leu Cys Gly Tyr Phe Ala Tyr Ser
385                 390                 395                 400

Phe Asn Asp Arg Thr Ala Pro Arg Phe Gly Leu Tyr Arg Tyr Ala Ala
                405                 410                 415

Asp Gln Phe Glu Pro Lys Ala Ser Met Lys His Tyr Arg Lys Ile Ile
            420                 425                 430

Asp Ser Asn Gly Phe
```

435

<210> SEQ ID NO 7
<211> LENGTH: 949
<212> TYPE: PRT
<213> ORGANISM: Homo sapiens

<400> SEQUENCE: 7

```
Glu Pro Gly Asp Gly Ala Gln Thr Trp Ala Arg Phe Ser Arg Pro Pro
1               5                   10                  15

Ala Pro Glu Ala Ala Gly Leu Phe Gln Gly Thr Phe Pro Asp Gly Phe
            20                  25                  30

Leu Trp Ala Val Gly Ser Ala Ala Tyr Gln Thr Glu Gly Gly Trp Gln
        35                  40                  45

Gln His Gly Lys Gly Ala Ser Ile Trp Asp Thr Phe Thr His His Pro
    50                  55                  60

Leu Ala Pro Pro Gly Asp Ser Arg Asn Ala Ser Leu Pro Leu Gly Ala
65                  70                  75                  80

Pro Ser Pro Leu Gln Pro Ala Thr Gly Asp Val Ala Ser Asp Ser Tyr
                85                  90                  95

Asn Asn Val Phe Arg Asp Thr Glu Ala Leu Arg Glu Leu Gly Val Thr
            100                 105                 110

His Tyr Arg Phe Ser Ile Ser Trp Ala Arg Val Leu Pro Asn Gly Ser
        115                 120                 125

Ala Gly Val Pro Asn Arg Glu Gly Leu Arg Tyr Tyr Arg Arg Leu Leu
    130                 135                 140

Glu Arg Leu Arg Glu Leu Gly Val Gln Pro Val Val Thr Leu Tyr His
145                 150                 155                 160

Trp Asp Leu Pro Gln Arg Leu Gln Asp Ala Tyr Gly Gly Trp Ala Asn
                165                 170                 175

Arg Ala Leu Ala Asp His Phe Arg Asp Tyr Ala Glu Leu Cys Phe Arg
            180                 185                 190

His Phe Gly Gly Gln Val Lys Tyr Trp Ile Thr Ile Asp Asn Pro Tyr
        195                 200                 205

Val Val Ala Trp His Gly Tyr Ala Thr Gly Arg Leu Ala Pro Gly Ile
    210                 215                 220

Arg Gly Ser Pro Arg Leu Gly Tyr Leu Val Ala His Asn Leu Leu Leu
225                 230                 235                 240

Ala His Ala Lys Val Trp His Leu Tyr Asn Thr Ser Phe Arg Pro Thr
                245                 250                 255

Gln Gly Gly Gln Val Ser Ile Ala Leu Ser Ser His Trp Ile Asn Pro
            260                 265                 270

Arg Arg Met Thr Asp His Ser Ile Lys Glu Cys Gln Lys Ser Leu Asp
        275                 280                 285

Phe Val Leu Gly Trp Phe Ala Lys Pro Val Phe Ile Asp Gly Asp Tyr
    290                 295                 300

Pro Glu Ser Met Lys Asn Asn Leu Ser Ser Ile Leu Pro Asp Phe Thr
305                 310                 315                 320

Glu Ser Glu Lys Lys Phe Ile Lys Gly Thr Ala Asp Phe Phe Ala Leu
                325                 330                 335

Cys Phe Gly Pro Thr Leu Ser Phe Gln Leu Leu Asp Pro His Met Lys
            340                 345                 350

Phe Arg Gln Leu Glu Ser Pro Asn Leu Arg Gln Leu Leu Ser Trp Ile
        355                 360                 365
```

```
Asp Leu Glu Phe Asn His Pro Gln Ile Phe Ile Val Glu Asn Gly Trp
    370                 375                 380

Phe Val Ser Gly Thr Thr Lys Arg Asp Ala Lys Tyr Met Tyr Tyr
385                 390                 395                 400

Leu Lys Lys Phe Ile Met Glu Thr Leu Lys Ala Ile Lys Leu Asp Gly
                405                 410                 415

Val Asp Val Ile Gly Tyr Thr Ala Trp Ser Leu Met Asp Gly Phe Glu
                420                 425                 430

Trp His Arg Gly Tyr Ser Ile Arg Arg Gly Leu Phe Tyr Val Asp Phe
                435                 440                 445

Leu Ser Gln Asp Lys Met Leu Leu Pro Lys Ser Ser Ala Leu Phe Tyr
    450                 455                 460

Gln Lys Leu Ile Glu Lys Asn Gly Phe Pro Pro Leu Pro Glu Asn Gln
465                 470                 475                 480

Pro Leu Glu Gly Thr Phe Pro Cys Asp Phe Ala Trp Gly Val Val Asp
                485                 490                 495

Asn Tyr Ile Gln Val Asp Thr Thr Leu Ser Gln Phe Thr Asp Leu Asn
                500                 505                 510

Val Tyr Leu Trp Asp Val His His Ser Lys Arg Leu Ile Lys Val Asp
                515                 520                 525

Gly Val Val Thr Lys Lys Arg Lys Ser Tyr Cys Val Asp Phe Ala Ala
    530                 535                 540

Ile Gln Pro Gln Ile Ala Leu Leu Gln Glu Met His Val Thr His Phe
545                 550                 555                 560

Arg Phe Ser Leu Asp Trp Ala Leu Ile Leu Pro Leu Gly Asn Gln Ser
                565                 570                 575

Gln Val Asn His Thr Ile Leu Gln Tyr Tyr Arg Cys Met Ala Ser Glu
                580                 585                 590

Leu Val Arg Val Asn Ile Thr Pro Val Val Ala Leu Trp Gln Pro Met
                595                 600                 605

Ala Pro Asn Gln Gly Leu Pro Arg Leu Leu Ala Arg Gln Gly Ala Trp
    610                 615                 620

Glu Asn Pro Tyr Thr Ala Leu Ala Phe Ala Glu Tyr Ala Arg Leu Cys
625                 630                 635                 640

Phe Gln Glu Leu Gly His His Val Lys Leu Trp Ile Thr Met Asn Glu
                645                 650                 655

Pro Tyr Thr Arg Asn Met Thr Tyr Ser Ala Gly His Asn Leu Leu Lys
                660                 665                 670

Ala His Ala Leu Ala Trp His Val Tyr Asn Glu Lys Phe Arg His Ala
    675                 680                 685

Gln Asn Gly Lys Ile Ser Ile Ala Leu Gln Ala Asp Trp Ile Glu Pro
690                 695                 700

Ala Cys Pro Phe Ser Gln Lys Asp Lys Glu Val Ala Glu Arg Val Leu
705                 710                 715                 720

Glu Phe Asp Ile Gly Trp Leu Ala Glu Pro Ile Phe Gly Ser Gly Asp
                725                 730                 735

Tyr Pro Trp Val Met Arg Asp Trp Leu Asn Gln Arg Asn Asn Phe Leu
                740                 745                 750

Leu Pro Tyr Phe Thr Glu Asp Glu Lys Lys Leu Ile Gln Gly Thr Phe
    755                 760                 765

Asp Phe Leu Ala Leu Ser His Tyr Thr Thr Ile Leu Val Asp Ser Glu
770                 775                 780

Lys Glu Asp Pro Ile Lys Tyr Asn Asp Tyr Leu Glu Val Gln Glu Met
```

```
                785                 790                 795                 800
        Thr Asp Ile Thr Trp Leu Asn Ser Pro Ser Gln Val Ala Val Pro
                        805                 810                 815

Trp Gly Leu Arg Lys Val Leu Asn Trp Leu Lys Phe Lys Tyr Gly Asp
                        820                 825                 830

Leu Pro Met Tyr Ile Ile Ser Asn Gly Ile Asp Gly Leu His Ala
                        835                 840                 845

Glu Asp Asp Gln Leu Arg Val Tyr Tyr Met Gln Asn Tyr Ile Asn Glu
                        850                 855                 860

Ala Leu Lys Ala His Ile Leu Asp Gly Ile Asn Leu Cys Gly Tyr Phe
        865                 870                 875                 880

Ala Tyr Ser Phe Asn Asp Arg Thr Ala Pro Arg Phe Gly Leu Tyr Arg
                        885                 890                 895

Tyr Ala Ala Asp Gln Phe Glu Pro Lys Ala Ser Met Lys His Tyr Arg
                        900                 905                 910

Lys Ile Ile Asp Ser Asn Gly Phe Pro Gly Pro Glu Thr Leu Glu Arg
                        915                 920                 925

Phe Cys Pro Glu Glu Phe Thr Val Cys Thr Glu Cys Ser Phe Phe His
                        930                 935                 940

Thr Arg Lys Ser Leu
        945

<210> SEQ ID NO 8
<211> LENGTH: 33
<212> TYPE: PRT
<213> ORGANISM: Homo sapiens

<400> SEQUENCE: 8

Met Pro Ala Ser Ala Pro Pro Arg Arg Pro Arg Pro Pro Pro Ser
1               5                   10                  15

Leu Ser Leu Leu Leu Val Leu Leu Gly Leu Gly Gly Arg Arg Leu Arg
                20                  25                  30

Ala

<210> SEQ ID NO 9
<211> LENGTH: 25
<212> TYPE: PRT
<213> ORGANISM: Homo sapiens

<400> SEQUENCE: 9

Met Ser Val Leu Thr Gln Val Leu Ala Leu Leu Leu Leu Trp Leu Thr
1               5                   10                  15

Gly Thr Arg Cys Arg Arg Leu Arg Ala
                20                  25

<210> SEQ ID NO 10
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
ggaggtggag gttcaggagg tggaggttca ggaggtggag gttca               45

<210> SEQ ID NO 11
<211> LENGTH: 15
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Gly Gly Gly Gly Ser Gly Gly Gly Gly Ser Gly Gly Gly Gly Ser
1               5                   10                  15

<210> SEQ ID NO 12
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gly Gly Gly Gly Ser
1               5

<210> SEQ ID NO 13
<211> LENGTH: 1
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Gly
1

<210> SEQ ID NO 14
<211> LENGTH: 2
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Gly Gly
1

<210> SEQ ID NO 15
<211> LENGTH: 2
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Gly Ser
1

<210> SEQ ID NO 16
<211> LENGTH: 3
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 16

Gly Gly Ser
1

<210> SEQ ID NO 17
<211> LENGTH: 1
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Ala
1

<210> SEQ ID NO 18
<211> LENGTH: 2
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Ala Ala
1

<210> SEQ ID NO 19
<211> LENGTH: 1228
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
                20                  25                  30

Ala Glu Pro Gly Asp Gly Ala Gln Thr Trp Ala Arg Phe Ser Arg Pro
            35                  40                  45

Pro Ala Pro Glu Ala Ala Gly Leu Phe Gln Gly Thr Phe Pro Asp Gly
        50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

```
Ser Ala Gly Val Pro Asn Arg Glu Gly Leu Arg Tyr Arg Arg Leu
            165                 170                 175

Leu Glu Arg Leu Arg Glu Leu Gly Val Gln Pro Val Val Thr Leu Tyr
        180                 185                 190

His Trp Asp Leu Pro Gln Arg Leu Gln Asp Ala Tyr Gly Gly Trp Ala
            195                 200                 205

Asn Arg Ala Leu Ala Asp His Phe Arg Asp Tyr Ala Glu Leu Cys Phe
        210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
            245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
        290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
            325                 330                 335

Tyr Pro Glu Ser Met Lys Asn Asn Leu Ser Ser Ile Leu Pro Asp Phe
        340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
        370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
            405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Pro Lys Ser Ser Ala Leu Phe
        485                 490                 495

Tyr Gln Lys Leu Ile Glu Lys Asn Gly Phe Pro Pro Leu Pro Glu Asn
        500                 505                 510

Gln Pro Leu Glu Gly Thr Phe Pro Cys Asp Phe Ala Trp Gly Val Val
        515                 520                 525

Asp Asn Tyr Ile Gln Val Asp Thr Thr Leu Ser Gln Phe Thr Asp Leu
        530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
            565                 570                 575
```

```
Ala Ile Gln Pro Gln Ile Ala Leu Leu Gln Glu Met His Val Thr His
            580                 585                 590

Phe Arg Phe Ser Leu Asp Trp Ala Leu Ile Leu Pro Leu Gly Asn Gln
        595                 600                 605

Ser Gln Val Asn His Thr Ile Leu Gln Tyr Tyr Arg Cys Met Ala Ser
    610                 615                 620

Glu Leu Val Arg Val Asn Ile Thr Pro Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
                660                 665                 670

Cys Phe Gln Glu Leu Gly His His Val Lys Leu Trp Ile Thr Met Asn
            675                 680                 685

Glu Pro Tyr Thr Arg Asn Met Thr Tyr Ser Ala Gly His Asn Leu Leu
        690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
        755                 760                 765

Asp Tyr Pro Trp Val Met Arg Asp Trp Leu Asn Gln Arg Asn Asn Phe
770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
            820                 825                 830

Met Thr Asp Ile Thr Trp Leu Asn Ser Pro Ser Gln Val Ala Val Val
        835                 840                 845

Pro Trp Gly Leu Arg Lys Val Leu Asn Trp Leu Lys Phe Lys Tyr Gly
850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Gly Ser Gly Gly Gly Ser Gly Gly Gly
            980                 985                 990

Gly Ser Gly Gly Gly Gly Ser Leu  Lys Tyr Pro Asn Ala  Ser Pro Leu
```

```
                995                1000               1005
Leu Gly Ser Ser Trp Gly Gly Leu Ile His Leu Tyr Thr Ala Thr
    1010                1015                1020

Ala Arg Asn Ser Tyr His Leu Gln Ile His Lys Asn Gly His Val
    1025                1030                1035

Asp Gly Ala Pro His Gln Thr Ile Tyr Ser Ala Leu Met Ile Arg
    1040                1045                1050

Ser Glu Asp Ala Gly Phe Val Val Ile Thr Gly Val Met Ser Arg
    1055                1060                1065

Arg Tyr Leu Cys Met Asp Phe Arg Gly Asn Ile Phe Gly Ser His
    1070                1075                1080

Tyr Phe Asp Pro Glu Asn Cys Arg Phe Gln His Gln Thr Leu Glu
    1085                1090                1095

Asn Gly Tyr Asp Val Tyr His Ser Pro Gln Tyr His Phe Leu Val
    1100                1105                1110

Ser Leu Gly Arg Ala Lys Arg Ala Phe Leu Pro Gly Met Asn Pro
    1115                1120                1125

Pro Pro Tyr Ser Gln Phe Leu Ser Arg Arg Asn Glu Ile Pro Leu
    1130                1135                1140

Ile His Phe Asn Thr Pro Ile Pro Arg Arg His Thr Gln Ser Ala
    1145                1150                1155

Glu Asp Asp Ser Glu Arg Asp Pro Leu Asn Val Leu Lys Pro Arg
    1160                1165                1170

Ala Arg Met Thr Pro Ala Pro Ala Ser Cys Ser Gln Glu Leu Pro
    1175                1180                1185

Ser Ala Glu Asp Asn Ser Pro Met Ala Ser Asp Pro Leu Gly Val
    1190                1195                1200

Val Arg Gly Gly Arg Val Asn Thr His Ala Gly Gly Thr Gly Pro
    1205                1210                1215

Glu Gly Cys Arg Pro Phe Ala Lys Phe Ile
    1220                1225

<210> SEQ ID NO 20
<211> LENGTH: 1220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Met Ser Val Leu Thr Gln Val Leu Ala Leu Leu Leu Trp Leu Thr
1               5                   10                  15

Gly Leu Gly Gly Arg Arg Leu Arg Ala Glu Pro Gly Asp Gly Ala Gln
            20                  25                  30

Thr Trp Ala Arg Phe Ser Arg Pro Pro Ala Pro Glu Ala Ala Gly Leu
        35                  40                  45

Phe Gln Gly Thr Phe Pro Asp Gly Phe Leu Trp Ala Val Gly Ser Ala
    50                  55                  60

Ala Tyr Gln Thr Glu Gly Gly Trp Gln Gln His Gly Lys Gly Ala Ser
65                  70                  75                  80

Ile Trp Asp Thr Phe Thr His His Pro Leu Ala Pro Pro Gly Asp Ser
                85                  90                  95

Arg Asn Ala Ser Leu Pro Leu Gly Ala Pro Ser Pro Leu Gln Pro Ala
            100                 105                 110
```

-continued

```
Thr Gly Asp Val Ala Ser Asp Ser Tyr Asn Asn Val Phe Arg Asp Thr
        115                 120                 125

Glu Ala Leu Arg Glu Leu Gly Val Thr His Tyr Arg Phe Ser Ile Ser
        130                 135                 140

Trp Ala Arg Val Leu Pro Asn Gly Ser Ala Gly Val Pro Asn Arg Glu
145                 150                 155                 160

Gly Leu Arg Tyr Tyr Arg Arg Leu Leu Glu Arg Leu Arg Glu Leu Gly
                165                 170                 175

Val Gln Pro Val Val Thr Leu Tyr His Trp Asp Leu Pro Gln Arg Leu
                180                 185                 190

Gln Asp Ala Tyr Gly Gly Trp Ala Asn Arg Ala Leu Ala Asp His Phe
            195                 200                 205

Arg Asp Tyr Ala Glu Leu Cys Phe Arg His Phe Gly Gly Gln Val Lys
        210                 215                 220

Tyr Trp Ile Thr Ile Asp Asn Pro Tyr Val Val Ala Trp His Gly Tyr
225                 230                 235                 240

Ala Thr Gly Arg Leu Ala Pro Gly Ile Arg Gly Ser Pro Arg Leu Gly
                245                 250                 255

Tyr Leu Val Ala His Asn Leu Leu Leu Ala His Ala Lys Val Trp His
                260                 265                 270

Leu Tyr Asn Thr Ser Phe Arg Pro Thr Gln Gly Gly Gln Val Ser Ile
        275                 280                 285

Ala Leu Ser Ser His Trp Ile Asn Pro Arg Arg Met Thr Asp His Ser
        290                 295                 300

Ile Lys Glu Cys Gln Lys Ser Leu Asp Phe Val Leu Gly Trp Phe Ala
305                 310                 315                 320

Lys Pro Val Phe Ile Asp Gly Asp Tyr Pro Glu Ser Met Lys Asn Asn
                325                 330                 335

Leu Ser Ser Ile Leu Pro Asp Phe Thr Glu Ser Glu Lys Lys Phe Ile
                340                 345                 350

Lys Gly Thr Ala Asp Phe Phe Ala Leu Cys Phe Gly Pro Thr Leu Ser
        355                 360                 365

Phe Gln Leu Leu Asp Pro His Met Lys Phe Arg Gln Leu Glu Ser Pro
        370                 375                 380

Asn Leu Arg Gln Leu Leu Ser Trp Ile Asp Leu Glu Phe Asn His Pro
385                 390                 395                 400

Gln Ile Phe Ile Val Glu Asn Gly Trp Phe Val Ser Gly Thr Thr Lys
                405                 410                 415

Arg Asp Asp Ala Lys Tyr Met Tyr Tyr Leu Lys Lys Phe Ile Met Glu
                420                 425                 430

Thr Leu Lys Ala Ile Lys Leu Asp Gly Val Asp Val Ile Gly Tyr Thr
        435                 440                 445

Ala Trp Ser Leu Met Asp Gly Phe Glu Trp His Arg Gly Tyr Ser Ile
450                 455                 460

Arg Arg Gly Leu Phe Tyr Val Asp Phe Leu Ser Gln Asp Lys Met Leu
465                 470                 475                 480

Leu Pro Lys Ser Ser Ala Leu Phe Tyr Gln Lys Leu Ile Glu Lys Asn
                485                 490                 495

Gly Phe Pro Pro Leu Pro Glu Asn Gln Pro Leu Glu Gly Thr Phe Pro
                500                 505                 510

Cys Asp Phe Ala Trp Gly Val Val Asp Asn Tyr Ile Gln Val Asp Thr
        515                 520                 525
```

-continued

Thr Leu Ser Gln Phe Thr Asp Leu Asn Val Tyr Leu Trp Asp Val His
530                 535                 540

His Ser Lys Arg Leu Ile Lys Val Asp Gly Val Val Thr Lys Lys Arg
545                 550                 555                 560

Lys Ser Tyr Cys Val Asp Phe Ala Ala Ile Gln Pro Gln Ile Ala Leu
            565                 570                 575

Leu Gln Glu Met His Val Thr His Phe Arg Phe Ser Leu Asp Trp Ala
            580                 585                 590

Leu Ile Leu Pro Leu Gly Asn Gln Ser Gln Val Asn His Thr Ile Leu
            595                 600                 605

Gln Tyr Tyr Arg Cys Met Ala Ser Glu Leu Val Arg Val Asn Ile Thr
610                 615                 620

Pro Val Val Ala Leu Trp Gln Pro Met Ala Pro Asn Gln Gly Leu Pro
625                 630                 635                 640

Arg Leu Leu Ala Arg Gln Gly Ala Trp Glu Asn Pro Tyr Thr Ala Leu
            645                 650                 655

Ala Phe Ala Glu Tyr Ala Arg Leu Cys Phe Gln Glu Leu Gly His His
            660                 665                 670

Val Lys Leu Trp Ile Thr Met Asn Glu Pro Tyr Thr Arg Asn Met Thr
675                 680                 685

Tyr Ser Ala Gly His Asn Leu Leu Lys Ala His Ala Leu Ala Trp His
690                 695                 700

Val Tyr Asn Glu Lys Phe Arg His Ala Gln Asn Gly Lys Ile Ser Ile
705                 710                 715                 720

Ala Leu Gln Ala Asp Trp Ile Glu Pro Ala Cys Pro Phe Ser Gln Lys
            725                 730                 735

Asp Lys Glu Val Ala Glu Arg Val Leu Glu Phe Asp Ile Gly Trp Leu
            740                 745                 750

Ala Glu Pro Ile Phe Gly Ser Gly Asp Tyr Pro Trp Val Met Arg Asp
            755                 760                 765

Trp Leu Asn Gln Arg Asn Asn Phe Leu Leu Pro Tyr Phe Thr Glu Asp
770                 775                 780

Glu Lys Lys Leu Ile Gln Gly Thr Phe Asp Phe Leu Ala Leu Ser His
785                 790                 795                 800

Tyr Thr Thr Ile Leu Val Asp Ser Glu Lys Glu Asp Pro Ile Lys Tyr
            805                 810                 815

Asn Asp Tyr Leu Glu Val Gln Glu Met Thr Asp Ile Thr Trp Leu Asn
            820                 825                 830

Ser Pro Ser Gln Val Ala Val Val Pro Trp Gly Leu Arg Lys Val Leu
            835                 840                 845

Asn Trp Leu Lys Phe Lys Tyr Gly Asp Leu Pro Met Tyr Ile Ile Ser
850                 855                 860

Asn Gly Ile Asp Asp Gly Leu His Ala Glu Asp Asp Gln Leu Arg Val
865                 870                 875                 880

Tyr Tyr Met Gln Asn Tyr Ile Asn Glu Ala Leu Lys Ala His Ile Leu
            885                 890                 895

Asp Gly Ile Asn Leu Cys Gly Tyr Phe Ala Tyr Ser Phe Asn Asp Arg
            900                 905                 910

Thr Ala Pro Arg Phe Gly Leu Tyr Arg Tyr Ala Ala Asp Gln Phe Glu
            915                 920                 925

Pro Lys Ala Ser Met Lys His Tyr Arg Lys Ile Ile Asp Ser Asn Gly
930                 935                 940

Phe Pro Gly Pro Glu Thr Leu Glu Arg Phe Cys Pro Glu Glu Phe Thr

```
                945                 950                 955                 960
Val Cys Thr Glu Cys Ser Phe Phe His Thr Arg Lys Ser Leu Gly Ser
                    965                 970                 975
Gly Gly Gly Gly Ser Gly Gly Gly Gly Ser Gly Gly Gly Gly Ser Leu
                    980                 985                 990
Lys Tyr Pro Asn Ala Ser Pro Leu Leu Gly Ser Ser Trp Gly Gly Leu
                    995                 1000                1005
Ile His Leu Tyr Thr Ala Thr Ala Arg Asn Ser Tyr His Leu Gln
        1010                1015                1020
Ile His Lys Asn Gly His Val Asp Gly Ala Pro His Gln Thr Ile
        1025                1030                1035
Tyr Ser Ala Leu Met Ile Arg Ser Glu Asp Ala Gly Phe Val Val
        1040                1045                1050
Ile Thr Gly Val Met Ser Arg Arg Tyr Leu Cys Met Asp Phe Arg
        1055                1060                1065
Gly Asn Ile Phe Gly Ser His Tyr Phe Asp Pro Glu Asn Cys Arg
        1070                1075                1080
Phe Gln His Gln Thr Leu Glu Asn Gly Tyr Asp Val Tyr His Ser
        1085                1090                1095
Pro Gln Tyr His Phe Leu Val Ser Leu Gly Arg Ala Lys Arg Ala
        1100                1105                1110
Phe Leu Pro Gly Met Asn Pro Pro Pro Tyr Ser Gln Phe Leu Ser
        1115                1120                1125
Arg Arg Asn Glu Ile Pro Leu Ile His Phe Asn Thr Pro Ile Pro
        1130                1135                1140
Arg Arg His Thr Gln Ser Ala Glu Asp Asp Ser Glu Arg Asp Pro
        1145                1150                1155
Leu Asn Val Leu Lys Pro Arg Ala Arg Met Thr Pro Ala Pro Ala
        1160                1165                1170
Ser Cys Ser Gln Glu Leu Pro Ser Ala Glu Asp Asn Ser Pro Met
        1175                1180                1185
Ala Ser Asp Pro Leu Gly Val Val Arg Gly Gly Arg Val Asn Thr
        1190                1195                1200
His Ala Gly Gly Thr Gly Pro Glu Gly Cys Arg Pro Phe Ala Lys
        1205                1210                1215
Phe Ile
        1220

<210> SEQ ID NO 21
<211> LENGTH: 762
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Met Pro Ala Ser Ala Pro Pro Arg Arg Pro Arg Pro Pro Pro Ser
1               5                   10                  15

Leu Ser Leu Leu Leu Val Leu Leu Gly Leu Gly Arg Arg Leu Arg
                20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60
```

```
Phe Leu Trp Ala Val Gly Ser Ala Ala Tyr Gln Thr Glu Gly Gly Trp
 65                  70                  75                  80

Gln Gln His Gly Lys Gly Ala Ser Ile Trp Asp Thr Phe Thr His His
                 85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
450                 455                 460

Glu Trp His Arg Gly Tyr Ser Ile Arg Arg Gly Leu Phe Tyr Val Asp
465                 470                 475                 480
```

```
Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Ser Gly Gly Gly Ser Gly Gly Gly Gly Ser
        515                 520                 525

Gly Gly Gly Gly Ser Leu Lys Tyr Pro Asn Ala Ser Pro Leu Leu Gly
        530                 535                 540

Ser Ser Trp Gly Gly Leu Ile His Leu Tyr Thr Ala Thr Ala Arg Asn
545                 550                 555                 560

Ser Tyr His Leu Gln Ile His Lys Asn Gly His Val Asp Gly Ala Pro
                565                 570                 575

His Gln Thr Ile Tyr Ser Ala Leu Met Ile Arg Ser Glu Asp Ala Gly
            580                 585                 590

Phe Val Val Ile Thr Gly Val Met Ser Arg Arg Tyr Leu Cys Met Asp
        595                 600                 605

Phe Arg Gly Asn Ile Phe Gly Ser His Tyr Phe Asp Pro Glu Asn Cys
        610                 615                 620

Arg Phe Gln His Gln Thr Leu Glu Asn Gly Tyr Asp Val Tyr His Ser
625                 630                 635                 640

Pro Gln Tyr His Phe Leu Val Ser Leu Gly Arg Ala Lys Arg Ala Phe
                645                 650                 655

Leu Pro Gly Met Asn Pro Pro Tyr Ser Gln Phe Leu Ser Arg Arg
            660                 665                 670

Asn Glu Ile Pro Leu Ile His Phe Asn Thr Pro Ile Pro Arg Arg His
        675                 680                 685

Thr Gln Ser Ala Glu Asp Ser Glu Arg Asp Pro Leu Asn Val Leu
        690                 695                 700

Lys Pro Arg Ala Arg Met Thr Pro Ala Pro Ala Ser Cys Ser Gln Glu
705                 710                 715                 720

Leu Pro Ser Ala Glu Asp Asn Ser Pro Met Ala Ser Asp Pro Leu Gly
                725                 730                 735

Val Val Arg Gly Gly Arg Val Asn Thr His Ala Gly Gly Thr Gly Pro
            740                 745                 750

Glu Gly Cys Arg Pro Phe Ala Lys Phe Ile
        755                 760

<210> SEQ ID NO 22
<211> LENGTH: 752
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Met Pro Ala Ser Ala Pro Pro Arg Arg Pro Arg Pro Pro Pro Ser
1               5                   10                  15

Leu Ser Leu Leu Leu Val Leu Leu Gly Leu Gly Gly Arg Arg Leu Pro
            20                  25                  30

Leu Pro Glu Asn Gln Pro Leu Glu Gly Thr Phe Pro Cys Asp Phe Ala
        35                  40                  45

Trp Gly Val Val Asp Asn Tyr Ile Gln Val Asp Thr Thr Leu Ser Gln
    50                  55                  60

Phe Thr Asp Leu Asn Val Tyr Leu Trp Asp Val His His Ser Lys Arg
```

```
              65                  70                  75                  80
Leu Ile Lys Val Asp Gly Val Val Thr Lys Arg Lys Ser Tyr Cys
                85                  90                  95
Val Asp Phe Ala Ala Ile Gln Pro Gln Ile Ala Leu Leu Gln Glu Met
                100                 105                 110
His Val Thr His Phe Arg Phe Ser Leu Asp Trp Ala Leu Ile Leu Pro
                115                 120                 125
Leu Gly Asn Gln Ser Gln Val Asn His Thr Ile Leu Gln Tyr Tyr Arg
            130                 135                 140
Cys Met Ala Ser Glu Leu Val Arg Val Asn Ile Thr Pro Val Val Ala
145                 150                 155                 160
Leu Trp Gln Pro Met Ala Pro Asn Gln Gly Leu Pro Arg Leu Leu Ala
                165                 170                 175
Arg Gln Gly Ala Trp Glu Asn Pro Tyr Thr Ala Leu Ala Phe Ala Glu
                180                 185                 190
Tyr Ala Arg Leu Cys Phe Gln Glu Leu Gly His His Val Lys Leu Trp
            195                 200                 205
Ile Thr Met Asn Glu Pro Tyr Thr Arg Asn Met Thr Tyr Ser Ala Gly
        210                 215                 220
His Asn Leu Leu Lys Ala His Ala Leu Ala Trp His Val Tyr Asn Glu
225                 230                 235                 240
Lys Phe Arg His Ala Gln Asn Gly Lys Ile Ser Ile Ala Leu Gln Ala
                245                 250                 255
Asp Trp Ile Glu Pro Ala Cys Pro Phe Ser Gln Lys Asp Lys Glu Val
                260                 265                 270
Ala Glu Arg Val Leu Glu Phe Asp Ile Gly Trp Leu Ala Glu Pro Ile
            275                 280                 285
Phe Gly Ser Gly Asp Tyr Pro Trp Val Met Arg Asp Trp Leu Asn Gln
        290                 295                 300
Arg Asn Asn Phe Leu Leu Pro Tyr Phe Thr Glu Asp Glu Lys Lys Leu
305                 310                 315                 320
Ile Gln Gly Thr Phe Asp Phe Leu Ala Leu Ser His Tyr Thr Thr Ile
                325                 330                 335
Leu Val Asp Ser Glu Lys Glu Asp Pro Ile Lys Tyr Asn Asp Tyr Leu
            340                 345                 350
Glu Val Gln Glu Met Thr Asp Ile Thr Trp Leu Asn Ser Pro Ser Gln
            355                 360                 365
Val Ala Val Val Pro Trp Gly Leu Arg Lys Val Leu Asn Trp Leu Lys
            370                 375                 380
Phe Lys Tyr Gly Asp Leu Pro Met Tyr Ile Ile Ser Asn Gly Ile Asp
385                 390                 395                 400
Asp Gly Leu His Ala Glu Asp Gln Leu Arg Val Tyr Tyr Met Gln
                405                 410                 415
Asn Tyr Ile Asn Glu Ala Leu Lys Ala His Ile Leu Asp Gly Ile Asn
            420                 425                 430
Leu Cys Gly Tyr Phe Ala Tyr Ser Phe Asn Asp Arg Thr Ala Pro Arg
            435                 440                 445
Phe Gly Leu Tyr Arg Tyr Ala Ala Asp Gln Phe Glu Pro Lys Ala Ser
        450                 455                 460
Met Lys His Tyr Arg Lys Ile Ile Asp Ser Asn Gly Phe Pro Gly Pro
465                 470                 475                 480
Glu Thr Leu Glu Arg Phe Cys Pro Glu Glu Phe Thr Val Cys Thr Glu
                485                 490                 495
```

Cys Ser Phe Phe His Thr Arg Lys Ser Leu Gly Ser Gly Gly Gly
              500                 505                 510

Ser Gly Gly Gly Ser Gly Gly Gly Ser Leu Lys Tyr Pro Asn
              515                 520                 525

Ala Ser Pro Leu Leu Gly Ser Ser Trp Gly Gly Leu Ile His Leu Tyr
530                 535                 540

Thr Ala Thr Ala Arg Asn Ser Tyr His Leu Gln Ile His Lys Asn Gly
545                 550                 555                 560

His Val Asp Gly Ala Pro His Gln Thr Ile Tyr Ser Ala Leu Met Ile
              565                 570                 575

Arg Ser Glu Asp Ala Gly Phe Val Val Ile Thr Gly Val Met Ser Arg
              580                 585                 590

Arg Tyr Leu Cys Met Asp Phe Arg Gly Asn Ile Phe Gly Ser His Tyr
              595                 600                 605

Phe Asp Pro Glu Asn Cys Arg Phe Gln His Gln Thr Leu Glu Asn Gly
              610                 615                 620

Tyr Asp Val Tyr His Ser Pro Gln Tyr His Phe Leu Val Ser Leu Gly
625                 630                 635                 640

Arg Ala Lys Arg Ala Phe Leu Pro Gly Met Asn Pro Pro Tyr Ser
              645                 650                 655

Gln Phe Leu Ser Arg Arg Asn Glu Ile Pro Leu Ile His Phe Asn Thr
              660                 665                 670

Pro Ile Pro Arg Arg His Thr Gln Ser Ala Glu Asp Ser Glu Arg
              675                 680                 685

Asp Pro Leu Asn Val Leu Lys Pro Arg Ala Arg Met Thr Pro Ala Pro
              690                 695                 700

Ala Ser Cys Ser Gln Glu Leu Pro Ser Ala Glu Asp Asn Ser Pro Met
705                 710                 715                 720

Ala Ser Asp Pro Leu Gly Val Val Arg Gly Gly Arg Val Asn Thr His
              725                 730                 735

Ala Gly Gly Thr Gly Pro Glu Gly Cys Arg Pro Phe Ala Lys Phe Ile
              740                 745                 750

<210> SEQ ID NO 23
<211> LENGTH: 1215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Met Pro Ala Ser Ala Pro Pro Arg Arg Pro Arg Pro Pro Pro Ser
1                 5                   10                  15

Leu Ser Leu Leu Leu Val Leu Leu Gly Leu Gly Gly Arg Arg Leu Arg
              20                  25                  30

Ala Glu Pro Gly Asp Gly Ala Gln Thr Trp Ala Arg Phe Ser Arg Pro
              35                  40                  45

Pro Ala Pro Glu Ala Ala Gly Leu Phe Gln Gly Thr Phe Pro Asp Gly
              50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
              85                  90                  95

-continued

Pro Leu Ala Pro Pro Gly Asp Ser Arg Asn Ala Ser Leu Pro Leu Gly
            100                 105                 110

Ala Pro Ser Pro Leu Gln Pro Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
        180                 185                 190

His Trp Asp Leu Pro Gln Arg Leu Gln Asp Ala Tyr Gly Gly Trp Ala
    195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
    450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Ser Gly Thr Phe Pro Asp Gly Phe Leu Trp Ala

-continued

```
            515                 520                 525
Val Gly Ser Ala Ala Tyr Gln Thr Glu Gly Gly Trp Gln Gln His Gly
    530                 535                 540

Lys Gly Ala Ser Ile Trp Asp Thr Phe Thr His His Pro Leu Ala Pro
545                 550                 555                 560

Pro Gly Asp Ser Arg Asn Ala Ser Leu Pro Leu Gly Ala Pro Ser Pro
                565                 570                 575

Leu Gln Pro Ala Thr Gly Asp Val Ala Ser Asp Ser Tyr Asn Asn Val
            580                 585                 590

Phe Arg Asp Thr Glu Ala Leu Arg Glu Leu Gly Val Thr His Tyr Arg
        595                 600                 605

Phe Ser Ile Ser Trp Ala Arg Val Leu Pro Asn Gly Ser Ala Gly Val
        610                 615                 620

Pro Asn Arg Glu Gly Leu Arg Tyr Tyr Arg Arg Leu Leu Glu Arg Leu
625                 630                 635                 640

Arg Glu Leu Gly Val Gln Pro Val Val Thr Leu Tyr His Trp Asp Leu
                645                 650                 655

Pro Gln Arg Leu Gln Asp Ala Tyr Gly Gly Trp Ala Asn Arg Ala Leu
            660                 665                 670

Ala Asp His Phe Arg Asp Tyr Ala Glu Leu Cys Phe Arg His Phe Gly
        675                 680                 685

Gly Gln Val Lys Tyr Trp Ile Thr Ile Asp Asn Pro Tyr Val Val Ala
    690                 695                 700

Trp His Gly Tyr Ala Thr Gly Arg Leu Ala Pro Gly Ile Arg Gly Ser
705                 710                 715                 720

Pro Arg Leu Gly Tyr Leu Val Ala His Asn Leu Leu Leu Ala His Ala
                725                 730                 735

Lys Val Trp His Leu Tyr Asn Thr Ser Phe Arg Pro Thr Gln Gly Gly
            740                 745                 750

Gln Val Ser Ile Ala Leu Ser Ser His Trp Ile Asn Pro Arg Arg Met
    755                 760                 765

Thr Asp His Ser Ile Lys Glu Cys Gln Lys Ser Leu Asp Phe Val Leu
        770                 775                 780

Gly Trp Phe Ala Lys Pro Val Phe Ile Asp Gly Asp Tyr Pro Glu Ser
785                 790                 795                 800

Met Lys Asn Asn Leu Ser Ser Ile Leu Pro Asp Phe Thr Glu Ser Glu
                805                 810                 815

Lys Lys Phe Ile Lys Gly Thr Ala Asp Phe Phe Ala Leu Cys Phe Gly
            820                 825                 830

Pro Thr Leu Ser Phe Gln Leu Leu Asp Pro His Met Lys Phe Arg Gln
        835                 840                 845

Leu Glu Ser Pro Asn Leu Arg Gln Leu Leu Ser Trp Ile Asp Leu Glu
        850                 855                 860

Phe Asn His Pro Gln Ile Phe Ile Val Glu Asn Gly Trp Phe Val Ser
865                 870                 875                 880

Gly Thr Thr Lys Arg Asp Asp Ala Lys Tyr Met Tyr Leu Lys Lys
                885                 890                 895

Phe Ile Met Glu Thr Leu Lys Ala Ile Lys Leu Asp Gly Val Asp Val
            900                 905                 910

Ile Gly Tyr Thr Ala Trp Ser Leu Met Asp Gly Phe Glu Trp His Arg
        915                 920                 925

Gly Tyr Ser Ile Arg Arg Gly Leu Phe Tyr Val Asp Phe Leu Ser Gln
    930                 935                 940
```

-continued

Asp Lys Met Leu Leu Pro Lys Ser Ser Ala Leu Phe Tyr Gln Lys Leu
945                 950                 955                 960

Ile Glu Lys Asn Gly Phe Pro Glu Phe Gly Ser Gly Gly Gly Gly Ser
                965                 970                 975

Gly Gly Gly Gly Ser Gly Gly Gly Ser Leu Lys Tyr Pro Asn Ala
            980                 985                 990

Ser Pro Leu Leu Gly Ser Ser Trp Gly Gly Leu Ile His Leu Tyr Thr
            995                1000                1005

Ala Thr Ala Arg Asn Ser Tyr His Leu Gln Ile His Lys Asn Gly
        1010                1015                1020

His Val Asp Gly Ala Pro His Gln Thr Ile Tyr Ser Ala Leu Met
        1025                1030                1035

Ile Arg Ser Glu Asp Ala Gly Phe Val Val Ile Thr Gly Val Met
        1040                1045                1050

Ser Arg Arg Tyr Leu Cys Met Asp Phe Arg Gly Asn Ile Phe Gly
        1055                1060                1065

Ser His Tyr Phe Asp Pro Glu Asn Cys Arg Phe Gln His Gln Thr
        1070                1075                1080

Leu Glu Asn Gly Tyr Asp Val Tyr His Ser Pro Gln Tyr His Phe
        1085                1090                1095

Leu Val Ser Leu Gly Arg Ala Lys Arg Ala Phe Leu Pro Gly Met
        1100                1105                1110

Asn Pro Pro Pro Tyr Ser Gln Phe Leu Ser Arg Arg Asn Glu Ile
        1115                1120                1125

Pro Leu Ile His Phe Asn Thr Pro Ile Pro Arg Arg His Thr Gln
        1130                1135                1140

Ser Ala Glu Asp Asp Ser Glu Arg Asp Pro Leu Asn Val Leu Lys
        1145                1150                1155

Pro Arg Ala Arg Met Thr Pro Ala Pro Ala Ser Cys Ser Gln Glu
        1160                1165                1170

Leu Pro Ser Ala Glu Asp Asn Ser Pro Met Ala Ser Asp Pro Leu
        1175                1180                1185

Gly Val Val Arg Gly Gly Arg Val Asn Thr His Ala Gly Gly Thr
        1190                1195                1200

Gly Pro Glu Gly Cys Arg Pro Phe Ala Lys Phe Ile
        1205                1210                1215

<210> SEQ ID NO 24
<211> LENGTH: 1189
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Met Pro Ala Ser Ala Pro Pro Arg Arg Pro Arg Pro Pro Pro Ser
1               5                   10                  15

Leu Ser Leu Leu Leu Val Leu Leu Gly Leu Gly Gly Arg Arg Leu Pro
                20                  25                  30

Leu Pro Glu Asn Gln Pro Leu Glu Gly Thr Phe Pro Cys Asp Phe Ala
            35                  40                  45

Trp Gly Val Val Asp Asn Tyr Ile Gln Val Asp Thr Thr Leu Ser Gln
        50                  55                  60

```
Phe Thr Asp Leu Asn Val Tyr Leu Trp Asp Val His His Ser Lys Arg
 65                  70                  75                  80

Leu Ile Lys Val Asp Gly Val Val Thr Lys Lys Arg Lys Ser Tyr Cys
                 85                  90                  95

Val Asp Phe Ala Ala Ile Gln Pro Gln Ile Ala Leu Leu Gln Glu Met
            100                 105                 110

His Val Thr His Phe Arg Phe Ser Leu Asp Trp Ala Leu Ile Leu Pro
            115                 120                 125

Leu Gly Asn Gln Ser Gln Val Asn His Thr Ile Leu Gln Tyr Tyr Arg
    130                 135                 140

Cys Met Ala Ser Glu Leu Val Arg Val Asn Ile Thr Pro Val Val Ala
145                 150                 155                 160

Leu Trp Gln Pro Met Ala Pro Asn Gln Gly Leu Pro Arg Leu Leu Ala
                165                 170                 175

Arg Gln Gly Ala Trp Glu Asn Pro Tyr Thr Ala Leu Ala Phe Ala Glu
                180                 185                 190

Tyr Ala Arg Leu Cys Phe Gln Glu Leu Gly His His Val Lys Leu Trp
            195                 200                 205

Ile Thr Met Asn Glu Pro Tyr Thr Arg Asn Met Thr Tyr Ser Ala Gly
    210                 215                 220

His Asn Leu Leu Lys Ala His Ala Leu Ala Trp His Val Tyr Asn Glu
225                 230                 235                 240

Lys Phe Arg His Ala Gln Asn Gly Lys Ile Ser Ile Ala Leu Gln Ala
                245                 250                 255

Asp Trp Ile Glu Pro Ala Cys Pro Phe Ser Gln Lys Asp Lys Glu Val
            260                 265                 270

Ala Glu Arg Val Leu Glu Phe Asp Ile Gly Trp Leu Ala Glu Pro Ile
            275                 280                 285

Phe Gly Ser Gly Asp Tyr Pro Trp Val Met Arg Asp Trp Leu Asn Gln
    290                 295                 300

Arg Asn Asn Phe Leu Leu Pro Tyr Phe Thr Glu Asp Glu Lys Lys Leu
305                 310                 315                 320

Ile Gln Gly Thr Phe Asp Phe Leu Ala Leu Ser His Tyr Thr Thr Ile
                325                 330                 335

Leu Val Asp Ser Glu Lys Glu Asp Pro Ile Lys Tyr Asn Asp Tyr Leu
            340                 345                 350

Glu Val Gln Glu Met Thr Asp Ile Thr Trp Leu Asn Ser Pro Ser Gln
            355                 360                 365

Val Ala Val Val Pro Trp Gly Leu Arg Lys Val Leu Asn Trp Leu Lys
    370                 375                 380

Phe Lys Tyr Gly Asp Leu Pro Met Tyr Ile Ile Ser Asn Gly Ile Asp
385                 390                 395                 400

Asp Gly Leu His Ala Glu Asp Asp Gln Leu Arg Val Tyr Tyr Met Gln
                405                 410                 415

Asn Tyr Ile Asn Glu Ala Leu Lys Ala His Ile Leu Asp Gly Ile Asn
            420                 425                 430

Leu Cys Gly Tyr Phe Ala Tyr Ser Phe Asn Asp Arg Thr Ala Pro Arg
            435                 440                 445

Phe Gly Leu Tyr Arg Tyr Ala Ala Asp Gln Phe Glu Pro Lys Ala Ser
    450                 455                 460

Met Lys His Tyr Arg Lys Ile Ile Asp Ser Asn Gly Phe Pro Gly Pro
465                 470                 475                 480

Glu Thr Leu Glu Arg Phe Cys Pro Glu Glu Phe Thr Val Cys Thr Glu
```

```
                   485              490              495
Cys Ser Phe Phe His Thr Arg Lys Ser Leu Gly Thr Phe Pro Cys Asp
        500                  505                 510
Phe Ala Trp Gly Val Val Asp Asn Tyr Ile Gln Val Asp Thr Thr Leu
        515                  520                 525
Ser Gln Phe Thr Asp Leu Asn Val Tyr Leu Trp Asp Val His His Ser
        530                  535                 540
Lys Arg Leu Ile Lys Val Asp Gly Val Val Thr Lys Arg Lys Ser
545                 550                 555                 560
Tyr Cys Val Asp Phe Ala Ala Ile Gln Pro Gln Ile Ala Leu Leu Gln
                565                 570                 575
Glu Met His Val Thr His Phe Arg Phe Ser Leu Asp Trp Ala Leu Ile
            580                 585                 590
Leu Pro Leu Gly Asn Gln Ser Gln Val Asn His Thr Ile Leu Gln Tyr
        595                 600                 605
Tyr Arg Cys Met Ala Ser Glu Leu Val Arg Val Asn Ile Thr Pro Val
    610                 615                 620
Val Ala Leu Trp Gln Pro Met Ala Pro Asn Gln Gly Leu Pro Arg Leu
625                 630                 635                 640
Leu Ala Arg Gln Gly Ala Trp Glu Asn Pro Tyr Thr Ala Leu Ala Phe
                645                 650                 655
Ala Glu Tyr Ala Arg Leu Cys Phe Gln Glu Leu Gly His His Val Lys
            660                 665                 670
Leu Trp Ile Thr Met Asn Glu Pro Tyr Thr Arg Asn Met Thr Tyr Ser
        675                 680                 685
Ala Gly His Asn Leu Leu Lys Ala His Ala Leu Ala Trp His Val Tyr
    690                 695                 700
Asn Glu Lys Phe Arg His Ala Gln Asn Gly Lys Ile Ser Ile Ala Leu
705                 710                 715                 720
Gln Ala Asp Trp Ile Glu Pro Ala Cys Pro Phe Ser Gln Lys Asp Lys
                725                 730                 735
Glu Val Ala Glu Arg Val Leu Glu Phe Asp Ile Gly Trp Leu Ala Glu
            740                 745                 750
Pro Ile Phe Gly Ser Gly Asp Tyr Pro Trp Val Met Arg Asp Trp Leu
        755                 760                 765
Asn Gln Arg Asn Asn Phe Leu Leu Pro Tyr Phe Thr Glu Asp Glu Lys
    770                 775                 780
Lys Leu Ile Gln Gly Thr Phe Asp Phe Leu Ala Leu Ser His Tyr Thr
785                 790                 795                 800
Thr Ile Leu Val Asp Ser Glu Lys Glu Asp Pro Ile Lys Tyr Asn Asp
                805                 810                 815
Tyr Leu Glu Val Gln Glu Met Thr Asp Ile Thr Trp Leu Asn Ser Pro
            820                 825                 830
Ser Gln Val Ala Val Pro Trp Gly Leu Arg Lys Val Leu Asn Trp
        835                 840                 845
Leu Lys Phe Lys Tyr Gly Asp Leu Pro Met Tyr Ile Ile Ser Asn Gly
    850                 855                 860
Ile Asp Asp Gly Leu His Ala Glu Asp Gln Leu Arg Val Tyr Tyr
865                 870                 875                 880
Met Gln Asn Tyr Ile Asn Glu Ala Leu Lys Ala His Ile Leu Asp Gly
                885                 890                 895
Ile Asn Leu Cys Gly Tyr Phe Ala Tyr Ser Phe Asn Asp Arg Thr Ala
            900                 905                 910
```

```
Pro Arg Phe Gly Leu Tyr Arg Tyr Ala Ala Asp Gln Phe Glu Pro Lys
        915                 920                 925

Ala Ser Met Lys His Tyr Arg Lys Ile Ile Asp Ser Asn Gly Phe Gly
        930                 935                 940

Ser Gly Gly Gly Ser Gly Gly Gly Ser Gly Gly Gly Ser
945                 950                 955                 960

Leu Lys Tyr Pro Asn Ala Ser Pro Leu Leu Gly Ser Ser Trp Gly Gly
            965                 970                 975

Leu Ile His Leu Tyr Thr Ala Thr Ala Arg Asn Ser Tyr His Leu Gln
            980                 985                 990

Ile His Lys Asn Gly His Val Asp Gly Ala Pro His Gln Thr Ile Tyr
            995                 1000                1005

Ser Ala Leu Met Ile Arg Ser Glu Asp Ala Gly Phe Val Val Ile
        1010                1015                1020

Thr Gly Val Met Ser Arg Arg Tyr Leu Cys Met Asp Phe Arg Gly
        1025                1030                1035

Asn Ile Phe Gly Ser His Tyr Phe Asp Pro Glu Asn Cys Arg Phe
        1040                1045                1050

Gln His Gln Thr Leu Glu Asn Gly Tyr Asp Val Tyr His Ser Pro
        1055                1060                1065

Gln Tyr His Phe Leu Val Ser Leu Gly Arg Ala Lys Arg Ala Phe
        1070                1075                1080

Leu Pro Gly Met Asn Pro Pro Tyr Ser Gln Phe Leu Ser Arg
        1085                1090                1095

Arg Asn Glu Ile Pro Leu Ile His Phe Asn Thr Pro Ile Pro Arg
        1100                1105                1110

Arg His Thr Gln Ser Ala Glu Asp Asp Ser Glu Arg Asp Pro Leu
        1115                1120                1125

Asn Val Leu Lys Pro Arg Ala Arg Met Thr Pro Ala Pro Ala Ser
        1130                1135                1140

Cys Ser Gln Glu Leu Pro Ser Ala Glu Asp Asn Ser Pro Met Ala
        1145                1150                1155

Ser Asp Pro Leu Gly Val Val Arg Gly Gly Arg Val Asn Thr His
        1160                1165                1170

Ala Gly Gly Thr Gly Pro Glu Gly Cys Arg Pro Phe Ala Lys Phe
        1175                1180                1185

Ile

<210> SEQ ID NO 25
<211> LENGTH: 1219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
                20                  25                  30

Gly Ser Ser Trp Gly Gly Leu Ile His Leu Tyr Thr Ala Thr Ala Arg
            35                  40                  45

Asn Ser Tyr His Leu Gln Ile His Lys Asn Gly His Val Asp Gly Ala
```

```
            50                  55                  60
Pro His Gln Thr Ile Tyr Ser Ala Leu Met Ile Arg Ser Glu Asp Ala
 65                  70                  75                  80

Gly Phe Val Val Ile Thr Gly Val Met Ser Arg Arg Tyr Leu Cys Met
                     85                  90                  95

Asp Phe Arg Gly Asn Ile Phe Gly Ser His Tyr Phe Asp Pro Glu Asn
                100                 105                 110

Cys Arg Phe Gln His Gln Thr Leu Glu Asn Gly Tyr Asp Val Tyr His
                115                 120                 125

Ser Pro Gln Tyr His Phe Leu Val Ser Leu Gly Arg Ala Lys Arg Ala
                130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Ser Glu Arg Asp Pro Leu Asn Val
                180                 185                 190

Leu Lys Pro Arg Ala Arg Met Thr Pro Ala Pro Ala Ser Cys Ser Gln
                195                 200                 205

Glu Leu Pro Ser Ala Glu Asp Asn Ser Pro Met Ala Ser Asp Pro Leu
                210                 215                 220

Gly Val Arg Gly Gly Arg Val Asn Thr His Ala Gly Gly Thr Gly
225                 230                 235                 240

Pro Glu Gly Cys Arg Pro Phe Ala Lys Phe Ile Gly Ser Gly Gly Gly
                245                 250                 255

Gly Ser Gly Gly Gly Ser Gly Gly Gly Ser Leu Lys Glu Pro
                260                 265                 270

Gly Asp Gly Ala Gln Thr Trp Ala Arg Phe Ser Arg Pro Pro Ala Pro
                275                 280                 285

Glu Ala Ala Gly Leu Phe Gln Gly Thr Phe Pro Asp Gly Phe Leu Trp
                290                 295                 300

Ala Val Gly Ser Ala Ala Tyr Gln Thr Glu Gly Gly Trp Gln Gln His
305                 310                 315                 320

Gly Lys Gly Ala Ser Ile Trp Asp Thr Phe Thr His His Pro Leu Ala
                325                 330                 335

Pro Pro Gly Asp Ser Arg Asn Ala Ser Leu Pro Leu Gly Ala Pro Ser
                340                 345                 350

Pro Leu Gln Pro Ala Thr Gly Asp Val Ala Ser Asp Ser Tyr Asn Asn
                355                 360                 365

Val Phe Arg Asp Thr Glu Ala Leu Arg Glu Leu Gly Val Thr His Tyr
370                 375                 380

Arg Phe Ser Ile Ser Trp Ala Arg Val Leu Pro Asn Gly Ser Ala Gly
385                 390                 395                 400

Val Pro Asn Arg Glu Gly Leu Arg Tyr Tyr Arg Arg Leu Leu Glu Arg
                405                 410                 415

Leu Arg Glu Leu Gly Val Gln Pro Val Val Thr Leu Tyr His Trp Asp
                420                 425                 430

Leu Pro Gln Arg Leu Gln Asp Ala Tyr Gly Gly Trp Ala Asn Arg Ala
                435                 440                 445

Leu Ala Asp His Phe Arg Asp Tyr Ala Glu Leu Cys Phe Arg His Phe
                450                 455                 460

Gly Gly Gln Val Lys Tyr Trp Ile Thr Ile Asp Asn Pro Tyr Val Val
465                 470                 475                 480
```

```
Ala Trp His Gly Tyr Ala Thr Gly Arg Leu Ala Pro Gly Ile Arg Gly
            485                 490                 495

Ser Pro Arg Leu Gly Tyr Leu Val Ala His Asn Leu Leu Leu Ala His
            500                 505                 510

Ala Lys Val Trp His Leu Tyr Asn Thr Ser Phe Arg Pro Thr Gln Gly
            515                 520                 525

Gly Gln Val Ser Ile Ala Leu Ser Ser His Trp Ile Asn Pro Arg Arg
            530                 535                 540

Met Thr Asp His Ser Ile Lys Glu Cys Gln Lys Ser Leu Asp Phe Val
545                 550                 555                 560

Leu Gly Trp Phe Ala Lys Pro Val Phe Ile Asp Gly Asp Tyr Pro Glu
            565                 570                 575

Ser Met Lys Asn Asn Leu Ser Ser Ile Leu Pro Asp Phe Thr Glu Ser
            580                 585                 590

Glu Lys Lys Phe Ile Lys Gly Thr Ala Asp Phe Phe Ala Leu Cys Phe
            595                 600                 605

Gly Pro Thr Leu Ser Phe Gln Leu Leu Asp Pro His Met Lys Phe Arg
            610                 615                 620

Gln Leu Glu Ser Pro Asn Leu Arg Gln Leu Leu Ser Trp Ile Asp Leu
625                 630                 635                 640

Glu Phe Asn His Pro Gln Ile Phe Ile Val Glu Asn Gly Trp Phe Val
            645                 650                 655

Ser Gly Thr Thr Lys Arg Asp Asp Ala Lys Tyr Met Tyr Tyr Leu Lys
            660                 665                 670

Lys Phe Ile Met Glu Thr Leu Lys Ala Ile Lys Leu Asp Gly Val Asp
            675                 680                 685

Val Ile Gly Tyr Thr Ala Trp Ser Leu Met Asp Gly Phe Glu Trp His
            690                 695                 700

Arg Gly Tyr Ser Ile Arg Arg Gly Leu Phe Tyr Val Asp Phe Leu Ser
705                 710                 715                 720

Gln Asp Lys Met Leu Leu Pro Lys Ser Ser Ala Leu Phe Tyr Gln Lys
            725                 730                 735

Leu Ile Glu Lys Asn Gly Phe Pro Pro Leu Pro Glu Asn Gln Pro Leu
            740                 745                 750

Glu Gly Thr Phe Pro Cys Asp Phe Ala Trp Gly Val Val Asp Asn Tyr
            755                 760                 765

Ile Gln Val Asp Thr Thr Leu Ser Gln Phe Thr Asp Leu Asn Val Tyr
            770                 775                 780

Leu Trp Asp Val His His Ser Lys Arg Leu Ile Lys Val Asp Gly Val
785                 790                 795                 800

Val Thr Lys Lys Arg Lys Ser Tyr Cys Val Asp Phe Ala Ala Ile Gln
            805                 810                 815

Pro Gln Ile Ala Leu Leu Gln Glu Met His Val Thr His Phe Arg Phe
            820                 825                 830

Ser Leu Asp Trp Ala Leu Ile Leu Pro Leu Gly Asn Gln Ser Gln Val
            835                 840                 845

Asn His Thr Ile Leu Gln Tyr Tyr Arg Cys Met Ala Ser Glu Leu Val
            850                 855                 860

Arg Val Asn Ile Thr Pro Val Val Ala Leu Trp Gln Pro Met Ala Pro
865                 870                 875                 880

Asn Gln Gly Leu Pro Arg Leu Leu Ala Arg Gln Gly Ala Trp Glu Asn
            885                 890                 895
```

Pro Tyr Thr Ala Leu Ala Phe Ala Glu Tyr Ala Arg Leu Cys Phe Gln
            900                 905                 910

Glu Leu Gly His His Val Lys Leu Trp Ile Thr Met Asn Glu Pro Tyr
        915                 920                 925

Thr Arg Asn Met Thr Tyr Ser Ala Gly His Asn Leu Leu Lys Ala His
    930                 935                 940

Ala Leu Ala Trp His Val Tyr Asn Glu Lys Phe Arg His Ala Gln Asn
945                 950                 955                 960

Gly Lys Ile Ser Ile Ala Leu Gln Ala Asp Trp Ile Glu Pro Ala Cys
                965                 970                 975

Pro Phe Ser Gln Lys Asp Lys Glu Val Ala Glu Arg Val Leu Glu Phe
            980                 985                 990

Asp Ile Gly Trp Leu Ala Glu Pro Ile Phe Gly Ser Gly Asp Tyr Pro
        995                 1000                1005

Trp Val Met Arg Asp Trp Leu Asn Gln Arg Asn Asn Phe Leu Leu
    1010                1015                1020

Pro Tyr Phe Thr Glu Asp Glu Lys Lys Leu Ile Gln Gly Thr Phe
    1025                1030                1035

Asp Phe Leu Ala Leu Ser His Tyr Thr Thr Ile Leu Val Asp Ser
    1040                1045                1050

Glu Lys Glu Asp Pro Ile Lys Tyr Asn Asp Tyr Leu Glu Val Gln
    1055                1060                1065

Glu Met Thr Asp Ile Thr Trp Leu Asn Ser Pro Ser Gln Val Ala
    1070                1075                1080

Val Val Pro Trp Gly Leu Arg Lys Val Leu Asn Trp Leu Lys Phe
    1085                1090                1095

Lys Tyr Gly Asp Leu Pro Met Tyr Ile Ile Ser Asn Gly Ile Asp
    1100                1105                1110

Asp Gly Leu His Ala Glu Asp Gln Leu Arg Val Tyr Tyr Met
    1115                1120                1125

Gln Asn Tyr Ile Asn Glu Ala Leu Lys Ala His Ile Leu Asp Gly
    1130                1135                1140

Ile Asn Leu Cys Gly Tyr Phe Ala Tyr Ser Phe Asn Asp Arg Thr
    1145                1150                1155

Ala Pro Arg Phe Gly Leu Tyr Arg Tyr Ala Ala Asp Gln Phe Glu
    1160                1165                1170

Pro Lys Ala Ser Met Lys His Tyr Arg Lys Ile Ile Asp Ser Asn
    1175                1180                1185

Gly Phe Pro Gly Pro Glu Thr Leu Glu Arg Phe Cys Pro Glu Glu
    1190                1195                1200

Phe Thr Val Cys Thr Glu Cys Ser Phe Phe His Thr Arg Lys Ser
    1205                1210                1215

Leu

<210> SEQ ID NO 26
<211> LENGTH: 700
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Met Leu Gly Ala Arg Leu Arg Leu Trp Val Cys Ala Leu Cys Ser Val
1               5                   10                  15

```
Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Arg Val Asn Thr His Ala Gly Gly Thr Gly
225                 230                 235                 240

Pro Glu Gly Cys Arg Pro Phe Ala Lys Phe Ile Gln Gly Thr Phe Pro
                245                 250                 255

Asp Gly Phe Leu Trp Ala Val Gly Ser Ala Ala Tyr Gln Thr Glu Gly
            260                 265                 270

Gly Trp Gln Gln His Gly Lys Gly Ala Ser Ile Trp Asp Thr Phe Thr
        275                 280                 285

His His Pro Leu Ala Pro Pro Gly Asp Ser Arg Asn Ala Ser Leu Pro
    290                 295                 300

Leu Gly Ala Pro Ser Pro Leu Gln Pro Ala Thr Gly Asp Val Ala Ser
305                 310                 315                 320

Asp Ser Tyr Asn Asn Val Phe Arg Asp Thr Glu Ala Leu Arg Glu Leu
                325                 330                 335

Gly Val Thr His Tyr Arg Phe Ser Ile Ser Trp Ala Arg Val Leu Pro
            340                 345                 350

Asn Gly Ser Ala Gly Val Pro Asn Arg Glu Gly Leu Arg Tyr Tyr Arg
        355                 360                 365

Arg Leu Leu Glu Arg Leu Arg Glu Leu Gly Val Gln Pro Val Val Thr
    370                 375                 380

Leu Tyr His Trp Asp Leu Pro Gln Arg Leu Gln Asp Ala Tyr Gly Gly
385                 390                 395                 400

Trp Ala Asn Arg Ala Leu Ala Asp His Phe Arg Asp Tyr Ala Glu Leu
                405                 410                 415

Cys Phe Arg His Phe Gly Gly Gln Val Lys Tyr Trp Ile Thr Ile Asp
            420                 425                 430
```

Asn Pro Tyr Val Val Ala Trp His Gly Tyr Ala Thr Gly Arg Leu Ala
            435                 440                 445

Pro Gly Ile Arg Gly Ser Pro Arg Leu Gly Tyr Leu Val Ala His Asn
        450                 455                 460

Leu Leu Leu Ala His Ala Lys Val Trp His Leu Tyr Asn Thr Ser Phe
465                 470                 475                 480

Arg Pro Thr Gln Gly Gln Val Ser Ile Ala Leu Ser Ser His Trp
            485                 490                 495

Ile Asn Pro Arg Arg Met Thr Asp His Ser Ile Lys Glu Cys Gln Lys
            500                 505                 510

Ser Leu Asp Phe Val Leu Gly Trp Phe Ala Lys Pro Val Phe Ile Asp
        515                 520                 525

Gly Asp Tyr Pro Glu Ser Met Lys Asn Asn Leu Ser Ser Ile Leu Pro
        530                 535                 540

Asp Phe Thr Glu Ser Glu Lys Lys Phe Ile Lys Gly Thr Ala Asp Phe
545                 550                 555                 560

Phe Ala Leu Cys Phe Gly Pro Thr Leu Ser Phe Gln Leu Leu Asp Pro
                565                 570                 575

His Met Lys Phe Arg Gln Leu Glu Ser Pro Asn Leu Arg Gln Leu Leu
            580                 585                 590

Ser Trp Ile Asp Leu Glu Phe Asn His Pro Gln Ile Phe Ile Val Glu
        595                 600                 605

Asn Gly Trp Phe Val Ser Gly Thr Thr Lys Arg Asp Asp Ala Lys Tyr
        610                 615                 620

Met Tyr Tyr Leu Lys Lys Phe Ile Met Glu Thr Leu Lys Ala Ile Lys
625                 630                 635                 640

Leu Asp Gly Val Asp Val Ile Gly Tyr Thr Ala Trp Ser Leu Met Asp
                645                 650                 655

Gly Phe Glu Trp His Arg Gly Tyr Ser Ile Arg Arg Gly Leu Phe Tyr
            660                 665                 670

Val Asp Phe Leu Ser Gln Asp Lys Met Leu Leu Pro Lys Ser Ser Ala
            675                 680                 685

Leu Phe Tyr Gln Lys Leu Ile Glu Lys Asn Gly Phe
690                 695                 700

<210> SEQ ID NO 27
<211> LENGTH: 688
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met

```
                     85                  90                  95
Asp Phe Arg Gly Asn Ile Phe Gly Ser His Tyr Phe Asp Pro Glu Asn
                100                 105                 110
Cys Arg Phe Gln His Gln Thr Leu Glu Asn Gly Tyr Asp Val Tyr His
            115                 120                 125
Ser Pro Gln Tyr His Phe Leu Val Ser Leu Gly Arg Ala Lys Arg Ala
        130                 135                 140
Phe Leu Pro Gly Met Asn Pro Pro Tyr Ser Gln Phe Leu Ser Arg
145                 150                 155                 160
Arg Asn Glu Ile Pro Leu Ile His Phe Asn Thr Pro Ile Pro Arg Arg
                165                 170                 175
His Thr Gln Ser Ala Glu Asp Ser Glu Arg Asp Pro Leu Asn Val
            180                 185                 190
Leu Lys Pro Arg Ala Arg Met Thr Pro Ala Pro Ala Ser Cys Ser Gln
        195                 200                 205
Glu Leu Pro Ser Ala Glu Asp Asn Ser Pro Met Ala Ser Asp Pro Leu
    210                 215                 220
Gly Val Val Arg Gly Gly Arg Val Asn Thr His Ala Gly Gly Thr Gly
225                 230                 235                 240
Pro Glu Gly Cys Arg Pro Phe Ala Lys Phe Ile Gly Thr Phe Pro Cys
                245                 250                 255
Asp Phe Ala Trp Gly Val Val Asp Asn Tyr Ile Gln Val Asp Thr Thr
            260                 265                 270
Leu Ser Gln Phe Thr Asp Leu Asn Val Tyr Leu Trp Asp Val His His
        275                 280                 285
Ser Lys Arg Leu Ile Lys Val Asp Gly Val Val Thr Lys Lys Arg Lys
    290                 295                 300
Ser Tyr Cys Val Asp Phe Ala Ala Ile Gln Pro Gln Ile Ala Leu Leu
305                 310                 315                 320
Gln Glu Met His Val Thr His Phe Arg Phe Ser Leu Asp Trp Ala Leu
                325                 330                 335
Ile Leu Pro Leu Gly Asn Gln Ser Gln Val Asn His Thr Ile Leu Gln
            340                 345                 350
Tyr Tyr Arg Cys Met Ala Ser Glu Leu Val Arg Val Asn Ile Thr Pro
        355                 360                 365
Val Val Ala Leu Trp Gln Pro Met Ala Pro Asn Gln Gly Leu Pro Arg
    370                 375                 380
Leu Leu Ala Arg Gln Gly Ala Trp Glu Asn Pro Tyr Thr Ala Leu Ala
385                 390                 395                 400
Phe Ala Glu Tyr Ala Arg Leu Cys Phe Gln Glu Leu Gly His His Val
                405                 410                 415
Lys Leu Trp Ile Thr Met Asn Glu Pro Tyr Thr Arg Asn Met Thr Tyr
            420                 425                 430
Ser Ala Gly His Asn Leu Leu Lys Ala His Ala Leu Ala Trp His Val
        435                 440                 445
Tyr Asn Glu Lys Phe Arg His Ala Gln Asn Gly Lys Ile Ser Ile Ala
    450                 455                 460
Leu Gln Ala Asp Trp Ile Glu Pro Ala Cys Pro Phe Ser Gln Lys Asp
465                 470                 475                 480
Lys Glu Val Ala Glu Arg Val Leu Glu Phe Asp Ile Gly Trp Leu Ala
                485                 490                 495
Glu Pro Ile Phe Gly Ser Gly Asp Tyr Pro Trp Val Met Arg Asp Trp
            500                 505                 510
```

-continued

Leu Asn Gln Arg Asn Asn Phe Leu Leu Pro Tyr Phe Thr Glu Asp Glu
            515                 520                 525

Lys Lys Leu Ile Gln Gly Thr Phe Asp Phe Leu Ala Leu Ser His Tyr
    530                 535                 540

Thr Thr Ile Leu Val Asp Ser Glu Lys Glu Asp Pro Ile Lys Tyr Asn
545                 550                 555                 560

Asp Tyr Leu Glu Val Gln Glu Met Thr Asp Ile Thr Trp Leu Asn Ser
                565                 570                 575

Pro Ser Gln Val Ala Val Pro Trp Gly Leu Arg Lys Val Leu Asn
            580                 585                 590

Trp Leu Lys Phe Lys Tyr Gly Asp Leu Pro Met Tyr Ile Ile Ser Asn
        595                 600                 605

Gly Ile Asp Asp Gly Leu His Ala Glu Asp Gln Leu Arg Val Tyr
    610                 615                 620

Tyr Met Gln Asn Tyr Ile Asn Glu Ala Leu Lys Ala His Ile Leu Asp
625                 630                 635                 640

Gly Ile Asn Leu Cys Gly Tyr Phe Ala Tyr Ser Phe Asn Asp Arg Thr
                645                 650                 655

Ala Pro Arg Phe Gly Leu Tyr Arg Tyr Ala Ala Asp Gln Phe Glu Pro
            660                 665                 670

Lys Ala Ser Met Lys His Tyr Arg Lys Ile Ile Asp Ser Asn Gly Phe
        675                 680                 685

<210> SEQ ID NO 28
<211> LENGTH: 1149
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

```
His Thr Gln Ser Ala Glu Asp Asp Ser Glu Arg Asp Pro Leu Asn Val
                180                 185                 190
Leu Lys Pro Arg Ala Arg Met Thr Pro Ala Pro Ala Ser Cys Ser Gln
            195                 200                 205
Glu Leu Pro Ser Ala Glu Asp Asn Ser Pro Met Ala Ser Asp Pro Leu
        210                 215                 220
Gly Val Val Arg Gly Gly Arg Val Asn Thr His Ala Gly Gly Thr Gly
225                 230                 235                 240
Pro Glu Gly Cys Arg Pro Phe Ala Lys Phe Ile Gln Gly Thr Phe Pro
                245                 250                 255
Asp Gly Phe Leu Trp Ala Val Gly Ser Ala Ala Tyr Gln Thr Glu Gly
            260                 265                 270
Gly Trp Gln Gln His Gly Lys Gly Ala Ser Ile Trp Asp Thr Phe Thr
        275                 280                 285
His His Pro Leu Ala Pro Pro Gly Asp Ser Arg Asn Ala Ser Leu Pro
290                 295                 300
Leu Gly Ala Pro Ser Pro Leu Gln Pro Ala Thr Gly Asp Val Ala Ser
305                 310                 315                 320
Asp Ser Tyr Asn Asn Val Phe Arg Asp Thr Glu Ala Leu Arg Glu Leu
                325                 330                 335
Gly Val Thr His Tyr Arg Phe Ser Ile Ser Trp Ala Arg Val Leu Pro
            340                 345                 350
Asn Gly Ser Ala Gly Val Pro Asn Arg Glu Gly Leu Arg Tyr Tyr Arg
        355                 360                 365
Arg Leu Leu Glu Arg Leu Arg Glu Leu Gly Val Gln Pro Val Val Thr
370                 375                 380
Leu Tyr His Trp Asp Leu Pro Gln Arg Leu Gln Asp Ala Tyr Gly Gly
385                 390                 395                 400
Trp Ala Asn Arg Ala Leu Ala Asp His Phe Arg Asp Tyr Ala Glu Leu
                405                 410                 415
Cys Phe Arg His Phe Gly Gly Gln Val Lys Tyr Trp Ile Thr Ile Asp
            420                 425                 430
Asn Pro Tyr Val Val Ala Trp His Gly Tyr Ala Thr Gly Arg Leu Ala
        435                 440                 445
Pro Gly Ile Arg Gly Ser Pro Arg Leu Gly Tyr Leu Val Ala His Asn
450                 455                 460
Leu Leu Leu Ala His Ala Lys Val Trp His Leu Tyr Asn Thr Ser Phe
465                 470                 475                 480
Arg Pro Thr Gln Gly Gly Gln Val Ser Ile Ala Leu Ser Ser His Trp
                485                 490                 495
Ile Asn Pro Arg Arg Met Thr Asp His Ser Ile Lys Glu Cys Gln Lys
            500                 505                 510
Ser Leu Asp Phe Val Leu Gly Trp Phe Ala Lys Pro Val Phe Ile Asp
        515                 520                 525
Gly Asp Tyr Pro Glu Ser Met Lys Asn Asn Leu Ser Ser Ile Leu Pro
530                 535                 540
Asp Phe Thr Glu Ser Glu Lys Lys Phe Ile Lys Gly Thr Ala Asp Phe
545                 550                 555                 560
Phe Ala Leu Cys Phe Gly Pro Thr Leu Ser Phe Gln Leu Leu Asp Pro
                565                 570                 575
His Met Lys Phe Arg Gln Leu Glu Ser Pro Asn Leu Arg Gln Leu Leu
            580                 585                 590
Ser Trp Ile Asp Leu Glu Phe Asn His Pro Gln Ile Phe Ile Val Glu
```

```
                595                 600                 605
Asn Gly Trp Phe Val Ser Gly Thr Thr Lys Arg Asp Asp Ala Lys Tyr
610                 615                 620

Met Tyr Tyr Leu Lys Lys Phe Ile Met Glu Thr Leu Lys Ala Ile Lys
625                 630                 635                 640

Leu Asp Gly Val Asp Val Ile Gly Tyr Thr Ala Trp Ser Leu Met Asp
                645                 650                 655

Gly Phe Glu Trp His Arg Gly Tyr Ser Ile Arg Arg Gly Leu Phe Tyr
            660                 665                 670

Val Asp Phe Leu Ser Gln Asp Lys Met Leu Leu Pro Lys Ser Ser Ala
            675                 680                 685

Leu Phe Tyr Gln Lys Leu Ile Glu Lys Asn Gly Phe Gln Gly Thr Phe
            690                 695                 700

Pro Asp Gly Phe Leu Trp Ala Val Gly Ser Ala Ala Tyr Gln Thr Glu
705                 710                 715                 720

Gly Gly Trp Gln Gln His Gly Lys Gly Ala Ser Ile Trp Asp Thr Phe
                725                 730                 735

Thr His His Pro Leu Ala Pro Pro Gly Asp Ser Arg Asn Ala Ser Leu
                740                 745                 750

Pro Leu Gly Ala Pro Ser Pro Leu Gln Pro Ala Thr Gly Asp Val Ala
            755                 760                 765

Ser Asp Ser Tyr Asn Asn Val Phe Arg Asp Thr Glu Ala Leu Arg Glu
770                 775                 780

Leu Gly Val Thr His Tyr Arg Phe Ser Ile Ser Trp Ala Arg Val Leu
785                 790                 795                 800

Pro Asn Gly Ser Ala Gly Val Pro Asn Arg Glu Gly Leu Arg Tyr Tyr
                805                 810                 815

Arg Arg Leu Leu Glu Arg Leu Arg Glu Leu Gly Val Gln Pro Val Val
            820                 825                 830

Thr Leu Tyr His Trp Asp Leu Pro Gln Arg Leu Gln Asp Ala Tyr Gly
            835                 840                 845

Gly Trp Ala Asn Arg Ala Leu Ala Asp His Phe Arg Asp Tyr Ala Glu
850                 855                 860

Leu Cys Phe Arg His Phe Gly Gly Gln Val Lys Tyr Trp Ile Thr Ile
865                 870                 875                 880

Asp Asn Pro Tyr Val Val Ala Trp His Gly Tyr Ala Thr Gly Arg Leu
                885                 890                 895

Ala Pro Gly Ile Arg Gly Ser Pro Arg Leu Gly Tyr Leu Val Ala His
            900                 905                 910

Asn Leu Leu Leu Ala His Ala Lys Val Trp His Leu Tyr Asn Thr Ser
            915                 920                 925

Phe Arg Pro Thr Gln Gly Gly Gln Val Ser Ile Ala Leu Ser Ser His
930                 935                 940

Trp Ile Asn Pro Arg Arg Met Thr Asp His Ser Ile Lys Glu Cys Gln
945                 950                 955                 960

Lys Ser Leu Asp Phe Val Leu Gly Trp Phe Ala Lys Pro Val Phe Ile
                965                 970                 975

Asp Gly Asp Tyr Pro Glu Ser Met Lys Asn Asn Leu Ser Ser Ile Leu
            980                 985                 990

Pro Asp Phe Thr Glu Ser Glu Lys Lys Phe Ile Lys Gly Thr Ala Asp
            995                 1000                1005

Phe Phe Ala Leu Cys Phe Gly Pro Thr Leu Ser Phe Gln Leu Leu
            1010                1015                1020
```

```
Asp Pro His Met Lys Phe Arg Gln Leu Glu Ser Pro Asn Leu Arg
    1025                1030                1035

Gln Leu Leu Ser Trp Ile Asp Leu Glu Phe Asn His Pro Gln Ile
    1040                1045                1050

Phe Ile Val Glu Asn Gly Trp Phe Val Ser Gly Thr Thr Lys Arg
    1055                1060                1065

Asp Asp Ala Lys Tyr Met Tyr Tyr Leu Lys Lys Phe Ile Met Glu
    1070                1075                1080

Thr Leu Lys Ala Ile Lys Leu Asp Gly Val Asp Val Ile Gly Tyr
    1085                1090                1095

Thr Ala Trp Ser Leu Met Asp Gly Phe Glu Trp His Arg Gly Tyr
    1100                1105                1110

Ser Ile Arg Arg Gly Leu Phe Tyr Val Asp Phe Leu Ser Gln Asp
    1115                1120                1125

Lys Met Leu Leu Pro Lys Ser Ser Ala Leu Phe Tyr Gln Lys Leu
    1130                1135                1140

Ile Glu Lys Asn Gly Phe
    1145
```

<210> SEQ ID NO 29
<211> LENGTH: 1125
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 29

```
Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
                20                  25                  30

Gly Ser Ser Trp Gly Gly Leu Ile His Leu Tyr Thr Ala Thr Ala Arg
            35                  40                  45

Asn Ser Tyr His Leu Gln Ile His Lys Asn Gly His Val Asp Gly Ala
        50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
                100                 105                 110

Cys Arg Phe Gln His Gln Thr Leu Glu Asn Gly Tyr Asp Val Tyr His
            115                 120                 125

Ser Pro Gln Tyr His Phe Leu Val Ser Leu Gly Arg Ala Lys Arg Ala
        130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205
```

```
Glu Leu Pro Ser Ala Glu Asp Asn Ser Pro Met Ala Ser Asp Pro Leu
    210                 215                 220
Gly Val Val Arg Gly Arg Val Asn Thr His Ala Gly Gly Thr Gly
225                 230                 235                 240
Pro Glu Gly Cys Arg Pro Phe Ala Lys Phe Ile Gly Thr Phe Pro Cys
                    245                 250                 255
Asp Phe Ala Trp Gly Val Val Asp Asn Tyr Ile Gln Val Asp Thr Thr
                260                 265                 270
Leu Ser Gln Phe Thr Asp Leu Asn Val Tyr Leu Trp Asp Val His His
            275                 280                 285
Ser Lys Arg Leu Ile Lys Val Asp Gly Val Val Thr Lys Lys Arg Lys
290                 295                 300
Ser Tyr Cys Val Asp Phe Ala Ala Ile Gln Pro Gln Ile Ala Leu Leu
305                 310                 315                 320
Gln Glu Met His Val Thr His Phe Arg Phe Ser Leu Asp Trp Ala Leu
                    325                 330                 335
Ile Leu Pro Leu Gly Asn Gln Ser Gln Val Asn His Thr Ile Leu Gln
                340                 345                 350
Tyr Tyr Arg Cys Met Ala Ser Glu Leu Val Arg Val Asn Ile Thr Pro
            355                 360                 365
Val Val Ala Leu Trp Gln Pro Met Ala Pro Asn Gln Gly Leu Pro Arg
370                 375                 380
Leu Leu Ala Arg Gln Gly Ala Trp Glu Asn Pro Tyr Thr Ala Leu Ala
385                 390                 395                 400
Phe Ala Glu Tyr Ala Arg Leu Cys Phe Gln Glu Leu Gly His His Val
                    405                 410                 415
Lys Leu Trp Ile Thr Met Asn Glu Pro Tyr Thr Arg Asn Met Thr Tyr
                420                 425                 430
Ser Ala Gly His Asn Leu Leu Lys Ala His Ala Leu Ala Trp His Val
            435                 440                 445
Tyr Asn Glu Lys Phe Arg His Ala Gln Asn Gly Lys Ile Ser Ile Ala
            450                 455                 460
Leu Gln Ala Asp Trp Ile Glu Pro Ala Cys Pro Phe Ser Gln Lys Asp
465                 470                 475                 480
Lys Glu Val Ala Glu Arg Val Leu Glu Phe Asp Ile Gly Trp Leu Ala
                485                 490                 495
Glu Pro Ile Phe Gly Ser Gly Asp Tyr Pro Trp Val Met Arg Asp Trp
                500                 505                 510
Leu Asn Gln Arg Asn Asn Phe Leu Leu Pro Tyr Phe Thr Glu Asp Glu
            515                 520                 525
Lys Lys Leu Ile Gln Gly Thr Phe Asp Phe Leu Ala Leu Ser His Tyr
530                 535                 540
Thr Thr Ile Leu Val Asp Ser Glu Lys Glu Asp Pro Ile Lys Tyr Asn
545                 550                 555                 560
Asp Tyr Leu Glu Val Gln Glu Met Thr Asp Ile Thr Trp Leu Asn Ser
                565                 570                 575
Pro Ser Gln Val Ala Val Pro Trp Gly Leu Arg Lys Val Leu Asn
            580                 585                 590
Trp Leu Lys Phe Lys Tyr Gly Asp Leu Pro Met Tyr Ile Ile Ser Asn
            595                 600                 605
Gly Ile Asp Asp Gly Leu His Ala Glu Asp Asp Gln Leu Arg Val Tyr
            610                 615                 620
Tyr Met Gln Asn Tyr Ile Asn Glu Ala Leu Lys Ala His Ile Leu Asp
```

-continued

```
            625                 630                 635                 640
    Gly Ile Asn Leu Cys Gly Tyr Phe Ala Tyr Ser Phe Asn Asp Arg Thr
                        645                 650                 655
    Ala Pro Arg Phe Gly Leu Tyr Arg Tyr Ala Ala Asp Gln Phe Glu Pro
                        660                 665                 670
    Lys Ala Ser Met Lys His Tyr Arg Lys Ile Ile Asp Ser Asn Gly Phe
                        675                 680                 685
    Gly Thr Phe Pro Cys Asp Phe Ala Trp Gly Val Val Asp Asn Tyr Ile
            690                 695                 700
    Gln Val Asp Thr Thr Leu Ser Gln Phe Thr Asp Leu Asn Val Tyr Leu
705                         710                 715                 720
    Trp Asp Val His His Ser Lys Arg Leu Ile Lys Val Asp Gly Val Val
                        725                 730                 735
    Thr Lys Lys Arg Lys Ser Tyr Cys Val Asp Phe Ala Ala Ile Gln Pro
                        740                 745                 750
    Gln Ile Ala Leu Leu Gln Glu Met His Val Thr His Phe Arg Phe Ser
                        755                 760                 765
    Leu Asp Trp Ala Leu Ile Leu Pro Leu Gly Asn Gln Ser Gln Val Asn
            770                 775                 780
    His Thr Ile Leu Gln Tyr Tyr Arg Cys Met Ala Ser Glu Leu Val Arg
785                         790                 795                 800
    Val Asn Ile Thr Pro Val Val Ala Leu Trp Gln Pro Met Ala Pro Asn
                        805                 810                 815
    Gln Gly Leu Pro Arg Leu Leu Ala Arg Gln Gly Ala Trp Glu Asn Pro
                        820                 825                 830
    Tyr Thr Ala Leu Ala Phe Ala Glu Tyr Ala Arg Leu Cys Phe Gln Glu
                        835                 840                 845
    Leu Gly His His Val Lys Leu Trp Ile Thr Met Asn Glu Pro Tyr Thr
            850                 855                 860
    Arg Asn Met Thr Tyr Ser Ala Gly His Asn Leu Leu Lys Ala His Ala
865                         870                 875                 880
    Leu Ala Trp His Val Tyr Asn Glu Lys Phe Arg His Ala Gln Asn Gly
                        885                 890                 895
    Lys Ile Ser Ile Ala Leu Gln Ala Asp Trp Ile Glu Pro Ala Cys Pro
                        900                 905                 910
    Phe Ser Gln Lys Asp Lys Glu Val Ala Glu Arg Val Leu Glu Phe Asp
                        915                 920                 925
    Ile Gly Trp Leu Ala Glu Pro Ile Phe Gly Ser Gly Asp Tyr Pro Trp
            930                 935                 940
    Val Met Arg Asp Trp Leu Asn Gln Arg Asn Asn Phe Leu Leu Pro Tyr
945                         950                 955                 960
    Phe Thr Glu Asp Glu Lys Lys Leu Ile Gln Gly Thr Phe Asp Phe Leu
                        965                 970                 975
    Ala Leu Ser His Tyr Thr Thr Ile Leu Val Asp Ser Glu Lys Glu Asp
                        980                 985                 990
    Pro Ile Lys Tyr Asn Asp Tyr Leu  Glu Val Gln Glu Met  Thr Asp Ile
                995                 1000                1005
    Thr Trp  Leu Asn Ser Pro Ser  Gln Val Ala Val  Pro Trp Gly
            1010                1015                1020
    Leu Arg  Lys Val Leu Asn Trp  Leu Lys Phe Lys Tyr  Gly Asp Leu
            1025                1030                1035
    Pro Met  Tyr Ile Ile Ser Asn  Gly Ile Asp Asp Gly  Leu His Ala
            1040                1045                1050
```

Glu Asp Asp Gln Leu Arg Val Tyr Tyr Met Gln Asn Tyr Ile Asn
    1055                1060                1065

Glu Ala Leu Lys Ala His Ile Leu Asp Gly Ile Asn Leu Cys Gly
    1070                1075                1080

Tyr Phe Ala Tyr Ser Phe Asn Asp Arg Thr Ala Pro Arg Phe Gly
    1085                1090                1095

Leu Tyr Arg Tyr Ala Ala Asp Gln Phe Glu Pro Lys Ala Ser Met
    1100                1105                1110

Lys His Tyr Arg Lys Ile Ile Asp Ser Asn Gly Phe
    1115                1120                1125

<210> SEQ ID NO 30
<211> LENGTH: 2157
<212> TYPE: DNA
<213> ORGANISM: Homo sapiens

<400> SEQUENCE: 30
gctcccagcc aagaacctcg gggccgctgc gcggtgggga ggagttcccc gaaacccggc        60
cgctaagcga ggcctcctcc tcccgcagat ccgaacggcc tgggcggggt caccccggct       120
gggacaagaa gccgccgcct gcctgcccgg gcccggggag ggggctgggg ctggggccgg       180
aggcggggtg tgagtgggtg tgtgcggggg gcggaggctt gatgcaatcc cgataagaaa       240
tgctcgggtc tcttgggcac ctacccgtgg ggcccgtaag gcgctactat ataaggctgc       300
cggcccggag ccgccgcgcc gtcagagcag gagcgctgcg tccaggatct agggccacga       360
ccatcccaac ccggcactca cagccccgca gcgcatcccg gtcgccgccc agcctcccgc       420 accccccatcg ccggagctgc gccgagagcc cagggaggt gccatgcgga gcgggtgtgt        480
ggtggtccac gtatggatcc tggccggcct ctggctggcc gtggccgggc gccccctcgc       540
cttctcggac gcggggcccc acgtgcacta cggctggggc gaccccatcc gcctgcggca       600
cctgtacacc tccggccccc acgggctctc cagctgcttc ctgcgcatcc gtgccgacgg       660
cgtcgtggac tgcgcgcggg gccagagcgc gcacagtttg ctggagatca aggcagtcgc       720
tctgcggacc gtggccatca agggcgtgca cagcgtgcgg tacctctgca tgggcgccga       780
cggcaagatg caggggctgc ttcagtactc ggaggaagac tgtgctttcg aggaggagat       840
ccgcccagat ggctacaatg tgtaccgatc cgagaagcac cgcctcccgg tctccctgag       900
cagtgccaaa cagcggcagc tgtacaagaa cagaggcttt cttccactct ctcatttcct       960
gcccatgctg cccatggtcc cagaggagcc tgaggacctc agggcccact ggaatctga       1020 catgttctct tcgcccctgg agaccgacag catggaccca tttgggcttg tcaccggact      1080
ggaggccgtg aggagtccca gctttgagaa gtaactgaga ccatgcccgg gcctcttcac      1140
tgctgccagg ggctgtggta cctgcagcgt ggggacgtg cttctacaag aacagtcctg       1200
agtccacgtt ctgtttagct ttaggaagaa acatctagaa gttgtacata ttcagagttt      1260
tccattggca gtgccagttt ctagccaata gacttgtctg atcataacat tgtaagcctg      1320
tagcttgccc agctgctgcc tgggccccca ttctgctccc tcgaggttgc tggacaagct      1380
gctgcactgt ctcagttctg cttgaatacc tccatcgatg gggaactcac ttcctttgga      1440
aaaattctta tgtcaagctg aaattctcta atttttctc atcacttccc caggagcagc       1500
cagaagacag gcagtagttt taatttcagg aacaggtgat ccactctgta aaacagcagg      1560
taaatttcac tcaaccccat gtgggaattg atctatatct ctacttccag ggaccatttg      1620
cccttcccaa atccctccag gccagaactg actggagcag gcatggccca ccaggcttca      1680

```
ggagtagggg aagcctggag ccccactcca gccctgggac aacttgagaa ttccccctga    1740
ggccagttct gtcatggatg ctgtcctgag aataacttgc tgtcccggtg tcacctgctt    1800
ccatctccca gcccaccagc cctctgccca cctcacatgc ctccccatgg attggggcct    1860
cccaggcccc ccaccttatg tcaacctgca cttcttgttc aaaaatcagg aaagaaaag     1920 atttgaagac cccaagtctt gtcaataact tgctgtgtgg aagcagcggg ggaagaccta    1980
gaaccctttc cccagcactt ggttttccaa catgatattt atgagtaatt tattttgata    2040
tgtacatctc ttattttctt acattattta tgcccccaaa ttatatttat gtatgtaagt    2100
gaggtttgtt ttgtatatta aaatggagtt tgtttgtaaa aaaaaaaaaa aaaaaa        2157
```

<210> SEQ ID NO 31
<211> LENGTH: 216
<212> TYPE: PRT
<213> ORGANISM: Homo sapiens

<400> SEQUENCE: 31

```
Met Arg Ser Gly Cys Val Val His Val Trp Ile Leu Ala Gly Leu
1               5                   10                  15

Trp Leu Ala Val Ala Gly Arg Pro Leu Ala Phe Ser Asp Ala Gly Pro
            20                  25                  30

His Val His Tyr Gly Trp Gly Asp Pro Ile Arg Leu Arg His Leu Tyr
        35                  40                  45

Thr Ser Gly Pro His Gly Leu Ser Ser Cys Phe Leu Arg Ile Arg Ala
    50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Glu Ile Arg Pro
        115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205

Val Arg Ser Pro Ser Phe Glu Lys
    210                 215
```

<210> SEQ ID NO 32
<211> LENGTH: 940
<212> TYPE: DNA
<213> ORGANISM: Homo sapiens

<400> SEQUENCE: 32

```
ctgtcagctg aggatccagc cgaaagagga gccaggcact caggccacct gagtctactc    60
acctggacaa ctggaatctg gcaccaattc taaaccactc agcttctccg agctcacacc    120
```

```
ccggagatca cctgaggacc cgagccattg atggactcgg acgagaccgg gttcgagcac      180
tcaggactgt gggtttctgt gctggctggt cttctgctgg gagcctgcca ggcacacccc      240
atccctgact ccagtcctct cctgcaattc gggggccaag tccggcagcg gtacctctac      300
acagatgatg cccagcagac agaagcccac ctggagatca gggaggatgg gacggtgggg      360
ggcgctgctg accagagccc cgaaagtctc ctgcagctga aagccttgaa gccgggagtt      420
attcaaatct gggagtcaa gacatccagg ttcctgtgcc agcggccaga tggggccctg       480
tatggatcgc tccactttga ccctgaggcc tgcagcttcc gggagctgct tcttgaggac      540
ggatacaatg tttaccagtc cgaagcccac ggcctcccgc tgcacctgcc agggaacaag      600
tccccacacc gggaccctgc accccgagga ccagctcgct tcctgccact accaggcctg      660 cccccccgcac tcccggagcc acccggaatc ctggccccccc agcccccccga tgtgggctcc    720 tcggacccctc tgagcatggt gggaccttcc cagggccgaa gccccagcta cgcttcctga    780
agccagaggc tgtttactat gacatctcct ctttatttat taggttattt atcttattta      840
tttttttatt tttcttactt gagataataa agagttccag aggagaaaaa aaaaaaaaaa      900
aaaaaaaaaa aaaaaaaaaa aaaaaaaaaa aaaaaaaaa                             940
```

<210> SEQ ID NO 33
<211> LENGTH: 209
<212> TYPE: PRT
<213> ORGANISM: Homo sapiens

<400> SEQUENCE: 33

```
Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser
```

<210> SEQ ID NO 34

<211> LENGTH: 3018
<212> TYPE: DNA
<213> ORGANISM: Homo sapiens

<400> SEQUENCE: 34

```
cggcaaaaag agggaatcc agtctaggat cctcacacca gctacttgca agggagaagg      60
aaaaggccag taaggcctgg gccaggagag tcccgacagg agtgtcaggt ttcaatctca     120
gcaccagcca ctcagagcag ggcacgatgt tgggggcccg cctcaggctc tgggtctgtg    180
ccttgtgcag cgtctgcagc atgagcgtcc tcagagccta tcccaatgcc tccccactgc    240
tcggctccag ctggggtggc ctgatccacc tgtacacagc cacagccagg aacagctacc    300
acctgcagat ccacaagaat ggccatgtgg atggcgcacc ccatcagacc atctacagtg    360
ccctgatgat cagatcagag gatgctggct tgtggtgat tacaggtgtg atgagcagaa     420
gatacctctg catggatttc agaggcaaca tttttggatc acactatttc gacccggaga    480
actgcaggtt ccaacaccag acgctggaaa acgggtacga cgtctaccac tctcctcagt    540
atcacttcct ggtcagtctg ggccgggcga agagagcctt cctgccaggc atgaacccac    600
ccccgtactc ccagttcctg tcccggagga acgagatccc cctaattcac ttcaacaccc    660
ccataccacg gcggcacacc cggagcgcgc aggacgactc ggagcgggac ccctgaacg    720
tgctgaagcc ccgggcccgg atgacccgg ccccggcctc ctgttcacag gagctcccga    780
gcgccgagga caacagcccg atggccagtg acccattagg ggtggtcagg ggcggtcgag    840
tgaacacgca cgctggggga acgggcccgg aaggctgccg cccttcgcc aagttcatct    900
agggtcgctg gaagggcacc ctctttaacc catccctcag caaacgcagc tcttcccaag    960
gaccaggtcc cttgacgttc cgaggatggg aaaggtgaca ggggcatgta tggaatttgc   1020
tgcttctctg gggtcccttc cacaggaggt cctgtgagaa ccaacctttg aggcccaagt   1080
catggggttt caccgccttc ctcactccat atagaacacc tttcccaata ggaaacccca   1140
acaggtaaac tagaaatttc cccttcatga aggtagagag aaggggtctc tcccaacata   1200
tttctcttcc ttgtgcctct cctctttatc acttttaagc ataaaaaaa aaaaaaaaa    1260
aaaaaaaaaa aaaagcagtg ggttcctgag ctcaagactt tgaaggtgta gggaagagga   1320
aatcggagat cccagaagct tctccactgc cctatgcatt tatgttagat gccccgatcc   1380
cactggcatt tgagtgtgca aaccttgaca ttaacagctg aatggggcaa gttgatgaaa   1440
acactacttt caagccttcg ttcttccttg agcatctctg gggaagagct gtcaaaagac   1500
tggtggtagg ctggtgaaaa cttgacagct agacttgatg cttgctgaaa tgaggcagga   1560
atcataatag aaaactcagc ctccctacag ggtgagcacc ttctgtctcg ctgtctccct   1620
ctgtgcagcc acagccagag ggcccagaat ggccccactc tgttcccaag cagttcatga   1680
tacagcctca cctttggcc ccatctctgg tttttgaaaa tttggtctaa ggaataaata    1740
gcttttacac tggctcacga aaatctgccc tgctagaatt tgcttttcaa aatgaaata    1800
aattccaact ctcctaagag gcatttaatt aaggctctac ttccaggttg agtaggaatc   1860
cattctgaac aaactacaaa aatgtgactg ggaaggggc tttgagagac tgggactgct    1920
ctgggttagg ttttctgtgg actgaaaaat cgtgtccttt tctctaaatg aagtggcatc   1980
aaggactcag ggggaaagaa atcaggggac atgttataga agttatgaaa agacaaccac   2040
atggtcaggc tcttgtctgt ggtctctagg gctctgcagc agcagtggct cttcgattag   2100
ttaaaactct cctaggctga cacatctggg tctcaatccc cttggaaatt cttggtgcat   2160
taaatgaagc cttaccccat tactgcggtt cttcctgtaa ggggctcca ttttcctccc    2220
```

```
tctctttaaa tgaccaccta aaggacagta tattaacaag caaagtcgat tcaacaacag    2280
cttcttccca gtcactttt tttttctcac tgccatcaca tactaacctt atactttgat     2340
ctattctttt tggttatgag agaaatgttg ggcaactgtt tttacctgat ggttttaagc    2400
tgaacttgaa ggactggttc ctattctgaa acagtaaaac tatgtataat agtatatagc    2460
catgcatggc aaatatttta atatttctgt tttcatttcc tgttggaaat attatcctgc    2520
ataatagcta ttggaggctc ctcagtgaaa gatcccaaaa ggattttggt ggaaaactag    2580
ttgtaatctc acaaactcaa cactaccatc aggggttttc tttatggcaa agccaaaata    2640
gctcctacaa tttcttatat ccctcgtcat gtggcagtat ttatttattt atttggaagt    2700
ttgcctatcc ttctatattt atagatattt ataaaaatgt aacccctttt tcctttcttc    2760
tgtttaaaat aaaaataaaa tttatctcag cttctgttag cttatcctct ttgtagtact    2820
acttaaaagc atgtcggaat ataagaataa aaaggattat gggagggaa cattagggaa     2880 atccagagaa ggcaaaattg aaaaaaagat tttagaattt taaaattttc aaagatttct    2940
tccattcata aggagactca atgattttaa ttgatctaga cagaattatt taagttttat    3000
caatattgga tttctggt                                                  3018

<210> SEQ ID NO 35
<211> LENGTH: 251
<212> TYPE: PRT
<213> ORGANISM: Homo sapiens

<400> SEQUENCE: 35

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220
```

Gly Val Val Arg Gly Arg Val Asn Thr His Ala Gly Gly Thr Gly
225                 230                 235                 240

Pro Glu Gly Cys Arg Pro Phe Ala Lys Phe Ile
            245                 250

<210> SEQ ID NO 36
<211> LENGTH: 251
<212> TYPE: PRT
<213> ORGANISM: Homo sapiens

<400> SEQUENCE: 36

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Arg Val Asn Thr His Ala Gly Gly Thr Gly
225                 230                 235                 240

Pro Glu Gly Cys Arg Pro Phe Ala Lys Phe Ile
            245                 250

<210> SEQ ID NO 37
<211> LENGTH: 431
<212> TYPE: PRT
<213> ORGANISM: Homo sapiens

<400> SEQUENCE: 37

Tyr Asp Thr Phe Pro Lys Asn Phe Phe Trp Gly Ile Gly Thr Gly Ala
1               5                   10                  15

Leu Gln Val Glu Gly Ser Trp Lys Lys Asp Gly Lys Gly Pro Ser Ile
            20                  25                  30

Trp Asp His Phe Ile His Thr His Leu Lys Asn Val Ser Ser Thr Asn
        35                  40                  45

Gly Ser Ser Asp Ser Tyr Ile Phe Leu Glu Lys Asp Leu Ser Ala Leu
50                  55                  60

Asp Phe Ile Gly Val Ser Phe Tyr Gln Phe Ser Ile Ser Trp Pro Arg
65                  70                  75                  80

Leu Phe Pro Asp Gly Ile Val Thr Val Ala Asn Ala Lys Gly Leu Gln
                85                  90                  95

Tyr Tyr Ser Thr Leu Leu Asp Ala Leu Val Leu Arg Asn Ile Glu Pro
            100                 105                 110

Ile Val Thr Leu Tyr His Trp Asp Leu Pro Leu Ala Leu Gln Glu Lys
            115                 120                 125

Tyr Gly Gly Trp Lys Asn Asp Thr Ile Ile Asp Ile Phe Asn Asp Tyr
130                 135                 140

Ala Thr Tyr Cys Phe Gln Met Phe Gly Asp Arg Val Lys Tyr Trp Ile
145                 150                 155                 160

Thr Ile His Asn Pro Tyr Leu Val Ala Trp His Gly Tyr Gly Thr Gly
                165                 170                 175

Met His Ala Pro Gly Glu Lys Gly Asn Leu Ala Ala Val Tyr Thr Val
            180                 185                 190

Gly His Asn Leu Ile Lys Ala His Ser Lys Val Trp His Asn Tyr Asn
            195                 200                 205

Thr His Phe Arg Pro His Gln Lys Gly Trp Leu Ser Ile Thr Leu Gly
210                 215                 220

Ser His Trp Ile Glu Pro Asn Arg Ser Glu Asn Thr Met Asp Ile Phe
225                 230                 235                 240

Lys Cys Gln Gln Ser Met Val Ser Val Leu Gly Trp Phe Ala Asn Pro
                245                 250                 255

Ile His Gly Asp Gly Asp Tyr Pro Glu Gly Met Arg Lys Lys Leu Phe
            260                 265                 270

Ser Val Leu Pro Ile Phe Ser Glu Ala Glu Lys His Glu Met Arg Gly
            275                 280                 285

Thr Ala Asp Phe Phe Ala Phe Ser Phe Gly Pro Asn Asn Phe Lys Pro
290                 295                 300

Leu Asn Thr Met Ala Lys Met Gly Gln Asn Val Ser Leu Asn Leu Arg
305                 310                 315                 320

Glu Ala Leu Asn Trp Ile Lys Leu Glu Tyr Asn Asn Pro Arg Ile Leu
                325                 330                 335

Ile Ala Glu Asn Gly Trp Phe Thr Asp Ser Arg Val Lys Thr Glu Asp
            340                 345                 350

Thr Thr Ala Ile Tyr Met Met Lys Asn Phe Leu Ser Gln Val Leu Gln
            355                 360                 365

Ala Ile Arg Leu Asp Glu Ile Arg Val Phe Gly Tyr Thr Ala Trp Ser
370                 375                 380

Leu Leu Asp Gly Phe Glu Trp Gln Asp Ala Tyr Thr Ile Arg Arg Gly
385                 390                 395                 400

Leu Phe Tyr Val Asp Phe Asn Ser Lys Gln Lys Glu Arg Lys Pro Lys
                405                 410                 415

Ser Ser Ala His Tyr Tyr Lys Gln Ile Ile Arg Glu Asn Gly Phe
            420                 425                 430

<210> SEQ ID NO 38
<211> LENGTH: 397
<212> TYPE: PRT
<213> ORGANISM: Homo sapiens

<400> SEQUENCE: 38

-continued

```
Thr Arg Pro Ala Gln Cys Thr Asp Phe Val Asn Ile Lys Lys Gln Leu
1               5                   10                  15

Glu Met Leu Ala Arg Met Lys Val Thr His Tyr Arg Phe Ala Leu Asp
            20                  25                  30

Trp Ala Ser Val Leu Pro Thr Gly Asn Leu Ser Ala Val Asn Arg Gln
        35                  40                  45

Ala Leu Arg Tyr Tyr Arg Cys Val Val Ser Glu Gly Leu Lys Leu Gly
    50                  55                  60

Ile Ser Ala Met Val Thr Leu Tyr Tyr Pro Thr His Ala His Leu Gly
65                  70                  75                  80

Leu Pro Glu Pro Leu Leu His Ala Asp Gly Trp Leu Asn Pro Ser Thr
                85                  90                  95

Ala Glu Ala Phe Gln Ala Tyr Ala Gly Leu Cys Phe Gln Glu Leu Gly
            100                 105                 110

Asp Leu Val Lys Leu Trp Ile Thr Ile Asn Glu Pro Asn Arg Leu Ser
            115                 120                 125

Asp Ile Tyr Asn Arg Ser Gly Asn Asp Thr Tyr Gly Ala Ala His Asn
    130                 135                 140

Leu Leu Val Ala His Ala Leu Ala Trp Arg Leu Tyr Asp Arg Gln Phe
145                 150                 155                 160

Arg Pro Ser Gln Arg Gly Ala Val Ser Leu Ser Leu His Ala Asp Trp
                165                 170                 175

Ala Glu Pro Ala Asn Pro Tyr Ala Asp Ser His Trp Arg Ala Ala Glu
            180                 185                 190

Arg Phe Leu Gln Phe Glu Ile Ala Trp Phe Ala Glu Pro Leu Phe Lys
        195                 200                 205

Thr Gly Asp Tyr Pro Ala Ala Met Arg Glu Tyr Ile Ala Ser Lys His
    210                 215                 220

Arg Arg Gly Leu Ser Ser Ser Ala Leu Pro Arg Leu Thr Glu Ala Glu
225                 230                 235                 240

Arg Arg Leu Leu Lys Gly Thr Val Asp Phe Cys Ala Leu Asn His Phe
                245                 250                 255

Thr Thr Arg Phe Val Met His Glu Gln Leu Ala Gly Ser Arg Tyr Asp
            260                 265                 270

Ser Asp Arg Asp Ile Gln Phe Leu Gln Asp Ile Thr Arg Leu Ser Ser
        275                 280                 285

Pro Thr Arg Leu Ala Val Ile Pro Trp Gly Val Arg Lys Leu Leu Arg
    290                 295                 300

Trp Val Arg Arg Asn Tyr Gly Asp Met Asp Ile Tyr Ile Thr Ala Ser
305                 310                 315                 320

Gly Ile Asp Asp Gln Ala Leu Glu Asp Asp Arg Leu Arg Lys Tyr Tyr
                325                 330                 335

Leu Gly Lys Tyr Leu Gln Glu Val Leu Lys Ala Tyr Leu Ile Asp Lys
            340                 345                 350

Val Arg Ile Lys Gly Tyr Tyr Ala Phe Lys Leu Ala Glu Glu Lys Ser
        355                 360                 365

Lys Pro Arg Phe Gly Phe Phe Thr Ser Asp Phe Lys Ala Lys Ser Ser
    370                 375                 380

Ile Gln Phe Tyr Asn Lys Val Ile Ser Ser Arg Gly Phe
385                 390                 395
```

<210> SEQ ID NO 39
<211> LENGTH: 946

```
<212> TYPE: PRT
<213> ORGANISM: Homo sapiens

<400> SEQUENCE: 39

Gly Phe Ser Gly Asp Gly Arg Ala Ile Trp Ser Lys Asn Pro Asn Phe
1               5                   10                  15

Thr Pro Val Asn Glu Ser Gln Leu Phe Leu Tyr Asp Thr Phe Pro Lys
            20                  25                  30

Asn Phe Phe Trp Gly Ile Gly Thr Gly Ala Leu Gln Val Glu Gly Ser
        35                  40                  45

Trp Lys Lys Asp Gly Lys Gly Pro Ser Ile Trp Asp His Phe Ile His
    50                  55                  60

Thr His Leu Lys Asn Val Ser Ser Thr Asn Gly Ser Ser Asp Ser Tyr
65                  70                  75                  80

Ile Phe Leu Glu Lys Asp Leu Ser Ala Leu Asp Phe Ile Gly Val Ser
                85                  90                  95

Phe Tyr Gln Phe Ser Ile Ser Trp Pro Arg Leu Phe Pro Asp Gly Ile
            100                 105                 110

Val Thr Val Ala Asn Ala Lys Gly Leu Gln Tyr Tyr Ser Thr Leu Leu
        115                 120                 125

Asp Ala Leu Val Leu Arg Asn Ile Glu Pro Ile Val Thr Leu Tyr His
    130                 135                 140

Trp Asp Leu Pro Leu Ala Leu Gln Glu Lys Tyr Gly Gly Trp Lys Asn
145                 150                 155                 160

Asp Thr Ile Ile Asp Ile Phe Asn Asp Tyr Ala Thr Tyr Cys Phe Gln
                165                 170                 175

Met Phe Gly Asp Arg Val Lys Tyr Trp Ile Thr Ile His Asn Pro Tyr
            180                 185                 190

Leu Val Ala Trp His Gly Tyr Gly Thr Gly Met His Ala Pro Gly Glu
        195                 200                 205

Lys Gly Asn Leu Ala Ala Val Tyr Thr Val Gly His Asn Leu Ile Lys
    210                 215                 220

Ala His Ser Lys Val Trp His Asn Tyr Asn Thr His Phe Arg Pro His
225                 230                 235                 240

Gln Lys Gly Trp Leu Ser Ile Thr Leu Gly Ser His Trp Ile Glu Pro
                245                 250                 255

Asn Arg Ser Glu Asn Thr Met Asp Ile Phe Lys Cys Gln Gln Ser Met
            260                 265                 270

Val Ser Val Leu Gly Trp Phe Ala Asn Pro Ile His Gly Asp Gly Asp
        275                 280                 285

Tyr Pro Glu Gly Met Arg Lys Lys Leu Phe Ser Val Leu Pro Ile Phe
    290                 295                 300

Ser Glu Ala Glu Lys His Glu Met Arg Gly Thr Ala Asp Phe Phe Ala
305                 310                 315                 320

Phe Ser Phe Gly Pro Asn Asn Phe Lys Pro Leu Asn Thr Met Ala Lys
                325                 330                 335

Met Gly Gln Asn Val Ser Leu Asn Leu Arg Glu Ala Leu Asn Trp Ile
            340                 345                 350

Lys Leu Glu Tyr Asn Asn Pro Arg Ile Leu Ile Ala Glu Asn Gly Trp
        355                 360                 365

Phe Thr Asp Ser Arg Val Lys Thr Glu Asp Thr Thr Ala Ile Tyr Met
    370                 375                 380

Met Lys Asn Phe Leu Ser Gln Val Leu Gln Ala Ile Arg Leu Asp Glu
385                 390                 395                 400
```

```
Ile Arg Val Phe Gly Tyr Thr Ala Trp Ser Leu Leu Asp Gly Phe Glu
            405                 410                 415

Trp Gln Asp Ala Tyr Thr Ile Arg Arg Gly Leu Phe Tyr Val Asp Phe
        420                 425                 430

Asn Ser Lys Gln Lys Glu Arg Lys Pro Lys Ser Ser Ala His Tyr Tyr
            435                 440                 445

Lys Gln Ile Ile Arg Glu Asn Gly Phe Ser Leu Lys Glu Ser Thr Pro
        450                 455                 460

Asp Val Gln Gly Gln Phe Pro Cys Asp Phe Ser Trp Gly Val Thr Glu
465                 470                 475                 480

Ser Val Leu Lys Pro Glu Ser Val Ala Ser Ser Pro Gln Phe Ser Asp
            485                 490                 495

Pro His Leu Tyr Val Trp Asn Ala Thr Gly Asn Arg Leu Leu His Arg
        500                 505                 510

Val Glu Gly Val Arg Leu Lys Thr Arg Pro Ala Gln Cys Thr Asp Phe
        515                 520                 525

Val Asn Ile Lys Lys Gln Leu Glu Met Leu Ala Arg Met Lys Val Thr
        530                 535                 540

His Tyr Arg Phe Ala Leu Asp Trp Ala Ser Val Leu Pro Thr Gly Asn
545                 550                 555                 560

Leu Ser Ala Val Asn Arg Gln Ala Leu Arg Tyr Tyr Arg Cys Val Val
            565                 570                 575

Ser Glu Gly Leu Lys Leu Gly Ile Ser Ala Met Val Thr Leu Tyr Tyr
        580                 585                 590

Pro Thr His Ala His Leu Gly Leu Pro Glu Pro Leu Leu His Ala Asp
            595                 600                 605

Gly Trp Leu Asn Pro Ser Thr Ala Glu Ala Phe Gln Ala Tyr Ala Gly
        610                 615                 620

Leu Cys Phe Gln Glu Leu Gly Asp Leu Val Lys Leu Trp Ile Thr Ile
625                 630                 635                 640

Asn Glu Pro Asn Arg Leu Ser Asp Ile Tyr Asn Arg Ser Gly Asn Asp
            645                 650                 655

Thr Tyr Gly Ala Ala His Asn Leu Leu Val Ala His Ala Leu Ala Trp
        660                 665                 670

Arg Leu Tyr Asp Arg Gln Phe Arg Pro Ser Gln Arg Gly Ala Val Ser
            675                 680                 685

Leu Ser Leu His Ala Asp Trp Ala Glu Pro Ala Asn Pro Tyr Ala Asp
        690                 695                 700

Ser His Trp Arg Ala Ala Glu Arg Phe Leu Gln Phe Glu Ile Ala Trp
705                 710                 715                 720

Phe Ala Glu Pro Leu Phe Lys Thr Gly Asp Tyr Pro Ala Ala Met Arg
            725                 730                 735

Glu Tyr Ile Ala Ser Lys His Arg Arg Gly Leu Ser Ser Ser Ala Leu
        740                 745                 750

Pro Arg Leu Thr Glu Ala Glu Arg Leu Leu Lys Gly Thr Val Asp
        755                 760                 765

Phe Cys Ala Leu Asn His Phe Thr Thr Arg Phe Val Met His Glu Gln
        770                 775                 780

Leu Ala Gly Ser Arg Tyr Asp Ser Asp Arg Asp Ile Gln Phe Leu Gln
785                 790                 795                 800

Asp Ile Thr Arg Leu Ser Ser Pro Thr Arg Leu Ala Val Ile Pro Trp
            805                 810                 815
```

```
Gly Val Arg Lys Leu Leu Arg Trp Val Arg Arg Asn Tyr Gly Asp Met
                820                 825                 830

Asp Ile Tyr Ile Thr Ala Ser Gly Ile Asp Asp Gln Ala Leu Glu Asp
            835                 840                 845

Asp Arg Leu Arg Lys Tyr Tyr Leu Gly Lys Tyr Leu Gln Glu Val Leu
850                 855                 860

Lys Ala Tyr Leu Ile Asp Lys Val Arg Ile Lys Gly Tyr Tyr Ala Phe
865                 870                 875                 880

Lys Leu Ala Glu Glu Lys Ser Lys Pro Arg Phe Gly Phe Phe Thr Ser
                885                 890                 895

Asp Phe Lys Ala Lys Ser Ser Ile Gln Phe Tyr Asn Lys Val Ile Ser
            900                 905                 910

Ser Arg Gly Phe Pro Phe Glu Asn Ser Ser Arg Cys Ser Gln Thr
                915                 920                 925

Gln Glu Asn Thr Glu Cys Thr Val Cys Leu Phe Leu Val Gln Lys Lys
930                 935                 940

Pro Leu
945

<210> SEQ ID NO 40
<211> LENGTH: 1195
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Glu Pro Gly Asp Gly Ala Gln Thr Trp Ala Arg Phe Ser Arg Pro Pro
1               5                   10                  15

Ala Pro Glu Ala Ala Gly Leu Phe Gln Gly Thr Phe Pro Asp Gly Phe
                20                  25                  30

Leu Trp Ala Val Gly Ser Ala Ala Tyr Gln Thr Glu Gly Gly Trp Gln
            35                  40                  45

Gln His Gly Lys Gly Ala Ser Ile Trp Asp Thr Phe Thr His His Pro
        50                  55                  60

Leu Ala Pro Pro Gly Asp Ser Arg Asn Ala Ser Leu Pro Leu Gly Ala
65                  70                  75                  80

Pro Ser Pro Leu Gln Pro Ala Thr Gly Asp Val Ala Ser Asp Ser Tyr
                85                  90                  95

Asn Asn Val Phe Arg Asp Thr Glu Ala Leu Arg Glu Leu Gly Val Thr
                100                 105                 110

His Tyr Arg Phe Ser Ile Ser Trp Ala Arg Val Leu Pro Asn Gly Ser
            115                 120                 125

Ala Gly Val Pro Asn Arg Glu Gly Leu Arg Tyr Tyr Arg Arg Leu Leu
        130                 135                 140

Glu Arg Leu Arg Glu Leu Gly Val Gln Pro Val Val Thr Leu Tyr His
145                 150                 155                 160

Trp Asp Leu Pro Gln Arg Leu Gln Asp Ala Tyr Gly Gly Trp Ala Asn
                165                 170                 175

Arg Ala Leu Ala Asp His Phe Arg Asp Tyr Ala Glu Leu Cys Phe Arg
                180                 185                 190

His Phe Gly Gly Gln Val Lys Tyr Trp Ile Thr Ile Asp Asn Pro Tyr
            195                 200                 205

Val Val Ala Trp His Gly Tyr Ala Thr Gly Arg Leu Ala Pro Gly Ile
```

-continued

```
             210                 215                 220
Arg Gly Ser Pro Arg Leu Gly Tyr Leu Val Ala His Asn Leu Leu Leu
225                 230                 235                 240

Ala His Ala Lys Val Trp His Leu Tyr Asn Thr Ser Phe Arg Pro Thr
                245                 250                 255

Gln Gly Gly Gln Val Ser Ile Ala Leu Ser Ser His Trp Ile Asn Pro
                260                 265                 270

Arg Arg Met Thr Asp His Ser Ile Lys Glu Cys Gln Lys Ser Leu Asp
                275                 280                 285

Phe Val Leu Gly Trp Phe Ala Lys Pro Val Phe Ile Asp Gly Asp Tyr
                290                 295                 300

Pro Glu Ser Met Lys Asn Asn Leu Ser Ser Ile Leu Pro Asp Phe Thr
305                 310                 315                 320

Glu Ser Glu Lys Lys Phe Ile Lys Gly Thr Ala Asp Phe Phe Ala Leu
                325                 330                 335

Cys Phe Gly Pro Thr Leu Ser Phe Gln Leu Leu Asp Pro His Met Lys
                340                 345                 350

Phe Arg Gln Leu Glu Ser Pro Asn Leu Arg Gln Leu Leu Ser Trp Ile
                355                 360                 365

Asp Leu Glu Phe Asn His Pro Gln Ile Phe Ile Val Glu Asn Gly Trp
                370                 375                 380

Phe Val Ser Gly Thr Thr Lys Arg Asp Asp Ala Lys Tyr Met Tyr Tyr
385                 390                 395                 400

Leu Lys Lys Phe Ile Met Glu Thr Leu Lys Ala Ile Lys Leu Asp Gly
                405                 410                 415

Val Asp Val Ile Gly Tyr Thr Ala Trp Ser Leu Met Asp Gly Phe Glu
                420                 425                 430

Trp His Arg Gly Tyr Ser Ile Arg Arg Gly Leu Phe Tyr Val Asp Phe
                435                 440                 445

Leu Ser Gln Asp Lys Met Leu Leu Pro Lys Ser Ser Ala Leu Phe Tyr
                450                 455                 460

Gln Lys Leu Ile Glu Lys Asn Gly Phe Pro Pro Leu Pro Glu Asn Gln
465                 470                 475                 480

Pro Leu Glu Gly Thr Phe Pro Cys Asp Phe Ala Trp Gly Val Val Asp
                485                 490                 495

Asn Tyr Ile Gln Val Asp Thr Thr Leu Ser Gln Phe Thr Asp Leu Asn
                500                 505                 510

Val Tyr Leu Trp Asp Val His His Ser Lys Arg Leu Ile Lys Val Asp
                515                 520                 525

Gly Val Val Thr Lys Lys Arg Lys Ser Tyr Cys Val Asp Phe Ala Ala
                530                 535                 540

Ile Gln Pro Gln Ile Ala Leu Leu Gln Glu Met His Val Thr His Phe
545                 550                 555                 560

Arg Phe Ser Leu Asp Trp Ala Leu Ile Leu Pro Leu Gly Asn Gln Ser
                565                 570                 575

Gln Val Asn His Thr Ile Leu Gln Tyr Tyr Arg Cys Met Ala Ser Glu
                580                 585                 590

Leu Val Arg Val Asn Ile Thr Pro Val Val Ala Leu Trp Gln Pro Met
                595                 600                 605

Ala Pro Asn Gln Gly Leu Pro Arg Leu Leu Ala Arg Gln Gly Ala Trp
                610                 615                 620

Glu Asn Pro Tyr Thr Ala Leu Ala Phe Ala Glu Tyr Ala Arg Leu Cys
625                 630                 635                 640
```

```
Phe Gln Glu Leu Gly His His Val Lys Leu Trp Ile Thr Met Asn Glu
                645                 650                 655

Pro Tyr Thr Arg Asn Met Thr Tyr Ser Ala Gly His Asn Leu Leu Lys
            660                 665                 670

Ala His Ala Leu Ala Trp His Val Tyr Asn Glu Lys Phe Arg His Ala
        675                 680                 685

Gln Asn Gly Lys Ile Ser Ile Ala Leu Gln Ala Asp Trp Ile Glu Pro
    690                 695                 700

Ala Cys Pro Phe Ser Gln Lys Asp Lys Glu Val Ala Glu Arg Val Leu
705                 710                 715                 720

Glu Phe Asp Ile Gly Trp Leu Ala Glu Pro Ile Phe Gly Ser Gly Asp
                725                 730                 735

Tyr Pro Trp Val Met Arg Asp Trp Leu Asn Gln Arg Asn Asn Phe Leu
            740                 745                 750

Leu Pro Tyr Phe Thr Glu Asp Glu Lys Lys Leu Ile Gln Gly Thr Phe
        755                 760                 765

Asp Phe Leu Ala Leu Ser His Tyr Thr Thr Ile Leu Val Asp Ser Glu
    770                 775                 780

Lys Glu Asp Pro Ile Lys Tyr Asn Asp Tyr Leu Glu Val Gln Glu Met
785                 790                 795                 800

Thr Asp Ile Thr Trp Leu Asn Ser Pro Ser Gln Val Ala Val Val Pro
                805                 810                 815

Trp Gly Leu Arg Lys Val Leu Asn Trp Leu Lys Phe Lys Tyr Gly Asp
            820                 825                 830

Leu Pro Met Tyr Ile Ile Ser Asn Gly Ile Asp Asp Gly Leu His Ala
        835                 840                 845

Glu Asp Asp Gln Leu Arg Val Tyr Tyr Met Gln Asn Tyr Ile Asn Glu
    850                 855                 860

Ala Leu Lys Ala His Ile Leu Asp Gly Ile Asn Leu Cys Gly Tyr Phe
865                 870                 875                 880

Ala Tyr Ser Phe Asn Asp Arg Thr Ala Pro Arg Phe Gly Leu Tyr Arg
                885                 890                 895

Tyr Ala Ala Asp Gln Phe Glu Pro Lys Ala Ser Met Lys His Tyr Arg
            900                 905                 910

Lys Ile Ile Asp Ser Asn Gly Phe Pro Gly Pro Glu Thr Leu Glu Arg
        915                 920                 925

Phe Cys Pro Glu Glu Phe Thr Val Cys Thr Glu Cys Ser Phe Phe His
    930                 935                 940

Thr Arg Lys Ser Leu Gly Ser Gly Gly Gly Ser Gly Gly Gly Gly
945                 950                 955                 960

Ser Gly Gly Gly Ser Leu Lys Tyr Pro Asn Ala Ser Pro Leu Leu
                965                 970                 975

Gly Ser Ser Trp Gly Gly Leu Ile His Leu Tyr Thr Ala Thr Ala Arg
            980                 985                 990

Asn Ser Tyr His Leu Gln Ile His Lys Asn Gly His Val Asp Gly Ala
        995                1000                1005

Pro His Gln Thr Ile Tyr Ser Ala Leu Met Ile Arg Ser Glu Asp
       1010                1015                1020

Ala Gly Phe Val Val Ile Thr Gly Val Met Ser Arg Arg Tyr Leu
       1025                1030                1035

Cys Met Asp Phe Arg Gly Asn Ile Phe Gly Ser His Tyr Phe Asp
       1040                1045                1050
```

Pro Glu  Asn Cys Arg Phe Gln  His Gln Thr Leu Glu  Asn Gly Tyr
    1055              1060             1065

Asp Val  Tyr His Ser Pro Gln  Tyr His Phe Leu Val  Ser Leu Gly
    1070              1075             1080

Arg Ala  Lys Arg Ala Phe Leu  Pro Gly Met Asn Pro  Pro Pro Tyr
    1085              1090             1095

Ser Gln  Phe Leu Ser Arg Arg  Asn Glu Ile Pro Leu  Ile His Phe
    1100              1105             1110

Asn Thr  Pro Ile Pro Arg Arg  His Thr Arg Ser Ala  Glu Asp Asp
    1115              1120             1125

Ser Glu  Arg Asp Pro Leu Asn  Val Leu Lys Pro Arg  Ala Arg Met
    1130              1135             1140

Thr Pro  Ala Pro Ala Ser Cys  Ser Gln Glu Leu Pro  Ser Ala Glu
    1145              1150             1155

Asp Asn  Ser Pro Met Ala Ser  Asp Pro Leu Gly Val  Val Arg Gly
    1160              1165             1170

Gly Arg  Val Asn Thr His Ala  Gly Gly Thr Gly Pro  Glu Gly Cys
    1175              1180             1185

Arg Pro  Phe Ala Lys Phe Ile
    1190              1195

<210> SEQ ID NO 41
<211> LENGTH: 1195
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Glu Pro Gly Asp Gly Ala Gln  Thr Trp Ala Arg Phe  Ser Arg Pro Pro
1              5                  10                  15

Ala Pro Glu Ala Ala Gly Leu  Phe Gln Gly Thr Phe  Pro Asp Gly Phe
            20                  25                  30

Leu Trp Ala Val Gly Ser Ala  Ala Tyr Gln Thr Glu  Gly Gly Trp Gln
        35                  40                  45

Gln His Gly Lys Gly Ala Ser  Ile Trp Asp Thr Phe  Thr His His Pro
    50                  55                  60

Leu Ala Pro Pro Gly Asp Ser  Arg Asn Ala Ser Leu  Pro Leu Gly Ala
65                  70                  75                  80

Pro Ser Pro Leu Gln Pro Ala  Thr Gly Asp Val Ala  Ser Asp Ser Tyr
            85                  90                  95

Asn Asn Val Phe Arg Asp Thr  Glu Ala Leu Arg Glu  Leu Gly Val Thr
            100                 105                 110

His Tyr Arg Phe Ser Ile Ser  Trp Ala Arg Val Leu  Pro Asn Gly Ser
        115                 120                 125

Ala Gly Val Pro Asn Arg Glu  Gly Leu Arg Tyr Tyr  Arg Arg Leu Leu
    130                 135                 140

Glu Arg Leu Arg Glu Leu Gly  Val Gln Pro Val Val  Thr Leu Tyr His
145                 150                 155                 160

Trp Asp Leu Pro Gln Arg Leu  Gln Asp Ala Tyr Gly  Gly Trp Ala Asn
            165                 170                 175

Arg Ala Leu Ala Asp His Phe  Arg Asp Tyr Ala Glu  Leu Cys Phe Arg
            180                 185                 190

His Phe Gly Gly Gln Val Lys  Tyr Trp Ile Thr Ile  Asp Asn Pro Tyr

```
            195                 200                 205
Val Val Ala Trp His Gly Tyr Ala Thr Gly Arg Leu Ala Pro Gly Ile
210                 215                 220

Arg Gly Ser Pro Arg Leu Gly Tyr Leu Val Ala His Asn Leu Leu Leu
225                 230                 235                 240

Ala His Ala Lys Val Trp His Leu Tyr Asn Thr Ser Phe Arg Pro Thr
                245                 250                 255

Gln Gly Gly Gln Val Ser Ile Ala Leu Ser Ser His Trp Ile Asn Pro
                260                 265                 270

Arg Arg Met Thr Asp His Ser Ile Lys Glu Cys Gln Lys Ser Leu Asp
            275                 280                 285

Phe Val Leu Gly Trp Phe Ala Lys Pro Val Phe Ile Asp Gly Asp Tyr
290                 295                 300

Pro Glu Ser Met Lys Asn Asn Leu Ser Ser Ile Leu Pro Asp Phe Thr
305                 310                 315                 320

Glu Ser Glu Lys Lys Phe Ile Lys Gly Thr Ala Asp Phe Phe Ala Leu
                325                 330                 335

Cys Phe Gly Pro Thr Leu Ser Phe Gln Leu Leu Asp Pro His Met Lys
                340                 345                 350

Phe Arg Gln Leu Glu Ser Pro Asn Leu Arg Gln Leu Leu Ser Trp Ile
            355                 360                 365

Asp Leu Glu Phe Asn His Pro Gln Ile Phe Ile Val Glu Asn Gly Trp
370                 375                 380

Phe Val Ser Gly Thr Thr Lys Arg Asp Asp Ala Lys Tyr Met Tyr Tyr
385                 390                 395                 400

Leu Lys Lys Phe Ile Met Glu Thr Leu Lys Ala Ile Lys Leu Asp Gly
                405                 410                 415

Val Asp Val Ile Gly Tyr Thr Ala Trp Ser Leu Met Asp Gly Phe Glu
                420                 425                 430

Trp His Arg Gly Tyr Ser Ile Arg Arg Gly Leu Phe Tyr Val Asp Phe
            435                 440                 445

Leu Ser Gln Asp Lys Met Leu Leu Pro Lys Ser Ser Ala Leu Phe Tyr
450                 455                 460

Gln Lys Leu Ile Glu Lys Asn Gly Phe Pro Pro Leu Pro Glu Asn Gln
465                 470                 475                 480

Pro Leu Glu Gly Thr Phe Pro Cys Asp Phe Ala Trp Gly Val Val Asp
                485                 490                 495

Asn Tyr Ile Gln Val Asp Thr Thr Leu Ser Gln Phe Thr Asp Leu Asn
                500                 505                 510

Val Tyr Leu Trp Asp Val His His Ser Lys Arg Leu Ile Lys Val Asp
            515                 520                 525

Gly Val Val Thr Lys Lys Arg Lys Ser Tyr Cys Val Asp Phe Ala Ala
530                 535                 540

Ile Gln Pro Gln Ile Ala Leu Leu Gln Glu Met His Val Thr His Phe
545                 550                 555                 560

Arg Phe Ser Leu Asp Trp Ala Leu Ile Leu Pro Leu Gly Asn Gln Ser
                565                 570                 575

Gln Val Asn His Thr Ile Leu Gln Tyr Tyr Arg Cys Met Ala Ser Glu
                580                 585                 590

Leu Val Arg Val Asn Ile Thr Pro Val Val Ala Leu Trp Gln Pro Met
            595                 600                 605

Ala Pro Asn Gln Gly Leu Pro Arg Leu Leu Ala Arg Gln Gly Ala Trp
610                 615                 620
```

```
Glu Asn Pro Tyr Thr Ala Leu Ala Phe Ala Glu Tyr Ala Arg Leu Cys
625                 630                 635                 640

Phe Gln Glu Leu Gly His His Val Lys Leu Trp Ile Thr Met Asn Glu
            645                 650                 655

Pro Tyr Thr Arg Asn Met Thr Tyr Ser Ala Gly His Asn Leu Leu Lys
            660                 665                 670

Ala His Ala Leu Ala Trp His Val Tyr Asn Glu Lys Phe Arg His Ala
        675                 680                 685

Gln Asn Gly Lys Ile Ser Ile Ala Leu Gln Ala Asp Trp Ile Glu Pro
    690                 695                 700

Ala Cys Pro Phe Ser Gln Lys Asp Lys Glu Val Ala Glu Arg Val Leu
705                 710                 715                 720

Glu Phe Asp Ile Gly Trp Leu Ala Glu Pro Ile Phe Gly Ser Gly Asp
                725                 730                 735

Tyr Pro Trp Val Met Arg Asp Trp Leu Asn Gln Arg Asn Asn Phe Leu
            740                 745                 750

Leu Pro Tyr Phe Thr Glu Asp Glu Lys Lys Leu Ile Gln Gly Thr Phe
        755                 760                 765

Asp Phe Leu Ala Leu Ser His Tyr Thr Thr Ile Leu Val Asp Ser Glu
770                 775                 780

Lys Glu Asp Pro Ile Lys Tyr Asn Asp Tyr Leu Glu Val Gln Glu Met
785                 790                 795                 800

Thr Asp Ile Thr Trp Leu Asn Ser Pro Ser Gln Val Ala Val Val Pro
                805                 810                 815

Trp Gly Leu Arg Lys Val Leu Asn Trp Leu Lys Phe Lys Tyr Gly Asp
            820                 825                 830

Leu Pro Met Tyr Ile Ile Ser Asn Gly Ile Asp Asp Gly Leu His Ala
        835                 840                 845

Glu Asp Asp Gln Leu Arg Val Tyr Tyr Met Gln Asn Tyr Ile Asn Glu
850                 855                 860

Ala Leu Lys Ala His Ile Leu Asp Gly Ile Asn Leu Cys Gly Tyr Phe
865                 870                 875                 880

Ala Tyr Ser Phe Asn Asp Arg Thr Ala Pro Arg Phe Gly Leu Tyr Arg
                885                 890                 895

Tyr Ala Ala Asp Gln Phe Glu Pro Lys Ala Ser Met Lys His Tyr Arg
            900                 905                 910

Lys Ile Ile Asp Ser Asn Gly Phe Pro Gly Pro Glu Thr Leu Glu Arg
        915                 920                 925

Phe Cys Pro Glu Glu Phe Thr Val Cys Thr Glu Cys Ser Phe Phe His
930                 935                 940

Thr Arg Lys Ser Leu Gly Ser Gly Gly Gly Ser Gly Gly Gly Gly
945                 950                 955                 960

Ser Gly Gly Gly Ser Leu Lys Tyr Pro Asn Ala Ser Pro Leu Leu
                965                 970                 975

Gly Ser Ser Trp Gly Gly Leu Ile His Leu Tyr Thr Ala Thr Ala Arg
            980                 985                 990

Asn Ser Tyr His Leu Gln Ile His  Lys Asn Gly His Val  Asp Gly Ala
            995                 1000                1005

Pro His  Gln Thr Ile Tyr Ser  Ala Leu Met Ile Arg  Ser Glu Asp
        1010                1015                1020

Ala Gly  Phe Val Val Ile Thr  Gly Val Met Ser Arg  Arg Tyr Leu
        1025                1030                1035
```

```
Cys Met Asp Phe Arg Gly Asn Ile Phe Gly Ser His Tyr Phe Asp
    1040                1045                1050

Pro Glu Asn Cys Arg Phe Gln His Gln Thr Leu Glu Asn Gly Tyr
    1055                1060                1065

Asp Val Tyr His Ser Pro Gln Tyr His Phe Leu Val Ser Leu Gly
    1070                1075                1080

Arg Ala Lys Arg Ala Phe Leu Pro Gly Met Asn Pro Pro Pro Tyr
    1085                1090                1095

Ser Gln Phe Leu Ser Arg Arg Asn Glu Ile Pro Leu Ile His Phe
    1100                1105                1110

Asn Thr Pro Ile Pro Arg Arg His Thr Gln Ser Ala Glu Asp Asp
    1115                1120                1125

Ser Glu Arg Asp Pro Leu Asn Val Leu Lys Pro Arg Ala Arg Met
    1130                1135                1140

Thr Pro Ala Pro Ala Ser Cys Ser Gln Glu Leu Pro Ser Ala Glu
    1145                1150                1155

Asp Asn Ser Pro Met Ala Ser Asp Pro Leu Gly Val Val Arg Gly
    1160                1165                1170

Gly Arg Val Asn Thr His Ala Gly Gly Thr Gly Pro Glu Gly Cys
    1175                1180                1185

Arg Pro Phe Ala Lys Phe Ile
    1190                1195

<210> SEQ ID NO 42
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Tyr Pro Asn Ala Ser Pro Leu Leu Gly Ser Ser Trp Gly Gly Leu Ile
1               5                   10                  15

His Leu Tyr Thr Ala Thr Ala Arg Asn Ser Tyr His Leu Gln Ile His
            20                  25                  30

Lys Asn Gly His Val Asp Gly Ala Pro His Gln Thr Ile Tyr Ser Ala
        35                  40                  45

Leu Met Ile Arg Ser Glu Asp Ala Gly Phe Val Val Ile Thr Gly Val
    50                  55                  60

Met Ser Arg Arg Tyr Leu Cys Met Asp Phe Arg Gly Asn Ile Phe Gly
65                  70                  75                  80

Ser His Tyr Phe Asp Pro Glu Asn Cys Arg Phe Gln His Gln Thr Leu
                85                  90                  95

Glu Asn Gly Tyr Asp Val Tyr His Ser Pro Gln Tyr His Phe Leu Val
            100                 105                 110

Ser Leu Gly Arg Ala Lys Arg Ala Phe Leu Pro Gly Met Asn Pro Pro
        115                 120                 125

Pro Tyr Ser Gln Phe Leu Ser Arg Arg Asn Glu Ile Pro Leu Ile His
    130                 135                 140

Phe Asn Thr Pro Ile Pro Arg Arg His Thr Arg Ser Ala Glu Asp Asp
145                 150                 155                 160

Ser Glu Arg Asp Pro Leu Asn Val Leu Lys Pro Arg Ala Arg Met Thr
                165                 170                 175

Pro Ala Pro Ala Ser Cys Ser Gln Glu Leu Pro Ser Ala Glu Asp Asn
```

```
                180             185             190
Ser Pro Met Ala Ser Asp Pro Leu Gly Val Val Arg Gly Gly Arg Val
        195                 200                 205

Asn Thr His Ala Gly Gly Thr Gly Pro Glu Gly Cys Arg Pro Phe Ala
        210                 215                 220

Lys Phe Ile
225

<210> SEQ ID NO 43
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Tyr Pro Asn Ala Ser Pro Leu Leu Gly Ser Ser Trp Gly Gly Leu Ile
1               5                   10                  15

His Leu Tyr Thr Ala Thr Ala Arg Asn Ser Tyr His Leu Gln Ile His
            20                  25                  30

Lys Asn Gly His Val Asp Gly Ala Pro His Gln Thr Ile Tyr Ser Ala
        35                  40                  45

Leu Met Ile Arg Ser Glu Asp Ala Gly Phe Val Val Ile Thr Gly Val
50                  55                  60

Met Ser Arg Arg Tyr Leu Cys Met Asp Phe Arg Gly Asn Ile Phe Gly
65                  70                  75                  80

Ser His Tyr Phe Asp Pro Glu Asn Cys Arg Phe Gln His Gln Thr Leu
                85                  90                  95

Glu Asn Gly Tyr Asp Val Tyr His Ser Pro Gln Tyr His Phe Leu Val
            100                 105                 110

Ser Leu Gly Arg Ala Lys Arg Ala Phe Leu Pro Gly Met Asn Pro Pro
        115                 120                 125

Pro Tyr Ser Gln Phe Leu Ser Arg Arg Asn Glu Ile Pro Leu Ile His
130                 135                 140

Phe Asn Thr Pro Ile Pro Arg Arg His Thr Gln Ser Ala Glu Asp Asp
145                 150                 155                 160

Ser Glu Arg Asp Pro Leu Asn Val Leu Lys Pro Arg Ala Arg Met Thr
                165                 170                 175

Pro Ala Pro Ala Ser Cys Ser Gln Glu Leu Pro Ser Ala Glu Asp Asn
            180                 185                 190

Ser Pro Met Ala Ser Asp Pro Leu Gly Val Val Arg Gly Gly Arg Val
        195                 200                 205

Asn Thr His Ala Gly Gly Thr Gly Pro Glu Gly Cys Arg Pro Phe Ala
        210                 215                 220

Lys Phe Ile
225

<210> SEQ ID NO 44
<211> LENGTH: 982
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44
```

Met Pro Ala Ser Ala Pro Pro Arg Arg Pro Arg Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

-continued

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
            435                 440                 445

Gly Val Asp Val Ile Gly Tyr Thr Ala Trp Ser Leu Met Asp Gly Phe
            450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
            485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
            515                 520                 525

Asp Asn Tyr Ile Gln Val Asp Thr Thr Leu Ser Gln Phe Thr Asp Leu
            530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
            565                 570                 575

Ala Ile Gln Pro Gln Ile Ala Leu Leu Gln Glu Met His Val Thr His
            580                 585                 590

Phe Arg Phe Ser Leu Asp Trp Ala Leu Ile Leu Pro Leu Gly Asn Gln
            595                 600                 605

Ser Gln Val Asn His Thr Ile Leu Gln Tyr Tyr Arg Cys Met Ala Ser
610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
            645                 650                 655

Trp Glu Asn Pro Tyr Thr Ala Leu Ala Phe Ala Glu Tyr Ala Arg Leu
            660                 665                 670

Cys Phe Gln Glu Leu Gly His His Val Lys Leu Trp Ile Thr Met Asn
            675                 680                 685

Glu Pro Tyr Thr Arg Asn Met Thr Tyr Ser Ala Gly His Asn Leu Leu
            690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
            725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
            755                 760                 765

Asp Tyr Pro Trp Val Met Arg Asp Trp Leu Asn Gln Arg Asn Asn Phe
            770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
            805                 810                 815

Glu Lys Glu Asp Pro Ile Lys Tyr Asn Asp Tyr Leu Glu Val Gln Glu
            820                 825                 830

Met Thr Asp Ile Thr Trp Leu Asn Ser Pro Ser Gln Val Ala Val Val

```
                835                 840                 845

Pro Trp Gly Leu Arg Lys Val Leu Asn Trp Leu Lys Phe Lys Tyr Gly
    850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
                900                 905                 910

Phe Ala Tyr Ser Phe Asn Asp Arg Thr Ala Pro Arg Phe Gly Leu Tyr
                915                 920                 925

Arg Tyr Ala Ala Asp Gln Phe Glu Pro Lys Ala Ser Met Lys His Tyr
            930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu
                980

<210> SEQ ID NO 45
<211> LENGTH: 974
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Met Ser Val Leu Thr Gln Val Leu Ala Leu Leu Leu Trp Leu Thr
1               5                   10                  15

Gly Leu Gly Gly Arg Arg Leu Arg Ala Glu Pro Gly Asp Gly Ala Gln
            20                  25                  30

Thr Trp Ala Arg Phe Ser Arg Pro Pro Ala Pro Glu Ala Ala Gly Leu
        35                  40                  45

Phe Gln Gly Thr Phe Pro Asp Gly Phe Leu Trp Ala Val Gly Ser Ala
    50                  55                  60

Ala Tyr Gln Thr Glu Gly Gly Trp Gln Gln His Gly Lys Gly Ala Ser
65                  70                  75                  80

Ile Trp Asp Thr Phe Thr His His Pro Leu Ala Pro Pro Gly Asp Ser
                85                  90                  95

Arg Asn Ala Ser Leu Pro Leu Gly Ala Pro Ser Pro Leu Gln Pro Ala
            100                 105                 110

Thr Gly Asp Val Ala Ser Asp Ser Tyr Asn Asn Val Phe Arg Asp Thr
        115                 120                 125

Glu Ala Leu Arg Glu Leu Gly Val Thr His Tyr Arg Phe Ser Ile Ser
    130                 135                 140

Trp Ala Arg Val Leu Pro Asn Gly Ser Ala Gly Val Pro Asn Arg Glu
145                 150                 155                 160

Gly Leu Arg Tyr Tyr Arg Arg Leu Leu Glu Arg Leu Arg Glu Leu Gly
                165                 170                 175

Val Gln Pro Val Val Thr Leu Tyr His Trp Asp Leu Pro Gln Arg Leu
            180                 185                 190

Gln Asp Ala Tyr Gly Gly Trp Ala Asn Arg Ala Leu Ala Asp His Phe
        195                 200                 205
```

```
Arg Asp Tyr Ala Glu Leu Cys Phe Arg His Phe Gly Gly Gln Val Lys
    210             215                 220

Tyr Trp Ile Thr Ile Asp Asn Pro Tyr Val Val Ala Trp His Gly Tyr
225             230             235                 240

Ala Thr Gly Arg Leu Ala Pro Gly Ile Arg Gly Ser Pro Arg Leu Gly
                245             250                 255

Tyr Leu Val Ala His Asn Leu Leu Ala His Ala Lys Val Trp His
            260             265             270

Leu Tyr Asn Thr Ser Phe Arg Pro Thr Gln Gly Gly Gln Val Ser Ile
        275             280             285

Ala Leu Ser Ser His Trp Ile Asn Pro Arg Arg Met Thr Asp His Ser
    290             295             300

Ile Lys Glu Cys Gln Lys Ser Leu Asp Phe Val Leu Gly Trp Phe Ala
305             310             315                 320

Lys Pro Val Phe Ile Asp Gly Asp Tyr Pro Glu Ser Met Lys Asn Asn
                325             330             335

Leu Ser Ser Ile Leu Pro Asp Phe Thr Glu Ser Glu Lys Lys Phe Ile
            340             345             350

Lys Gly Thr Ala Asp Phe Ala Leu Cys Phe Gly Pro Thr Leu Ser
        355             360             365

Phe Gln Leu Leu Asp Pro His Met Lys Phe Arg Gln Leu Glu Ser Pro
    370             375             380

Asn Leu Arg Gln Leu Leu Ser Trp Ile Asp Leu Glu Phe Asn His Pro
385             390             395             400

Gln Ile Phe Ile Val Glu Asn Gly Trp Phe Val Ser Gly Thr Thr Lys
            405             410             415

Arg Asp Asp Ala Lys Tyr Met Tyr Tyr Leu Lys Lys Phe Ile Met Glu
                420             425             430

Thr Leu Lys Ala Ile Lys Leu Asp Gly Val Asp Val Ile Gly Tyr Thr
            435             440             445

Ala Trp Ser Leu Met Asp Gly Phe Glu Trp His Arg Gly Tyr Ser Ile
    450             455             460

Arg Arg Gly Leu Phe Tyr Val Asp Phe Leu Ser Gln Asp Lys Met Leu
465             470             475             480

Leu Pro Lys Ser Ser Ala Leu Phe Tyr Gln Lys Leu Ile Glu Lys Asn
                485             490             495

Gly Phe Pro Pro Leu Pro Glu Asn Gln Pro Leu Glu Gly Thr Phe Pro
            500             505             510

Cys Asp Phe Ala Trp Gly Val Val Asp Asn Tyr Ile Gln Val Asp Thr
            515             520             525

Thr Leu Ser Gln Phe Thr Asp Leu Asn Val Tyr Leu Trp Asp Val His
    530             535             540

His Ser Lys Arg Leu Ile Lys Val Asp Gly Val Val Thr Lys Lys Arg
545             550             555             560

Lys Ser Tyr Cys Val Asp Phe Ala Ala Ile Gln Pro Gln Ile Ala Leu
                565             570             575

Leu Gln Glu Met His Val Thr His Phe Arg Phe Ser Leu Asp Trp Ala
            580             585             590

Leu Ile Leu Pro Leu Gly Asn Gln Ser Gln Val Asn His Thr Ile Leu
        595             600             605

Gln Tyr Tyr Arg Cys Met Ala Ser Glu Leu Val Arg Val Asn Ile Thr
    610             615             620
```

Pro Val Val Ala Leu Trp Gln Pro Met Ala Pro Asn Gln Gly Leu Pro
625                 630                 635                 640

Arg Leu Leu Ala Arg Gln Gly Ala Trp Glu Asn Pro Tyr Thr Ala Leu
            645                 650                 655

Ala Phe Ala Glu Tyr Ala Arg Leu Cys Phe Gln Glu Leu Gly His His
        660                 665                 670

Val Lys Leu Trp Ile Thr Met Asn Glu Pro Tyr Thr Arg Asn Met Thr
    675                 680                 685

Tyr Ser Ala Gly His Asn Leu Leu Lys Ala His Ala Leu Ala Trp His
690                 695                 700

Val Tyr Asn Glu Lys Phe Arg His Ala Gln Asn Gly Lys Ile Ser Ile
705                 710                 715                 720

Ala Leu Gln Ala Asp Trp Ile Glu Pro Ala Cys Pro Phe Ser Gln Lys
            725                 730                 735

Asp Lys Glu Val Ala Glu Arg Val Leu Glu Phe Asp Ile Gly Trp Leu
        740                 745                 750

Ala Glu Pro Ile Phe Gly Ser Gly Asp Tyr Pro Trp Val Met Arg Asp
    755                 760                 765

Trp Leu Asn Gln Arg Asn Asn Phe Leu Leu Pro Tyr Phe Thr Glu Asp
770                 775                 780

Glu Lys Lys Leu Ile Gln Gly Thr Phe Asp Phe Leu Ala Leu Ser His
785                 790                 795                 800

Tyr Thr Thr Ile Leu Val Asp Ser Glu Lys Glu Asp Pro Ile Lys Tyr
            805                 810                 815

Asn Asp Tyr Leu Glu Val Gln Glu Met Thr Asp Ile Thr Trp Leu Asn
        820                 825                 830

Ser Pro Ser Gln Val Ala Val Val Pro Trp Gly Leu Arg Lys Val Leu
    835                 840                 845

Asn Trp Leu Lys Phe Lys Tyr Gly Asp Leu Pro Met Tyr Ile Ile Ser
850                 855                 860

Asn Gly Ile Asp Asp Gly Leu His Ala Glu Asp Gln Leu Arg Val
865                 870                 875                 880

Tyr Tyr Met Gln Asn Tyr Ile Asn Glu Ala Leu Lys Ala His Ile Leu
            885                 890                 895

Asp Gly Ile Asn Leu Cys Gly Tyr Phe Ala Tyr Ser Phe Asn Asp Arg
        900                 905                 910

Thr Ala Pro Arg Phe Gly Leu Tyr Arg Tyr Ala Ala Asp Gln Phe Glu
    915                 920                 925

Pro Lys Ala Ser Met Lys His Tyr Arg Lys Ile Ile Asp Ser Asn Gly
930                 935                 940

Phe Pro Gly Pro Glu Thr Leu Glu Arg Phe Cys Pro Glu Glu Phe Thr
945                 950                 955                 960

Val Cys Thr Glu Cys Ser Phe Phe His Thr Arg Lys Ser Leu
            965                 970

<210> SEQ ID NO 46
<211> LENGTH: 4380
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 46
atgcccgcca gcgccccgcc gcgccgcccg cggccgccgc cgccgtcgct gtcgctgctg    60

```
ctggtgctgc tgggcctggg cggccgccgc ctgcgtgcgg agccgggcga cggcgcgcag    120
acctgggccc gtttctcgcg gcctcctgcc cccgaggccg cgggcctctt ccagggcacc    180
ttccccgacg gcttcctctg ggccgtgggc agcgccgcct accagaccga gggcggctgg    240
cagcagcacg gcaagggtgc gtccatctgg gatacgttca cccaccaccc cctggcaccc    300
ccgggagact cccggaacgc cagtctgccg ttgggcgccc cgtcgccgct gcagcccgcc    360
accggggacg tagccagcga cagctacaac aacgtcttcc gcgacacgga ggcgctgcgc    420
gagctcgggg tcactcacta ccgcttctcc atctcgtggg cgcgagtgct ccccaatggc    480
agcgcgggcc tccccaaccg cgaggggctg cgctactacc ggcgcctgct ggagcggctg    540
cgggagctgg gcgtgcagcc cgtggtcacc ctgtaccact gggacctgcc ccagcgcctg    600
caggacgcct acgcggctg gccaaccgc gccctggccg accacttcag ggattacgcg    660
gagctctgct ccgccactt cggcggtcag gtcaagtact ggatcaccat cgacaacccc    720
tacgtggtgg cctggcacgg ctacgccacc gggcgcctgg cccccggcat ccggggcagc    780
ccgcggctcg ggtacctggt ggcgcacaac ctcctcctgg ctcatgccaa agtctggcat    840
ctctacaata cttctttccg tcccactcag ggaggtcagg tgtccattgc cctaagctct    900
cactggatca atcctcgaag aatgaccgac cacagcatca agaatgtca aaatctctg    960 gactttgtac taggttggtt tgccaaaccc gtatttattg atggtgacta tcccgagagc    1020
atgaagaata acctttcatc tattctgcct gattttactg aatctgagaa aagttcatc    1080 aaaggaactg ctgactttt tgctctttgc tttggaccca ccttgagttt tcaacttttg    1140
gaccctcaca tgaagttccg ccaattggaa tctcccaacc tgaggcaact gctttcctgg    1200
attgaccttg aatttaacca tcctcaaata tttattgtgg aaaatggctg gtttgtctca    1260
gggaccacca agagagatga tgccaaatat atgtattacc tcaaaaagtt catcatggaa    1320
accttaaaag ccatcaagct ggatggggtg gatgtcatcg ggtataccgc atggtccctc    1380
atggatggtt tcgagtggca cagaggttac agcatcaggc gtggactctt ctatgttgac    1440
tttctaagcc aggacaagat gttgttgcca aagtcttcag ccttgttcta ccaaaagctg    1500
atagagaaaa atggcttccc tccttttacct gaaaatcagc ccctagaagg gacatttccc    1560
tgtgactttg cttggggagt tgttgacaac tacattcaag tagataccac tctgtctcag    1620
tttaccgacc tgaatgttta cctgtgggat gtccaccaca gtaaaaggct tattaaagtg    1680 gatgggttg tgaccaagaa gaggaaatcc tactgtgttg actttgctgc catccagccc    1740
cagatcgctt tactccagga aatgcacgtt acacattttc gcttctccct ggactgggcc    1800
ctgattctcc ctctgggtaa ccagtcccag gtgaaccaca ccatcctgca gtactatcgc    1860
tgcatggcca gcgagcttgt ccgtgtcaac atcaccccag tggtggccct gtggcagcct    1920
atggccccga ccaaggact gccgcgcctc ctggccaggc agggcgcctg ggagaacccc    1980
tacactgccc tggcctttgc agagtatgcc cgactgtgct ttcaagagct cggccatcac    2040
gtcaagcttt ggataacgat gaatgagccg tatacaagga atatgacata cagtgctggc    2100
cacaaccttc tgaaggccca tgccctggct tggcatgtgt acaatgaaaa gtttaggcat    2160
gctcagaatg ggaaaatatc catagccttg caggctgatt ggatagaacc tgcctgccct    2220 ttctccccaaa aggacaaaga ggtggccgag agagttttgg aatttgacat tggctggctg    2280
gctgagccca ttttcggctc tggagattat ccatgggtga tgggactg gctgaaccaa    2340 agaaacaatt ttcttcttcc ttatttcact gaagatgaaa aaagctaat ccagggtacc    2400
```

```
tttgactttt tggctttaag ccattatacc accatccttg tagactcaga aaagaagat    2460
ccaataaaat acaatgatta cctagaagtg caagaaatga ccgacatcac gtggctcaac    2520
tcccccagtc aggtggcggt agtgccctgg gggttgcgca aagtgctgaa ctggctgaag    2580
ttcaagtacg gagacctccc catgtacata atatccaacg gaatcgatga cgggctgcat    2640
gctgaggacg accagctgag ggtgtattat atgcagaatt acataaacga agctctcaaa    2700
gcccacatac tggatggtat caatctttgc ggatactttg cttattcgtt taacgaccgc    2760
acagctccga ggtttggcct ctatcgttat gctgcagatc agtttgagcc caaggcatcc    2820
atgaaacatt acaggaaaat tattgacagc aatggtttcc cgggcccaga aactctggaa    2880
agattttgtc cagaagaatt caccgtgtgt actgagtgca gttttttttca caccgaaag    2940
tctttaggat ccggaggtgg aggttcagga ggtggaggtt caggaggtgg aggttcactt    3000
aagtatccca atgcctcccc actgctcggc tccagctggg gtggcctgat ccacctgtac    3060
acagccacag ccaggaacag ctaccacctg cagatccaca agaatggcca tgtggatggc    3120
gcaccccatc agaccatcta cagtgccctg atgatcagat cagaggatgc tggctttgtg    3180
gtgattacag gtgtgatgag cagaagatac ctctgcatgg atttcagagg caacattttt    3240
ggatcacact atttcgaccc ggagaactgc aggttccaac accagacgct ggaaaacggg    3300
tacgacgtct accactctcc tcagtatcac ttcctggtca gtctgggccg ggcgaagaga    3360
gccttcctgc caggcatgaa cccacccccg tactcccagt cctgtcccg gaggaacgag    3420
atcccctaa ttcacttcaa cacccccata ccacggcggc acccagag cgccgaggac    3480
gactcggagc gggaccccct gaacgtgctg aagccccggg cccggatgac cccggccccg    3540
gcctcctgtt cacaggagct cccgagcgcc gaggacaaca gcccgatggc cagtgaccca    3600
ttaggggtgg tcaggggcgg tcgagtgaac acgcacgctg ggggaacggg cccggaaggc    3660
tgccgcccct tcgccaagtt catcggaggt ggaggttcaa aaacccacac gtgtcctcct    3720
tgtcctgccc cagaagcagc aggtggtcca tcagtttttc ttttccctcc caaacccaag    3780
gatacgctga tgatctctcg cacgcctgag gtgacatgcg tcgtagtaga cgtgagccac    3840
gaagatcccg aggtgaagtt caattggtat gtggacggag tagaagtgca taacgcgaaa    3900
actaagccgc gcgaggaaca atataacagt acttacaggg tggtatccgt gctcacagtc    3960
ctgcaccagg actggctgaa cggtaaggaa tacaagtgca agtaagcaa caaggcactt    4020
cccgcgccta ttgagaaaac aatctccaag gcgaagggac aaccaagaga acctcaggtt    4080
tacactctcc cgccttccag ggaagagatg accaaaaatc aagtttccct gacttgcctc    4140
gtcaaaggat tctaccttc cgacattgct gttgaatggg aaagcaatgg acaaccagag    4200
aacaactaca agacaacacc cccggtgctg gatagtgacg gatctttctt tctctactca    4260
aagctgaccg tggataagtc caggtggcag cagggaaacg tgttttcctg ctctgtcatg    4320
catgaagcgc tgcataatca ctatacccag aagtctctga gcttgagccc aggcaagtaa    4380
```

<210> SEQ ID NO 47
<211> LENGTH: 1459
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 47

Met Pro Ala Ser Ala Pro Pro Arg Arg Pro Arg Pro Pro Pro Pro Ser

```
1               5                   10                  15
Leu Ser Leu Leu Leu Val Leu Leu Gly Leu Gly Gly Arg Arg Leu Arg
                20                  25                  30
Ala Glu Pro Gly Asp Gly Ala Gln Thr Trp Ala Arg Phe Ser Arg Pro
                35                  40                  45
Pro Ala Pro Glu Ala Ala Gly Leu Phe Gln Gly Thr Phe Pro Asp Gly
                50                  55                  60
Phe Leu Trp Ala Val Gly Ser Ala Ala Tyr Gln Thr Glu Gly Gly Trp
65                  70                  75                  80
Gln Gln His Gly Lys Gly Ala Ser Ile Trp Asp Thr Phe Thr His His
                85                  90                  95
Pro Leu Ala Pro Pro Gly Asp Ser Arg Asn Ala Ser Leu Pro Leu Gly
                100                 105                 110
Ala Pro Ser Pro Leu Gln Pro Ala Thr Gly Asp Val Ala Ser Asp Ser
                115                 120                 125
Tyr Asn Asn Val Phe Arg Asp Thr Glu Ala Leu Arg Glu Leu Gly Val
                130                 135                 140
Thr His Tyr Arg Phe Ser Ile Ser Trp Ala Arg Val Leu Pro Asn Gly
145                 150                 155                 160
Ser Ala Gly Val Pro Asn Arg Glu Gly Leu Arg Tyr Tyr Arg Arg Leu
                165                 170                 175
Leu Glu Arg Leu Arg Glu Leu Gly Val Gln Pro Val Val Thr Leu Tyr
                180                 185                 190
His Trp Asp Leu Pro Gln Arg Leu Gln Asp Ala Tyr Gly Gly Trp Ala
                195                 200                 205
Asn Arg Ala Leu Ala Asp His Phe Arg Asp Tyr Ala Glu Leu Cys Phe
                210                 215                 220
Arg His Phe Gly Gly Gln Val Lys Tyr Trp Ile Thr Ile Asp Asn Pro
225                 230                 235                 240
Tyr Val Val Ala Trp His Gly Tyr Ala Thr Gly Arg Leu Ala Pro Gly
                245                 250                 255
Ile Arg Gly Ser Pro Arg Leu Gly Tyr Leu Val Ala His Asn Leu Leu
                260                 265                 270
Leu Ala His Ala Lys Val Trp His Leu Tyr Asn Thr Ser Phe Arg Pro
                275                 280                 285
Thr Gln Gly Gly Gln Val Ser Ile Ala Leu Ser Ser His Trp Ile Asn
                290                 295                 300
Pro Arg Arg Met Thr Asp His Ser Ile Lys Glu Cys Gln Lys Ser Leu
305                 310                 315                 320
Asp Phe Val Leu Gly Trp Phe Ala Lys Pro Val Phe Ile Asp Gly Asp
                325                 330                 335
Tyr Pro Glu Ser Met Lys Asn Asn Leu Ser Ser Ile Leu Pro Asp Phe
                340                 345                 350
Thr Glu Ser Glu Lys Lys Phe Ile Lys Gly Thr Ala Asp Phe Phe Ala
                355                 360                 365
Leu Cys Phe Gly Pro Thr Leu Ser Phe Gln Leu Leu Asp Pro His Met
                370                 375                 380
Lys Phe Arg Gln Leu Glu Ser Pro Asn Leu Arg Gln Leu Leu Ser Trp
385                 390                 395                 400
Ile Asp Leu Glu Phe Asn His Pro Gln Ile Phe Ile Val Glu Asn Gly
                405                 410                 415
Trp Phe Val Ser Gly Thr Thr Lys Arg Asp Asp Ala Lys Tyr Met Tyr
                420                 425                 430
```

```
Tyr Leu Lys Lys Phe Ile Met Glu Thr Leu Lys Ala Ile Lys Leu Asp
        435                 440                 445
Gly Val Asp Val Ile Gly Tyr Thr Ala Trp Ser Leu Met Asp Gly Phe
    450                 455                 460
Glu Trp His Arg Gly Tyr Ser Ile Arg Arg Gly Leu Phe Tyr Val Asp
465                 470                 475                 480
Phe Leu Ser Gln Asp Lys Met Leu Leu Pro Lys Ser Ser Ala Leu Phe
                485                 490                 495
Tyr Gln Lys Leu Ile Glu Lys Asn Gly Phe Pro Pro Leu Pro Glu Asn
            500                 505                 510
Gln Pro Leu Glu Gly Thr Phe Pro Cys Asp Phe Ala Trp Gly Val Val
        515                 520                 525
Asp Asn Tyr Ile Gln Val Asp Thr Thr Leu Ser Gln Phe Thr Asp Leu
530                 535                 540
Asn Val Tyr Leu Trp Asp Val His His Ser Lys Arg Leu Ile Lys Val
545                 550                 555                 560
Asp Gly Val Val Thr Lys Lys Arg Lys Ser Tyr Cys Val Asp Phe Ala
                565                 570                 575
Ala Ile Gln Pro Gln Ile Ala Leu Leu Gln Glu Met His Val Thr His
            580                 585                 590
Phe Arg Phe Ser Leu Asp Trp Ala Leu Ile Leu Pro Leu Gly Asn Gln
        595                 600                 605
Ser Gln Val Asn His Thr Ile Leu Gln Tyr Tyr Arg Cys Met Ala Ser
    610                 615                 620
Glu Leu Val Arg Val Asn Ile Thr Pro Val Val Ala Leu Trp Gln Pro
625                 630                 635                 640
Met Ala Pro Asn Gln Gly Leu Pro Arg Leu Leu Ala Arg Gln Gly Ala
                645                 650                 655
Trp Glu Asn Pro Tyr Thr Ala Leu Ala Phe Ala Glu Tyr Ala Arg Leu
            660                 665                 670
Cys Phe Gln Glu Leu Gly His His Val Lys Leu Trp Ile Thr Met Asn
        675                 680                 685
Glu Pro Tyr Thr Arg Asn Met Thr Tyr Ser Ala Gly His Asn Leu Leu
    690                 695                 700
Lys Ala His Ala Leu Ala Trp His Val Tyr Asn Glu Lys Phe Arg His
705                 710                 715                 720
Ala Gln Asn Gly Lys Ile Ser Ile Ala Leu Gln Ala Asp Trp Ile Glu
                725                 730                 735
Pro Ala Cys Pro Phe Ser Gln Lys Asp Lys Glu Val Ala Glu Arg Val
            740                 745                 750
Leu Glu Phe Asp Ile Gly Trp Leu Ala Glu Pro Ile Phe Gly Ser Gly
        755                 760                 765
Asp Tyr Pro Trp Val Met Arg Asp Trp Leu Asn Gln Arg Asn Asn Phe
    770                 775                 780
Leu Leu Pro Tyr Phe Thr Glu Asp Glu Lys Lys Leu Ile Gln Gly Thr
785                 790                 795                 800
Phe Asp Phe Leu Ala Leu Ser His Tyr Thr Thr Ile Leu Val Asp Ser
                805                 810                 815
Glu Lys Glu Asp Pro Ile Lys Tyr Asn Asp Tyr Leu Glu Val Gln Glu
            820                 825                 830
Met Thr Asp Ile Thr Trp Leu Asn Ser Pro Ser Gln Val Ala Val Val
        835                 840                 845
```

-continued

Pro Trp Gly Leu Arg Lys Val Leu Asn Trp Leu Lys Phe Lys Tyr Gly
850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
            885                 890                 895

Glu Ala Leu Lys Ala His Ile Leu Asp Gly Ile Asn Leu Cys Gly Tyr
                900                 905                 910

Phe Ala Tyr Ser Phe Asn Asp Arg Thr Ala Pro Arg Phe Gly Leu Tyr
            915                 920                 925

Arg Tyr Ala Ala Asp Gln Phe Glu Pro Lys Ala Ser Met Lys His Tyr
930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Gly Ser Gly Gly Gly Ser Gly Gly Gly
            980                 985                 990

Gly Ser Gly Gly Gly Gly Ser Leu Lys Tyr Pro Asn Ala Ser Pro Leu
            995                 1000                1005

Leu Gly Ser Ser Trp Gly Gly Leu Ile His Leu Tyr Thr Ala Thr
1010                1015                1020

Ala Arg Asn Ser Tyr His Leu Gln Ile His Lys Asn Gly His Val
1025                1030                1035

Asp Gly Ala Pro His Gln Thr Ile Tyr Ser Ala Leu Met Ile Arg
1040                1045                1050

Ser Glu Asp Ala Gly Phe Val Val Ile Thr Gly Val Met Ser Arg
1055                1060                1065

Arg Tyr Leu Cys Met Asp Phe Arg Gly Asn Ile Phe Gly Ser His
1070                1075                1080

Tyr Phe Asp Pro Glu Asn Cys Arg Phe Gln His Gln Thr Leu Glu
1085                1090                1095

Asn Gly Tyr Asp Val Tyr His Ser Pro Gln Tyr His Phe Leu Val
1100                1105                1110

Ser Leu Gly Arg Ala Lys Arg Ala Phe Leu Pro Gly Met Asn Pro
1115                1120                1125

Pro Pro Tyr Ser Gln Phe Leu Ser Arg Arg Asn Glu Ile Pro Leu
1130                1135                1140

Ile His Phe Asn Thr Pro Ile Pro Arg Arg His Thr Gln Ser Ala
1145                1150                1155

Glu Asp Asp Ser Glu Arg Asp Pro Leu Asn Val Leu Lys Pro Arg
1160                1165                1170

Ala Arg Met Thr Pro Ala Pro Ala Ser Cys Ser Gln Glu Leu Pro
1175                1180                1185

Ser Ala Glu Asp Asn Ser Pro Met Ala Ser Asp Pro Leu Gly Val
1190                1195                1200

Val Arg Gly Gly Arg Val Asn Thr His Ala Gly Thr Gly Pro
1205                1210                1215

Glu Gly Cys Arg Pro Phe Ala Lys Phe Ile Gly Gly Gly Ser
1220                1225                1230

Lys Thr His Thr Cys Pro Pro Cys Pro Ala Pro Glu Ala Ala Gly
1235                1240                1245

Gly Pro Ser Val Phe Leu Phe Pro Pro Lys Pro Lys Asp Thr Leu

|  | 1250 |  |  |  | 1255 |  |  |  | 1260 |  |
|---|---|---|---|---|---|---|---|---|---|---|

Met Ile Ser Arg Thr Pro Glu Val Thr Cys Val Val Asp Val
    1265                    1270                1275

Ser His Glu Asp Pro Glu Val Lys Phe Asn Trp Tyr Val Asp Gly
    1280                    1285                1290

Val Glu Val His Asn Ala Lys Thr Lys Pro Arg Glu Glu Gln Tyr
    1295                    1300                1305

Asn Ser Thr Tyr Arg Val Val Ser Val Leu Thr Val Leu His Gln
    1310                    1315                1320

Asp Trp Leu Asn Gly Lys Glu Tyr Lys Cys Lys Val Ser Asn Lys
    1325                    1330                1335

Ala Leu Pro Ala Pro Ile Glu Lys Thr Ile Ser Lys Ala Lys Gly
    1340                    1345                1350

Gln Pro Arg Glu Pro Gln Val Tyr Thr Leu Pro Pro Ser Arg Glu
    1355                    1360                1365

Glu Met Thr Lys Asn Gln Val Ser Leu Thr Cys Leu Val Lys Gly
    1370                    1375                1380

Phe Tyr Pro Ser Asp Ile Ala Val Glu Trp Glu Ser Asn Gly Gln
    1385                    1390                1395

Pro Glu Asn Asn Tyr Lys Thr Thr Pro Pro Val Leu Asp Ser Asp
    1400                    1405                1410

Gly Ser Phe Phe Leu Tyr Ser Lys Leu Thr Val Asp Lys Ser Arg
    1415                    1420                1425

Trp Gln Gln Gly Asn Val Phe Ser Cys Ser Val Met His Glu Ala
    1430                    1435                1440

Leu His Asn His Tyr Thr Gln Lys Ser Leu Ser Leu Ser Pro Gly
    1445                    1450                1455

Lys

<210> SEQ ID NO 48
<211> LENGTH: 4353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 48
atgcccgcca gcgccccgcc gcgccgcccg cggccgccgc cgccgtcgct gtcgctgctg    60
ctggtgctgc tgggcctggg cggccgccgc ctgcgtgcgg agccgggcga cggcgcgcag   120
acctgggccc gtttctcgcg gcctcctgcc cccgaggccg cgggcctctt ccagggcacc   180
ttccccgacg gcttcctctg gccgtgggc agcgccgcct accagaccga gggcggctgg   240
cagcagcacg gcaagggtgc gtccatctgg gatacgttca cccaccaccc cctggcaccc   300
ccgggagact cccggaacgc cagtctgccg ttgggcgccc gtcgccgct gcagcccgcc   360 accggggacg tagccagcga cagctacaac aacgtcttcc gcgacacgga ggcgctgcgc   420
gagctcgggg tcactcacta ccgcttctcc atctcgtggg cgcgagtgct ccccaatggc   480
agcgcgggcg tccccaaccg cgaggggctg cgctactacc ggcgcctgct ggagcggctg   540
cgggagctgg gcgtgcagcc cgtggtcacc ctgtaccact gggacctgcc ccagcgcctg   600
caggacgcct acggcggctg gccaaccgc gccctggccg accacttcag ggattacgcg   660
gagctctgct tccgccactt cggcggtcag gtcaagtact ggatcaccat cgacaacccc   720

```
tacgtggtgg cctggcacgg ctacgccacc gggcgcctgg cccccggcat ccggggcagc    780
ccgcggctcg ggtacctggt ggcgcacaac ctcctcctgg ctcatgccaa agtctggcat    840
ctctacaata cttctttccg tcccactcag ggaggtcagg tgtccattgc cctaagctct    900
cactggatca atcctcgaag aatgaccgac cacagcatca agaatgtca aaaatctctg     960
gactttgtac taggttggtt tgccaaaccc gtatttattg atggtgacta tcccgagagc   1020
atgaagaata acctttcatc tattctgcct gattttactg aatctgagaa aaagttcatc   1080
aaaggaactg ctgactttt tgctctttgc tttggaccca ccttgagttt tcaacttttg    1140
gaccctcaca tgaagttccg ccaattggaa tctcccaacc tgaggcaact gctttcctgg   1200
attgaccttg aatttaacca tcctcaaata tttattgtgg aaaatggctg gtttgtctca   1260
gggaccacca agagagatga tgccaaatat atgtattacc tcaaaaagtt catcatggaa   1320
accttaaaag ccatcaagct ggatggggtg gatgtcatcg ggtataccgc atggtccctc   1380
atggatggtt tcgagtggca cagaggttac agcatcaggc gtggactctt ctatgttgac   1440
tttctaagcc aggacaagat gttgttgcca aagtcttcag ccttgttcta ccaaaagctg   1500
atagagaaaa atggcttccc tcctttacct gaaaatcagc ccctagaagg gacatttccc   1560
tgtgactttg cttggggagt tgttgacaac tacattcaag tagataccac tctgtctcag   1620
tttaccgacc tgaatgttta cctgtgggat gtccaccaca gtaaaaggct tattaaagtg   1680
gatggggttg tgaccaagaa gaggaaatcc tactgtgttg actttgctgc catccagccc   1740
cagatcgctt tactccagga aatgcacgtt acacattttc gcttctccct ggactgggcc   1800
ctgattctcc ctctgggtaa ccagtcccag gtgaaccaca ccatcctgca gtactatcgc   1860
tgcatggcca gcgagcttgt ccgtgtcaac atcaccccag tggtggccct gtggcagcct   1920
atggccccga accaaggact gccgcgcctc ctggccaggc agggcgcctg ggagaacccc   1980
tacactgccc tggcctttgc agagtatgcc cgactgtgct ttcaagagct cggccatcac   2040
gtcaagcttt ggataacgat gaatgagccg tatacaagga atatgacata cagtgctggc   2100
cacaaccttc tgaaggccca tgccctggct tggcatgtgt acaatgaaaa gtttaggcat   2160
gctcagaatg ggaaaatatc catagccttg caggctgatt ggatagaacc tgcctgccct   2220
ttctcccaaa aggacaaaga ggtggccgag agagttttgg aatttgacat tggctggctg   2280
gctgagccca ttttcggctc tggagattat ccatgggtga tgagggactg gctgaaccaa   2340
agaaacaatt ttcttcttcc ttatttcact gaagatgaaa aaaagctaat ccagggtacc   2400
tttgactttt tggcttttaag ccattatacc accatccttg tagactcaga aaaagaagat   2460
ccaataaaat acaatgatta cctagaagtg caagaaatga ccgacatcac gtggctcaac   2520
tcccccagtc aggtggcggt agtgccctgg ggggttgcgca aagtgctgaa ctggctgaag   2580
ttcaagtacg agagacctccc catgtacata atatccaacg gaatcgatga cgggctgcat   2640
gctgaggacg accagctgag ggtgtattat atgcagaatt acataaacga agctctcaaa   2700
gcccacatac tggatggtat caatctttgc ggatactttg cttattcgtt taacgaccgc   2760
acagctccga ggtttggcct ctatcgttat gctgcagatc agtttgagcc caaggcatcc   2820
atgaaacatt acaggaaaat tattgacagc aatggttttcc cgggcccaga aactctggaa   2880
agattttgtc cagaagaatt caccgtgtgt actgagtgca gttttttttca caccccgaaag   2940
tctttaggat ccggaggtgg aggttcagga ggtggaggtt caggaggtgg aggttcactt   3000
aagtatccca tgcctccccc actgctcggc tccagctggg gtggcctgat ccacctgtac   3060
acagccacag ccaggaacag ctaccacctg cagatccaca agaatggcca tgtggatggc   3120
```

```
gcaccccatc agaccatcta cagtgccctg atgatcagat cagaggatgc tggctttgtg    3180
gtgattacag gtgtgatgag cagaagatac ctctgcatgg atttcagagg caacattttt    3240
ggatcacact atttcgaccc ggagaactgc aggttccaac accagacgct ggaaaacggg    3300
tacgacgtct accactctcc tcagtatcac ttcctggtca gtctgggccg ggcgaagaga    3360
gccttcctgc caggcatgaa cccacccccg tactcccagt tcctgtcccg gaggaacgag    3420 atcccectaa ttcacttcaa cacccccata ccacggcggc acaccagag cgccgaggac    3480 gactcggagc gggaccccct gaacgtgctg aagccccggg cccggatgac cccggccccg    3540
gcctcctgtt cacaggagct cccgagcgcc gaggacaaca gcccgatggc cagtgaccca    3600
ttaggggtgg tcaggggcgg tcgagtgaac acgcacgctg ggggaacggg cccggaaggc    3660
tgccgcccct tcgccaagtt catcggaggt ggaggttcag ccccagaagc agcaggtggt    3720
ccatcagttt ttctttttccc tcccaaaccc aaggatacgc tgatgatctc tcgcacgcct    3780
gaggtgacat gcgtcgtagt agacgtgagc acgaagatc ccgaggtgaa gttcaattgg    3840
tatgtggacg gagtagaagt gcataacgcg aaaactaagc cgcgcgagga acaatataac    3900
agtacttaca gggtggtatc cgtgctcaca gtcctgcacc aggactggct gaacggtaag    3960
gaatacaagt gcaaagtaag caacaaggca cttcccgcgc ctattgagaa aacaatctcc    4020
aaggcgaagg gacaaccaag agaacctcag gtttacactc tcccgccttc cagggaagag    4080
atgaccaaaa atcaagtttc cctgacttgc ctcgtcaaag gattctaccc ttccgacatt    4140
gctgttgaat gggaaagcaa tggacaacca gagacaact acaagacaac accccggtg    4200 ctggatagtg acggatcttt ctttctctac tcaaagctga ccgtggataa gtccaggtgg    4260
cagcagggaa acgtgttttc ctgctctgtc atgcatgaag cgctgcataa tcactatacc    4320
cagaagtctc tgagcttgag cccaggcaag taa                                 4353
```

<210> SEQ ID NO 49
<211> LENGTH: 1450
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 49

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

```
Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
        515                 520                 525

Asp Asn Tyr Ile Gln Val Asp Thr Thr Leu Ser Gln Phe Thr Asp Leu
530                 535                 540

Asn Val Tyr Leu Trp Asp Val His His Ser Lys Arg Leu Ile Lys Val
```

```
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
                580                 585                 590

Phe Arg Phe Ser Leu Asp Trp Ala Leu Ile Leu Pro Leu Gly Asn Gln
                595                 600                 605

Ser Gln Val Asn His Thr Ile Leu Gln Tyr Tyr Arg Cys Met Ala Ser
    610                 615                 620

Glu Leu Val Arg Val Asn Ile Thr Pro Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
                660                 665                 670

Cys Phe Gln Glu Leu Gly His His Val Lys Leu Trp Ile Thr Met Asn
            675                 680                 685

Glu Pro Tyr Thr Arg Asn Met Thr Tyr Ser Ala Gly His Asn Leu Leu
        690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
        755                 760                 765

Asp Tyr Pro Trp Val Met Arg Asp Trp Leu Asn Gln Arg Asn Asn Phe
    770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
            805                 810                 815

Glu Lys Glu Asp Pro Ile Lys Tyr Asn Asp Tyr Leu Glu Val Gln Glu
        820                 825                 830

Met Thr Asp Ile Thr Trp Leu Asn Ser Pro Ser Gln Val Ala Val Val
    835                 840                 845

Pro Trp Gly Leu Arg Lys Val Leu Asn Trp Leu Lys Phe Lys Tyr Gly
850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
    930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
            965                 970                 975
```

-continued

```
His Thr Arg Lys Ser Leu Gly Ser Gly Gly Gly Ser Gly Gly Gly
            980             985             990

Gly Ser Gly Gly Gly Gly Ser Leu Lys Tyr Pro Asn Ala Ser Pro Leu
        995             1000            1005

Leu Gly Ser Ser Trp Gly Gly Leu Ile His Leu Tyr Thr Ala Thr
    1010            1015            1020

Ala Arg Asn Ser Tyr His Leu Gln Ile His Lys Asn Gly His Val
    1025            1030            1035

Asp Gly Ala Pro His Gln Thr Ile Tyr Ser Ala Leu Met Ile Arg
    1040            1045            1050

Ser Glu Asp Ala Gly Phe Val Val Ile Thr Gly Val Met Ser Arg
    1055            1060            1065

Arg Tyr Leu Cys Met Asp Phe Arg Gly Asn Ile Phe Gly Ser His
    1070            1075            1080

Tyr Phe Asp Pro Glu Asn Cys Arg Phe Gln His Gln Thr Leu Glu
    1085            1090            1095

Asn Gly Tyr Asp Val Tyr His Ser Pro Gln Tyr His Phe Leu Val
    1100            1105            1110

Ser Leu Gly Arg Ala Lys Arg Ala Phe Leu Pro Gly Met Asn Pro
    1115            1120            1125

Pro Pro Tyr Ser Gln Phe Leu Ser Arg Arg Asn Glu Ile Pro Leu
    1130            1135            1140

Ile His Phe Asn Thr Pro Ile Pro Arg Arg His Thr Gln Ser Ala
    1145            1150            1155

Glu Asp Asp Ser Glu Arg Asp Pro Leu Asn Val Leu Lys Pro Arg
    1160            1165            1170

Ala Arg Met Thr Pro Ala Pro Ala Ser Cys Ser Gln Glu Leu Pro
    1175            1180            1185

Ser Ala Glu Asp Asn Ser Pro Met Ala Ser Asp Pro Leu Gly Val
    1190            1195            1200

Val Arg Gly Gly Arg Val Asn Thr His Ala Gly Gly Thr Gly Pro
    1205            1210            1215

Glu Gly Cys Arg Pro Phe Ala Lys Phe Ile Gly Gly Gly Gly Ser
    1220            1225            1230

Ala Pro Glu Ala Ala Gly Gly Pro Ser Val Phe Leu Phe Pro Pro
    1235            1240            1245

Lys Pro Lys Asp Thr Leu Met Ile Ser Arg Thr Pro Glu Val Thr
    1250            1255            1260

Cys Val Val Val Asp Val Ser His Glu Asp Pro Glu Val Lys Phe
    1265            1270            1275

Asn Trp Tyr Val Asp Gly Val Glu Val His Asn Ala Lys Thr Lys
    1280            1285            1290

Pro Arg Glu Glu Gln Tyr Asn Ser Thr Tyr Arg Val Val Ser Val
    1295            1300            1305

Leu Thr Val Leu His Gln Asp Trp Leu Asn Gly Lys Glu Tyr Lys
    1310            1315            1320

Cys Lys Val Ser Asn Lys Ala Leu Pro Ala Pro Ile Glu Lys Thr
    1325            1330            1335

Ile Ser Lys Ala Lys Gly Gln Pro Arg Glu Pro Gln Val Tyr Thr
    1340            1345            1350

Leu Pro Pro Ser Arg Glu Glu Met Thr Lys Asn Gln Val Ser Leu
    1355            1360            1365
```

```
Thr Cys Leu Val Lys Gly Phe Tyr Pro Ser Asp Ile Ala Val Glu
    1370            1375                1380

Trp Glu Ser Asn Gly Gln Pro Glu Asn Asn Tyr Lys Thr Thr Pro
    1385                1390                1395

Pro Val Leu Asp Ser Asp Gly Ser Phe Phe Leu Tyr Ser Lys Leu
    1400                1405                1410

Thr Val Asp Lys Ser Arg Trp Gln Gln Gly Asn Val Phe Ser Cys
    1415                1420                1425

Ser Val Met His Glu Ala Leu His Asn His Tyr Thr Gln Lys Ser
    1430                1435                1440

Leu Ser Leu Ser Pro Gly Lys
    1445                1450
```

<210> SEQ ID NO 50
<211> LENGTH: 1449
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 50

```
atgttggggg cccgcctcag gctctgggtc tgtgccttgt gcagcgtctg cagcatgagc      60
gtcctcagag cctatcccaa tgcctcccca ctgctcggct ccagctgggg tggcctgatc     120
cacctgtaca gccacagc caggaacagc taccacctgc agatccacaa gaatggccat      180
gtggatggcg caccccatca gaccatctac agtgccctga tgatcagatc agaggatgct     240
ggctttgtgg tgattacagg tgtgatgagc agaagatacc tctgcatgga tttcagaggc     300
aacattttg gatcacacta tttcgacccg gagaactgca ggttccaaca ccagacgctg     360
gaaaacgggt acgacgtcta ccactctcct cagtatcact tcctggtcag tctgggccgg     420
gcgaagagag ccttcctgcc aggcatgaac ccaccccgt actcccagtt cctgtcccgg     480
aggaacgaga tccccctaat tcacttcaac acccccatac acggcggca cacccagagc     540
gccgaggacg actcggagcg ggacccctg aacgtgctga gccccgggc ccggatgacc      600
ccggccccgg cctcctgttc acaggagctc ccgagcgccg aggacaacag cccgatggcc     660
agtgacccat taggggtggt caggggcggt cgagtgaaca cgcacgctgg gggaacgggc     720
ccggaaggct gccgccctt cgccaagttc atcggaggtg gaggttcaaa acccacacg      780
tgtcctcctt gtcctgcccc agaagcagca ggtggtccat cagttttct tttccctccc     840
aaacccaagg atacgctgat gatctctcgc acgcctgagg tgacatgcgt cgtagtagac     900
gtgagccacg aagatcccga ggtgaagttc aattggtatg tggacggagt agaagtgcat     960
aacgcgaaaa ctaagccgcg cgaggaacaa tataacagta cttacagggt ggtatccgtg    1020
ctcacagtcc tgcaccagga ctggctgaac ggtaaggaat acaagtgcaa agtaagcaac    1080
aaggcacttc ccgcgcctat tgagaaaaca atctccaagg cgaagggaca accaagagaa    1140
cctcaggttt acactctccc gccttccagg gaagagatga ccaaaaatca gtttccctg    1200
acttgcctcg tcaaaggatt ctaccctttcc gacattgctg ttgaatggga agcaatgga    1260
caaccagaga caactacaa gacaacaccc ccggtgctgg atagtgacgg atctttcttt    1320
ctctactcaa agctgaccgt ggataagtcc aggtggcagc agggaaacgt gttttcctgc    1380
tctgtcatgc atgaagcgct gcataatcac tatacccaga gtctctgag cttgagccca    1440
ggcaagtaa                                                           1449
```

<210> SEQ ID NO 51
<211> LENGTH: 482
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 51

```
Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile Gly Gly Gly Gly Ser
                245                 250                 255

Lys Thr His Thr Cys Pro Pro Cys Pro Ala Pro Glu Ala Ala Gly Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350
```

```
Glu Tyr Lys Cys Lys Val Ser Asn Lys Ala Leu Pro Ala Pro Ile Glu
            355                 360                 365
Lys Thr Ile Ser Lys Ala Lys Gly Gln Pro Arg Glu Pro Gln Val Tyr
    370                 375                 380
Thr Leu Pro Pro Ser Arg Glu Glu Met Thr Lys Asn Gln Val Ser Leu
385                 390                 395                 400
Thr Cys Leu Val Lys Gly Phe Tyr Pro Ser Asp Ile Ala Val Glu Trp
                405                 410                 415
Glu Ser Asn Gly Gln Pro Glu Asn Asn Tyr Lys Thr Thr Pro Pro Val
            420                 425                 430
Leu Asp Ser Asp Gly Ser Phe Phe Leu Tyr Ser Lys Leu Thr Val Asp
        435                 440                 445
Lys Ser Arg Trp Gln Gln Gly Asn Val Phe Ser Cys Ser Val Met His
    450                 455                 460
Glu Ala Leu His Asn His Tyr Thr Gln Lys Ser Leu Ser Leu Ser Pro
465                 470                 475                 480
Gly Lys
```

<210> SEQ ID NO 52
<211> LENGTH: 1422
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 52

```
atgttggggg cccgcctcag gctctgggtc tgtgccttgt gcagcgtctg cagcatgagc      60
gtcctcagag cctatcccaa tgcctcccca ctgctcggct ccagctgggg tggcctgatc     120
cacctgtaca gccacagc caggaacagc taccacctgc agatccacaa gaatggccat      180
gtggatggcg caccccatca gaccatctac agtgccctga tgatcagatc agaggatgct     240
ggctttgtgg tgattacagg tgtgatgagc agaagatacc tctgcatgga tttcagaggc     300
aacatttttg gatcacacta tttcgacccg gagaactgca ggttccaaca ccagacgctg     360
gaaaacgggt acgacgtcta ccactctcct cagtatcact tcctggtcag tctgggccgg     420
gcgaagagag ccttcctgcc aggcatgaac ccaccccgt actcccagtt cctgtcccgg     480
aggaacgaga tccccctaat tcacttcaac acccccatac acggcggca cacccagagc     540
gccgaggacg actcggagcg ggaccccctg aacgtgctga gccccgggc ccggatgacc     600
ccggccccgg cctcctgttc acaggagctc ccgagcgccg aggacaacag cccgatggcc     660
agtgacccat tagggtggt caggggcggt cgagtgaaca cgcacgctgg gggaacgggc     720
ccggaaggct gccgccctt cgccaagttc atcggaggtg gaggttcagc cccagaagca     780
gcaggtggtc catcagtttt tctttcccct cccaaaccca aggatacgct gatgatctct     840
cgcacgcctg aggtgacatg cgtcgtagta gacgtgagcc acgaagatcc cgaggtgaag     900
ttcaattggt atgtggacgg agtagaagtg cataacgcga aaactaagcc gcgcgaggaa     960
caatataaca gtacttacag ggtggtatcc gtgctcacag tcctgcacca ggactggctg    1020
aacggtaagg aatacaagtg caaagtaagc aacaaggcac ttcccgcgcc tattgagaaa    1080
acaatctcca aggcgaaggg acaaccaaga gaacctcagg tttacactct cccgccttcc    1140
agggaagaga tgaccaaaaa tcaagttttc ctgacttgcc tcgtcaaagg attctaccct    1200
tccgacattg ctgttgaatg ggaaagcaat ggacaaccag agaacaacta caagacaaca    1260
```

-continued

```
cccccggtgc tggatagtga cggatctttc tttctctact caaagctgac cgtggataag    1320
tccaggtggc agcagggaaa cgtgttttcc tgctctgtca tgcatgaagc gctgcataat    1380
cactataccc agaagtctct gagcttgagc ccaggcaagt aa                        1422
```

<210> SEQ ID NO 53
<211> LENGTH: 473
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 53

```
Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile Gly Gly Gly Ser
                245                 250                 255

Ala Pro Glu Ala Ala Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320
```

```
Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470

<210> SEQ ID NO 54
<211> LENGTH: 1228
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65              70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
```

```
                195                 200                 205
Asn Arg Ala Leu Ala Asp His Phe Arg Asp Tyr Ala Glu Leu Cys Phe
            210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
            275                 280                 285

Thr Gln Gly Gly Gln Val Ser Ile Ala Leu Ser Ser His Trp Ile Asn
            290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
            355                 360                 365

Leu Cys Phe Gly Pro Thr Leu Ser Phe Gln Leu Leu Asp Pro His Met
370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
            435                 440                 445

Gly Val Asp Val Ile Gly Tyr Thr Ala Trp Ser Leu Met Asp Gly Phe
450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
            515                 520                 525

Asp Asn Tyr Ile Gln Val Asp Thr Thr Leu Ser Gln Phe Thr Asp Leu
            530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
            580                 585                 590

Phe Arg Phe Ser Leu Asp Trp Ala Leu Ile Leu Pro Leu Gly Asn Gln
            595                 600                 605

Ser Gln Val Asn His Thr Ile Leu Gln Tyr Tyr Arg Cys Met Ala Ser
            610                 615                 620
```

```
Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
            660                 665                 670

Cys Phe Gln Glu Leu Gly His His Val Lys Leu Trp Ile Thr Met Asn
        675                 680                 685

Glu Pro Tyr Thr Arg Asn Met Thr Tyr Ser Ala Gly His Asn Leu Leu
    690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
        755                 760                 765

Asp Tyr Pro Trp Val Met Arg Asp Trp Leu Asn Gln Arg Asn Asn Phe
    770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
            820                 825                 830

Met Thr Asp Ile Thr Trp Leu Asn Ser Pro Ser Gln Val Ala Val Val
        835                 840                 845

Pro Trp Gly Leu Arg Lys Val Leu Asn Trp Leu Lys Phe Lys Tyr Gly
    850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
    930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Gly Ser Gly Gly Gly Ser Gly Gly Gly
            980                 985                 990

Gly Ser Gly Gly Gly Gly Ser Leu Lys Tyr Pro Asn Ala Ser Pro Leu
        995                 1000                1005

Leu Gly Ser Ser Trp Gly Gly Leu Ile His Leu Tyr Thr Ala Thr
        1010                1015                1020

Ala Arg Asn Ser Tyr His Leu Gln Ile His Lys Asn Gly His Val
        1025                1030                1035
```

-continued

```
Asp Gly Ala Pro His Gln Thr Ile Tyr Ser Ala Leu Met Ile Arg
    1040                1045                1050

Ser Glu Asp Ala Gly Phe Val Val Ile Thr Gly Val Met Ser Arg
    1055                1060                1065

Arg Tyr Leu Cys Met Asp Phe Arg Gly Asn Ile Phe Gly Ser His
    1070                1075                1080

Tyr Phe Asp Pro Glu Asn Cys Arg Phe Gln His Gln Thr Leu Glu
    1085                1090                1095

Asn Gly Tyr Asp Val Tyr His Ser Pro Gln Tyr His Phe Leu Val
    1100                1105                1110

Ser Leu Gly Arg Ala Lys Arg Ala Phe Leu Pro Gly Met Asn Pro
    1115                1120                1125

Pro Pro Tyr Ser Gln Phe Leu Ser Arg Arg Asn Glu Ile Pro Leu
    1130                1135                1140

Ile His Phe Asn Thr Pro Ile Pro Arg Arg His Thr Gln Ser Ala
    1145                1150                1155

Glu Asp Asp Ser Glu Arg Asp Pro Leu Asn Val Leu Lys Pro Arg
    1160                1165                1170

Ala Arg Met Thr Pro Ala Pro Ala Ser Ser Ser Gln Glu Leu Pro
    1175                1180                1185

Ser Ala Glu Asp Asn Ser Pro Met Ala Ser Asp Pro Leu Gly Val
    1190                1195                1200

Val Arg Gly Gly Arg Val Asn Thr His Ala Gly Gly Thr Gly Pro
    1205                1210                1215

Glu Gly Cys Arg Pro Phe Ala Lys Phe Ile
    1220                1225
```

<210> SEQ ID NO 55
<211> LENGTH: 1228
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 55

```
Met Pro Ala Ser Ala Pro Pro Arg Arg Pro Arg Pro Pro Pro Ser
1               5                   10                  15

Leu Ser Leu Leu Leu Val Leu Leu Gly Leu Gly Gly Arg Arg Leu Arg
                20                  25                  30

Ala Glu Pro Gly Asp Gly Ala Gln Thr Trp Ala Arg Phe Ser Arg Pro
                35                  40                  45

Pro Ala Pro Glu Ala Ala Gly Leu Phe Gln Gly Thr Phe Pro Asp Gly
            50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
                100                 105                 110

Ala Pro Ser Pro Leu Gln Pro Ala Thr Gly Asp Val Ala Ser Asp Ser
            115                 120                 125

Tyr Asn Asn Val Phe Arg Asp Thr Glu Ala Leu Arg Glu Leu Gly Val
            130                 135                 140

Thr His Tyr Arg Phe Ser Ile Ser Trp Ala Arg Val Leu Pro Asn Gly
```

-continued

```
            145                 150                 155                 160
Ser Ala Gly Val Pro Asn Arg Glu Gly Leu Arg Tyr Tyr Arg Arg Leu
                165                 170                 175
Leu Glu Arg Leu Arg Glu Leu Gly Val Gln Pro Val Val Thr Leu Tyr
                180                 185                 190
His Trp Asp Leu Pro Gln Arg Leu Gln Asp Ala Tyr Gly Gly Trp Ala
                195                 200                 205
Asn Arg Ala Leu Ala Asp His Phe Arg Asp Tyr Ala Glu Leu Cys Phe
            210                 215                 220
Arg His Phe Gly Gly Gln Val Lys Tyr Trp Ile Thr Ile Asp Asn Pro
225                 230                 235                 240
Tyr Val Val Ala Trp His Gly Tyr Ala Thr Gly Arg Leu Ala Pro Gly
                245                 250                 255
Ile Arg Gly Ser Pro Arg Leu Gly Tyr Leu Val Ala His Asn Leu Leu
                260                 265                 270
Leu Ala His Ala Lys Val Trp His Leu Tyr Asn Thr Ser Phe Arg Pro
            275                 280                 285
Thr Gln Gly Gly Gln Val Ser Ile Ala Leu Ser Ser His Trp Ile Asn
        290                 295                 300
Pro Arg Arg Met Thr Asp His Ser Ile Lys Glu Cys Gln Lys Ser Leu
305                 310                 315                 320
Asp Phe Val Leu Gly Trp Phe Ala Lys Pro Val Phe Ile Asp Gly Asp
                325                 330                 335
Tyr Pro Glu Ser Met Lys Asn Asn Leu Ser Ser Ile Leu Pro Asp Phe
                340                 345                 350
Thr Glu Ser Glu Lys Lys Phe Ile Lys Gly Thr Ala Asp Phe Phe Ala
            355                 360                 365
Leu Cys Phe Gly Pro Thr Leu Ser Phe Gln Leu Asp Pro His Met
        370                 375                 380
Lys Phe Arg Gln Leu Glu Ser Pro Asn Leu Arg Gln Leu Leu Ser Trp
385                 390                 395                 400
Ile Asp Leu Glu Phe Asn His Pro Gln Ile Phe Ile Val Glu Asn Gly
                405                 410                 415
Trp Phe Val Ser Gly Thr Thr Lys Arg Asp Asp Ala Lys Tyr Met Tyr
                420                 425                 430
Tyr Leu Lys Lys Phe Ile Met Glu Thr Leu Lys Ala Ile Lys Leu Asp
            435                 440                 445
Gly Val Asp Val Ile Gly Tyr Thr Ala Trp Ser Leu Met Asp Gly Phe
        450                 455                 460
Glu Trp His Arg Gly Tyr Ser Ile Arg Arg Gly Leu Phe Tyr Val Asp
465                 470                 475                 480
Phe Leu Ser Gln Asp Lys Met Leu Leu Pro Lys Ser Ser Ala Leu Phe
                485                 490                 495
Tyr Gln Lys Leu Ile Glu Lys Asn Gly Phe Pro Pro Leu Pro Glu Asn
                500                 505                 510
Gln Pro Leu Glu Gly Thr Phe Pro Cys Asp Phe Ala Trp Gly Val Val
            515                 520                 525
Asp Asn Tyr Ile Gln Val Asp Thr Thr Leu Ser Gln Phe Thr Asp Leu
        530                 535                 540
Asn Val Tyr Leu Trp Asp Val His His Ser Lys Arg Leu Ile Lys Val
545                 550                 555                 560
Asp Gly Val Val Thr Lys Lys Arg Lys Ser Tyr Cys Val Asp Phe Ala
                565                 570                 575
```

```
Ala Ile Gln Pro Gln Ile Ala Leu Leu Gln Glu Met His Val Thr His
            580                 585                 590

Phe Arg Phe Ser Leu Asp Trp Ala Leu Ile Leu Pro Leu Gly Asn Gln
        595                 600                 605

Ser Gln Val Asn His Thr Ile Leu Gln Tyr Tyr Arg Cys Met Ala Ser
    610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
            660                 665                 670

Cys Phe Gln Glu Leu Gly His His Val Lys Leu Trp Ile Thr Met Asn
        675                 680                 685

Glu Pro Tyr Thr Arg Asn Met Thr Tyr Ser Ala Gly His Asn Leu Leu
    690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
        755                 760                 765

Asp Tyr Pro Trp Val Met Arg Asp Trp Leu Asn Gln Arg Asn Asn Phe
    770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
            820                 825                 830

Met Thr Asp Ile Thr Trp Leu Asn Ser Pro Ser Gln Val Ala Val Val
        835                 840                 845

Pro Trp Gly Leu Arg Lys Val Leu Asn Trp Leu Lys Phe Lys Tyr Gly
    850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
    930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Gly Ser Gly Gly Gly Ser Gly Gly Gly Gly
            980                 985                 990
```

```
Gly Ser Gly Gly Gly Gly Ser Leu Lys Tyr Pro Asn Ala Ser Pro Leu
            995                 1000                1005

Leu Gly Ser Ser Trp Gly Gly Leu Ile His Leu Tyr Thr Ala Thr
        1010                1015                1020

Ala Arg Asn Ser Tyr His Leu Gln Ile His Lys Asn Gly His Val
        1025                1030                1035

Asp Gly Ala Pro His Gln Thr Ile Tyr Ser Ala Leu Met Ile Arg
        1040                1045                1050

Ser Glu Asp Ala Gly Phe Val Val Ile Thr Gly Val Met Ser Arg
        1055                1060                1065

Arg Tyr Leu Cys Met Asp Phe Arg Gly Asn Ile Phe Gly Ser His
        1070                1075                1080

Tyr Phe Asp Pro Glu Asn Cys Arg Phe Gln His Gln Thr Leu Glu
        1085                1090                1095

Asn Gly Tyr Asp Val Tyr His Ser Pro Gln Tyr His Phe Leu Val
        1100                1105                1110

Ser Leu Gly Arg Ala Lys Arg Ala Phe Leu Pro Gly Met Asn Pro
        1115                1120                1125

Pro Pro Tyr Ser Gln Phe Leu Ser Arg Arg Asn Glu Ile Pro Leu
        1130                1135                1140

Ile His Phe Asn Thr Pro Ile Pro Arg Arg His Thr Gln Ser Ala
        1145                1150                1155

Glu Asp Asp Ser Glu Arg Asp Pro Leu Asn Val Leu Lys Pro Arg
        1160                1165                1170

Ala Arg Met Thr Pro Ala Pro Ala Ser Cys Ser Gln Glu Leu Pro
        1175                1180                1185

Ser Ala Glu Asp Asn Ser Pro Met Ala Ser Asp Pro Leu Gly Val
        1190                1195                1200

Val Arg Gly Gly Arg Val Asn Thr His Ala Gly Gly Thr Gly Pro
        1205                1210                1215

Glu Gly Ser Arg Pro Phe Ala Lys Phe Ile
        1220                1225

<210> SEQ ID NO 56
<211> LENGTH: 1228
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Met Pro Ala Ser Ala Pro Pro Arg Arg Pro Arg Pro Pro Pro Ser
1               5                   10                  15

Leu Ser Leu Leu Leu Val Leu Leu Gly Leu Gly Gly Arg Arg Leu Arg
                20                  25                  30

Ala Glu Pro Gly Asp Gly Ala Gln Thr Trp Ala Arg Phe Ser Arg Pro
            35                  40                  45

Pro Ala Pro Glu Ala Ala Gly Leu Phe Gln Gly Thr Phe Pro Asp Gly
        50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
```

-continued

Ala Pro Ser Pro Leu Gln Pro Ala Thr Gly Asp Val Ala Ser Asp Ser
100              105                 110                 115

Tyr Asn Asn Val Phe Arg Asp Thr Glu Ala Leu Arg Glu Leu Gly Val
    120                 125                 130                 135 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
    450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
        515                 520                 525

```
Asp Asn Tyr Ile Gln Val Asp Thr Thr Leu Ser Gln Phe Thr Asp Leu
    530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
                580                 585                 590

Phe Arg Phe Ser Leu Asp Trp Ala Leu Ile Leu Pro Leu Gly Asn Gln
        595                 600                 605

Ser Gln Val Asn His Thr Ile Leu Gln Tyr Tyr Arg Cys Met Ala Ser
    610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
                660                 665                 670

Cys Phe Gln Glu Leu Gly His His Val Lys Leu Trp Ile Thr Met Asn
                675                 680                 685

Glu Pro Tyr Thr Arg Asn Met Thr Tyr Ser Ala Gly His Asn Leu Leu
    690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
                740                 745                 750

Leu Glu Phe Asp Ile Gly Trp Leu Ala Glu Pro Ile Phe Gly Ser Gly
                755                 760                 765

Asp Tyr Pro Trp Val Met Arg Asp Trp Leu Asn Gln Arg Asn Asn Phe
    770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
                820                 825                 830

Met Thr Asp Ile Thr Trp Leu Asn Ser Pro Ser Gln Val Ala Val Val
            835                 840                 845

Pro Trp Gly Leu Arg Lys Val Leu Asn Trp Leu Lys Phe Lys Tyr Gly
850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
                900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
    930                 935                 940
```

```
Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Gly Ser Gly Gly Gly Ser Gly Gly Gly
            980                 985                 990

Gly Ser Gly Gly Gly Gly Ser Leu Lys Tyr Pro Asn Ala Ser Pro Leu
        995                 1000                1005

Leu Gly Ser Ser Trp Gly Gly Leu Ile His Leu Tyr Thr Ala Thr
    1010                1015                1020

Ala Arg Asn Ser Tyr His Leu Gln Ile His Lys Asn Gly His Val
    1025                1030                1035

Asp Gly Ala Pro His Gln Thr Ile Tyr Ser Ala Leu Met Ile Arg
    1040                1045                1050

Ser Glu Asp Ala Gly Phe Val Val Ile Thr Gly Val Met Ser Arg
    1055                1060                1065

Arg Tyr Leu Cys Met Asp Phe Arg Gly Asn Ile Phe Gly Ser His
    1070                1075                1080

Tyr Phe Asp Pro Glu Asn Cys Arg Phe Gln His Gln Thr Leu Glu
    1085                1090                1095

Asn Gly Tyr Asp Val Tyr His Ser Pro Gln Tyr His Phe Leu Val
    1100                1105                1110

Ser Leu Gly Arg Ala Lys Arg Ala Phe Leu Pro Gly Met Asn Pro
    1115                1120                1125

Pro Pro Tyr Ser Ala Phe Leu Ser Arg Arg Asn Glu Ile Pro Leu
    1130                1135                1140

Ile His Phe Asn Thr Pro Ile Pro Arg Arg His Thr Gln Ser Ala
    1145                1150                1155

Glu Asp Asp Ser Glu Arg Asp Pro Leu Asn Val Leu Lys Pro Arg
    1160                1165                1170

Ala Arg Met Thr Pro Ala Pro Ala Ser Cys Ser Gln Glu Leu Pro
    1175                1180                1185

Ser Ala Glu Asp Asn Ser Pro Met Ala Ser Asp Pro Leu Gly Val
    1190                1195                1200

Val Arg Gly Gly Arg Val Asn Thr His Ala Gly Thr Gly Pro
    1205                1210                1215

Glu Gly Cys Arg Pro Phe Ala Lys Phe Ile
    1220                1225
```

<210> SEQ ID NO 57
<211> LENGTH: 1228
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 57

```
Met Pro Ala Ser Ala Pro Pro Arg Arg Pro Arg Pro Pro Pro Ser
1               5                   10                  15

Leu Ser Leu Leu Leu Val Leu Leu Gly Leu Gly Gly Arg Arg Leu Arg
                20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
```

```
            50                  55                  60
Phe Leu Trp Ala Val Gly Ser Ala Ala Tyr Gln Thr Glu Gly Gly Trp
 65                  70                  75                  80

Gln Gln His Gly Lys Gly Ala Ser Ile Trp Asp Thr Phe Thr His His
                 85                  90                  95

Pro Leu Ala Pro Pro Gly Asp Ser Arg Asn Ala Ser Leu Pro Leu Gly
                100                 105                 110

Ala Pro Ser Pro Leu Gln Pro Ala Thr Gly Asp Val Ala Ser Asp Ser
                115                 120                 125

Tyr Asn Asn Val Phe Arg Asp Thr Glu Ala Leu Arg Glu Leu Gly Val
            130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
                180                 185                 190

His Trp Asp Leu Pro Gln Arg Leu Gln Asp Ala Tyr Gly Gly Trp Ala
                195                 200                 205

Asn Arg Ala Leu Ala Asp His Phe Arg Asp Tyr Ala Glu Leu Cys Phe
210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
                260                 265                 270

Leu Ala His Ala Lys Val Trp His Leu Tyr Asn Thr Ser Phe Arg Pro
            275                 280                 285

Thr Gln Gly Gly Gln Val Ser Ile Ala Leu Ser Ser His Trp Ile Asn
290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
                340                 345                 350

Thr Glu Ser Glu Lys Lys Phe Ile Lys Gly Thr Ala Asp Phe Phe Ala
                355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
                420                 425                 430

Tyr Leu Lys Lys Phe Ile Met Glu Thr Leu Lys Ala Ile Lys Leu Asp
            435                 440                 445

Gly Val Asp Val Ile Gly Tyr Thr Ala Trp Ser Leu Met Asp Gly Phe
        450                 455                 460

Glu Trp His Arg Gly Tyr Ser Ile Arg Arg Gly Leu Phe Tyr Val Asp
465                 470                 475                 480
```

```
Phe Leu Ser Gln Asp Lys Met Leu Leu Pro Lys Ser Ala Leu Phe
            485                 490                 495
Tyr Gln Lys Leu Ile Glu Lys Asn Gly Phe Pro Leu Pro Glu Asn
            500                 505                 510
Gln Pro Leu Glu Gly Thr Phe Pro Cys Asp Phe Ala Trp Gly Val Val
            515                 520                 525
Asp Asn Tyr Ile Gln Val Asp Thr Thr Leu Ser Gln Phe Thr Asp Leu
            530                 535                 540
Asn Val Tyr Leu Trp Asp Val His His Ser Lys Arg Leu Ile Lys Val
545                 550                 555                 560
Asp Gly Val Val Thr Lys Lys Arg Lys Ser Tyr Cys Val Asp Phe Ala
                565                 570                 575
Ala Ile Gln Pro Gln Ile Ala Leu Leu Gln Glu Met His Val Thr His
            580                 585                 590
Phe Arg Phe Ser Leu Asp Trp Ala Leu Ile Leu Pro Leu Gly Asn Gln
            595                 600                 605
Ser Gln Val Asn His Thr Ile Leu Gln Tyr Tyr Arg Cys Met Ala Ser
            610                 615                 620
Glu Leu Val Arg Val Asn Ile Thr Pro Val Val Ala Leu Trp Gln Pro
625                 630                 635                 640
Met Ala Pro Asn Gln Gly Leu Pro Arg Leu Leu Ala Arg Gln Gly Ala
                645                 650                 655
Trp Glu Asn Pro Tyr Thr Ala Leu Ala Phe Ala Glu Tyr Ala Arg Leu
                660                 665                 670
Cys Phe Gln Glu Leu Gly His His Val Lys Leu Trp Ile Thr Met Asn
            675                 680                 685
Glu Pro Tyr Thr Arg Asn Met Thr Tyr Ser Ala Gly His Asn Leu Leu
            690                 695                 700
Lys Ala His Ala Leu Ala Trp His Val Tyr Asn Glu Lys Phe Arg His
705                 710                 715                 720
Ala Gln Asn Gly Lys Ile Ser Ile Ala Leu Gln Ala Asp Trp Ile Glu
                725                 730                 735
Pro Ala Cys Pro Phe Ser Gln Lys Asp Lys Glu Val Ala Glu Arg Val
            740                 745                 750
Leu Glu Phe Asp Ile Gly Trp Leu Ala Glu Pro Ile Phe Gly Ser Gly
            755                 760                 765
Asp Tyr Pro Trp Val Met Arg Asp Trp Leu Asn Gln Arg Asn Asn Phe
            770                 775                 780
Leu Leu Pro Tyr Phe Thr Glu Asp Glu Lys Lys Leu Ile Gln Gly Thr
785                 790                 795                 800
Phe Asp Phe Leu Ala Leu Ser His Tyr Thr Thr Ile Leu Val Asp Ser
                805                 810                 815
Glu Lys Glu Asp Pro Ile Lys Tyr Asn Asp Tyr Leu Glu Val Gln Glu
            820                 825                 830
Met Thr Asp Ile Thr Trp Leu Asn Ser Pro Ser Gln Val Ala Val Val
            835                 840                 845
Pro Trp Gly Leu Arg Lys Val Leu Asn Trp Leu Lys Phe Lys Tyr Gly
            850                 855                 860
Asp Leu Pro Met Tyr Ile Ile Ser Asn Gly Ile Asp Asp Gly Leu His
865                 870                 875                 880
Ala Glu Asp Asp Gln Leu Arg Val Tyr Tyr Met Gln Asn Tyr Ile Asn
                885                 890                 895
```

Glu Ala Leu Lys Ala His Ile Leu Asp Gly Ile Asn Leu Cys Gly Tyr
              900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
    930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Gly Ser Gly Gly Gly Ser Gly Gly Gly
            980                 985                 990

Gly Ser Gly Gly Gly Gly Ser Leu Lys Tyr Pro Asn Ala Ser Pro Leu
        995                 1000                1005

Leu Gly Ser Ser Trp Gly Gly Leu Ile His Leu Tyr Thr Ala Thr
    1010                1015                1020

Ala Arg Asn Ser Tyr His Leu Gln Ile His Lys Asn Gly His Val
    1025                1030                1035

Asp Gly Ala Pro His Gln Thr Ile Tyr Ser Ala Leu Met Ile Arg
    1040                1045                1050

Ser Glu Asp Ala Gly Phe Val Val Ile Thr Gly Val Met Ser Arg
    1055                1060                1065

Arg Tyr Leu Cys Met Asp Phe Arg Gly Asn Ile Phe Gly Ser His
    1070                1075                1080

Tyr Phe Asp Pro Glu Asn Cys Arg Phe Gln His Gln Thr Leu Glu
    1085                1090                1095

Asn Gly Tyr Asp Val Tyr His Ser Pro Gln Tyr His Phe Leu Val
    1100                1105                1110

Ser Leu Gly Arg Ala Lys Arg Ala Phe Leu Pro Gly Met Asn Pro
    1115                1120                1125

Pro Pro Tyr Ser Gln Phe Leu Ser Arg Arg Asn Glu Ile Pro Leu
    1130                1135                1140

Ile His Phe Asn Thr Pro Ile Pro Arg Arg His Thr Gln Ser Ala
    1145                1150                1155

Glu Asp Asp Ser Glu Arg Asp Pro Leu Asn Val Leu Lys Pro Arg
    1160                1165                1170

Ala Arg Met Thr Pro Ala Pro Ala Ser Ser Ser Gln Glu Leu Pro
    1175                1180                1185

Ser Ala Glu Asp Asn Ser Pro Met Ala Ser Asp Pro Leu Gly Val
    1190                1195                1200

Val Arg Gly Gly Arg Val Asn Thr His Ala Gly Gly Thr Gly Pro
    1205                1210                1215

Glu Gly Ser Arg Pro Phe Ala Lys Phe Ile
    1220                1225

<210> SEQ ID NO 58
<211> LENGTH: 1228
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Met Pro Ala Ser Ala Pro Pro Arg Arg Pro Arg Pro Pro Pro Ser

```
           1               5                   10                  15
         Leu Ser Leu Leu Leu Val Leu Leu Gly Leu Gly Gly Arg Arg Leu Arg
                          20                  25                  30

Ala Glu Pro Gly Asp Gly Ala Gln Thr Trp Ala Arg Phe Ser Arg Pro
                          35                  40                  45

Pro Ala Pro Glu Ala Ala Gly Leu Phe Gln Gly Thr Phe Pro Asp Gly
                          50                  55                  60

Phe Leu Trp Ala Val Gly Ser Ala Ala Tyr Gln Thr Glu Gly Gly Trp
         65                   70                  75                  80

Gln Gln His Gly Lys Gly Ala Ser Ile Trp Asp Thr Phe Thr His His
                          85                  90                  95

Pro Leu Ala Pro Pro Gly Asp Ser Arg Asn Ala Ser Leu Pro Leu Gly
                          100                 105                 110

Ala Pro Ser Pro Leu Gln Pro Ala Thr Gly Asp Val Ala Ser Asp Ser
                          115                 120                 125

Tyr Asn Asn Val Phe Arg Asp Thr Glu Ala Leu Arg Glu Leu Gly Val
                          130                 135                 140

Thr His Tyr Arg Phe Ser Ile Ser Trp Ala Arg Val Leu Pro Asn Gly
         145                 150                 155                 160

Ser Ala Gly Val Pro Asn Arg Glu Gly Leu Arg Tyr Tyr Arg Arg Leu
                          165                 170                 175

Leu Glu Arg Leu Arg Glu Leu Gly Val Gln Pro Val Val Thr Leu Tyr
                          180                 185                 190

His Trp Asp Leu Pro Gln Arg Leu Gln Asp Ala Tyr Gly Gly Trp Ala
                          195                 200                 205

Asn Arg Ala Leu Ala Asp His Phe Arg Asp Tyr Ala Glu Leu Cys Phe
         210                 215                 220

Arg His Phe Gly Gly Gln Val Lys Tyr Trp Ile Thr Ile Asp Asn Pro
         225                 230                 235                 240

Tyr Val Val Ala Trp His Gly Tyr Ala Thr Gly Arg Leu Ala Pro Gly
                          245                 250                 255

Ile Arg Gly Ser Pro Arg Leu Gly Tyr Leu Val Ala His Asn Leu Leu
                          260                 265                 270

Leu Ala His Ala Lys Val Trp His Leu Tyr Asn Thr Ser Phe Arg Pro
                          275                 280                 285

Thr Gln Gly Gly Gln Val Ser Ile Ala Leu Ser Ser His Trp Ile Asn
                          290                 295                 300

Pro Arg Arg Met Thr Asp His Ser Ile Lys Glu Cys Gln Lys Ser Leu
         305                 310                 315                 320

Asp Phe Val Leu Gly Trp Phe Ala Lys Pro Val Phe Ile Asp Gly Asp
                          325                 330                 335

Tyr Pro Glu Ser Met Lys Asn Asn Leu Ser Ser Ile Leu Pro Asp Phe
                          340                 345                 350

Thr Glu Ser Glu Lys Lys Phe Ile Lys Gly Thr Ala Asp Phe Phe Ala
                          355                 360                 365

Leu Cys Phe Gly Pro Thr Leu Ser Phe Gln Leu Leu Asp Pro His Met
                          370                 375                 380

Lys Phe Arg Gln Leu Glu Ser Pro Asn Leu Arg Gln Leu Leu Ser Trp
         385                 390                 395                 400

Ile Asp Leu Glu Phe Asn His Pro Gln Ile Phe Ile Val Glu Asn Gly
                          405                 410                 415

Trp Phe Val Ser Gly Thr Thr Lys Arg Asp Asp Ala Lys Tyr Met Tyr
                          420                 425                 430
```

Tyr Leu Lys Lys Phe Ile Met Glu Thr Leu Lys Ala Ile Lys Leu Asp
            435                 440                 445

Gly Val Asp Val Ile Gly Tyr Thr Ala Trp Ser Leu Met Asp Gly Phe
        450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
                500                 505                 510

Gln Pro Leu Glu Gly Thr Phe Pro Cys Asp Phe Ala Trp Gly Val Val
        515                 520                 525

Asp Asn Tyr Ile Gln Val Asp Thr Thr Leu Ser Gln Phe Thr Asp Leu
530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
                580                 585                 590

Phe Arg Phe Ser Leu Asp Trp Ala Leu Ile Leu Pro Leu Gly Asn Gln
        595                 600                 605

Ser Gln Val Asn His Thr Ile Leu Gln Tyr Tyr Arg Cys Met Ala Ser
        610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
                660                 665                 670

Cys Phe Gln Glu Leu Gly His His Val Lys Leu Trp Ile Thr Met Asn
        675                 680                 685

Glu Pro Tyr Thr Arg Asn Met Thr Tyr Ser Ala Gly His Asn Leu Leu
        690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
                740                 745                 750

Leu Glu Phe Asp Ile Gly Trp Leu Ala Glu Pro Ile Phe Gly Ser Gly
        755                 760                 765

Asp Tyr Pro Trp Val Met Arg Asp Trp Leu Asn Gln Arg Asn Asn Phe
        770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
                820                 825                 830

Met Thr Asp Ile Thr Trp Leu Asn Ser Pro Ser Gln Val Ala Val Val
                835                 840                 845

Pro Trp Gly Leu Arg Lys Val Leu Asn Trp Leu Lys Phe Lys Tyr Gly
850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
            885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
            915                 920                 925

Arg Tyr Ala Ala Asp Gln Phe Glu Pro Lys Ala Ser Met Lys His Tyr
930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Gly Ser Gly Gly Gly Ser Gly Gly Gly
            980                 985                 990

Gly Ser Gly Gly Gly Gly Ser Leu Lys Tyr Pro Asn Ala Ser Pro Leu
            995                 1000                1005

Leu Gly Ser Ser Trp Gly Gly Leu Ile His Leu Tyr Thr Ala Thr
1010                1015                1020

Ala Arg Asn Ser Tyr His Leu Gln Ile His Lys Asn Gly His Val
1025                1030                1035

Asp Gly Ala Pro His Gln Thr Ile Tyr Ser Ala Leu Met Ile Arg
1040                1045                1050

Ser Glu Asp Ala Gly Phe Val Val Ile Thr Gly Val Met Ser Arg
1055                1060                1065

Arg Tyr Leu Cys Met Asp Phe Arg Gly Asn Ile Phe Gly Ser His
1070                1075                1080

Tyr Phe Asp Pro Glu Asn Cys Arg Phe Gln His Gln Thr Leu Glu
1085                1090                1095

Asn Gly Tyr Asp Val Tyr His Ser Pro Gln Tyr His Phe Leu Val
1100                1105                1110

Ser Leu Gly Arg Ala Lys Arg Ala Phe Leu Pro Gly Met Asn Pro
1115                1120                1125

Pro Pro Tyr Ser Ala Phe Leu Ser Arg Arg Asn Glu Ile Pro Leu
1130                1135                1140

Ile His Phe Asn Thr Pro Ile Pro Arg Arg His Thr Gln Ser Ala
1145                1150                1155

Glu Asp Asp Ser Glu Arg Asp Pro Leu Asn Val Leu Lys Pro Arg
1160                1165                1170

Ala Arg Met Thr Pro Ala Pro Ala Ser Ser Ser Gln Glu Leu Pro
1175                1180                1185

Ser Ala Glu Asp Asn Ser Pro Met Ala Ser Asp Pro Leu Gly Val
1190                1195                1200

Val Arg Gly Gly Arg Val Asn Thr His Ala Gly Gly Thr Gly Pro
1205                1210                1215

Glu Gly Ser Arg Pro Phe Ala Lys Phe Ile
1220                1225

<210> SEQ ID NO 59
<211> LENGTH: 482
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 59

```
Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Ser Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile Gly Gly Gly Gly Ser
                245                 250                 255

Lys Thr His Thr Cys Pro Pro Cys Pro Ala Pro Glu Ala Ala Gly Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380
```

```
Thr Leu Pro Pro Ser Arg Glu Glu Met Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
450                 455                 460

Glu Ala Leu His Asn His Tyr Thr Gln Lys Ser Leu Ser Leu Ser Pro
465                 470                 475                 480

Gly Lys

<210> SEQ ID NO 60
<211> LENGTH: 482
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Ser Glu Arg Asp Pro Leu Asn Val Leu
            180                 185                 190

Lys Pro Arg Ala Arg Met Thr Pro Ala Pro Ala Ser Cys Ser Gln Glu
        195                 200                 205

Leu Pro Ser Ala Glu Asp Asn Ser Pro Met Ala Ser Asp Pro Leu Gly
    210                 215                 220

Val Val Arg Gly Gly Arg Val Asn Thr His Ala Gly Gly Thr Gly Pro
225                 230                 235                 240

Glu Gly Ser Arg Pro Phe Ala Lys Phe Ile Gly Gly Gly Ser
```

```
            245                 250                 255
Lys Thr His Thr Cys Pro Pro Cys Pro Ala Pro Glu Ala Ala Gly Gly
            260                 265                 270

Pro Ser Val Phe Leu Phe Pro Pro Lys Pro Lys Asp Thr Leu Met Ile
            275                 280                 285

Ser Arg Thr Pro Glu Val Thr Cys Val Val Val Asp Val Ser His Glu
            290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
            325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
            355                 360                 365

Lys Thr Ile Ser Lys Ala Lys Gly Gln Pro Arg Glu Pro Gln Val Tyr
            370                 375                 380

Thr Leu Pro Pro Ser Arg Glu Glu Met Thr Lys Asn Gln Val Ser Leu
385                 390                 395                 400

Thr Cys Leu Val Lys Gly Phe Tyr Pro Ser Asp Ile Ala Val Glu Trp
            405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
            435                 440                 445

Lys Ser Arg Trp Gln Gln Gly Asn Val Phe Ser Cys Ser Val Met His
            450                 455                 460

Glu Ala Leu His Asn His Tyr Thr Gln Lys Ser Leu Ser Leu Ser Pro
465                 470                 475                 480

Gly Lys

<210> SEQ ID NO 61
<211> LENGTH: 482
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
            35                  40                  45

Asn Ser Tyr His Leu Gln Ile His Lys Asn Gly His Val Asp Gly Ala
            50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
            85                  90                  95

Asp Phe Arg Gly Asn Ile Phe Gly Ser His Tyr Phe Asp Pro Glu Asn
            100                 105                 110
```

```
Cys Arg Phe Gln His Gln Thr Leu Glu Asn Gly Tyr Asp Val Tyr His
            115                 120                 125

Ser Pro Gln Tyr His Phe Leu Val Ser Leu Gly Arg Ala Lys Arg Ala
130                 135                 140

Phe Leu Pro Gly Met Asn Pro Pro Tyr Ser Ala Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile Gly Gly Gly Ser
                245                 250                 255

Lys Thr His Thr Cys Pro Pro Cys Pro Ala Pro Glu Ala Ala Gly Gly
                260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
        290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Glu Glu Met Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Lys

<210> SEQ ID NO 62
<211> LENGTH: 482
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 62

```
Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Ser Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Ser Arg Pro Phe Ala Lys Phe Ile Gly Gly Gly Gly Ser
                245                 250                 255

Lys Thr His Thr Cys Pro Pro Cys Pro Ala Pro Glu Ala Ala Gly Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Glu Glu Met Thr Lys Asn Gln Val Ser Leu
385                 390                 395                 400
```

```
Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
450                 455                 460

Glu Ala Leu His Asn His Tyr Thr Gln Lys Ser Leu Ser Leu Ser Pro
465                 470                 475                 480

Gly Lys

<210> SEQ ID NO 63
<211> LENGTH: 482
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Ala Phe Leu Ser Arg Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Ser Glu Arg Asp Pro Leu Asn Val
            180                 185                 190

Leu Lys Pro Arg Ala Arg Met Thr Pro Ala Pro Ala Ser Ser Ser Gln
        195                 200                 205

Glu Leu Pro Ser Ala Glu Asp Asn Ser Pro Met Ala Ser Asp Pro Leu
210                 215                 220

Gly Val Val Arg Gly Gly Arg Val Asn Thr His Ala Gly Gly Thr Gly
225                 230                 235                 240

Pro Glu Gly Ser Arg Pro Phe Ala Lys Phe Ile Gly Gly Gly Ser
                245                 250                 255

Lys Thr His Thr Cys Pro Pro Cys Pro Ala Pro Glu Ala Ala Gly Gly
            260                 265                 270
```

```
Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
        290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
                340                 345                 350

Glu Tyr Lys Cys Lys Val Ser Asn Lys Ala Leu Pro Ala Pro Ile Glu
            355                 360                 365

Lys Thr Ile Ser Lys Ala Lys Gly Gln Pro Arg Glu Pro Gln Val Tyr
        370                 375                 380

Thr Leu Pro Pro Ser Arg Glu Glu Met Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
                420                 425                 430

Leu Asp Ser Asp Gly Ser Phe Phe Leu Tyr Ser Lys Leu Thr Val Asp
            435                 440                 445

Lys Ser Arg Trp Gln Gln Gly Asn Val Phe Ser Cys Ser Val Met His
        450                 455                 460

Glu Ala Leu His Asn His Tyr Thr Gln Lys Ser Leu Ser Leu Ser Pro
465                 470                 475                 480

Gly Lys

<210> SEQ ID NO 64
<211> LENGTH: 473
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
                20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
                100                 105                 110

Cys Arg Phe Gln His Gln Thr Leu Glu Asn Gly Tyr Asp Val Tyr His
            115                 120                 125

Ser Pro Gln Tyr His Phe Leu Val Ser Leu Gly Arg Ala Lys Arg Ala
```

```
                130                 135                 140
Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Ser Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile Gly Gly Gly Gly Ser
                245                 250                 255

Ala Pro Glu Ala Ala Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470

<210> SEQ ID NO 65
<211> LENGTH: 473
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65

Met Leu Gly Ala Arg Leu Arg Leu Trp Val Cys Ala Leu Cys Ser Val
1               5                   10                  15
```

```
Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
            165                 170                 175

His Thr Gln Ser Ala Glu Asp Ser Glu Arg Asp Pro Leu Asn Val
        180                 185                 190

Leu Lys Pro Arg Ala Arg Met Thr Pro Ala Pro Ala Ser Cys Ser Gln
    195                 200                 205

Glu Leu Pro Ser Ala Glu Asp Asn Ser Pro Met Ala Ser Asp Pro Leu
210                 215                 220

Gly Val Val Arg Gly Gly Arg Val Asn Thr His Ala Gly Gly Thr Gly
225                 230                 235                 240

Pro Glu Gly Ser Arg Pro Phe Ala Lys Phe Ile Gly Gly Gly Ser
            245                 250                 255

Ala Pro Glu Ala Ala Gly Gly Pro Ser Val Phe Leu Phe Pro Pro Lys
        260                 265                 270

Pro Lys Asp Thr Leu Met Ile Ser Arg Thr Pro Glu Val Thr Cys Val
    275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
            325                 330                 335

Gln Asp Trp Leu Asn Gly Lys Glu Tyr Lys Cys Lys Val Ser Asn Lys
        340                 345                 350

Ala Leu Pro Ala Pro Ile Glu Lys Thr Ile Ser Lys Ala Lys Gly Gln
    355                 360                 365

Pro Arg Glu Pro Gln Val Tyr Thr Leu Pro Pro Ser Arg Glu Glu Met
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
            405                 410                 415

Tyr Lys Thr Thr Pro Pro Val Leu Asp Ser Asp Gly Ser Phe Phe Leu
        420                 425                 430
```

Tyr Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470

<210> SEQ ID NO 66
<211> LENGTH: 473
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Ala Phe Leu Ser Arg Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile Gly Gly Gly Ser
                245                 250                 255

Ala Pro Glu Ala Ala Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu

```
                305                 310                 315                 320
Gln Tyr Asn Ser Thr Tyr Arg Val Val Ser Val Leu Thr Val Leu His
                325                 330                 335
Gln Asp Trp Leu Asn Gly Lys Glu Tyr Lys Cys Lys Val Ser Asn Lys
                340                 345                 350
Ala Leu Pro Ala Pro Ile Glu Lys Thr Ile Ser Lys Ala Lys Gly Gln
                355                 360                 365
Pro Arg Glu Pro Gln Val Tyr Thr Leu Pro Pro Ser Arg Glu Glu Met
                370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
                420                 425                 430
Tyr Ser Lys Leu Thr Val Asp Lys Ser Arg Trp Gln Gln Gly Asn Val
                435                 440                 445
Phe Ser Cys Ser Val Met His Glu Ala Leu His Asn His Tyr Thr Gln
                450                 455                 460
Lys Ser Leu Ser Leu Ser Pro Gly Lys
465                 470

<210> SEQ ID NO 67
<211> LENGTH: 473
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Met Leu Gly Ala Arg Leu Arg Leu Trp Val Cys Ala Leu Cys Ser Val
1               5                   10                  15
Cys Ser Met Ser Val Leu Arg Ala Tyr Pro Asn Ala Ser Pro Leu Leu
                20                  25                  30
Gly Ser Ser Trp Gly Gly Leu Ile His Leu Tyr Thr Ala Thr Ala Arg
                35                  40                  45
Asn Ser Tyr His Leu Gln Ile His Lys Asn Gly His Val Asp Gly Ala
                50                  55                  60
Pro His Gln Thr Ile Tyr Ser Ala Leu Met Ile Arg Ser Glu Asp Ala
65                  70                  75                  80
Gly Phe Val Val Ile Thr Gly Val Met Ser Arg Arg Tyr Leu Cys Met
                85                  90                  95
Asp Phe Arg Gly Asn Ile Phe Gly Ser His Tyr Phe Asp Pro Glu Asn
                100                 105                 110
Cys Arg Phe Gln His Gln Thr Leu Glu Asn Gly Tyr Asp Val Tyr His
                115                 120                 125
Ser Pro Gln Tyr His Phe Leu Val Ser Leu Gly Arg Ala Lys Arg Ala
                130                 135                 140
Phe Leu Pro Gly Met Asn Pro Pro Tyr Ser Gln Phe Leu Ser Arg Arg
145                 150                 155                 160
Arg Asn Glu Ile Pro Leu Ile His Phe Asn Thr Pro Ile Pro Arg Arg
                165                 170                 175
His Thr Gln Ser Ala Glu Asp Asp Ser Glu Arg Asp Pro Leu Asn Val
                180                 185                 190
```

-continued

Leu Lys Pro Arg Ala Arg Met Thr Pro Ala Pro Ala Ser Ser Ser Gln
        195                 200                 205

Glu Leu Pro Ser Ala Glu Asp Asn Ser Pro Met Ala Ser Asp Pro Leu
    210                 215                 220

Gly Val Val Arg Gly Arg Val Asn Thr His Ala Gly Gly Thr Gly
225                 230                 235                 240

Pro Glu Gly Ser Arg Pro Phe Ala Lys Phe Ile Gly Gly Gly Ser
                245                 250                 255

Ala Pro Glu Ala Ala Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470

<210> SEQ ID NO 68
<211> LENGTH: 473
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

```
Pro His Gln Thr Ile Tyr Ser Ala Leu Met Ile Arg Ser Glu Asp Ala
 65                  70                  75                  80

Gly Phe Val Val Ile Thr Gly Val Met Ser Arg Arg Tyr Leu Cys Met
                 85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Ala Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Ser Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Ser Arg Pro Phe Ala Lys Phe Ile Gly Gly Gly Ser
                245                 250                 255

Ala Pro Glu Ala Ala Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470
```

```
<210> SEQ ID NO 69
<211> LENGTH: 473
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Asp Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile Gly Gly Gly Ser
                245                 250                 255

Ala Pro Glu Ala Ala Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365
```

```
Pro Arg Glu Pro Gln Val Tyr Thr Leu Pro Pro Ser Arg Glu Glu Met
        370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470

<210> SEQ ID NO 70
<211> LENGTH: 473
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Asp Ser Gln Phe Leu Ser Arg Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Ser Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240
```

-continued

```
Pro Glu Gly Ser Arg Pro Phe Ala Lys Phe Ile Gly Gly Gly Ser
            245                 250                 255

Ala Pro Glu Ala Ala Gly Gly Pro Ser Val Phe Leu Phe Pro Pro Lys
        260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470

<210> SEQ ID NO 71
<211> LENGTH: 473
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
```

```
        115                 120                 125
Ser Pro Gln Tyr His Phe Leu Val Ser Leu Gly Arg Ala Lys Arg Ala
130                 135                 140

Phe Leu Pro Gly Met Asn Pro Pro Cys Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Gln Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Arg Val Asn Thr His Ala Gly Gly Thr Gly
225                 230                 235                 240

Pro Glu Gly Cys Arg Pro Phe Ala Lys Phe Ile Gly Gly Gly Ser
                245                 250                 255

Ala Pro Glu Ala Ala Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470

<210> SEQ ID NO 72
<211> LENGTH: 473
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72
```

```
Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Cys Ser Gln Phe Leu Ser Arg
145                 150                 155                 160

Arg Asn Glu Ile Pro Leu Ile His Phe Asn Thr Pro Ile Pro Arg Arg
            165                 170                 175

His Thr Gln Ser Ala Glu Asp Asp Ser Glu Arg Asp Pro Leu Asn Val
        180                 185                 190

Leu Lys Pro Arg Ala Arg Met Thr Pro Ala Pro Ala Ser Ser Ser Gln
    195                 200                 205

Glu Leu Pro Ser Ala Glu Asp Asn Ser Pro Met Ala Ser Asp Pro Leu
210                 215                 220

Gly Val Val Arg Gly Gly Arg Val Asn Thr His Ala Gly Gly Thr Gly
225                 230                 235                 240

Pro Glu Gly Ser Arg Pro Phe Ala Lys Phe Ile Gly Gly Gly Ser
                245                 250                 255

Ala Pro Glu Ala Ala Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415
```

```
Tyr Lys Thr Thr Pro Pro Val Leu Asp Ser Asp Gly Ser Phe Phe Leu
                420             425                 430

Tyr Ser Lys Leu Thr Val Asp Lys Ser Arg Trp Gln Gln Gly Asn Val
        435             440                 445

Phe Ser Cys Ser Val Met His Glu Ala Leu His Asn His Tyr Thr Gln
    450             455                 460

Lys Ser Leu Ser Leu Ser Pro Gly Lys
465             470

<210> SEQ ID NO 73
<211> LENGTH: 1422
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 73
atgttggggg cccgcctcag gctctgggtc tgtgccttgt gcagcgtctg cagcatgagc      60
gtcctcagag cctatcccaa tgcctcccca ctgctcggct ccagctgggg tggcctgatc     120
cacctgtaca cagccacagc caggaacagc taccacctgc agatccacaa gaatggccat     180
gtggatggcg cacccatca gaccatctac agtgccctga tgatcagatc agaggatgct     240
ggctttgtgg tgattacagg tgtgatgagc agaagatacc tctgcatgga tttcagaggc     300
aacatttttg gatcacacta tttcgacccg gagaactgca ggttccaaca ccagacgctg     360
gaaaacgggt acgacgtcta ccactctcct cagtatcact tcctggtcag tctgggccgg     420
gcgaagagag ccttcctgcc aggcatgaac ccaccccgg actcccagtt cctgtcccgg     480
aggaacgaga tcccctaat tcacttcaac accccatac cacggcggca cccagagc     540 gccgaggacg actcggagcg ggacccctg aacgtgctga gccccgggc ccggatgacc     600 ccggccccgg cctcctgttc acaggagctc ccgagcgccg aggacaacag cccgatggcc     660
agtgacccat taggggtggt caggggcggt cgagtgaaca cgcacgctgg ggaacgggc     720 ccggaaggct gccgcccctt cgccaagttc atcggaggtg aggttcagc cccagaagca     780 gcaggtggtc catcagtttt tcttttccct cccaaaccca aggatacgct gatgatctct     840
cgcacgcctg aggtgacatg cgtcgtagta gacgtgagcc acgaagatcc cgaggtgaag     900
ttcaattggt atgtggacgg agtagaagtg cataacgcga aaactaagcc gcgcgaggaa     960
caatataaca gtacttacag ggtggtatcc gtgctcacag tcctgcacca ggactggctg    1020
aacggtaagg aatacaagtg caaagtaagc aacaaggcac tcccgcgcc tattgagaaa    1080 acaatctcca aggcgaaggg acaaccaaga gaacctcagg tttacactct cccgccttcc    1140
agggaagaga tgaccaaaaa tcaagtttcc ctgacttgcc tcgtcaaagg attctaccct    1200
tccgacattg ctgttgaatg ggaaagcaat ggacaaccag agaacaacta caagacaaca    1260
cccccggtgc tggatagtga cggatctttc tttctctact caaagctgac cgtggataag    1320
tccaggtggc agcagggaaa cgtgttttcc tgctctgtca tgcatgaagc gctgcataat    1380
cactataccc agaagtctct gagcttgagc ccaggcaagt aa                      1422

<210> SEQ ID NO 74
<211> LENGTH: 1422
<212> TYPE: DNA
<213> ORGANISM: Artificial Sequence
<220> FEATURE:
<221> NAME/KEY: source
```

<223> OTHER INFORMATION: /note="Description of Artificial Sequence:
      Synthetic polynucleotide"

<400> SEQUENCE: 74

```
atgttggggg cccgcctcag gctctgggtc tgtgccttgt gcagcgtctg cagcatgagc      60
gtcctcagag cctatcccaa tgcctcccca ctgctcggct ccagctgggg tggcctgatc     120
cacctgtaca cagccacagc caggaacagc taccacctgc agatccacaa gaatggccat     180
gtggatggcg caccccatca gaccatctac agtgccctga tgatcagatc agaggatgct     240
ggctttgtgg tgattacagg tgtgatgagc agaagatacc tctgcatgga tttcagaggc     300
aacatttttg gatcacacta tttcgacccg gagaactgca ggttccaaca ccagacgctg     360
gaaaacgggt acgacgtcta ccactctcct cagtatcact tcctggtcag tctgggccgg     420
gcgaagagag ccttcctgcc aggcatgaac caccccccgg actcccagtt cctgtcccgg     480
aggaacgaga tcccctaat tcacttcaac accccccatac acggcggca cacccagagc     540
gccgaggacg actcggagcg ggacccccctg aacgtgctga gccccgggc ccggatgacc     600
ccggccccgg cctcctcttc acaggagctc ccgagcgccg aggacaacag cccgatggcc     660
agtgacccat taggggtggt caggggcggt cgagtgaaca cgcacgctgg gggaacgggc     720
ccggaaggct cccgcccctt cgccaagttc atcggaggtg gaggttcagc cccagaagca     780
gcaggtggtc catcagtttt tcttttccct cccaaaccca aggatacgct gatgatctct     840
cgcacgcctg aggtgacatg cgtcgtagta gacgtgagcc acgaagatcc cgaggtgaag     900
ttcaattggt atgtggacgg agtagaagtg cataacgcga aaactaagcc gcgcgaggaa     960
caatataaca gtacttacag ggtggtatcc gtgctcacag tcctgcacca ggactggctg    1020
aacggtaagg aatacaagtg caaagtaagc aacaaggcac ttcccgcgcc tattgagaaa    1080
acaatctcca aggcgaaggg acaaccaaga gaacctcagg tttacactct cccgccttcc    1140
agggaagaga tgaccaaaaa tcaagttccc ctgacttgcc tcgtcaaagg attctaccct    1200
tccgacattg ctgttgaatg ggaaagcaat ggacaaccag agaacaacta caagacaaca    1260
cccccggtgc tggatagtga cggatctttc tttctctact caaagctgac cgtggataag    1320
tccaggtggc agcagggaaa cgtgttttcc tgctctgtca tgcatgaagc gctgcataat    1380
cactataccc agaagtctct gagcttgagc ccaggcaagt aa                       1422
```

<210> SEQ ID NO 75
<211> LENGTH: 1422
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 75

```
atgttggggg cccgcctcag gctctgggtc tgtgccttgt gcagcgtctg cagcatgagc      60
gtcctcagag cctatcccaa tgcctcccca ctgctcggct ccagctgggg tggcctgatc     120
cacctgtaca cagccacagc caggaacagc taccacctgc agatccacaa gaatggccat     180
gtggatggcg caccccatca gaccatctac agtgccctga tgatcagatc agaggatgct     240
ggctttgtgg tgattacagg tgtgatgagc agaagatacc tctgcatgga tttcagaggc     300
aacatttttg gatcacacta tttcgacccg gagaactgca ggttccaaca ccagacgctg     360
gaaaacgggt acgacgtcta ccactctcct cagtatcact tcctggtcag tctgggccgg     420
```

| | |
|---|---|
| gcgaagagag ccttcctgcc aggcatgaac ccaccccgt gctcccagtt cctgtcccgg | 480 |
| aggaacgaga tcccctaat tcacttcaac accccatac cacggcggca cacccagagc | 540 |
| gccgaggacg actcggagcg ggacccctg aacgtgctga agccccgggc ccggatgacc | 600 |
| ccggccccgg cctcctgttc acaggagctc ccgagcgccg aggacaacag cccgatggcc | 660 |
| agtgacccat taggggtggt caggggcggt cgagtgaaca cgcacgctgg gggaacgggc | 720 |
| ccggaaggct gccgcccctt cgccaagttc atcggaggtg gaggttcagc cccagaagca | 780 |
| gcaggtggtc catcagtttt tcttttccct cccaaaccca aggatacgct gatgatctct | 840 |
| cgcacgcctg aggtgacatg cgtcgtagta cgtgagcc acgaagatcc cgaggtgaag | 900 |
| ttcaattggt atgtggacgg agtagaagtg cataacgcga aaactaagcc gcgcgaggaa | 960 |
| caatataaca gtacttacag ggtggtatcc gtgctcacag tcctgcacca ggactggctg | 1020 |
| aacggtaagg aatacaagtg caaagtaagc aacaaggcac ttcccgcgcc tattgagaaa | 1080 |
| acaatctcca aggcgaaggg acaaccaaga gaacctcagg tttacactct cccgccttcc | 1140 |
| agggaagaga tgaccaaaaa tcaagtttcc ctgacttgcc tcgtcaaagg attctaccct | 1200 |
| tccgacattg ctgttgaatg ggaaagcaat ggacaaccag agaacaacta caagacaaca | 1260 |
| cccccggtgc tggatagtga cggatctttc tttctctact caaagctgac cgtggataag | 1320 |
| tccaggtggc agcagggaaa cgtgttttcc tgctctgtca tgcatgaagc gctgcataat | 1380 |
| cactataccc agaagtctct gagcttgagc ccaggcaagt aa | 1422 |

<210> SEQ ID NO 76
<211> LENGTH: 1422
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 76

| | |
|---|---|
| atgttggggg cccgcctcag gctctgggtc tgtgccttgt gcagcgtctg cagcatgagc | 60 |
| gtcctcagag cctatcccaa tgcctcccca ctgctcggct ccagctgggg tggcctgatc | 120 |
| cacctgtaca cagccacagc caggaacagc taccacctgc agatccacaa gaatggccat | 180 |
| gtggatggcg cacccatca gaccatctac agtgccctga tgatcagatc agaggatgct | 240 |
| ggctttgtgg tgattacagg tgtgatgagc agaagatacc tctgcatgga tttcagaggc | 300 |
| aacattttg gatcacacta tttcgacccg gagaactgca ggttccaaca ccagacgctg | 360 |
| gaaaacgggt acgacgtcta ccactctcct cagtatcact tcctggtcag tctgggccgg | 420 |
| gcgaagagag ccttcctgcc aggcatgaac ccaccccgt gctcccagtt cctgtcccgg | 480 |
| aggaacgaga tcccctaat tcacttcaac accccatac cacggcggca cacccagagc | 540 |
| gccgaggacg actcggagcg ggacccctg aacgtgctga agccccgggc ccggatgacc | 600 |
| ccggccccgg cctcctcttc acaggagctc ccgagcgccg aggacaacag cccgatggcc | 660 |
| agtgacccat taggggtggt caggggcggt cgagtgaaca cgcacgctgg gggaacgggc | 720 |
| ccggaaggct cccgcccctt cgccaagttc atcggaggtg gaggttcagc cccagaagca | 780 |
| gcaggtggtc catcagtttt tcttttccct cccaaaccca aggatacgct gatgatctct | 840 |
| cgcacgcctg aggtgacatg cgtcgtagta cgtgagcc acgaagatcc cgaggtgaag | 900 |
| ttcaattggt atgtggacgg agtagaagtg cataacgcga aaactaagcc gcgcgaggaa | 960 |
| caatataaca gtacttacag ggtggtatcc gtgctcacag tcctgcacca ggactggctg | 1020 |

-continued

```
aacggtaagg aatacaagtg caaagtaagc aacaaggcac ttcccgcgcc tattgagaaa    1080
acaatctcca aggcgaaggg acaaccaaga gaacctcagg tttacactct cccgccttcc    1140
agggaagaga tgaccaaaaa tcaagtttcc ctgacttgcc tcgtcaaagg attctaccct    1200
tccgacattg ctgttgaatg ggaaagcaat ggacaaccag agaacaacta caagacaaca    1260
cccccggtgc tggatagtga cggatctttc tttctctact caaagctgac cgtggataag    1320
tccaggtggc agcagggaaa cgtgttttcc tgctctgtca tgcatgaagc gctgcataat    1380
cactataccc agaagtctct gagcttgagc ccaggcaagt aa                      1422
```

<210> SEQ ID NO 77
<211> LENGTH: 929
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 77

```
Glu Pro Gly Asp Gly Ala Gln Thr Trp Ala Arg Phe Ser Arg Pro Pro
1               5                   10                  15

Ala Pro Glu Ala Ala Gly Leu Phe Gln Gly Thr Phe Pro Asp Gly Phe
            20                  25                  30

Leu Trp Ala Val Gly Ser Ala Ala Tyr Gln Thr Glu Gly Gly Trp Gln
        35                  40                  45

Gln His Gly Lys Gly Ala Ser Ile Trp Asp Thr Phe Thr His His Pro
    50                  55                  60

Leu Ala Pro Pro Gly Asp Ser Arg Asn Ala Ser Leu Pro Leu Gly Ala
65                  70                  75                  80

Pro Ser Pro Leu Gln Pro Ala Thr Gly Asp Val Ala Ser Asp Ser Tyr
                85                  90                  95

Asn Asn Val Phe Arg Asp Thr Glu Ala Leu Arg Glu Leu Gly Val Thr
            100                 105                 110

His Tyr Arg Phe Ser Ile Ser Trp Ala Arg Val Leu Pro Asn Gly Ser
        115                 120                 125

Ala Gly Val Pro Asn Arg Glu Gly Leu Arg Tyr Tyr Arg Arg Leu Leu
    130                 135                 140

Glu Arg Leu Arg Glu Leu Gly Val Gln Pro Val Val Thr Leu Tyr His
145                 150                 155                 160

Trp Asp Leu Pro Gln Arg Leu Gln Asp Ala Tyr Gly Gly Trp Ala Asn
                165                 170                 175

Arg Ala Leu Ala Asp His Phe Arg Asp Tyr Ala Glu Leu Cys Phe Arg
            180                 185                 190

His Phe Gly Gly Gln Val Lys Tyr Trp Ile Thr Ile Asp Asn Pro Tyr
        195                 200                 205

Val Val Ala Trp His Gly Tyr Ala Thr Gly Arg Leu Ala Pro Gly Ile
    210                 215                 220

Arg Gly Ser Pro Arg Leu Gly Tyr Leu Val Ala His Asn Leu Leu Leu
225                 230                 235                 240

Ala His Ala Lys Val Trp His Leu Tyr Asn Thr Ser Phe Arg Pro Thr
                245                 250                 255

Gln Gly Gly Gln Val Ser Ile Ala Leu Ser Ser His Trp Ile Asn Pro
            260                 265                 270

Arg Arg Met Thr Asp His Ser Ile Lys Glu Cys Gln Lys Ser Leu Asp
```

```
              275                 280                 285
Phe Val Leu Gly Trp Phe Ala Lys Pro Val Phe Ile Asp Gly Asp Tyr
    290                 295                 300
Pro Glu Ser Met Lys Asn Asn Leu Ser Ser Ile Leu Pro Asp Phe Thr
305                 310                 315                 320
Glu Ser Glu Lys Lys Phe Ile Lys Gly Thr Ala Asp Phe Phe Ala Leu
                325                 330                 335
Cys Phe Gly Pro Thr Leu Ser Phe Gln Leu Leu Asp Pro His Met Lys
                340                 345                 350
Phe Arg Gln Leu Glu Ser Pro Asn Leu Arg Gln Leu Leu Ser Trp Ile
                355                 360                 365
Asp Leu Glu Phe Asn His Pro Gln Ile Phe Ile Val Glu Asn Gly Trp
                370                 375                 380
Phe Val Ser Gly Thr Thr Lys Arg Asp Asp Ala Lys Tyr Met Tyr Tyr
385                 390                 395                 400
Leu Lys Lys Phe Ile Met Glu Thr Leu Lys Ala Ile Lys Leu Asp Gly
                405                 410                 415
Val Asp Val Ile Gly Tyr Thr Ala Trp Ser Leu Met Asp Gly Phe Glu
                420                 425                 430
Trp His Arg Gly Tyr Ser Ile Arg Arg Gly Leu Phe Tyr Val Asp Phe
                435                 440                 445
Leu Ser Gln Asp Lys Met Leu Leu Pro Lys Ser Ser Ala Leu Phe Tyr
                450                 455                 460
Gln Lys Leu Ile Glu Lys Asn Gly Phe Pro Pro Leu Pro Glu Asn Gln
465                 470                 475                 480
Pro Leu Glu Gly Thr Phe Pro Cys Asp Phe Ala Trp Gly Val Val Asp
                485                 490                 495
Asn Tyr Ile Gln Val Asp Thr Thr Leu Ser Gln Phe Thr Asp Leu Asn
                500                 505                 510
Val Tyr Leu Trp Asp Val His His Ser Lys Arg Leu Ile Lys Val Asp
                515                 520                 525
Gly Val Val Thr Lys Lys Arg Lys Ser Tyr Cys Val Asp Phe Ala Ala
                530                 535                 540
Ile Gln Pro Gln Ile Ala Leu Leu Gln Glu Met His Val Thr His Phe
545                 550                 555                 560
Arg Phe Ser Leu Asp Trp Ala Leu Ile Leu Pro Leu Gly Asn Gln Ser
                565                 570                 575
Gln Val Asn His Thr Ile Leu Gln Tyr Tyr Arg Cys Met Ala Ser Glu
                580                 585                 590
Leu Val Arg Val Asn Ile Thr Pro Val Val Ala Leu Trp Gln Pro Met
                595                 600                 605
Ala Pro Asn Gln Gly Leu Pro Arg Leu Leu Ala Arg Gln Gly Ala Trp
                610                 615                 620
Glu Asn Pro Tyr Thr Ala Leu Ala Phe Ala Glu Tyr Ala Arg Leu Cys
625                 630                 635                 640
Phe Gln Glu Leu Gly His His Val Lys Leu Trp Ile Thr Met Asn Glu
                645                 650                 655
Pro Tyr Thr Arg Asn Met Thr Tyr Ser Ala Gly His Asn Leu Leu Lys
                660                 665                 670
Ala His Ala Leu Ala Trp His Val Tyr Asn Glu Lys Phe Arg His Ala
                675                 680                 685
Gln Asn Gly Lys Ile Ser Ile Ala Leu Gln Ala Asp Trp Ile Glu Pro
                690                 695                 700
```

```
Ala Cys Pro Phe Ser Gln Lys Asp Lys Glu Val Ala Glu Arg Val Leu
705                 710                 715                 720

Glu Phe Asp Ile Gly Trp Leu Ala Glu Pro Ile Phe Gly Ser Gly Asp
            725                 730                 735

Tyr Pro Trp Val Met Arg Asp Trp Leu Asn Gln Arg Asn Asn Phe Leu
        740                 745                 750

Leu Pro Tyr Phe Thr Glu Asp Lys Lys Leu Ile Gln Gly Thr Phe
    755                 760                 765

Asp Phe Leu Ala Leu Ser His Tyr Thr Thr Ile Leu Val Asp Ser Glu
    770                 775                 780

Lys Glu Asp Pro Ile Lys Tyr Asn Asp Tyr Leu Glu Val Gln Glu Met
785                 790                 795                 800

Thr Asp Ile Thr Trp Leu Asn Ser Pro Ser Gln Val Ala Val Val Pro
            805                 810                 815

Trp Gly Leu Arg Lys Val Leu Asn Trp Leu Lys Phe Lys Tyr Gly Asp
            820                 825                 830

Leu Pro Met Tyr Ile Ile Ser Asn Gly Ile Asp Asp Gly Leu His Ala
            835                 840                 845

Glu Asp Asp Gln Leu Arg Val Tyr Tyr Met Gln Asn Tyr Ile Asn Glu
850                 855                 860

Ala Leu Lys Ala His Ile Leu Asp Gly Ile Asn Leu Cys Gly Tyr Phe
865                 870                 875                 880

Ala Tyr Ser Phe Asn Asp Arg Thr Ala Pro Arg Phe Gly Leu Tyr Arg
            885                 890                 895

Tyr Ala Ala Asp Gln Phe Glu Pro Lys Ala Ser Met Lys His Tyr Arg
            900                 905                 910

Lys Ile Ile Asp Ser Asn Gly Phe Pro Gly Pro Glu Thr Leu Glu Arg
            915                 920                 925

Phe

<210> SEQ ID NO 78
<211> LENGTH: 929
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

Glu Pro Gly Asp Gly Ala Gln Thr Trp Ala Arg Phe Ser Arg Pro Pro
1               5                   10                  15

Ala Pro Glu Ala Ala Gly Leu Phe Gln Gly Thr Phe Pro Asp Gly Phe
            20                  25                  30

Leu Trp Ala Val Gly Ser Ala Ala Tyr Gln Thr Glu Gly Gly Trp Gln
        35                  40                  45

Gln His Gly Lys Gly Ala Ser Ile Trp Asp Thr Phe Thr His His Pro
    50                  55                  60

Leu Ala Pro Pro Gly Asp Ser Arg Asn Ala Ser Leu Pro Leu Gly Ala
65                  70                  75                  80

Pro Ser Pro Leu Gln Pro Ala Thr Gly Asp Val Ala Ser Asp Ser Tyr
                85                  90                  95

Asn Asn Val Phe Arg Asp Thr Glu Ala Leu Arg Glu Leu Gly Val Thr
            100                 105                 110

His Tyr Arg Phe Ser Ile Ser Trp Ala Arg Val Leu Pro Asn Gly Ser
```

```
            115                 120                 125
Ala Gly Val Pro Asn Arg Glu Gly Leu Arg Tyr Tyr Arg Arg Leu Leu
130                 135                 140

Glu Arg Leu Arg Glu Leu Gly Val Gln Pro Val Val Thr Leu Tyr His
145                 150                 155                 160

Trp Asp Leu Pro Gln Arg Leu Gln Asp Ala Tyr Gly Gly Trp Ala Asn
                165                 170                 175

Arg Ala Leu Ala Asp His Phe Arg Asp Tyr Ala Glu Leu Cys Phe Arg
                180                 185                 190

His Phe Gly Gly Gln Val Lys Tyr Trp Ile Thr Ile Asp Asn Pro Tyr
            195                 200                 205

Val Val Ala Trp His Gly Tyr Ala Thr Gly Arg Leu Ala Pro Gly Ile
210                 215                 220

Arg Gly Ser Pro Arg Leu Gly Tyr Leu Val Ala His Asn Leu Leu Leu
225                 230                 235                 240

Ala His Ala Lys Val Trp His Leu Tyr Asn Thr Ser Phe Arg Pro Thr
                245                 250                 255

Gln Gly Gly Gln Val Ser Ile Ala Leu Ser Ser His Trp Ile Asn Pro
                260                 265                 270

Arg Arg Met Thr Asp His Ser Ile Lys Glu Cys Gln Lys Ser Leu Asp
                275                 280                 285

Phe Val Leu Gly Trp Phe Ala Lys Pro Val Phe Ile Asp Gly Asp Tyr
290                 295                 300

Pro Glu Ser Met Lys Asn Asn Leu Ser Ser Ile Leu Pro Asp Phe Thr
305                 310                 315                 320

Glu Ser Glu Lys Lys Phe Ile Lys Gly Thr Ala Asp Phe Phe Ala Leu
                325                 330                 335

Cys Phe Gly Pro Thr Leu Ser Phe Gln Leu Leu Asp Pro His Met Lys
                340                 345                 350

Phe Arg Gln Leu Glu Ser Pro Asn Leu Arg Gln Leu Leu Ser Trp Ile
                355                 360                 365

Asp Leu Glu Phe Asn His Pro Gln Ile Phe Ile Val Glu Asn Gly Trp
370                 375                 380

Phe Val Ser Gly Thr Thr Lys Arg Asp Asp Ala Lys Tyr Met Tyr Tyr
385                 390                 395                 400

Leu Lys Lys Phe Ile Met Glu Thr Leu Lys Ala Ile Lys Leu Asp Gly
                405                 410                 415

Val Asp Val Ile Gly Tyr Thr Ala Trp Ser Leu Met Asp Gly Phe Glu
                420                 425                 430

Trp His Arg Gly Tyr Ser Ile Arg Arg Gly Leu Phe Tyr Val Asp Phe
                435                 440                 445

Leu Ser Gln Asp Lys Met Leu Leu Pro Lys Ser Ser Ala Leu Phe Tyr
450                 455                 460

Gln Lys Leu Ile Glu Lys Asn Gly Phe Pro Pro Leu Pro Glu Asn Gln
465                 470                 475                 480

Pro Leu Glu Gly Thr Phe Pro Cys Asp Phe Ala Trp Gly Val Val Asp
                485                 490                 495

Asn Tyr Ile Gln Val Asp Thr Thr Leu Ser Gln Phe Thr Asp Leu Asn
                500                 505                 510

Val Tyr Leu Trp Asp Val His His Ser Lys Arg Leu Ile Lys Val Asp
            515                 520                 525

Gly Ala Val Thr Lys Lys Arg Lys Ser Tyr Cys Val Asp Phe Ala Ala
530                 535                 540
```

-continued

```
Ile Gln Pro Gln Ile Ala Leu Leu Gln Glu Met His Val Thr His Phe
545                 550                 555                 560

Arg Phe Ser Leu Asp Trp Ala Leu Ile Leu Pro Leu Gly Asn Gln Ser
            565                 570                 575

Gln Val Asn His Thr Ile Leu Gln Tyr Tyr Arg Cys Met Ala Ser Glu
        580                 585                 590

Leu Val Arg Val Asn Ile Thr Pro Val Val Ala Leu Trp Gln Pro Met
    595                 600                 605

Ala Pro Asn Gln Gly Leu Pro Arg Leu Leu Ala Arg Gln Gly Ala Trp
610                 615                 620

Glu Asn Pro Tyr Thr Ala Leu Ala Phe Ala Glu Tyr Ala Arg Leu Cys
625                 630                 635                 640

Phe Gln Glu Leu Gly His His Val Lys Leu Trp Ile Thr Met Asn Glu
            645                 650                 655

Pro Tyr Thr Arg Asn Met Thr Tyr Ser Ala Gly His Asn Leu Leu Lys
        660                 665                 670

Ala His Ala Leu Ala Trp His Val Tyr Asn Glu Lys Phe Arg His Ala
    675                 680                 685

Gln Asn Gly Lys Ile Ser Ile Ala Leu Gln Ala Asp Trp Ile Glu Pro
690                 695                 700

Ala Cys Pro Phe Ser Gln Lys Asp Lys Glu Val Ala Glu Arg Val Leu
705                 710                 715                 720

Glu Phe Asp Ile Gly Trp Leu Ala Glu Pro Ile Phe Gly Ser Gly Asp
            725                 730                 735

Tyr Pro Trp Val Met Arg Asp Trp Leu Asn Gln Arg Asn Asn Phe Leu
        740                 745                 750

Leu Pro Tyr Phe Thr Glu Asp Glu Lys Glu Leu Ile Gln Gly Thr Phe
    755                 760                 765

Asp Phe Leu Ala Leu Ser His Tyr Thr Thr Ile Leu Val Asp Ser Glu
770                 775                 780

Lys Glu Asp Pro Ile Lys Tyr Asn Asp Tyr Leu Glu Val Gln Glu Met
785                 790                 795                 800

Thr Asp Ile Thr Trp Leu Asn Ser Pro Ser Gln Val Ala Val Val Pro
            805                 810                 815

Trp Gly Leu Arg Lys Val Leu Asn Trp Leu Lys Phe Lys Tyr Gly Asp
        820                 825                 830

Leu Pro Met Tyr Ile Ile Ser Asn Gly Ile Asp Asp Gly Leu His Ala
    835                 840                 845

Glu Asp Asp Gln Leu Arg Val Tyr Tyr Met Gln Asn Tyr Ile Asn Glu
850                 855                 860

Ala Leu Lys Ala His Ile Leu Asp Gly Ile Asn Leu Cys Gly Tyr Phe
865                 870                 875                 880

Ala Tyr Ser Phe Asn Asp Arg Thr Ala Pro Arg Phe Gly Leu Tyr Arg
            885                 890                 895

Tyr Ala Ala Asp Gln Phe Glu Pro Lys Ala Ser Met Lys His Tyr Arg
        900                 905                 910

Lys Ile Ile Asp Ser Asn Gly Phe Pro Gly Pro Glu Thr Leu Glu Arg
    915                 920                 925

Phe
```

<210> SEQ ID NO 79
<211> LENGTH: 1175
<212> TYPE: PRT

-continued

<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Glu Pro Gly Asp Gly Ala Gln Thr Trp Ala Arg Phe Ser Arg Pro Pro
1               5                   10                  15

Ala Pro Glu Ala Ala Gly Leu Phe Gln Gly Thr Phe Pro Asp Gly Phe
            20                  25                  30

Leu Trp Ala Val Gly Ser Ala Ala Tyr Gln Thr Glu Gly Gly Trp Gln
        35                  40                  45

Gln His Gly Lys Gly Ala Ser Ile Trp Asp Thr Phe Thr His His Pro
    50                  55                  60

Leu Ala Pro Pro Gly Asp Ser Arg Asn Ala Ser Leu Pro Leu Gly Ala
65                  70                  75                  80

Pro Ser Pro Leu Gln Pro Ala Thr Gly Asp Val Ala Ser Asp Ser Tyr
                85                  90                  95

Asn Asn Val Phe Arg Asp Thr Glu Ala Leu Arg Glu Leu Gly Val Thr
            100                 105                 110

His Tyr Arg Phe Ser Ile Ser Trp Ala Arg Val Leu Pro Asn Gly Ser
        115                 120                 125

Ala Gly Val Pro Asn Arg Glu Gly Leu Arg Tyr Tyr Arg Arg Leu Leu
    130                 135                 140

Glu Arg Leu Arg Glu Leu Gly Val Gln Pro Val Val Thr Leu Tyr His
145                 150                 155                 160

Trp Asp Leu Pro Gln Arg Leu Gln Asp Ala Tyr Gly Gly Trp Ala Asn
                165                 170                 175

Arg Ala Leu Ala Asp His Phe Arg Asp Tyr Ala Glu Leu Cys Phe Arg
            180                 185                 190

His Phe Gly Gly Gln Val Lys Tyr Trp Ile Thr Ile Asp Asn Pro Tyr
        195                 200                 205

Val Val Ala Trp His Gly Tyr Ala Thr Gly Arg Leu Ala Pro Gly Ile
    210                 215                 220

Arg Gly Ser Pro Arg Leu Gly Tyr Leu Val Ala His Asn Leu Leu Leu
225                 230                 235                 240

Ala His Ala Lys Val Trp His Leu Tyr Asn Thr Ser Phe Arg Pro Thr
                245                 250                 255

Gln Gly Gly Gln Val Ser Ile Ala Leu Ser Ser His Trp Ile Asn Pro
            260                 265                 270

Arg Arg Met Thr Asp His Ser Ile Lys Glu Cys Gln Lys Ser Leu Asp
        275                 280                 285

Phe Val Leu Gly Trp Phe Ala Lys Pro Val Phe Ile Asp Gly Asp Tyr
    290                 295                 300

Pro Glu Ser Met Lys Asn Asn Leu Ser Ser Ile Leu Pro Asp Phe Thr
305                 310                 315                 320

Glu Ser Glu Lys Lys Phe Ile Lys Gly Thr Ala Asp Phe Phe Ala Leu
                325                 330                 335

Cys Phe Gly Pro Thr Leu Ser Phe Gln Leu Leu Asp Pro His Met Lys
            340                 345                 350

Phe Arg Gln Leu Glu Ser Pro Asn Leu Arg Gln Leu Leu Ser Trp Ile
        355                 360                 365

Asp Leu Glu Phe Asn His Pro Gln Ile Phe Ile Val Glu Asn Gly Trp
    370                 375                 380

-continued

Phe Val Ser Gly Thr Thr Lys Arg Asp Asp Ala Lys Tyr Met Tyr Tyr
385                 390                 395                 400

Leu Lys Lys Phe Ile Met Glu Thr Leu Lys Ala Ile Lys Leu Asp Gly
            405                 410                 415

Val Asp Val Ile Gly Tyr Thr Ala Trp Ser Leu Met Asp Gly Phe Glu
            420                 425                 430

Trp His Arg Gly Tyr Ser Ile Arg Arg Gly Leu Phe Tyr Val Asp Phe
            435                 440                 445

Leu Ser Gln Asp Lys Met Leu Leu Pro Lys Ser Ser Ala Leu Phe Tyr
450                 455                 460

Gln Lys Leu Ile Glu Lys Asn Gly Phe Pro Pro Leu Pro Glu Asn Gln
465                 470                 475                 480

Pro Leu Glu Gly Thr Phe Pro Cys Asp Phe Ala Trp Gly Val Val Asp
            485                 490                 495

Asn Tyr Ile Gln Val Asp Thr Thr Leu Ser Gln Phe Thr Asp Leu Asn
            500                 505                 510

Val Tyr Leu Trp Asp Val His Ser Lys Arg Leu Ile Lys Val Asp
            515                 520                 525

Gly Val Val Thr Lys Lys Arg Lys Ser Tyr Cys Val Asp Phe Ala Ala
530                 535                 540

Ile Gln Pro Gln Ile Ala Leu Leu Gln Glu Met His Val Thr His Phe
545                 550                 555                 560

Arg Phe Ser Leu Asp Trp Ala Leu Ile Leu Pro Leu Gly Asn Gln Ser
            565                 570                 575

Gln Val Asn His Thr Ile Leu Gln Tyr Tyr Arg Cys Met Ala Ser Glu
            580                 585                 590

Leu Val Arg Val Asn Ile Thr Pro Val Val Ala Leu Trp Gln Pro Met
            595                 600                 605

Ala Pro Asn Gln Gly Leu Pro Arg Leu Leu Ala Arg Gln Gly Ala Trp
610                 615                 620

Glu Asn Pro Tyr Thr Ala Leu Ala Phe Ala Glu Tyr Ala Arg Leu Cys
625                 630                 635                 640

Phe Gln Glu Leu Gly His His Val Lys Leu Trp Ile Thr Met Asn Glu
            645                 650                 655

Pro Tyr Thr Arg Asn Met Thr Tyr Ser Ala Gly His Asn Leu Leu Lys
            660                 665                 670

Ala His Ala Leu Ala Trp His Val Tyr Asn Glu Lys Phe Arg His Ala
            675                 680                 685

Gln Asn Gly Lys Ile Ser Ile Ala Leu Gln Ala Asp Trp Ile Glu Pro
            690                 695                 700

Ala Cys Pro Phe Ser Gln Lys Asp Lys Glu Val Ala Glu Arg Val Leu
705                 710                 715                 720

Glu Phe Asp Ile Gly Trp Leu Ala Glu Pro Ile Phe Gly Ser Gly Asp
            725                 730                 735

Tyr Pro Trp Val Met Arg Asp Trp Leu Asn Gln Arg Asn Asn Phe Leu
            740                 745                 750

Leu Pro Tyr Phe Thr Glu Asp Glu Lys Lys Leu Ile Gln Gly Thr Phe
            755                 760                 765

Asp Phe Leu Ala Leu Ser His Tyr Thr Thr Ile Leu Val Asp Ser Glu
            770                 775                 780

Lys Glu Asp Pro Ile Lys Tyr Asn Asp Tyr Leu Glu Val Gln Glu Met
785                 790                 795                 800

Thr Asp Ile Thr Trp Leu Asn Ser Pro Ser Gln Val Ala Val Val Pro
            805                 810                 815

Trp Gly Leu Arg Lys Val Leu Asn Trp Leu Lys Phe Lys Tyr Gly Asp
        820                 825                 830

Leu Pro Met Tyr Ile Ile Ser Asn Gly Ile Asp Asp Gly Leu His Ala
            835                 840                 845

Glu Asp Asp Gln Leu Arg Val Tyr Tyr Met Gln Asn Tyr Ile Asn Glu
    850                 855                 860

Ala Leu Lys Ala His Ile Leu Asp Gly Ile Asn Leu Cys Gly Tyr Phe
865                 870                 875                 880

Ala Tyr Ser Phe Asn Asp Arg Thr Ala Pro Arg Phe Gly Leu Tyr Arg
                885                 890                 895

Tyr Ala Ala Asp Gln Phe Glu Pro Lys Ala Ser Met Lys His Tyr Arg
            900                 905                 910

Lys Ile Ile Asp Ser Asn Gly Phe Pro Gly Pro Glu Thr Leu Glu Arg
        915                 920                 925

Phe Gly Ser Gly Gly Gly Gly Ser Gly Gly Gly Gly Ser Gly Gly Gly
    930                 935                 940

Gly Ser Leu Lys Tyr Pro Asn Ala Ser Pro Leu Leu Gly Ser Ser Trp
945                 950                 955                 960

Gly Gly Leu Ile His Leu Tyr Thr Ala Thr Ala Arg Asn Ser Tyr His
                965                 970                 975

Leu Gln Ile His Lys Asn Gly His Val Asp Gly Ala Pro His Gln Thr
            980                 985                 990

Ile Tyr Ser Ala Leu Met Ile Arg  Ser Glu Asp Ala Gly  Phe Val Val
        995                 1000                1005

Ile Thr  Gly Val Met Ser Arg  Arg Tyr Leu Cys Met  Asp Phe Arg
    1010                1015                1020

Gly Asn  Ile Phe Gly Ser His  Tyr Phe Asp Pro Glu  Asn Cys Arg
    1025                1030                1035

Phe Gln  His Gln Thr Leu Glu  Asn Gly Tyr Asp Val  Tyr His Ser
    1040                1045                1050

Pro Gln  Tyr His Phe Leu Val  Ser Leu Gly Arg Ala  Lys Arg Ala
    1055                1060                1065

Phe Leu  Pro Gly Met Asn Pro  Pro Pro Tyr Ser Gln  Phe Leu Ser
    1070                1075                1080

Arg Arg  Asn Glu Ile Pro Leu  Ile His Phe Asn Thr  Pro Ile Pro
    1085                1090                1095

Arg Arg  His Thr Gln Ser Ala  Glu Asp Asp Ser Glu  Arg Asp Pro
    1100                1105                1110

Leu Asn  Val Leu Lys Pro Arg  Ala Arg Met Thr Pro  Ala Pro Ala
    1115                1120                1125

Ser Cys  Ser Gln Glu Leu Pro  Ser Ala Glu Asp Asn  Ser Pro Met
    1130                1135                1140

Ala Ser  Asp Pro Leu Gly Val  Val Arg Gly Gly Arg  Val Asn Thr
    1145                1150                1155

His Ala  Gly Gly Thr Gly Pro  Glu Gly Cys Arg Pro  Phe Ala Lys
    1160                1165                1170

Phe Ile
    1175

<210> SEQ ID NO 80
<211> LENGTH: 1195
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 80

```
Glu Pro Gly Asp Gly Ala Gln Thr Trp Ala Arg Phe Ser Arg Pro Pro
1               5                   10                  15

Ala Pro Glu Ala Ala Gly Leu Phe Gln Gly Thr Phe Pro Asp Gly Phe
            20                  25                  30

Leu Trp Ala Val Gly Ser Ala Ala Tyr Gln Thr Glu Gly Gly Trp Gln
        35                  40                  45

Gln His Gly Lys Gly Ala Ser Ile Trp Asp Thr Phe Thr His His Pro
    50                  55                  60

Leu Ala Pro Pro Gly Asp Ser Arg Asn Ala Ser Leu Pro Leu Gly Ala
65                  70                  75                  80

Pro Ser Pro Leu Gln Pro Ala Thr Gly Asp Val Ala Ser Asp Ser Tyr
                85                  90                  95

Asn Asn Val Phe Arg Asp Thr Glu Ala Leu Arg Glu Leu Gly Val Thr
            100                 105                 110

His Tyr Arg Phe Ser Ile Ser Trp Ala Arg Val Leu Pro Asn Gly Ser
        115                 120                 125

Ala Gly Val Pro Asn Arg Glu Gly Leu Arg Tyr Tyr Arg Arg Leu Leu
    130                 135                 140

Glu Arg Leu Arg Glu Leu Gly Val Gln Pro Val Val Thr Leu Tyr His
145                 150                 155                 160

Trp Asp Leu Pro Gln Arg Leu Gln Asp Ala Tyr Gly Gly Trp Ala Asn
                165                 170                 175

Arg Ala Leu Ala Asp His Phe Arg Asp Tyr Ala Glu Leu Cys Phe Arg
            180                 185                 190

His Phe Gly Gly Gln Val Lys Tyr Trp Ile Thr Ile Asp Asn Pro Tyr
        195                 200                 205

Val Val Ala Trp His Gly Tyr Ala Thr Gly Arg Leu Ala Pro Gly Ile
    210                 215                 220

Arg Gly Ser Pro Arg Leu Gly Tyr Leu Val Ala His Asn Leu Leu Leu
225                 230                 235                 240

Ala His Ala Lys Val Trp His Leu Tyr Asn Thr Ser Phe Arg Pro Thr
                245                 250                 255

Gln Gly Gly Gln Val Ser Ile Ala Leu Ser Ser His Trp Ile Asn Pro
            260                 265                 270

Arg Arg Met Thr Asp His Ser Ile Lys Glu Cys Gln Lys Ser Leu Asp
        275                 280                 285

Phe Val Leu Gly Trp Phe Ala Lys Pro Val Phe Ile Asp Gly Asp Tyr
    290                 295                 300

Pro Glu Ser Met Lys Asn Asn Leu Ser Ser Ile Leu Pro Asp Phe Thr
305                 310                 315                 320

Glu Ser Glu Lys Lys Phe Ile Lys Gly Thr Ala Asp Phe Phe Ala Leu
                325                 330                 335

Cys Phe Gly Pro Thr Leu Ser Phe Gln Leu Leu Asp Pro His Met Lys
            340                 345                 350

Phe Arg Gln Leu Glu Ser Pro Asn Leu Arg Gln Leu Leu Ser Trp Ile
        355                 360                 365

Asp Leu Glu Phe Asn His Pro Gln Ile Phe Ile Val Glu Asn Gly Trp
    370                 375                 380
```

```
Phe Val Ser Gly Thr Thr Lys Arg Asp Asp Ala Lys Tyr Met Tyr Tyr
385                 390                 395                 400

Leu Lys Lys Phe Ile Met Glu Thr Leu Lys Ala Ile Lys Leu Asp Gly
            405                 410                 415

Val Asp Val Ile Gly Tyr Thr Ala Trp Ser Leu Met Asp Gly Phe Glu
            420                 425                 430

Trp His Arg Gly Tyr Ser Ile Arg Arg Gly Leu Phe Tyr Val Asp Phe
            435                 440                 445

Leu Ser Gln Asp Lys Met Leu Leu Pro Lys Ser Ser Ala Leu Phe Tyr
450                 455                 460

Gln Lys Leu Ile Glu Lys Asn Gly Phe Pro Pro Leu Pro Glu Asn Gln
465                 470                 475                 480

Pro Leu Glu Gly Thr Phe Pro Cys Asp Phe Ala Trp Gly Val Val Asp
            485                 490                 495

Asn Tyr Ile Gln Val Asp Thr Thr Leu Ser Gln Phe Thr Asp Leu Asn
            500                 505                 510

Val Tyr Leu Trp Asp Val His Ser Lys Arg Leu Ile Lys Val Asp
            515                 520                 525

Gly Val Val Thr Lys Lys Arg Lys Ser Tyr Cys Val Asp Phe Ala Ala
530                 535                 540

Ile Gln Pro Gln Ile Ala Leu Leu Gln Glu Met His Val Thr His Phe
545                 550                 555                 560

Arg Phe Ser Leu Asp Trp Ala Leu Ile Leu Pro Leu Gly Asn Gln Ser
            565                 570                 575

Gln Val Asn His Thr Ile Leu Gln Tyr Tyr Arg Cys Met Ala Ser Glu
            580                 585                 590

Leu Val Arg Val Asn Ile Thr Pro Val Val Ala Leu Trp Gln Pro Met
            595                 600                 605

Ala Pro Asn Gln Gly Leu Pro Arg Leu Leu Ala Arg Gln Gly Ala Trp
610                 615                 620

Glu Asn Pro Tyr Thr Ala Leu Ala Phe Ala Glu Tyr Ala Arg Leu Cys
625                 630                 635                 640

Phe Gln Glu Leu Gly His His Val Lys Leu Trp Ile Thr Met Asn Glu
            645                 650                 655

Pro Tyr Thr Arg Asn Met Thr Tyr Ser Ala Gly His Asn Leu Leu Lys
            660                 665                 670

Ala His Ala Leu Ala Trp His Val Tyr Asn Glu Lys Phe Arg His Ala
            675                 680                 685

Gln Asn Gly Lys Ile Ser Ile Ala Leu Gln Ala Asp Trp Ile Glu Pro
            690                 695                 700

Ala Cys Pro Phe Ser Gln Lys Asp Lys Glu Val Ala Glu Arg Val Leu
705                 710                 715                 720

Glu Phe Asp Ile Gly Trp Leu Ala Glu Pro Ile Phe Gly Ser Gly Asp
            725                 730                 735

Tyr Pro Trp Val Met Arg Asp Trp Leu Asn Gln Arg Asn Asn Phe Leu
            740                 745                 750

Leu Pro Tyr Phe Thr Glu Asp Glu Lys Lys Leu Ile Gln Gly Thr Phe
            755                 760                 765

Asp Phe Leu Ala Leu Ser His Tyr Thr Thr Ile Leu Val Asp Ser Glu
            770                 775                 780

Lys Glu Asp Pro Ile Lys Tyr Asn Asp Tyr Leu Glu Val Gln Glu Met
785                 790                 795                 800
```

-continued

```
Thr Asp Ile Thr Trp Leu Asn Ser Pro Ser Gln Val Ala Val Val Pro
            805                 810                 815

Trp Gly Leu Arg Lys Val Leu Asn Trp Leu Lys Phe Lys Tyr Gly Asp
            820                 825                 830

Leu Pro Met Tyr Ile Ile Ser Asn Gly Ile Asp Asp Gly Leu His Ala
            835                 840                 845

Glu Asp Asp Gln Leu Arg Val Tyr Tyr Met Gln Asn Tyr Ile Asn Glu
850                 855                 860

Ala Leu Lys Ala His Ile Leu Asp Gly Ile Asn Leu Cys Gly Tyr Phe
865                 870                 875                 880

Ala Tyr Ser Phe Asn Asp Arg Thr Ala Pro Arg Phe Gly Leu Tyr Arg
            885                 890                 895

Tyr Ala Ala Asp Gln Phe Glu Pro Lys Ala Ser Met Lys His Tyr Arg
            900                 905                 910

Lys Ile Ile Asp Ser Asn Gly Phe Pro Gly Pro Glu Thr Leu Glu Arg
            915                 920                 925

Phe Cys Pro Glu Glu Phe Thr Val Cys Thr Glu Cys Ser Phe Phe His
            930                 935                 940

Thr Arg Lys Ser Leu Gly Ser Gly Gly Gly Ser Gly Gly Gly Gly
945                 950                 955                 960

Ser Gly Gly Gly Gly Ser Leu Lys Tyr Pro Asn Ala Ser Pro Leu Leu
            965                 970                 975

Gly Ser Ser Trp Gly Gly Leu Ile His Leu Tyr Thr Ala Thr Ala Arg
            980                 985                 990

Asn Ser Tyr His Leu Gln Ile His Lys Asn Gly His Val Asp Gly Ala
            995                 1000                1005

Pro His Gln Thr Ile Tyr Ser Ala Leu Met Ile Arg Ser Glu Asp
        1010            1015            1020

Ala Gly Phe Val Val Ile Thr Gly Val Met Ser Arg Arg Tyr Leu
        1025            1030            1035

Cys Met Asp Phe Arg Gly Asn Ile Phe Gly Ser His Tyr Phe Asp
        1040            1045            1050

Pro Glu Asn Cys Arg Phe Gln His Gln Thr Leu Glu Asn Gly Tyr
        1055            1060            1065

Asp Val Tyr His Ser Pro Gln Tyr His Phe Leu Val Ser Leu Gly
        1070            1075            1080

Arg Ala Lys Arg Ala Phe Leu Pro Gly Met Asn Pro Pro Pro Tyr
        1085            1090            1095

Ser Gln Phe Leu Ser Arg Arg Asn Glu Ile Pro Leu Ile His Phe
        1100            1105            1110

Asn Thr Pro Ile Pro Arg Arg His Thr Gln Ser Ala Glu Asp Asp
        1115            1120            1125

Ser Glu Arg Asp Pro Leu Asn Val Leu Lys Pro Arg Ala Arg Met
        1130            1135            1140

Thr Pro Ala Pro Ala Ser Cys Ser Gln Glu Leu Pro Ser Ala Glu
        1145            1150            1155

Asp Asn Ser Pro Met Ala Ser Asp Pro Leu Gly Val Val Arg Gly
        1160            1165            1170

Gly Arg Val Asn Thr His Ala Gly Gly Thr Gly Pro Glu Gly Cys
        1175            1180            1185

Arg Pro Phe Ala Lys Phe Ile
        1190            1195
```

-continued

```
<210> SEQ ID NO 81
<211> LENGTH: 1208
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81
```

Met Pro Ala Ser Ala Pro Pro Arg Arg Pro Pro Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

```
Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
                420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
    450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
    515                 520                 525

Asp Asn Tyr Ile Gln Val Asp Thr Thr Leu Ser Gln Phe Thr Asp Leu
530                 535                 540

Asn Val Tyr Leu Trp Asp Val His His Ser Lys Arg Leu Ile Lys Val
545                 550                 555                 560

Asp Gly Ala Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
            580                 585                 590

Phe Arg Phe Ser Leu Asp Trp Ala Leu Ile Leu Pro Leu Gly Asn Gln
            595                 600                 605

Ser Gln Val Asn His Thr Ile Leu Gln Tyr Tyr Arg Cys Met Ala Ser
    610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
                660                 665                 670

Cys Phe Gln Glu Leu Gly His His Val Lys Leu Trp Ile Thr Met Asn
        675                 680                 685

Glu Pro Tyr Thr Arg Asn Met Thr Tyr Ser Ala Gly His Asn Leu Leu
    690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
        755                 760                 765

Asp Tyr Pro Trp Val Met Arg Asp Trp Leu Asn Gln Arg Asn Asn Phe
    770                 775                 780
```

```
Leu Leu Pro Tyr Phe Thr Glu Asp Glu Lys Glu Leu Ile Gln Gly Thr
785                 790                 795                 800

Phe Asp Phe Leu Ala Leu Ser His Tyr Thr Thr Ile Leu Val Asp Ser
            805                 810                 815

Glu Lys Glu Asp Pro Ile Lys Tyr Asn Asp Tyr Leu Glu Val Gln Glu
                820                 825                 830

Met Thr Asp Ile Thr Trp Leu Asn Ser Pro Ser Gln Val Ala Val Val
            835                 840                 845

Pro Trp Gly Leu Arg Lys Val Leu Asn Trp Leu Lys Phe Lys Tyr Gly
850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
                900                 905                 910

Phe Ala Tyr Ser Phe Asn Asp Arg Thr Ala Pro Arg Phe Gly Leu Tyr
            915                 920                 925

Arg Tyr Ala Ala Asp Gln Phe Glu Pro Lys Ala Ser Met Lys His Tyr
930                 935                 940

Arg Lys Ile Ile Asp Ser Asn Gly Phe Pro Gly Pro Glu Thr Leu Glu
945                 950                 955                 960

Arg Phe Gly Ser Gly Gly Gly Ser Gly Gly Gly Ser Gly Gly
                965                 970                 975

Gly Gly Ser Leu Lys Tyr Pro Asn Ala Ser Pro Leu Leu Gly Ser Ser
            980                 985                 990

Trp Gly Gly Leu Ile His Leu Tyr  Thr Ala Thr Ala Arg  Asn Ser Tyr
            995                 1000                1005

His Leu  Gln Ile His Lys Asn  Gly His Val Asp Gly  Ala Pro His
     1010                1015                1020

Gln Thr  Ile Tyr Ser Ala Leu  Met Ile Arg Ser Glu  Asp Ala Gly
     1025                1030                1035

Phe Val  Val Ile Thr Gly Val  Met Ser Arg Arg Tyr  Leu Cys Met
     1040                1045                1050

Asp Phe  Arg Gly Asn Ile Phe  Gly Ser His Tyr Phe  Asp Pro Glu
     1055                1060                1065

Asn Cys  Arg Phe Gln His Gln  Thr Leu Glu Asn Gly  Tyr Asp Val
     1070                1075                1080

Tyr His  Ser Pro Gln Tyr His  Phe Leu Val Ser Leu  Gly Arg Ala
     1085                1090                1095

Lys Arg  Ala Phe Leu Pro Gly  Met Asn Pro Pro Pro  Tyr Ser Gln
     1100                1105                1110

Phe Leu  Ser Arg Arg Asn Glu  Ile Pro Leu Ile His  Phe Asn Thr
     1115                1120                1125

Pro Ile  Pro Arg Arg His Thr  Gln Ser Ala Glu Asp  Asp Ser Glu
     1130                1135                1140

Arg Asp  Pro Leu Asn Val Leu  Lys Pro Arg Ala Arg  Met Thr Pro
     1145                1150                1155

Ala Pro  Ala Ser Cys Ser Gln  Glu Leu Pro Ser Ala  Glu Asp Asn
     1160                1165                1170

Ser Pro  Met Ala Ser Asp Pro  Leu Gly Val Val Arg  Gly Gly Arg
     1175                1180                1185

Val Asn  Thr His Ala Gly Gly  Thr Gly Pro Glu Gly  Cys Arg Pro
```

Phe Ala Lys Phe Ile
    1205

<210> SEQ ID NO 82
<211> LENGTH: 1175
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

Glu Pro Gly Asp Gly Ala Gln Thr Trp Ala Arg Phe Ser Arg Pro Pro
1               5                   10                  15

Ala Pro Glu Ala Ala Gly Leu Phe Gln Gly Thr Phe Pro Asp Gly Phe
            20                  25                  30

Leu Trp Ala Val Gly Ser Ala Ala Tyr Gln Thr Glu Gly Gly Trp Gln
        35                  40                  45

Gln His Gly Lys Gly Ala Ser Ile Trp Asp Thr Phe Thr His His Pro
    50                  55                  60

Leu Ala Pro Pro Gly Asp Ser Arg Asn Ala Ser Leu Pro Leu Gly Ala
65                  70                  75                  80

Pro Ser Pro Leu Gln Pro Ala Thr Gly Asp Val Ala Ser Asp Ser Tyr
                85                  90                  95

Asn Asn Val Phe Arg Asp Thr Glu Ala Leu Arg Glu Leu Gly Val Thr
            100                 105                 110

His Tyr Arg Phe Ser Ile Ser Trp Ala Arg Val Leu Pro Asn Gly Ser
        115                 120                 125

Ala Gly Val Pro Asn Arg Glu Gly Leu Arg Tyr Tyr Arg Arg Leu Leu
    130                 135                 140

Glu Arg Leu Arg Glu Leu Gly Val Gln Pro Val Val Thr Leu Tyr His
145                 150                 155                 160

Trp Asp Leu Pro Gln Arg Leu Gln Asp Ala Tyr Gly Gly Trp Ala Asn
                165                 170                 175

Arg Ala Leu Ala Asp His Phe Arg Asp Tyr Ala Glu Leu Cys Phe Arg
            180                 185                 190

His Phe Gly Gly Gln Val Lys Tyr Trp Ile Thr Ile Asp Asn Pro Tyr
        195                 200                 205

Val Val Ala Trp His Gly Tyr Ala Thr Gly Arg Leu Ala Pro Gly Ile
    210                 215                 220

Arg Gly Ser Pro Arg Leu Gly Tyr Leu Val Ala His Asn Leu Leu Leu
225                 230                 235                 240

Ala His Ala Lys Val Trp His Leu Tyr Asn Thr Ser Phe Arg Pro Thr
                245                 250                 255

Gln Gly Gly Gln Val Ser Ile Ala Leu Ser Ser His Trp Ile Asn Pro
            260                 265                 270

Arg Arg Met Thr Asp His Ser Ile Lys Glu Cys Gln Lys Ser Leu Asp
        275                 280                 285

Phe Val Leu Gly Trp Phe Ala Lys Pro Val Phe Ile Asp Gly Asp Tyr
    290                 295                 300

Pro Glu Ser Met Lys Asn Asn Leu Ser Ser Ile Leu Pro Asp Phe Thr
305                 310                 315                 320

Glu Ser Glu Lys Lys Phe Ile Lys Gly Thr Ala Asp Phe Phe Ala Leu
                325                 330                 335

```
Cys Phe Gly Pro Thr Leu Ser Phe Gln Leu Leu Asp Pro His Met Lys
            340                 345                 350

Phe Arg Gln Leu Glu Ser Pro Asn Leu Arg Gln Leu Leu Ser Trp Ile
            355                 360                 365

Asp Leu Glu Phe Asn His Pro Gln Ile Phe Ile Val Glu Asn Gly Trp
        370                 375                 380

Phe Val Ser Gly Thr Thr Lys Arg Asp Asp Ala Lys Tyr Met Tyr Tyr
385                 390                 395                 400

Leu Lys Lys Phe Ile Met Glu Thr Leu Lys Ala Ile Lys Leu Asp Gly
                405                 410                 415

Val Asp Val Ile Gly Tyr Thr Ala Trp Ser Leu Met Asp Gly Phe Glu
            420                 425                 430

Trp His Arg Gly Tyr Ser Ile Arg Arg Gly Leu Phe Tyr Val Asp Phe
            435                 440                 445

Leu Ser Gln Asp Lys Met Leu Leu Pro Lys Ser Ser Ala Leu Phe Tyr
        450                 455                 460

Gln Lys Leu Ile Glu Lys Asn Gly Phe Pro Pro Leu Pro Glu Asn Gln
465                 470                 475                 480

Pro Leu Glu Gly Thr Phe Pro Cys Asp Phe Ala Trp Gly Val Val Asp
                485                 490                 495

Asn Tyr Ile Gln Val Asp Thr Thr Leu Ser Gln Phe Thr Asp Leu Asn
            500                 505                 510

Val Tyr Leu Trp Asp Val His His Ser Lys Arg Leu Ile Lys Val Asp
            515                 520                 525

Gly Ala Val Thr Lys Lys Arg Lys Ser Tyr Cys Val Asp Phe Ala Ala
        530                 535                 540

Ile Gln Pro Gln Ile Ala Leu Leu Gln Glu Met His Val Thr His Phe
545                 550                 555                 560

Arg Phe Ser Leu Asp Trp Ala Leu Ile Leu Pro Leu Gly Asn Gln Ser
                565                 570                 575

Gln Val Asn His Thr Ile Leu Gln Tyr Tyr Arg Cys Met Ala Ser Glu
            580                 585                 590

Leu Val Arg Val Asn Ile Thr Pro Val Val Ala Leu Trp Gln Pro Met
            595                 600                 605

Ala Pro Asn Gln Gly Leu Pro Arg Leu Leu Ala Arg Gln Gly Ala Trp
        610                 615                 620

Glu Asn Pro Tyr Thr Ala Leu Ala Phe Ala Glu Tyr Ala Arg Leu Cys
625                 630                 635                 640

Phe Gln Glu Leu Gly His His Val Lys Leu Trp Ile Thr Met Asn Glu
                645                 650                 655

Pro Tyr Thr Arg Asn Met Thr Tyr Ser Ala Gly His Asn Leu Leu Lys
            660                 665                 670

Ala His Ala Leu Ala Trp His Val Tyr Asn Glu Lys Phe Arg His Ala
            675                 680                 685

Gln Asn Gly Lys Ile Ser Ile Ala Leu Gln Ala Asp Trp Ile Glu Pro
        690                 695                 700

Ala Cys Pro Phe Ser Gln Lys Asp Lys Glu Val Ala Glu Arg Val Leu
705                 710                 715                 720

Glu Phe Asp Ile Gly Trp Leu Ala Glu Pro Ile Phe Gly Ser Gly Asp
                725                 730                 735

Tyr Pro Trp Val Met Arg Asp Trp Leu Asn Gln Arg Asn Asn Phe Leu
            740                 745                 750
```

```
Leu Pro Tyr Phe Thr Glu Asp Glu Lys Glu Leu Ile Gln Gly Thr Phe
        755                 760                 765

Asp Phe Leu Ala Leu Ser His Tyr Thr Thr Ile Leu Val Asp Ser Glu
        770                 775                 780

Lys Glu Asp Pro Ile Lys Tyr Asn Asp Tyr Leu Glu Val Gln Glu Met
785                 790                 795                 800

Thr Asp Ile Thr Trp Leu Asn Ser Pro Ser Gln Val Ala Val Val Pro
                805                 810                 815

Trp Gly Leu Arg Lys Val Leu Asn Trp Leu Lys Phe Lys Tyr Gly Asp
                820                 825                 830

Leu Pro Met Tyr Ile Ile Ser Asn Gly Ile Asp Asp Gly Leu His Ala
                835                 840                 845

Glu Asp Asp Gln Leu Arg Val Tyr Tyr Met Gln Asn Tyr Ile Asn Glu
850                 855                 860

Ala Leu Lys Ala His Ile Leu Asp Gly Ile Asn Leu Cys Gly Tyr Phe
865                 870                 875                 880

Ala Tyr Ser Phe Asn Asp Arg Thr Ala Pro Arg Phe Gly Leu Tyr Arg
                885                 890                 895

Tyr Ala Ala Asp Gln Phe Glu Pro Lys Ala Ser Met Lys His Tyr Arg
                900                 905                 910

Lys Ile Ile Asp Ser Asn Gly Phe Pro Gly Pro Glu Thr Leu Glu Arg
915                 920                 925

Phe Gly Ser Gly Gly Gly Ser Gly Gly Gly Ser Gly Gly Gly
        930                 935                 940

Gly Ser Leu Lys Tyr Pro Asn Ala Ser Pro Leu Leu Gly Ser Ser Trp
945                 950                 955                 960

Gly Gly Leu Ile His Leu Tyr Thr Ala Thr Ala Arg Asn Ser Tyr His
                965                 970                 975

Leu Gln Ile His Lys Asn Gly His Val Asp Gly Ala Pro His Gln Thr
                980                 985                 990

Ile Tyr Ser Ala Leu Met Ile Arg Ser Glu Asp Ala Gly Phe Val Val
                995                 1000                1005

Ile Thr Gly Val Met Ser Arg Arg Tyr Leu Cys Met Asp Phe Arg
1010                1015                1020

Gly Asn Ile Phe Gly Ser His Tyr Phe Asp Pro Glu Asn Cys Arg
1025                1030                1035

Phe Gln His Gln Thr Leu Glu Asn Gly Tyr Asp Val Tyr His Ser
1040                1045                1050

Pro Gln Tyr His Phe Leu Val Ser Leu Gly Arg Ala Lys Arg Ala
1055                1060                1065

Phe Leu Pro Gly Met Asn Pro Pro Tyr Ser Gln Phe Leu Ser
1070                1075                1080

Arg Arg Asn Glu Ile Pro Leu Ile His Phe Asn Thr Pro Ile Pro
1085                1090                1095

Arg Arg His Thr Gln Ser Ala Glu Asp Asp Ser Glu Arg Asp Pro
1100                1105                1110

Leu Asn Val Leu Lys Pro Arg Ala Arg Met Thr Pro Ala Pro Ala
1115                1120                1125

Ser Cys Ser Gln Glu Leu Pro Ser Ala Glu Asp Asn Ser Pro Met
1130                1135                1140

Ala Ser Asp Pro Leu Gly Val Val Arg Gly Gly Arg Val Asn Thr
1145                1150                1155

His Ala Gly Gly Thr Gly Pro Glu Gly Cys Arg Pro Phe Ala Lys
```

Phe Ile
   1175

<210> SEQ ID NO 83
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 83
gacggcgcgc agacctgggc                                              20

<210> SEQ ID NO 84
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 84
tagctctaga ctaaaatctt tccagagttt ctg                               33

<210> SEQ ID NO 85
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 85
tagctctaga ctatttcatg gatgccttgg gct                               33

<210> SEQ ID NO 86
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 86
tagctctaga ctaagctgtg cggtcgttaa acg                               33

<210> SEQ ID NO 87
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 87
tagctctaga ctagtgggct ttgagagctt cgt                               33

<210> SEQ ID NO 88
<211> LENGTH: 33
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 88
tagctctaga ctactcagca tgcagcccgt cat                                    33

<210> SEQ ID NO 89
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 89
tagctctaga ctacttgaac ttcagccagt tca                                    33

<210> SEQ ID NO 90
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 90
tagctctaga ctaggggag ttgagccacg tga                                     33

<210> SEQ ID NO 91
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 91
tagctctaga ctatattgga tcttcttttt ctg                                    33

<210> SEQ ID NO 92
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 92
tagctctaga ctagtcaaag gtaccctgga tta                                    33

<210> SEQ ID NO 93
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 93
tagctctaga ctagtttctt tggttcagcc agt                                    33
```

<210> SEQ ID NO 94
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 94
tagctctaga ctactcagcc agccagccaa tgt                                    33

<210> SEQ ID NO 95
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 95
tagctctaga ctaggagaaa gggcaggcag gtt                                    33

<210> SEQ ID NO 96
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 96
tagctctaga ctactgagca tgcctaaact ttt                                    33

<210> SEQ ID NO 97
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 97
tagctctaga ctagttgtgg ccagcactgt atg                                    33

<210> SEQ ID NO 98
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 98
tagctctaga ctacttgacg tgatggccga gct                                    33

<210> SEQ ID NO 99
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 99
tagctctaga ctaagtgtag gggttctccc agg                33

<210> SEQ ID NO 100
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 100
tagctctaga ctaggccata ggctgccaca ggg                33

<210> SEQ ID NO 101
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 101
tagctctaga ctacatgcag cgatagtact gca                33

<210> SEQ ID NO 102
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 102
tagctctaga ctaaatcagg gcccagtcca ggg                33

<210> SEQ ID NO 103
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 103
tagctctaga ctagatctgg ggctggatgg cag                33

<210> SEQ ID NO 104
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 104
tagctctaga ctacccatcc actttaataa gcc                33

<210> SEQ ID NO 105
<211> LENGTH: 33

-continued

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 105
tagctctaga ctaggtaaac tgagacagag tgg                                  33

<210> SEQ ID NO 106
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 106
tagctctaga ctagtcacag ggaaatgtcc ctt                                  33

<210> SEQ ID NO 107
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 107
tagctctaga ctactctatc agcttttggt aga                                  33

<210> SEQ ID NO 108
<211> LENGTH: 1585
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 108
```

Met Pro Ala Ser Ala Pro Pro Arg Arg Pro Arg Pro Pro Pro Ser
1               5                   10                  15

Leu Ser Leu Leu Leu Val Leu Leu Gly Leu Gly Arg Arg Leu Arg
                20                  25                  30

Ala Glu Pro Gly Asp Gly Ala Gln Thr Trp Ala Arg Phe Ser Arg
            35                  40                  45

Pro Ala Pro Glu Ala Ala Gly Leu Phe Gln Gly Thr Phe Pro Asp Gly
        50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly

```
                145                 150                 155                 160
            Ser Ala Gly Val Pro Asn Arg Glu Gly Leu Arg Tyr Tyr Arg Arg Leu
                                165                 170                 175

Leu Glu Arg Leu Arg Glu Leu Gly Val Gln Pro Val Val Thr Leu Tyr
                                180                 185                 190

His Trp Asp Leu Pro Gln Arg Leu Gln Asp Ala Tyr Gly Gly Trp Ala
                                195                 200                 205

Asn Arg Ala Leu Ala Asp His Phe Arg Asp Tyr Ala Glu Leu Cys Phe
                    210                 215                 220

Arg His Phe Gly Gly Gln Val Lys Tyr Trp Ile Thr Ile Asp Asn Pro
            225                 230                 235                 240

Tyr Val Val Ala Trp His Gly Tyr Ala Thr Gly Arg Leu Ala Pro Gly
                                245                 250                 255

Ile Arg Gly Ser Pro Arg Leu Gly Tyr Leu Val Ala His Asn Leu Leu
                                260                 265                 270

Leu Ala His Ala Lys Val Trp His Leu Tyr Asn Thr Ser Phe Arg Pro
                    275                 280                 285

Thr Gln Gly Gly Gln Val Ser Ile Ala Leu Ser Ser His Trp Ile Asn
                    290                 295                 300

Pro Arg Arg Met Thr Asp His Ser Ile Lys Glu Cys Gln Lys Ser Leu
            305                 310                 315                 320

Asp Phe Val Leu Gly Trp Phe Ala Lys Pro Val Phe Ile Asp Gly Asp
                                325                 330                 335

Tyr Pro Glu Ser Met Lys Asn Asn Leu Ser Ser Ile Leu Pro Asp Phe
                                340                 345                 350

Thr Glu Ser Glu Lys Lys Phe Ile Lys Gly Thr Ala Asp Phe Phe Ala
                    355                 360                 365

Leu Cys Phe Gly Pro Thr Leu Ser Phe Gln Leu Asp Pro His Met
                    370                 375                 380

Lys Phe Arg Gln Leu Glu Ser Pro Asn Leu Arg Gln Leu Leu Ser Trp
            385                 390                 395                 400

Ile Asp Leu Glu Phe Asn His Pro Gln Ile Phe Ile Val Glu Asn Gly
                                405                 410                 415

Trp Phe Val Ser Gly Thr Thr Lys Arg Asp Asp Ala Lys Tyr Met Tyr
                                420                 425                 430

Tyr Leu Lys Lys Phe Ile Met Glu Thr Leu Lys Ala Ile Lys Leu Asp
                    435                 440                 445

Gly Val Asp Val Ile Gly Tyr Thr Ala Trp Ser Leu Met Asp Gly Phe
                    450                 455                 460

Glu Trp His Arg Gly Tyr Ser Ile Arg Arg Gly Leu Phe Tyr Val Asp
            465                 470                 475                 480

Phe Leu Ser Gln Asp Lys Met Leu Leu Pro Lys Ser Ser Ala Leu Phe
                                485                 490                 495

Tyr Gln Lys Leu Ile Glu Lys Asn Gly Phe Pro Pro Leu Pro Glu Asn
                                500                 505                 510

Gln Pro Leu Glu Gly Thr Phe Pro Cys Asp Phe Ala Trp Gly Val Val
                    515                 520                 525

Asp Asn Tyr Ile Gln Val Asp Thr Thr Leu Ser Gln Phe Thr Asp Leu
                    530                 535                 540

Asn Val Tyr Leu Trp Asp Val His His Ser Lys Arg Leu Ile Lys Val
            545                 550                 555                 560

Asp Gly Val Val Thr Lys Lys Arg Lys Ser Tyr Cys Val Asp Phe Ala
                                565                 570                 575
```

```
Ala Ile Gln Pro Gln Ile Ala Leu Leu Gln Glu Met His Val Thr His
            580                 585                 590

Phe Arg Phe Ser Leu Asp Trp Ala Leu Ile Leu Pro Leu Gly Asn Gln
        595                 600                 605

Ser Gln Val Asn His Thr Ile Leu Gln Tyr Tyr Arg Cys Met Ala Ser
    610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
            660                 665                 670

Cys Phe Gln Glu Leu Gly His His Val Lys Leu Trp Ile Thr Met Asn
        675                 680                 685

Glu Pro Tyr Thr Arg Asn Met Thr Tyr Ser Ala Gly His Asn Leu Leu
    690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
        755                 760                 765

Asp Tyr Pro Trp Val Met Arg Asp Trp Leu Asn Gln Arg Asn Asn Phe
    770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
            820                 825                 830

Met Thr Asp Ile Thr Trp Leu Asn Ser Pro Ser Gln Val Ala Val Val
        835                 840                 845

Pro Trp Gly Leu Arg Lys Val Leu Asn Trp Leu Lys Phe Lys Tyr Gly
    850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
    930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Gly Ser Gly Gly Gly Ser Gly Gly Gly Gly
            980                 985                 990
```

```
Gly Ser Gly Gly Gly Gly Ser Leu  Lys Glu Ala His Lys  Ser Glu Ile
            995               1000                 1005

Ala His Arg Tyr Asn Ala Leu  Gly Glu Gln His Phe  Lys Gly Leu
    1010              1015                 1020

Val Leu Ile Ala Phe Ser Gln  Tyr Leu Gln Lys Ala  Ser Tyr Asp
    1025              1030                 1035

Glu His Ala Lys Leu Val Gln  Glu Val Thr Asp Phe  Ala Lys Thr
    1040              1045                 1050

Cys Val Ala Asp Glu Ser Ala  Ala Asn Cys Asp Lys  Ser Leu His
    1055              1060                 1065

Thr Leu Phe Gly Asp Lys Leu  Cys Ala Ile Pro Asn  Leu Arg Glu
    1070              1075                 1080

Asn Tyr Gly Glu Leu Ala Asp  Cys Cys Thr Lys Gln  Glu Pro Glu
    1085              1090                 1095

Arg Asn Glu Cys Phe Leu Gln  His Lys Asp Asp Asn  Pro Ser Leu
    1100              1105                 1110

Pro Pro Phe Glu Arg Pro Glu  Ala Glu Ala Met Cys  Thr Ser Phe
    1115              1120                 1125

Lys Glu Asn Pro Thr Thr Phe  Met Gly His Tyr Leu  His Glu Val
    1130              1135                 1140

Ala Arg Arg His Pro Tyr Phe  Tyr Ala Pro Glu Leu  Leu Tyr Tyr
    1145              1150                 1155

Ala Glu Gln Tyr Asn Glu Ile  Leu Thr Gln Cys Cys  Ala Glu Ala
    1160              1165                 1170

Asp Lys Glu Ser Cys Leu Thr  Pro Lys Leu Asp Gly  Val Lys Glu
    1175              1180                 1185

Lys Ala Leu Val Ser Ser Val  Arg Gln Arg Met Lys  Cys Ser Ser
    1190              1195                 1200

Met Gln Lys Phe Gly Glu Arg  Ala Phe Lys Ala Trp  Ala Val Ala
    1205              1210                 1215

Arg Leu Ser Gln Thr Phe Pro  Asn Ala Asp Phe Ala  Glu Ile Thr
    1220              1225                 1230

Lys Leu Ala Thr Asp Leu Thr  Lys Val Asn Lys Glu  Cys Cys His
    1235              1240                 1245

Gly Asp Leu Leu Glu Cys Ala  Asp Asp Arg Ala Glu  Leu Ala Lys
    1250              1255                 1260

Tyr Met Cys Glu Asn Gln Ala  Thr Ile Ser Ser Lys  Leu Gln Thr
    1265              1270                 1275

Cys Cys Asp Lys Pro Leu Leu  Lys Lys Ala His Cys  Leu Ser Glu
    1280              1285                 1290

Val Glu His Asp Thr Met Pro  Ala Asp Leu Pro Ala  Ile Ala Ala
    1295              1300                 1305

Asp Phe Val Glu Asp Gln Glu  Val Cys Lys Asn Tyr  Ala Glu Ala
    1310              1315                 1320

Lys Asp Val Phe Leu Gly Thr  Phe Leu Tyr Glu Tyr  Ser Arg Arg
    1325              1330                 1335

His Pro Asp Tyr Ser Val Ser  Leu Leu Leu Arg Leu  Ala Lys Lys
    1340              1345                 1350

Tyr Glu Ala Thr Leu Glu Lys  Cys Cys Ala Glu Ala  Asn Pro Pro
    1355              1360                 1365

Ala Cys Tyr Gly Thr Val Leu  Ala Glu Phe Gln Pro  Leu Val Glu
    1370              1375                 1380

Glu Pro Lys Asn Leu Val Lys  Thr Asn Cys Asp Leu  Tyr Glu Lys
```

```
                  1385                1390                1395
Leu Gly Glu Tyr Gly Phe Gln Asn Ala Ile Leu Val Arg Tyr Thr
    1400                1405                1410

Gln Lys Ala Pro Gln Val Ser Thr Pro Thr Leu Val Glu Ala Ala
    1415                1420                1425

Arg Asn Leu Gly Arg Val Gly Thr Lys Cys Cys Thr Leu Pro Glu
    1430                1435                1440

Asp Gln Arg Leu Pro Cys Val Glu Asp Tyr Leu Ser Ala Ile Leu
    1445                1450                1455

Asn Arg Val Cys Leu Leu His Glu Lys Thr Pro Val Ser Glu His
    1460                1465                1470

Val Thr Lys Cys Cys Ser Gly Ser Leu Val Glu Arg Arg Pro Cys
    1475                1480                1485

Phe Ser Ala Leu Thr Val Asp Glu Thr Tyr Val Pro Lys Glu Phe
    1490                1495                1500

Lys Ala Glu Thr Phe Thr Phe His Ser Asp Ile Cys Thr Leu Pro
    1505                1510                1515

Glu Lys Glu Lys Gln Ile Lys Lys Gln Thr Ala Leu Ala Glu Leu
    1520                1525                1530

Val Lys His Lys Pro Lys Ala Thr Ala Glu Gln Leu Lys Thr Val
    1535                1540                1545

Met Asp Asp Phe Ala Gln Phe Leu Asp Thr Cys Cys Lys Ala Ala
    1550                1555                1560

Asp Lys Asp Thr Cys Phe Ser Thr Glu Gly Pro Asn Leu Val Thr
    1565                1570                1575

Arg Ala Lys Asp Ala Leu Ala
    1580                1585

<210> SEQ ID NO 109
<211> LENGTH: 251
<212> TYPE: PRT
<213> ORGANISM: Macaca mulatta

<400> SEQUENCE: 109

Met Leu Gly Ala Arg Leu Arg Leu Trp Val Cys Ala Leu Cys Ser Val
1               5                   10                  15

Cys Ser Met Ser Val Ile Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asn Pro Glu Asn
            100                 105                 110

Cys Arg Phe Arg His Trp Thr Leu Glu Asn Gly Tyr Asp Val Tyr His
        115                 120                 125

Ser Pro Gln His His Phe Leu Val Ser Leu Gly Arg Ala Lys Arg Ala
    130                 135                 140

Phe Leu Pro Gly Met Asn Pro Pro Tyr Ser Gln Phe Leu Ser Arg
145                 150                 155                 160
```

```
Arg Asn Glu Ile Pro Leu Ile His Phe Asn Thr Pro Arg Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Val Ala Ser Asp Pro Leu
    210                 215                 220

Gly Val Val Arg Gly Gly Arg Val Asn Thr His Ala Gly Gly Thr Gly
225                 230                 235                 240

Pro Glu Ala Cys Arg Pro Phe Pro Lys Phe Ile
                245                 250

<210> SEQ ID NO 110
<211> LENGTH: 245
<212> TYPE: PRT
<213> ORGANISM: Bos sp.

<400> SEQUENCE: 110

Met Leu Gly Ala Arg Leu Gly Leu Trp Val Cys Thr Leu Ser Cys Val
1               5                   10                  15

Val Gln Ala Tyr Pro Asn Ser Ser Pro Leu Leu Gly Ser Ser Trp Gly
            20                  25                  30

Gly Leu Thr His Leu Tyr Thr Ala Thr Ala Arg Asn Ser Tyr His Leu
        35                  40                  45

Gln Ile His Gly Asp Gly His Val Asp Gly Ser Pro Gln Gln Thr Val
    50                  55                  60

Tyr Ser Ala Leu Met Ile Arg Ser Glu Asp Ala Gly Phe Val Val Ile
65                  70                  75                  80

Thr Gly Val Met Ser Arg Arg Tyr Leu Cys Met Asp Phe Thr Gly Asn
                85                  90                  95

Ile Phe Gly Ser His His Phe Ser Pro Glu Ser Cys Arg Phe Arg Gln
            100                 105                 110

Arg Thr Leu Glu Asn Gly Tyr Asp Val Tyr His Ser Pro Gln His Arg
        115                 120                 125

Phe Leu Val Ser Leu Gly Arg Ala Lys Arg Ala Phe Leu Pro Gly Thr
    130                 135                 140

Asn Pro Pro Pro Tyr Ala Gln Phe Leu Ser Arg Arg Asn Glu Ile Pro
145                 150                 155                 160

Leu Pro His Phe Ala Ala Thr Ala Arg Pro Arg Arg His Thr Arg Ser
                165                 170                 175

Ala His Asp Ser Gly Asp Pro Leu Ser Val Leu Lys Pro Arg Ala Arg
            180                 185                 190

Ala Thr Pro Val Pro Ala Ala Cys Ser Gln Glu Leu Pro Ser Ala Glu
        195                 200                 205

Asp Ser Gly Pro Ala Ala Ser Asp Pro Leu Gly Val Leu Arg Gly His
    210                 215                 220

Arg Leu Asp Val Arg Ala Gly Ser Ala Gly Ala Glu Arg Cys Arg Pro
225                 230                 235                 240

Phe Pro Gly Phe Ala
                245

<210> SEQ ID NO 111
<211> LENGTH: 251
<212> TYPE: PRT
<213> ORGANISM: Mus sp.
```

<400> SEQUENCE: 111

```
Met Leu Gly Thr Cys Leu Arg Leu Leu Val Gly Val Leu Cys Thr Val
1               5                   10                  15

Cys Ser Leu Gly Thr Ala Arg Ala Tyr Pro Asp Thr Ser Pro Leu Leu
            20                  25                  30

Gly Ser Asn Trp Gly Ser Leu Thr His Leu Tyr Thr Ala Thr Ala Arg
        35                  40                  45

Thr Ser Tyr His Leu Gln Ile His Arg Asp Gly His Val Asp Gly Thr
    50                  55                  60

Pro His Gln Thr Ile Tyr Ser Ala Leu Met Ile Thr Ser Glu Asp Ala
65                  70                  75                  80

Gly Ser Val Val Ile Thr Gly Ala Met Thr Arg Arg Phe Leu Cys Met
            85                  90                  95

Asp Leu His Gly Asn Ile Phe Gly Ser Leu His Phe Ser Pro Glu Asn
            100                 105                 110

Cys Lys Phe Arg Gln Trp Thr Leu Glu Asn Gly Tyr Asp Val Tyr Leu
        115                 120                 125

Ser Gln Lys His His Tyr Leu Val Ser Leu Gly Arg Ala Lys Arg Ile
    130                 135                 140

Phe Gln Pro Gly Thr Asn Pro Pro Phe Ser Gln Phe Leu Ala Arg
145                 150                 155                 160

Arg Asn Glu Val Pro Leu Leu His Phe Tyr Thr Val Arg Pro Arg Arg
            165                 170                 175

His Thr Arg Ser Ala Glu Asp Pro Pro Glu Arg Asp Pro Leu Asn Val
        180                 185                 190

Leu Lys Pro Arg Pro Arg Ala Thr Pro Val Pro Val Ser Cys Ser Arg
    195                 200                 205

Glu Leu Pro Ser Ala Glu Glu Gly Pro Ala Ala Ser Asp Pro Leu
    210                 215                 220

Gly Val Leu Arg Arg Gly Arg Gly Asp Ala Arg Gly Gly Ala Gly Gly
225                 230                 235                 240

Ala Asp Arg Cys Arg Pro Phe Pro Arg Phe Val
            245                 250
```

<210> SEQ ID NO 112
<211> LENGTH: 251
<212> TYPE: PRT
<213> ORGANISM: Rattus sp.

<400> SEQUENCE: 112

```
Met Leu Gly Ala Cys Leu Arg Leu Leu Val Gly Ala Leu Cys Thr Val
1               5                   10                  15

Cys Ser Leu Gly Thr Ala Arg Ala Tyr Ser Asp Thr Ser Pro Leu Leu
            20                  25                  30

Gly Ser Asn Trp Gly Ser Leu Thr His Leu Tyr Thr Ala Thr Ala Arg
        35                  40                  45

Asn Ser Tyr His Leu Gln Ile His Arg Asp Gly His Val Asp Gly Thr
    50                  55                  60

Pro His Gln Thr Ile Tyr Ser Ala Leu Met Ile Thr Ser Glu Asp Ala
65                  70                  75                  80

Gly Ser Val Val Ile Ile Gly Ala Met Thr Arg Arg Phe Leu Cys Met
            85                  90                  95

Asp Leu Arg Gly Asn Ile Phe Gly Ser Tyr His Phe Ser Pro Glu Asn
            100                 105                 110
```

-continued

```
Cys Arg Phe Arg Gln Trp Thr Leu Glu Asn Gly Tyr Asp Val Tyr Leu
        115                 120                 125

Ser Pro Lys His His Tyr Leu Val Ser Leu Gly Arg Ser Lys Arg Ile
    130                 135                 140

Phe Gln Pro Gly Thr Asn Pro Pro Phe Ser Gln Phe Leu Ala Arg
145                 150                 155                 160

Arg Asn Glu Val Pro Leu Leu His Phe Tyr Thr Ala Arg Pro Arg Arg
                165                 170                 175

His Thr Arg Ser Ala Glu Asp Pro Pro Glu Arg Asp Pro Leu Asn Val
            180                 185                 190

Leu Lys Pro Arg Pro Arg Ala Thr Pro Ile Pro Val Ser Cys Ser Arg
            195                 200                 205

Glu Leu Pro Ser Ala Glu Glu Gly Gly Pro Ala Ala Ser Asp Pro Leu
        210                 215                 220

Gly Val Leu Arg Arg Gly Arg Gly Asp Ala Arg Arg Gly Ala Gly Gly
225                 230                 235                 240

Thr Asp Arg Cys Arg Pro Phe Pro Arg Phe Val
                245                 250
```

<210> SEQ ID NO 113
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 113

Gly Ser Gly Gly
1

<210> SEQ ID NO 114
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 114

Leu Lys Glu Ala
1

<210> SEQ ID NO 115
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 6xHis tag"

<400> SEQUENCE: 115

His His His His His His
1               5

<210> SEQ ID NO 116
<211> LENGTH: 4
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 116

Met Pro Ala Ser
1

<210> SEQ ID NO 117
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

Glu Pro Gly Asp
1
```